US009695239B2

(12) United States Patent
Barth et al.

(10) Patent No.: US 9,695,239 B2
(45) Date of Patent: Jul. 4, 2017

(54) MICROTUBULE-MODIFYING COMPOUND

(71) Applicant: Fraunhofer-Gesellschaft zur Förderung der angewandten Forschung E.V., Munich (DE)

(72) Inventors: Stefan Barth, Munich (DE); Theopilus Thepen, Munich (DE); Dmitrij Hristodorov, Aachen (DE); Radoslav Mladenov, Aachen (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 14/436,568

(22) PCT Filed: Oct. 24, 2013

(86) PCT No.: PCT/EP2013/072257
§ 371 (c)(1),
(2) Date: Apr. 17, 2015

(87) PCT Pub. No.: WO2014/064187
PCT Pub. Date: May 1, 2014

(65) Prior Publication Data

US 2015/0259418 A1 Sep. 17, 2015

(30) Foreign Application Priority Data

Oct. 24, 2012 (EP) .................................... 12189804

(51) Int. Cl.

| | |
|---|---|
| ***C12P 21/06*** | (2006.01) |
| ***C12N 15/00*** | (2006.01) |
| ***C07H 21/04*** | (2006.01) |
| ***C12P 21/08*** | (2006.01) |
| ***C07K 16/00*** | (2006.01) |
| ***C07K 16/28*** | (2006.01) |
| ***C07K 14/52*** | (2006.01) |
| ***C07K 14/54*** | (2006.01) |
| ***C07K 14/47*** | (2006.01) |

(52) U.S. Cl.
CPC ............ *C07K 16/283* (2013.01); *C07K 14/47* (2013.01); *C07K 14/521* (2013.01); *C07K 14/54* (2013.01); *C07K 16/2878* (2013.01); *C07K 16/2896* (2013.01); *C07K 2317/622* (2013.01); *C07K 2319/21* (2013.01); *C07K 2319/33* (2013.01)

(58) Field of Classification Search
None
See application file for complete search history.

(56) References Cited

U.S. PATENT DOCUMENTS 4,946,778 A 8/1990 Ladner et al.
9,045,739 B2 * 6/2015 Barth .................... C12N 15/62

FOREIGN PATENT DOCUMENTS

WO WO-2012/045752 A1 4/2012

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Cawley, D.B., et al. Epidermal growth factor-toxin A chain conjugates: EGF-ricin A is a potent toxin while EGF-diphtheria fragment a is nontoxic. *Cell.* 1980; 22:563-570.
Hu, C.C., et al. Investigation of a plasmid containing a novel immunotoxin VEGF165-PE38 gene for antiangiogenic therapy in a malignant glioma model. *Int J Cancer.* 2010; 127:2222-2229.
Murphy, J.R., et al. Genetic construction, expression, and melanoma-selective cytotoxicity of a diphtheria toxin-related alpha-melanocyte-stimulating hormone fusion protein. *Proc Natl Acad Sci U S A.* 1986; 83:8258-8262.
Williams, D.P., et al. Diphtheria toxin receptor binding domain substitution with interleukin-2: genetic construction and properties of a diphtheria toxin-related interleukin-2 fusion protein. *Protein Eng.* 1987; 1:493-498.
Kreitman, R.J. Recombinant immunotoxins for the treatment of chemoresistant hematologic malignancies. *Curr Pharm Des.* 2009; 15:2652-2664.
Blythman, H.E., et al. Immunotoxins: hybrid molecules of monoclonal antibodies and a toxin subunit specifically kill tumour cells. *Nature.* 1981; 290:145-146.
Chaudhary, V.K., D.J. FitzGerald, and I. Pastan A proper amino terminus of diphtheria toxin is important for cytotoxicity. *Biochem Biophys Res Commun.* 1991; 180:545-551.
Kondo, T., et al. Activity of immunotoxins constructed with modified Pseudomonas exotoxin A lacking the cell recognition domain. *J Biol Chem.* 1988; 263:9470-9475.
Kreitman, R.J., et al. Single-chain immunotoxin fusions between anti-Tac and Pseudomonas exotoxin: relative importance of the two toxin disulfide bonds. *Bioconjug Chem.* 1993; 4:112-120.
Siegall, C.B., et al. Functional analysis of domains II, Ib, and III of Pseudomonas exotoxin. *J Biol Chem.* 1989; 264:14256-14261.

(Continued)

*Primary Examiner* — Shulamith H Shafer
(74) *Attorney, Agent, or Firm* — Venable LLP; Keith G. Haddaway; Kerri M. Patterson

(57) ABSTRACT

A compound formed from at least one component A comprising a binding domain for extra-cellular surface structures of a diseased proliferating cell that internalized upon binding of component A of said compound, and at least one component B, characterized in that component B is a polypeptide which amino acid sequence comprises a microtubule-associated protein (MAP) or comprises at least a partial sequence of the MAP, the partial sequence having maintained the binding function of the MAP to a microtubule.

16 Claims, 60 Drawing Sheets

(56) References Cited

OTHER PUBLICATIONS

Williams, D.P., et al. Structure/function analysis of interleukin-2-toxin (DAB486-IL-2). Fragment B sequences required for the delivery of fragment A to the cytosol of target cells. *J Biol Chem.* 1990; 265:11885-11889.
Madhumathi, J. and R.S. Verma Therapeutic targets and recent advances in protein immunotoxins. *Curr Opin Microbiol.* 2012; 15(3):300-9.
Kreitman, R.J. Immunotoxins for targeted cancer therapy. *AAPS J.* 2006: 8:E532-551.
Roscoe, D.M., et al. Primate antibody response to immunotoxin: serological and computer-aided analysis of epitopes on a truncated form of Pseudomonas exotoxin. *Infect Immun.* 1994; 62:5055-5065.
Roscoe, D.M., L.H. Pai, and I. Pastan Identification of epitopes on a mutant form of Pseudomonas exotoxin using serum from humans treated with Pseudomonas exotoxin containing immunotoxins. *Eur J Immunol.* 1997; 27:1459-1468.
Graham, M.L. Pegaspargase: a review of clinical studies. *Adv Drug Deliv Rev.* 2003; 55:1293-1302.
Reddy, K.R. Development and pharmacokinetics and pharmacodynamics of pegylated interferon alfa-2a (40 kD). *Semin Liver Dis.* 2004; 24 Suppl 2:33-38.
Tsutsumi, Y., et al. Site-specific chemical modification with polyethylene glycol of recombinant immunotoxin anti-Tac(Fv)-PE38 (LMB-2) improves antitumor activity and reduces animal toxicity and immunogenicity. *Proc Natl Acad Sci U S A.* 2000; 97:8548-8553.
Li, Z., et al. Immunotoxins and cancer therapy. *Cell Mol Immunol.* 2005; 2:106-112.
Mathew, M. and R.S. Verma Humanized immunotoxins: a new generation of immunotoxins for targeted cancer therapy. *Cancer Sci.* 2009; 100:1359-1365.
Huhn, M., et al. Human angiogenin fused to human CD30 ligand (Ang-CD30L) exhibits specific cytotoxicity against CD30-positive lymphoma. *Cancer Res.* 2001; 61:8737-8742.
Tur, M.K., et al. Immunokinases, a novel class of immunotherapeutics for targeted cancer therapy. *Curr Pharm Des.* 2009; 15:2693-2699.
Tur, M.K., et al. Targeted restoration of down-regulated DAPK2 tumor suppressor activity induces apoptosis in Hodgkin lymphoma cells. *J Immunother.* 2009; 32:431-441.
ten Cate, B., et al. Targeted elimination of leukemia stem cells; a new therapeutic approach in hemato-oncology. *Curr Drug Targets.* 2010; 11:95-110.
Wan, L., et al. Expression, purification, and refolding of a novel immunotoxin containing humanized single-chain fragment variable antibody against CTLA4 and the N-terminal fragment of human perforin. *Protein Expr Purif.* 2006; 48:307-313.
Barth, S., et al. Compatible-solute-supported periplasmic expression of functional recombinant proteins under stress conditions. *Appl Environ Microbiol.* 2000; 66:1572-1579.
Hetzel, C., et al. Small cleavable adapters enhance the specific cytotoxicity of a humanized immunotoxin directed against CD64-positive cells. *J Immunother.* 2008; 31:370-376.
Hristodorov, Dimitrij et al., "Macrophage-Targeted Therapy: CD64-Based Immunotoxins for Treatment of Chronic Inflammatory Diseases," Toxins, vol. 4, No. 9, Sep. 2012, pp. 676-694.
Mathew, Mrudula et al., "Humanized Immunotoxins: A New Generation of Immunotoxins for Targeted Cancer Therapy," Cancer Science, Japanese Cancer Association, Tokyo, JP, vol. 100, No. 8, Aug. 1, 2009, pp. 1359-1365.
Olson, K.R. et al., "Analysis of Map 4 Function in Living Cells Using Green Fluorescent Protein (GFP) Chimeras," The Journal of Cell Biology: JCB, The Rockefeller University Press, vol. 130, No. 3, Aug. 1, 1995, pp. 639-650.
Sluchanko, N.N. et al., "Phosphorylation of More Than One Site is Required for Tight Interaction of Human Tau Protein with 14-3-3zeta." FEBS Letters, Elsevier, Amsterdam, NL, vol. 583, No. 17, Sep. 3, 2009, pp. 2739-2742.
Stahnke, Bettina et al., "Granzyme B-H22 (scFV), a human Immunotoxin in Targeting CD 64 in Acute Myeloid Leukemia of Monocytic Subtypes," Molecular Cancer Therapeutics, vol. 7, No. 9, Sep. 2008, pp. 2924-2932.
International Search Report of PCT/EP2013/072257 dated Dec. 3, 2013 with Written Opinion of the International Searching Authority.
International Preliminary Report on Patentability in International Application No. PCT/EP2013/072257, dated Apr. 28, 2015.
Drechsel et al., "Modulation of the Dynamic Instability of Tubulin Assembly by the Microtubule-Associated Protein Tau," Molecular Biology of the Cell, vol. 33, pp. 1141-1154 (Oct. 1992).
Fukuoka et al., "Antimitotic Agents," Jpn. J. Cancer and Chemotherapy, vol. 24, No. 11, pp. 1519-1525 (1997).
Noetzel et al., "A comparision of the ability of XMAP215 and tau to inhibit the microtubule destabilizing activity of XKCM1," Phil. Trans. R. Soc. B., vol. 360, pp. 591-594 (Mar. 29, 2005).

* cited by examiner

Fig. 3

ID 1: Microtubule-associated protein tau (MAPT), *Homo sapiens*

ATGGCTGAACCCCGCCAGGAGTTCGAAGTGATGGAAGATCACGCTGGGACGTACGGGTTGGGGGACAGGAAAGATCAGGGGGGCTACACCATGC
ACCAAGACCAAGAGGGTGACACGGACGCTGGCCTGAAAGCTGAAGAAGCAGGCATTGGAGACACCCCCAGCCTGGAAGACGAAGCTGCTGGTCA
CGTGACCCAAGCTCGCATGGTCAGTAAAAGCAAAGACGGGACTGGAAGCGATGACAAAAAAGCCAAGGGGGCTGATGGTAAAACGAAGATCGCC
ACACCGCGGGGAGCAGCCCCTCCAGGCCAGAAGGGCCAGGCCAACGCCACCAGGATTCCAGCAAAAACCCCGCCCGCTCCAAAGACACCACCCA
GCTCTGGTGAACCTCCAAAATCAGGGGATCGCAGCGGCTACAGCAGCCCCGGCTCCCCAGGCACTCCCGGCAGCCGCTCCCGCACCCCGGCCCT
TCCAACCCCACCCACCCGGGAGCCCAAGAAGGTGGCAGTGGTCCGTACTCCACCCAAGTcGCCGTCTTCCGCCAAGAGCCGCCTGCAGACAGCC
CCCGTGCCCATGCCAGACCTGAAGAATGTCAAGTCCAAGATCGGCGCCACTGAGAACCTGAAGCACCAGCCGGGAGGCGGGAAGGTGCAGATAA
TTAATAAGAAGCTGGATCTTAGCAACGTCCAGTCCAAGTGTGGCTCAAAGGATAATATCAAACACGTCCCGGGAGGCGGCAGTGTGCAAATAGT
CTACAAACCAGTTGACCTGAGCAAGGTGACCTCCAAGTGTGGCTCATTAGGCAACATCCATCATAAACCAGGAGGTGGCCAGGTGGAAGTAAAA
TCTGAGAAGCTTGACTTCAAGGACAGAGTCCAGTCGAAGATTGGGTCCCTGGACAATATCACCCACGTCCCTGGCGGAGGAAATAAAAAGATTG
AAACCCACAAGCTGACCTTCCGCGAGAACGCCAAAGCCAAGACAGACCACGGGGCGGAGATCGTGTACAAGTCGCCAGTGGTGTCTGGGGACAC
GTCTCCACGGCATCTCAGCAATGTCTCCTCCACCGGCAGCATCGACATGGTAGACTCGCCCCAGCTCGCCACGCTAGCTGACGAGGTGTCTGCC
TCCCTGGCCAAGCAGGGTTTGCCCAAAAAAAAAAGGAAAGTGTGA

ID 2: H22(scFv), *Homo sapiens*

ATGGCCCAGGTGCAGCTGGTGGAGAGCGGTGGAGGTGTTGTGCAACCTGGCCGGTCCCTGCGCCTGTCCTGCTCCTCGTCTGGCTTCATTTTCA
GTGACAATTACATGTATTGGGTGAGACAGGCACCTGGAAAAGGTCTTGAGTGGGTTGCAACCATTAGTGATGGTGGTAGTTACACCTACTATCC
AGACAGTGTGAAGGGAAGATTTACAATATCGAGAGACAACAGCAAGAACACATTGTTCCTGCAAATGGACAGCCTGAGACCCGAAGACACCGGG
GTCTATTTTTGTGCAAGAGGCTACTATAGGTACGAGGGGGCTATGGACTACTGGGGCCAAGGGACCCCGGTCACCGTGAGCTCAGGAGGTGGCG
GCTCCGGAGGTGGAGGCAGCGGAGGGGGCGGATCCGACATCCAGCTGACCCAGAGCCCAAGCAGCCTGAGCGCCAGCGTGGGTGACAGAGTGAC
CATCACCTGTAAGTCCAGTCAAAGTGTTTTATACAGTTCAAATCAGAAGAACTACTTGGCCTGGTACCAGCAGAAGCCAGGTAAGGCTCCAAAG
CTGCTGATCTACTGGGCATCCACTAGGGAATCTGGTGTGCCAAGCAGATTCAGCGGTAGCGGTAGCGGTACCGACTTCACCTTCACCATCAGCA
GCCTCCAGCCAGAGGACATCGCCACCTACTACTGCCATCAATACCTCTCCTCGTGGACGTTCGGCCAAGGGACCAAGCTGGAGATCAAA

ID 3: H22(scFv)-MAPT

ATGGCCCAGGTGCAGCTGGTGGAGAGCGGTGGAGGTGTTGTGCAACCTGGCCGGTCCCTGCGCCTGTCCTGCTCCTCGTCTGGCTTCATTTTCA
GTGACAATTACATGTATTGGGTGAGACAGGCACCTGGAAAAGGTCTTGAGTGGGTTGCAACCATTAGTGATGGTGGTAGTTACACCTACTATCC
AGACAGTGTGAAGGGAAGATTTACAATATCGAGAGACAACAGCAAGAACACATTGTTCCTGCAAATGGACAGCCTGAGACCCGAAGACACCGGG
GTCTATTTTTGTGCAAGAGGCTACTATAGGTACGAGGGGGCTATGGACTACTGGGGCCAAGGGACCCCGGTCACCGTGAGCTCAGGAGGTGGCG
GCTCCGGAGGTGGAGGCAGCGGAGGGGGCGGATCCGACATCCAGCTGACCCAGAGCCCAAGCAGCCTGAGCGCCAGCGTGGGTGACAGAGTGAC
CATCACCTGTAAGTCCAGTCAAAGTGTTTTATACAGTTCAAATCAGAAGAACTACTTGGCCTGGTACCAGCAGAAGCCAGGTAAGGCTCCAAAG
CTGCTGATCTACTGGGCATCCACTAGGGAATCTGGTGTGCCAAGCAGATTCAGCGGTAGCGGTAGCGGTACCGACTTCACCTTCACCATCAGCA
GCCTCCAGCCAGAGGACATCGCCACCTACTACTGCCATCAATACCTCTCCTCGTGGACGTTCGGCCAAGGGACCAAGCTGGAGATCAAAGCGGC
CGCAATGGCTGAACCCCGCCAGGAGTTCGAAGTGATGGAAGATCACGCTGGGACGTACGGGTTGGGGGACAGGAAAGATCAGGGGGGCTACACC
ATGCACCAAGACCAAGAGGGTGACACGGACGCTGGCCTGAAAGCTGAAGAAGCAGGCATTGGAGACACCCCCAGCCTGGAAGACGAAGCTGCTG
GTCACGTGACCCAAGCTCGCATGGTCAGTAAAAGCAAAGACGGGACTGGAAGCGATGACAAAAAAGCCAAGGGGGCTGATGGTAAAACGAAGAT
CGCCACACCGCGGGGAGCAGCCCCTCCAGGCCAGAAGGGCCAGGCCAACGCCACCAGGATTCCAGCAAAAACCCCGCCCGCTCCAAAGACACCA
CCCAGCTCTGGTGAACCTCCAAAATCAGGGGATCGCAGCGGCTACAGCAGCCCCGGCTCCCCAGGCACTCCCGGCAGCCGCTCCCGCACCCCGG
CCCTTCCAACCCCACCCACCCGGGAGCCCAAGAAGGTGGCAGTGGTCCGTACTCCACCCAAGTcGCCGTCTTCCGCCAAGAGCCGCCTGCAGAC
AGCCCCCGTGCCCATGCCAGACCTGAAGAATGTCAAGTCCAAGATCGGCGCCACTGAGAACCTGAAGCACCAGCCGGGAGGCGGGAAGGTGCAG
ATAATTAATAAGAAGCTGGATCTTAGCAACGTCCAGTCCAAGTGTGGCTCAAAGGATAATATCAAACACGTCCCGGGAGGCGGCAGTGTGCAAA
TAGTCTACAAACCAGTTGACCTGAGCAAGGTGACCTCCAAGTGTGGCTCATTAGGCAACATCCATCATAAACCAGGAGGTGGCCAGGTGGAAGT
AAAATCTGAGAAGCTTGACTTCAAGGACAGAGTCCAGTCGAAGATTGGGTCCCTGGACAATATCACCCACGTCCCTGGCGGAGGAAATAAAAAG
ATTGAAACCCACAAGCTGACCTTCCGCGAGAACGCCAAAGCCAAGACAGACCACGGGGCGGAGATCGTGTACAAGTCGCCAGTGGTGTCTGGGG
ACACGTCTCCACGGCATCTCAGCAATGTCTCCTCCACCGGCAGCATCGACATGGTAGACTCGCCCCAGCTCGCCACGCTAGCTGACGAGGTGTC
TGCCTCCCTGGCCAAGCAGGGTTTGCCCAAAAAAAAAAGGAAAGTGTGA

ID 4: 425(scFv), *Mus sp.*

ATGGCCGAGGTGCAACTGCAGCAGTCTGGGGCTGAACTGGTGAAGCCTGGGGCTTCAGTGAAGTTGTCCTGCAAGGCTTCCGGCTACACCTTCA
CCAGCCACTGGATGCACTGGGTGAAGCAGAGGGCTGGACAAGGCCTTGAGTGGATCGGAGAGTTTAATCCCAGCAACGGCCGTACTAACTACAA
TGAGAAATTCAAGAGCAAGGCCACACTGACTGTAGACAAATCCTCCAGCACAGCCTACATGCAACTCAGCAGCCTGACATCTGAGGACTCTGCG
GTCTATTACTGTGCCAGTCGGGACTATGATTACGACGGACGGTACTTTGACTACTGGGGCCAAGGGACCACGGTCACCGTCTCCTCAGGTGGCG
GTGGCTCGGGCGGTGGTGGGTCGGGTGGTGGCGGATCTGACATCGAGCTCACCCAGTCTCCAGCAATCATGTCTGCATCTCCAGGGGAGAAGGT
CACTATGACCTGCAGTGCCAGCTCAAGTGTAACTTACATGTATTGGTACCAGCAGAAGCCAGGATCCTCCCCCAGACTCCTGATTTATGACACA
TCCAACCTGGCTTCTGGAGTCCCTGTTCGTTTCAGTGGCAGTGGGTCTGGGACCTCTTACTCTCTCACAATCAGCCGAATGGAGGCTGAAGATG
CTGCCACTTATTACTGCCAGCAGTGGAGTAGTCACATATTCACGTTCGGCTCGGGGACAGAACTCGAGATCAAA

ID 5: 425(scFv)-MAPT

ATGGCCGAGGTGCAACTGCAGCAGTCTGGGGCTGAACTGGTGAAGCCTGGGGCTTCAGTGAAGTTGTCCTGCAAGGCTTCCGGCTACACCTTCA
CCAGCCACTGGATGCACTGGGTGAAGCAGAGGGCTGGACAAGGCCTTGAGTGGATCGGAGAGTTTAATCCCAGCAACGGCCGTACTAACTACAA
TGAGAAATTCAAGAGCAAGGCCACACTGACTGTAGACAAATCCTCCAGCACAGCCTACATGCAACTCAGCAGCCTGACATCTGAGGACTCTGCG
GTCTATTACTGTGCCAGTCGGGACTATGATTACGACGGACGGTACTTTGACTACTGGGGCCAAGGGACCACGGTCACCGTCTCCTCAGGTGGCG
GTGGCTCGGGCGGTGGTGGGTCGGGTGGTGGCGGATCTGACATCGAGCTCACCCAGTCTCCAGCAATCATGTCTGCATCTCCAGGGGAGAAGGT
CACTATGACCTGCAGTGCCAGCTCAAGTGTAACTTACATGTATTGGTACCAGCAGAAGCCAGGATCCTCCCCCAGACTCCTGATTTATGACACA

Fig. 3 (Continued)

TCCAACCTGGCTTCTGGAGTCCCTGTTCGTTTCAGTGGCAGTGGGTCTGGGACCTCTTACTCTCTCACAATCAGCCGAATGGAGGCTGAAGATG
CTGCCACTTATTACTGCCAGCAGTGGAGTAGTCACATATTCACGTTCGGCTCGGGGACAGAACTCGAGATCAAAGCGGCCGCAATGGCTGAACC
CCGCCAGGAGTTCGAAGTGATGGAAGATCACGCTGGGACGTACGGGTTGGGGGACAGGAAAGATCAGGGGGGCTACACCATGCACCAAGACCAA
GAGGGTGACACGGACGCTGGCCTGAAAGCTGAAGAAGCAGGCATTGGAGACACCCCCAGCCTGGAAGACGAAGCTGCTGGTCACGTGACCCAAG
CTCGCATGGTCAGTAAAAGCAAAGACGGGACTGGAAGCGATGACAAAAAAGCCAAGGGGGCTGATGGTAAAACGAAGATCGCCACACCGCGGGG
AGCAGCCCCTCCAGGCCAGAAGGGCCAGGCCAACGCCACCAGGATTCCAGCAAAAACCCCGCCCGCTCCAAAGACACCACCCAGCTCTGGTGAA
CCTCCAAAATCAGGGGATCGCAGCGGCTACAGCAGCCCCGGCTCCCCAGGCACTCCCGGCAGCCGCTCCCGCACCCCGGCCCTTCCAACCCCAC
CCACCCGGGAGCCCAAGAAGGTGGCAGTGGTCCGTACTCCACCCAAGTCGCCGTCTTCCGCCAAGAGCCGCCTGCAGACAGCCCCCGTGCCCAT
GCCAGACCTGAAGAATGTCAAGTCCAAGATCGGCGCCACTGAGAACCTGAAGCACCAGCCGGGAGGCGGGAAGGTGCAGATAATTAATAAGAAG
CTGGATCTTAGCAACGTCCAGTCCAAGTGTGGCTCAAAGGATAATATCAAACACGTCCCGGGAGGCGGCAGTGTGCAAATAGTCTACAAACCAG
TTGACCTGAGCAAGGTGACCTCCAAGTGTGGCTCATTAGGCAACATCCATCATAAACCAGGAGGTGGCCAGGTGGAAGTAAAATCTGAGAAGCT
TGACTTCAAGGACAGAGTCCAGTCGAAGATTGGGTCCCTGGACAATATCACCCACGTCCCTGGCGGAGGAAATAAAAAGATTGAAACCCACAAG
CTGACCTTCCGCGAGAACGCCAAAGCCAAGACAGACCACGGGGCGGAGATCGTGTACAAGTCGCCAGTGGTGTCTGGGGACACGTCTCCACGGC
ATCTCAGCAATGTCTCCTCCACCGGCAGCATCGACATGGTAGACTCGCCCCAGCTCGCCACGCTAGCTGACGAGGTGTCTGCCTCCCTGGCCAA
GCAGGGTTTGCCCAAAAAAAAAAGGAAAGTGTGA

**ID 6: Ki4(scFv), *Mus sp.***

ATGGCCCAGGTCAAGCTGCAGGAGTCAGGGACTGAACTGGCAAAGCCTGGGGCCGCAGTGAAGATGTCCTGCAAGGCTTCTGGCTACACCTTTA
CTGACTACTGGATGCACTGGGTTAAACAGAGGCCTGGACAGGGTCTGGAATGGATTGGATACATTAATCCTAACACTGCTTATACTGACTACAA
TCAGAAATTCAAGGACAAGGCCACATTGACTGCAGACAAATCCTCCAGCACAGCCTACATGCAACTGCGCAGCCTGACCTCTGAGGATTCTGCA
GTCTATTACTGTGCAAAAAAGACAACTCAGACTACGTGGGGGTTTCCTTTTTGGGGCCAAGGGACCACGGTCACCGTCTCCTCAGGTGGAGGCG
GTTCAGGCGGAGGTGGCTCTGGCGGTGGCGGATCGGACATTGTGCTGACCCAGTCTCCAAAATCCATGGCCATGTCAGTCGGAGAGAGGGTCAC
CTTGAGCTGCAAGGCCAGTGAGAATGTGGATTCTTTTGTTTCCTGGTATCAACAGAAACCAGGCCAGTCTCCTAAACTGCTGATATACGGGGCC
TCCAACCGGTACACTGGGGTCCCCGATCGCTTCGCAGGCAGTGGATCTGGAAGAGATTTCACTCTGACCATCAGCAGTGTGCAGGCTGAAGACC
TTGCAGATTATCACTGTGGACAGAATTACAGGTATCCGCTCACGTTCGGTGCTGGCACCAAGCTGGAAATCAAACGG

ID 7: Ki4(scFv)-MAPT

ATGGCCCAGGTCAAGCTGCAGGAGTCAGGGACTGAACTGGCAAAGCCTGGGGCCGCAGTGAAGATGTCCTGCAAGGCTTCTGGCTACACCTTTA
CTGACTACTGGATGCACTGGGTTAAACAGAGGCCTGGACAGGGTCTGGAATGGATTGGATACATTAATCCTAACACTGCTTATACTGACTACAA
TCAGAAATTCAAGGACAAGGCCACATTGACTGCAGACAAATCCTCCAGCACAGCCTACATGCAACTGCGCAGCCTGACCTCTGAGGATTCTGCA
GTCTATTACTGTGCAAAAAAGACAACTCAGACTACGTGGGGGTTTCCTTTTTGGGGCCAAGGGACCACGGTCACCGTCTCCTCAGGTGGAGGCG
GTTCAGGCGGAGGTGGCTCTGGCGGTGGCGGATCGGACATTGTGCTGACCCAGTCTCCAAAATCCATGGCCATGTCAGTCGGAGAGAGGGTCAC
CTTGAGCTGCAAGGCCAGTGAGAATGTGGATTCTTTTGTTTCCTGGTATCAACAGAAACCAGGCCAGTCTCCTAAACTGCTGATATACGGGGCC
TCCAACCGGTACACTGGGGTCCCCGATCGCTTCGCAGGCAGTGGATCTGGAAGAGATTTCACTCTGACCATCAGCAGTGTGCAGGCTGAAGACC
TTGCAGATTATCACTGTGGACAGAATTACAGGTATCCGCTCACGTTCGGTGCTGGCACCAAGCTGGAAATCAAACGG

**ID 8: scFv35, *Homo sapiens***

ATGACCCAGTCTCCATCCTCCCTGTCTGCATCTGTAGGAGACAGAGTCACCATCGCTTGCCGGGCAAGTCAGACCATTAGCAACTATTTAAATT
GGTATCAGCAGAAACCAGGGAAAGCCCCTAAGCTCCTGATCTATGGTGCATCCAGTTTGCAAAGTGGGGTCCCATCAAGGTTCAGTGGCAGTGG
ATCTGGGACAGATTTCACTCTCACCATCAGCAGTCTGCAACCTGAAGATTTTGCAACTTACTACTGTCAACAGAGTTACAGTACCCCTCCGACG
TACACTTTTGGCCAGGGGACCAAGCTGGAGATCAAAGGTGGCGGTGGCTCGGGCGGTGGTGGGTCGGGTGGCAGCGGATCATCGGGGGGCGACT
TGGTCCAGCCGGGGGGGTCCCTGAGAGTCTCCTGTGTAGCCTCTGGATTTACATTTAGGACCTATGTGATGAACTGGGTCCGCCAGGCTCCAGG
AAAGGGGCTGGAGTGGGTGGCCCACATAAGTCCAGAGGGAACTGAAGAATACTATGCGGACCCTGTGAAGGGCCGATTTACCGTCTCCAGAGAC
AACGCGAAGAATTCAGTATTTCTGCAAATGAATAGTCTGAGAGGCGAGGACACGGCTGTGTATTATTGCGCGAGAGTCCGACGCTATGGTCCCT
CTACGCTCAGTCCGTTCACCTGGAAgGACAATCACTACGCCATGGACGTCTGGGGCCAAGGGACAACGGTCACCGTCTCTCCA

ID 9: scFv35-MAPT

ATGACCCAGTCTCCATCCTCCCTGTCTGCATCTGTAGGAGACAGAGTCACCATCGCTTGCCGGGCAAGTCAGACCATTAGCAACTATTTAAATT
GGTATCAGCAGAAACCAGGGAAAGCCCCTAAGCTCCTGATCTATGGTGCATCCAGTTTGCAAAGTGGGGTCCCATCAAGGTTCAGTGGCAGTGG
ATCTGGGACAGATTTCACTCTCACCATCAGCAGTCTGCAACCTGAAGATTTTGCAACTTACTACTGTCAACAGAGTTACAGTACCCCTCCGACG
TACACTTTTGGCCAGGGGACCAAGCTGGAGATCAAAGGTGGCGGTGGCTCGGGCGGTGGTGGGTCGGGTGGCAGCGGATCATCGGGGGGCGACT
TGGTCCAGCCGGGGGGGTCCCTGAGAGTCTCCTGTGTAGCCTCTGGATTTACATTTAGGACCTATGTGATGAACTGGGTCCGCCAGGCTCCAGG
AAAGGGGCTGGAGTGGGTGGCCCACATAAGTCCAGAGGGAACTGAAGAATACTATGCGGACCCTGTGAAGGGCCGATTTACCGTCTCCAGAGAC
AACGCGAAGAATTCAGTATTTCTGCAAATGAATAGTCTGAGAGGCGAGGACACGGCTGTGTATTATTGCGCGAGAGTCCGACGCTATGGTCCCT
CTACGCTCAGTCCGTTCACCTGGAAgGACAATCACTACGCCATGGACGTCTGGGGCCAAGGGACAACGGTCACCGTCTCTCCAgcGGCCGCAAT
GGCTGAACCCCGCCAGGAGTTCGAAGTGATGGAAGATCACGCTGGGACGTACGGGTTGGGGGACAGGAAAGATCAGGGGGGCTACACCATGCAC
CAAGACCAAGAGGGTGACACGGACGCTGGCCTGAAAGCTGAAGAAGCAGGCATTGGAGACACCCCCAGCCTGGAAGACGAAGCTGCTGGTCACG
TGACCCAAGCTCGCATGGTCAGTAAAAGCAAAGACGGGACTGGAAGCGATGACAAAAAAGCCAAGGGGGCTGATGGTAAAACGAAGATCGCCAC
ACCGCGGGGAGCAGCCCCTCCAGGCCAGAAGGGCCAGGCCAACGCCACCAGGATTCCAGCAAAAACCCCGCCCGCTCCAAAGACACCACCCAGC
TCTGGTGAACCTCCAAAATCAGGGGATCGCAGCGGCTACAGCAGCCCCGGCTCCCCAGGCACTCCCGGCAGCCGCTCCCGCACCCCGGCCCTTC
CAACCCCACCCACCCGGGAGCCCAAGAAGGTGGCAGTGGTCCGTACTCCACCCAAGTcGCCGTCTTCCGCCAAGAGCCGCCTGCAGACAGCCCC
CGTGCCCATGCCAGACCTGAAGAATGTCAAGTCCAAGATCGGCGCCACTGAGAACCTGAAGCACCAGCCGGGAGGCGGGAAGGTGCAGATAATT
AATAAGAAGCTGGATCTTAGCAACGTCCAGTCCAAGTGTGGCTCAAAGGATAATATCAAACACGTCCCGGGAGGCGGCAGTGTGCAAATAGTCT
ACAAACCAGTTGACCTGAGCAAGGTGACCTCCAAGTGTGGCTCATTAGGCAACATCCATCATAAACCAGGAGGTGGCCAGGTGGAAGTAAAATC
TGAGAAGCTTGACTTCAAGGACAGAGTCCAGTCGAAGATTGGGTCCCTGGACAATATCACCCACGTCCCTGGCGGAGGAAATAAAAAGATTGAA
ACCCACAAGCTGACCTTCCGCGAGAACGCCAAAGCCAAGACAGACCACGGGGCGGAGATCGTGTACAAGTCGCCAGTGGTGTCTGGGGACACGT
CTCCACGGCATCTCAGCAATGTCTCCTCCACCGGCAGCATCGACATGGTAGACTCGCCCCAGCTCGCCACGCTAGCTGACGAGGTGTCTGCCTC
CCTGGCCAAGCAGGGTTTGCCCAAAAAAAAAAGGAAAGTGTGA

Fig. 3 (Continued)

ID 10: anti-EpCAM(scFv), *Homo sapiens*

ATGGCCCAGGTGCAGCTGGTGCAGTCTGGGGCTGAGGTGAAGAAGCCTGGGTCCTCGGTGAGGGTCTCCTGCAAGGCTTCTGGAGGCACCTTCA
GCAGCTATGCTATCAGCTGGGTGCGACAGGCCCCTGGACAAGGGCTTGAGTGGATGGGAGGGATCATCCCTATCTTTGGTACAGCAAACTACGC
ACAGAAGTTCCAGGGCAGAGTCACGATTACCGCGGACGAATCCACGAGCACAGCCTACATGGAGCTGAGCAGCCTGAGATCTGAGGACACGGCT
GTGTATTACTGTGCAAGAGACCCGTTTCTTCACTATTGGGGCCAAGGTACCCTGGTCACCGTCTCGAGTGGTGGAGGCGGTTCAGGCGGAGGTG
GCTCTGGCGGTGGCGGATCGGAAATTGAGCTCACTCAGTCTCCACTCTCCCTGCCCGTCACCCCTGGAGAGCCGGCCTCCATCTCCTGCAGGTC
TAGTCAGAGCCTCCTGCATAGTAATGGATACAACTATTTGGATTGGTACCTGCAGAAGCCAGGGCAGTCTCCACAGCTCCTGATCTATTTGGGT
TCTAATCGGGCCTCCGGGGTCCCTGACAGGTTCAGTGGCAGTGGATCAGGCACAGATTTTACACTGAAAATCAGCAGAGTGGAGGCTGAGGATG
TTGGGGTTTATTACTGCATGCAAGCTCTACAAACTTTCACTTTCGGCCCTGGGACCAAGGTGGAGATCAAACGT

ID 11: anti-EpCAM(scFv)-MAPT

ATGGCCCAGGTGCAGCTGGTGCAGTCTGGGGCTGAGGTGAAGAAGCCTGGGTCCTCGGTGAGGGTCTCCTGCAAGGCTTCTGGAGGCACCTTCA
GCAGCTATGCTATCAGCTGGGTGCGACAGGCCCCTGGACAAGGGCTTGAGTGGATGGGAGGGATCATCCCTATCTTTGGTACAGCAAACTACGC
ACAGAAGTTCCAGGGCAGAGTCACGATTACCGCGGACGAATCCACGAGCACAGCCTACATGGAGCTGAGCAGCCTGAGATCTGAGGACACGGCT
GTGTATTACTGTGCAAGAGACCCGTTTCTTCACTATTGGGGCCAAGGTACCCTGGTCACCGTCTCGAGTGGTGGAGGCGGTTCAGGCGGAGGTG
GCTCTGGCGGTGGCGGATCGGAAATTGAGCTCACTCAGTCTCCACTCTCCCTGCCCGTCACCCCTGGAGAGCCGGCCTCCATCTCCTGCAGGTC
TAGTCAGAGCCTCCTGCATAGTAATGGATACAACTATTTGGATTGGTACCTGCAGAAGCCAGGGCAGTCTCCACAGCTCCTGATCTATTTGGGT
TCTAATCGGGCCTCCGGGGTCCCTGACAGGTTCAGTGGCAGTGGATCAGGCACAGATTTTACACTGAAAATCAGCAGAGTGGAGGCTGAGGATG
TTGGGGTTTATTACTGCATGCAAGCTCTACAAACTTTCACTTTCGGCCCTGGGACCAAGGTGGAGATCAAACGTGCGGCCGCAATGGCTGAACC
CCGCCAGGAGTTCGAAGTGATGGAAGATCACGCTGGGACGTACGGGTTGGGGGACAGGAAAGATCAGGGGGGCTACACCATGCACCAAGACCAA
GAGGGTGACACGGACGCTGGCCTGAAAGCTGAAGAAGCAGGCATTGGAGACACCCCCAGCCTGGAAGACGAAGCTGCTGGTCACGTGACCCAAG
CTCGCATGGTCAGTAAAAGCAAAGACGGGACTGGAAGCGATGACAAAAAAGCCAAGGGGGCTGATGGTAAAACGAAGATCGCCACACCGCGGGG
AGCAGCCCCTCCAGGCCAGAAGGGCCAGGCCAACGCCACCAGGATTCCAGCAAAAACCCCGCCCGCTCCAAAGACACCACCCAGCTCTGGTGAA
CCTCCAAAATCAGGGGATCGCAGCGGCTACAGCAGCCCCGGCTCCCCAGGCACTCCCGGCAGCCGCTCCCGCACCCCGGCCCTTCCAACCCCAC
CCACCCGGGAGCCCAAGAAGGTGGCAGTGGTCCGTACTCCACCCAAGTCGCCGTCTTCCGCCAAGAGCCGCCTGCAGACAGCCCCCGTGCCCAT
GCCAGACCTGAAGAATGTCAAGTCCAAGATCGGCGCCACTGAGAACCTGAAGCACCAGCCGGGAGGCGGGAAGGTGCAGATAATTAATAAGAAG
CTGGATCTTAGCAACGTCCAGTCCAAGTGTGGCTCAAAGGATAATATCAAACACGTCCCGGGAGGCGGCAGTGTGCAAATAGTCTACAAACCAG
TTGACCTGAGCAAGGTGACCTCCAAGTGTGGCTCATTAGGCAACATCCATCATAAACCAGGAGGTGGCCAGGTGGAAGTAAAATCTGAGAAGCT
TGACTTCAAGGACAGAGTCCAGTCGAAGATTGGGTCCCTGGACAATATCACCCACGTCCCTGGCGGAGGAAATAAAAAGATTGAAACCCACAAG
CTGACCTTCCGCGAGAACGCCAAAGCCAAGACAGACCACGGGGCGGAGATCGTGTACAAGTCGCCAGTGGTGTCTGGGGACACGTCTCCACGGC
ATCTCAGCAATGTCTCCTCCACCGGCAGCATCGACATGGTAGACTCGCCCCAGCTCGCCACGCTAGCTGACGAGGTGTCTGCCTCCCTGGCCAA
GCAGGGTTTGCCCAAAAAAAAAAGGAAAGTGTGA

ID 12: EGF, *Homo sapiens*

ATGGCCCAGCCGGCCAATAGTGACTCTGAATGTCCCCTGTCCCACGATGGGTACTGCCTCCATGATGGTGTGTGCATGTATATTGAAGCATTGG
ACAAGTATGCATGCAACTGTGTTGTTGGCTACATCGGGGAGCGATGTCAGTACCGAGACCTGAAGTGGTGGGAACTGCGC

ID 13: EGF-MAPT, *Homo sapiens*

ATGGCCCAGCcggccAATAGTGACTCTGAATGTCCCCTGTCCCACGATGGGTACTGCCTCCATGATGGTGTGTGCATGTATATTGAAGCATTGG
ACAAGTATGCATGCAACTGTGTTGTTGGCTACATCGGGGAGCGATGTCAGTACCGAGACCTGAAGTGGTGGGAACTGCGCgcGGCCGCAATGGC
TGAACCCCGCCAGGAGTTCGAAGTGATGGAAGATCACGCTGGGACGTACGGGTTGGGGGACAGGAAAGATCAGGGGGGCTACACCATGCACCAA
GACCAAGAGGGTGACACGGACGCTGGCCTGAAAGCTGAAGAAGCAGGCATTGGAGACACCCCCAGCCTGGAAGACGAAGCTGCTGGTCACGTGA
CCCAAGCTCGCATGGTCAGTAAAAGCAAAGACGGGACTGGAAGCGATGACAAAAAAGCCAAGGGGGCTGATGGTAAAACGAAGATCGCCACACC
GCGGGGAGCAGCCCCTCCAGGCCAGAAGGGCCAGGCCAACGCCACCAGGATTCCAGCAAAAACCCCGCCCGCTCCAAAGACACCACCCAGCTCT
GGTGAACCTCCAAAATCAGGGGATCGCAGCGGCTACAGCAGCCCCGGCTCCCCAGGCACTCCCGGCAGCCGCTCCCGCACCCCGGCCCTTCCAA
CCCCACCCACCCGGGAGCCCAAGAAGGTGGCAGTGGTCCGTACTCCACCCAAGTcGCCGTCTTCCGCCAAGAGCCGCCTGCAGACAGCCCCCGT
GCCCATGCCAGACCTGAAGAATGTCAAGTCCAAGATCGGCGCCACTGAGAACCTGAAGCACCAGCCGGGAGGCGGGAAGGTGCAGATAATTAAT
AAGAAGCTGGATCTTAGCAACGTCCAGTCCAAGTGTGGCTCAAAGGATAATATCAAACACGTCCCGGGAGGCGGCAGTGTGCAAATAGTCTACA
AACCAGTTGACCTGAGCAAGGTGACCTCCAAGTGTGGCTCATTAGGCAACATCCATCATAAACCAGGAGGTGGCCAGGTGGAAGTAAAATCTGA
GAAGCTTGACTTCAAGGACAGAGTCCAGTCGAAGATTGGGTCCCTGGACAATATCACCCACGTCCCTGGCGGAGGAAATAAAAAGATTGAAACC
CACAAGCTGACCTTCCGCGAGAACGCCAAAGCCAAGACAGACCACGGGGCGGAGATCGTGTACAAGTCGCCAGTGGTGTCTGGGGACACGTCTC
CACGGCATCTCAGCAATGTCTCCTCCACCGGCAGCATCGACATGGTAGACTCGCCCCAGCTCGCCACGCTAGCTGACGAGGTGTCTGCCTCCCT
GGCCAAGCAGGGTTTGCCCAAAAAAAAAAGGAAAGTGTGA A431 cells L3.6pl cells MCF-7 cells

ID 14: KIF1, *Homo sapiens*
ATGGCGAACGTTCCGTGGGCAGAGGTCTGCGAGAAATTCCAGGCGGCGCTCGCTCTGTCGCGGGTGGAACTGCATAAAAATCCGGAGAAGGAAC
CATACAAGTCCAAATACAGCGCCCGGGCGCTACTGGAAGAGGTCAAGGCGCTGCTCGGCCCTGCGCCTGAGGACGAGGATGAGCGGCCTGAGGC
CGAGGACGGCCCGGGTGCCGGTGACCACGCCCTGGGGCTGCCGGCTGAGGTGGTGGAGCCCGAGGGGCCCGTCGCCCAGCGAGCGGTGAGGCTG
GCAGTCATCGAGTTCCACCTCGGGGTGAACCACATCGACACGGAGGAGCTGTCGGCGGGGGAGGAGCACCTGGTGAAATGCCTGCGGCTGCTGC
GCAGGTACCGGCTCTCGCACGACTGCATCTCTCTCTGCATCCAGGCGCAGAATAACCTGGGTATCTTGTGGTCTGAAAGAGAAGAAATTGAAAC
TGCACAGGCTTACCTAGAGTCATCAGAAGCACTATATAATCAGTATATGAAAGAGGTTGGGAGTCCTCCTCTTGATCCTACTGAGCGTTTTCTT
CCTGAAGAAGAGAAACTTACTGAACAAGAGAGATCAAAAAGATTTGAAAAGGTTTATACTCATAACCTATATTACCTAGCTCAAGTCTACCAGC
ATCTGGAAATGTTTGAGAAGGCTGCTCACTATTGCCATAGTACACTAAAACGCCAGCTTGAGCACAATGCCTACCATCCTATAGAGTGGGCTAT
CAATGCTGCTACCTTGTCACAGTTTTACATCAATAAGCTATGCTTTATGGAGGCCAGGCACTGTTTATCAGCTGCTAATGTCATTTTTGGTCAA
ACTGGAAAGATCTCAGCCACAGAAGACACTCCTGAAGCTGAAGGAGAAGTGCCAGAGCTTTATCATCAAAGAAAGGGGGAAATAGCAAGGTGCT
GGATCAAATACTGTTTGACTCTCATGCAGAATGCCCAACTCTCCATGCAGGACAACATAGGAGAGCTTGATCTTGATAAACAGTCTGAACTTAG
AGCTTTAAGGAAAAAAGAACTAGATGAGGAGGAAAGCATTCGGAAAAAAGCTGTGCAGTTTGGAACCGGTGAACTGTGTGATGCCATCTCTGCA
GTAGAAGAGAAAGTGAGCTACTTGAGACCTTTAGATTTTGAAGAAGCCAGAGAACTTTTCTTATTGGGTCAGCACTATGTCTTTGAGGCAAAAG
AGTTCTTTCAGATTGATGGTTATGTCACTGACCATATTGAAGTTGTCCAAGACCACAGTGCTCTGTTTAAGGTGCTTGCATTCTTTGAAACTGA
CATGGAGAGACGGTGCAAGATGCATAAACGCAGAATAGCCATGCTAGAGCCCCTAACTGTAGACCTGAATCCACAGTATTATCTGTTGGTCAAC
AGACAGATCCAGTTTGAAATTGCACATGCTTACTATGATATGATGGATTTGAAGGTTGCCATTGCTGACAGGCTAAGGGATCCTGATTCACACA
TTGTAAAAAAAATAAATAATCTTAATAAGTCAGCACTGAAGTACTACCAGCTCTTCTTAGACTCCCTGAGAGACCCAAATAAAGTATTCCCTGA
GCATATAGGGGAAGATGTTCTTCGCCCTGCCATGTTAGCTAAGTTTCGAGTTGCCCGTCTCTATGGCAAAATCATTACTGCAGATCCCAAGAAA
GAGCTGGAAAATTTGGCAACATCATTGGAACATTACAAATTTATTGTTGATTACTGTGAAAAGCATCCTGAGGCCGCCCAGGAAATAGAAGTTG
AGCTAGAACTTAGTAAAGAGATGGTTAGTCTTCTCCCAACAAAAATGGAGAGATTCAGAACCAAGATGGCCCTGACTTAA ID15: KIF2A, *Homo sapiens*
ATGGCAACGGCCAACTTCGGCAAGATCCAGATCGGGATTTACGTGGAGATCAAGCGCAGCGATGGCCGAATACATCAAGCAATGGTAACATCTT
TAAATGAAGATAATGAAAGTGTAACTGTTGAATGGATAGAAAATGGAGATACAAAAGGCAAAGAGATTGACCTGGAGAGCATCTTTTCACTTAA
CCCTGACCTTGTTCCTGATGAAGAAATTGAACCCAGTCCAGAAACACCTCCACCTCCAGCATCCTCAGCCAAAGTAAACAAAATTGTAAAGAAT
CGACGGACTGTAGCTTCTATTAAGAATGACCCTCCTTCAAGAGATAATAGAGTGGTTGGTTCAGCACGTGCACGGCCCAGTCAATTTCCTGAAC
AGTCTTCCTCTGCACAACAGAATGGTAGTGTTTCAGATATATCTCCAGTTCAAGCTGCAAAAAAGGAATTTGGACCCCCTTCACGTAGAAAATC
TAATTGTGTGAAAGAAGTAGAAAAACTGCAAGAAAAACGAGAGAAAAGGAGATTGCAACAGCAAGAACTTAGAGAAAAAAGAGCCCAGGACGTT
GATGCTACAAACCCAAATTATGAAATTATGTGTATGATCAGAGACTTTAGAGGAAGTTTGGATTATAGACCATTAACAACAGCAGATCCTATTG
ATGAACATAGGATATGTGTGTGTGTAAGAAAACGACCACTCAATAAAAAAGAAACTCAAATGAAAGATCTTGATGTAATCACAATTCCTAGTAA
AGATGTTGTGATGGTACATGAACCAAAACAAAAAGTAGATTTAACAAGGTACCTAGAAAACCAAACATTTCGTTTTGATTATGCCTTTGATGAC
TCAGCTCCTAATGAAATGGTTTACAGGTTTACTGCTAGACCACTAGTGGAAACTATATTTGAAAGGGGAATGGCTACATGCTTTGCTTATGGGC
AGACTGGAAGTGCAAAAACTCATACTATGGGTGGTGACTTTTCAGGAAAGAACCAAGATTGTTCTAAAGGAATTTATGCATTAGCAGCTCGAGA
TGTCTTTTTAATGCTAAAGAAGCCAAACTATAAGAAGCTAGAACTTCAAGTATATGCAACCTTCTTTGAAATTTATAGTGGAAAGGTGTTTGAC
TTGCTAAACAGGAAAACAAAATTAAGAGTTCTAGAAGATGGAAAACAGCAGGTTCAAGTGGTGGGATTACAGGAACGGGAGGTCAAATGTGTTG
AAGATGTACTGAAACTCATTGACATAGGCAACAGTTGCAGAACATCCGGTCAAACATCTGCAAATGCACATTCATCTCGGAGCCATGCAGTGTT
TCAGATTATTCTTAGAAGGAAAGGAAAACTACATGGCAAATTTTCTCTCATTGATTTGGCTGGAAATGAAAGAGGAGCTGATACTTCCAGTGCG
GACAGGCAAACTAGGCTTGAAGGTGCTGAAATTAATAAAAGCCTTTTAGCACTCAAGGAGTGCATCAGAGCCTTAGGTAGAAATAAACCTCATA
CTCCTTTCCGTGCAAGTAAACTCACTCAGGTGTTAAGAGATTCTTTCATAGGTGAAAACTCTCGTACCTGCATGATTGCCACAATCTCTCCAGG
AATGGCATCCTGTGAAAATACTCTTAATACATTAAGATATGCAAATAGAGTAAAGGAGTTTGGAATTAGTCCATCAGACATTCCCTTCTCACAG
GGTAGTGGCAGTCGCCCTGATCTCTCTCCTTCTTATGAATATGACGACTTTTCTCCTTCAGTTACCAGGGTCAAAGAATTGACTGTAGATCCAA
CTGCTGCTGGTGATGTTCGTCCAATAATGCACCATCCACCAAACCAGATTGATGACTTAGAGACACAGTGGGGTGTGGGGAGTTCCCCTCAGAG
AGATGATCTAAAACTTCTTTGTGAACAAAATGAAGAAGAAGTCTCTCCACAGTTGTTTACTTTCCACGAAGCTGTTTCACAAATGGTAGAAATG
GAAGAACAAGTTGTAGAAGATCACAGGGCAGTGTTCCAGGAATCTATTCGGTGGTTAGAAGATGAAAAGGCCCTCTTAGAGATGACTGAAGAAG
TAGATTATGATGTCGATTCATATGCTACACAACTTGAAGCTATTCTTGAGCAAAAAATAGACATTTTAACTGAACTGCGGGATAAAGTGAAATC
TTTCCGTGCAGCTCTACAAGAGGAGGAACAAGCCAGCAAGCAAATCAACCCGAAGAGACCCCGTGCCCTTTAA ID16: KIF4A, *Homo sapiens*
ATGAAGGAAGAGGTGAAGGGAATTCCCGTAAGAGTGGCGCTGCGTTGTCGCCCTCTGGTCCCCAAAGAGATTAGCGAGGGCTGCCAGATGTGCC
TTTCCTTCGTGCCCGGAGAGCCTCAGGTGGTGGTTGGTACAGATAAATCCTTCACCTACGATTTTGTATTTGATCCCTCTACTGAACAGGAAGA
AGTCTTCAATACAGCAGTAGCGCCACTCATAAAGGTGTATTTAAAGGATATAATGCAACGGTCCTGGCCTATGGGCAGACTGGCTCTGGAAAA
ACCTATTCAATGGGAGGTGCATATACTGCAGAGCAAGAGAATGAACCAACAGTTGGGGTTATTCCTAGGGTAATACAACTGCTCTTCAAAGAAA
TTGATAAAAAGAGTGACTTTGAATTTACTCTGAAAGTGTCTTACTTAGAGATTTACAATGAAGAAATTTTGGATCTTCTATGCCCATCTCGTGA
GAAAGCTCAAATAAATATACGAGAGGATCCTAAGGAAGGCATAAAGATTGTGGGACTCACTGAGAAGACTGTTTTGGTTGCCTTGGATACTGTT
TCCTGTTTGGAACAGGGCAACAACTCTAGGACTGTGGCCTCCACGGCTATGAACTCCCAGTCGTCCCGATCTCATGCCATCTTTACAATCTCCT
TAGAGCAAAGAAAGAAAAGTGACAAGAATAGCAGCTTTCGCTCCAAGCTGCATCTTGTAGACCTCGCTGGATCAGAAAGACAGAAGAAAACCAA
GGCTGAAGGGGATCGTCTAAAAGAGGGTATTAATATTAACCGAGGCCTCCTATGCTTGGGAAATGTAATCAGTGCTCTTGGAGATGACAAAAAG
GGTGGCTTTGTGCCCTACAGAGATTCCAAGTTGACTCGACTGCTTCAAGATTCTCTAGGAGGTAATAGCCATACTCTTATGATAGCCTGTGTGA
GTCCTGCTGACTCCAATCTAGAGGAAACATTAAATACCCTTCGCTATGCTGACAGAGCAAGAAAAATCAAGAACAAACCTATTGTTAATATTGA
TCCCCAGACAGCTGAACTTAATCATCTAAAGCAACAGGTACAACAGCTACAAGTCTTGTTGCTACAGGCCCATGGAGGTACCCTGCCTGGATCT
ATAACTGTGGAACCATCAGAGAATCTACAATCCCTGATGGAGAAGAATCAGTCCCTGGTAGAGGAGAATGAAAAATTAAGTCGTGGTCTGAGCG

Fig. 9 (Continued)

AGGCAGCTGGTCAGACAGCCCAGATGTTGGAGAGGATCATTTTGACAGAGCAAGCGAATGAAAAAATGAACGCCAAGCTAGAAGAGCTCAGGCA
GCATGCGGCCTGCAAACTGGATCTTCAAAAGCTAGTGGAGACTTTGGAAGACCAGGAATTGAAAGAAAATGTAGAGATAATTTGTAACCTGCAG
CAATTGATTACCCAGTTATCGGATGAAACTGTTGCTTGCATGGCTGCAGCCATTGATACTGCGGTGGAGCAAGAAGCCCAAGTAGAAACCAGTC
CAGAGACGAGCAGGTCTTCTGACGCTTTTACCACTCAGCATGCTCTCCGTCAAGCGCAGATGTCTAAGGAGCTGGTTGAGTTGAATAAAGCGCT
TGCACTGAAAGAGGCCCTGGCTAGGAAGATGACTCAGAATGACAGCCAACTGCAGCCCATTCAGTACCAATACCAGGATAACATAAAAGAGCTA
GAATTAGAAGTCATCAATCTGCAAAAGGAAAAGGAAGAATTGGTTCTTGAACTTCAGACAGCAAAGAAGGATGCCAACCAAGCCAAGTTGAGTG
AGCGCCGCCGCAAACGTCTCCAGGAGCTGGAGGGTCAAATTGCTGATCTGAAGAAGAAACTGAATGAGCAGTCCAAACTTCTGAAACTAAAGGA
ATCCACAGAGCGTACTGTCTCCAAACTGAACCAGGAGATACGGATGATGAAAAACCAGCGGGTACAGTTAATGCGTCAAATGAAAGAAGATGCT
GAGAAGTTTAGACAGTGGAAGCAGAAAAAAGACAAAGAAGTAATACAGTTAAAAGAACGAGACCGTAAGAGGCAATATGAGCTGCTGAAACTTG
AAAGAAACTTCCAGAAACAATCCAATGTGCTCAGACGTAAAACGGAGGAGGCAGCAGCTGCCAACAAGCGTCTCAAGGATGCTCTCCAGAAACA
ACGGGAGGTTGCAGATAAGCGGAAAGAGACTCAGAGCCGTGGAATGGAAGGCACTGCAGCTCGAGTGAAGAATTGGCTTGGAAACGAAATTGAG
GTTATGGTCAGTACTGAGGAAGCCAAACGCCATCTGAATGACCTCCTTGAAGATAGAAAGATCCTGGCTCAAGATGTGGCTCAACTCAAAGAAA
AAAAGGAATCTGGGGAGAATCCACCTCCTAAACTCCGGAGGCGTACATTCTCCCTTACTGAAGTGCGTGGTCAAGTTTCGGAGTCAGAAGATTC
TATTACAAAGCAGATTGAAAGCCTAGAGACTGAAATGGAATTCAGGAGTGCTCAGATTGCTGACCTACAGCAGAAGCTGCTGGATGCAGAAAGT
GAAGACAGACCAAAACAACGCTGGGAGAATATTGCCACCATTCTGGAAGCCAAGTGTGCCCTGAAATATTTGATTGGAGAGCTGGTCTCCTCCA
AAATACAGGTCAGCAAACTTGAAAGCAGCCTGAAACAGAGCAAGACCAGCTGTGCTGACATGCAGAAGATGCTGTTTGAGGAACGAAATCATTT
TGCCGAGATAGAGACAGAGTTACAAGCTGAGCTGGTCAGAATGGAGCAACAGCACCAAGAGAAGGTGCTGTACCTTCTCAGCCAGCTGCAGCAA
AGCCAAATGGCAGAGAAGCAGTTAGAGGAATCAGTCAGTGAAAAGGAACAGCAGCTGCTGAGCACACTGAAGTGTCAGGATGAAGAACTTGAGA
AAATGCGAGAAGTGTGTGAGCAAAATCAGCAGCTTCTCCGAGAGAATGAAATCATCAAGCAGAAACTGACCCTCCTCCAGGTAGCCAGCAGACA
GAAACATCTTCCTAAGGATACCCTTCTATCTCCAGACTCTTCTTTTGAATATGTCCCACCTAAGCCAAAACCTTCTCGTGTTAAAGAAAAGTTC
CTGGAGCAAAGCATGGACATCGAGGATCTAAAATATTGTTCAGAGCATTCTGTGAATGAGCATGAGGATGGTGATGGTGATGATGATGAGGGGG
ATGACGAGGAATGGAAGCCAACAAAATTAGTTAAGGTGTCCAGGAAGAACATCCAAGGGTGTTCCTGCAAGGGCTGGTGTGGAAACAAGCAGTG
TGGGTGCAGGAAGCAAAAGTCAGACTGTGGTGTGGACTGTTGCTGTGACCCCACAAAGTGTCGGAACCGCCAGCAAGGCAAGGATAGCTTGGGC
ACTGTTGAACGGACCCAGGATTCCGAAGGCTCCTTCAAACTGGAGGATCCTACCGAGGTGACCCCAGGATTGAGCTTCTTTAATCCCGTCTGTG
CCACCCCCAATAGCAAGATCCTGAAAGAGATGTGCGATGTGGAGCAGGTGCTGTCAAAGAAGACTCCCCCAGCTCCCTCCCCTTTTGACCTCCC
AGAGTTGAAACATGTAGCAACAGAATACCAAGAAAACAAGGCTCCAGGGAAGAAAAAGAAACGGGCTCTGGCCAGCAACACCAGCTTCTTCTCT
GGCTGCTCCCCTATCGAAGAAGAGGCCCACTGA

ID 17: KIF5A, *Homo sapiens*

ATGGCGGAGACCAACAACGAATGTAGCATCAAGGTGCTCTGCCGATTCCGGCCCCTGAACCAGGCTGAGATTCTGCGGGGAGACAAGTTCATCC
CCATTTTCCAAGGGGACGACAGCGTCGTTATTGGGGGGAAGCCATATGTTTTTGACCGTGTATTCCCCCCAAACACGACTCAAGAGCAAGTTTA
TCATGCATGTGCCATGCAGATTGTCAAAGATGTCCTTGCTGGCTACAATGGCACCATTTTTGCTTATGGACAGACATCCTCAGGGAAAACACAT
ACCATGGAGGGAAAGCTGCACGACCCTCAGCTGATGGGAATCATTCCTCGAATTGCCCGAGACATCTTCAACCACATCTACTCCATGGATGAGA
ACCTTGAGTTCCACATCAAGGTTTCTTACTTTGAAATTTACCTGGACAAAATTCGTGACCTTCTGGATGTGACCAAGACAAATCTGTCCGTGCA
CGAGGACAAGAACCGGGTGCCATTTGTCAAGGGTTGTACTGAACGCTTTGTGTCCAGCCCGGAGGAGATTCTGGATGTGATTGATGAAGGGAAA
TCAAATCGTCATGTGGCTGTCACCAACATGAATGAACACAGCTCTCGGAGCCACAGCATCTTCCTCATCAACATCAAGCAGGAGAACATGGAAA
CGGAGCAGAAGCTCAGTGGGAAGCTGTATCTGGTGGACCTGGCAGGGAGTGAGAAGGTCAGCAAGACTGGAGCAGAGGGAGCCGTGCTGGACGA
GGCAAAGAATATCAACAAGTCACTGTCAGCTCTGGGCAATGTGATCTCCGCACTGGCTGAGGGCACTAAAAGCTATGTTCCATATCGTGACAGC
AAAATGACAAGGATTCTCCAGGACTCTCTCGGGGGAAACTGCCGGACGACTATGTTCATCTGTTGCTCACCATCCAGTTATAATGATGCAGAGA
CCAAGTCCACCCTGATGTTTGGGCAGCGGGCAAAGACCATTAAGAACACTGCCTCAGTAAATTTGGAGTTGACTGCTGAGCAGTGGAAGAAGAA
ATATGAGAAGGAGAAGGAGAAGACAAAGGCCCAGAAGGAGACGATTGCGAAGCTGGAGGCTGAGCTGAGCCGGTGGCGCAATGGAGAGAATGTG
CCTGAGACAGAGCGCCTGGCTGGGGAGGAGGCAGCCCTGGGAGCCGAGCTCTGTGAGGAGACCCCTGTGAATGACAACTCATCCATCGTGGTGC
GCATCGCGCCCGAGGAGCGGCAGAAATACGAGGAGGAGATCCGCCGTCTCTATAAGCAGCTTGACGACAAGGATGATGAAATCAACCAACAAAG
CCAACTCATAGAGAAGCTCAAGCAGCAAATGCTGGACCAGGAAGAGCTGCTGGTGTCCACCCGAGGAGACAACGAGAAGGTCCAGCGGGAGCTG
AGCCACCTGCAATCAGAGAACGATGCCGCTAAGGATGAGGTGAAGGAAGTGCTGCAGGCCCTGGAGGAGCTGGCTGTGAACTATGACCAGAAGT
CCCAGGAGGTGGAGGAGAAGAGCCAGCAGAACCAGCTTCTGGTGGATGAGCTGTCTCAGAAGGTGGCCACCATGCTGTCCCTGGAGTCTGAGTT
GCAGCGGCTACAGGAGGTCAGTGGACACCAGCGAAAACGAATTGCTGAGGTGCTGAACGGGCTGATGAAGGATCTGAGCGAGTTCAGTGTCATT
GTGGGCAACGGGGAGATTAAGCTGCCAGTGGAGATCAGTGGGGCCATCGAGGAGGAGTTCACTGTGGCCCGACTCTACATCAGCAAAATCAAAT
CAGAAGTCAAGTCTGTGGTCAAGCGGTGCCGGCAGCTGGAGAACCTCCAGGTGGAGTGTCACCGCAAGATGGAAGTGACCGGGCGGGAGCTCTC
ATCCTGCCAGCTCCTCATCTCTCAGCATGAGGCCAAGATCCGCTCGCTTACGGAATACATGCAGAGCGTGGAGCTAAAGAAGCGGCACCTGGAA
GAGTCCTATGACTCCTTGAGCGATGAGCTGGCCAAGCTCCAGGCCCAGGAAACTGTGCATGAAGTGGCCCTGAAGGACAAGGAGCCTGACACTC
AGGATGCAGATGAAGTGAAGAAGGCTCTGGAGCTGCAGATGGAGAGTCACCGGGAGGCCCATCACCGGCAGCTGGCCCGGCTCCGGGACGAGAT
CAACGAGAAGCAGAAGACCATTGATGAGCTCAAAGACCTAAATCAGAAGCTCCAGTTAGAGCTAGAGAAGCTTCAGGCTGACTACGAGAAGCTG
AAGAGCGAAGAACACGAGAAGAGCACCAAGCTGCAGGAGCTGACATTTCTGTACGAGCGACATGAGCAGTCCAAGCAGGACCTCAAGGGTCTGG
AGGAGACAGTTGCCCGGGAACTCCAGACCCTCCACAACCTTCGCAAGCTGTTCGTTCAAGACGTCACGACTCGAGTCAAGAAAAGTGCAGAAAT
GGAGCCCGAAGACAGTGGGGGGATTCACTCCCAAAAGCAGAAGATTTCCTTTCTTGAGAACAACCTGGAACAGCTTACAAAGGTTCACAAACAG
CTGGTACGTGACAATGCAGATCTGCGTTGTGAGCTTCCTAAATTGGAAAAACGACTTAGGGCTACGGCTGAGAGAGTTAAGGCCCTGGAGGGTG
CACTGAAGGAGGCCAAGGAGGGCGCCATGAAGGACAAGCGCCGGTACCAGCAGGAGGTGGACCGCATCAAGGAGGCCGTTCGCTACAAGAGCTC
GGGCAAACGGGGCCATTCTGCCCAGATTGCCAAACCCGTCCGGCCTGGCCACTACCCAGCATCCTCACCCACCAACCCCTATGGCACCCGGAGC
CCTGAGTGCATCAGTTACACCAACAGCCTCTTCCAGAACTACCAGAATCTCTACCTGCAGGCCACACCCAGCTCCACCTCAGATATGTACTTTG
CAAACTCCTGTACCAGCAGTGGAGCCACATCTTCTGGCGGCCCCTTGGCTTCCTACCAGAAGGCCAACATGGACAATGGAAATGCCACAGATAT
CAATGACAATAGGAGTGACCTGCCGTGTGGCTATGAGGCTGAGGACCAGGCCAAGCTTTTCCCTCTCCACCAAGAGACAGCAGCCAGCTAA

ID 18: KIF5B, *Homo sapiens*

ATGGCGGACCTGGCCGAGTGCAACATCAAAGTGATGTGTCGCTTCAGACCTCTCAACGAGTCTGAAGTGAACCGCGGCGACAAGTACATCGCCA
AGTTTCAGGGAGAAGACACGGTCGTGATCGCGTCCAAGCCTTATGCATTTGATCGGGTGTTCCAGTCAAGCACATCTCAAGAGCAAGTGTATAA
TGACTGTGCAAAGAAGATTGTTAAAGATGTACTTGAAGGATATAATGGAACAATATTTGCATATGGACAAACATCCTCTGGGAAGACACACACA
ATGGAGGGTAAACTTCATGATCCAGAAGGCATGGGAATTATTCCAAGAATAGTGCAAGATATTTTTAATTATATTTACTCCATGGATGAAAATT
TGGAATTTCATATTAAGGTTTCATATTTTGAAATATATTTGGATAAGATAAGGGACCTGTTAGATGTTTCAAAGACCAACCTTTCAGTTCATGA
AGACAAAAACCGAGTTCCCTATGTAAAGGGGTGCACAGAGCGTTTTGTATGTAGTCCAGATGAAGTTATGGATACCATAGATGAAGGAAAATCC
AACAGACATGTAGCAGTTACAAATATGAATGAACATAGCTCTAGGAGTCACAGTATATTTCTTATTAATGTCAAACAAGAGAACACACAAACGG
AACAAAAGCTGAGTGGAAAACTTTATCTGGTTGATTTAGCTGGTAGTGAAAAGGTTAGTAAAACTGGAGCTGAAGGTGCTGTGCTGGATGAAGC
TAAAAACATCAACAAGTCACTTTCTGCTCTTGGAAATGTTATTTCTGCTTTGGCTGAGGGTAGTACATATGTTCCATATCGAGATAGTAAAATG
ACAAGAATCCTTCAAGATTCATTAGGTGGCAACTGTAGAACCACTATTGTAATTTGCTGCTCTCCATCATCATACAATGAGTCTGAAACAAAAT
CTACACTCTTATTTGGCCAAAGGGCCAAAACAATTAAGAACACAGTTTGTGTCAATGTGGAGTTAACTGCAGAACAGTGGAAAAAGAAGTATGA
AAAAGAAAAAGAAAAAAATAAGATCCTGCGGAACACTATTCAGTGGCTTGAAAATGAGCTCAACAGATGGCGTAATGGGGAGACGGTGCCTATT
GATGAACAGTTTGACAAAGAGAAAGCCAACTTGGAAGCTTTCACAGTGGATAAAGATATTACTCTTACCAATGATAAACCAGCAACCGCAATTG
GAGTTATAGGAAATTTTACTGATGCTGAAAGAAGAAAGTGTGAAGAAGAAATTGCTAAATTATACAAACAGCTTGATGACAAGGATGAAGAAAT
TAACCAGCAAAGTCAACTGGTAGAGAAACTGAAGACGCAAATGTTGGATCAGGAGGAGCTTTTGGCATCTACCAGAAGGGATCAAGACAATATG
CAAGCTGAGCTGAATCGCCTTCAAGCAGAAAATGATGCCTCTAAAGAAGAAGTGAAAGAAGTTTTACAGGCCCTAGAAGAACTTGCTGTCAATT

Fig. 9 (Continued)

ATGATCAGAAGTCTCAGGAAGTTGAAGACAAAACTAAGGAATATGAATTGCTTAGTGATGAATTGAATCAGAAATCGGCAACTTTAGCGAGTAT
AGATGCTGAGCTTCAGAAACTTAAGGAAATGACCAACCACCAGAAAAAACGAGCAGCTGAGATGATGGCATCTTTACTAAAAGACCTTGCAGAA
ATAGGAATTGCTGTGGGAAATAATGATGTAAAGCAGCCTGAGGGAACTGGCATGATAGATGAAGAGTTCACTGTTGCAAGACTCTACATTAGCA
AAATGAAGTCAGAAGTAAAAACCATGGTGAAACGTTGCAAGCAGTTAGAAAGCACACAAACTGAGAGCAACAAAAAAATGGAAGAAAATGAAAA
GGAGTTAGCAGCATGTCAGCTTCGTATCTCTCAACATGAAGCCAAAATCAAGTCATTGACTGAATACCTTCAAAATGTGGAACAAAAGAAAAGA
CAGTTGGAGGAATCTGTCGATGCCCTCAGTGAAGAACTAGTCCAGCTTCGAGCACAAGAGAAAGTCCATGAAATGGAAAAGGAGCACTTAAATA
AGGTTCAGACTGCAAATGAAGTTAAGCAAGCTGTTGAACAGCAGATCCAGAGCCATAGAGAAACTCATCAAAAACAGATCAGTAGTTTGAGAGA
TGAAGTAGAAGCAAAAGCAAAACTTATTACTGATCTTCAAGACCAAAACCAGAAAATGATGTTAGAGCAGGAACGTCTAAGAGTAGAACATGAG
AAGTTGAAAGCCACAGATCAGGAAAAGAGCAGAAAACTACATGAACTTACGGTTATGCAAGATAGACGAGAACAAGCAAGACAAGACTTGAAGG
GTTTGGAAGAGACAGTGGCAAAAGAACTTCAGACTTTACACAACCTGCGCAAACTCTTTGTTCAGGACCTGGCTACAAGAGTTAAAAAGAGTGC
TGAGATTGATTCTGATGACACCGGAGGCAGCGCTGCTCAGAAGCAAAAAATCTCCTTTCTTGAAAATAATCTTGAACAGCTCACTAAAGTGCAC
AAACAGTTGGTACGTGATAATGCAGATCTCCGCTGTGAACTTCCTAAGTTGGAAAAGCGACTTCGAGCTACAGCTGAGAGAGTGAAAGCTTTGG
AATCAGCACTGAAAGAAGCTAAAGAAAATGCATCTCGTGATCGCAAACGCTATCAGCAAGAAGTAGATCGCATAAAGGAAGCAGTCAGGTCAAA
GAATATGGCCAGAAGAGGGCATTCTGCACAGATTGCTAAACCTATTCGTCCCGGGCAACATCCAGCAGCTTCTCCAACTCACCCAAGTGCAATT
CGTGGAGGAGGTGCATTTGTTCAGAACAGCCAGCCAGTGGCAGTGCGAGGTGGAGGAGGCAAACAAGTGTAA

ID 19: KIF6, *Homo sapiens*
ATGGTGAAGCAGACTATCCAGATATTCGCGAGGGTGAAGCCCCCTGTCCGGAAGCACCAACAAGGGATTTATTCCATAGATGAAGATGAAAAAT
TAATACCTAGCTTGGAAATCATCTTACCACGTGATTTGGCAGATGGGTTTGTGAATAATAAGCGAGAAAGCTACAAATTTAAATTTCAAAGAAT
TTTTGATCAGGATGCAAACCAAGAGACCGTTTTTGAAAACATTGCCAAACCAGTTGCTGGGAGTGTCCTGGCAGGTTACAATGGTACCATCTTT
GCATATGGGCAAACAGGCAGCGGGAAGACATTCACTATCACAGGGGGTGCAGAGCGTTACAGTGACAGAGGCATTATCCCAAGGACACTGTCAT
ACATTTTTGAACAGTTACAAAAGGACAGCAGCAAAATATATACAACACACATTTCCTATTTGGAAATCTACAATGAATGTGGTTATGATCTTTT
GGATCCAAGACATGAAGCCTCCAGTTTGGAAGATTTGCCGAAAGTGACAATACTGGAGGATCCTGATCAGAACATTCACCTGAAAAACTTGACT
CTCCATCAGGCAACCACAGAGGAAGAAGCTCTGAATTTGCTTTTTTTAGGAGACACCAACCGAATGATTGCAGAGACTCCTATGAACCAAGCTT
CAACCCGTTCCCACTGCATTTTCACCATTCATTTGTCAAGCAAGGAACCAGGATCTGCAACTGTACGACATGCCAAACTCCATCTGGTTGACCT
GGCTGGTTCAGAGCGAGTTGCAAAGACTGGAGTAGGGGGCCATCTTCTAACAGAGGCCAAGTATATCAACTTGTCACTACATTACTTAGAACAG
GTTATCATTGCCCTTTCAGAAAAGCACCGTTCGCACATTCCTTATAGAAACTCCATGATGACCAGTGTCCTAAGAGACAGTTTGGGAGGGAACT
GCATGACAACTATGATTGCAACACTCTCCTTGGAGAAAAGGAATCTTGATGAGTCTATATCAACCTGCAGATTTGCACAGCGAGTGGCACTCAT
AAAGAATGAAGCTGTTCTTAATGAAGAAATTAACCCCAGATTAGTGATTAAACGCCTACAAAAGGAAATCCAGGAACTGAAGGATGAACTGGCC
ATGGTCACTGGGGAGCAGAGGACAGAGGCACTCACAGAAGCAGAGCTCCTTCAGCTGGAAAAACTAATAACATCCTTTTTGGAAGACCAGGATT
CAGACAGTAGATTAGAGGTTGGCGCGGATATGCGTAAAGTTCATCACTGTTTTCATCATTTAAAGAAACTATTGAATGACAAGAAGATCCTTGA
AAACAATACAGTCTCCTCTGAAAGCAAAGACCAAGATTGTCAAGAACCATTAAAAGAAGAAGAATATAGAAAGCTACGAGATATTCTGAAACAG
AGAGATAACGAAATCAATATCCTGGTCAACATGTTAAAAAAAGAAAAGAAGAAAGCTCAGGAGGCTCTCCACTTGGCTGGCATGGATAGACGTG
AATTCAGACAGTCCCAGAGCCCACCCTTCCGCCTAGGAAACCCAGAAGAAGGTCAAAGAATGCGACTATCCTCAGCTCCCTCACAGGCCCAGGA
CTTCAGCATTTTGGGGAAAAGATCCAGTTTGCTCCACAAGAAAATAGGAATGAGAGAGGAAATGTCATTAGGATGCCAGGAGGCTTTTGAAATC
TTCAAGAGGGACCACGCTGACAGCGTTACCATCGATGACAACAAACAGATTCTGAAACAGAGATTTTCTGAAGCCAAGGCCCTGGGAGAAAGTA
TAAATGAAGCAAGAAGTAAAATTGGTCACCTGAAGGAAGAAATCACCCAGCGGCATATACAGCAAGTAGCCCTAGGAATCTCGGAAAACATGGC
CGTGCCTCTGATGCCAGACCAGCAGGAGGAGAAGCTGCGATCACAACTGGAGGAAGAAAAGAGAAGGTATAAAACAATGTTCACTCGCCTGAAA
GCCCTGAAGGTGGAGATCGAGCACTTGCAGCTGCTCATGGACAAAGCCAAGGTGAAGCTACAGAAAGAGTTTGAAGTCTGGTGGCAGAGGAGG
CCACCAACCTGCAGGTAAATTCTCCAGCAGTGAATTCACTCGATCACACGAAGCCATTTCTCCAGACATCTGACTCCCAGCATGAATGGTCCCA
ACTCCTCTCTAACAAAAGTTCTGGAGGCTGGGAAGTCCAAGATCAAGGCACTGGCAGATTCGATGTCTGTGATGTGAATGCCAGGAAAATCCTG
CCCTCGCCTTGCCCCAGTCCACACAGCCAGAAACAGAGCAGCACCAGCACCCCACTGGAAGACAGCATCCCCAAGAGGCCAGTGTCGTCCATCC
CTCTCACCGGAGACAGCCAGACGGACTCGGACATCATCGCCTTCATCAAGGCCAGACAGAGCATTCTGCAGAAGCAATGTTTGGGAAGCAATTG
A ID 20: KIF7, *Homo sapiens*
ATGGGGCTGGAGGCTCAGAGGCTGCCAGGGGCTGAGGAGGCCCCAGTGCGGGTTGCCCTGCGAGTTCGACCACTGCTGCCCAAGGAGCTGCTGC
ACGGGCATCAGAGCTGCCTGCAGGTGGAGCCAGGGCTTGGCCGCGTCACTCTGGGCCGTGACCGACACTTTGGCTTCCACGTGGTGCTGGCCGA
GGATGCGGGGCAGGAGGCCGTGTACCAGGCCTGCGTTCAGCCCCTCCTTGAGGCCTTCTTCGAGGGCTTCAATGCCACTGTCTTTGCCTATGGT
CAGACGGGCTCAGGGAAGACATACACCATGGGGGAGGCCAGTGTGGCCTCCCTCCTTGAGGATGAGCAGGGCATTGTCCCGAGGGCCATGGCCG
AGGCCTTCAAGCTCATCGATGAGAACGACCTGCTTGACTGTCTGGTACATGTGTCCTACCTGGAAGTGTACAAGGAGGAGTTCCGAGACCTGCT
CGAGGTGGGCACTGCCAGCCGTGACATCCAGCTCCGGGAAGATGAGCGCGGGAATGTTGTGCTGTGCGGGGTGAAGGAGGTCGACGTGGAGGGC
CTGGATGAGGTGCTGAGCCTCCTGGAGATGGGCAACGCGGCGCGGCACACGGGAGCCACGCACCTCAACCACCTGTCTAGCCGCTCACACACGG
TCTTCACCGTGACCCTGGAGCAGCGGGGCGCGCCCCCAGCCGCCTACCCCGCCCCGCCCCGGGCCAGCTGCTCGTCTCCAAGTTCCACTTCGT
GGACCTGGCGGGCTCAGAGAGGGTGCTCAAGACGGGCAGCACCGGCGAGCGGCTCAAGGAGAGCATCCAGATCAACAGCAGCCTCCTGGCGCTG
GGCAACGTCATCAGCGCCCTGGGGGACCCTCAGCGCCGGGGCAGCCACATACCCTACCGCGACTCCAAGATCACCCGGATCCTCAAAGACTCGC
TGGGCGGGAACGCCAAGACGGTGATGATCGCCTGCGTCAGCCCTTCCTCCTCCGACTTCGACGAGACCCTCAACACCCTCAACTACGCCAGCCG
CGCCCAGAACATCCGCAACCGCGCCACGGTCAACTGGCGGCCCGAGGCCGAGCGGCCACCCGAAGAGACGGCGAGCGGCGCGCGGGGTCCGCCA
CGGCACCGCTCCGAGACCCGCATCATCCACCGCGGCCGGCGCGCCCCAGGCCCAGCCACCGCCTCCGCGGCGGCCGCCATGCGCCTGGGCGCCG
AGTGCGCGCGCTACCGGGCCTGCACCGACGCCGCCTACAGCCTCTTGCGCGAGCTGCAGGCCGAGCCCGGGCTGCCCGGCGCCGCCGCCCGCAA
GGTGCGCGACTGGCTGTGCGCCGTCGAGGGCGAGCGCAGCGCCCTGAGCTCCGCCTCCGGGCCCGATAGCGGCATCGAGAGCGCCTCCGTCGAG
GACCAGGCGGCGCAGGGGGCCGGCGGGCGAAAGGAGGATGAGGGGGCGCAGCAGCTGCTGACCCTGCAGAACCAGGTGGCGCGGCTGGAGGAG
AGAACCGAGACTTTCTGGCTGCGCTGGAGGACGCCATGGAGCAGTACAAACTGCAGAGCGACCGGCTGCGTGAGCAGCAGGAGGAGATGGTGGA
ACTGCGGCTGCGGTTAGAGCTGGTGCGGCCAGGCTGGGGGGGCCCGCGGCTCCTGAATGGCCTGCCTCCCGGGTCCTTTGTGCCTCGACCTCAT
ACAGCCCCCCTGGGGGGTGCCCACGCCCATGTGCTGGGCATGGTGCCGCCTGCCTGCCTCCCTGGAGATGAAGTTGGCTCTGAGCAGAGGGGAG
AGCAGGTGACAAATGGCAGGGAGGCTGGAGCTGAGTTGCTGACTGAGGTGAACAGGCTGGGAAGTGGCTCTTCAGCTGCTTCAGAGGAGGAAGA
GGAGGAGGAGGAGCCGCCCAGGCGGACCTTACACCTGCGCAGAAATAGGATCAGCAACTGCAGTCAGAGGGCGGGGGCACGCCCAGGGAGTCTG
CCAGAGAGGAAGGGCCCAGAGCTTTGCCTTGAGGAGTTGGATGCAGCCATTCCAGGGTCCAGAGCAGTTGGTGGAGCAAGGCCCGAGTTCAGG
CCCGCCAGGTCCCCCCTGCCACAGCCTCAGAGTGGCGGCTGGCCCAGGCCCAGCAGAAGATCCGGGAGCTGGCTATCAACATCCGCATGAAGGA
GGAGCTTATTGGCGAGCTGGTCCGCACAGGAAAGGCAGCTCAGGCCCTGAACCGCCAGCACAGCCAGCGTATCCGGGAGCTGGAGCAGGAGGCA
GAGCAGGTGCGGGCCGAGCTGAGTGAAGGCCAGAGGCAGCTGCGGGAGCTCGAGGGCAAGGAGCTCCAGGATGCTGGCGAGCGGTCTCGGCTCC
AGGAGTTCCGCAGGAGGGTCGCTGCGGCCCAGAGCCAGGTGCAGGTGCTGAAGGAGAAGAAGCAGGCTACGGAGCGGCTGGTGTCACTGTCGGC
CCAGAGTGAGAAGCGACTGCAGGAGCTCGAGCGGAACGTGCAGCTCATGCGGCAGCAGCAGGGACAGCTGCAGAGGCGGCTTCGCGAGGAGACG
GAGCAGAAGCGGCGCCTGGAGGCAGAAATGAGCAAGCGGCAGCACCGCGTCAAGGAGCTGGAGCTGAAGCATGAGCAACAGCAGAAGATCCTGA
AGATTAAGACGGAAGAGATCGCGGCATTCCAGAGGAAGAGGCGCAGTGGCAGCAACGGCTCTGTGGTCAGCCTGGAACAGCAGCAGAAGATTGA
GGAGCAGAAGAAGTGGCTGGACCAGGAGATGGAGAAGGTGCTACAGCAGCGGCGGGCGCTGGAGGAGCTGGGGGAGGAGCTCCACAAGCGGGAG
GCCATCCTGGCCAAGAAGGAGGCCCTGATGCAGGAGAAGACGGGGCTGGAGAGCAAGCGCCTGAGATCCAGCCAGGCCCTCAACGAGGACATCG
TGCGAGTGTCCAGCCGGCTGGAGCACCTGGAGAAGGAGCTGTCCGAGAAGAGCGGGCAGCTGCGGCAGGGCAGCGCCCAGAGCCAGCAGCAGAT
CCGCGGGGAGATCGACAGCCTGCGCCAGGAGAAGGACTCGCTGCTCAAGCAGCGCCTGGAGATCGACGGCAAGCTGAGGCAGGGGAGTCTGCTG
TCCCCCGAGGAGGAGCGGACGCTGTTCCAGTTGGATGAGGCCATCGAGGCCCTGGATGCTGCCATTGAGTATAAGAATGAGGCCATCACATGCC

Fig. 9 (Continued)

GCCAGCGGGTGCTTCGGGCCTCAGCCTCGTTGCTGTCCCAGTGCGAGATGAACCTCATGGCCAAGCTCAGCTACCTCTCATCCTCAGAGACCAG
AGCCCTCCTCTGCAAGTATTTTGACAAGGTGGTGACGCTCCGAGAGGAGCAGCACCAGCAGCAGATTGCCTTCTCGGAACTGGAGATGCAGCTG
GAGGAGCAGCAGAGGCTGGTGTACTGGCTGGAGGTGGCCCTGGAGCGGCAGCGCCTGGAGATGGACCGCCAGCTGACCCTGCAGCAGAAGGAGC
ACGAGCAGAACATGCAGCTGCTCCTGCAGCAGAGTCGAGACCACCTCGGTGAAGGGTTAGCAGACAGCAGGAGGCAGTATGAGGCCCGGATTCA
AGCTCTGGAGAAGGAACTGGGCCGTTACATGTGGATAAACCAGGAACTGAAACAGAAGCTCGGCGGTGTGAACGCTGTAGGCCACAGCAGGGGT
GGGGAGAAGAGGAGCCTGTGCTCGGAGGGCAGACAGGCTCCTGGAAATGAAGATGAGCTCCACCTGGCACCCGAGCTTCTCTGGCTGTCCCCC
TCACTGAGGGGCCCCCCGCACCCGGAGGAGACGCGGACTTGGTCCACGCTCCGTTACCCTTGACCTGGAAACGCTCGAGCCTGTGTGGTGA
GGAGCAGGGGTCCCCCGAGGAACTGAGGCAGCGGGAGGCGGCTGAGCCCCTGGTGGGGCGGGTGCTTCCTGTGGGTGAGGCAGGCCTGCCCTGG
AACTTTGGGCCTTTGTCCAAGCCCCGGCGGGAACTGCGACGAGCCAGCCCGGGGATGATTGATGTCCGGAAAAACCCCCTGTAA

ID21: KIF9, *Homo sapiens*
ATGGGTACTAGGAAAAAAGTTCATGCATTTGTCCGTGTCAAACCCACCGATGACTTTGCTCATGAAATGATCAGATACGGAGATGACAAAAGAA
GCATTGATATTCACTTAAAAAAGACATTCGGAGAGGAGTTGTCAATAACCAACAGACAGACTGGTCGTTTAAGTTGGATGGAGTTCTTCACGA
TGCCTCCCAGGACTTGGTTTATGAGACAGTTGCAAAGGATGTGGTTTCTCAGGCCCTCGATGGCTATAATGGCACCATCATGTGTTATGGGCAG
ACGGGAGCTGGCAAGACATACACCATGATGGGGGCAACTGAGAATTACAAGCACCGGGGGATCCTCCCTCGTGCCCTGCAGCAGGTTTTTAGGA
TGATCGAAGAACGCCCCACACATGCCATCACTGTGCGTGTTTCCTACTTGGAAATCTATAATGAGAGCCTGTTTGATCTCCTGTCCACTCTGCC
CTATGTTGGACCCTCAGTCACACCAATGACCATCGTGGAAAACCCTCAAGGAGTCTTCATTAAGGGCTTGTCAGTTCACCTCACAAGTCAGGAG
GAGGATGCATTCAGCCTCCTTTTTGAGGGTGAGACCAACAGGATTATAGCCTCCCACACTATGAACAAAAACTCTTCCAGATCACACTGCATTT
TCACCATCTACTTAGAGGCCCATTCCCGGACCTTATCAGAGGAAAAGTACATCACTTCCAAAATTAACTTGGTGGATCTGGCAGGCTCAGAGAG
GCTGGGGAAGTCTGGGTCTGAGGGCCAAGTCCTGAAGGAAGCCACCTACATCAACAAATCGCTCTCATTCCTGGAGCAGGCCATCATTGCCCTT
GGGGACCAGAAGCGGGACCACATCCCCTTTCGGCAGTGCAAGCTCACCCACGCTCTGAAGGACTCGTTAGGGGGAAACTGCAATATGGTCCTCG
TGACAAACATCTATGGAGAAGCTGCCCAGTTAGAAGAAACGCTATCTTCACTGAGATTTGCCAGCAGGATGAAGCTAGTCACCACTGAGCCTGC
CATCAATGAAAAGTATGATGCTGAGAGAATGGTCAAGAACCTGGAGAAGGAACTAGCACTACTCAAGCAGGAGCTGGCTATCCATGACAGCCTG
ACCAACCGCACCTTTGTGACCTATGACCCCATGGATGAAATCCAGATTGCTGAGATCAACTCCCAGGTGCGGAGGTACCTGGAGGGGACACTGG
ACGAGATCGACATAATCAGCCTTAGACAGATCAAGGAGGTGTTCAACCAGTTCCGGGTGGTTCTGAGCCAACAGGAACAGGAAGTGGAGTCCAC
TTTGCGCAGGAAGTACACCCTCATTGACAGGAATGACTTTGCAGCCATTTCTGCTATCCAGAAGGCGGGGCTTGTGGATGTTGATGGCCACCTA
GTGGGTGAGCCTGAAGGACAAAACTTTGGACTCGGAGTCGCCCCTTTCTCTACCAAACCTGGGAAGAAAGCCAAGTCCAAGAAGACATTCAAAG
AGCCACTCAGCTCCTTGGCAAGAAAGGAAGGTGCCAGCAGCCCTGTGAATGGGAAGGACTTGGATTACGTTTCCACCTCCAAGACCCAGCTGGT
CCCATCCTCCAAAGATGGGGATGTCAAAGACATGCTTTCGCGGGACCGGGAAACTTCCAGCATTGAGCCCCTTCCCTCAGACTCCCCGAAGGAG
GAATTACGCCCAATTAGGCCCGACACCCCACCCTCCAAACCAGTGGCCTTTGAGGAGTTTAAGAATGAGCAAGGTAGTGAGATCAACCGAATTT
TCAAAGAAAACAAATCCATCTTGAATGAACGGAGGAAAAGGGCCAGCGAGACCACACAGCACATCAATGCCATCAAGCGGGAGATTGATGTGAC
CAAGGAGGCCCTGAATTTCCAGAAGTCACTACGGGAGAAGCAAGGCAAGTACGAAAACAAGGGGCTGATGATCATCGATGAGGAAGAATTCCTG
CTGATCCTCAAGCTCAAAGACCTCAAGAAGCAGTACCGCAGCGAGTACCAGGACCTGCGTGACCTCAGGGCTGAGATCCAGTATTGCCAGCACC
TAGTGGATCAGTGTCGCCACCGCCTGCTCATGGAATTTGACATCTGGTACAATGAGTCCTTTGTCATCCCTGAGGACATGCAGATGGCACTGAA
GCCAGGCGGCAGCATCCGGCCAGGCATGGTCCCTGTGAACAGGATTGTGTCTCTGGGAGAAGATGACCAGGACAAATTCAGCCAGCTGCAGCAG
AGGGTGCTTCCTGAGGGCCCTGATTCCATCTCCTTCTACAATGCCAAAGTCAAGATAGAGCAGAAGCATAATTACTTGAAAACCATGATGGGCC
TCCAGCAGGCACATAGAAAATAG ID 22: KIF10, *Homo sapiens*
ATGGCGGAGGAAGGAGCCGTGGCCGTCTGCGTGCGAGTGCGGCCGCTGAACAGCAGAGAAGAATCACTTGGAGAAACTGCCCAAGTTTACTGGA
AAACTGACAATAATGTCATTTATCAAGTTGATGGAAGTAAATCCTTCAATTTTGATCGTGTCTTTCATGGTAATGAAACTACCAAAAATGTGTA
TGAAGAAATAGCAGCACCAATCATCGATTCTGCCATACAAGGCTACAATGGTACTATATTTGCCTATGGACAGACTGCTTCAGGAAAAACATAT
ACCATGATGGGTTCAGAAGATCATTTGGGAGTTATACCCAGGGCAATTCATGACATTTTCCAAAAAATTAAGAAGTTTCCTGATAGGGAATTTC
TCTTACGTGTATCTTACATGGAAATATACAATGAAACCATTACAGATTTACTCTGTGGCACTCAAAAAATGAAACCTTTAATTATTCGAGAAGA
TGTCAATAGGAATGTGTATGTTGCTGATCTCACAGAAGAAGTTGTATATACATCAGAAATGGCTTTGAAATGGATTACAAAGGGAGAAAAGAGC
AGGCATTATGGAGAAACAAAAATGAATCAAAGAAGCAGTCGTTCTCATACCATCTTTAGGATGATTTTGGAAAGCAGAGAGAAGGGTGAACCTT
CTAATTGTGAAGGATCTGTTAAGGTATCCCATTTGAATTTGGTTGATCTTGCAGGCAGTGAAAGAGCTGCTCAAACAGGCGCTGCAGGTGTGCG
GCTCAAGGAAGGCTGTAATATAAATCGAAGCTTATTTATTTTGGGACAAGTGATCAAGAAACTTAGTGATGGACAAGTTGGTGGTTTCATAAAT
TATCGAGATAGCAAGTTAACACGAATTCTCCAGAATTCCTTGGGAGGAAATGCAAAGACACGTATTATCTGCACAATTACTCCAGTATCTTTTG
ATGAAACACTTACTGCTCTCCAGTTTGCCAGTACTGCTAAATATATGAAGAATACTCCTTATGTTAATGAGGTATCAACTGATGAAGCTCTCCT
GAAAAGGTATAGAAAAGAAATAATGGATCTTAAAAAACAATTAGAGGAGGTTTCTTTAGAGACGCGGGCTCAGGCAATGGAAAAAGACCAATTG
GCCCAACTTTTGGAAGAAAAAGATTTGCTTCAGAAAGTACAGAATGAGAAAATTGAAAACTTAACACGGATGCTGGTGACCTCTTCTTCCCTCA
CGTTGCAACAGGAATTAAAGGCTAAAAGAAAACGAAGAGTTACTTGGTGCCTTGGCAAAATTAACAAAATGAAGAACTCAAACTATGCAGATCA
ATTTAATATACCAACAAATATAACAACAAAAACACATAAGCTTTCTATAAATTTATTACGAGAAATTGATGAATCTGTCTGTTCAGAGTCTGAT
GTTTTCAGTAACACTCTTGATACATTAAGTGAGATAGAATGGAATCCAGCAACAAAGCTACTAAATCAGGAGAATATAGAAAGTGAGTTGAACT
CACTTCGTGCTGACTATGATAATCTGGTATTAGACTATGAACAACTACGAACAGAAAAAGAAGAAATGGAATTGAAATTAAAAGAAAAGAATGA
TTTGGATGAATTTGAGGCTCTAGAAAGAAAAACTAAAAAAGATCAAGAGATGCAACTAATTCATGAAATTTCGAACTTAAAGAATTTAGTTAAG
CATGCAGAAGTATATAATCAAGATCTTGAGAATGAACTCAGTTCAAAAGTAGAGCTGCTTAGAGAAAAGGAAGACCAGATTAAGAAGCTACAGG
AATACATAGACTCTCAAAAGCTAGAAAATATAAAAATGGACTTGTCATACTCATTGGAAAGCATTGAAGACCCAAAACAAATGAAGCAGACTCT
GTTTGATGCTGAAACTGTAGCCCTTGATGCCAAGAGAGAATCAGCCTTTCTTAGAAGTGAAAATCTGGAGCTGAAGGAGAAAATGAAAGAACTT
GCAACTACATACAAGCAAATGGAAAATGATATTCAGTTATATCAAAGCCAGTTGGAGGCAAAAAAGAAAATGCAAGTTGATCTGGAGAAAGAAT
TACAATCTGCTTTTAATGAGATAACAAAACTCACCTCCCTTATAGATGGCAAAGTTCCAAAAGATTTGCTCTGTAATTTGGAATTGGAAGGAAA
GATTACTGATCTTCAGAAAGAACTAAATAAAGAAGTTGAAGAAAATGAAGCTTTGCGGGAAGAAGTCATTTTGCTTTCAGAATTGAAATCTTTA
CCTTCTGAAGTAGAAAGGCTGAGGAAAGAGATACAAGACAAATCTGAAGAGCTCCATATAATAACATCAGAAAAAGATAAATTGTTTTCTGAAG
TAGTTCATAAGGAGAGTAGAGTTCAAGGTTTACTTGAAGAAATTGGGAAAACAAAAGATGACCTAGCAACTACACAGTCGAATTATAAAAGCAC
TGATCAAGAATTCCAAAATTTCAAAACCCTTCATATGGACTTTGAGCAAAAGTATAAGATGGTCCTTGAGGAGAATGAGAGAATGAATCAGGAA
ATAGTTAATCTCTCTAAAGAAGCCCAAAAATTTGATTCGAGTTTGGGTGCTTTGAAGACCGAGCTTTCTTACAAGACCCAAGAACTTCAGGAGA
AAACACGTGAGGTTCAAGAAAGACTAAATGAGATGGAACAGCTGAAGGAACAATTAGAAAATAGAGATTCTACGCTGCAAACTGTAGAAAGGGA
GAAAACACTGATTACTGAGAAACTGCAGCAAACTTTAGAAGAAGTAAAAACTTTAACTCAAGAAAAAGATGATCTAAAACAACTCCAAGAAAGC
TTGCAAATTGAGAGGGACCAACTCAAAAGTGATATTCACGATACTGTTAACATGAATATAGATACTCAAGAACAATTACGAAATGCTCTTGAGT
CTCTGAAACAACATCAAGAAACAATTAATACACTAAAATCGAAAATTTCTGAGGAAGTTTCCAGGAATTTGCATATGGAGGAAAATACAGGAGA
AACTAAAGATGAATTTCAGCAAAAGATGGTTGGCATAGATAAAAAACAGGATTTGGAAGCTAAAAATACCCAAACACTAACTGCAGATGTTAAG
GATAATGAGATAATTGAGCAACAAAGGAAGATATTTTCTTTAATACAGGAGAAAAATGAACTCCAACAAATGTTAGAGAGTGTTATAGCAGAAA
AGGAACAATTGAAGACTGACCTAAAGGAAAATATTGAAATGACCATTGAAAACCAGGAAGAATTAAGACTTCTTGGGGATGAACTTAAAAAGCA
ACAAGAGATAGTTGCACAAGAAAAGAACCATGCCATAAAGAAAGAAGGAGAGCTTTCTAGGACCTGTGACAGACTGGCAGAAGTTGAAGAAAAA
CTAAAGGAAAAGAGCCAGCAACTCCAAGAAAAACAGCAACAACTTCTTAATGTACAAGAAGAGATGAGTGAGATGCAGAAAAAGATTAATGAAA
TAGAGAATTTAAAGAATGAATTAAAGAACAAAGAATTGACATTGGAACATATGGAAACAGAGAGGCTTGAGTTGGCTCAGAAACTTAATGAAAA
TTATGAGGAAGTGAAATCTATAACCAAAGAAAGAAAAGTTCTAAAGGAATTACAGAAGTCATTTGAAACAGAGAGAGACCACCTTAGAGGATAT
ATAAGAGAAATTGAAGCTACAGGCCTACAAACCAAAGAAGAACTAAAAATTGCTCATATTCACCTAAAAGAACACCAAGAAACTATTGATGAAC
TAAGAAGAAGCGTATCTGAGAAGACAGCTCAAATAATAAATACTCAGGACTTAGAAAAATCCCATACCAAATTACAAGAAGAGATCCCAGTGCT

Fig. 9 (Continued)

TCATGAGGAACAAGAGTTACTGCCTAATGTGAAAGAAGTCAGTGAGACTCAGGAAACAATGAATGAACTGGAGTTATTAACAGAACAGTCCACA
ACCAAGGACTCAACAACACTGGCAAGAATAGAAATGGAAAGGCTCAGGTTGAATGAAAAATTTCAAGAAAGTCAGGAAGAGATAAAATCTCTAA
CCAAGGAAAGAGACAACCTTAAAACGATAAAAGAAGCCCTTGAAGTTAAACATGACCAGCTGAAAGAACATATTAGAGAAACTTTGGCTAAAAT
CCAGGAGTCTCAAAGCAAACAAGAACAGTCCTTAAATATGAAAGAAAAAGACAATGAAACTACCAAAATCGTGAGTGAGATGGAGCAATTCAAA
CCCAAAGATTCAGCACTACTAAGGATAGAAATAGAAATGCTCGGATTGTCCAAAAGACTTCAAGAAAGTCATGATGAAATGAAATCTGTAGCTA
AGGAGAAAGATGACCTACAGAGGCTGCAAGAAGTTCTTCAATCTGAAAGTGACCAGCTCAAAGAAAACATAAAAGAAATTGTAGCTAAACACCT
GGAAACTGAAGAGGAACTTAAAGTTGCTCATTGTTGCCTGAAAGAACAAGAGGAAACTATTAATGAGTTAAGAGTGAATCTTTCAGAGAAGGAA
ACTGAAATATCAACCATTCAAAAGCAGTTAGAAGCAATCAATGATAAATTACAGAACAAGATCCAAGAGATTTATGAGAAAGAGGAACAATTTA
ATATAAAACAAATTAGTGAGGTTCAGGAAAAAGTGAATGAACTGAAACAATTCAAGGAGCATCGCAAAGCCAAGGATTCAGCACTACAAAGTAT
AGAAAGTAAGATGCTCGAGTTGACCAACAGACTTCAAGAAAGTCAAGAAGAAATACAAATTATGATTAAGGAAAAAGAGGAAATGAAAAGAGTA
CAGGAGGCCCTTCAGATAGAGAGAGACCAACTGAAAGAAAACACTAAAGAAATTGTAGCTAAAATGAAAGAATCTCAAGAAAAAGAATATCAGT
TTCTTAAGATGACAGCTGTCAATGAGACTCAGGAGAAAATGTGTGAAATAGAACACTTGAAGGAGCAATTTGAGACCCAGAAGTTAAACCTGGA
AAACATAGAAACGGAGAATATAAGGTTGACTCAGATACTACATGAAAACCTTGAAGAAATGAGATCTGTAACAAAAGAAAGAGATGACCTTAGG
AGTGTGGAGGAGACTCTCAAAGTAGAGAGAGACCAGCTCAAGGAAAACCTTAGAGAAACTATAACTAGAGACCTAGAAAAACAAGAGGAGCTAA
AAATTGTTCACATGCATCTGAAGGAGCACCAAGAAACTATTGATAAACTAAGAGGGATTGTTTCAGAGAAAACAAATGAAATATCAAATATGCA
AAAGGACTTAGAACACTCAAATGATGCCTTAAAAGCACAGGATCTGAAAATACAAGAGGAACTAAGAATTGCTCACATGCATCTGAAAGAGCAG
CAGGAAACTATTGACAAACTCAGAGGAATTGTTTCTGAGAAGACAGATAAACTATCAAATATGCAAAAAGATTTAGAAAATTCAAATGCTAAAT
TACAAGAAAAGATTCAAGAACTTAAGGCAAATGAACATCAACTTATTACGTTAAAAAAAGATGTCAATGAGACACAGAAAAAGTGTCTGAAAT
GGAGCAACTAAAGAAACAAATAAAAGACCAAAGCTTAACTCTGAGTAAATTAGAAATAGAGAATTTAAATTTGGCTCAGAAACTTCATGAAAAC
CTTGAAGAAATGAAATCTGTAATGAAAGAAAGAGATAATCTAAGAAGAGTAGAGGAGACACTCAAACTGGAGAGAGACCAACTCAAGGAAAGCC
TGCAAGAAACCAAAGCTAGAGATCTGGAAATACAACAGGAACTAAAAACTGCTCGTATGCTATCAAAAGAACACAAAGAAACTGTTGATAAACT
TAGAGAAAAAATTTCAGAAAAGACAATTCAAATTTCAGACATTCAAAAGGATTTAGATAAATCAAAAGATGAATTACAGAAAAAGATCCAAGAA
CTTCAGAAAAAAGAACTTCAACTGCTTAGAGTGAAAGAAGATGTCAATATGAGTCATAAAAAAATTAATGAAATGGAACAGTTGAAGAAGCAAT
TTGAGGCCCAAAACTTATCTATGCAAAGTGTGAGAATGGATAACTTCCAGTTGACTAAGAAACTTCATGAAAGCCTTGAAGAAATAAGAATTGT
AGCTAAAGAAAGAGATGAGCTAAGGAGGATAAAAGAATCTCTCAAAATGGAAAGGGACCAATTCATAGCAACCTTAAGGGAAATGATAGCTAGA
GACCGACAGAACCACCAAGTAAAACCTGAAAAAAGGTTACTAAGTGATGGACAACAGCACCTTACGGAAAGCCTGAGAGAAAAGTGCTCTAGAA
TAAAAGAGCTTTTGAAGAGATACTCAGAGATGGATGATCATTATGAGTGCTTGAATAGATTGTCTCTTGACTTGGAGAAGGAAATTGAATTCCA
AAAAGAGCTTTCAATGAGAGTTAAAGCAAACCTCTCACTTCCCTATTTACAAACCAAACACATTGAAAAACTTTTTACTGCAAACCAGAGATGC
TCCATGGAATTCCACAGAATCATGAAGAAACTGAAGTATGTGTTAAGCTATGTTACAAAAATAAAAGAAGAACAACATGAATCCATCAATAAAT
TTGAAATGGATTTTATTGATGAAGTGGAAAAGCAAAAGGAATTGCTAATTAAAATACAGCACCTTCAACAAGATTGTGATGTACCATCCAGAGA
ATTAAGGGATCTCAAATTGAACCAGAATATGGATCTACATATTGAGGAAATTCTCAAAGATTTCTCAGAAAGTGAGTTCCCTAGCATAAAGACT
GAATTTCAACAAGTACTAAGTAATAGGAAAGAAATGACACAGTTTTTGGAAGAGTGGTTAAATACTCGTTTTGATATAGAAAAGCTTAAAAATG
GCATCCAGAAAGAAAATGATAGGATTTGTCAAGTGAATAACTTCTTTAATAACAGAATAATTGCCATAATGAATGAATCAACAGAGTTTGAGGA
AAGAAGTGCTACCATATCCAAAGAGTGGGAACAGGACCTGAAATCACTGAAAGAGAAAAATGAAAAACTATTTAAAAACTACCAAACATTGAAG
ACTTCCTTGGCATCTGGTGCCCAGGTTAATCCTACCACACAAGACAATAAGAATCCTCATGTTACATCAAGAGCTACACAGTTAACCACAGAGA
AAATTCGAGAGCTGGAAAATTCACTGCATGAAGCTAAAGAAAGTGCTATGCATAAGGAAAGCAAGATTATAAAGATGCAGAAAGAACTTGAGGT
GACTAATGACATAATAGCAAAACTTCAAGCCAAAGTTCATGAATCAAATAAATGCCTTGAAAAAACAAAAGAGACAATTCAAGTACTTCAGGAC
AAAGTTGCTTTAGGAGCTAAGCCATATAAAGAAGAAATTGAAGATCTCAAAATGAAGCTTGTGAAAATAGACCTAGAGAAAATGAAAAATGCCA
AAGAATTTGAAAAGGAAATCAGTGCTACAAAAGCCACTGTAGAATATCAAAAGGAAGTTATAAGGCTATTGAGAGAAAATCTCAGAAGAAGTCA
ACAGGCCCAAGATACCTCAGTGATATCAGAACATACTGATCCTCAGCCTTCAAATAAACCCTTAACTTGTGGAGGTGGCAGCGGCATTGTACAA
AACACAAAAGCTCTTATTTTGAAAAGTGAACATATAAGGCTAGAAAAAGAAATTTCTAAGTTAAAGCAGCAAAATGAACAGCTAATAAAACAAA
AGAATGAATTGTTAAGCAATAATCAGCATCTTTCCAATGAGGTCAAAACTTGGAAGGAAAGAACCCTTAAAAGAGAGGCTCACAAACAAGTAAC
TTGTGAGAATTCTCCAAAGTCTCCTAAAGTGACTGGAACAGCTTCTAAAAAGAAACAAATTACACCCTCTCAATGCAAGGAACGGAATTTACAA
GATCCTGTGCCAAAGGAATCACCAAAATCTTGTTTTTTTGATAGCCGATCAAAGTCTTTACCATCACCTCATCCAGTTCGCTATTTTGATAACT
CAAGTTTAGGCCTTTGTCCAGAGGTGCAAAATGCAGGAGCAGAGAGTGTGGATTCTCAGCCAGGTCCTTGGCACGCCTCCTCAGGCAAGGATGT
GCCTGAGTGCAAAACTCAGTAG

ID 23: KIF11, *Homo sapiens*

ATGGCGTCGCAGCCAAATTCGTCTGCGAAGAAGAAAGAGGAGAAGGGGAAGAACATCCAGGTGGTGGTGAGATGCAGACCATTTAATTTGGCAG
AGCGGAAAGCTAGCGCCCATTCAATAGTAGAATGTGATCCTGTACGAAAAGAAGTTAGTGTACGAACTGGAGGATTGGCTGACAAGAGCTCAAG
GAAAACATACACTTTTGATATGGTGTTTGGAGCATCTACTAAACAGATTGATGTTTACCGAAGTGTTGTTTGTCCAATTCTGGATGAAGTTATT
ATGGGCTATAATTGCACTATCTTTGCGTATGGCCAAACTGGCACTGGAAAAACTTTTACAATGGAAGGTGAAAGGTCACCTAATGAAGAGTATA
CCTGGGAAGAGGATCCCTTGGCTGGTATAATTCCACGTACCCTTCATCAAATTTTTGAGAAACTTACTGATAATGGTACTGAATTTTCAGTCAA
AGTGTCTCTGTTGGAGATCTATAATGAAGAGCTTTTTGATCTTCTTAATCCATCATCTGATGTTTCTGAGAGACTACAGATGTTTGATGATCCC
CGTAACAAGAGAGGAGTGATAATTAAAGGTTTAGAAGAAATTACAGTACACAACAAGGATGAAGTCTATCAAATTTTAGAAAAGGGGGCAGCAA
AAAGGACAACTGCAGCTACTCTGATGAATGCATACTCTAGTCGTTCCCACTCAGTTTTCTCTGTTACAATACATATGAAAGAAACTACGATTGA
TGGAGAAGAGCTTGTTAAAATCGGAAAGTTGAACTTGGTTGATCTTGCAGGAAGTGAAAACATTGGCCGTTCTGGAGCTGTTGATAAGAGAGCT
CGGGAAGCTGGAAATATAAATCAATCCCTGTTGACTTTGGGAAGGGTCATTACTGCCCTTGTAGAAAGAACACCTCATGTTCCTTATCGAGAAT
CTAAACTAACTAGAATCCTCCAGGATTCTCTTGGAGGGCGTACAAGAACATCTATAATTGCAACAATTTCTCCTGCATCTCTCAATCTTGAGGA
AACTCTGAGTACATTGGAATATGCTCATAGAGCAAAGAACATATTGAATAAGCCTGAAGTGAATCAGAAACTCACCAAAAAAGCTCTTATTAAG
GAGTATACGGAGGAGATAGAACGTTTAAAACGAGATCTTGCTGCAGCCCGTGAGAAAAATGGAGTGTATATTTCTGAAGAAAATTTTAGAGTCA
TGAGTGGAAAATTAACTGTTCAAGAAGAGCAGATTGTAGAATTGATTGAAAAAATTGGTGCTGTTGAGGAGGAGCTGAATAGGGTTACAGAGTT
GTTTATGGATAATAAAAATGAACTTGACCAGTGTAAATCTGACCTGCAAAATAAAACACAAGAACTTGAAACCACTCAAAAACATTTGCAAGAA
ACTAAATTACAACTTGTTAAAGAAGAATATATCACATCAGCTTTGGAAAGTACTGAGGAGAAACTTCATGATGCTGCCAGCAAGCTGCTTAACA
CAGTTGAAGAAACTACAAAAGATGTATCTGGTCTCCATTCCAAACTGGATCGTAAGAAGGCAGTTGACCAACACAATGCAGAAGCTCAGGATAT
TTTTGGCAAAAACCTGAATAGTCTGTTTAATAATATGGAAGAATTAATTAAGGATGGCAGCTCAAAGCAAAAGGCCATGCTAGAAGTACATAAG
ACCTTATTTGGTAATCTGCTGTCTTCCAGTGTCTCTGCATTAGATACCATTACTACAGTAGCACTTGGATCTCTCACATCTATTCCAGAAAATG
TGTCTACTCATGTTTCTCAGATTTTTAATATGATACTAAAAGAACAATCATTAGCAGCAGAAAGTAAAACTGTACTACAGGAATTGATTAATGT
ACTCAAGACTGATCTTCTAAGTTCACTGGAAATGATTTTATCCCCAACTGTGGTGTCTATACTGAAAATCAATAGTCAACTAAAGCATATTTTC
AAGACTTCATTGACAGTGGCCGATAAGATAGAAGATCAAAAAAAGGAACTAGATGGCTTTCTCAGTATACTGTGTAACAATCTACATGAACTAC
AAGAAAATACCATTTGTTCCTTGGTTGAGTCACAAAAGCAATGTGGAAACCTAACTGAAGACCTGAAGACAATAAAGCAGACCCATTCCCAGGA
ACTTTGCAAGTTAATGAATCTTTGGACAGAGAGATTCTGTGCTTTGGAGGAAAAGTGTGAAAATATACAGAAACCACTTAGTAGTGTCCAGGAA
AATATACAGCAGAAATCTAAGGATATAGTCAACAAAATGACTTTTCACAGTCAAAAATTTTGTGCTGATTCTGATGGCTTCTCACAGGAACTCA
GAAATTTTAACCAAGAAGGTACAAAATTGGTTGAAGAATCTGTGAAACACTCTGATAAACTCAATGGCAACCTGGAAAAAATATCTCAAGAGAC
TGAACAGAGATGTGAATCTCTGAACACAAGAACAGTTTATTTTTCTGAACAGTGGGTATCTTCCTTAAATGAAAGGGAACAGGAACTTCACAAC
TTATTGGAGGTTGTAAGCCAATGTTGTGAGGCTTCAAGTTCAGACATCACTGAGAAATCAGATGGACGTAAGGCAGCTCATGAGAAACAGCATA
ACATTTTTCTTGATCAGATGACTATTGATGAAGATAAATTGATAGCACAAAATCTAGAACTTAATGAAACCATAAAAATTGGTTTGACTAAGCT
TAATTGCTTTCTGGAACAGGATCTGAAACTGGATATCCCAACAGGTACGACACCACAGAGGAAAAGTTATTTATACCCATCAACACTGGTAAGA
ACTGAACCACGTGAACATCTCCTTGATCAGCTGAAAAGGAAACAGCCTGAGCTGTTAATGATGCTAAACTGTTCAGAAAACAACAAAGAAGAGA
CAATTCCGGATGTGGATGTAGAAGAGGCAGTTCTGGGGCAGTATACTGAAGAACCTCTAAGTCAAGAGCCATCTGTAGATGCTGGTGTGGATTG

Fig. 9 (Continued)

TTCATCAATTGGCGGGGTTCCATTTTTCCAGCATAAAAAATCACATGGAAAAGACAAAGAAAACAGAGGCATTAACACACTGGAGAGGTCTAAA
GTGGAAGAAACTACAGAGCACTTGGTTACAAAGAGCAGATTACCTCTGCGAGCCCAGATCAACCTTTAA

ID 24: KIF12, *Homo sapiens*
ATGCAGAGGACCTTCGCCTGGCTGTTGGACCGCGTGCAGCACCTGGGTGCCCCTGTCACCCTTCGCGCCTCTTATCTGGAGATCTACAATGAGC
AGGTTCGGGACTTGCTGAGCCTGGGGTCTCCCCGGCCCCTCCCTGTTCGCTGGAACAAGACTCGGGGCTTCTATGTGGAGCAGCTGCGGGTGGT
GGAATTTGGGAGTCTGGAGGCCCTGATGGAACTTTTGCAAACGGGTCTCAGCCGTCGAAGGAACTCAGCCCACACCCTGAACCAGGCCTCCAGC
CGAAGCCATGCCCTGCTCACCCTTTACATCAGCCGTCAAACTGCCCAGCAGATGCCTTCTGTGGACCCTGGGGAGCCCCCTGTTGGTGGGAAGC
TGTGCTTTGTGGACCTGGCAGGCAGTGAGAAGGTAGCAGCCACGGGATCCCGTGGGGAGCTGATGCTTGAGGCTAACAGCATCAACCGAAGCCT
GCTGGCCCTGGGTCACTGCATCTCCCTGCTGCTGGACCCACAGCGGAAGCAGAGCCACATCCCTTTCCGGGACAGCAAGCTCACCAAGTTGCTG
GCAGACTCACTGGGAGGGCGCGGGGTCACCCTCATGGTGGCCTGCGTGTCCCCCTCAGCCCAGTGCCTTCCTGAGACTCTCAGCACCCTGCGAT
ATGCAAGCCGAGCTCAGCGGGTCACCACCCGACCACAGGCCCCCAAGTCTCCTGTGGCAAAGCAGCCCCAGCGTTTGGAGACAGAGATGCTGCA
GCTCCAGGAGGAGAACCGTCGCCTGCAGTTCCAGCTGGACCAAATGGACTGCAAGGCCTCAGGGCTCAGTGGAGCCCGGGTGGCCTGGGCCCAG
CGGAACCTGTACGGGATGCTACAGGAGTTCATGCTAGAGAATGAGAGGCTCAGGAAAGAAAAGAGCCAGCTGCAGAATAGCCGAGACCTGGCCC
AGAATGAGCAGCGCATCCTGGCCCAGCAGGTCCATGCACTAGAGAGGCGTCTCCTCTCTGCCTGCTACCATCACCAGCAGGGTCCTGGCCTGAC
CCCACCGTGTCCCTGCTTGATGGCCCCAGCTCCCCCTTGCCATGCACTGCCACCCCTCTACTCCTGCCCCTGCTGCCACATCTGCCCACTGTGT
CGAGTGCCCCTGGCCCACTGGGCCTGCCTGCCAGGGGAGCACCACCTGCCCCAGGTGTTGGACCCTGAGGCCTCAGGTGGCAGGCCCCCATCTG
CCCGGCCCCCACCCTGGGCACCCCCATGCAGCCCTGGCTCTGCCAAGTGCCCAAGAGAGAGGAGTCACAGTGACTGGACTCAGACCCGAGTCCT
GGCAGAGATGTTGACGGAGGAGGAGGTGGTACCTTCTGCACCTCCCCTGCCTGTGAGGCCCCCGAAGACATCACCAGGGCTCAGAGGTGGGGCC
GGGGTTCCAAACCTGGCCCAGAGACTGGAGGCCCTCAGAGACCAGATTGGCAGCTCCCTGCGACGTGGCCGCAGCCAGCCACCCTGCAGTGAGG
GCGCACGGAGCCCAGGCCAAGTCCTCCCTCCCCATTGA ID 25: KIF13B, *Homo sapiens*
ATGGGGGACTCCAAAGTGAAAGTGGCGGTGCGGATACGACCCATGAACCGGCGAGAGACTGACTTGCATACCAAATGTGTGGTGGATGTGGATG
CAAACAAGGTTATTCTTAATCCTGTAAATACGAATCTTTCCAAAGGAGATGCCCGGGGCCAGCCGAAGGTGTTTGCTTATGATCATTGTTTCTG
GTCTATGGATGAATCTGTCAAAGAAAAGTATGCAGGTCAAGATATTGTTTTCAAGTGCCTTGGAGAGAATATCCTGCAGAATGCTTTTGATGGC
TACAATGCATGTATCTTTGCCTATGGACAGACTGGCTCTGGAAAATCTTATACCATGATGGGCACAGCTGACCAACCTGGATTAATCCCAAGAC
TTTGCAGTGGACTCTTTGAACGAACTCAGAAAGAGGAAAATGAAGAACAGAGTTTTAAAGTAGAAGTGTCCTACATGGAAATTTATAATGAAAA
AGTTCGAGACCTTCTTGATCCCAAAGGAAGCCGTCAGACGTTGAAAGTCAGAGAGCATAGTGTGTTGGGACCTTATGTCGACGGACTTTCTAAA
CTGGCTGTCACAAGCTACAAGGATATTGAGTCGTTGATGTCTGAGGGTAACAAATCTCGCACAGTTGCTGCAACCAACATGAACGAGGAGAGTA
GCCGATCCCATGCAGTTTTCAAAATCACCCTCACACATACTCTCTACGATGTGAAGTCTGGGACATCTGGAGAGAAAGTGGGCAAACTCAGCCT
GGTGGATTTAGCTGGCAGTGAACGAGCAACGAAGACAGGCGCTGCAGGGGACAGGCTGAAGGAAGGGAGCAACATTAACAAGTCCCTCACAACC
CTCGGTCTGGTTATCTCAGCTCTTGCAGATCAGAGTGCTGGCAAAAACAAGAATAAATTTGTTCCATATCGTGACTCAGTTCTCACTTGGCTGC
TCAAAGACAGCCTCGGGGGTAACAGCAAGACCGCCATGGTGGCTACTGTGAGTCCTGCAGCTGATAACTATGATGAAACCCTCTCAACTCTGCG
GTATGCAGATCGAGCCAAGCACATTGTAAACCACGCTGTGGTGAATGAGGACCCTAATGCCCGAATTATCCGGGATCTCCGGGAAGAAGTTGAG
AAACTCCGGGAGCAGCTGACCAAAGCAGAGGCAATGAAATCTCCAGAGCTAAAGGACCGGCTGGAAGAATCTGAGAAGCTAATCCAGGAAATGA
CTGTGACCTGGGAGGAGAAATTAAGGAAAACGGAGGAGATTGCACAGGAACGACAGAAACAGCTTGAGAGTCTTGGAATATCTCTTCAGTCTTC
GGGAATCAAAGTTGGGGATGATAAATGCTTCCTTGTGAATCTGAATGCTGACCCAGCTCTGAATGAGCTTCTGGTGTACTATTTAAAGGAACAT
ACATTGATAGGGTCAGCAAATTCCCAAGATATCCAACTGTGCGGCATGGGAATTCTTCCTGAACACTGTATTATAGACATCACGTCAGAAGGCC
AGGTTATGCTGACTCCTCAGAAGAACACCAGAACATTTGTAAATGGGTCATCTGTCTCCAGTCCAATACAGCTACACCATGGGGACAGGATATT
ATGGGGAAACAATCATTTCTTCAGACTCAATTTGCCTAAAAAGAAAAAGAAAGCAGAACGAGAGGATGAGGACCAGGATCCCTCCATGAAGAAC
GAGAATAGTTCTGAGCAGCTGGATGTAGACGGAGACTCCTCCAGCGAGGTGTCCAGTGAAGTTAACTTTAATTACGAATACGCACAGATGGAGG
TCACCATGAAGGCCCTGGGCAGCAATGATCCGATGCAGTCCATATTAAACAGCTTAGAACAACAGCATGAAGAAGAAAAACGATCTGCACTGGA
GCGCCAGAGGCTTATGTATGAGCACGAATTGGAGCAGCTCCGGAGAAGGCTGTCTCCTGAGAAGCAGAACTGCCGGAGCATGGACAGGTTTTCT
TTCCACTCGCCCAGCGCTCAGCAACGCTTAAGACAGTGGGCTGAGGAGAGAGAAGCAACGTTGAATAACAGCCTGATGAGGCTGAGGGAACAAA
TTGTTAAGGCCAATCTATTGGTGAGAGAAGCTAATTACATTGCTGAGGAGCTGGATAAAAGAACAGAATACAAAGTTACCCTACAGATTCCAGC
CTCCAGCCTGGATGCCAACAGGAAGCGAGGCTCTCTTCTTAGTGAGCCTGCAATCCAGGTGAGAAGAAAAGGAAAAGGAAAGCAGATTTGGTCT
TTGGAAAAACTGGACAACAGGCTGTTGGATATGAGAGACCTTTATCAGGAGTGGAAAGAGTGTGAAGAAGATAACCCAGTAATACGATCATACT
TCAAACGTGCTGATCCATTCTATGATGAGCAGGAAAATCACAGTCTCATTGGGGTGGCCAATGTCTTCCTCGAGTCACTTTTCTATGATGTGAA
GTTACAATACGCTGTTCCCATCATCAACCAGAAAGGAGAGGTGGCAGGTCGGCTGCACGTGGAGGTGATGCGACTCAGTGGTGATGTTGGGGAG
AGGATCGCAGGAGGCGATGAGGTGGCAGAGGTCTCCTTTGAGAAGGAGACCCAGGAGAACAAACTGGTGTGCATGGTTAAAATCCTGCAAGCTA
CTGGGTTGCCACAGCATCTGTCCCACTTTGTGTTCTGCAAATACAGCTTCTGGGATCAACAGGAGCCGGTGATTGTCGCTCCTGAAGTGGACAC
CTCCTCCTCTTCCGTCAGCAAGGAGCCGCACTGCATGGTTGTCTTTGATCATTGCAATGAGTTTTCTGTTAACATCACCGAAGACTTTATCGAG
CATCTTTCCGAAGGAGCATTGGCAATTGAAGTATATGGACATAAAATAAACGATCCCCGGAAAAACCCCGCCCTGTGGGATTTGGGAATCATCC
AAGCAAAGACACGTAGTCTTCGGGACAGATGGAGTGAAGTGACCAGGAAATTGGAATTCTGGGTTCAAATCTTGGAACAGAATGAGAATGGTGA
ATACTGCCCTGTAGAAGTGATTTCTGCAAAGGATGTCCCAACAGGAGGAATCTTCCAGCTCCGGCAGGGGCAGTCCCGGAGAGTTCAAGTCGAA
GTGAAGTCAGTGCAGGAATCTGGGACTTTACCACTGATGGAAGAATGTATACTGTCTGTTGGCATTGGATGTGTCAAAGTTAGACCGCTCAGAG
CCCCCAGAACACATGAGACCTTCCATGAGGAAGAGGAAGACATGGACAGCTACCAGGATCGAGATTTAGAGAGACTTCGTAGAAAATGGCTAAA
TGCATTAACAAAACGTCAGGAGTACTTGGATCAACAATTGCAAAAGCTTGTCAGTAAACGTGATAAAACAGAGGATGATGCTGACCGTGAAGCG
CAGCTTCTGGAGATGCGGTTGACCCTAACTGAGGAGAGGAACGCGGTGATGGTCCCCTCTGCTGGCAGTGGTATTCCAGGGGCCCCAGCAGAAT
GGACCCCAGTACCTGGGATGGAGACACACATTCCTGTTATATTCCTGGACTTAAATGCTGATGATTTCAGCTCTCAGGATAATCTTGATGACCC
AGAAGCTGGTGGATGGGATGCGACCTTGACTGGGAAGAAGAAGAGGAGTTCTTTGAATTGCAGATTGTGAAGCAGCATGATGGGGAGGTGAAA
GCAGAAGCCTCCTGGGACTCCGCGGTGCATGGCTGCCCTCAGCTCAGCAGGGGCACGCCCGTGGACGAGCGGTTGTTCCTGATCGTGCGCGTGA
CGGTCCAGCTCAGCCACCCTGCTGACATGCAACTGGTGTTACGCAAGAGAATCTGTGTCAATGTTCACGGCCGCCAGGGTTTTGCACAGAGTCT
CCTAAAAAAGATGTCTCATCGAAGTTCTATTCCTGGCTGTGGAGTGACTTTTGAAATTGTCTCCAATATTCCAGAGGATGCCCAGGGAGTGGAA
GAACGGGAAGCATTAGCAAGAATGGCAGCCAATGTTGAAAACCCAGCTTCTGCTGACTCGGAGGCTTATATTGAAAAGTACCTCAGGAGCGTGC
TGGCTGTAGAAAACCTCCTGACTTTAGATCGTCTGCGCCAGGAAGTTGCAGTGAAGGAACAGTTAACAGGAAAAGGAAAGTTGAGCAGGAGGAG
TATCAGTTCTCCAAATGTGAACAGATTGTCTGGAAGCCGACAAGATCTCATTCCATCATACAGTCTAGGCAGCAACAAGGGCCGGTGGGAAAGT
CAGCAGGATGTATCCCAAACCACAGTTTCCAGAGGAATAGCTCCTGCCCCCGCCCTCTCTGTTTCTCCCCAAAATAACCATTCTCCAGATCCAG
GACTCAGTAACCTTGCAGCATCCTACTTGAATCCTGTCAAATCCTTCGTGCCGCAAATGCCAAAGCTCCTCAAGTCTCTCTTTCCCGTCCGCGA
TGAGAAGAGGGGCAAGCGGCCGTCTCCCCTCGCACACCAGCCCGTGCCCCGCATCATGGTGCAGTCAGCCAGCCCGGACATCAGGGTGACCAGG
ATGGAGGAGGCTCAGCCGGAGATGGGCCCTGACGTGCTGGTGCAGACGATGGGGGCCCCGGCCTTGAAGATCTGCGACAAACCTGCCAAAGTGC
CTTCCCCACCGCCTGTCATAGCTGTCACAGCGGTCACCCCGGCTCCGGAGGCACAGGACGGGCCCCCCAGCCCCCTGAGTGAAGCCTCTAGCGG
GTACTTCTCCCACAGCGTCTCCACCGCGACCCTGTCGGACGCCCTGGGCCCCGGCCTGGACGCTGCGGCCCCGCCGGGGTCCATGCCCACCGCC
CCTGAGGCCGAGCCCGAGGCGCCCATCAGCCACCCCCCACCGCCCACGGCCGTCCCCGCCGAGGAGCCCCCTGGCCCCCAGCAGCTCGTGAGCC
CCGGTCGGGAGCGCCCCGACCTCGAGGCCCCGGCGCCCGGCTCCCCGTTCCGCGTCCGGAGGGTGCGGGCCTCGGAGTTGCGCTCCTTCTCGCG
CATGCTGGCTGGGGACCCCGGCTGCTCCCCGGGGGCCGAGGGGAATGCGCCGGCCCCGGGCGCCGGGGGACAGGCCCTGGCCTCTGATTCCGAG
GAAGCTGACGAGGTCCCGGAGTGGCTCCGAGAGGGCGAGTTCGTCACCGTGGGCGCCCACAAAACGGGCGTGGTGAGATACGTGGGGCCTGCCG
ACTTCCAAGAGGGCACGTGGGTCGGCGTGGAGCTCGACCTGCCCTCAGGTAAGAATGACGGTTCCATCGGCGGGAAGCAGTACTTCAGGTGTAA
CCCTGGCTACGGGCTGCTGGTCAGGCCCAGCCGGGTCCGCAGGGCCACGGGCCCTGTGCGGCGGCGCAGCACAGGACTCCGGCTGGGTGCCCCC

Fig. 9 (Continued)

GAGGCCCGCCGGAGCGCCACCCTCTCGGGCTCCGCCACCAACCTGGCCTCGCTGACAGCTGCCCTGGCCAAGGCCGACAGGAGCCACAAGAACC
CTGAGAACCGGAAATCCTGGGCCAGCTGA

ID 26: KIF14, *Homo sapiens*
ATGTCATTACACAGTACTCATAATAGAAATAACAGCGGTGATATTCTTGATATTCCTTCTTCCCAAAATAGTTCATCACTGAATGCCCTCACCC
ACAGTAGCCGACTTAAGCTGCATTTGAAGTCGGATATGTCAGAATGTGAAAATGATGATCCATTATTGAGATCTGCAGGTAAAGTCAGAGACAT
AAATAGAACTTATGTTATTTCTGCCAGTAGAAAAACAGCAGACATGCCCCTTACCCCTAATCCTGTAGGTAGATTGGCACTTCAGAGGAGAACT
ACAAGGAACAAAGAATCATCTTTGCTTGTTAGTGAGTTGGAAGACACAACTGAAAAAACAGCAGAAACACGTCTTACATTACAACGTCGTGCTA
AAACAGATTCTGCAGAAAAGTGGAAAACAGCTGAAATAGATTCTGTCAAAATGACACTGAATGTGGGAGGTGAAACAGAAAATAATGGTGTTTC
TAAGGAAAGTAGAACAAATGTAAGGATTGTAAATAATGCTAAAAACTCTTTTGTTGCCTCTTCTGTACCTTTAGATGAAGATCCACAGGTCATT
GAAATGATGGCTGATAAGAAATACAAAGAAACATTTTCTGCCCCCAGTAGAGCAAATGAAAATGTTGCACTTAAGTACTCAAGTAATAGACCAC
CCATTGCTTCCCTGAGTCAGACTGAAGTTGTTAGATCAGGACACTTGACAACGAAACCTACTCAGAGCAAGTTGGATATCAAAGTGTTGGGAAC
AGGAAACTTGTATCATAGAAGTATTGGGAAGGAAATTGCAAAAACTTCAAATAAATTTGGGAGCTTAGAAAAAAGAACACCTACAAAATGTACA
ACAGAACACAAACTGACAACAAAGTGCAGCCTGCCTCAGCTTAAGAGCCCAGCTCCATCAATACTGAAGAATAGAATGTCTAACCTTCAAGTTA
AACAAAGACCAAAAAGTTCCTTTCTTGCAAATAAACAGGAAAGATCCGCAGAAAATACAATTCTTCCCGAAGAAGAAACTGTAGTTCAGAACAC
CTCTGCAGGAAAAGACCCCTTAAAAGTAGAGAATAGTCAAGTGACAGTGGCAGTACGCGTAAGACCTTTCACCAAGAGAGAGAAGATTGAAAAA
GCATCCCAGGTAGTCTTCATGAGTGGGAAAGAAATAACTGTGGAACACCCTGACACGAAACAAGTTTATAATTTTATTTATGATGTTTCATTCT
GGTCTTTTGATGAATGTCATCCTCACTACGCTAGCCAGACAACTGTCTATGAGAAGCTAGCAGCACCACTCCTAGAAAGAGCCTTCGAAGGCTT
CAATACCTGTCTTTTTGCTTATGGTCAGACTGGCTCTGGAAAATCATATACGATGATGGGATTTAGTGAAGAACCAGGAATAATTCCAAGATTT
TGTGAAGATCTTTTTTCTCAAGTAGCCAGAAAACAAACCCAAGAGGTCAGCTATCACATTGAAATGAGCTTCTTTGAAGTATATAATGAAAAAA
TTCACGACCTTCTGGTTTGTAAAGATGAAAATGGGCAGAGAAAGCAACCACTGAGAGTGAGGGAACATCCTGTTTATGGACCATATGTTGAAGC
ACTGTCAATGAACATTGTCAGTTCTTACGCTGATATCCAGAGTTGGCTAGAATTGGGAAATAAACAAAGAGCTACTGCTGCTACTGGTATGAAT
GATAAAAGTTCCCGATCTCATTCAGTTTTCACCCTGGTGATGACCCAGACCAAGACAGAATTTGTGGAAGGGGAAGAACACGATCACAGAATAA
CAAGTCGAATTAACCTAATAGATCTGGCAGGCAGTGAGCGCTGCTCTACGGCTCACACTAATGGAGATCGACTAAAGGAAGGTGTGAGTATTAA
TAAGTCCTTGCTAACTTTGGGAAAAGTTATATCTGCACTTTCGGAACAAGCAAACCAAAGGAGTGTTTTTATTCCTTATCGTGAATCTGTTCTT
ACATGGCTGTTAAAAGAAAGTCTGGGTGGAAATTCAAAAACTGCAATGATTGCTACGATTAGTCCCGCTGCCAGCAACATAGAAGAAACATTAA
GCACACTTAGATATGCTAACCAAGCCCGTTTAATAGTCAACATTGCTAAAGTAAATGAAGATATGAACGCTAAGTTAATTAGAGAATTGAAGGC
AGAAATTGCAAAGCTAAAAGCTGCTCAGAGAAACAGTCGGAATATTGACCCTGAACGATACAGGCTCTGTCGGCAAGAAATAACATCCTTAAGA
ATGAAACTGCATCAACAGGAGAGAGACATGGCAGAAATGCAAAGAGTGTGGAAAGAAAAGTTTGAACAAGCTGAAAAAAGAAAACTTCAAGAAA
CAAAAGAGTTACAGAAAGCAGGAATTATGTTTCAAATGGACAATCATTTACCAAACCTTGTTAATCTGAATGAAGATCCACAACTATCTGAGAT
GCTGCTATATATGATAAAAGAAGGAACAACTACAGTTGGAAAGTATAAACCAAACTCAAGCCATGATATTCAGTTATCTGGGGTGCTGATTGCT
GATGATCATTGTACTATCAAAAATTTTGGTGGGACAGTGAGTATTATCCCAGTTGGGGAAGCAAAGACATATGTAAATGGAAAACATATTTTGG
AAATCACAGTATTACGTCATGGTGATCGAGTGATTCTTGGTGGAGATCATTATTTTAGATTTAATCATCCAGTAGAAGTCCAGAAAGGAAAAAG
GCCATCTGGAAGAGATACTCCTATAAGTGAGGGTCCAAAAGACTTTGAATTTGCAAAAAATGAGTTGCTCATGGCACAGAGATCACAACTTGAA
GCAGAAATAAAAGAGGCTCAGTTGAAGGCAAAGGAAGAAATGATGCAAGGAATCCAGATTGCAAAAGAAATGGCTCAGCAAGAGCTTTCTTCTC
AAAAAGCTGCATATGAAAGCAAAATAAAAGCACTGGAAGCAGAACTGAGAGAAGAGTCTCAAAGGAAAAAAATGCAGGAAATAAATAACCAGAA
GGCTAATCACAAAATTGAGGAATTAGAAAAGGCAAAGCAGCATCTTGAACAGGAAATATATGTCAACAAAAAGCGATTAGAAATGGAAACATTG
GCTACAAAACAGGCTTTAGAAGACCATAGCATCCGCCATGCAAGAATTCTGGAAGCTTTAGAAACTGAAAAGCAAAAAATTGCTAAAGAAGTAC
AAATTCTACAGCAGAATCGGAATAATAGGGATAAAACTTTTACAGTGCAGACAACTTGGAGCTCTATGAAACTCTCAATGATGATTCAGGAAGC
CAATGCTATCAGCAGCAAATTGAAAACATACTATGTTTTTGGCAGACATGATATATCAGATAAAAGTAGTTCTGACACTTCTATTCGGGTTCGT
AACCTGAAACTAGGAATCTCAACATTCTGGAGTCTGGAAAAGTTTGAATCTAAACTTGCAGCAATGAAAGAACTTTATGAGAGTAATGGTAGTA
ACAGGGGTGAAGATGCCTTTTGTGATCCTGAAGATGAATGGGAACCCGACATTACAGATGCACCAGTTTCTTCACTTTCTAGAAGGAGGAGTAG
GAGTTTGATGAAGAACAGAAGAATTTCTGGTTGTTTACATGACATACAAGTCCATCCAATTAAGAATTTGCATTCTTCACATTCATCAGGTTTA
ATGGACAAATCAAGCACTATTTACTCAAATTCAGCAGAGTCCTTTCTTCCTGGAATTTGCAAAGAATTGATTGGTTCTTCGTTAGATTTTTTTG
GACAGAGTTATGATGAAGAAAGAACTATAGCAGACAGCCTAATTAATAGTTTTCTTAAAATTTATAATGGGCTATTTGCCATTTCCAAGGCTCA
TGAAGAACAAGATGAAGAAAGTCAAGATAACTTGTTTTCTTCTGATCGAGCAATCCAGTCACTTACTATTCAGACTGCATGTGCTTTTGAGCAG
CTAGTAGTGCTAATGAAACACTGGCTGAGTGATTTACTGCCTTGTACCAACATAGCAAGACTTGAGGATGAGTTGAGACAAGAAGTTAAAAAAC
TGGGAGGCTACTTACAGTTATTTTTGCAGGGATGCTGTTTGGATATTTCATCAATGATAAAAGAGGCTCAAAAGAATGCAATCCAAATTGTACA
ACAAGCTGTAAAGTATGTGGGGCAGTTAGCAGTTCTGAAAGGGAGCAAGCTACATTTTCTAGAAAACGGTAACAATAAAGCTGCCAGTGTCCAG
GAGGAATTCATGGATGCTGTTTGTGATGGTGTAGGCTTAGGAATGAAGATTTTATTAGATTCTGGACTGGAAAAAGCAAAAGAACTTCAGCATG
AACTCTTTAGGCAGTGTACAAAAAATGAGGTTACCAAAGAAATGAAAACTAATGCCATGGGATTGATTAGATCTCTTGAAAACATCTTTGCTGA
ATCGAAAATTAAAAGTTTCAGAAGGCAAGTACAAGAAGAAAACTTTGAATACCAAGATTTCAAGAGGATGGTTAATCGTGCTCCAGAATTCTTA
AAGTTAAAACATTGCTTAGAGAAAGCTATTGAAATTATTATTTCTGCACTGAAAGGATGCCATAGTGATATAAATCTTCTCCAGACTTGTGTTG
AAAGTATTCGCAACTTGGCCAGTGATTTTTACAGTGACTTCAGTGTGCCTTCTACTTCTGTTGGCAGCTATGAGAGTAGAGTAACTCACATTGT
CCACCAGGAACTAGAATCTCTAGCTAAGTCTCTCCTCTTTTGTTTTGAATCTGAAGAAAGCCCTGATTTGTTGAAACCCTGGGAAACTTATAAT
CAAAATACCAAAGAAGAACACCAACAATCTAAATCAAGCGGGATTGACGGCAGTAAGAATAAAGGTGTACCAAAGCGTGTCTATGAGCTCCATG
GCTCATCCCCAGCAGTGAGCTCAGAGGAATGCACACCCAGTAGGATTCAGTGGGTGTGA ID 27: KIF15, *Homo sapiens*
ATGGCACCCGGCTGCAAAACTGAGTTACGCAGCGTGACAAATGGTCAGTCTAACCAACCAAGTAATGAAGGTGATGCCATCAAAGTTTTTGTGC
GAATTCGTCCTCCTGCAGAAAGATCTGGGTCAGCTGATGGAGAGCAGAACTTATGCTTATCTGTGCTGTCCTCCACGAGTCTCCGGCTGCACTC
CAACCCTGAGCCCAAGACCTTCACGTTTGATCATGTTGCAGATGTGGATACCACTCAGGAATCTGTATTCGCAACTGTGGCTAAAAGCATTGTG
GAGTCTTGCATGAGCGGTTATAATGGTACCATCTTTGCATATGGACAGACTGGCTCAGGGAAGACATTTACTATGATGGGACCATCTGAATCTG
ATAATTTTTCTCATAACCTGAGAGGAGTAATCCCACGAAGTTTTGAATATTTGTTTTCCTTAATTGATCGTGAAAAAGAAAAGGCTGGAGCTGG
AAAGAGTTTCCTTTGTAAGTGTTCCTTTATTGAAATCTACAACGAGCAGATATATGATCTACTGGACTCTGCATCGGCTGGACTGTACTTAAGG
GAGCATATCAAGAAGGGAGTCTTTGTTGTTGGTGCGGTGGAGCAGGTGGTAACCTCAGCTGCTGAAGCCTATCAGGTGTTGTCTGGAGGATGGA
GGAATAGACGTGTGGCATCAACATCAATGAACAGAGAATCGTCTAGGTCTCATGCCGTCTTTACAATTACAATAGAGTCAATGGAGAAAAGTAA
TGAGATTGTGAATATACGGACCTCCCTACTCAACCTGGTGGATTTAGCAGGATCTGAAAGGCAAAAAGATACCCATGCAGAAGGGATGAGATTG
AAGGAAGCAGGTAACATAAATCGATCATTGAGCTGCCTGGGCCAAGTGATTACAGCACTTGTCGACGTGGGTAATGGAAAACAGAGACATGTTT
GCTACAGAGACTCCAAACTTACCTTCTTACTACGGGATTCCCTTGGAGGTAATGCCAAAACAGCCATAATTGCAAATGTTCATCCTGGATCCAG
GTGTTTTGGGGAAACCCTATCAACACTTAACTTTGCTCAAAGAGCCAAGCTGATTAAAAACAAGGCAGTAGTAAATGAAGACACCCAAGGAAAT
GTGAGCCAGCTCCAAGCTGAAGTGAAGAGGCTCAAAGAACAACTGGCGGAGCTTGCTTCAGGACAGACACCACCAGAAAGCTTCCTGACCAGAG
ACAAAAAGAAGACTAACTATATGGAGTATTTCCAGGAAGCAATGTTATTCTTTAAGAAATCTGAACAGGAAAAGAAGTCTCTGATAGAAAAAGT
TACCCAATTAGAAGACCTCACCCTCAAAAAGGAAAAATTTATTCAATCTAATAAAATGATTGTGAAATTCCGAGAGGATCAAATAATACGCTTG
GAAAAGCTCCACAAGGAATCCCGGGGAGGTTTTCTGCCTGAGGAGCAGGATCGTTTGCTCTCAGAATTAAGGAATGAGATTCAAACTCTGCGAG
AACAAATAGAGCACCACCCCAGAGTTGCAAAGTATGCTATGGAAAATCATTCCCTCAGGGAGGAGAATAGAAGACTGAGATTATTAGAGCCTGT
GAAAAGAGCTCAAGAAATGGATGCCCAGACCATTGCAAAACTAGAAAAAGCTTTCTCTGAAATAAGTGGCATGGAGAAAAGTGACAAAAATCAG
CAAGGATTTTCACCTAAAGCTCAGAAAGAGCCATGTTTGTTTGCAAACACTGAGAAGTTAAAAGCACAACTCCTGCAAATTCAGACAGAGCTGA
ATAATTCAAAGCAAGAATATGAAGAATTCAAAGAACTTACTAGGAAAAGGCAGCTAGAATTGGAATCAGAGCTTCAGTCTTTGCAAAAAGCGAA
CCTTAATCTTGAAAACCTTTTGGAAGCAACAAAAGCCTGCAAGCGGCAAGAAGTTTCTCAGCTGAATAAAATTCATGCTGAAACACTTAAGATT

Fig. 9 (Continued)

ATAACTACACCAACCAAGGCCTACCAACTTCATTCCCGACCAGTACCAAAATTAAGCCCTGAAATGGGAAGCTTTGGCTCTCTATACACTCAGA
ATTCTAGCATATTAGATAATGATATATTAAATGAGCCAGTTCCTCCTGAGATGAATGAACAAGCTTTTGAGGCCATTTCTGAAGAGCTTAGAAC
AGTGCAGGAACAAATGAGTGCTCTTCAAGCCAAACTGGATGAAGAAGAGCATAAAAACCTAAAGCTTCAGCAGCATGTTGACAAACTGGAACAT
CATTCTACCCAAATGCAGGAGCTTTTCTCATCAGAAAGAATTGATTGGACCAAACAGCAGGAAGAGCTTCTCTCACAGTTGAATGTCCTTGAAA
AGCAGCTTCAAGAGACTCAAACTAAAAATGACTTTTTGAAAAGTGAGGTACATGACCTGCGAGTAGTCCTTCATTCTGCTGACAAGGAGCTTTC
TTCAGTGAAATTGGAATATAGTTCATTCAAAACGAATCAGGAGAAAGAATTCAACAAACTTTCCGAAAGACACATGCATGTACAGCTTCAATTA
GATAATCTCAGGTTAGAAAACGAAAAGCTGCTTGAGAGCAAAGCCTGCCTACAGGATTCCTATGACAACTTACAAGAAATAATGAAATTTGAGA
TTGACCAACTTTCAAGAAACCTCCAAAACTTCAAAAAAGAAAATGAAACTCTGAAATCTGATCTGAATAATTTGATGGAGCTTCTTGAGGCAGA
AAAAGAACGCAATAACAAATTATCATTACAGTTTGAAGAAGATAAAGAAAACAGTTCTAAAGAAATCTTAAAAGTTCTTGAGGCTGTACGTCAG
GAGAAACAGAAAGAGACGGCCAAGTGTGAGCAGCAGATGGCAAAAGTACAGAAACTAGAAGAGAGCTTGCTTGCTACTGAAAAAGTGATCAGTT
CCCTGGAAAAGTCTAGAGATTCTGATAAGAAAGTTGTAGCTGACCTCATGAACCAGATCCAGGAGCTAAGAACATCGGTCTGTGAGAAAACAGA
AACTATAGACACCCTGAAACAAGAACTGAAGGACATAAATTGCAAATACAACTCTGCTTTGGTTGACAGAGAAGAGAGCAGAGTGTTGATCAAG
AAGCAGGAAGTGGATATTCTGGATCTGAAAGAAACCCTTAGGCTGAGAATACTTTCTGAGGACATAGAGAGGGATATGCTCTGTGAGGACCTGG
CTCATGCCACTGAGCAGCTGAACATGCTCACAGAGGCCTCAAAAAAACACTCGGGGCTGCTGCAGTCTGCCCAGGAAGAACTGACCAAGAAGGA
AGCCCTGATTCAGGAACTTCAGCACAAGCTAAACCAAAAGAAAGAGGAAGTAGAACAGAAGAAGAATGAATATAACTTCAAAATGAGGCAACTA
GAACATGTGATGGATTCTGCTGCTGAGGATCCCCAGAGTCCTAAGACACCACCTCACTTTCAAACACATTTGGCAAAACTCCTGGAAACACAAG
AACAAGAGATAGAAGATGGAAGAGCCTCTAAGACTTCTTTGGAACACCTTGTAACAAAGCTAAATGAAGACAGAGAAGTCAAAAATGCTGAAAT
CCTCAGAATGAAGGAGCAGTTGCGTGAAATGGAAAACCTACGCCTGGAAAGTCAGCAGTTAATAGAGAAAAACTGGCTCCTGCAAGGTCAGCTG
GATGATATTAAAAGACAAAAGGAAAACAGTGATCAGAATCATCCAGATAATCAACAGCTGAAGAATGAACAAGAAGAAAGTATCAAAGAAAGAC
TTGCAAAAAGTAAAATAGTTGAAGAAATGCTGAAAATGAAAGCAGACCTAGAAGAAGTCCAAAGTGCCCTTTACAACAAAGAGATGGAATGCCT
TAGAATGACTGATGAAGTCGAACGAACCCAAACTTTGGAGTCTAAAGCATTCCAGGAAAAAGAACAACTGAGATCAAAGCTGGAAGAAATGTAT
GAAGAAAGAGAGAGAACATCCCAGGAGATGGAAATGTTAAGGAAGCAGGTGGAGTGTCTTGCTGAGGAAAATGGAAAGTTGGTAGGTCACCAAA
ATTTGCATCAGAAGATTCAGTACGTAGTGCGACTAAAGAAGGAAAATGTCAGGCTTGCTGAGGAGACAGAAAAGTTGCGTGCCGAAAATGTATT
TTTAAAAGAAAAGAAAAGAAGTGAATCTTGA

ID 28: KIF17, *Homo sapiens*

ATGGCCTCCGAGGCGGTGAAGGTTGTCGTGCGCTGCCGTCCCATGAACCAGCGGGAGCGAGAGCTGCGCTGCCAGCCCGTGGTGACTGTGGACT
GCGCGCGCGCGCCCAGTGCTGCATCCAGAACCCGGGCGCCGCCGACGAGCCGCCCAAGCAGTTCACCTTCGACGGCGCCTACCACGTGGACCACGT
CACCGAGCAGATCTACAACGAGATCGCCTATCCGCTGGTGGAGGGCGTCACTGAGGGCTACAATGGCACCATCTTTGCCTACGGCCAGACAGGC
AGCGGGAAGTCCTTCACCATGCAGGGCCTGCCGGATCCGCCCTCCCAGAGAGGCATCATCCCCAGGGCCTTCGAGCACGTGTTCGAGAGCGTCC
AGTGTGCAGAGAACACTAAGTTCCTGGTCCGGGCCTCCTACCTGGAGATCTACAATGAAGATGTCCGGGACCTCCTTGGGGCTGACACCAAGCA
GAAGCTGGAGCTGAAGGAGCACCCAGAGAAGGGCGTGTACGTGAAGGGGCTGTCCATGCACACGGTGCACAGCGTGGCCCAGTGTGAGCACATC
ATGGAGACTGGCTGGAAGAACCGTTCGGTCGGCTACACGCTGATGAACAAGGATTCCTCACGCTCGCACTCCATCTTCACCATCAGCATCGAGA
TGTCTGCCGTGGATGAGCGGGGCAAGGACCACCTCCGGGCGGGCAAGCTGAACCTGGTGGACCTGGCGGGCAGCGAGCGGCAGTCCAAGACCGG
GGCCACGGGCGAGCGGCTCAAGGAGGCCACCAAGATCAACCTGTCGCTCTCGGCACTGGGCAATGTCATCTCGGCGCTGGTGGACGGGCGCTGT
AAGCACGTCCCCTACCGTGACTCGAAGCTGACGCGGCTGCTGCAGGACTCACTGGGCGGCAACACCAAGACGCTCATGGTGGCCTGCCTGTCGC
CTGCGGACAACAACTACGATGAGACACTCAGCACGCTGCGCTACGCCAACCGGGCCAAGAACATCAGGAACAAGCCGCGCATCAATGAGGACCC
CAAGGATGCGCTGCTTCGCGAGTACCAGGAGGAGATCAAGAAGCTCAAGGCCATCCTGACACAGCAGATGAGCCCCAGCAGCCTGTCAGCCCTG
CTGTCCAGGCAGGTGCCCCCAGACCCTGTGCAGGTGGAGGAGAAGCTGTTGCCCCAACCTGTGATCCAGCATGACGTGGAGGCCGAGAAGCAGC
TGATCCGGGAGGAGTATGAAGAGCGCCTGGCCCGGCTGAAAGCCGACTATAAGGCCGAGCAGGAGTCTCGGGCCAGGCTGGAGGAAGACATCAC
TGCCATGCGCAACTCATATGACGTCAGGCTGTCCACGCTGGAGGAGAACCTGCGGAAGGAGACAGAGGCTGTCCTGCAGGTGGGAGTCCTCTAC
AAGGCTGAGGTCATGTCCAGGGCTGAGTTTGCCAGCAGCGCTGAGTACCCGCCTGCTTTTCAGTATGAGACAGTGGTGAAACCCAAGGTCTTCT
CCACGACTGACACTCTGCCCAGTGACGATGTCTCCAAGACTCAGGTTTCCTCCAGGTTTGCGGAGCTGCCCAAGGTGGAACCCTCCAAATCTGA
GATTTCTCTGGGCTCCAGTGAGTCATCCTCGCTCGAAGAAACCTCTGTGTCCGAGGCTTTCCCTGGGCCTGAGGAGCCCTCCAACGTGGAGGTC
TCCATGCCCACTGAGGAGTCCAGGAGCAGATACTTCCTGGATGAGTGCCTCGGGCAGGAGGCCGCTGGGCACCTGCTGGGGGAACAGAACTACC
TCCCGCAAGAGGAGCCGCAGGAGGTGCCCCTGCAGGGGTTACTAGGCCTGCAGGACCCGTTTGCCGAGGTGGAAGCCAAGCTGGCCAGACTCTC
CTCCACCGTGGCCAGGACAGATGCACCCCAGGCAGACGTCCCCAAGGTCCCTGTGCAGGTCCCTGCGCCGACAGACCTGCTGGAGCCCAGTGAT
GCCAGGCCCGAAGCCGAGGCGGCTGATGACTTCCCGCCCAGGCCTGAGGTAGATCTGGCCTCGGAAGTGGCCTTAGAGGTGGTGCGGACAGCAG
AGCCTGGCGTGTGGTTGGAGGCTCAGGCCCCGGTGGCCCTGGTGGCTCAGCCTGAGCCCCTGCCGGCCACAGCTGGTGTGAAGAGGGAGAGCGT
GGGCATGGAGGTGGCAGTGCTGACTGATGACCCGCTGCCCGTTGTGGACCAGCAGCAGGTGCTGGCCCGTCTGCAGCTGTTGGAGCAGCAGGTT
GTGGGTGGAGAGCAGGCCAAGAACAAGGACCTGAAGGAGAAGCACAAGCGGCGCAAGCGCTACGCAGACGAGCGCAGGAAGCAGCTGGTGGCTG
CCCTGCAGAACTCGGATGAGGACAGCGGGGACTGGGTGCTGCTTAACGTCTACGACTCCATCCAGGAGGAAGTGCGGGCCAAGAGCAAGCTGCT
GGAGAAGATGCAGAGGAAGCTTCGGGCAGCAGAGGTGGAGATCAAAGATCTGCAGTCCGAGTTTCAGCTGGAGAAGATCGATTACTTGGCCACC
ATCCGCCGGCAGGAGCGTGACTCCATGCTCTTGCAGCAGCTCCTGGAGCAGGTGCAGCCCCTGATTCGCAGGGACTGTAACTACAGCAACCTGG
AGAAGATTCTGCGTGAGTCCTGCTGGGACGAAGATAACGGCTTCTGGAAGATCCCACATCCCGTCATCACAAAAACCAGCCTCCCAGTAGCAGT
TTCAACTGGGCCACAGAACAAACCAGCCCGCAAAACCTCTGCAGCAGACAATGGCGAGCCGAACATGGAGGACGACCGCTACAGGCTCATGCTC
AGTCGGAGCAACAGTGAAAACATTGCCAGCAACTACTTCCGATCTAAGCGGGCCAGCCAGATCCTCAGCACAGACGCCAGGAAGAGCCTCACAC
ATCACAACTCGCCACCAGGCCTCAGCTGCCCACTCAGCAACAACTCTGCCATCCCACCCACCCAGGCCCCTGAAATGCCCCAGCCCCGGCCCTT
CCGCCTCGAGTCCCTCGACATCCCTTTCACCAAGGCCAAGCGTAAGAAAAGCAAAAGCAACTTTGGCAGTGAGCCTCTGTGA

ID 29: KIF19, *Homo sapiens*

ATGAAGGACAGCGGGGACTCCAAGGACCAGCAACTCATGGTGGCGCTTCGGGTCCGGCCCATCAGCGTGGCAGAGCTGGAGGAAGGAGCTACCC
TCATCGCCCATAAAGTGGATGAGCAGATGGTGGTTCTCATGGACCCAATGGAGGATCCCGACGACATCCTGCGGGCGCATCGCTCCCGGGAGAA
GTCCTACCTGTTCGACGTGGCCTTTGACTTCACCGCCACCCAGGAGATGGTGTATCAGGCCACCACCAAGAGCCTCATCGAGGGCGTCATCTCA
GGCTACAATGCCACTGTCTTTGCCTATGGCCCCACAGGCTGTGGGAAAACCTACACCATGCTGGGCACAGACCAGGAGCCTGGCATCTATGTTC
AGACCCTCAACGACCTCTTCCGTGCCATCGAGGAGACCAGCAATGACATGGAGTATGAGGTCTCCATGTCCTACCTGGAGATCTACAATGAGAT
GATCCGGGACCTGCTGAACCCCTCCCTGGGCTACCTGGAGCTGCGGGAGGACTCTAAGGGGGTGATCCAGGTGGCCGGCATCACCGAAGTCTCC
ACCATCAATGCCAAGGAGATCATGCAGCTGCTGATGAAGGGGAACCGGCAGAGGACCCAGGAGCCCACGGCCGCCAACCAGACGTCCTCCCGCT
CCCACGCGGTACTGCAGGTGACCGTGCGCCAGCGCAGCCGGGTCAAGAACATCTTGCAGGAGGTGCGGCAGGGCCGCCTGTTCATGATCGACCT
GGCTGGCTCAGAGCGCGCCTCGCAGACACAGAATCGTGGGCAGCGTATGAAGGAGGGGGCCCACATCAACCGCTCACTGCTGGCACTGGGCAAC
TGCATCAACGCCCTGAGCGACAAGGGTAGCAACAAGTACATCAACTATCGCGACAGCAAGCTCACCCGGCTCCTGAAGGACTCTCTGGGAGGAA
ACAGCCGCACAGTGATGATCGCTCACATCAGTCCTGCGAGCAGTGCCTTCGAGGAGTCCCGGAACACCCTGACCTACGCCGGCCGGGCCAAGAA
CATTAAGACTAGGGTGAAGCAGAACCTCCTGAACGTCTCCTACCACATCGCCCAGTACACCAGCATCATCGCTGACCTGCGGGGCGAGATCCAG
CGACTCAAGCGCAAGATTGATGAGCAGACTGGGCGGGGCCAGGCCCGGGGCCGGCAGGATCGGGGTGACATCCGCCACATCCAAGCTGAGGTCC
AGCTGCACAGCGGGCAGGGTGAGAAGGCTGGCATGGGACAGCTTCGGGAGCAGCTCGCCAGCGCCTTCCAGGAGCAGATGGATGTGCGGAGGCG
CCTGCTGGAGCTGGAGAACCGCGCCATGGAGGTCCAGATTGACACCTCCCGACACCTGCTCACCATCGCCGGCTGGAAGCATGAGAAGTCCCGC
CGGGCCCTCAAATGGCGGGAGGAGCAGCGAAAGGAGTGCTACGCTAAGGACGACAGCGAGAAGGACTCAGACACAGGTGATGACCAACCAGACA
TCCTGGAGCCACCCGAGGTGGCCGCAGCCCGGGAGAGCATTGCAGCCCTGGTGGACGAGCAGAAGCAACTGCGCAAGCAGAAGCTGGCGCTGGA
GCAGCGCTGCCGGGAGCTGCGCGCGCGGGGCCGGCGCCTGGAGGAGACGCTGCCGCGGCGCATCGGCTCCGAGGAGCAGCGCGAGGTGCTCAGC
CTGCTGTGCCGCGTGCACGAGCTCGAGGTGGAGAACACCGAGATGCAGTCGCACGCGCTGCTCCGCGACGGTGCGCTCCGCCACCGCCACGAGG

Fig. 9 (Continued)

CCGTGCGCCGCCTGGAGCAGCACCGCAGTCTCTGCGACGAGATTATCCAGGGCCAGCGGCAGATCATCGACGACTACAACCTGGCCGTCCCGCA
GCGCCTGGAAGAGCTCTACGAAGTGTACCTGCGGGAGCTGGAGGAGGGCAGCCTGGAGCAGGCCACCATCATGGACCAAGTGGCCTCCAGGGCC
CTGCAGGACAGCTCCTTGCCCAAAATTACCCCAGCAGGAACCTCACTGACCCCAGATTCTGACCTGGAGAGTGTGAAGACATTGAGCTCTGATG
CCCAGCACCTGCAGAACAGCGCCCTCCCTCCCCTCAGCACAGAGAGTGAAGGCCACCACGTGTTCAAGGCTGGTACTGGGGCCTGGCAGGCAAA
AAGCTCCTCTGTGCCCACCCCACCTCCCATCCAGCTCGGCAGCCTGGTGACGCAGGAGGCCCCGGCTCAGGACAGCCTGGGCAGCTGGATCAAC
TCTTCCCCTGACAGCAGTGAGAACCTGTCGGAGATCCCCTTGTCCCACAAAGAGAGGAAGGAGATCCTGACTGGCACCAAGTGCATCTGGGTGA
AGGCCGCCCGGCGGCGCTCGCGGGCCCTGGGAACCGAGGGGCGACACCTGCTGGCACCCGCCACAGAGCGCAGCAGCCTGTCCCTGCACTCACT
GAGCGAGGGCGACGATGCGCGGCCACCAGGCCCACTGGCCTGCAAGCGGCCGCCCAGCCCCACACTACAGCATGCTGCCAGTGAGGACAACCTG
TCCAGCAGCACGGGCGAGGCCCCGTCCCGGGCAGTCGGACATCATGGGGACGGCCCCAGGCCCTGGCTGCGTGGCCAGAAGAAAAGCCTGGGCA
AGAAAAGGGAGGAGTCGCTGGAGGCAAAGAGAAGGAAGCGGAGGTCCCGATCCTTCGAGGTCACCGGGCAAGGGCTCTCCCACCCCAAGACACA
CCTCCTGGGGCCCCATCAGGCGGAGCGCATCTCGGACCACAGGATGCCAGTGTGCAGGCACCCAGCCCCTGGTATCCGGCATCTGGGAAAGGTC
ACGCTACCTTTGGCCAAAGTCAAACTCCCTCCAAGCCAGAACACGGGCCCGGGGGACTCCTCACCCCTGGCTGTTCCCCCCAACCCAGGTGGTG
GTTCTCGACGGGCTACCCGTGGCCCCGCCTGCCCCACGGCACAAGCACCCATGGCAAAGATGGATGCTCCCGGCATAACTGA

ID 30: KIF22, *Homo sapiens*
ATGGCCGCGGGCGGCTCGACGCAGCAGAGGCGACGCGAGATGGCGGCAGCTTCAGCGGCGGCGATCTCAGGAGCTGGTCGCTGTCGGCTAAGCA
AGATTGGAGCTACTCGTCGTCCACCTCCAGCTCGCGTAAGGGTGGCTGTGCGACTGCGGCCATTTGTGGATGGAACAGCGGGAGCAAGTGATCC
CCCCTGTGTGCGGGGCATGGACAGCTGCTCTCTAGAGATTGCTAACTGGAGGAACCACCAGGAGACTCTCAAATACCAGTTTGATGCCTTCTAT
GGGGAGAGGAGTACTCAGCAGGACATCTATGCAGGTTCAGTGCAGCCCATCCTAAGGCACTTGCTGGAAGGGCAGAATGCCAGTGTGCTTGCCT
ATGGACCCACAGGAGCTGGGAAGACGCACACAATGCTGGGCAGCCCAGAGCAACCTGGGGTGATCCCGCGGGCTCTCATGGACCTCCTGCAGCT
CACAAGGGAGGAGGGTGCCGAGGGCCGGCCATGGGCCCTTTCTGTCACCATGTCTTACCTAGAGATCTACCAGGAGAAGGTATTAGACCTCCTG
GACCCTGCTTCGGGAGACCTGGTAATCCGAGAAGACTGCCGGGGGAATATCCTGATTCCGGGTCTCTCCCAGAAGCCCATCAGTAGCTTTGCTG
ATTTTGAGCGGCACTTCCTGCCAGCCAGTCGAAATCGGACTGTAGGAGCCACCCGGCTCAACCAGCGCTCCTCCCGCAGTCATGCTGTGCTCCT
GGTCAAGGTGGACCAGCGGGAACGTTTGGCCCCATTTCGCCAGCGAGAGGGAAAACTCTACCTGATTGACTTGGCTGGGTCAGAGGACAACCGG
CGCACAGGCAACAAGGGCCTTCGGCTAAAAGAGAGTGGAGCCATCAACACCTCCCTGTTTGTCCTGGGCAAAGTGGTAGATGCGCTGAATCAGG
GCCTCCCTCGTGTACCTTATCGGGACAGCAAGCTCACTCGCCTATTGCAGGACTCTCTGGGTGGCTCAGCCCACAGTATCCTTATTGCCAACAT
TGCCCCTGAGAGACGCTTCTACCTAGACACAGTCTCCGCACTCAACTTTGCTGCCAGGTCCAAGGAGGTGATCAATCGGCCTTTTACCAATGAG
AGCCTGCAGCCTCATGCCTTGGGACCTGTTAAGCTGTCTCAGAAAGAATTGCTTGGTCCACCAGAGGCAAAGAGAGCCCGAGGCCCTGAGGAAG
AGGAGATCGGGAGCCCTGAGCCCATGGCAGCTCCAGCCTCTGCCTCCCAGAAACTCAGCCCCCTACAGAAGCTAAGCAGCATGGACCCGGCCAT
GCTGGAGCGCCTCCTCAGCTTGGACCGTCTGCTTGCCTCCCAGGGGAGCCAGGGGGCCCCTCTGTTGAGTACCCCAAAGCGAGAGCGGATGGTG
CTAATGAAGACAGTGGAAGAGAAGGACCTAGAGATTGAGAGGCTTAAGACGAAGCAAAAAGAACTGGAGGCCAAGATGTTGGCCCAGAAGGCTG
AGGAAAAGGAGAACCATTGTCCCACAATGCTCCGGCCCCTTTCACATCGCACAGTCACAGGGGCAAAGCCCCTGAAAAAGGCTGTGGTGATGCC
CCTACAGCTAATTCAGGAGCAGGCAGCATCCCCAAATGCCGAGATCCACATCCTGAAGAATAAAGGCCGGAAGAGAAAGCTGGAGTCCCTGGAT
GCCCTAGAGCCTGAGGAGAAGGCTGAGGACTGCTGGGAGCTACAGATCAGCCCGGAGCTACTGGCTCATGGGCGCCAAAAAATACTGGATCTGC
TGAACGAAGGCTCAGCCCGAGATCTCCGCAGTCTTCAGCGCATTGGCCCGAAGAAGGCCCAGCTAATCGTGGGCTGGCGGGAGCTCCACGGCCC
CTTCAGCCAGGTGGAGGACCTGGAACGCGTGGAGGGCATAACGGGGAAACAGATGGAGTCCTTCCTGAAGGCAAACATCCTGGGTCTCGCCGCC
GGCCAGCGCTGTGGCGCCTCCTGA ID 31: KIF23, *Homo sapiens*
ATGAAGTCAGCGAGAGCTAAGACACCCCGGAAACCTACCGTGAAAAAAGGGTCCCAAACGAACCTTAAAGACCCAGTTGGGGTATACTGTAGGG
TGCGCCCACTGGGCTTTCCTGATCAAGAGTGTTGCATAGAAGTGATCAATAATACAACTGTTCAGCTTCATACTCCTGAGGGCTACAGACTCAA
CCGAAATGGAGACTATAAGGAGACTCAGTATTCATTTAAACAAGTATTTGGCACTCACACCACCCAGAAGGAACTCTTTGATGTTGTGGCTAAT
CCCTTGGTCAATGACCTCATTCATGGCAAAAATGGTCTTCTTTTTACATATGGTGTGACGGGAAGTGGAAAAACTCACACAATGACTGGTTCTC
CAGGGGAAGGAGGGCTGCTTCCTCGTTGTTTGGACATGATCTTTAACAGTATAGGGTCATTTCAAGCTAAACGATATGTTTTCAAATCTAATGA
TAGGAATAGTATGGATATACAGTGTGAGGTTGATGCCTTATTAGAACGTCAGAAAAGAGAAGCTATGCCCAATCCAAAGACTTCTTCTAGCAAA
CGACAAGTAGATCCAGAGTTTGCAGATATGATAACTGTACAAGAATTCTGCAAAGCAGAAGAGGTTGATGAAGATAGTGTCTATGGTGTATTTG
TCTCTTATATTGAAATATATAATAATTACATATATGATCTATTGGAAGAGGTGCCGTTTGATCCCATAAAACCCAAACCTCCACAATCTAAATT
GCTTCGTGAAGATAAGAACCATAACATGTATGTTGCAGGATGTACAGAAGTTGAAGTGAAATCTACTGAGGAGGCTTTTGAAGTTTTCTGGAGA
GGCCAGAAAAAGAGACGTATTGCTAATACCCATTTGAATCGTGAGTCCAGCCGTTCCCATAGCGTGTTCAACATTAAATTAGTTCAGGCTCCCT
TGGATGCAGATGGAGACAATGTCTTACAGGAAAAAGAACAAATCACTATAAGTCAGTTGTCCTTGGTAGATCTTGCTGGAAGTGAAAGAACTAA
CCGGACCAGAGCAGAAGGGAACAGATTACGTGAAGCTGGTAATATTAATCAGTCACTAATGACGCTAAGAACATGTATGGATGTCCTAAGAGAG
AACCAAATGTATGGAACTAACAAGATGGTTCCATATCGAGATTCAAAGTTAACCCATCTGTTCAAGAACTACTTTGATGGGGAAGGAAAAGTGC
GGATGATCGTGTGTGTGAACCCCAAGGCTGAAGATTATGAAGAAAACTTGCAAGTCATGAGATTTGCGGAAGTGACTCAAGAAGTTGAAGTAGC
AAGACCTGTAGACAAGGCAATATGTGGTTTAACGCCTGGGAGGAGATACAGAAACCAGCCTCGAGGTCCAGTTGGAAATGAACCATTGGTTACT
GACGTGGTTTTGCAGAGTTTTCCACCTTTGCCATCATGCGAAATTTTGGATATCAACGATGAGCAGACACTTCCAAGGCTGATTGAAGCCTTAG
AGAAACGACATAACTTACGACAAATGATGATTGATGAGTTTAACAAACAATCTAATGCTTTTAAAGCTTTGTTACAAGAATTTGACAATGCTGT
TTTAAGTAAAGAAAACCACATGCAAGGGAAACTAAATGAAAAGGAGAAGATGATCTCAGGACAGAAATTGGAAATAGAACGACTGGAAAAGAAA
AACAAAACTTTAGAATATAAGATTGAGATTTTAGAGAAAACAACTACTATCTATGAGGAAGATAAACGCAATTTGCAACAGGAACTTGAAACTC
AGAACCAGAAACTTCAGCGACAGTTTTCTGACAAACGCAGATTAGAAGCCAGGTTGCAAGGCATGGTGACAGAAACGACAATGAAGTGGGAGAA
AGAATGTGAGCGTAGAGTGGCAGCCAAACAGCTGGAGATGCAGAATAAACTCTGGGTTAAAGATGAAAAGCTGAAACAACTGAAGGCTATTGTT
ACCGAACCTAAAACTGAGAAGCCAGAGAGACCCTCTCGGGAGCGAGATCGAGAAAAAGTTACTCAAAGATCTGTTTCTCCATCACCTGTGCCTC
TTTCTAGTAACTATATTGCTCAGATTTCCAACGGCCAGCAACTCATGAGCCAGCCACAGCTACATAGGCGCTCTAACTCTTGCAGCAGCATTTC
TGTAGCTTCCTGTATTTCGGAATGGGAGCAGAAAATTCCTACGTACAACACACCTCTCAAAGTCACATCTATTGCAAGGCGTAGGCAGCAGGAG
CCAGGACAAAGCAAAACTTGTATCGTGTCAGACAGAAGGCGAGGGATGTACTGGACTGAAGGCAGGGAGGTGGTTCCTACATTCAGAAATGAGA
TAGAAATAGAAGAGGATCATTGCGGCAGGTTACTCTTTCAACCTGATCAGAACGCACCACCAATTCGTCTCCGACACAGACGATCACGCTCTGC
AGGAGACAGATGGGTAGATCATAAGCCCGCCTCTAACATGCAAACTGAAACAGTCATGCAGCCACATGTCCCTCATGCCATCACAGTATCTGTT
GCAAATGAAAAGGCACTAGCTAAGTGTGAGAAGTACATGCTGACCCACCAGGAACTAGCCTCCGATGGGGAGATTGAAACTAAACTAATTAAGG
GTGATATTTATAAAACAAGGGGTGGTGGACAATCTGTTCAGTTTACTGATATTGAGACTTTAAAGCAAGAATCACCAAATGGTAGTCGAAAACG
AAGATCTTCCACAGTAGCACCTGCCCAACCAGATGGTGCAGAGTCTGAATGGACCGATGTAGAAACAAGGTGTTCTGTGGCTGTGGAGATGAGA
GCAGGATCCCAGCTGGGACCTGGATATCAGCATCACGCACAACCCAAGCGCAAAAAGCCATGA ID 32: KIF24, *Homo sapiens*
ATGGCATCCTGGTTATATGAATGTCTTTGTGAAGCTGAACTTGCACAGTATTATTCTCATTTCACTGCCCTTGGCCTTCAGAAAATAGATGAAT
TAGCCAAGATTACAATGAAGGACTACTCCAAATTAGGAGTCCATGACATGAACGACCGCAAACGTCTCTTCCAACTTATCAAAATTATTAAGAT
TATGCAAGAAGAAGATAAAGCAGTCAGTATCCCAGAGCGTCATCTTCAGACAAGCAGCCTGCGCATCAAATCTCAGGAATTAAGATCTGGCCCT
CGCAGACAGCTGAATTTTGATTCTCCTGCTGACAATAAAGACAGAAATGCCAGCAATGATGGGTTTGAAATGTGCAGTTTATCAGATTTCTCTG
CAAATGAACAGAAGTCCACTTACCTAAAAGTGCTAGAACACATGCTACCAGATGATTCCCAGTACCATACAAAAACAGGAATTCTGAATGCCAC
AGCTGGTGATTCCTATGTGCAAACAGAAATCAGCACTTCACTCTTTTCACCAAATTACCTTTCTGCAATACTGGGGGATTGTGATATTCCCATT
ATTCAAAGAATCTCTCATGTTTCAGGGTATAACTATGGAATCCCTCATTCTTGTATCAGACAGAACACTTCAGAGAAACAGAATCCTTGGACTG
AGATGGAGAAAATCAGAGTTTGTGTTCGAAAACGCCCCCTGGGCATGAGGGAGGTACGTCGTGGAGAAATTAATATTATTACTGTAGAAGACAA

Fig. 9 (Continued)

AGAAACTCTACTTGTGCATGAGAAGAAAGAAGCAGTTGACCTCACTCAATATATTCTGCAGCATGTTTTTTATTTTGATGAAGTCTTTGGTGAG
GCGTGCACCAATCAGGATGTATACATGAAGACTACTCACCCACTTATTCAGCATATTTTCAATGGAGGCAATGCCACTTGCTTTGCTTATGGAC
AGACAGGTGCTGGAAAGACCTACACCATGATAGGAACTCATGAGAACCCAGGATTGTATGCTCTAGCTGCCAAAGATATCTTCAGGCAACTAGA
AGTGTCCCAGCCAAGAAAGCACCTCTTTGTGTGGATCAGCTTCTATGAAATTTACTGTGGACAGCTTTATGACCTCCTAAATAGAAGAAAAAGG
CTCTTTGCAAGAGAAGATAGCAAGCACATGGTGCAGATAGTGGGACTGCAAGAGCTTCAGGTGGACAGTGTGGAGCTCCTCTTAGAGGTGATCT
TAAAGGGCAGCAAGGAGCGCAGCACTGGGGCCACTGGAGTTAATGCAGACTCCTCCCGCTCCCATGCCGTCATCCAAATTCAGATCAAAGATTC
AGCCAAGAGGACATTTGGCAGGATCTCTTTTATTGACTTGGCTGGCAGTGAAAGAGCAGCAGATGCAAGGGACTCAGATAGACAGACAAAGATG
GAAGGTGCAGAAATAAATCAGAGTCTACTGGCTCTGAAGGAATGTATCCGAGCACTGGATCAGGAACACACCCATACTCCCTTCAGGCAAAGCA
AACTAACTCAGGTCCTGAAGGACTCTTTCATCGGCAATGCCAAAACCTGCATGATCGCCAACATCTCACCAAGCCACGTGGCCACTGAACACAC
TCTCAACACCTTGCGCTATGCTGACCGGGTCAAAGAACTAAAGAAAGGCATTAAGTGTTGCACTTCAGTTACCAGTCGAAATCGGACATCTGGA
AACTCCTCTCCAAAACGAATTCAGAGCTCCCCTGGGGCTTTGTCAGAGGACAAATGTTCTCCCAAAAAAGTCAAGCTGGGATTTCAGCAGTCAC
TCACAGTGGCAGCCCCTGGTTCCACGAGAGGGAAGGTCCATCCTCTGACCAGCCACCCACCCAACATTCCTTTTACTTCTGCACCTAAGGTCTC
TGGTAAAAGGGGTGGCTCCAGAGGGAGTCCTTCACAAGAGTGGGTCATTCATGCTAGCCCTGTGAAAGGAACTGTGCGCTCTGGACATGTGGCC
AAAAAAAAGCCAGAAGAGTCAGCACCATTGTGCTCTGAGAAAAATCGAATGGGCAACAAAACTGTCCTTGGGTGGAAAGCAGGGCCTCAGGCC
CAGGAGAAGGCCTAGTGCGTGGTAAGCTGTCCACCAAGTGCAAGAAAGTGCAGACAGTGCAGCCAGTACAGAAGCAGCTTGTGTCTCGAGTTGA
GCTCTCCTTTGGCAACGCCCACCACAGGGCTGAGTACAGTCAAGACAGCCAGAGGGGCACGCCTGCTAGGCCTGCCTCTGAAGCTTGGACAAAC
ATCCCGCCACATCAGAAGGAGAGGGAGGAACATCTGCGTTTCTATCACCAGCAGTTCCAACAGCCACCTCTCCTCCAACAGAAGTTAAAATACC
AACCACTGAAAAGGTCTTTACGCCAGTACAGGCCCCCAGAGGGTCAGCTCACGAATGAGACTCCGCCTCTGTTCCACTCTTACTCTGAAAACCA
TGATGGAGCCCAAGTAGAGGAACTTGATGACAGTGATTTCAGTGAAGATTCTTTTTCACACATCTCTAGTCAGAGGGCCACAAAGCAAAGGAAC
ACCCTGGAGAATAGCGAAGACTCATTCTTCCTGCACCAGACGTGGGGACAGGGTCCTGAGAAGCAGGTGGCAGAAAGACAGCAGAGTCTGTTTT
CTAGCCCCAGGACAGGTGACAAGAAAGATCTAACTAAAAGCTGGGTGGACTCCAGGGACCCCATAAACCACAGAAGAGCAGCACTCGATCACAG
CTGCAGCCCAAGTAAGGGGCCCGTGGACTGGAGCAGAGAGAACTCTACTTCCTCAGGGCCTTCTCCCAGAGACAGCCTGGCAGAGAAGCCATAC
TGTTCACAGGTAGATTTCATATATAGACAGGAAAGAGGTGGAGGCTCTTCCTTTGATCTCAGAAAGGATGCCTCCCAAAGTGAGGTTTCTGGGG
AGAATGAGGGCAACTTGCCATCCCCAGAGGAAGATGGTTTCACTATCTCATTGTCCCACGTTGCAGTTCCTGGATCCCCAGACCAAAGAGACAC
AGTCACCACACCTCTGAGAGAAGTCAGTGCAGACGGCCCAATCCAGGTGACCAGCACTGTGAAAAACGGTCATGCTGTCCCAGGAGAGGATCCT
AGGGGGCAGTTAGGCACGCATGCTGAATATGCTTCTGGACTCATGTCTCCCCTCACCATGTCCCTCCTGGAGAACCCAGACAACGAAGGGTCTC
CTCCCTCGGAGCAGCTGGTCCAGGATGGGGCTACGCACAGTCTAGTGGCAGAGAGCACAGGGGGCCCAGTTGTGAGCCACACAGTGCCATCTGG
TGATCAAGAGGCAGCCTTGCCAGTGTCTTCAGCAACTAGGCACCTGTGGCTGTCCTCATCTCCCCCTGATAATAAGCCTGGTGGTGATCTTCCA
GCTCTGTCCCCATCACCCATCCGTCAGCACCCAGCTGACAAGCTGCCCAGCAGGGAGGCAGACCTAGGAGAGGCCTGCCAGAGCAGAGAGACTG
TACTTTTCTCCCACGAACACATGGGTAGTGAGCAGTATGATGCTGATGCAGAGGAGACGGGGCTGGATGGCTCCTGGGGTTTCCCAGGAAAGCC
CTTCACCACCATACATATGGGGGTACCCCATTCTGGACCTACACTCACCCCACGAACAGGAAGTAGTGATGTGGCTGACCAGCTCTGGGCCCAG
GAGAGAAAACATCCTACAAGGCTTGGTTGGCAGGAGTTTGGTTTGTCCACAGACCCCATCAAGTTGCCCTGCAACAGTGAAAATGTCACATGGC
TCAAACCCAGGCCGATCTCAAGGTGCTTAGCAAGGCCAAGTTCTCCCTTGGTTCCCAGCTGCTCTCCCAAGACTGCAGGGACACTCCGTCAGCC
CACCCTGGAGCAAGCGCAGCAGGTGGTCATCCGAGCACACCAGGAACAGCTGGATGAAATGGCTGAGCTCGGCTTCAAGGAGGAGACGCTGATG
AGCCAGCTGGCTTCTAATGATTTTGAAGATTTTGTGACCCAGCTGGATGAAATCATGGTTCTGAAATCCAAGTGTATCCAGAGTCTGAGGAGCC
AGCTGCAGCTCTATCTCACCTGCCACGGGCCCACCGCAGCCCCTGAGGGAACAGTGCCGTCTTAG

ID 33: KIF25, *Homo sapiens*

ATGACATGGACCTCAGGTCAGCTTCAGCGTGAGAAGCAGGCCAGGCCTGGGTCTGGAGCCGTCCTGGCCTTCCCAGATGACAAGGACCTCAGGG
TTTATGGTCCAGCAGAGTCTCAGAGCGCGGTCTTTGGAGATGTGTGCCCCCTACTCACTTCTCTCTTGGATGGGTACAATGTTTGTGTTATGGC
GTATGGACAGACGGGCAGCGGAAAGAGCTATACCATGCTGGGACGCCATTCGGACGACGGCCCTGTTCTGCCGCTTGACCCACAGAGTGACTTA
GGAATTATCCCTAGAGTGGCTGAGGAGCTCTTCAGGCTCATTTTGGAAAATACCTCAAGAAGCCCAAAGGTTGAAGTCTCCATAGTGGAAGTTT
ACAATAATGACATTTTTGACCTTCTGGCCAAAGACAGCATTGCAGCAGTGTCGGGGGTCAAGCGTGAGGTGGTGACAGCCAAGGATGGACGGAC
AGAGGTTGCGCTGCTGGCCTCTGAGGCTGTCGGCAGCGCCTCGAAACTGATGGAGCTCGTTCATGGAGGTCTGCAGCTCAGGGCGAAGCACCCC
ACCCTGGTGCACGCGGATTCCTCCAGGTCTCACCTGATAATTACGGTGACTCTAACCACAGCCTCCTGCTCTGACAGCACTGCAGACCAAGCCT
GCAGTGCCACCCTCCCCAGGGAGCAAACAGAGGCAGGAAGGGCAGGAAGGAGCCGCAGAGCTTCTCAAGGGGCCTTGGCTCCACAGCTGGTTCC
TGGGAACCCCGCAGGGCATGCGGAGCAGGTGCAGGCTCGACTACAGCTCGTGGACTCGGCCGGCAGCGAGTGCGTTGGTGTGTCTGGAGTGACC
GGGTTGGCCCTGAGGGAGATGGCGTGCATCAGCCGCAGCCTTGCGGCCCTGGCAGGCGTCCTGGGGGCTTTGTTGGAGCACCGTGGCCATGCCC
CGTACCGGAACAGCAGGCTCACCCACCTCCTTCAGGACTGCCTCGGAGGCGATGCGAAGTTACTGGTGATTCTCTGCATTTCTCCCAGCCAGAG
GCACCTGGCACAGACGTTGCAGGGCCTGGGTTTCGGGATCCGAGCTCGGCAAGTCCAGCGAGGCCCTGCCCGAAAGAAGCCGCCCAGCTCCCAA
ACGGAGGGGAAGAGGAGGCCGGATTGA

ID 34: KIF26, *Homo sapiens*

ATGGAAGAAATACCAGTAAAAGTTGCTGTAAGAATTAGACCTCTGCTTTGCAAAGAAGCTCTTCATAATCATCAAGTTTGTGTGAGAGTTATTC
CAAACAGCCAGCAAGTTATCATTGGGAGAGATAGAGTCTTCACTTTTGATTTTGTTTTTGGCAAAAATTCCACTCAAGATGAAGTTTATAACAC
ATGTATAAAGCCCCTAGTGTTGTCACTCATTGAGGGCTATAATGCAACTGTTTTTGCCTATGGACAAACTGGATCTGGGAAGACATACACCATT
GGAGGGGGCCATATTGCTTCAGTTGTGGAGGGCCAAAAGGGTATCATTCCTCGAGCTATTCAAGAAATATTTCAAAGCATCTCTGAACATCCTA
GCATTGACTTTAATGTAAAAGTATCTTATATAGAAGTGTACAAGGAAGACCTAAGAGATCTTCTAGAATTGGAGACATCCATGAAGGATCTTCA
CATCCGAGAAGATGAAAAAGGAAACACAGTGATTGTTGGGGCCAAGGAATGCCATGTGGAGAGTGCAGGTGAAGTGATGAGTCTTTTGGAGATG
GGGAATGCAGCCAGACATACAGGTACCACTCAAATGAATGAGCACTCCAGCAGATCACATGCAATTTTTACAATCAGCATTTGTCAAGTTCATA
AAAATATGGAGGCAGCTGAAGATGGATCATGGTATTCCCCTCGGCATATTGTCTCAAAGTTCCACTTTGTGGATTTGGCAGGATCAGAAAGAGT
AACCAAAACGGGGAATACTGGTGAACGGTTCAAAGAATCCATTCAAATCAATAGTGGATTGCTGGCTTTAGGAAATGTAATAAGCGCTCTTGGG
GACCCACGCAGGAAGAGTTCACATATTCCATATAGGGATGCTAAAATTACCCGGCTTCTGAAAGATTCTCTGGGAGGCAGTGCTAAGACTGTCA
TGATCACATGTGTCAGCCCCTCCTCCTCGAATTTTGATGAGTCCTTAAATTCTCTCAAATATGCCAACAGAGCACGGAACATTAGAAACAAACC
CACTGTAAACTTCAGCCCCGAGTCAGACCGTATAGATGAAATGGAATTTGAGATTAAATTGCTTCGAGAAGCTTTGCAAAGCCAGCAGGCTGGT
GTCAGCCAAACTACCCAGATCAATCGAGAAGGGAGTCCTGATACAAATAGGATTCATTCTCTTGAGGAGCAAGTAGCTCAGCTTCAAGGAGAAT
GTCTGGGTTACCAGTGTTGTGTAGAAGAAGCCTTTACCTTCCTGGTTGACCTAAAAGATACTGTCAGACTAAACGAAAAGCAGCAACACAAACT
GCAGGAGTGGTTTAACATGATCCAAGAGGTCAGGAAGGCTGTCCTCACCTCATTTCGAGGAATCGGAGGCACTGCAAGTCTGGAAGAAGGACCA
CAGCATGTTACAGTTCTCCAGCTGAAGAGAGAGCTTAAGAAATGCCAGTGTGTGCTTGCTGATGAAGTAGTATTTAATCAGAAGGAACTGG
AGGTGAAGGAACTGAAGAATCAAGTGCAGATGATGGTACAGGAAAACAAAGGGCATGCTGTATCTTTGAAAGAAGCGCAAAAAGTGAATAGACT
GCAGAATGAAAAAATAATAGAACAACAACTTCTTGTGGATCAACTGAGTGAAGAACTAACAAAACTTAACCTGTCAGTGACTTCTTCAGCTAAA
GAAAATTGTGGAGATGGGCCAGATGCCAGGATCCCTGAAAGGAGACCATATACTGTACCATTTGATACTCATTTGGGGCATTATATTTATATCC
CATCAAGACAAGATTCCAGGAAGGTCCACACAAGTCCGCCTATGTACTCTCTGGATCGAATATTTGCTGGATTTCGAACACGAAGTCAGATGCT
GTTGGGTCACATAGAAGAACAAGATAAGGTCCTCCACTGCCAATTTTCTGATAACAGTGATGATGAAGAATCAGAAGGCCAAGAGAAATCTGGA
ACTAGATGTAGAAGTCGTTCATGGATTCAGAAGCCAGACTCTGTTTGTTCCCTTGTTGAATTGAGTGATACTCAGGATGAAACACAAAAGTCAG
ATTTGGAGAATGAAGATTTAAAGATTGATTGTCTCCAGGAGAGTCAAGAATTGAATTTGCAAAAATTAAAGAATTCAGAACGCATACTTACTGA
AGCTAAACAAAAAATGAGAGAACTTACAATTAACATCAAGATGAAGGAAGATCTGATTAAAGAATTAATAAAAACAGGTAATGATGCCAAGTCT
GTAAGCAAGCAGTATTCTTTGAAAGTAACAAAGCTAGAGCATGATGCAGAACAGGCAAAAGTCGAACTGATTGAAACACAAAAGCAGCTACAGG
AGCTGGAAAACAAAGATCTTTCTGATGTTGCAATGAAGGTAAAATTACAGAAAGAGTTTCGTAAAAAGATGGATGCTGCAAAGCTGAGAGTTCA
GGTCTTGCAGAAGAAGCAACAAGATAGTAAGAAACTGGCATCACTGTCAATCCAAAATGAGAAACGTGCTAATGAGCTAGAGCAGAGTGTAGAT

Fig. 9 (Continued)

CACATGAAATATCAAAAGATACAGCTACAAAGAAAACTACGAGAAGAAAATGAAAAAAGGAAGCAACTGGATGCAGTAATTAAGCGGGACCAGC
AAAAAATCAAAGAAATACAATTAAAAACAGGACAGGAAGAAGGTCTAAAACCGAAAGCTGAGGACCTTGATGCATGTAACTTGAAAAGGAGAAA
AGGTTCGTTTGGAAGTATAGACCATCTCCAGAAATTGGATGAGCAAAAGAAATGGTTAGATGAAGAAGTAGAGAAAGTTCTGAACCAACGCCAA
GAATTAGAGGAGCTGGAAGCAGACTTAAAGAAACGGGAGGCCATAGTTTCTAAGAAGGAGGCTCTGTTACAGGAGAAGAGTCACCTGGAAAATA
AGAAATTGAGATCTAGTCAGGCCTTAAACACAGATAGTTTGAAAATATCAACTCGCCTGAACTTACTGGAACAAGAGTTGTCTGAAAAGAATGT
GCAGCTCCAGACCAGTACAGCTGAGGAGAAAACAAAGATTTCAGAACAAGTTGAAGTCCTCCAGAAAGAAAAGGATCAGCTCCAGAAACGCAGA
CACAATGTGGATGAAAAACTTAAAAATGGTAGAGTGTTATCACCTGAAGAAGAACATGTTCTTTTCCAACTTGAAGAAGGGATTGAAGCTTTGG
AAGCTGCAATTGAATACAGGAATGAAAGTATCCAGAATCGCCAGAAGTCACTTAGAGCATCATTCCATAACCTCTCTCGTGGTGAAGCAAATGT
CTTGGAAAAGCTAGCTTGCCTGAGTCCTGTTGAGATTAGAACTATTCTTTTCAGATATTTCAATAAGGTGGTGAATTTGCGAGAAGCTGAACGG
AAACAACAGTTATATAATGAAGAAATGAAAATGAAAGTTCTGGAACGGGATAATATGGTTCGTGAATTAGAATCTGCACTGGACCATCTAAAAT
TGCAGTGTGACCGGAGACTGACCCTCCAGCAAAAGGAACACGAACAAAAGATGCAGTTGCTATTACATCATTTCAAAGAACAAGATGGAGAAGG
CATTATGGAAACTTTCAAAACATATGAAGATAAAATCCAGCAGTTGGAAAAAGATCTTTATTTCTATAAGAAAACCAGCCGGGATCATAAGAAG
AAACTTAAGGAACTGGTAGGGGAAGCAATTCGGCGGCAACTAGCACCATCAGAGTATCAAGAGGCTGGAGATGGAGTCCTGAAGCCAGAAGGAG
GAGGCATGCTTTCAGAAGAATTAAAATGGGCATCCAGACCTGAAAGTATGAAATTAAGTGGAAGAGAAAGAGAAATGGACAGTTCAGCAAGCAG
CTTAAGAACACAGCCAAATCCTCAAAAGCTCTGGGAAGATATCCCAGAATTACCTCCAATTCATAGTTCTTTAGCACCCCCCAGTGGGCATATG
TTAGGTAATGAGAATAAAACAGAAACAGATGATAATCAGTTTACAAAATCTCACAGTCGACTGTCATCCCAAATTCAGGTTGTGGGAAATGTGG
GACGACTTCATGGTGTCACACCTGTAAAACTGTGTCGAAAAGAATTACGTCAAATTTCCGCCTTGGAACTATCATTGCGACGTTCCAGTCTTGG
AGTTGGCATTGGATCAATGGCTGCTGATTCCATCGAAGTATCTAGGAAACCAAGGACTTAAAAACTTAG

ID 35: KIF27, *Homo sapiens*

ATGGAAGAAATACCAGTAAAAGTTGCTGTAAGAATTAGACCTCTGCTTTGCAAAGAAGCTCTTCATAATCATCAAGTTTGTGTGAGAGTTATTC
CAAACAGCCAGCAAGTTATCATTGGAGAGATAGAGTCTTCACTTTTGATTTTGTTTTTGGCAAAAATTCCACTCAAGATGAAGTTTATAACAC
ATGTATAAAGCCCCTAGTGTTGTCACTCATTGAGGGCTATAATGCAACTGTTTTTGCCTATGGACAAACTGGATCTGGGAAGACATACACCATT
GGAGGGGGCCATATTGCTTCAGTTGTGGAGGGCCAAAAGGGTATCATTCCTCGAGCTATTCAAGAAATATTTCAAAGCATCTCTGAACATCCTA
GCATTGACTTTAATGTAAAAGTATCTTATATAGAAGTGTACAAGGAAGACCTAAGAGATCTTCTAGAATTGGAGACATCCATGAAGGATCTTCA
CATCCGAGAAGATGAAAAAGGAAACACAGTGATTGTTGGGGCCAAGGAATGCCATGTGGAGAGTGCAGGTGAAGTGATGAGTCTTTTGGAGATG
GGGAATGCAGCCAGACATACAGGTACCACTCAAATGAATGAGCACTCCAGCAGATCACATGCAATTTTTACAATCAGCATTTGTCAAGTTCATA
AAAATATGGAGGCAGCTGAAGATGGATCATGGTATTCCCCTCGGCATATTGTCTCAAAGTTCCACTTTGTGGATTTGGCAGGATCAGAAAGAGT
AACCAAAACGGGGAATACTGGTGAACGGTTCAAAGAATCCATTCAAATCAATAGTGGATTGCTGGCTTTAGGAAATGTAATAAGCGCTCTTGGG
GACCCACGCAGGAAGAGTTCACATATTCCATATAGGGATGCTAAAATTACCCGGCTTCTGAAAGATTCTCTGGGAGGCAGTGCTAAGACTGTCA
TGATCACATGTGTCAGCCCCTCCTCCTCGAATTTTGATGAGTCCTTAAATTCTCTCAAATATGCCAACAGAGCACGGAACATTAGAAACAAACC
CACTGTAAACTTCAGCCCCGAGTCAGACCGTATAGATGAAATGGAATTTGAGATTAAATTGCTTCGAGAAGCTTTGCAAAGCCAGCAGGCTGGT
GTCAGCCAAACTACCCAGATCAATCGAGAAGGGAGTCCTGATACAAATAGGATTCATTCTCTTGAGGAGCAAGTAGCTCAGCTTCAAGGAGAAT
GTCTGGGTTACCAGTGTTGTGTAGAAGAAGCCTTTACCTTCCTGGTTGACCTAAAAGATACTGTCAGACTAAACGAAAAGCAGCAACACAAACT
GCAGGAGTGGTTTAACATGATCCAAGAGGTCAGGAAGGCTGTCCTCACCTCATTTCGAGGAATCGGAGGCACTGCAAGTCTGGAAGAAGGACCA
CAGCATGTTACAGTTCTCCAGCTGAAGAGAGAGCTTAAGAAATGCCAGTGTGTGCTTGCTGCTGATGAAGTAGTATTTAATCAGAAGGAACTGG
AGGTGAAGGAACTGAAGAATCAAGTGCAGATGATGCTACAGGAAAACAAAGGGCATGCTGTATCTTTGAAAGAAGCGCAAAAAGTGAATAGACT
GCAGAATGAAAAAAATAATAGAACAACAACTTCTTGTGGATCAACTGAGTGAAGAACTAACAAAACTTAACCTGTCAGTGACTTCTTCAGCTAAA
GAAAATTGTGGAGATGGGCCAGATGCCAGGATCCCTGAAAGGAGACCATATACTGTACCATTTGATACTCATTTGGGGCATTATATTTATATCC
CATCAAGACAAGATTCCAGGAAGGTCCACACAAGTCCGCCTATGTACTCTCTGGATCGAATATTTGCTGGATTTCGAACACGAAGTCAGATGCT
GTTGGGTCACATAGAAGAACAAGATAAGGTCCTCCACTGCCAATTTTCTGATAACAGTGATGATGAAGAATCAGAAGGCCAAGAGAAATCTGGA
ACTAGATGTAGAAGTCGTTCATGGATTCAGAAGCCAGACTCTGTTTGTTCCCTTGTTGAATTGAGTGATACTCAGGATGAAACACAAAAGTCAG
ATTTGGAGAATGAAGATTTAAAGATTGATTGTCTCCAGGAGAGTCAAGAATTGAATTTGCAAAAATTAAAGAATTCAGAACGCATACTTACTGA
AGCTAAACAAAAAATGAGAGAACTTACAATTAACATCAAGATGAAGGAAGATCTGATTAAAGAATTAATAAAAACAGGTAATGATGCCAAGTCT
GTAAGCAAGCAGTATTCTTTGAAAGTAACAAAGCTAGAGCATGATGCAGAACAGGCAAAAGTCGAACTGATTGAAACACAAAAGCAGCTACAGG
AGCTGGAAAACAAAGATCTTTCTGATGTTGCAATGAAGGTAAAATTACAGAAAGAGTTTCGTAAAAAGATGGATGCTGCAAAGCTGAGAGTTCA
GGTCTTGCAGAAGAAGCAACAAGATAGTAAGAAACTGGCATCACTGTCAATCCAAAATGAGAAACGTGCTAATGAGCTAGAGCAGAGTGTAGAT
CACATGAAATATCAAAAGATACAGCTACAAAGAAAACTACGAGAAGAAAATGAAAAAAGGAAGCAACTGGATGCAGTAATTAAGCGGGACCAGC
AAAAAATCAAAGAAATACAATTAAAAACAGGACAGGAAGAAGGTCTAAAACCGAAAGCTGAGGACCTTGATGCATGTAACTTGAAAAGGAGAAA
AGGTTCGTTTGGAAGTATAGACCATCTCCAGAAATTGGATGAGCAAAAGAAATGGTTAGATGAAGAAGTAGAGAAAGTTCTGAACCAACGCCAA
GAATTAGAGGAGCTGGAAGCAGACTTAAAGAAACGGGAGGCCATAGTTTCTAAGAAGGAGGCTCTGTTACAGGAGAAGAGTCACCTGGAAAATA
AGAAATTGAGATCTAGTCAGGCCTTAAACACAGATAGTTTGAAAATATCAACTCGCCTGAACTTACTGGAACAAGAGTTGTCTGAAAAGAATGT
GCAGCTCCAGACCAGTACAGCTGAGGAGAAAACAAAGATTTCAGAACAAGTTGAAGTCCTCCAGAAAGAAAAGGATCAGCTCCAGAAACGCAGA
CACAATGTGGATGAAAAACTTAAAAATGGTAGAGTGTTATCACCTGAAGAAGAACATGTTCTTTTCCAACTTGAAGAAGGGATTGAAGCTTTGG
AAGCTGCAATTGAATACAGGAATGAAAGTATCCAGAATCGCCAGAAGTCACTTAGAGCATCATTCCATAACCTCTCTCGTGGTGAAGCAAATGT
CTTGGAAAAGCTAGCTTGCCTGAGTCCTGTTGAGATTAGAACTATTCTTTTCAGATATTTCAATAAGGTGGTGAATTTGCGAGAAGCTGAACGG
AAACAACAGTTATATAATGAAGAAATGAAAATGAAAGTTCTGGAACGGGATAATATGGTTCGTGAATTAGAATCTGCACTGGACCATCTAAAAT
TGCAGTGTGACCGGAGACTGACCCTCCAGCAAAAGGAACACGAACAAAAGATGCAGTTGCTATTACATCATTTCAAAGAACAAGATGGAGAAGG
CATTATGGAAACTTTCAAAACATATGAAGATAAAATCCAGCAGTTGGAAAAAGATCTTTATTTCTATAAGAAAACCAGCCGGGATCATAAGAAG
AAACTTAAGGAACTGGTAGGGGAAGCAATTCGGCGGCAACTAGCACCATCAGAGTATCAAGAGGCTGGAGATGGAGTCCTGAAGCCAGAAGGAG
GAGGCATGCTTTCAGAAGAATTAAAATGGGCATCCAGACCTGAAAGTATGAAATTAAGTGGAAGAGAAAGAGAAATGGACAGTTCAGCAAGCAG
CTTAAGAACACAGCCAAATCCTCAAAAGCTCTGGGAAGATATCCCAGAATTACCTCCAATTCATAGTTCTTTAGCACCCCCCAGTGGGCATATG
TTAGGTAATGAGAATAAAACAGAAACAGATGATAATCAGTTTACAAAATCTCACAGTCGACTGTCATCCCAAATTCAGGTTGTGGGAAATGTGG
GACGACTTCATGGTGTCACACCTGTAAAACTGTGTCGAAAAGAATTACGTCAAATTTCCGCCTTGGAACTATCATTGCGACGTTCCAGTCTTGG
AGTTGGCATTGGATCAATGGCTGCTGATTCCATCGAAGTATCTAGGAAACCAAGGACTTAAAAACTTAG

ID 36: KIFC1, *Homo sapiens*

ATGGATCCGCAGAGGTCCCCCCTATTGGAAGTAAAGGGGAACATAGAACTGAAGAGACCTCTGATTAAGGCCCCTTCCCAGCTGCCTCTCTCAG
GAAGCAGACTCAAGAGGAGGCCTGACCAGATGGAAGATGGCCTGGAGCCTGAGAAGAAACGGACAAGAGGCCTGGGTGCAACGACCAAAATTAC
CACATCCCACCCAAGAGTTCCATCCCTCACTACAGTGCCACAGACACAAGGCCAGACCACAGCTCAAAAAGTTTCCAAGAAGACAGGACCCCGG
TGTTCCACAGCTATTGCCACAGGGTTGAAGAACCAGAAGCCAGTTCCTGCTGTTCCTGTCCAGAAGTCTGGCACATCAGGTGTTCCTCCCATGG
CAGGAGGGAAGAAACCCAGCAAACGTCCAGCCTGGGACTTAAAGGGTCAGTTATGTGACCTAAATGCAGAACTAAAACGGTGCCGTGAGAGGAC
TCAAACGTTGGACCAAGAGAACCAGCAGCTTCAGGACCAGCTCAGAGATGCCCAGCAGCAGGTCAAGGCCCTGGGGACAGAGCGCACAACACTG
GAGGGGCATTTAGCCAAGGTACAGGCCCAGGCTGAGCAGGGCCAACAGGAGCTGAAGAACTTGCGTGCTTGTGTCCTGGAGCTGGAAGAGCGGC
TGAGCACGCAGGAGGGCTTGGTGCAAGAGCTTCAGAAAAAACAGGTGGAATTGCAGGAAGAACGGAGGGGACTGATGTCCCAACTAGAGGAGAA
GGAGAGGAGGCTGCAGACATCAGAAGCAGCCCTGTCAAGCAGCCAAGCAGAGGTGGCATCTCTGCGGCAGGAGACTGTGGCCCAGGCAGCCTTA
CTGACTGAGCGGGAAGAACGTCTTCATGGGCTAGAAATGGAGCGCCGGCGACTGCACAACCAGCTGCAGGAACTCAAGGGCAACATCCGTGTAT
TCTGCCGGGTCCGCCCTGTCCTGCCGGGGGAGCCCACTCCACCCCCTGGCCTCCTCCTGTTTCCCTCTGGCCCTGGTGGGCCCTCTGATCCTCC
AACCCGCCTTAGCCTCTCCCGGTCTGACGAGCGGCGTGGGACCCTGAGTGGGGCACCAGCTCCCCCAACTCGCCATGATTTTTCCTTTGACCGG
GTATTCCCACCAGGAAGTGGACAGGATGAAGTGTTTGAAGAGATTGCCATGCTTGTCCAGTCAGCCCTGGATGGCTATCCAGTATGCATCTTTG

Fig. 9 (Continued)

CCTATGGCCAGACAGGCAGTGGCAAGACCTTCACAATGGAGGGTGGGCCTGGGGGAGACCCCCAGTTGGAGGGGCTGATCCCTCGGGCCCTGCG
GCACCTCTTCTCTGTGGCTCAGGAGCTGAGTGGTCAGGGCTGGACCTACAGCTTTGTAGCAAGCTACGTAGAGATCTACAATGAGACTGTCCGG
GACCTGCTGGCCACTGGAACCCGGAAGGGTCAAGGGGGCGAGTGTGAGATTCGCCGTGCAGGGCCAGGGAGTGAGGAGCTCACTGTCACCAATG
CTCGATATGTCCCTGTCTCCTGTGAGAAAGAAGTGGACGCCCTGCTTCATCTGGCCCGCCAGAATCGGGCTGTGGCCCGCACAGCCCAGAATGA
ACGGTCATCACGCAGCCACAGTGTATTCCAGCTACAGATTTCTGGGGAGCACTCCAGCCGAGGCCTGCAGTGTGGGGCCCCCCTCAGTCTTGTG
GACCTGGCCGGGAGTGAGCGACTTGACCCCGGCTTAGCCCTCGGCCCCGGGGAGCGGGAACGCCTTCGGGAAACACAGGCCATTAACAGCAGCC
TGTCCACGCTGGGGCTGGTTATCATGGCCCTGAGCAACAAGGAGTCCCACGTGCCTTACCGGAACAGCAAACTGACCTACCTGCTGCAGAACTC
TCTGGGTGGTAGTGCTAAGATGCTCATGTTTGTGAACATTTCTCCACTGGAAGAGAACGTCTCCGAGTCCCTCAACTCTCTACGCTTTGCCTCC
AAGGTGAACCAGTGTGTTATTGGTACTGCTCAGGCCAACAGGAAGTGA

ID 37: KIFC2, *Homo sapiens*
ATGTACGCCTTTTACTCGTTGCTCATCTACATCTTCTACAGCCTCTTCCGCAGGGATGGTGGCGCCGCGGCGGCCGCGGAGCCCGGGGACCCCG
CCCAGAGAGCCCGCAAGCCCCGGGGTCGCCGGCGCCCAGACCTGCCCGCGCCAGAGCTGTGGACCGAGCTGACCGGCCTGGCCGCCAGCTCCGA
GCCTGAGGATGGGTCGGAAGGCGCAGCCGAGGGCCGCGCGGCCGCGGTGTCCCTGGAAGAGGCCCTACTGCGCCTCGCCGAGTTCCTCTCCGTC
CAGCTGGGGGCGGAAGAGAGCTGCGGGGGCCCGGCGGACCTGGGCCAGTCTGGCGAGGTCCCCTCACTGTTGACAGTGACCAGTCAGCTCTTGG
CCCTTCTGGCATGGCTTCGAAGCCCCAGGGGGAGGCAGGCCCTGCTCCAGGGGACTCAGCCAGCCCCTCGGGTCCGGCCCCCCTCTCCAGATGG
ATCCACATCCCAAGAAGAAAGCCCTTCCCACTTCACCGCAGTCCCAGGCGAGCCACTGGGGGATGAGACCCAGGGACAGCAGCCCCTCCAGTTG
GAGGAGGATCAGAGGGCGTGGCAGCGGCTGGAGCAGCTCATCCTGGGACAGCTGGAGGAGCTGAAGCAGCAGCTGGAACAGCAGGAGGAGGAGT
TGGGTCGACTGCGCCTGGGCGTGGGGGCGACGGACTCAGAGAAAAGGGTTCAGCATCTGACTCTGGAGAACGAGGCCCTGAAGCAGAGCCTGAG
TCTCATGCGGGACCTCCTGCTGCACTGGGGCCCCGGGCCCCCCATCAGGGCTCCGCAGGAGGAGGCAGAGGCATTGCTAGAGCTCCAGGGCCGG
CTTCAGGAGGCCCAAGACACCACAGAAGCCCTCCGAGCCCAGCTGGGGGTGCAGGAGGTGCAGCTGCAGGGCCTTCAAGGGGCCCTCCAGCAGC
TCCAGCAGGAGACGGAGCAGAACTGCAGGCGTGAGCTACAGCAGATGCATGGGCAGCTGGCAGGACTTCGGGCACGGATGGCCAGCCTGCGTCA
GGGCTGCGGGGACCTCCGAGGTTTGGTCAGCACCTTTACCCAGAGCTGTCAGGGTTCGCTGAGTGAGGCCCGGGGCCAGGTGTCCTGGGCCTTG
GGGGCACTGTCATCTGGAGGGCCTGGCACTCAGCTCCCTGAGGGGCAGCAAGGGCCCCCAGCCGGATGCCCAGGGCGGCTGCCAGAACTCAAGG
GAAATATCCGTGTGCTGTGTCGGCTGAGGCCAGGGACATCTTCTAGCCTTGTGAGTGTGGAGCCTGGCCCAGGGGGCACCGTCACCACCTGCTA
CCGGGGGCGCCATCGTCGATTCCGCCTAGACTGGGTCTTCCCTCCAGACGCCAGCCAGGAGGAGGTCTTCAGAGAGCTGGAACCTGCGGTGCTG
TCCTGCCTCCGAGGCTACAGCGTCTGCATCTTCACCTATGGCCAGACAGGCACCGGGAAGACCTACAGCATGGAGGGCCCTCCTGAGGACCCCG
GCATAGTTCCTAGGGCGCTGCAGTCGCTGTTCCGGGAGATGGGGGCCGGCCGGCAGCACCGGGTGACACTCAGCATGGTGGAGATCTACAATGA
GGCTGTCAGGGACCTCCTTGCTCCAGGGCCTCCCGAGCGCCTGGCCGTGAGGCAGGGCCCAGAAGGCCAGGGCGGGATCCAGGTGGCTGGCCTC
ACCCACTGGGACGTGCCCAACCTGGAGACATTGCACCAGATGCTGAAACTGGGGAGGAGCAACCGGGCCACCGCCGCCACCGCCATGAACCAGC
GCAGCTCCCGCTCGCATGCCCTGGTCACGCTGACGCTGCGCGCGGCGTCTCCACCGCGCGCTCCAGGCACCGCAGGCACGCTGCACCTGGTGGA
CCTGGCGGGATCCGAACGCGCACGGAAGGCAGGGGCGGCCGGCCCGCCGCGGGGAGACCCAGACGGCGCCCGGCGCCTGCGGGAGGCCCAGACC
ATAAACCGCTCGCTGCTGGCGCTAGGAGGCGTGATGGCCGCACTGCGGGCCCACCGGCCGCACGTGCCCTTCCGCGACTCGCAGCTCACGCGAC
TGCTGCAGCCGGCGCTGGGCCCAGGCACCACCGCGGTGCTGCTGCTGCAGGTGGGCGCCGGGGCGGGGCAGGTGTGCGTGCCGGTCGCCGCC
CACCCGGGCCCGCCCACCCGCGCCTCTTGCCCGCAGATCTCCACGCGGCCGGAGGATCTCGGGGAGACAGTCTGCTCCCTCAAGTTCGCCGACC
GAGTGGGTCAAGTGGAGCTGGGGCCAGCCCGGCGCCGCAGGGTCCCGCGCTCCTCCGGGACGCCTTCTTCCCTCAGCACCGACACTCCGCTCAC
CGGGACCCCCTGCACCCCTACGCCGTCCCCTGGCAGTCCTCCATGCCCCAGTCCCGACAACGGCTCGGGCTCGGCTCTCGCGCCCGCAGAGGGC
CTGCCCCTCTAGTCCTGGGTCGCGGCCCTGCCCATGGGGTCTCAGGCCAGGTCTCTGCTGGCAGAGGCGGTAG ID 38: KIFC3, *Homo sapiens*
ATGGTCCCCTCTCGCAGGACGTGGAACCTGGGAGCCACGCCCTCGCTGCGGGGCCTGTGGAGAGTGGGCCGGGCCCCGGAGCCCGAGCCGGGGA
TGGCTCGCCCCGCCCCAGCCCCAGCCAGCCCGGCCGCCCGCCCTTTCCCACACACCGGCCCGGGGAGGTTGAGAACTGGGCGTGGAAAAGATAC
CCCAGTCTGCGGTGACGAGGACTCCAGTGCCCGAAGTGCAGCTCGCCCAGCCCTAGCTCAGTGCCGAGCCCTTAGCGTGGACTGGGCTGGCCCC
GGAAGCCCCCACGGGCTCTACCTGACCCTGCAGGTAGAACACCTGAAGGAGAAGCTCATTAGCCAGGCCCAGGAAGTGAGCCGACTGCGATCTG
AGCTGGGGGGCACCGACTTGGAGAAGCACCGGGACCTGCTGATGGTGGAGAATGAGCGACTGAGGCAGGAGATGCGGCGCTGTGAGGCCGAGCT
GCAAGAGCTGCGCACAAAGCCAGCAGGTCCCTGCCCAGGTTGTGAGCACAGCCAGGAGAGCGCCCAGCTCCGTGACAAGCTGTCCCAGCTGCAG
CTGGAGATGGCGGAAAGCAAAGGCATGCTGTCAGAGCTGAACCTAGAGGTGCAGCAGAAGACCGACCGGCTGGCTGAGGTGGAGCTGCGACTCA
AGGACTGCCTGGCTGAGAAGGCACAGGAGGAGGAGCGGCTTAGTCGGCGCCTGCGTGACAGCCACGAGACCATTGCCAGCCTGCGGGCCCAGTC
CCCACCTGTCAAGTATGTCATCAAGACAGTGGAGGTGGAGTCGTCCAAGACCAAGCAGGCCCTCAGCGAGTCCCAGGCCCGGAACCAGCACCTG
CAGGAGCAGGTGGCTATGCAGAGGCAGGTGCTGAAGGAGATGGAACAGCAGCTGCAGAGCTCACACCAGCTGACCGCGCGGCTCCGGGCGCAGA
TTGCCATGTACGAGTCAGAGCTGGAGCGGGCCCATGGGCAGATGCTGGAGGAGATGCAGTCCCTGGAAGAGGACAAGAACCGGGCCATTGAGGA
GGCCTTTGCCAGAGCCCAGGTGGAGATGAAGGCTGTGCACGAGAATCTAGCAGGCGTCCGGACCAACTTGCTGACCTTGCAGCCGGCACTGCGG
ACCCTCACCAACGACTACAATGGGCTCAAGCGGCAGGTGCGCGGCTTCCCACTGCTGCTGCAGGAGGCCCTCAGGAGTGTCAAGGCCGAGATAG
GCCAGGCCATCGAGGAGGTCAACAGCAACAACCAGGAGCTGCTGCGCAAGTACCGCCGCGAGCTGCAGCTGCGTAAGAAGTGCCACAATGAGCT
CGTGCGGCTGAAAGGGAACATCCGAGTGATTGCTCGTGTCCGGCCAGTCACCAAAGAGGATGGGGAAGGACCTGAGGCCACCAATGCTGTGACT
TTCGATGCCGACGACGACTCCATCATCCACCTGCTGCACAAGGGCAAGCCTGTGTCCTTCGAGCTGGACAAGGTCTTCTCCCCACAGGCCTCGC
AGCAGGACGTGTTCCAGGAGGTGCAGGCCCTGGTCACCTCTTGCATTGATGGCTTCAATGTCTGCATCTTTGCGTACGGCCAGACGGGCGCCGG
CAAGACGTACACGATGGAGGGGACCGCTGAGAACCCAGGTATCAACCAGCGGGCCCTGCAGCTGCTCTTCTCCGAGGTGCAGGAGAAGGCGTCT
GACTGGGAGTACACCATCACCGTCAGCGCTGCGGAGATCTACAATGAGGTCCTCAGGGACCTGCTAGGGAAAGAGCCTCAGGAAAAACTGGAGA
TCCGGCTGTGCCCAGACGGCAGTGGGCAGCTGTATGTACCAGGGCTGACTGAGTTCCAAGTGCAGAGCGTGGACGACATCAACAAGGTGTTTGA
GTTTGGCCACACTAATCGCACGACCGAGTTCACCAACCTGAACGAGCACAGCTCCCGCTCGCACGCGCTGCTCATCGTGACGGTGCGAGGCGTG
GACTGCAGCACAGGCCTCCGCACCACGGGGAAGCTGAACCTGGTGGACTTGGCTGGCTCGGAGCGCGTGGGCAAGTCGGGGGCCGAGGGCAGCC
GCCTGCGGGAGGCGCAGCACATCAACAAGTCGCTGTCGGCTCTGGGGGACGTCATTGCTGCCCTGCGCTCCCGCCAGGGCCACGTGCCCTTCCG
CAACTCCAAGCTCACCTACCTGCTGCAGGATTCGCTTAGTGGTGACAGCAAGACCCTCATGGTGGTACAGGTGTCCCCCGTGGAGAAGAACACT
AGCGAGACGCTCTATTCCCTCAAGTTTGCTGAGAGGGTGCGCTCTGTGGAGCTGGGGCCTGGGCTACGCAGGGCAGAGCTTGGGTCCTGGTCAA
GCCAGGAGCATCTAGAGTGGGAGCCGGCTTGTCAGACGCCACAGCCCTCGGCACGGGCCCACTCAGCCCCCAGCTCTGGGACCAGTAGCCGCCC
TGGATCCATCCGGAGGAAGCTGCAGCCCTCGGGGAAGTCGCGGCCACTGCCTGTGTGA ID 39: DNAH1, *Homo sapiens*
ATGGAGCAGCCTAACAGTAAAGCCTATAGCCTGGGAAGGACCCCTCAGGGCCCAGAGTGCAGCAGTGCTCCTGCAGTCCAAGTGGGGACCCACA
GGGGCCTAGAGTATAACCCGGGGAAGATTCTTCCAGGATCAGACTATGGGTTGGGAAATCCTCCAGCCCTTGACCCCAAGCTCCCACATTTACC
CCTGCCCCCGGCCCCACCCACACTCTCAGACTTGGGGCAGCCACGGAAGTCACCCCTGACAGGCACTGATAAGAAGTACCCGCTGATGAAGCAG
CGTGGGTTCTACTCCGACATCCTCAGCCCTGGAACCTTAGATCAACTTGGGGAGGTATGTCGTGGCCCCCGAATGAGCCAGAACCTCCTGCGGC
AGGCTGACCTTGACAAGTTCACCCCAAGAGTCGGAAGCTTTGAGGTTCCTGAAGACTTCCAGGAGCGCATGGAGCAGCAGTGCATCGGGTCCAC
CACCCGGCTGCTCGCCCAGACTGACTTCCCACTGCAGGCCTACGAGCCCAAGATGCAGGTGCCTTTCCAGGTGCTGCCAGGCCAGCATCCTCGC
AAGATTGAGATCGAGAGGAGGAAACAGCAGTACCTGAGCCTGGACATTGAGCAGTTGCTGTTCAGCCAGGGCATCGACTCCAACAAGCTCATGC
CCAGGCACCTGGACCACCAGCACCCCCAAACCATCGAACAGGGCCATGACCCAATCTTCCCCATCTACCTCCCACTGAAGGTATTTGACAATGA
GGACTTTGACTGCCGGACTCCCAGAGAGTGGATCAACATGGGCTTGGAGCCAGGGTCTCTGGACAGGAAACCTGTCCCGGGAAAAGCCCTCTTG
CCCACTGATGACTTCCTGGGGCATGAGGACCCCAAGAGTCAGAAGCTGAAGTACAAATGGTGCGAGGTCGGCGTCCTGGACTACGACGAGGAGA
AGAAGCTATACCTGGTACACAAGACAGACGAGAAAGGCCTGGTGCGAGATGAGATGGGGAGGCCCATCCTGAATGCAGGGGTCACCACTGAAGG

Fig. 9 (Continued)

AAGGCCACCCCTTCAGGTCTGTCAGTACTGGGTGCCACGGATCCAGCTTCTCTTCTGCGCTGAGGACCCTTGCATGTTCGCACAACGTGTGGTC
CAGGCCAACGCCCTGCGCAAGAACACGGAAGCACTGCTGCTCTACAACTTGTATGTGGACTGCATGCCCTCTGACGGCCAGCATGTCATCAGTG
AACAGAGCCTGAGCAAGATCAAGCAGTGGGCCCTGAGCACGCCTCGGATGCGCAAAGGCCCCTCGGTTCTAGAGCACCTCAGCAGTCTTGCCAG
AGAAGTGAGCCTGGACTATGAGCGCAGCATGAACAAGATCAACTTTGACCACGTTGTCTCTTCCAAGCCCGAGACCTTCTCCTACGTCACCCTC
CCCAAGAAGGAGGAGGAGCAGGTGCCTGAGCGAGGGCTGGTGAGTGTCCCCAAGTACCACTTCTGGGAGCAGAAGGAGGACTTCACTTTCGTGT
CCCTGCTCACACGGCCAGAGGTCATCACGGCCCTCAGCAAGGTGAGGGCCGAGTGCAACAAGGTGACCGCCATGTCCCTGTTCCACTCGAGCCT
CTCCAAGTACAGCCACCTGGAGGAATTTGAGCAGATCCAGTCACAGACCTTCTCCCAGGTGCAGATGTTCCTCAAGGACAGCTGGATCAGCTCG
CTAAAGGTGGCCATGCGCAGCAGCCTGCGCGACATGAGCAAGGGCTGGTACAACCTCTACGAGACCAACTGGGAGGTGTACCTCATGTCCAAGC
TGCGCAAGCTGATGGAGCTGGTGAAGTACATGCTGCAGGACACACTGCGCTTCCTGGTGCAGGACTCACTTGCCAGCTTCTCACAGTTCATCAG
CGACACCTGTTGCAGCGTGCTCAACTGCACCGATGACATGGTCTGGGGTGACGACTTAATTAACAGCCCCTACAGGCCCCGGAAGAATCCCCTG
TTCATCATGGACCTGGTGCTGGACAGCTCTGGGGTGCACTATAGCACCCCACTGGAGCAGTTTGAGGCATCTCTGCTGAACCTCTTCGACAAGG
GCATCCTGGCCACCCATGCCGTGCCCCAGCTGGAGAAGCTGGTGATGGAGGACATCTTCATCAGCGGTGACCCCCTGCTGGAGTCCGTGGGCCT
TCATGAGCCACTGGTGGAAGAGCTACGGGCCACCATTGCCAGTGCCGTGTCCAAGGCCATGATCCCACTGCAGGCCTACGCCAAGGAGTACCGA
AAGTACCTGGAGCTGAACAACAATGACATTGCCTCCTTTCTCAAAACCTACCAGACGCAGGGCCTGTTGGCCCAGGAGGTGCGGGAGGTAGTGC
TCACCCACCTGCGGGAGAAGGAGATCCTGGACAGCTCGCTGCCCAGCAGCATCATCATTGGGCCTTTCTACATCAACACCGACAATGTCAAGCA
GAGCCTGTCCAAGAAACGCAAGGCCCTGGCCACTTCCGTGCTGGACATCCTTGCCAAGAACCTGCATAAGGAGGTGGATAGCATCTGCGAGGAG
TTCCGCAGCATCAGCCGCAAGATCTATGAGAAGCCCAACAGCATTGAGGAGCTGGCTGAGCTGCGAGAGTGGATGAAGGGCATCCCGGAGAGGC
TGGTGGGCCTGGAGGAGCGGATTGTGAAGGTCATGGATGACTACCAGGTCATGGATGAATTCCTCTACAACCTCAGCTCAGATGACTTCAATGA
CAAATGGATTGCCAGCAACTGGCCTTCTAAGATCCTTGGGCAGATAGAGCTGGTGCAGCAGCAGCATGTGGAGGATGAGGAGAAGTTCCGCAAA
ATCCAGATCATGGATCAGAACAACTTCCAAGAGAAGCTGGAAGGGCTGCAGCTGGTAGTAGCTGGCTTCTCCATCCATGTGGAGATTTCACGTG
CACACGAGATCGCCAACGAGGTGCGGCGTGTCAAGAAGCAGCTGAAGGACTGCCAGCAGCTGGCCATGCTCTACAACAACCGCGAGCGCATCTT
CAGCTTGCCCATCACCAATTATGACAAGCTCTCCAGGATGGTGAAGGAGTTCCAACCCTACCTGGACCTTTGGACCACAGCGTCTGACTGGCTG
CGCTGGTCGGAGAGCTGGATGAATGACCCCTCTCTGCCATCGATGCTGAGCAGCTGGAGAAGAACGTGGTTGAAGCCTTCAAGACCATGCACA
AGTGCGTGAAGCAGTTTAAGGACATGCCAGCCTGCCAGGAAGTGGCCTTGGACATCCGGGCCCGCATCGAGGAGTTCAAACCATACATCCCACT
GATCCAGGGGCTGCGCAACCCTGGCATGCGGATCCGGCACTGGGAGACACTGTCCAACCAGATCAACATCAATGTCAGGCCCAAGGCCAACCTG
ACCTTTGCTCGCTGCCTGGAGATGAACCTGCAGGACCATATCGAGAGCATCAGCAAGGTGGCTGAGGTGGCTGGCAAGGAGTACGCCATCGAGC
AGGCACTGGACAAGATGGAGAAGGAGTGGTCGACCATCCTGTTCAATGTACTGCCCTACAAGGCGACAGACACCTACATCCTGAAGAGCCCGGA
CGAGGCCTCACAGCTGCTGGACGACCACATCGTCATGACCCAGAATATGTCATTTTCACCCTACAAGAAGCCCTTTGAGCAGCGCATCAACTCC
TGGGAGAACAAACTGAAGCTGACCCAGGAGGTTCTGGAGGAGTGGCTGAACTGTCAGCGGTCCTGGCTCTACCTGGAGCCCATCTTTAGCTCTG
AGGACATCAACCAGCAGCTGCCTGTGGAGAGCAAGCGCTACCAGACCATGGAGCGGATCTGGAAGAAGATCATGAAGAATGCCTACGAGAACCG
GGAGGTGATCAATGTGTGTTCCGACCTGAGAATGCTGGACAGCCTGCGGGACTGCAACAAGATTCTGGACCTGGTGCAGAAGGGCCTCAGCGAG
TATCTGGAGACCAAGAGGAGCGCCTTCCCCAGATTCTACTTCCTGTCAGATGATGAACTACTAGAGATCTTGTCGCAGACAAAGGACCCCACGG
CCGTGCAGCCACACCTGCGCAAGTGCTTCGAGAACATCGCTCGGCTGCTATTCCAGGAGGACCTGGAGATCACGCACATGTACTCAGCCGAGGG
GGAGGAGGTACAGTTGTGCTTCTCCATCTACCCCTCCAGCAACGTGGAGGACTGGCTGCGGGAGGTGGAGCGCAGCATGAAGGCCAGTGTGCAC
GACATCATTGAGAAGGCCATCAGGGCCTACCCCACGATGCCCAGGACCCAGTGGGTTCTGAACTGGCCTGGCCAGGTGACCATCGCTGGGTGCC
AGACCTACTGGACCATGGAGGTGGCAGAGGCTCTGGAGGCCGGCAACCTCAGAAGCCAACTGTTCCCCCAGCTCTGCCAGCAGCTCAGTGATCT
GGTGGCCCTTGTGCGGGGGAAGCTGTCCCGCATGCAGCGGGCAGTGCTGTCAGCGCTAATCGTCATTGAGGTCCATGCCAAGGACGTGGTGAGC
AAGCTAATCCAGGAGAACGTGGTCAGCGTGAATGACTTCCAGTGGATCTCACAGCTGAGGTACTACTGGACAAATAATGACCTGTATATCCGTG
CTGTGAATGCTGAGTTCATCTATGGCTATGAGTACCTGGGCAACAGTGGGAGGCTGGTGATCACGCCCCTCACCGACAGGTGCTACCTGACACT
GACCGGAGCTCTGCACCTCAAGTTTGGGGGTGCCCCAGCTGGCCCAGCTGGCACAGGCAAAACTGAGACCACCAAAGACCTGGGTAAGGCCTTG
GCCATACAGACCGTTGTGTTCAACTGCTCTGACCAGCTCGACTTCATGGCCATGGGCAAGTTCTTCAAGGGCCTGGCCAGTGCTGGGGCCTGGG
CCTGCTTCGACGAGTTCAATCGCATCGACATCGAGGTGCTGTCTGTGGTGGCGCAGCAGATCACCACCATCCAGAAGGCGCAGCAGCAGCGGGT
GGAACGCTTCATGTTTGAGGGTGTGGAGATCCCACTGGTGCCATCCTGCGCAGTGTTTATCACCATGAACCCGGGCTACGCTGGCCGCACGGAG
CTGCCTGACAATCTGAAGGCGCTCTTCCGACCCGTGGCCATGATGGTTCCAGATTACGCCATGATCACTGAGATCTCCCTCTATTCCTTTGGCT
TTAATGAGGCCAGTGTGCTGGCTAAGAAGATCACAACCACCTTCAAGCTGTCTTCTGAGCAGCTCAGCTCCCAGGATCACTATGACTTCGGGAT
GAGAGCCGTGAAAACTGTGATCTCGGCTGCTGGAACCTCAAGCGAGAAAACCCCAGCATGAATGAGGAGCTGATCTGCCTCCGGGCCATCCGT
GATGTGAACGTGCCCAAGTTCCTGCAGGAGGACCTCAAGCTCTTCTCTGGCATCGTGTCCGACCTGTTTCCCACCATCAAGGAGGAGGACACGG
ACTACGGCATCCTGGATGAGGCCATCCGCGAGGCCTGCAGGAACAGCAACCTCAAGGATGTGGAGGGCTTCCTGACAAAGTGCATCCAGCTCTA
CGAGACCACGGTGGTACGACACGGCCTCATGCTCGTCGGGCCCACAGGCTCCGGCAAGAGTACTTGTTACAGAGTCCTGGCAGCTGCCATGACG
TCACTGAAAGGGCAGCCATCCATCAGTGGTGGCATGTACGAGGCTGTCAACTACTACGTGCTCAACCCCAAGTCCATCACGATGGGCCAGCTGT
ACGGGGAGTTTGACCTCCTCACCCATGAGTGGACAGACGGGATATTCTCCTCGTTCATCCGGGCGGGGGCCATCACCTCCGACACCAACAAGAA
GTGGTACATGTTCGATGGGCCGGTGGATGCCATCTGGATTGAGAACATGAACACGGTGCTGGATGACAACAAGAAGCTGTGCCTCAGCTCTGGG
GAGATCATCAAGCTCACAGAGGCAATGACCATGATGTTCGAGGTGCAAGACCTGGCGGTGGCTTCACCAGCTACAGTCTCCCGCTGTGGCATGG
TGTACCTGGAGCCCAGCATCCTGGGGCTCATGCCCTTCATCGAGTGCTGGCTGAGGAAGCTGCCTCCCTTGCTGAAGCCCTATGAGGAGCATTT
CAAGGCCCTCTTTGTCAGCTTCCTGGAGGAATCCATCTCCTTCGTTCGGTCCTCAGTGAAGGAGGTGATCGCCTCAACCAACTGCAACCTGACC
ATGAGCCTCCTCAAGCTGCTGGACTGCTTCTTCAAGCCCTTTCTGCCTAGAGAGGGCCTCAAGAAAATACCCTCTGAAAAGCTGAGTCGCATCG
TAGAGTTGATCGAGCCCTGGTTCATCTTCTCCCTGATCTGGAGCGTGGGTGCCACTGGGGACAGCAGTGGCCGCACCAGTTTCAGCCACTGGCT
AAGGCTCAAGATGGAGAACGAACAGCTGACTCTGCTTTTCCCAGAAGAGGGGCTGGTGTTCGATTACAGGCTGGAGGACGCGGGCATCAGTGGC
ACCAACGACAGTGAGGATGAAGAGGAGGAATACAAGCAGGTTGCCTGGGTGAAGTGGATGGACTCCTCAGCTCCATTCACCATGGTACCAGACA
CCAACTACTGCAACATCATTGTGCCCACCATGGACACCGTGCAGATGTCCCATTTACTGGACATGCTGCTCACCAACAAGAAGCCCGTGCTGTG
CATTGGGCCAACAGGCACGGGGAAGACGCTCACCATCTCTGACAAGCTCCTCAAGAACCTGGCACTGGATTACATCAGCCACTTCCTCACCTTC
TCAGCCCGCACTTCAGCCAACCAGACCCAGGACTTCATTGACAGCAAGCTGGACAAGAGGCGGAAGGGTGTGTTTGGACCACCTCTGGGCGCA
ACTTTATCTTCTTCATCGATGACCTGAACATGCCGGCCCTGGAGACCTACGGTGCACAGCCACCCATCGAGCTGTTGCGCCAGTGGATGGACCA
CGGCGGCTGGTACGACCGCAAGATCATTGGTGCCTTCAAGAACCTAGTGGACATCAACTTTGTCTGTGCCATGGGCCCCCCGGGTGGAGGCAGG
AACACCGTCACCCCGCGGCTGATGCGTCACTTCAACTACCTGTCTTTCGCTGAGATGGACGAGGTCAGCAAGAAACGCATCTTCTCCACCATCC
TGGGCAACTGGTTGGATGGACTCCTTGGAGAAAAAAGCTACCGGGAGCGTGTGCCTGGGGCCCCCCACATTGCCCACTTCACGGAGCCCCTTGT
GGAAGCCACCATCATGGTGTATGCAACCATCACCTCCCAGCTGCTGCCCACTCCAGCCAAGTCCCACTACACCTTCAACCTGAGGGACCTCTCC
AAGGTCTTCCAAGGCATGCTCATGGCTGACCCGGCCAAGGTCGAGGACCAAGTGCAGCTGCTGCGACTGTGGTATCACGAGAACTGCCGCGTGT
TCCGGGACCGACTGGTGAATGAGGAGGACCGCAGCTGGTTCGACCAGCTCCTCAAGCGCTGCATGGAGCAGTGGGAGGTGACCTTCAACAAGGT
CTGCCCCTTCCAGCCCATTCTTTACGGGGACTTCATGTCACCAGGCTCCGATGTCAAGTCCTACGAGCTCATCACCAGTGAGAGTAAGATGATG
CAGGTGATAGAGGAGTACATAGAGGACTACAACCAGATCAACACGGCCAAGCTGAAGCTGGTCCTCTTCATGGACGCCATGAGCCACATCTGTC
GCATCAGCCGCACCCTACGCCAGGCGCTGGGCAATGCACTCCTGCTGGGCGTGGGTGGCAGCGGCCGCAGCTCCCTCACAAGGCTCGCCTCGCA
CATGGCCGAGTACGAGTGCTTCCAGATTGAACTATCCAAGAACTACGGCATGTCCGAGTGGCGAGATGATGTGAAGAAGGTCCTGCTCAAGGCG
GGCCTACAGAACCTACCCATCACCTTCCTCTTCTCAGACACCCAGATCAAGAACGAATCCTTCCTGGAAGATATCAACAACGTCCTAAACTCTG
GTGACATTCCCAATCTGTATACTGCGGACGAGCAGGACCAGATCGTCAGCACCATGCGGCCCTATATCCAGGAGCAGGGCCTACAGCCCACCAA
GGCCAACCTCATGGCTGCTTACACAGGGCGTGTGCGCAGCAACATCCACATGGTGCTGTGCATGAGCCCCATCGGAGAGGTCTTCCGAGCTCGT
CTGAGGCAGTTTCCCTCCCTGGTCAACTGCTGTACCATCGACTGGTTTAACGAGTGGCCGGCAGAAGCCCTGAAGTCTGTGGCCACCGTGTTCC
TCAATGAGATCCCAGAACTGGAATCCTCCCAGGAAGAAATCCAAGGACTGATCCAGGTCTGTGTGTACATCCACCAGTCGGTGTCCAAGAAGTG
CATCGAGTACCTGGCAGAGCTGACCCGCCACAACTATGTGACCCCCAAGAGCTACTTGGAGCTGCTTCATATTTTCTCCATCCTCATCGGGCAG
AAGAAACTGGAGCTGAAAACTGCCAAGAACCGCATGAAGAGCGGCCTCGACAAGCTGCTGCGCACTTCTGAGGATGTAGCCAAGATGCAGGAGG

Fig. 9 (Continued)

ACCTGGAGAGTATGCACCCCCTGCTGGAGGAGGCTGCCAAGGACACCATGCTCACCATGGAGCAGATCAAGGTGGATACGGCCATCGCCGAGGA
GACCCGGAATTCAGTGCAGACAGAGGAGATCAAAGCCAATGAGAAGGCCAAGAAGGCACAAGCTATTGCTGACGATGCCCAGAAGGACCTGGAC
GAGGCGTTGCCAGCCCTGGATGCGGCTCTGGCCAGCCTGCGCAACCTCAACAAGAACGATGTGACCGAGGTACGTGCCATGCAGCGGCCACCCC
CGGGTGTGAAACTGGTCATAGAAGCTGTGTGCATTATGAAAGGCATCAAGCCCAAGAAGGTGCCTGGAGAAAAGCCAGGCACCAAGGTGGATGA
CTACTGGGAGCCTGGCAAGGGGCTGCTGCAGGACCCGGGCCACTTCCTTGAGAGCCTCTTCAAGTTTGACAAGGACAACATTGGGGATGTGGTG
ATCAAAGCCATCCAGCCGTACATCGATAATGAAGAGTTCCAGCCAGCCACCATTGCCAAGGTGTCCAAGGCTTGCACCTCCATCTGCCAGTGGG
TGCGCGCCATGCACAAGTACCACTTTGTGGCCAAGGCCGTGGAGCCCAAGCGGCAAGCCCTGCTGGAGGCCCAGGATGACCTGGGGGTGACACA
GAGGATCCTGGATGAGGCAAAACAGCGCCTTCGTGAGGTGGAGGACGGCATCGCCACAATGCAGGCTAAGTACCGGGAATGCATTACCAAGAAG
GAGGAGCTGGAGCTGAAGTGTGAGCAGTGTGAGCAGCGGCTGGGCCGAGCTGGCAAGCTCATCAACGGGCTGTCGGATGAGAAGGTGCGCTGGC
AGGAGACGGTGGAGAACCTGCAGTACATGCTCAACAACATCTCCGGCGATGTCCTGGTGGCCGCTGGCTTTGTGGCCTACCTGGGCCCCTTCAC
GGGCCAGTACCGCACGGTGCTCTACGACAGCTGGGTCAAGCAGCTCAGGAGCCACAATGTCCCACACACCTCCGAGCCCACGCTAATCGGGACG
CTGGGGAACCCTGTGAAGATCCGATCGTGGCAGATCGCTGGCCTCCCCAACGACACACTGTCAGTGGAGAACGGGGTCATCAACCAGTTTTCCC
AGCGCTGGACCCACTTCATTGACCCTCAGAGCCAGGCCAACAAATGGATCAAGAACATGGAGAAGGACAATGGGCTGGATGTGTTCAAGTTGAG
TGACCGCGACTTCCTGCGCAGCATGGAGAACGCCATCCGCTTTGGCAAGCCATGTCTCCTGGAGAACGTGGGCGAGGAGCTAGACCCAGCCCTG
GAGCCAGTGCTGCTCAAGCAGACGTACAAGCAGCAGGGAAACACGGTGCTGAAGCTGGGGGACACGGTGATCCCCTACCATGAGGACTTCAGGA
TGTACATCACCACCAAGCTGCCCAACCCACACTACACGCCCGAGATCTCCACCAAACTCACCCTCATCAACTTCACCCTGTCGCCCAGTGGCCT
AGAGGACCAGCTACTGGGCCAGGTAGTGGCAGAGGAGCGACCCGACCTGGAGGAGGCCAAGAACCAGCTGATTATCAGTAATGCCAAGATGCGC
CAGGAGCTGAAGGACATTGAGGACCAGATCCTGTACCGGCTCAGCTCCTCCGAGGGCAACCCTGTAGATGACATGGAACTCATCAAGGTGCTGG
AAGCCTCCAAGATGAAGGCTGCTGAGATCCAGGCCAAAGTCAGGATTGCAGAGCAGACGGAGAAGGACATCGACCTGACGCGCATGGAGTACAT
ACCCGTGGCCATCCGCACCCAGATCCTCTTCTTCTGTGTGTCCGACCTGGCCAACGTGGACCCCATGTACCAGTACTCCCTTGAGTGGTTTCTC
AACATCTTCCTCTCGGGCATCGCCAACTCAGAGAGAGCAGACAACCTGAAGAAGCGCATCTCCAACATCAACCGCTACCTGACCTACAGCCTCT
ACAGCAACGTCTGCCGCAGCCTCTTTGAGAAGCACAAGCTGATGTTTGCCTTCCTGCTGTGTGTTCGCATCATGATGAACGAGGGCAAAATCAA
CCAGAGTGAGTGGCGATACCTCCTGTCTGGGGGCTCCATCTCGATCATGACTGAGAATCCGGCACCGGACTGGCTGTCAGACCGGGCTTGGCGA
GACATCCTAGCACTCTCGAACCTGCCAACCTTTTCCTCCTTCTCTTCCGACTTCGTGAAGCACCTCTCAGAATTCCGGGTCATCTTCGACAGCC
TTGAGCCCCACCGGGAGCCTTTGCCTGGCATCTGGGACCAGTACCTAGACCAGTTCCAGAAGCTGCTAGTCCTCCGCTGCCTGCGTGGGGACAA
GGTTACCAACGCCATGCAGGACTTTGTGGCCACCAACCTGGAGCCACGCTTCATTGAACCCCAGACAGCCAATCTGTCAGTGGTGTTCAAAGAC
TCCAACTCCACCACACCCCTCATCTTTGTGCTGTCACCCGGCACAGACCCTGCTGCCGACCTCTACAAGTTTGCCGAAGAAATGAAGTTCTCCA
AAAAGCTCTCTGCCATCTCCCTGGGCCAGGGGCAGGGCCCTCGGGCAGAAGCCATGATGCGCAGCTCCATAGAGAGGGGCAAATGGGTCTTCTT
CCAGAACTGCCACCTGGCACCAAGCTGGATGCCAGCCCTAGAACGCCTCATCGAGCACATCAACCCCGACAAGGTACACAGGGACTTCCGCCTC
TGGCTCACCAGCCTGCCCAGCAACAAGTTCCCAGTGTCCATCCTGCAGAACGGCTCCAAGATGACCATTGAGCCGCCACGCGGTGTCAGGGCCA
ACCTGCTGAAGTCCTATAGTAGCCTTGGTGAAGACTTCCTCAACTCCTGCCACAAGGTGATGGAGTTCAAGTCTCTGCTGCTGTCTCTGTGCTT
GTTCCATGGGAACGCCCTGGAGCGCCATAAGTTTGGGCCCCTGGGCTTCAACATCCCCTATGAGTTCACGGATGGAGATCTGCGCATCTGCATC
AGCCAGCTCAAGATGTTCCTGGACGAATATGATGACATCCCCTACAAGGTCCTCAAGTACACGGCAGGGGAGATCAATTACGGGGGCCGTGTCA
CTGATGACTGGGACCGGCGCTGCATCATGAACATCTTGGAGGACTTCTACAACCCTGACGTGCTCTCCCCTGAGCACAGCTACAGCGCCTCGGG
CATCTACCACCAGATCCCGCCTACCTACGACCTCCACGGCTACCTCTCCTACATCAAGAGCCTCCCACTCAATGATATGCCTGAGATCTTTGGC
CTGCATGACAATGCCAACATCACCTTTGCCCAGAACGAGACGTTCGCCCTCCTGGGCACCATCATCCAGCTGCAACCCAAATCATCTTCTGCAG
GCAGCCAGGGCCGGGAGGAGATAGTGGAGGACGTCACCCAAAACATTCTGCTCAAGGTGCCTGAGCCTATCAACTTGCAATGGGTGATGGCCAA
GTACCCAGTGCTGTATGAGGAATCAATGAACACAGTACTAGTACAAGAGGTCATTAGGTACAATCGGCTGCTGCAGGTGATCACACAGACACTG
CAAGACCTACTCAAGGCACTCAAGGGGCTGGTAGTGATGTCCTCTCAGCTGGAGCTGATGGCTGCCAGCCTGTACAACAATACTGTGCCTGAGC
TCTGGAGTGCCAAGGCCTACCCATCGCTCAAGCCTCTGTCATCATGGGTCATGGACCTGCTGCAACGCCTGGACTTTCTGCAGGCCTGGATCCA
AGATGGCATCCCAGCTGTCTTCTGGATCAGTGGATTCTTCTTCCCCCAGGCTTTCTTAACAGGCACTCTGCAGAATTTTGCCCGCAAATTTGTC
ATCTCCATTGACACCATCTCCTTTGATTTCAAGGTGATGTTTGAGGCACCATCAGAGTTAACACAAAGACCCCAAGTAGGGTGCTATATCCATG
GATTATTCCTGGAAGGTGCCCGCTGGGATCCAGAGGCCTTCCAGCTGGCTGAGTCTCAGCCCAAGGAGCTGTACACAGAGATGGCCGTTATCTG
GCTCTTGCCAACACCCAACCGCAAGGCCCAGGACCAGGACTTTTACCTGTGCCCCATCTACAAGACACTGACTCGTGCTGGAACACTATCAACC
ACAGGACACTCTACCAACTATGTCATTGCTGTGGAGATCCCCACCCATCAGCCCCAGCGACACTGGATAAAGCGTGGTGTGGCCCTCATCTGTG
CCCTGGACTACTAG

ID 40: DNAH2, *Homo*
*sapiens*ATGTCCAGCAAAGCTGAGAAGAAGCAGCGATTGAGTGGCCGAGGAAGCTCCCAGGCAAGCTGGTCAGGGCGGGCCACTCGGGCTGCT
GTGGCCACACAGGAGCAGGGGAATGCCCCGGCTGTCAGTGAGCCAGAGCTGCAGGCTGAGCTCCCCAAGGAGGAGCCTGAGCCACGGTTGGAGG
GACCTCAAGCACAGAGTGAAGAATCAGTGGAGCCCGAGGCAGATGTGAAGCCCCTCTTCCTTTCCCGAGCTGCGCTGACAGGACTGGCGGATGC
AGTGTGGACACAGGAGCATGATGCCATTCTGGAACACTTTGCCCAGGACCCTACAGAATCCATCCTCACCATCTTCATTGACCCTTGTTTTGGG
CTGAAGCTAGAGCTGGGCATGCCTGTACAGACCCAGAACCAGCTTGTCTACTTCATTCGCCAAGCACCAGTTCCCATCACCTGGGAGAACTTCG
AGGCAACTGTGCAGTTTGGGACGGTGCGGGGCCCCTATATCCCGGCCCTGCTTCGGCTGCTCGGTGGAGTCTTTGCCCCTCAGATCTTTGCAAA
CACAGGCTGGCCTGAGAGCATTAGAAATCATTTTGCTTCTCATCTGCACAAGTTCTTGGCCTGCCTGACAGACACTCGGTACAAACTGGAGGGG
CACACGGTCCTCTACATCCCTGCAGAGGCCATGAACATGAAGCCTGAGATGGTGATAAAGGACAAAGAGCTGGTGCAACGGCTAGAGACCTCCA
TGATCCACTGGACCCGGCAGATAAAGGAGATGCTCAGTGCCCAGGAGACTGTGGAGACAGGAGAAAATTTAGGTCCTCTGGAGGAGATTGAGTT
CTGGCGCAACCGATGCATGGACCTGTCTGGCATCAGTAAGCAGCTGGTGAAGAAGGGAGTGAAGCACGTTGAATCCATCCTGCACCTTGCCAAG
TCGTCCTACTTGGCGCCCTTTATGAAACTGGCACAGCAGATCCAGGATGGCTCTCGTCAAGCACAGTCAAACCTGACCTTTTTGTCAATCCTGA
AGGAACCTTACCAGGAGTTGGCTTTCATGAAGCCCAAGGACATCTCTAGCAAGCTCCCTAAGCTGATCAGTCTCATCCGCATCATCTGGGTCAA
CTCTCCCCACTACAACACTCGGGAGAGACTGACCTCGCTCTTCCGAAAGGTATGTGACTGTCAGTATCACTTCGCCCGCTGGGAAGATGGCAAG
CAGGGTCCCCTTCCTTGCTTCTTTGGTGCCCAGGGGCCACAGATAACACGGAACTTGCTGGAGATTGAGGACATCTTTCATAAAAATCTGCACA
CGCTGCGAGCCGTTCGCGGGGGTATCCTGGATGTCAAGAACACCTGTTGGCATGAAGACTACAATAAGTTCCGTGCCGGAATCAAGGACCTGGA
GGTGATGACCCAGAACCTGATCACCTCAGCCTTCGAGTTGGTGCGGGACGTGCCGCACGGCGTGCTTCTGCTGGACACCTTCCACAGGCTTGCC
TCCCGCGAGGCTATCAAGCGGACTTATGACAAGAAGGCGGTGGATCTCTACATGCTGTTCAATAGCGAGCTGGCCCTGGTGAACCGTGAACGGA
ACAAGAAATGGCCAGACCTGGAGCCCTACGTGGCCCAGTATTCCGGAAAGGCGCGCTGGGTGCACATCCTCCGGCGTCGCATCGACAGAGTCAT
GACCTGCCTTGCTGGTGCTCATTTCCTGCCCCGTATTGGGACTGGAAAGGAGAGTGTGCACACCTATCAGCAGATGGTCCAGGCCATTGATGAG
CTGGTTCGAAAAACCTTCCAAGAGTGGACATCAAGTCTGGACAAGGATTGCATTCGGCGGTTGGATACCCCATTGCTGCGAATCAGCCAGGAGA
AGGCGGGCATGCTGGATGTCAACTTTGACAAGTCCCTTCTGATTCTCTTTGCGGAAATTGACTACTGGGAGCGGCTGCTGTTTGAGACGCCCCA
TTACGTGGTGAACGTAGCTGAGCGAGCCGAGGACCTGCGCATTCTGCGTGAAAATCTGCTACTCGTTGCTAGAGACTACAATAGGATTATTGCC
ATGCTGTCCCCAGATGAGCAGGCCCTATTCAAAGAGCGTATTCGGCTCCTGGATAAGAAGATCCACCCGGGACTCAAGAAACTGCACTGGGCCT
TGAAGGGGGCCAGTGCCTTCTTCATCACGGAGTGCCGTATACATGCCAGCAAGGTGCAGATGATTGTGAATGAGTTCAAGGCATCCACTCTGAC
CATTGGCTGGCGAGCCCAAGAGATGTCAGAGAAGCTGCTGGTACGCATTAGTGGCAAACGGGTATACAGGGACCTGGAATTTGAAGAGGACCAA
AGAGAGCATCGGGCAGCTGTACAGCAGAAATTGATGAACCTGCACCAGGATGTGGTGACCATCATGACCAACTCCTATGAGGTCTTCAAGAATG
ATGGTCCTGAGATTCAGCAGCAGTGGATGCTGTACATGATTCGGCTGGACCGCATGATGGAGGATGCCCTGCGCCTGAATGTGAAGTGGTCACT
GCTAGAACTATCCAAGGCTATCAACGGGGATGGAAAGACCAGCCCAAACCCACTCTTCCAAGTCCTTGTCATTTTGAAGAATGATCTGCAAGGA
AGTGTGGCACAGGTGGAATTCTCACCCACTCTGCAGACTTTGGCAGGTGTGGTCAATGACATTGGCAACCACCTCTTTTCCACCATCTCTGTCT
TCTGCCACCTCCCTGACATTCTCACCAAGCGCAAGTTACATCGTGAACCCATCCAAACAGTTGTGGAGCAAGATGAGGACATCAAGAAGATCCA
GACCCAAATCAGCAGCGGCATGACTAACAACGCAAGCCTGCTGCAGAACTACCTCAAGACCTGGGACATGTACCGGGAGATCTGGGAGATCAAC
AAGGACTCCTTCATTCATCGCTACCAGCGCCTCAACCCTCCTGTCTCTTCTTTTGTTGCCGACATTGCCCGCTACACGGAAGTTGCTAATAACG

Fig. 9 (Continued)

TGCAGAAGGAGGAGACAGTCACCAACATCCAGTTTGTGCTGCTGGACTGTTCGCACCTCAAGTTCTCCCTGGTGCAGCACTGCAATGAATGGCA
GAACAAGTTCGCGACTCTGCTCAGGGAGATGGCTGCTGGGCGCCTCCTGGAGCTGCACACCTACCTGAAGGAGAACGCAGAGAAAATCAGCCGC
CCTCCGCAGACACTGGAGGAACTGGGGGTCAGCTTGCAGCTCGTGGATGCCCTGAAGCACGACTTGGCCAACGTGGAGACTCAGATCCCTCCCA
TACACGAGCAATTTGCCATTCTTGAAAAGTACGAGGTGCCAGTCGAGGACAGTGTCCTGGAGATGCTGGACAGTCTCAACGGGGAGTGGGTTGT
CTTCCAACAAACTCTGCTGGACAGTAAGCAAATGCTGAAGAAACACAAGGAGAAATTCAAGACAGGCCTGATCCACTCGGCAGATGACTTCAAG
AAGAAAGCACATACACTTCTGGAAGATTTCGAATTCAAAGGCCATTTCACCAGCAACGTGGGATACATGTCTGCCTTAGACCAGATTACACAAG
TGCGGGCCATGCTGATGGCCATGCGGGAAGAGGAAAATAGTCTCCGAGCCAACCTGGGCATCTTCAAGATCGAGCAGCCACCCTCCAAGGACCT
TCAGAACCTGGAGAAGGAGCTCGATGCCCTCCAGCAAATCTGGGAGATCGCACGAGACTGGGAGGAGAACTGGAATGAGTGGAAGACTGGCCGG
TTCCTGATCCTGCAGACGGAAACCATGGAGACCACGGCCCACGGGCTGTTTCGTCGCCTCACAAAATTAGCCAAAGAGTATAAGGACCGAAACT
GGGAAATTATTGAAACCACTCGCTCAAAAATAGAGCAGTTCAAGAGGACCATGCCTCTCATCTCAGACCTGCGGAACCCTGCCCTTAGAGAGAG
GCACTGGGACCAGGTCCGGGATGAGATCCAGCGGGAGTTTGATCAGGAATCTGAAAGCTTCACCTTGGAGCAGATTGTGGAGCTTGGGATGGAT
CAGCATGTGGAGAAAATTGGGGAGATCTCTGCTTCAGCAACTAAAGAGCTGGCTATAGAAGTGGCTTTACAAAACATTGCCAAGACCTGGGATG
TGACTCAGCTCGACATAGTACCCTACAAGGATAAGGGCCATCATCGGCTCAGAGGTACAGAAGAAGTATTCCAGGCACTGGAAGATAACCAGGT
AGCTCTGTCTACCATGAAGGCATCACGCTTTGTCAAGGCCTTTGAGAAGGATGTGGACCACTGGGAACGCTGCCTCTCCCTCATTTTGGAGGTT
ATTGAGATGATTCTCACAGTGCAGCGTCAGTGGATGTACTTAGAGAATATCTTCCTAGGAGAAGACATCCGCAAGCAGCTGCCCAATGAATCGA
CCTTATTTGACCAGGTCAACAGCAACTGGAAAGCCATCATGGACAGGATGAACAAGGACAACAATGCTCTCCGGAGCACCCATCACCCAGGCCT
CCTGGACACATTGATAGAAATGAATACAATCCTGGAAGATATTCAGAAATCTCTGGATATGTATTTAGAGACCAAGCGACATATTTTCCCCCGC
TTCTACTTCTTGTCCAATGATGACCTGCTGGAGATTCTGGGCCAGTCCCGAAACCCAGAGGCTGTGCAGCCACACCTCAAAAAATGCTTTGACA
ACATCAAGTTGCTGAGAATCCAGAAGGTTGGAGGGCCCAGCAGCAAATGGGAAGCTGTGGGGATGTTCTCGGGCGACGGCGAGTACATTGACTT
CCTCCACTCAGTATTTTTAGAAGGCCCTGTGGAGTCCTGGCTTGGCGATGTGGAACAGACCATGAGGGTGACCCTGCGGGACCTTCTCCGGAAC
TGCCACCTGGCCCTCAGGAAGTTCCTCAACAAGAGGGACAAATGGGTGAAGGAGTGGGCTGGCCAGGTGGTGATCACTGCCAGTCAGATCCAGT
GGACGGCTGATGTCACCAAGTGCCTGCTGACAGCGAAGGAGCGGGCAGACAAGAAAATCCTCAAGGTCATGAAGAAGAACCAGGTGTCAATCCT
GAATAAGTATTCAGAAGCCATCAGGGGGAACTTGACCAAGATCATGCGGCTTAAAATTGTGGCTCTGGTGACGATAGAAATTCATGCCCGGGAT
GTGTTGGAGAAGCTTTACAAGAGTGGCCTCATGGATGTCAATTCCTTTGACTGGCTCAGCCAACTTCGGTTCTACTGGGAGAAGGATCTTGATG
ACTGTGTCATCCGCCAGACCAACACGCAATTTCAGTATAATTATGAGTACTTGGGTAACTCGGGCCGGCTCGTCATCACCCCCCTGACGGACAG
GTGTTACATGACACTGACCACGGCATTGCACCTGCACCGAGGGGGCTCCCCCAAAGGCCCTGCAGGCACAGGCAAGACCGAGACCGTCAAGGAC
CTGGGCAAGGCCCTGGGCATATATGTCATTGTGGTCAACTGCTCTGAGGGCCTGGACTACAAGTCCATGGGCCGAATGTACTCAGGTCTGGCCC
AGACTGGAGCTTGGGGCTGCTTTGATGAGTTTAACCGCATCAACATCGAGGTGCTGTCAGTGGTGGCCCACCAGATCCTGTGCATCCTGTCTGC
CCTGGCTGCCGGCCTCACCCATTTCCATTTTGATGGCTTTGAAATAAATCTGGTGTGGTCCTGTGGGATCTTCATTACCATGAATCCTGGCTAT
GCTGGCCGCACAGAGCTTCCCGAAAATCTTAAATCCATGTTCCGCCCAATTGCCATGGTGGTGCCTGACTCCACCCTCATTGCAGAAATCATTC
TCTTTGGAGAGGGCTTTGGCAACTGCAAGATTCTGGCCAAGAAGGTGTACACACTCTACTCACTGGCTGTGCAGCAGCTGTCCAGACAGGACCA
CTATGACTTTGGCCTGCGTGCCCTCACCTCCCTTCTGCGCTATGCTGGCAAGAAGCGCCGCCTACAGCCGGATCTGACTGATGAAGAGGTTCTG
CTGCTCTCAATGAGAGATATGAACATCGCCAAGCTCACTTCAGTTGATGCACCCCTGTTCAATGCCATCGTGCAAGATCTGTTTCCCAACATTG
AGCTGCCTGTCATTGACTATGGCAAGCTGCGGGAGACCGTTGAGCAGGAGATTCGAGACATGGGCCTGCAAAGCACGCCGTTCACCCTCACCAA
GGTTTTCCAGTTGTATGAAACCAAGAACTCCCGCCACTCCACCATGATCGTGGGCTGCACGGGCAGCGGCAAGACTGCCTCATGGCGCATTCTA
CAGGCCTCCCTGTCCTCTCTGTGCCGCGCCGGAGACCCTAACTTCAACATTGTTAGAGAGTTCCCTTTGAACCCCAAGGCATTGTCCCTAGGGG
AACTGTATGGGGAATATGACCTCAGCACCAATGAATGGACAGATGGCATCTTGTCCAGTGTCATGCGGACGGCATGTGCAGATGAGAAACCCGA
CGAGAAGTGGATCCTGTTCGATGGCCCCGTGGACACACTGTGGATCGAGAACATGAACTCCGTCATGGACGATAACAAGGTGTTGACCCTCATC
AACGGCGAGCGCATCGCGATGCCCGAGCAGGTGTCTCTCCTGTTTGAAGTGGAGGACCTGGCAATGGCCTCTCCGGCCACTGTATCCCGCTGCG
GGATGGTCTACACTGACTACGCTGACCTGGGCTGGAAGCCCTATGTTCAGTCATGGCTGGAGAAGAGGCCAAAGGCTGAGGTGGAGCCCCTTCA
ACGCATGTTCGAAAAGCTCATCAACAAGATGCTGGCCTTTAAGAAGGACAACTGCAAGGAGCTGGTGCCCCTGCCCGAGTACAGCGGTATCACC
TCCCTCTGCAAGCTGTACTCTGCCCTGGCCACGCCAGAGAATGGGGTGAACCCAGCTGACGGCGAGAACTATGTCACCATGGTAGAGATGACAT
TTGTGTTCAGCATGATCTGGTCTGTGTGTGCCTCTGTGGATGAGGAGGGCCGGAAGAGGATCGACAGCTACCTCCGAGAGATCGAGGGCTCCTT
TCCCAATAAGGACACGGTATATGAGTATTTTGTGGACCCCAAAATACGGAGTTGGACATCATTTGAGGACAAGCTCCCTAAGAGTTGGCGCTAC
CCTCCAAACGCCCCCTTCTATAAGATCATGGTGCCCACCGTCGACACTGTTCGCTACAACTACCTGGTGAGCAGCTTGGTGGCCAACCAGAATC
CCATTCTGCTGGTGGGTCCCGTGGGGACTGGGAAGACCTCCATCGCCCAGAGCGTTCTGCAGTCCCTGCCCTCCAGCCAGTGGTCGGTGCTCGT
TGTCAACATGTCCGCACAGACCACATCCAATAACGTGCAGAGCATCATTGAGAGCAGGGTTGAGAAGCGAACCAAGGGTGTCTACGTGCCATTC
GGGGGCAAAAGCATGATCACCTTTATGGATGACCTAAATATGCCCGCTAAGGACATGTTTGGGTCCCAGCCACCCCTGGAGCTGATCCGCCTCT
GGATTGACTATGGCTTCTGGTATGACCGTACGAAGCAGACCATCAAGTACATTCGAGAAATGTTCCTGATGGCTGCCATGGGCCCCCCTGGGGG
TGGACGGACTGTCATCTCCCCAAGGCTACGGAGTCGCTTCAACATTATCAACATGACCTTCCCCACAAAGTCCCAGATCATCCGCATATTCGGC
ACCATGATCAATCAGAAGCTTCAGGACTTTGAGGAAGAGGTGAAGCCCATTGGGAACGTGGTGACAGAGGCCACCCTGGACATGTACAACACCG
TGGTACAGCGCTTCCTGCCCACGCCCACCAAGATGCATTACCTCTTCAACCTTCGAGACATCTCCAAGGTGTTCCAGGGCATGCTTAGAGCCAA
CAAGGACTTCCATGATACCAAGTCCAGCATCACACGGCTCTGGATCCATGAATGTTTCAGAGTCTTCTCTGACCGGCTGGTTGATGCGGCAGAC
ACAGAAGCCTTCATGGGCATCATAAGCGACAAGCTCGGCTCCTTCTTTGACCTCACATTTCATCATCTCTGTCCCAGCAAGCGTCCTCCTATCT
TTGGGGATTTCCTGAAGGAGCCCAAGGTGTATGAAGACCTCACGGATCTGACAGTGCTGAAGACAGTCATGGAGACAGCTCTAAATGAGTATAA
CCTGTCACCCTCTGTCGTGCCCATGCAGCTAGTGCTCTTCCGAGAGGCTATTGAACACATCACACGGATCGTGCGGGTCATTGGACAGCCTCGG
GGCAACATGCTCCTGGTGGGTATCGGGGGCAGCGGACGCCAGAGTCTGGCCCGCCTGGCTTCATCCATCTGCGACTACACCACCTTCCAGATCG
AGGTCACCAAACATTATCGGAAGCAGGAGTTCCGAGATGATATCAAGCGTCTGTATCGCCAGGCTGGGGTGGAGCTCAAGACCACGTCCTTCAT
TTTTGTGGACACCCAAATAGCTGATGAGTCCTTCCTAGAGGACATCAACAACATCCTCAGCTCAGGCGAGGTGCCCAATCTCTACAAGCCTGAT
GAATTTGAAGAGATCCAGTCGCATATCATAGACCAGGCCCGGGTGGAGCAGGTGCCTGAGTCATCGGACAGCCTCTTCGCCTACCTCATTGAAC
GCGTGCAGAACAACCTGCACATCGTGCTCTGCCTCAGCCCCATGGGGGATCCCTTCAGGAACTGGATCCGCCAGTACCCAGCCTTGGTGAACTG
CACAACCATCAACTGGTTCTCAGAGTGGCCCCAAGAGGCCCTGCTCGAGGTGGCTGAGAAGTGCCTCATAGGAGTAGACCTGGGAACTCAGGAG
AATATCCACAGGAAGGTGGCCCAGATCTTTGTCACTATGCACTGGTCAGTAGCTCAGTATTCCCAGAAGATGCTGTTGGAACTGCGGAGACACA
ACTATGTCACACCCACCAAATACCTGGAACTCCTGTCTGGATATAAGAAGTTGCTGGGAGAAAAACGGCAGGAGCTGCTGGCCCAAGCCAATAA
ACTGCGGACAGGCTTGTTCAAGATCGACGAAACTAGGGAAAAGGTGCAAGTGATGTCGTTGGAGCTGGAGGATGCCAAGAAGAAGGTGGCTGAG
TTCCAGAAGCAGTGTGAGGAGTACCTGGTCATCATTGTGCAGCAGAAGCGGGAGGCAGATGAGCAGCAGAAGGCCGTAACAGCCAACAGTGAAA
AGATTGCAGTTGAGGAAATCAAGTGTCAGGCACTGGCTGACAATGCCCAGAAAGATCTAGAAGAGGCACTGCCCGCCCTGGAAGAGGCCATGCG
GGCCCTGGAGTCTCTGAACAAGAAGGATATAGGAGAGATCAAGTCTTATGGACGGCCCCCAGCCCAAGTGGAGATAGTGATGCAGGCAGTTATG
ATTCTTCGAGGCAACGAGCCCACATGGGCAGAGGCCAAGAGGCAGCTAGGGGAACAGAACTTCATCAAGTCACTGATCAACTTTGATAAAGACA
ATATCTCAGATAAGGTTCTGAAGAAGATTGGGGCCTACTGCGCCCAGCCTGACTTCCAGCCTGATATCATCGGCCGCGTCTCCCTGGCTGCCAA
GTCCCTCTGCATGTGGGTGCGGGCCATGGAGCTGTATGGGCGGCTATATCGGGTGGTGGAGCCCAAGCGAATCCGAATGAACGCTGCCTTGGCT
CAGCTTCGGGAGAAGCAAGCCGCGCTCGCTGAGGCCCAGGAGAAGCTGCGGGAGGTAGCTGAGAAACTGGAGATGCTAAAGAAACAGTATGATG
AGAAGCTGGCACAGAAGGAGGAGCTTCGCAAGAAGTCTGAAGAGATGGAGCTGAAGCTGGAGCGAGCTGGGATGCTCGTGTCGGGGTTGGCTGG
CGAGAAGGCCAGATGGGAGGAGACAGTCCAGGGCCTGGAGGAGGACCTGGGCTACCTGGTGGGGGACTGTCTCCTGGCAGCTGCCTTCCTGTCC
TACATGGGACCCTTCCTGACCAACTACCGGGATGAGATTGTCAACCAAATCTGGATCGGGAAGATCTGGGAGCTTCAGGTTCCTTGCTCCCCTT
CTTTCGCCATCGATAACTTCCTGTGCAATCCTACCAAAGTCCGGGACTGGAACATCCAAGGGTTGCCCTCAGACGCCTTCTCCACTGAGAATGG
CATCATCGTCACCCGAGGCAACAGGTGGGCACTGATGATCGACCCTCAGGCCCAGGCCCTGAAATGGATTAAGAACATGGAAGGAGGCCAGGGC
CTGAAGATCATCGACCTGCAGATGAGCGATTACCTGCGAATCCTAGAACACGCCATTCACTTTGGATACCCGGTGCTACTTCAGAACGTGCAGG
AATATCTGGACCCCACACTGAACCCCATGCTCAACAAATCTGTAGCCCGAATCGGTGGTCGGCTGTTGATGCGCATTGGCGATAAGGAGGTGGA
ATATAATACCAATTTCCGTTTCTACATCACCACCAAGCTCTCCAACCCCCACTACAGCCCAGAGACCTCAGCCAAGACCACCATCGTCAACTTT

Fig. 9 (Continued)

GCTGTTAAAGAACAGGGCCTGGAGGCCCAGCTGCTGGGCATTGTGGTGCGGAAGGAGCGGCCTGAGCTGGAGGAGCAGAAGGACTCACTGGTCA
TCAACATCGCGGCTGGTAAAAGGAAGCTCAAGGAGCTGGAGGATGAGATCCTGCGGCTGCTGAATGAGGCCACCGGCTCCCTGCTGGATGATGT
GCAGCTGGTGAACACGCTGCATACCTCCAAGATCACAGCCACAGAGGTGACTGAGCAGCTGGAGACCAGTGAGACCACAGAGATCAACACTGAC
TTGGCGCGGGAGGCTTACCGCCCATGCGCCCAGCGGGCATCAATCCTGTTCTTCGTGCTCAATGATATGGGCTGCATCGACCCCATGTACCAGT
TCTCACTGGATGCCTACATCAGCCTCTTTATTCTCAGCATTGACAAAAGCCACCGCAGCAATAAGCTGGAGGACCGCATTGACTACCTGAATGA
CTACCACACCTACGCTGTCTACAGGTACACCTGCCGTACCCTTTTCGAACGCCACAAACTACTATTCAGTTTTCATATGTGTGCCAAAATCTTG
GAGACTTCTGGCAAGCTCAACATGGATGAATACAACTTCTTTCTACGTGGGGGTGTGGTCTTGGATCGGGAGGGCCAAATGGACAATCCATGTA
GTAGCTGGCTTGCAGATGCCTACTGGGATAACATCACAGAGCTAGACAAACTGACCAACTTCCACGGACTCATGAACTCCTTTGAGCAGTACCC
TCGTGACTGGCACCTGTGGTATACCAATGCTGCCCCGGAGAAGGCGATGCTGCCAGGTGAGTGGGAAAATGCCTGCAATGAAATGCAACGGATG
CTGATCGTTCGCTCCCTGCGCCAGGACCGCGTGGCCTTCTGCGTGACCTCCTTCATCATCACCAACCTTGGCTCCCGCTTCATCGAGCCGCCTG
TGCTGAATATGAAGTCGGTGCTGGAGGATTCAACCCCACGATCCCCACTCGTGTTCATCCTGTCCCCTGGTGTGGACCCCACCAGTGCCCTGCT
GCAGCTGGCAGAGCACATGGGCATGGCCCAGCGCTTCCACGCCCTGTCCCTGGGCCAGGGCCAGGCCCCCATCGCTGCTCGGCTCCTCCGAGAG
GGTGTGACTCAGGGACACTGGGTGTTCCTGGCAAACTGCCACCTGTCACTGTCTTGGATGCCTAATCTGGACAAGCTGGTGGAGCAGCTGCAGG
TGGAGGATCCTCATCCATCCTTCCGCCTCTGGCTCAGCTCCATCCCCCACCCAGACTTCCCTATCTCAATCTTGCAGGTCAGCATCAAGATGAC
CACAGAGCCACCAAAGGGCCTAAAGGCCAACATGACACGTCTTTACCAACTGATGTCAGAACCACAGTTTTCCCGCTGCTCCAAACCTGCCAAA
TATAAGAAGCTGCTGTTTTCACTCTGTTTCTTCCACTCTGTGTTACTTGAACGCAAAAAGTTCCTGCAGCTTGGCTGGAACATCATCTATGGCT
TCAATGACTCCGACTTTGAGGTGTCAGAAAACTTGCTGAGCCTCTATCTCGATGAGTACGAGGAGACACCTTGGGACGCACTTAAGTACCTCAT
TGCCGGCATCAACTATGGTGGACATGTCACAGATGACTGGGACCGGCGCCTGCTGACCACCTACATCAATGATTATTTCTGTGACCAGTCTCTA
TCAACTCCCTTCCACCGGTTGTCAGCACTGGAGACTTATTTCATCCCCAAGGATGGCAGCCTCGCTTCTTACAAGGAATACATCAGCTTATTGC
CTGGCATGGACCCCCCTGAGGCCTTTGGCCAGCACCCCAATGCTGATGTGGCCTCTCAGATCACTGAGGCACAAACCCTCTTTGATACTTTGCT
TTCCTTGCAACCTCAGATTACACCCACCAGGGCTGGAGGCCAGACCCGGGAAGAGAAGGTCCTTGAGTTGGCCGCTGATGTGAAGCAGAAGATC
CCTGAAATGATCGACTATGAGGGGACTCAAAAACTGCTAGCTCTCGACCCCTCCCCCCTCAATGTGGTCCTTCTGCAGGAGATCCAGAGATACA
ACACACTGATGCAGACCATCCTGTTCTCACTGACAGACCTAGAGAAAGGCATCCAGGGTCTCATCGTCATGTCTACAAGCCTGGAAGAGATTTT
CAATTGCATCTTTGATGCCCATGTTCCTCCGCTCTGGGAAAGGCATACCCCTCACAAAAGCCATTGGCTGCCTGGACCCGGGACTTGGCCATG
CGTGTGGAGCAGTTTGAGCTGTGGGCCAGCCGGGCCCGGCCTCCTGTGATCTTCTGGTTGTCTGGTTTCACCTTTCCCACTGGCTTCCTCACTG
CTGTGCTGCAGTCTTCAGCTCGCCAAAACAACGTTTCAGTGGACAGCCTCTCCTGGGAGTTTATCGTTTCCACTGTGGATGACAGCAACCTAGT
GTATCCCCCCAAGGATGGTGTCTGGGTCCGGGGCCTGTACCTGGAAGGTGCTGGCTGGGACCGGAAGAACTCCTGCTTGGTGGAGGCAGAGCCC
ATGCAGCTTGTCTGCCTCATGCCCACGATCCACTTCCGGCCTGCAGAGAGCCGCAAGAAGAGCGCCAAGGGCATGTACTCCTGCCCCTGCTATT
ACTATCCCAACCGGGCAGGCAGCTCAGACCGAGCCTCCTTTGTCATCGGCATTGACCTGCGGTCTGGGGCCATGACACCTGATCATTGGATCAA
GAGGGGCACTGCTCTACTCATGAGCCTGGACAGCTGA

ID 41: DNAH3, *Homo sapiens*

ATGGGAGCTACAGGGCGCCTCGAGCTCACACTGGCCGCCCCTCCCCATCCGGGCCCAGCCTTTCAGCGTTCAAAAGCCAGGGAGACCCAAGGAG
AGGAGGAAGGGAGTGAAATGCAGATCGCCAAAAGTGACTCCATACATCACATGAGCCACTCCCAGGGGCAGCCAGAGCTGCCTCCTCTGCCTGC
TTCTGCTAATGAGGAACCGTCTGGACTCTATCAGACTGTCATGTCACACAGCTTTTACCCGCCCTTGATGCAACGCACGTCATGGACCTTGGCT
GCACCCTTCAAAGAACAGCATCACCACCGTGGACCCAGTGATTCCATCGCCAACAACTACTCCTTGATGGCCCAGGACCTGAAGCTGAAAGATC
TGCTGAAGGTCTACCAACCGGCCACCATCAGTGTCCCTAGGGACAGGACCGGTCAGGGGCTGCCATCATCAGGAAATAGAAGCTCATCAGAGCC
CATGAGGAAAAAAACGAAGTTTTCCTCCAGAAACAAAGAGGATTCCACTAGGATCAAGTTGGCCTTCAAGACGTCAATCTTCTCACCCATGAAG
AAGGAGGTAAAGACATCTTTGACGTTCCCAGGAAGCAGACCAATGAGTCCAGAACAGCAGCTCGATGTCATGTTACAGCAGGAGATGGAAATGG
AAAGTAAAGAAAAGAAGCCATCTGAATGGAGCCTGGAGAGATACTATTACTATCTGACCAATGGAATTCGCAAAGACATGATTGCCCCTGAGGA
GGGTGAAGTGATGGTTCGGATTTCAAAGCTGATTTCTAACACGCTGCTGACGAGTCCCTTCCTGGAGCCCCTGATGGTGGTCCTCGTGCAGGAG
AAGGAGAATGACTATTACTGTAGCCTCATGAAAAGCATCGTTGATTACATCCTCATGGACCCAATGGAGAGAAAACGGCTCTTTATTGAGAGCA
TCCCCCGCTTGTTTCCTCAAAGAGTGATCCGGGCCCCTGTGCCCTGGCACAGTGTCTACAGGAGCGCCAAGAAGTGGAACGAGGAGCATCTGCA
CACGGTGAACCCCATGATGCTCAGGCTGAAAGAACTGTGGTTTGCAGAGACCTCAGGTTTGTTCGAACAGCAGAAATACTAGCGGGA
AAATTGCCTCTGCAGCCTCAGGAATTTTGGGATGTGATCCAGAAACACTGCCTGGAGGCACACCAGACTCTTCTCAACAAGTGGATCCCCACCT
GCGCCCAGCTTTTTACCTCACGGAAGGAGCACTGGATTCATTTTGCTCCCAAGAGCAACTATGACTCAAGTCGAAACATTGAGGAATATTTTGC
TTCTGTGGCATCATTCATGTCGCTGCAGCTTAGGGAGCTGGTCATTAAGTCACTTGAGGACCTCGTTTCCCTTTTCATGATACACAAAGATGGG
AATGATTTTAAGGAGCCCTACCAAGAGATGAAGTTTTTCATACCTCAGCTAATCATGATCAAACTTGAAGTCAGTGAACCCATTATTGTCTTCA
ATCCATCTTTTGATGGCTGCTGGGAATTAATACGTGACTCTTTCCTGGAAATTATTAAGAACTCTAATGGGATCCCCAAGCTGAAATACATACC
ACTTAAGTTCTCCTTCACTGCTGCTGCTGCTGATCGGCAATGTGTGAAAGCAGCTGAGCCAGGAGAGCCCAGCATGCACGCGGCTGCCACTGCA
ATGGCAGAGCTGAAAGGATATAATCTGCTCCTTGGAACTGTTAACGCAGAAGAAAAACTTGTTTCTGATTTTTTGATTCAAACTTTCAAGGTAT
TTCAGAAAAATCAAGTTGGCCCCTGCAAATATTTAAATGTCTACAAAAAGTATGTTGACTTATTGGATAACACGGCAGAGCAAAACATCGCTGC
GTTCCTGAAAGAAAATCATGACATTGATGATTTTGTGACGAAGATCAATGCCATAAAGAAACGGAGAAATGAAATTGCATCCATGAACATCACC
GTGCCTTTAGCCATGTTCTGCCTTGATGCTACGGCCCTAAATCATGATCTCTGTGAGCGAGCTCAAAATCTTAAAGACCATCTGATTCAATTCC
AAGTGGATGTAAACCGAGACACCAATACCAGCATTTGTAATCAGTACAGCCACATCGCAGACAAAGTCAGTGAGGTTCCTGCCAACACTAAGGA
GCTGGTATCCCTCATTGAATTCCTAAAGAAATCCAGTGCTGTCACTGTGTTCAAACTCAGGAGGCAACTTAGAGATGCAAGTGAACGGCTGGAG
TTCCTGATGGACTATGCAGACTTGCCGTACCAGATTGAAGATATCTTTGACAACAGCCGGAACTTGCTCCTTCACAAGAGGGATCAGGCAGAAA
TGGATCTGATTAAAAGATGCTCAGAATTTGAGTTGAGACTTGAGGGCTACCACAGAGAACTGGAAAGTTTTAGGAAGCGCGAAGTGATGACTAC
AGAAGAAATGAAGCACAATGTTGAAAAGCTTAATGAGCTTTCAAAGAACCTAAATCGGGCGTTTGCAGAGTTTGAGTTGATCAATAAGGAGGAA
GAGCTATTGGAAAAGGAGAAGACTACTTACCCTCTTCTGCAGGCCATGCTGAAGAACAAAGTACCTTATGAGCAGCTGTGGTCGACAGCCTATG
AGTTCAGCATCAAGTCAGAGGAATGGATGAATGGACCCCTCTTCTTACTGAATGCTGAGCAAATTGCGGAGGAGATAGGGAATATGTGGAGGAC
AACGTATAAACTGATCAAGACCTTGTCTGATGTGCCTGCACCCAGGCGCTTAGCAGAGAATGTGAAGATCAAGATCGATAAGTTCAAGCAGTAC
ATTCCCATCCTCAGTATTTCCTGCAACCCAGGAATGAAAGACCGACACTGGCAGCAGATCAGTGAGATTGTTGGCTATCAGATAAAGCCCACCG
AAACGACCTGCCTCTCAAATATGCTCGAATTTGGATTCGGCAAATTCGTTGAAAAATTGGAGCCCATTGGTGCAGCTGCCAGCAAGGAATACTC
TCTGGAGAAAAACTTGGATAGAATGAAGTTGGATTGGGTTAACGTGACGTTCAGCTTCGTGAAATACAGGGACACTGATACAAACATCTTGTGT
GCAATTGATGACATTCAAATGCTACTTGATGATCACGTGATAAAGACCCAGACCATGTGTGGCTCCCCATTCATCAAACCAATAGAAGCAGAAT
GCCGGAAATGGAAGAAAAGCTAATTCGGATACAGAACAATTTGGATGCCTGGTTGAAATGCCAAGCCACCTGGCTGTACCTGGAACCAATCTT
CAGTTCAGAGGACATCATAGCCCAGATGCCAGAAGAGGGGAGGAAATTTGGCATTGTTGATAGTTACTGGAAATCACTTATGTCCCAAGCGGTG
AAAGATAACAGGATTCTGGTGGCAGCCGACCAGCCACGGATGGCAGAGAAGCTTCAAGAAGCCAACTTTCTCTTGGAGGACATCCAGAAAGGGC
TGAATGATTACTTGGAGAAGAAGAGACTATTCTTCCCCAGATTCTTCTTCCTATCAAACGATGAGCTGCTGGAAATCTTGTCCGAGACAAAGGA
CCCTCTCCGAGTGCAGCCGCACTTGAAGAAGTGCTTTGAAGGAATTGCCAAGCTTGAGTTTACAGACAATCTGGAAATTGTGGGCATGATCAGC
TCGGAAAAAGAAACTGTTCCATTCATACAGAAAATCTACCCAGCTAATGCCAAGGGCATGGTGGAAAAGTGGCTCCAGCAGGTGGAGCAGATGA
TGCTGGCCAGTATGCGAGAAGTCATTGGACTTGGGATTGAAGCATATGTCAAGGTCCCTCGAAATCACTGGGTCTTACAGTGGCCTGGACAGGT
GGTTATCTGTGTCTCCTCCATCTTTTGGACCCAGGAGGTGTCCCAAGCCCTGGCGGAAAATACCTTACTGGATTTTCTGAAAAAGAGCAATGAT
CAGATTGCGCAGATTGTCCAGCTGGTGCGAGGGAAGCTGAGCAGTGGAGCTCGACTCACTCTCGGGGCCCTCACGGTCATCGATGTCCACGCCC
GCGACGTGGTGGCCAAGTTATCTGAGGACAGGGTCTCCGATCTGAATGATTTCCAATGGATCTCACAGCTGCGCTACTACTGGGTGGCCAAGGA
TGTGCAGGTGCAGATTATCACCACAGAAGCCTTGTATGGCTATGAGTACCTGGGAAACTCCCCCCGGCTGGTGATCACACCCCTCACCGACCGC
TGCTACAGGACACTGATGGGAGCTTTGAAGCTGAACCTTGGGGGTGCTCCAGAGGGTCCAGCTGGGACTGGCAAGACAGAAACCACCAAAGATT
TGGCCAAAGCCTTGGCTAAGCAGTGTGTGGTCTTCAACTGCTCCGATGGTTTGGATTACAAAGCTATGGGGAAGTTCTTCAAGGGGCTGGCACA
GGCTGGAGCATGGGCGTGCTTTGATGAGTTCAACAGGATCGAGGTAGAAGTGCTGTCTGTGGTCGCTCAGCAGATCCTCAGCATCCAACAAGCC
ATCATTCGGAAGCTAAAGACATTCATCTTTGAAGGGACTGAGCTCTCTCTGAACCCAACCTGCGCTGTGTTCATCACCATGAACCCCGGGTATG

Fig. 9 (Continued)

CTGGCAGGGCTGAACTGCCCGACAATCTCAAGGCCTTGTTCCGGACAGTGGCCATGATGGTCCCAGATTACGCCCTCATTGGAGAAATCTCCCT
CTACTCCATGGGGTTTCTGGACTCCAGAAGTCTCGCCCAGAAGATCGTTGCGACCTACCGCCTGTGCTCGGAACAACTGTCCTCTCAGCATCAC
TATGACTACGGTATGCGCGCTGTCAAGTCTGTGCTTACTGCCGCAGGAAACCTGAAGCTCAAGTATCCAGAGGAGAATGAAAGTGTCCTGCTGC
TCCGGGCATTGCTTGATGTCAATCTGGCCAAGTTCTTAGCGCAAGATGTCCCTCTGTTTCAGGGAATTATATCTGATTTATTTCCTGGAGTTGT
TCTTCCAAAGCCAGACTATGAAGTTTTTCTGAAAGTGCTGAATGATAACATCAAAAAGATGAAACTCCAGCCAGTACCTTGGTTTATAGGGAAA
ATTATCCAGATCTACGAAATGATGCTGGTGAGACATGGCTATATGATTGTAGGAGACCCCATGGGCGGCAAGACCTCTGCTTATAAAGTGTTGG
CTGCAGCTCTCGGCGATTTACACGCAGCCAATCAGATGGAGGAGTTTGCTGTGGAGTACAAGATCATCAACCCCAAGGCTATCACGATGGGGCA
GCTGTATGGGTGCTTTGACCAAGTGAGCCACGAGTGGATGGATGGTGTCCTTGCCAATGCTTTCCGGGAGCAAGCGTCTTCACTCTCTGATGAT
CGCAAGTGGATTATATTTGATGGGCCAGTGGATGCTATTTGGATTGAAAATATGAACACTGTTCTGGATGACAATAAAAAGCTGTGTCTCATGA
GTGGGGAAATTATCCAGATGAACTCCAAGATGAGCCTGATCTTCGAGCCCGCCGACCTCGAGCAAGCCTCTCCAGCCACTGTGAGCAGGTGTGG
GATGATCTACATGGAGCCCATCAACTAGGCTGGAAGCCCCTGAAGGATTCCTACATGGACACCCTGCCCTCCAGTCTCACCAAGGAGCACAAA
GAATTGGTCAATGACATGTTCATGTGGCTTGTCCAGCCCTGCCTGGAATTTGGTCGCCTTCATTGTAAATTTGTTGTCCAGACATCTCCCATCC
ACCTTGCCTTCTCAATGATGAGACTGTACTCTTCTCTGCTTGATGAAATCAGGGCAGTAGAAGAGGAGGAAATGGAATTAGGTGAAGGCCTGTC
AAGTCAACAGATCTTTCTCTGGCTCCAAGGACTGTTTCTCTTTTCCTTGGTGTGGACCGTGGCTGGCACCATCAACGCAGACAGCAGAAAGAAA
TTTGATGTGTTTTTCCGCAACCTGATCATGGGCATGGATGATAACCACCCAAGGCCCAAAAGCGTCAAACTCACCAAAAACAACATCTTTCCAG
AAAGAGGAAGCATCTATGATTTTTATTTTATCAAACAAGCTAGTGGACATTGGGAAACGTGGACACAGTATATCACCAAAGAGGAGGAAAAAGT
TCCAGCTGGTGCAAAGGTCTCAGAACTCATCATCCCCACAATGGAGACAGCCCGGCAGTCCTTCTTCTTGAAAACCTACTTAGACCATGAGATT
CCAATGCTGTTCGTGGGTCCCACAGGCACTGGCAAATCAGCCATCACCAACAACTTCCTTCTCCACCTTCCCAAAAATACGTACCTACCCAACT
GCATCAATTTCTCTGCCAGAACCTCAGCCAATCAGACCCAGGATATCATCATGTCCAAGCTGGATCGACGACGGAAGGGCCTTTTCGGGCCTCC
CATAGGGAAGAAAGCAGTGGTGTTTGTGGATGACCTCAACATGCCAGCCAAAGAGGTGTATGGGGCCCAGCCACCCATCGAGCTCCTGAGGCAG
TGGATTGACCATGGTTACTGGTTTGACAAAAAAGACACAACCAGGCTGGACATCGTGGACATGCTGCTCGTGACAGCCATGGGGCCCCCCGGGG
GAGGAAGGAATGACATTACTGGACGATTCACTCGCCATCTGAATATCATTTCCATCAATGCCTTTGAGGATGACATTTTAACCAAGATTTTCAG
TTCGATTGTTGACTGGCACTTCGGGAAAGGGTTTGATGTGATGTTTTTAAGGTACGGAAAGATGCTGGTCCAAGCTACTAAGACAATTTATAGA
GATGCAGTGGAGAACTTCTTGCCAACTCCCTCGAAGTCACATTACGTCTTTAACCTGCGGGACTTCTCACGAGTGATTCAAGGGGTCCTGCTGT
GCCCTCACACACACCTGCAGGATGTAGAAAAATGTATCCGGCTTTGGATCCATGAGGTTTATCGGGTCTTCTATGATCGTCTGATTGACAAGGA
GGACAGACAGGTCTTTTTCAACATGGTGAAGGAAACCACCTCCAATTGCTTCAAGCAGACCATAGAGAAGGTGCTTATCCACTTGTCACCCACT
GGAAAGATAGTCGATGATAACATTCGAAGCCTCTTCTTTGGAGATTATTTCAAGCCAGAAAGTGACCAAAAAATCTACGATGAGATCACTGACC
TGAAACAGCTGACTGTGGTCATGGAGCACTATCTGGAAGAATTCAACAACATCAGCAAGGCCCCCATGTCCCTGGTCATGTTCAGGTTTGCCAT
TGAGCACATCTCTAGGATCTGCCGTGTCCTGAAGCAGGACAAAGGCCACCTGCTCCTGGTGGGCATAGGGGGCAGCGGGCGGCAAAGTGCCGCC
AAACTGTCCACATTCATGAACGCATACGAGCTATACCAGATTGAGATCACCAAGAACTACGCAGGCAATGACTGGCGAGAAGATCTTAAGAAGA
TCATACTGCAGGTCGGTGTGGCCACCAAGAGCACCGTGTTCCTCTTCGCCGACAACCAGATCAAGGATGAATCATTCGTGGAGGACATCAACAT
GCTTCTGAACACAGGTGACGTGCCTAACATCTTCCCTGCTGACGAGAAGGCTGACATCGTGGAGAAGATGCAGACTGCAGCCAGGACCCAAGGA
GAGAAGGTTGAAGTCACTCCTCTTTCTATGTATAACTTCTTTATTGAGAGGGTAATTAACAAAATCTCCTTTTCATTAGCCATGAGTCCAATAG
GGGATGCCTTCAGGAACCGCCTGCGGATGTTCCCTTCGCTGATCAATTGCTGTACGATTGATTGGTTCCAGTCCTGGCCCACAGATGCCCTAGA
GTTGGTGGCTAACAAATTTCTAGAGGATGTGGAGCTTGATGACAACATTCGGGTAGAGGTCGTGTCCATGTGCAAATATTTCCAAGAGAGCGTC
AAGAAGCTGTCACTCGATTATTACAACAAACTTCGAAGACACAACTATGTTACCCCCACCTCCTACCTTGAATTGATTCTAACCTTCAAGACGC
TCCTGAATAGCAAGAGGCAAGAGGTGGCTATGATGAGGAACCGCTACCTGACAGGCTTGCAGAAACTCGACTTTGCAGCTTCTCAGGTAGCGGT
TATGCAAAGAGAACTGACAGCTCTTCAACCTCAACTCATCCTCACCTCCGAGGAAACTGCCAAGATGATGGTGAAAATTGAAGCGGAGACGAGA
GAAGCTGATGGAAAGAAACTTCTGGTGCAGGCAGATGAAAAAGAAGCCAATGTTGCTGCTGCCATTGCCCAAGGAATCAAGAACGAATGTGAGG
GGGACCTAGCTGAGGCAATGCCTGCACTCGAGGCTGCACTAGCTGCTCTGGACACCCTGAACCCGGCCGACATCTCGCTGGTGAAGTCGATGCA
GAACCCACCAGGCCCTGTCAAACTGGTCATGGAGAGCATCTGCATCATGAAAGGGATGAAGCCAGAGAGGAAGCCAGACCCCAGTGGCTCCGGT
AAGATGATAGAAGATTACTGGGGGGTATCCAAAAAGATTCTTGGGGATCTGAAATTCTTGGAGAGTCTTAAGACATATGACAAAGACAACATCC
CCCCACTGACCATGAAGCGGATCCGGGAAAGGTTTATCAATCACCCGGAATTCCAGCCAGCTGTCATTAAAAATGTATCGTCGGCCTGCGAGGG
TCTGTGCAAGTGGGTGAGGGCCATGGAGGTGTACGATCGCGTGGCCAAGGTGGTGGCTCCCAAACGGGAGCGACTGAGGGAGGCAGAGGGGAAG
CTGGCTGCACAGATGCAGAAGCTGAACCAGAAAAGAGCAGAGCTGAAGCTGGTGGTAGATCGGCTCCAGGCCCTGAATGACGACTTTGAAGAGA
TGAACACCAAGAAAAAGGACTTGGAGGAAAACATTGAAATCTGCTCCCAAAAGCTGGTCAGGGCAGAGAAACTGATCAGTGGTCTTGGGGGAGA
GAAGGACAGATGGACCGAAGCTGCCCGACAGCTGGGGATCCGCTATACTAATCTGACTGGTGACGTGTTGCTGTCCTCAGGAACTGTGGCTTAC
CTGGGCGCTTTTACAGTGGATTATCGGGTCCAGTGCCAAAATCAGTGGTTGGCTGAATGTAAGGACAAGGTCATCCCTGGCTTCAGTGACTTCA
GTCTCAGCCACACGTTAGGGGATCCCATAAAAATCCGTGCCTGGCAGATTGCTGGGCTTCCCGTTGACTCCTTCTCCATCGACAATGGCATCAT
TGTATCCAATTCCAGACGCTGGGCCTTAATGATTGACCCTCACGGGCAGGCCAATAAATGGATTAAGAACATGGAGAAGGCGAATAAACTGGCT
GTCATCAAGTTCTCTGATAGCAACTACATGAGGATGCTGGAAAACGCGCTGCAGTTAGGCACCCCTGTCTTGATTGAAAACATTGGAGAAGAGC
TGGATGCTTCTATCGAACCTATCTTGCTCAAGGCAACATTCAAACAGCAAGGAGTTGAGTACATGAGGCTGGGTGAAAACATCATTGAATATTC
CAGGGATTTTAAGTTATACATCACAACCCGTTTGAGGAATCCACATTACCTCCCAGAAGTTGCCGTGAAGGTCTGTCTCCTCAACTTCATGATC
ACCCCCTTGGGTCTCCAAGATCAACTCCTTGGCATCGTGGCTGCGAAGGAGAAGCCAGAGCTGGAAGAGAAAAAGAACCAGTTGATTGTGGAAA
GTGCCAAGAACAAGAAGCATCTCAAGGAAATTGAAGATAAGATCTTGGAGGTTCTCTCCATGTCCAAGGGTAACATCCTGGAGGATGAAACCGC
CATCAAAGTTCTGTCCTCCTCCAAAGTGCTATCTGAAGAGATCTCAGAGAAACAGAAAGTTGCTTCCATGACAGAAACGCAGATTGACGAGACT
CGGATGGGCTACAAGCCAGTGGCTGTGCATTCTGCCACCATCTTCTTTGTATCTCGGACCTGGCCAACATCGAGCCGATGTACCAGTACTCCC
TGACTTGGTTCATAAATCTCTACATGCATTCCTTGACCCACAGCACGAAGAGCGAGGAACTGAATCTGCGCATCAAGTACATCATTGACCATTT
CACCCTGAGCATCTACAACAACGTGTGCCGTTCTCTGTTTGAGAAGGACAAGCTACTCTTCTCTCTCCTCCTGACCATCGGCATCATGAAACAG
AAGAAGGAAATTACGGAGGAGGTGTGGTACTTCCTTCTCACTGGAGGCATCGCACTGGATAACCCCTACCCCAATCCAGCTCCCCAATGGCTGT
CTGAGAAGGCATGGGCAGAGATTGTCCGTGCATCTGCCTTACCCAAACTGCATGGCCTGATGGAGCATTTGGAACAGAACCTGGGTGAATGGAA
GCTGATCTATGACTCGGCCTGGCCCCATGAGGAGCAACTCCCTGGGTCTTGGAAGTTCTCTCAAGGATTGGAGAAGATGGTGATCCTTCGATGT
TTGCGGCCTGACAAAATGGTGCCAGCGGTCCGGGAGTTCATTGCTGAACATATGGGAAAGCTGTATATCGAAGCCCCTACGTTCGATCTCCAGG
GATCCTACAATGATTCCAGCTGCTGTGCGCCTTTGATTTTTGTGTTGTCTCCAAGTGCAGACCCAATGGCAGGCCTGCTGAAGTTTGCTGATGA
TCTTGGTATGGGAGGTACCAGAACACAGACCATCTCCCTTGGCCAAGGCCAAGGCCCTATTGCTGCCAAAATGATCAACAATGCCATCAAAGAC
GGGACCTGGGTGGTCTTACAGAACTGCCACCTGGCCGCAAGCTGGATGCCTACCCTGGAGAAGATTTGTGAGGAGGTGATTGTTCCTGAGAGCA
CCAATGCCAGATTCAGACTCTGGCTAACCAGCTATCCATCAGAGAAGTTTCCAGTCAGCATTCTCCAGAATGGAATCAAAATGACCAATGAGCC
CCCCAAAGGGCTCCGGGCCAACCTGTTGCGCTCCTACCTCAATGACCCCATCTCAGATCCTGTGTTCTTCCAAAGCTGTGCAAAGGCGGTGATG
TGGCAAAAGATGTTATTTGGCCTTTGTTTCTTCCACGCCGTTGTTCAAGAGAGAAGAAACTTCGGCCCCCTAGGGTGGAATATTCCCTATGAAT
TCAACGAATCTGACCTGAGGATTAGTATGTGGCAGATCCAGATGTTTCTCAATGACTACAAGGAGGTGCCCTTTGATGCTCTGACCTACCTGAC
AGGGGAATGTAATTACGGAGGCAGAGTGACTGATGACAAAGACCGGCGTCTCCTGCTGTCACTTCTGTCCATGTTCTACTGTAAGGAAATTGAG
GAGGACTATTACTCCCTCGCTCCTGGAGACACTTACTACATCCCTCCTCATGGCTCCTACCAGTCCTATATCGACTATCTCAGGAATCTCCCCA
TCACAGCCCACCCAGAAGTGTTCGGCCTCCATGAGAACGCAGACATCACCAAAGACAACCAGGAAACCAACCAGCTGTTTGAGGGGGTCCTGCT
GACCCTCCCTAGACAGTCAGGAGGAAGTGGCAAGTCCCCTCAGGAAGTGGTTGAGGAGTTGGCACAAGACATTCTCTCCAAGCTTCCCAGAGAC
TTTGACCTGGAAGAGGTCATGAAGTTGTACCCCGTGGTCTATGAAGAATCCATGAATACCGTCCTAAGGCAGGAGCTCATCAGATTCAACAGGC
TGACCAAAGTGGTTCGGAGGAGCCTCATCAATCTTGGCCGAGCCATCAAAGGACAGGTCCTGATGTCCTCGGAGCTAGAGGAAGTCTTTAACAG
CATGCTTGTGGGTAAAGTGCCAGCCATGTGGGCAGCCAAGTCTTACCCATCACTGAAGCCTCTGGGGGGCTACGTGGCTGACCTGCTGGCCCGC
CTGACCTTCTTCCAGGAATGGATTGACAAGGGGCCCCCTGTGGTATTTTGGATCTCTGGATTCTACTTCACACAGTCTTTTTTGACTGGCGTCT
CTCAAAATTATGCCCGGAAATATACCATCCCCATTGACCACATTGGATTTGAGTTTGAGGTAACCCCACAAGAAACAGTGATGGAGAATAACCC
CGAAGATGGGGCCTACATCAAAGGGCTCTTCTTAGAAGGTGCCCGTTGGGACAGGAAAACGATGCAGATTGGGGAATCTCTCCCCAAAATCCTC

Fig. 9 (Continued)

TATGACCCACTGCCCATCATTTGGCTGAAACCTGGGGAGAGCGCAATGTTTCTGCATCAGGACATCTATGTGTGTCCAGTCTACAAAACAAGTG
CCCGCAGAGGAACCCTCTCCACCACAGGCCACTCTACCAACTATGTCCTCTCCATTGAGCTTCCAACAGACATGCCCCAGAAGCACTGGATAAA
CCGAGGGGTGGCCTCACTGTGCCAGCTGGATAACTGAID 42: DNAH5, *Homo sapiens*
ATGTTTAGGATTGGGAGGAGACAGCTCTGGAAGCATAGCGTCACTCGAGTTTTAACGCAAAGACTGAAGGGAGAGAAGGAAGCCAAGCGGGCTC
TTTTGGATGCGAGGCATAACTACTTATTTGCAATTGTGGCTTCCTGTTTGGACCTGAACAAAACCGAAGTGGAGGATGCCATTCTTGAAGGGAA
TCAGATTGAAAGAATTGATCAACTTTTTGCTGTTGGAGGTCTCCGACACCTCATGTTTTACTATCAAGATGTGGAGGAAGCAGAAACAGGACAA
CTTGGCTCTCTAGGAGGGGTAAATCTTGTTTCTGGAAAGATTAAAAAACCTAAGGTGTTCGTGACCGAGGGAAACGATGTGGCTCTTACTGGGG
TATGTGTGTTCTTCATCAGGACTGACCCTTCCAAAGCCATCACCCCTGACAACATCCACCAGGAGGTGAGTTTTAACATGTTAGATGCGGCAGA
TGGAGGCCTGCTCAACAGTGTGAGACGTTTGCTGTCGGACATCTTCATTCCTGCTCTCAGAGCCACGAGCCATGGCTGGGGCGAGCTCGAGGGC
CTTCAGGACGCAGCTAACATTCGCCAGGAGTTCTTGAGCTCCCTGGAAGGCTTTGTGAACGTCCTGTCGGGTGCACAGGAGAGTCTGAAGGAGA
AGGTGAACCTTCGAAAGTGTGACATACTTGAACTGAAAACCCTAAAGGAACCTACGGACTACTTGACTCTAGCAAATAACCCTGAGACTTTGGG
AAAAATAGAGGATTGCATGAAAGTATGGATCAAACAGACAGAACAGGTTCTTGCTGAAAACAATCAGCTGCTGAAGGAAGCGGATGACGTTGGG
CCACGAGCGGAGCTGGAGCACTGGAAAAAAAGACTCTCCAAGTTTAACTACCTTTTGGAACAATTGAAAAGCCCGGATGTGAAGGCTGTGCTGG
CAGTGCTTGCGGCGGCCAAGTCGAAACTGCTGAAGACTTGGCGGGAGATGGATATTCGAATCACTGATGCAACTAATGAAGCAAAGGACAATGT
GAAATACTTGTATACACTTGAAAAATGTTGTGACCCTTTGTACAGCAGTGATCCCCTATCCATGATGGATGCTATTCCTACACTTATAAATGCA
ATTAAAATGATCTATAGTATCTCTCATTACTATAATACCTCTGAGAAGATCACATCTCTGTTTGTAAAGGTGACAAATCAGATTATATCTGCAT
GTAAAGCCTATATTACCAATAATGGAACCGCTTCCATCTGGAACCAGCCACAGGATGTTGTTGAAGAAAAAATACTATCTGCGATTAAACTGAA
ACAGGAATACCAGCTCTGCTTTCACAAGACAAAACAAAAGCTTAAACAAAATCCAAATGCAAAACAATTTGATTTTAGCGAGATGTATATTTTT
GGAAAATTCGAAACTTTTCACCGACGCCTTGCCAAGATAATAGACATCTTTACAACCCTCAAGACGTATTCAGTCCTGCAAGATTCCACAATTG
AAGGGCTGGAAGACATGGCCACTAAATACCAGGGCATTGTGGCAACCATAAAGAAAAAGGAATACAATTTCCTAGACCAGCGGAAAATGGATTT
TGACCAAGATTACGAAGAGTTTTGCAAGCAGACTAATGACCTTCATAACGAGTTGCGGAAGTTCATGGATGTTACATTTGCAAAGATTCAAAAC
ACAAATCAAGCTCTAAGAATGTTGAAGAAATTTGAAAGATTGAATATACCTAATCTTGGTATTGATGACAAATATCAACTTATCCTTGAGAACT
ATGGGGCTGACATTGATATGATTTCAAAGCTGTATACAAAGCAGAAATACGATCCTCCTCTGGCTCGAAACCAGCCTCCCATCGCTGGAAAGAT
TTTGTGGGCCCGCCAGCTCTTCCATAGGATTCAGCAGCCCATGCAGCTTTTCCAGCAGCACCCAGCTGTGCTAAGCACGGCAGAAGCCAAACCT
ATAATTCGCAGTTACAACAGGATGGCCAAGGTCCTCCTGGAGTTTGAGGTCCTCTTCCACAGGGCGTGGCTTCGGCAAATTGAAGAAATTCATG
TAGGTCTTGAGGCTTCATTATTGGTGAAGGCTCCAGGCACAGGGGAATTGTTTGTAAACTTTGACCCTCAGATATTAATCTTATTTAGAGAAAC
AGAGTGCATGGCCCAGATGGGTCTGGAAGTCTCTCCACTGGCAACTTCCCTCTTCCAGAAACGAGATAGATACAAAAGGAACTTCAGTAACATG
AAGATGATGCTAGCTGAATATCAGAGAGTGAAGTCAAAAATACCTGCTGCCATTGAGCAATTGATTGTCCCTCACTTGGCCAAAGTGGATGAAG
CTCTCCAACCTGGCTTGGCTGCACTGACCTGGACATCACTGAATATTGAGGCTTATTTAGAAAACACTTTTGCAAAGATCAAGGACCTGGAGTT
GCTGCTTGACAGGGTCAATGATTTGATTGAGTTCCGCATTGATGCCATTCTAGAAGAAATGAGCAGCACGCCTCTTTGTCAGCTTCCCCAGGAG
GAGCCACTAACCTGTGAAGAGTTTCTCCAAATGACAAAGGATCTTTGTGTAAATGGTGCACAAATACTACATTTTAAAGCTCATTAGTGGAGG
AGGCAGTCAATGAGCTTGTAAATATGTTGCTGGATGTGGAAGTTTTATCTGAAGAAGAAAGTGAAAAAATATCCAATGAGAATAGTGTTAATTA
CAAAAATGAAAGTTCAGCAAAAAGAGAAGAAGGAAATTTTGACACCTTGACATCATCTATTAATGCCAGGGCCAATGCCCTGCTTTTGACGACA
GTCACGAGGAAAAAGAAAGAAACTGAGATGTTAGGGGAAGAAGCCCGCGAGTTACTCTCTCATTTCAACCATCAGAACATGGATGCTCTTCTGA
AAGTTACAAGGAATACACTAGAGGCCATTCGCAAACGTATTCATTCCTCTCACACAATTAACTTCCGGGACAGTAACAGTGCCTCTAACATGAA
GCAGAACAGTTTGCCCATTTTCCGGGCAAGCGTCACTCTGGCCATTCCCAACATCGTCATGGCCCCTGCCCTGGAAGATGTACAGCAGACCCTG
AACAAAGCCGTGGAGTGCATCATCAGTGTCCCTAAGGGGGTCAGACAGTGGAGCAGTGAACTGTTGTCCAAGAAAAAGATACAAGAAAGAAAAA
TGGCTGCTTTGCAGAGTAATGAAGACAGTGATTCTGATGTTGAAATGGAGAAAATGAACTTCAAGATACCTTGGAGATAGCATCTGTAAATTT
ACCCATTCCCGTGCAAACCAAGAACTATTATAAGAATGTTTCTGAAAACAAAGAGATTGTAAAATTAGTTTCTGTGCTTAGCACAATTATCAAC
TCCACCAAAAAGGAAGTTATTACATCCATGGATTGCTTCAAACGCTACAATCACATTTGGCAAAAGGGAAAAGAAGAAGCCATTAAGACATTTA
TTACACAGAGCCCCTTGCTTTCTGAATTTGAGTCCCAGATTCTCTATTTCCAAAACCTAGAGCAGGAAATTAATGCTGAGCCTGAATATGTCTG
TGTGGGTTCCATTGCTCTGTACACAGCTGACTTGAAGTTCGCCCTGACTGCTGAGACAAAGGCCTGGATGGTTGTCATTGGACGCCACTGTAAC
AAAAAATACCGGAGTGAGATGGAAAACATTTTTATGCTTATTGAAGAATTCAATAAGAAACTAAATCGTCCAATTAAGGACCTAGATGATATTC
GGATTGCAATGGCAGCGCTGAAAGAAATAAGGGAGGAGCAAATCTCCATTGACTTTCAAGTAGGACCTATTGAGGAATCTTATGCCCTGCTTAA
CAGATATGGACTTCTGATAGCAAGGGAAGAGATAGACAAAGTTGATACACTGCACTATGCTTGGGAGAAGCTGCTGGCACGTGCTGGCGAAGTC
CAGAATAAATTAGTCTCACTGCAGCCCAGTTTCAAGAAAGAGCTTATTAGTGCTGTGGAGGTATTCCTCCAAGATTGTCACCAGTTTTATCTGG
ACTATGATTTGAATGGTCCAATGGCTAGCGGCTTGAAGCCCCAGGAAGCCAGTGACAGGCTTATCATGTTTCAGAATCAATTTGATAATATCTA
TCGGAAATACATCACATATACTGGAGGAGAGGAGCTTTTTGGCCTGCCAGCTACACAGTATCCTCAGCTTCTTGAAATAAAGAAGCAACTAAAT
CTTCTACAGAAAATATATACTCTGTACAACAGTGTCATAGAAACTGTAAATAGCTATTATGATATTCTTTGGTCAGAGGTGAATATTGAAAAAA
TTAACAATGAACTCTTAGAATTCCAGAACAGATGTCGAAAGCTTCCCCGGGCCTTGAAGGACTGGCAGGCTTTTTTGGACCTGAAGAAGATCAT
TGATGATTTCAGCGAGTGTTGCCCGCTGCTGGAATACATGGCCAGTAAAGCCATGATGGAGCGGCACTGGGAAAGGATAACCACCCTCACCGGG
CACAGTCTGGATGTGGGGAATGAAAGCTTTAAGTTAAGAAATATCATGGAGGCACCTCTTCTGAAATATAAAGAGGAAATAGAGGACATCTGTA
TCAGTGCGGTGAAAGAGAGAGACATTGAGCAAAAGCTGAAGCAAGTGATTAATGAATGGGACAATAAAACATTCACCTTCGGCAGCTTTAAAAC
CCGTGGAGAGCTCCTCTTGAGAGGAGACAGTACCTCGGAAATCATCGCCAACATGGAGGACAGCTTGATGTTGCTGGGATCCCTACTGAGCAAC
AGGTACAATATGCCATTCAAAGCCCAGATTCAAAAATGGGTGCAGTACCTTTCCAACTCAACAGACATCATCGAGAGCTGGATGACGGTGCAAA
ACCTGTGGATTTATTTAGAAGCTGTCTTTGTGGGAGGAGACATTGCCAAGCAGCTGCCCAAGGAAGCCAAGCGGTTTTCTAACATAGATAAATC
TTGGGTGAAGATCATGACTCGGGCACATGAAGTGCCCAGTGTAGTCCAGTGCTGTGTTGGAGATGAGACCCTGGGGCAGCTGTTACCACACTTG
CTGGACCAGTTGGAAATATGCCAGAAATCCCTTACTGGGTACTTGGAGAAAAAACGACTGTGCTTTCCTCGGTTTTTCTTCGTCTCAGATCCTG
CCCTTCTAGAGATTCTGGGGCAGGCGTCGGACTCCCACACTATACAGGCCCATTTGCTGAATGTGTTTGACAACATTAAATCTGTCAAGTTCCA
CGAAAAGATCTATGATCGAATTCTGTCAATTTCCTCTCAAGAGGGTGAGACGATTGAATTGGATAAACCTGTCATGGCAGAGGGCAATGTGGAA
GTTTGGCTTAATTCTCTTTTGGAAGAATCTCAGTCCTCATTGCATCTTGTGATTCGCCAGGCAGCCGCAAATATTCAAGAAACAGGTTTCCAAC
TAACTGAATTTCTTTCATCCTTCCCTGCTCAGGTTGGATTATTAGGAATTCAGATGATATGGACACGGGATTCAGAAGAAGCCCTTAGAAATGC
CAAGTTTGATAAAAAAATCATGCAGAAAACTAATCAGGCTTTCCTGGAGCTACTCAATACATTGATAGACGTCACCACGAGGGATCTGAGTTCC
ACGGAACGAGTGAAATACGAGACTCTGATTACTATTCATGTGCACCAAAGGGATATCTTTGATGACCTGTGTCATATGCATATCAAGAGTCCCA
TGGACTTTGAGTGGCTGAAACAGTGCAGATTTTACTTTAACGAAGATTCTGACAAGATGATGATTCACATCACAGATGTGGCGTTCATATACCA
GAATGAATTTTTAGGCTGCACTGACAGGCTTGTAATAACTCCACTTACAGACAGATGTTACATCACGCTGGCTCAAGCTCTGGGAATGAGCATG
GGGGGAGCCCCTGCTGGACCTGCAGGCACAGGCAAAACAGAAACCACTAAAGACATGGGACGATGCCTCGGGAAATACGTCGTGGTTTTCAATT
GTTCAGACCAGATGGATTTCCGAGGACTTGGACGGATTTTTAAGGGACTGGCACAGTCTGGATCCTGGGGTTGTTTTGATGAATTTAACCGTAT
TGATCTACCAGTTCTCTCGGTTGCAGCCCAGCAAATTTCCATTATTCTGACATGTAAAAAGGAGCACAAAAAGTCTTTTATCTTTACTGATGGA
GATAATGTGACTATGAACCCTGAATTTGGCTTTTCTTAACCATGAATCCTGGCTATGCCGGACGGCAGGAACTCCCTGAAAACTTGAAGATTA
ATTTCCGCTCAGTGGCCATGATGGTGCCTGACCGTCAGATTATCATAAGGGTGAAGTTGGCTAGTTGTGGCTTCATTGACAACGTTGTTTTGGC
CAGGAAGTTTTTCACGCTCTACAAACTGTGTGAGGAGCAGCTTTCTAAGCAGGTTCATTATGACTTTGGCCTGCGTAACATTCTGTCAGTTCTT
CGGACCTTGGGAGCAGCAAAAAGAGCCAATCCAATGGATACGGAGTCCACGATTGTCATGCGTGTACTACGGGACATGAATCTTTCTAAACTGA
TTGATGAGGATGAACCCTTGTTTTTGAGTTTGATTGAAGATCTCTTTCCAAATATTCTTCTGGACAAGGCAGGTTACCCTGAACTGGAAGCAGC
AATTAGTAGACAGGTTGAAGAAGCTGGTTTAATCAACCATCCTCCTTGGAAACTGAAGGTCATCCAGCTATTCGAAACGCAGAGAGTGCGACAT
GGGATGATGACTCTGGGGCCCAGTGGGGCTGGAAGACCACCTGCATCCACACCTTGATGAGAGCCATGACAGATTGTGGAAAACCACATCGGG
AAATGAGGATGAATCCCAAAGCGATTACTGCCCCACAGATGTTTGGTCGGCTGGACGTTGCCACAAATGACTGGACTGATGGGATATTTTCTAC
GCTTTGGAGGAAAACATTAAGAGCAAAGAAAGGGGAACATATCTGGATAATTCTTGATGGTCCAGTAGATGCCATCTGGATTGAAAATCTGAAT
TCTGTTTTGGATGATAACAAAACTCTAACCCTTGCCAATGGTGATCGGATTCCCATGGCTCCAAACTGCAAGATCATTTTCGAGCCTCATAACA
TTGACAATGCTTCTCCTGCCACCGTCTCAAGAAATGGAATGGTTTTCATGAGCTCTTCTATCCTTGATTGGAGTCCTATTCTTGAGGGTTTTCT

Fig. 9 (Continued)

TAAGAAACGCTCACCTCAAGAAGCAGAAATTCTTCGTCAGCTGTACACCGAGTCTTTCCCAGACTTGTATCGCTTCTGTATCCAGAACTTAGAA
TACAAGATGGAGGTGCTGGAGGCCTTTGTCATCACACAGAGCATTAACATGCTTCAAGGCCTGATTCCTCTGAAGGAGCAAGGCGGGGAGGTGA
GCCAGGCTCACCTGGGGCGGCTGTTCGTGTTCGCGCTGCTGTGGAGCGCGGGGGCGGCGCTGGAGCTGGACGGACGGCGCCGCCTGGAGCTCTG
GCTGCGCTCTCGGCCCACAGGGACGCTGGAGCTGCCGCCGCCAGCGGGGCCCGGGGACACCGCCTTCGACTACTATGTGGCGCCCGATGGTACA
TGGACGCACTGGAACACGCGTACCCAGGAATACCTGTATCCGTCTGATACCACCCCAGAGTATGGTTCTATTCTGGTGCCAAATGTTGACAATG
TGAGGACTGACTTTCTAATTCAAACCATTGCTAAACAGGGCAAGGCTGTGCTATTAATTGGTGAACAAGGAACAGCCAAAACAGTAATAATTAA
AGGATTTATGTCAAAATATGATCCTGAATGTCACATGATCAAGAGTCTGAATTTTTCTTCTGCAACCACCCCACTGATGTTCCAGAGGACGATA
GAGAGCTATGTGGATAAACGAATGGGTACAACATATGGCCCTCCTGCGGGAAAGAAGATGACTGTTTTTATTGATGATGTGAATATGCCAATAA
TCAATGAGTGGGGAGATCAGGTTACGAATGAGATAGTGCGACAGCTGATGGAACAAAATGGATTCTATAATCTAGAGAAGCCTGGGGAGTTCAC
CAGCATCGTGGACATCCAGTTTTTGGCAGCCATGATCCATCCTGGTGGTGGACGCAATGACATACCCCAAAGACTCAAGAGGCAGTTCTCTATA
TTTAATTGCACGTTGCCCTCTGAAGCTTCTGTGGACAAGATCTTTGGTGTGATTGGGGTAGGCCACTACTGTACTCAGAGGGGGTTTCTCAGAAG
AAGTGAGAGATTCTGTGACAAAATTGGTGCCTCTGACACGCCGACTATGGCAGATGACCAAGATTAAAATGCTTCCTACCCCTGCAAAATTCCA
TTATGTGTTTAACCTACGAGATCTTTCTCGGGTCTGGCAGGGAATGCTGAACACTACTTCAGAGGTCATCAAGGAACCAAATGATCTGTTAAAG
CTGTGGAAGCATGAGTGTAAACGTGTTATAGCTGACCGTTTCACAGTGTCCAGTGATGTGACCTGGTTTGATAAGGCTTTAGTAAGTTTGGTAG
AGGAGGAGTTTGGTGAAGAGAAAAAACTCTTGGTGGATTGTGGAATTGACACATATTTTGTGGATTTCTTGAGAGATGCACCTGAAGCTGCAGG
TGAAACATCTGAAGAGGCTGATGCTGAAACACCTAAAATTTATGAGCCAATTGAATCTTTTAGTCACCTAAAAGAGCGTCTGAATATGTTCCTG
CAGCTCTATAATGAGAGCATCCGTGGCGCCGGCATGGACATGGTGTTCTTTGCAGATGCCATGGTTCACTTAGTCAAGATCTCTCGTGTCATTC
GTACTCCTCAGGGAAATGCCCTCCTGGTCGGGGTGGGCGGATCAGGAAAGCAGAGCCTGACGAGGTTGGCTTCATTCATTGCTGGCTACGTTTC
CTTCCAGATCACTCTGACGAGATCCTACAACACATCAAATCTGATGGAAGATCTGAAGGTTTTGTATCGAACAGCTGGTCAGCAAGGCAAAGGA
ATCACTTTTATTTTCACAGACAATGAGATTAAAGATGAGTCATTTTTGGAATATATGAACAATGTTTTATCATCAGGTGAGGTCTCTAACCTAT
TTGCTCGAGATGAAATTGATGAAATTAATAGCGACCTGGCATCAGTCATGAAAAAAGAATTCCCCAGGTGCCTTCCTACCAATGAGAACCTGCA
CGACTACTTCATGAGTCGGGTCCGACAGAACCTTCATATTGTGCTCTGCTTCTCGCCAGTGGGGGAGAAATTTCGAAACAGAGCTTTGAAGTTC
CCTGCCCTAATTTCAGGATGCACAATTGACTGGTTCAGCCGATGGCCCAAAGATGCTTTAGTTGCTGTGTCTGAACACTTCCTCACTTCCTATG
ATATTGACTGCAGTTTGGAAATCAAGAAGGAGGTGGTCCAATGCATGGGCTCCTTCCAGGATGGGGTGGCTGAGAAGTGTGTTGATTATTTTCA
GAGATTCCGACGTTCTACCCACGTGACGCCCAAATCATACCTCTCCTTTATTCAGGGCTATAAGTTCATATATGGAGAAAAGCATGTGGAGGTG
CGGACCCTGGCCAACAGAATGAATACTGGATTGGAAAAGCTCAAAGAAGCTTCAGAGTCTGTTGCAGCCTTGAGTAAAGAACTGGAAGCGAAAG
AAAAGGAGCTACAAGTGGCCAACGATAAAGCCGACATGGTCTTAAAAGAAGTGACAATGAAAGCACAGGCTGCTGAAAAGGTCAAGGCTGAGGT
ACAGAAGGTGAAGGACAGGGCCCAGGCCATTGTGGACAGCATCTCTAAAGACAAAGCCATTGCTGAAGAAAAACTGGAAGCAGCAAAACCAGCT
TTAGAAGAGGCAGAAGCTGCATTGCAGACCATCAGGCCTTCGGACATCGCCACTGTTCGCACGTTGGGCCGCCCCCCTCACCTCATCATGCGGA
TCATGGATTGCGTACTGCTGCTGTTTCAAAGGAAAGTCAGTGCTGTGAAAATTGACCTGGAAAAAAGCTGTACCATGCCCTCCTGGCAGGAATC
CTTAAAATTGATGACTGCAGGGAACTTTTTACAGAACTTACAGCAATTCCCAAAAGACACAATCAATGAAGAGGTGATAGAATTTTTGAGTCCT
TACTTTGAAATGCCTGACTATAACATCGAAACTGCTAAACGCGTATGTGGAAATGTAGCTGGTCTTTGTTCCTGGACGAAAGCTATGGCTTCCT
TCTTTTCTATAAACAAAGAAGTACTGCCTCTGAAGGCCAACTTGGTGGTGCAAGAGAATCGCCATCTCCTGGCCATGCAGGATCTGCAGAAAGC
CCAGGCCGAGTTGGATGACAAGCAGGCGGAACTTGACGTGGTGCAGGCTGAGTATGAACAGGCCATGACTGAAAAGCAGACCTTGCTTGAAGAT
GCAGAGCGATGCAGACACAAGATGCAGACAGCTTCCACGCTCATCAGTGGCTTGGCAGGTGAAAAAGAAAGATGGACAGAGCAAAGCCAAGAGT
TTGCTGCACAAACTAAAAGACTTGTAGGGGATGTACTGTTGGCTACAGCTTTTCTATCTTATTCTGGTCCATTTAACCAAGAGTTTCGTGATCT
TCTGTTAAATGACTGGCGGAAGGAAATGAAAGCCCGGAAAATTCCATTTGGAAAGAACCTAAATCTCAGTGAGATGTTGATTGATGCTCCTACT
ATTAGTGAATGGAACCTCCAAGGTCTGCCAAATGATGACTTGTCCATTCAAAATGGAATTATTGTCACGAAGGCATCTCGTTACCCTTTGTTAA
TTGATCCACAGACTCAAGGCAAGATCTGGATTAAAAATAAAGAAAGCCGAAATGAACTCCAGATCACGTCTTTAAATCACAAGTACTTCAGAAA
CCACCTGGAAGACAGCCTTTCTCTTGGAAGGCCTTTGCTTATTGAAGATGTTGGAGAGGAACTAGATCCAGCACTAGATAATGTTTTGGAAAGA
AACTTCATTAAAACTGGGTCTACCTTTAAGGTGAAAGTTGGTGACAAGGAAGTAGATGTGTTGGATGGCTTTAGACTCTACATTACCACCAAAT
TGCCTAACCCAGCCTACACCCCTGAGATAAGTGCCCGTACCTCCATCATTGACTTCACTGTCACCATGAAAGGTCTAGAAGATCAGTTACTGGG
GAGGGTCATTCTCACAGAGAAGCAGGAATTGGAGAAAGAAAGAACTCATCTGATGGAAGATGTAACTGCAAACAAAAGAAGGATGAAGGAACTA
GAAGATAACTTGCTTTACCGCCTGACAAGTACCCAGGGGTCCCTGGTAGAAGATGAAAGTCTCATTGTCGTGCTGAGTAACACAAAAAGGACAG
CCGAGGAGGTGACACAGAAGCTAGAAATTTCTGCTGAGACAGAAGTTCAAATTAACTCAGCCCGGGAGGAATACAGACCTGTGGCTACGCGGGG
CAGCATCCTCTACTTCCTCATTACTGAGATGCGCTTGGTTAATGAGATGTATCAGACTTCGCTTCGCCAGTTTCTGGGCTTATTTGACCTTTCC
TTAGCCAGGTCTGTCAAGAGCCCGATTACAAGCAAGAGGATTGCTAATATCATCGAGCACATGACCTACGAGGTTTATAAGTATGCTGCCCGAG
GGCTGTACGAGGAGCACAAATTCCTGTTCACCTTGTTGCTTACCCTAAAGATTGACATCCAGAGGAACCGAGTCAAGCATGAAGAGTTTCTCAC
TCTTATTAAAGGAGGTGCCTCATTAGACCTTAAAGCTTGTCCTCCAAAACCATCAAAATGGATCCTGGACATAACATGGCTGAATTTGGTGGAA
CTTAGCAAACTCAGACAGTTTTCAGATGTCCTTGACCAGATATCGAGAAATGAGAAAATGTGGAAAATTTGGTTTGATAAGGAAAACCCGGAGG
AGGAACCTCTTCCAAATGCCTATGATAAATCTCTTGACTGCTTCAGACGTCTTCTCCTTATTAGATCCTGGTGTCCTGACAGAACCATCGCCCA
GGCCCGCAAGTACATCGTGGACTCCATGGGAGAAAAATATGCCGAAGGTGTTATTTTAGACTTGGAGAAGACGTGGGAGGAATCTGATCCACGG
ACGCCACTCATCTGTCTCCTGTCTATGGGCTCAGACCCCACAGATTCCATCATTGCCTTGGGGAAGAGATTAAAAATAGAAACCCGTTATGTGT
CCATGGGCCAGGGCCAGGAAGTCCATGCTCGGAAGCTCTTGCAGCAGACCATGGCGAACGGAGGATGGGCACTTCTGCAGAACTGCCATCTGGG
ACTTGATTTCATGGATGAGCTGATGGACATAATCATAGAAACTGAGCTTGTACATGATGCGTTCCGCCTCTGGATGACCACCGAGGCTCATAAG
CAGTTTCCCATTACACTCCTTCAGATGTCCATTAAATTTGCCAACGATCCTCCACAAGGACTCCGGGCAGGACTGAAAAGAACATATAGTGGTG
TCAGCCAAGACCTGCTGGACGTGAGCTCTGGGTCCCAGTGGAAGCCCATGCTGTACGCAGTGGCTTTCCTGCACTCCACTGTCCAGGAGAGGCG
CAAGTTCGGTGCCCTGGGGTGGAATATCCCCTACGAATTTAACCAAGCGGACTTTAATGCCACTGTGCAGTTCATCCAAAACCACTTGGATGAC
ATGGATGTCAAAAAGGGTGTCTCCTGGACCACCATCCGCTACATGATAGGAGAGATTCAATATGGAGGCAGAGTCACTGACGACTATGATAAGA
GATTGTTGAACACATTTGCTAAGGTTTGGTTCAGTGAAAATATGTTTGGACCAGATTTCAGTTTTTACCAAGGATACAATATTCCAAAATGCAG
CACAGTGGATAACTATCTTCAGTATATCCAGAGTTTGCCTGCCTATGACAGCCCTGAGGTGTTTGGGCTGCACCCCAATGCTGACATCACCTAC
CAGAGCAAGCTGGCCAAGGACGTGCTGGACACCATCCTAGGCATCCAACCCAAGGACACCTCTGGTGGAGGGGATGAGACCCGGGAGGCGGTGG
TGGCCCGGCTGGCTGATGATATGCTGGAGAAGCTGCCCCCAGACTATGTCCCCTTTGAAGTAAAAGAGAGGCTGCAGAAGATGGGGCCATTCCA
GCCTATGAACATTTTCCTCAGGCAGGAAATAGACAGAATGCAAAGGGTACTCAGCCTTGTCCGCAGCACCCTCACTGAGCTGAAACTTGCTATT
GATGGCACCATCATCATGAGCGAAAATCTGCGAGATGCATTGGATTGCATGTTTGATGCTAGAATCCCTGCTTGGTGGAAAAAAGCTTCTTGGA
TTTCTAGTACACTGGGTTTCTGGTTTACTGAACTTATAGAAAGAAACAGCCAGTTTACCTCGTGGGTTTTCAATGGCCGACCTCACTGCTTTTG
GATGACGGGTTTTTTTAACCCCCAGGGATTTTTAACTGCAATGCGACAGGAAATAACTCGGGCCAACAAAGGCTGGGCTCTGGACAATATGGTG
CTTTGCAATGAAGTCACCAAATGGATGAAGGACGACATTTCTGCCCCTCCCACAGAGGGTGTCTATGTCTATGGCTTATATCTTGAAGGTGCTG
GCTGGGACAAGAGGAACATGAAACTCATTGAATCAAAGCCAAAAGTGCTCTTTGAGTTCATGCCTGTCATAAGGATTTATGCAGAAAACAATAC
TTTACGAGATCCTCGGTTTTACTCCTGTCCCATCTATAAGAAGCCAGTTCGAACGGACTTGAACTACATTGCCGCTGTGGATCTCAGGACAGCC
CAGACCCCTGAACACTGGGTGCTCCGTGGGGTTGCCCTTCTGTGTGATGTCAAGTAA

ID 43: DNAH6, *Homo sapiens*

ATGACTTTTCGGGCCACAGATAGTGAATTTGACCTGACAAATATTGAAGAGTATGCCGAAAATTCTGCACTTTCAAGACTGAATAATATAAAAG
CCAAACAAAGAGTGAGTTATGTGACATCCACAGAAAATGAATCTGATACACAAATCCTAACGTTTAGGCACATTACAAAAGCTCAGGAGAAGAC
AAGAAAACGACAGCAGCCTATAAAACTAGAGCCTTTGCCAGTGCTAAAAGTCTACCAAGATCATAAGCAGCCAGAATACATACATGAACAGAAC
CGATTTCAGTTAATGACTGCAGGAATCATTAAACGTCCAGTAAGCATAGCAAAAAAAAGTTTTGCCACATCATCTACTCAGTTTCTTGAGCATC
AAGATGCTGTGAAAAAAATGCAGATTCATCGGCCCTATGTTGAGGTGTTCTCTCCCTCTCCTCCTAAACTGCCACATACTGGTATTGGAAAAAG
AGGTCTCTTTGGGACTAGATCTTCAGCTTACCCTAAGTACACTTTTCACGACCGAGAAGAAGTTGTTAAAGCCAACATTCGTGATCCCTTGCAA
ATCATTAAAATAATACGTGAAAATGAACATCTTGGATTTCTTTATATGATCCCTGCAGTGCCAAGATCATCCATTGAATATGATACATATAATC

Fig. 9 (Continued)

TAAAAGTTGTAAGTTATGAGAACATCAATAAAAATGACTACTATACTATTAGCCAAAGGGCAGTAACACACATTTATAATGAAGACATTGAATT
TATCGAAATTGATCGATGGGAACAGGAATATCTGTATCACAGAGAACTCACTAAGATTCCCATATTTTCACTGTTCCGGAAATGGAAGGCTTTT
AGTGTATGGAGGAAGAATGTCCGCTCCAAGAAAATCACTGGATGTCAAAAATCTCTACAAAAAAATTTGTTCATTGTTAATCCTCATTTGCGAC
CAGCTCTTCTTAAAATAAATGAATTGTGTTATCATTTGAGTTTTATGGGACTTTGTTATATTGAAAAGTGTCACACCTACACCCTGCAGGAATT
TAAGGCCGCACAAGTCATACGGCTAGCAGAGGTGACAGAACGCCTAGGAGAATTTCGAAATGAGGCAAAATATGTAGTCAGGAGGGCTTGTCGA
TTTGCTTTGCGTGCTGCAGGATTTGTTCCTGATGACTGTGCATTTGGACCTTTTGAGGATTATCATAAAGTGCAGAGCAGTGGAAGTTTCATTA
ATACACCACATGAGTTGCCCACTTATGGAGACTCTGAGAAAATGACATATACAGAACAGGCCAGCAAAAGGCATTATTGCATGAGGCTGACGTG
CTTTATTCGTCTAAACGACTATCTAATTGAGAACACAATGCACATCTTAACGGTAAATGCTGTTAATTCGCTTTTGAACCATCTCACTGACAAG
CTAAAACGAACACCTTCAGCAGATGTCATTCAGAAATGGATTACTGAAGAGAAGCCTGAAGTCCCTGATAAAAAGGGGACCCTTATGGTGGAAA
AGCAAGAAGAAGATGAATCTCTCATCCCCATGTTTCTCACAGAACTAATGTTGACAGTCCAGTCACTGCTCTTTGAGCCTTCTCTGGAAGACTT
TCTGGATGGTATTTTGGGTGCAGTTAATCACTGTCAAAACACTGTGTTATCAGTTCCTAATCTCGTGCCTGATTCGTATTTTGATGCTTTCACC
AGCCCTTATATTAACAACAAACTTGAAGGAAAAACCTGTGGAACTGGGCCAAGTTTAGCAGCAGTATTTGAGGATGATAAGAATTTTCACACAA
TTATTTCTCAAATAAAGGAAACCATTCAGGCCGCATTTGAATCAGCCCGCATCTATGCAGCTACCTTTGAAAAGTTCCAGATATTCTTCAAGGA
AAATGAAAGTCTTGATTTACAAGCTCTTAAACTTCAGGAACCTGATATTAACTTTTTTAGTGAACAACTGGAAAAATATCACAAACAGCACAAG
GACGCAGTAGCGCTCAGACCCACCAGAAATGTAGGATTGCTGCTCATTGATACTAGGCTTCTAAGAGAAAAATTAATTCCATCACCTTTGCGAT
GCTTAGAGGTGCTAAATTTTATGCTTCCTCGTCAAAGCAAGAAAAAAGTGGATGCCATTATCTTTGAGGCACAAGATGCAGAGTATAAACTTGA
GTTTGTTCCAACTACTACCACAGAATATGTTCATAGCTTATTATTTCTTGATGAAATTCAGGAACGGATTGAAAGCCTTGAAGATGAGGGGAAT
ATAGTGACTCAAATGTACAAGCTTATGGAACAATATCAGGTGCCCACACCTCCTGAAGACTTTGCTGTTTTTGCAACTATGAAGCCATCCATTG
TTGCTGTTCGGAATGCCATTGATAAATCAGTGGGTGATAGAGAATCAAGCATTAAGCAATTTTGTGTGCATTTGGGTAGTGATCTTGAAGAATT
AAACAACGAAGTGAATGAAGTAAAACTGCAAGCACAGGATCCACAGATTTTAGATATCTCTGCTGACCAAGACAAAATAAGGCTCATATTGAAT
AATCTGCAATCTGTTCTGGCTGATCTTCAGAAACGTGCATTTCAGTATAAGTCCTATCAGAAGAATTTTAAGGTAGAAGTGTCCAAGTTTGAAG
CTTTGGAAGAAGTCAGTGCTGAACTGAAGCTCAAACAATTGCTCTGGATTCTTTCTCTGAATGGGATAAACTCCAACAAGAATGGTTAAAGTC
CAAATTTGATTGCCTGGATCCAGAAGTCCTAAACGGTCAAGTTTCTAAATATGCTAAATTTGTGACTCAACTGGAAAAAGGCTTGCCACCCAAC
AGTGTAGTGCCCCAGCTCAAATACAAGGTGGAAAAAATGAAAGAAAAGCTTCCAGTTATCATTGACTTGAGGAACCCGACTTTGAAGGCAAGAC
ATTGGGCAGCTATTGAACAAACAGTTGATGCCACTCTAGTGGATGCTGAAATTCCATTAACCTTGGAGAGGCTCTCCCAGTTGCATGTTTTTGA
CTTTGGTCAAGAAATCCAGGACATATCTGGACAGGCTTCTGGAGAAGCTGCCTTAGAAGCAATTCTTAAAAAGGTGGAGGACTCTTGGAAAACA
ACTGAATTTGTCATTCTGCCTCACCGTGACTCCAAAGATGTGTTTATACTGGGCGGCACAGATGACATACAGGTCCTTCTTGATGATAGCACCA
TCAATGTTGCAACTCTTGCCTCATCACGTTACCTTGGTCCACTGAAAACTCGAGTGGATGAATGGCAAAAACAACTTGCTTTATTTAATCAAAC
ACTGGAAGAGTGGCTGACCTGCCAGAGAAACTGGCTCTACCTAGAAAGTATTTTCAATGCTCCAGACATTCAGAGGCAATTGCCTGCAGAGGCC
AAGATGTTCCTTCAGGTGGATAAGTCATGGAAAGAAATCATGAGAAAGGTGAATCGGCTGCCTAATGCTCTTCGAGCCGCTACTCAGCCAGGAC
TTCTGGAAACTTTTCAAAACAATAATGCATTACTTGACCAAATTCAGAAGTGCCTAGAGGCATACTTAGAATCAAAAAGAGTTATCTTTCCAAG
GTTTTACTTCTTGTCAAATGATGAACTTCTGGAGATTTTGGCCCAGACACGAAATCCACAGGCCGTGCAGCCACACTTAAGGAAATGCTTCGAC
TCCATTTCAAAGCTCGAATTTGCTCTCATGCCTCCTGCCGAAGGAAAGATTCCTGGTATTGATGGAGAACCAGAAAAGGTTTATACTAATGATA
TTTTAGCAATGCTGTCACCAGAGGGAGAAAGGGTTAGCTTGGGGAAAGGCCTCAAGGCCCGAGGCAATGTAGAGGAATGGCTTGGTAAAGTGGA
AGAAGCCATGTTCACATCTCTGCGTCGCCTGTGCAAAGCTGCCATCGCTGACTATCAGGGGAAACTGAGGACAGACTGGGTGGTTGCTGGCCAC
CCTTCTCAAGTTATCCTGACTGTTTCTCAAATTATGTGGTGCCGTGATTTGACTGAATGTCTGGAAACAGAACACAGTAATCATATACAGGCCC
TGAAGAATTTTGAAAAAGTAAATTTTGAGAGATTAAATGCCCTAGCTGCAATAGTTCAAGGCAGTCTTCCTAAATTACACAGAAACATCCTAAC
TGCATTGATTACTATTGATGTGCATGCAAGAGATATAGTCACTGAACTTGTTCAATCCAAGGTGGAGACAGTTGAATCTTTTGACTGGCAGAGA
CAACTGCGCTATTACTGGGATATAGACCTGGATAATTGTGTGGCTAGAATGGCGCTCTCTCAGTACACTTATGGCTATGAATATTTGGGTGCAT
GCCCAAGATTGGTTATTACTCCACTCACAGATCGCTGCTATCTTTGCCTCATGGGAGCTTTGCAGCTTGACCTTGGGGGTGCACCAGCTGGTCC
TGCTGGCACTGGGAAAACAGAGACTACCAAAGATCTGGCAAAAGCTCTTGCCATCCAGTGTGTGGTCTTTAACTGTTCAGATGGTTTGGACTAC
AAGATGATGGGGCGCTTCTTCAGTGGCTTGGCACAGTCAGGGGCCTGGTGCTGCTTTGATGAATTTAATCGAATTGACATAGAAGTTCTGTCCG
TCATCGCGCAGCAACTCATTACCATTAGGAACGCCAAAGCGGCAAAGCTCTCTAGATTCATGTTTGAGGGGCGGGAAATAAAGTTGGTGATGAC
TTGTGCAGCCTTCATCACAATGAATCCTGGCTATGCAGGGAGAACTGAATTGCCAGATAATTTGAAAGCCCTGTTTAGACCATTTGCGATGATG
GTTCCAAATTATGCCTTGATTGCAGAGGTAATTCTATATTCTGAAGGATTTGAATCCAGTAAAATATTAGCAAGAAAAATGACTCAGATGTATA
AGCTTTGCAGTGAGCAGCTGTCTCAGCAGGATCACTACGACTTTGGCATGAGAGCTGTGAAGTCTGTCCTGGTCATGGCTGGATCTTTAAAAAG
AGAAAACCCAGACCTAAATGAAGATGTGGTGTTGATAAGAGCTTTACAAGACTCCAATTTGCCAAAATTTCTAACAGATGATGCTCTTCTGTTC
AGTGGAATCATATCTGACCTTTTTCCTGGAGTCCAAATTCCAGAACATGATTATGGTATTTTACAATCAACAATTGTGGATGTCATGAATAGAC
AAAATCTTCAGCCTGAGATGTGTATGGTTAGAAAGGTGATACAGTTTTATGAAACTATGCTAGTAAGGCATGGTGTTATGTTAGTCGGGCCAAC
AGGAGGCGGCAAGACCACAGTTTACCGAATACTAGCAGAAACTTTAGGGAATTTACAAAAACTTGGGATAGAAAATTCCTTTTACCAAGCAGTT
AAAACATATGTTCTCAACCCTAAATCAATTACCATGGGTGAATTATATGGAGAGGTTAATAACTTAACCTTGGAATGGAAAGATGGTTTGATGG
CACTAAGTGTCCGAGCAGCTGTGAATGATACTTCAGAAGACCATAAATGGATCATCAGTGATGGGCCAGTAGATGCTCTTTGGATTGAAAACAT
GAATACAGTGCTGGATGATAACAAGATGCTTTGCCTGGCTAACAGTGAGAGGATTAAACTCACACCTCAAATTCACATGCTTTTTGAGGTGCAA
GATCTGCGGGTTGCCTCCCCTGCAACAGTCAGTCGATGTGGAATGGTGTTTGTGGATCCTGAAGAACTGAAATGGATGCCTTATGTTAAAACTT
GGATGAAGGGTATTTCTAAAAAACTGACTGAGGAAACCCAAGAATATATATTGAATCTTTTCCAACGTTATGTTGATGAAGGTTTACATTTTAT
CAATAAAAAGTGCAGCCAAGCAATTCCACAAGTGGACATCAGCAAAGTTACTACACTCTGTTGCTTATTGGAGTCCTTGATACTTGGGAAAGAT
GGAGTTAACTTGGCAATGGAACAAACAAAATTGAACACTATACTATGTCAGACTTTTGTATTCTGTTATTTGTGGTCTTTGGGTGGAAACCTAA
CTGAAAACTACTATGATTCTTTTGATACATTTATTAGAACACAATTTGATGATAATCCTGATGCCAGGCTTCCCAATTCTGGTGATCTGTGGAG
CATTCATATGGACTTTGACACCAAACGGCTGGATCCCTGGGAACGAATCATACCTACTTTCAAATACAACCGAGATGTTCCATTTTTTGAAATG
CTTGTCCCCACAACTGACACAGTGCGCTATGGGTATCTAATGGAAAAACTACTGGCAGTCAAGCATTCCGTGTTGTTTACTGGAATAACTGGAG
TGGGCAAGTCTGTGATTGCAAAAGGATTGCTAAATAAAATTCAAGAATCAGCTGGCTATGTCCCTGTTTATCTAAATTTTTCTGCTCAAACTTC
ATCTGCAAGGACACAAGAGATCATTGAGTCAAAACTGGAGAGAAAAAGAAAAAATATTCTAGGAGCACCGGGAAACAAACGAATTGTGATTTTT
GTTGATGATTTAAACATGCCCAGACTGGATCGCTATGGCTCTCAGCCTCCGATTGAATTACTTCGGCAGTATCAAGATTTTGGGGGATTTTATG
ACAGAAACAAACTGTTTTGGAAAGAAATACAGGATGTAACAATCATATCGGCATGTGCACCTCCAGGCGGTGGCCGCAACCCTGTGACTCCCCG
CTTCATCAGACACTTCAGCATGCTGTGCCTCCCAATGCCCTCAGAGCACAGTCTGAAACAGATTTTTCAGGCCATCTTAAATGGTTTCCTGAGT
GACTTTCCACCAGCTGTAAAGCAAACTGCATCAAGCATTGTAGAAGCCTCAGTTGAGATTTATAACAAAATGAGTGTTGACCTCCTGCCAACAC
CCGCCAAGTCCCATTATGTCTTTAACTTGAGGGACTTATCCAAATGTGTGCAAGGTATCCTCCAATGTGATCCAGGAACAATAAGAGAAGAAAT
TCAGATATTTAGACTCTTTTGCCATGAGTGCCAAAGGGTCTTCCATGATCGCTTGATTAATAATGAAGATAAGCACTATTTCCATGTTATTCTG
ACAGAAATGCCAACAAACATTTTGGAATTGCAATTGACCTGGAATATTTTTTGAATAAGCCCATCATATTTGGAGATTTCATTAAGTTTGGAG
CAGATAAAGCTGATCGGATTTATGATGACATGCCTGATATAGAGAAAACTGCAAATGTTCTACAGGACTATCTTGATGATTATAATCTCACAAA
TCCCAAAGAAGTAAAGTTGGTGTTCTTCCAGGATGCTATAGAACATGTTTCAAGGATTGCTCGGATGATACGTCAAGAAAGAGGCAATGCCCTG
CTTGTTGGAGTAGGAGGCACAGGAAAGCAGTCACTCACGAGACTTGCAGCTCATATATGCGGTTACAAATGTTTGCAGATTGAACTCAGCCGGG
GATATAATTATGATAGTTTTCATGAAGACCTGAGGAAGTTGTACAAAATGGCTGGTGTAGAAGACAAGAATATGGTTTTCCTTTTCACTGACAC
CCAGATTGTAGTGGAGGAGTTCCTAGAAGATATAAATAACATCCTGAACTCAGGTGAAGTGCCTAATTTATTTGAAAAGGATGAACTGGAGCAG
GTTTTAGCGGCCACCAGACCAAGAGCAAAAGAAGTAGGAATTTCTGAGGGGAACAGAGACGAGGTGTTTCAATACTTTATCAGCAAAGTGCGTC
AGAAGCTGCACATTGTTCTCTGCATGAGCCCAGTTGGGGAGGCCTTTCGGTCCCGATGCAGGATGTTTCCATCCCTTGTGAATTGCTGCACCAT
TGACTGGTTTGTGCAGTGGCCCAGAGAAGCACTTCTTTCTGTGTCAAAGACATTTTTCTCACAAGTCGATGCTGGAAATGAAGAACTGAAAGAA
AAGCTTCCCTTGATGTGCGTGAACGTTCACTTGAGTGTCTCCAGCATGGCAGAGCGCTATTACAATGAGCTGCGCAGGCGGTACTACACGACAC
CCACCTCCTACCTGGAGCTTATCAATCTTTACCTGTCTATGCTGTCTGAAAAAAGGAAGCAGATTATTTCAGCACGAGATCGGGTGAAGAATGG
TCTCACCAAGCTACTAGAAACAAACATACTAGTAGATAAAATGAAACTAGATCTTTCAGCTTTAGAGCCTGTACTTTTAGCAAAATCAGAAGAT

Fig. 9 (Continued)

GTTGAAGCCCTGATGGAAAAATTGGCAGTGGATCAAGAAAGTGCCGATCAGGTCCGTAACACTGTGCAGGAGGATGAAGCAACAGCAAAAGTCA
AAGCTGAAGAAACCCAAGCAATAGCTGATGATGCTCAAAGAGATCTTGACGAGGCACTACCTGCACTAGATGCTGCCAATAAAGCACTGGATTC
CTTAGATAAGGCAGATATATCTGAAATCAGAGTTTTTACAAAGCCCCCAGATTTGGTCATGACAGTAATGGAAGCAATCTCCATTCTTTTGAAT
GCCAAGCCTGATTGGCCATCAGCAAAGCAACTTCTTGGTGACTCTAACTTTCTAAAAAGGCTTTTAGAATATGATAAGGAGAACATAAAGCCTC
AGATATTGGCAAAGCTTCAAAAGTATATTAATAATCCTGATTTTGTGCCTGAAAAAGTGGAGAAAGTGTCCAAAGCATGTAAATCTATGTGCAT
GTGGGTAAGAGCTATGGATTTGTACTCTCGAGTGGTCAAGGTCGTCGAACCAAAAAGACAAAAGCTCCGCGCCGCACAGGCTGAACTTGACATT
ACCATGGCTACCCTGAGAGAAAAGCAAGCATTACTAAGACAAGTAGAAGATCAAATACAGGCCTTACAAGATGAATATGACAAAGGTGTAAATG
AAAAAGAAAGCCTGGCAAAGACCATGGCCCTGACAAAAGCACGTCTAGTACGTGCTGGAAAGCTGACAGCAGCATTAGAAGATGAGCAGGTTCG
ATGGGAAGAAAGCATACAGAAGTTTGAGGAAGAAATATCAAATATCACTGGGAACGTGTTCATAGCAGCAGCTTGTGTGGCCTACTATGGGGCT
TTCACAGCCCAGTACAGGCAGTCACTTATAGAGTGTTGGATCCAGGACTGTCAGTCTCTGGAGATCCCAATCGATCCTTCCTTCAGTCTCATTA
ACATTCTTGGAGATCCCTACGAGATACGGCAGTGGAACACTGATGGGCTGCCCCGTGACTTGATATCAACAGAAAATGGCATTTTGGTTACTCA
AGGCAGAAGATGGCCTTTGATGATTGATCCCCAAGATCAGGCAAACCGTTGGATAAGGAACAAGGAAAGCAAAAGTGGTTTAAAGATCATTAAG
CTTACAGATAGTAATTTCTTACGAATACTCGAGAATTCAATCCGACTTGGTTTACCTGTCTTACTGGAAGAGCTTAAGGAAACCTTGGATCCAG
CTCTAGAACCCATTCTTTTGAAACAAATTTTTATCAGTGGTGGCCGACTACTCATCCGTCTTGGAGACTCAGACATTGATTATGACAAAAACTT
TAGGTTCTATATGACAACCAAAATGCCAAATCCCCACTATCTGCCTGAGGTATGCATTAAAGTTACCATTATCAATTTCACTGTAACAAAATCA
GGCCTGGAGGATCAGTTGTTAAGTGATGTGGTGCGACTTGAAAAACCCAGGTTGGAAGAACAAAGAATTAAGCTCATCGTGAGGATCAACACTG
ATAAAAACCAGTTGAAAACTATCGAAGAGAAAATCCTGAGAATGCTCTTTACCTCTGAAGGAAATATTCTGGACAATGAAGAACTTATTGACAC
ACTCCAGGATTCAAAGATCACTTCTGGTGCCATTAAAACCAGGCTGGAAGAAGCAGAGTCCACTGAGCAGATGATCAATGTGGCTCGTGAGAAG
TATCGTCCAGTGGCCACTCAAGGCTCTGTAATGTACTTTGTCATTGCAAGCCTCTCAGAAATAGATCCTATGTACCAGTACTCATTAAAATACT
TTAAACAGTTGTTCAATACCACCATTGAAACTTCTGTAAAGACAGAAAATCTACAACAGCGCCTGGACGTACTACTAGAACAAACTCTCCTAAC
TGCTTATGTCAATGTTTCAAGAGGACTTTTTGAGCAACATAAACTCATCTACAGCTTTATGCTTTGTGTTGAGATGATGCGTCAGCAAGGAACC
CTATCTGATGCTGAATGGAATTTCTTTCTCCGAGGTTCTGCAGGATTGGAAAAGGAACGCCCACCTAAGCCTGAAGCTCCCTGGCTACCTACTG
CTACATGGTTCGCATGCTGTGACTTGGAAGAATCATTTCCAGTTTTTCACGGACTTACCCAAAATATATTGTCACATCCTATTTCCATACGCTT
AGGATCTTTTGAGACTTATATTAACCCACAGAAATGGGAAGGCTATTCTAAAATGAAACACGAAGATAAACACATGAGACAGGAAAAGGAGGCA
GCACACCAAGATCCATGGAGTGCAGGATTGAGTTCTTTCCATAAGCTAATTCTTATTAAATGTTGTAAAGAAGAAAAGGTGGTTTTTGCTCTTA
CAGACTTTGTGATAGAAAATCTTGGAAAACAGTTTATAGAGACACCACCTGTGGACCTGCCTACCCTGTATCAAGACATGTCATGCAACACTCC
CCTGGTATTCATCCTAAGCACAGGCTCAGATCCCATGGGTGCATTTCAGAGGTTTGCCAGGGAAAGTGGATATTCAGAACGGGTGCAGTCAATT
TCACTGGGGCAAGGACAAGGACCTATTGCTGAAAAAATGGTCAAGGATGCAATGAAATCAGGAAACTGGGTATTTTTGCAAAATTGCCATCTTG
CTGTTTCTTGGATGTTGGCAATGGAAGAGCTCATTAAAACCTTCACAGATCCAGATAGTGCTATCAAGGACACTTTTCGACTTTTTTAAGCTC
CATGCCTAGTAATACATTTCCTGTTACAGTTCTTCAAAATTCTGTCAAGGTGACCAATGAGCCTCCAAAAGGCTTACGTGCAAATATCAGACGA
GCATTTACTGAAATGACACCTTCGTTTTTTGAAGAAAATATACTTGGAAAAAAATGGAGACAAATAATATTTGGCATTTGTTTCTTCCATGCAA
TTATTCAGGAGAGAAAGAAGTTTGGCCCCCTTGGTTGGAATATCTGCTATGAATTTAATGACAGTGACAGGGAATGTGCTTTACTGAATCTCAA
ACTCTATTGTAAAGAAGGAAAGATTCCCTGGGATGCACTAATTTACATTACTGGTGAAATTACTTATGGTGGTAGAGTCACAGACAGCTGGGAC
CAAAGATGCCTTCGTACTATCTTGAAAAGATTTTTTTCTCCTGAAACATTAGAAGAAGATTATAAATACTCTGAATCAGGCATCTATTTTGCAC
CCATGGCTGACAGCCTACAAGAGTTTAAGGACTACATTGAAAATCTGCCTTTGATCGATGACCCAGAAATTTTTGGAATGCATGAAAATGCTAA
TCTAGTCTTCCAGTACAAAGAGACCAGCACTTTAATCAACACCATACTTGAGGTTCAGCCAAGGTCATCTACTGGTGGAGAGGGAAAAAGCAAT
GACGAAATTGTTCAAGAACTTGTTGCTTCTGTCCAGACCAGAGTTCCAGAAAAACTGGAAATGGAGGGTGCTTCTGAGAGCCTTTTTGTCAAGG
ATCTTCAAGGACGTCTGAACTCCTTGACCACCGTTCTTGGACAGGAAGTGGACCGGTTTAACAACCTGCTGAAGTTAATTCATACTTCTCTGGA
AACACTCAACAAAGCCATCGCTGGATTTGTGGTGATGTCTGAAGAAATGGAAAAAGTGTATAACAGTTTCCTCAACAACCAGGTTCCCGCTCTG
TGGTCCAACACAGCCTACCCATCCCTGAAGCCACTAGGATCATGGGTCAAAGACCTTATCCTGAGGACCTCATTTGTGGATCTGTGGCTCAAAA
GAGGACAGCCTAAGTCCTACTGGATCTCTGGTTTCTTCTTTCCTCAAGGATTTCTAACAGGAACTCTTCAAAATCATGCTCGAAAATACAATTT
GCCTATAGATGAGCTGAGTTTCAAATACAGCGTAATTCCCACCTATCGGGATCAAGCTGCAGTGATAGAAGCTGCCAAGACAGTGCAATTTGGA
CAAGAACTGCCCATGGACATGGAGTTGCCCTCTCCTGAGGATGGTGTTCTTGTTCATGGGATGTTCATGGATGCTTCTCGATGGGATGATAAGG
AGATGGTGATAGAAGATGCATTGCCCGGACAGATGAATCCAGTGCTGCCTGTGGTGCATTTTGAACCACAACAAAACTATAAGCCAAGCCCAAC
ACTTTACCACTGCCCACTTTATAAAACAGGAGCCCGGGCAGGAACACTCTCAACCACAGGACATTCAACCAATTTTGTGGTAACCGTCCTGTTA
CCCTCCAAGCGGTCCAAAGACTACTGGATTGCCAAGGGATCAGCTTTGCTCTGCCAGCTGAGCGAATGA

ID 44: DNAH7, *Homo sapiens*

ATGAGCAGTGAGCAGGATAAATCGGCCAGCAAAGAAAAATCCAAGAAACCAGTAAGATTTCTACCACAGCTGTCTATGGAGAAATTAGCCAGCA
AAGAAAAGTTCAAGGCACCAGCAAGAGCTTTACCACAGCTGTCTATGGTGAGTACAAAGCCCCACTGGCAGCAGGCAGCTCCATCATTCCATTT
GAGTGTAAAGCAGGATGATGAGAGTCCAGAACCATTTAGTGTTAAAAATGAACAGTCCCATGCTGAATACATGGAACGTTTTGGAAAAAAGGGC
AAATTACCCCACCAAGTTGATGATAGTTATGTTGGACCATCTACTTCCAAATCAAAGGGCAAATCTCCACATAAAGAACGAGAAAACTTTAGAA
GTACTCTTGTTAATGTCATTATGCAACAAGATGCTGACTTAGACTCAGCTGTCCCTGATGGAAGCACAATTCCAAAACCGACCGCTTCTGCTAT
AGAGAAAGACATCTTGAGATATTACTATTATATTCACCATGGAATTGATACAGACCATGTAGCCCCAATGGAAGATTCTTGGCTAGAACACGTA
CTGGATTTAGTTCCACAACATCTGAAAGTCTTCACTGACAGCATAGTTACATTATCTGATGAAATGAGAGAGGATTATCTTCTTAGTGTAAGGA
AATCCATAGTTGATTTTGTTTTAAAAGATCCTCGAGAGAAAGGAGATGATAAGAAGACAGATGAACTTCCAGCCCATCGTGCTGAAATGGAAAT
TCTGCCAAAACCTTGGAGGAAATCTTTTTTAGCTGCAAGCAGTTATATTAGGGATCACTTGAATGCAATGAACCCCACAATGCTGGCTGTACTA
GATTTGTGGCACACTAATTTTAAAAAATTACGTTTAGTTGATATCAAAGAATTTCATAATTGCCAGGATGCATTAGAGCTGTCAAGTTTTCAGA
ACATTATCATGAGACACATGGACTCTGCCAAAGAGACTCTACTTAAAATGTGGTTTCCAGAAGTGCAGAATATTTATTACCAAGGTAATAAAAA
AAAGCAATTGCCAACTGGTGACAGCAGTGCCAAATTGGAATCTTTTTTCAACTGTGCTGCTGCACTTATGACTTTACAGCTGCAGGACCTCACT
TTAGTCTCCATGCAAGATTTCACGGACTTAATTGCACAACCCCCAGATTCTGTTAGAGCTTTTGAACATCCAGGTTTCATCATGAGGCTGATTC
TTGATAATGACACCATTAAGTTTGAACCTGAGTTGAGTGACTATATAGATATCTTTCTAAATGTTTATGACGTCATGATTAAAGCTGTCAGTTT
TGTGCCAAGAGTTGAGACAAAATTGTATTCCAAGTGGGAAAGTAAGTCTAAACCAACAACCTTGAAGCCCATAATTCTGAATGAAATTGTAGAT
GCTCACAAAGAAAAGATCAAGGAAGTTATTATGAAAGAGAGTGTGGCACCTACTGAGCACCTCAGACTCTATGACAAGTATGACTTTTTAATTA
CCAGAAAAGCTGAGCGAGATGTTGATAACTTCCTCGCAGAAAATCATAGTTATGAAAAAATAATAGATGAAATTTGCAAATACCAGAAACTAAT
AGAGGAAATACAGTACACATCCATAAAGACTATTCGTTTAGGAATGTTTGAAATGCACTGTGAGGAATTAATCAGAGCTTTGGTGAAGCGAGCA
GATATTATTTGTGGGAAACTTCTAGCTAAAATGTTCAGAGATCATCAGGAAGTAAATACAAGATTATGCGATGAATTTGAGAGGATAGCTGAAA
AAGCTCTTAGCACTCCTCCAAATACAGCAGAACTAATGGAAATGAAGGCTTACATTCAGAAAGTGGAGGTAACTGATATGATTGAACTAGAACA
GAGATTAGTGGATTCCAAAAACTGCCTCGCCTTCCTCATCGAGTATGTCAACTTTTCTCCAGCAGACATGAGGCTAAATAATAGTGTTTTCCAG
TGGTATGGAAGGATGGGAGAAATTTTTGAAGAACACAGGAAAATCATTAAACAGAAAATAGAACAATATCAAGAAGGTCTGAAGTTACGGTGTG
AACGGTTTGTGGAGGAATTGGAGAGTTATGCTAAGCAATCAGAAGAATTTTATTCATTTGGAGATCTTCAGGATGTTCAGCGGTACCTAAAAAA
GGCTCAAATACTGAATGGAAAGTTGGATTTAGCTGCAGATAAGATTGAGCAGTTTAATGCTGAAGAGGAAGCATTTGGTTGGCTACCATCTGTA
TATCCTCAACGTAAAAAAATCCAAGATGGCTTGAACCCTTATCTTCGTCTTTATGAAACTGCTGTCGAATTTAGCAGCAACTATAGAGCATGGA
CAGAAGGGCCATATCATAAAGTGAATCCAGACCAAGTAGAAGCAGATATTGGAAATTACTGGAGAGGATTATATAAACTGGAGAAAACCTTTCA
TGATTCTCCATATGCATTGGCAATGACAAAAAAAGTAAGATCAAAGGTGGAAGATTTCAAGCAGCACATTCCTCTCATTCAAGTGATCTGTAAT
CCTGGTTTGCGCCCCAGGCACTGGGAGGCCATGTCTGCCATTGTTGGTTACCCTTTGCAGCCATCAGATGACTCCACAGTCTCCTCTTTTTTAG
ACATGAATCTGGAACCATATATAGACCGATTTGAAGGTATTAGTGAAGCAGCTAGCAAAGAATATTCTCTTGAAAAGGCGATGGAGAAGATGAT
TACTGAGTGGGATGCAGTGGAATTTGTCATCCATTCTTATAGAGAAACTGGGACATTTATTTTGGCATCAGTTGATGAAATTCAGATGTTGTTG
GATGACCATATTATTAAAACACAAACTATGCGAGGATCTCCTTTCATTAAGCCTTATGAAAAACAAATGAGAGAATGGGAGGGCAAGCTCCTAC
TGCTTCAGGAGATTCTGGATGAATGGCTCAAAGTCCAAGCCACGTGGCTGTATCTGGAGCCCATTTTCAGCTCTCCAGACATTATGTCTCAAAT

Fig. 9 (Continued)

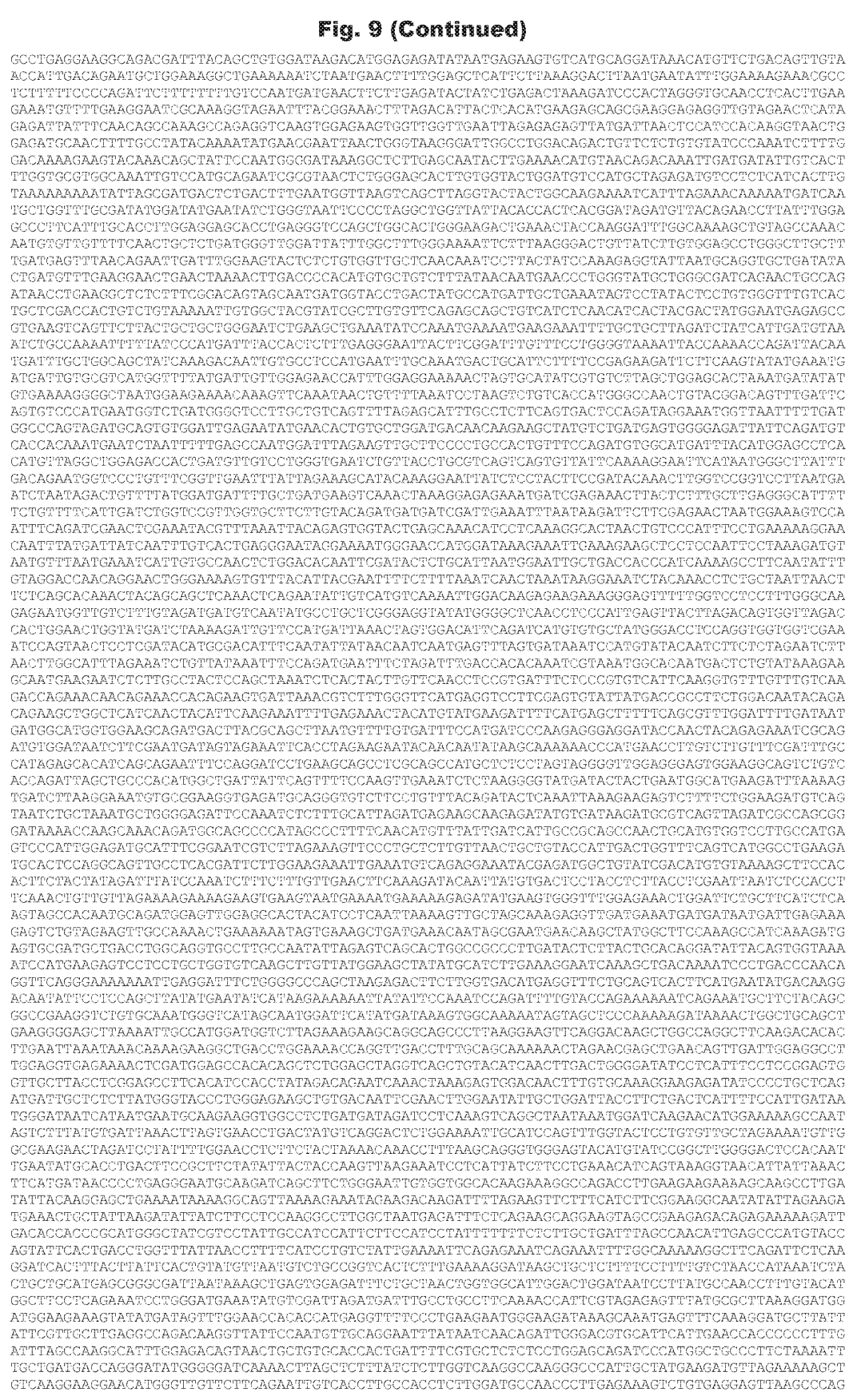

GCCTGAGGAAGGCAGACGATTTACAGCTGTGGATAAGACATGGAGAGATATAATGAGAAGTGTCATGCAGGATAAACATGTTCTGACAGTTGTA
ACCATTGACAGAATGCTGGAAAGGCTGAAAAAATCTAATGAACTTTTGGAGCTCATTCTTAAAGGACTTAATGAATATTTGGAAAAGAAACGCC
TCTTTTTCCCCAGATTCTTTTTTTTGTCCAATGATGAACTTCTTGAGATACTATCTGAGACTAAAGATCCCACTAGGGTGCAACCTCACTTGAA
GAAATGTTTTGAAGGAATCGCAAAGGTAGAATTTACGGAAACTTTAGACATTACTCACATGAAGAGCAGCGAAGGAGAGGTTGTAGAACTCATA
GAGATTATTTCAACAGCCAAAGCCAGAGGTCAAGTGGAGAAGTGGTTGGTTGAATTAGAGAGAGTTATGATTAACTCCATCCACAAGGTAACTG
GAGATGCAACTTTTGCCTATACAAAATATGAACGAATTAACTGGGTAAGGGATTGGCCTGGACAGACTGTTCTCTGTGTATCCCAAATCTTTTG
GACAAAAGAAGTACAAACAGCTATTCCAATGGGATAAAGGCTCTTGAGCAATACTTGAAAACATGTAACAGACAAATTGATGATATTGTCACT
TTGGTGCGTGGCAAATTGTCCATGCAGAATCGCGTAACTCTGGGAGCACTTGTGGTACTGGATGTCCATGCTAGAGATGTCCTCTCATCACTTG
TAAAAAAAAATATTAGCGATGACTCTGACTTTGAATGGTTAAGTCAGCTTAGGTACTACTGGCAAGAAAATCATTTAGAAACAAAAATGATCAA
TGCTGGTTTGCGATATGGATATGAATATCTGGGTAATTCCCCTAGGCTGGTTATTACACCACTCACGGATAGATGTTACAGAACCTTATTTGGA
GCCCTTCATTTGCACCTTGGAGGAGCACCTGAGGGTCCAGCTGGCACTGGGAAGACTGAAACTACCAAGGATTTGGCAAAAGCTGTAGCCAAAC
AATGTGTTGTTTTCAACTGCTCTGATGGGTTGGATTATTTGGCTTTGGGAAAATTCTTTAAGGGACTGTTATCTTGTGGAGCCTGGGCTTGCTT
TGATGAGTTTAACAGAATTGATTTGGAAGTACTCTCTGTGGTTGCTCAACAAATCCTTACTATCCAAAGAGGTATTAATGCAGGTGCTGATATA
CTGATGTTTGAAGGAACTGAACTAAAACTTGACCCCACATGTGCTGTCTTTATAACAATGAACCCTGGGTATGCTGGGCGATCAGAACTGCCAG
ATAACCTGAAGGCTCTCTTTCGGACAGTAGCAATGATGGTACCTGACTATGCCATGATTGCTGAAATAGTCCTATACTCCTGTGGGTTTGTCAC
TGCTCGACCACTGTCTGTAAAAATTGTGGCTACGTATCGCTTGTGTTCAGAGCAGCTGTCATCTCAACATCACTACGACTATGGAATGAGAGCC
GTGAAGTCAGTTCTTACTGCTGCTGGGAATCTGAAGCTGAAATATCCAAATGAAAATGAAGAAATTTTGCTGCTTAGATCTATCATTGATGTAA
ATCTGCCAAAATTTTTATCCCATGATTTACCACTCTTTGAGGGAATTACTTCGGATTTGTTTCCTGGGGTAAAATTACCAAAACCAGATTACAA
TGATTTGCTGGCAGCTATCAAAGACAATTGTGCCTCCATGAATTTGCAAATGACTGCATTCTTTTCCGAGAAGATTCTTCAAGTATATGAAATG
ATGATTGTGCGTCATGGTTTTATGATTGTTGGAGAACCATTTGGAGGAAAAACTAGTGCATATCGTGTCTTAGCTGGAGCACTAAATGATATAT
GTGAAAAGGGGCTAATGGAAGAAAACAAAGTTCAAATAACTGTTTTAAATCCTAAGTCTGTCACCATGGGCCAACTGTACGGACAGTTTGATTC
AGTGTCCCATGAATGGTCTGATGGGTCCTTGCTGTCAGTTTTAGAGCATTTGCCTCTTCAGTGACTCCAGATAGGAAATGGTTAATTTTTGAT
GGCCCAGTAGATGCAGTGTGGATTGAGAATATGAACACTGTGCTGGATGACAACAAGAAGCTATGTCTGATGAGTGGGGAGATTATTCAGATGT
CACCACAAATGAATCTAATTTTTGAGCCAATGGATTTAGAAGTTGCTTCCCCTGCCACTGTTTCCAGATGTGGCATGATTTACATGGAGCCTCA
CATGTTAGGCTGGAGACCACTGATGTTGTCCTGGGTGAATCTGTTACCTGCGTCAGTCAGTGTTATTCAAAAGGAATTCATAATGGGCTTATTT
GACAGAATGGTCCCTGTTTCGGTTGAATTTATTAGAAAGCATACAAAGGAATTATCTCCTACTTCCGATACAAACTTGGTCCGGTCCTTAATGA
ATCTAATAGACTGTTTTATGGATGATTTTGCTGATGAAGTCAAACTAAAGGAGAGAAATGATCGAGAAACTTACTCTTTGCTTGAGGGCATTTT
TCTGTTTTCATTGATCTGGTCCGTTGGTGCTTCTTGTACAGATGATGATCGATTGAAATTTAATAAGATTCTTCGAGAACTAATGGAAAGTCCA
ATTTCAGATCGAACTCGAAATACGTTTAAATTACAGAGTGGTACTGAGCAAACATCCTCAAAGGCACTAACTGTCCCATTTCCTGAAAAAGGAA
CAATTTATGATTATCAATTTGTCACTGAGGGAATAGGAAAATGGGAACCATGGATAAAGAAATTGAAAGAAGCTCCTCCAATTCCTAAAGATGT
AATGTTTAATGAAATCATTGTGCCAACTCTGGACACAATTCGATACTCTGCATTAATGGAATTGCTGACCACCCATCAAAAGCCTTCAATATTT
GTAGGACCAACAGGAACTGGAAAAGTGTTTACATTACGAATTTTCTTTTAAATCAACTAAATAAGGAAATCTACAAACCTCTGCTAATTAACT
TCTCAGCACAAACTACAGCAGCTCAAACTCAGAATATTGTCATGTCAAAATTGGACAAGAGAAGAAAGGGAGTTTTTGGTCCTCCTTTGGGCAA
GAGAATGGTTGTCTTTGTAGATGATGTCAATATGCCTGCTCGGGAGGTATATGGGGCTCAACCTCCCATTGAGTTACTTAGACAGTGGTTAGAC
CACTGGAACTGGTATGATCTAAAAGATTGTTCCATGATTAAACTAGTGGACATTCAGATCATGTGTGCTATGGGACCTCCAGGTGGTGGTCGAA
ATCCAGTAACTCCTCGATACATGCGACATTTCAATATTATAACAATCAATGAGTTTAGTGATAAATCCATGTATACAATCTTCTCTAGAATCTT
AACTTGGCATTTAGAAATCTGTTATAAATTTCCAGATGAATTTCTAGATTTGACCACACAAATCGTAAATGGCACAATGACTCTGTATAAAGAA
GCAATGAAGAATCTCTTGCCTACTCCAGCTAAATCTCACTACTTGTTCAACCTCCGTGATTTCTCCCGTGTCATTCAAGGTGTTTGTTTGTCAA
GACCAGAAACAACAGAAACCACAGAAGTGATTAAACGTCTTTGGGTTCATGAGGTCCTTCGAGTGTATTATGACCGCCTTCTGGACAATACAGA
CAGAAGCTGGCTCATCAACTACATTCAAGAAATTTTGAGAAACTACATGTATGAAGATTTTCATGAGCTTTTTCAGCGTTTGGATTTTGATAAT
GATGGCATGGTGGAAGCAGATGACTTACGCAGCTTAATGTTTTGTGATTTCCATGATCCCAAGAGGGAGGATACCAACTACAGAGAAATCGCAG
ATGTGGATAATCTTCGAATGATAGTAGAAATTCACCTAGAAGAATACAACAATATAAGCAAAAAACCCATGAACCTTGTCTTGTTTCGATTTGC
CATAGAGCACATCAGCAGAATTTCCAGGATCCTGAAGCAGCCTCGCAGCCATGCTCTCCTAGTAGGGGTTGGAGGGAGTGGAAGGCAGTCTGTC
ACCAGATTAGCTGCCCACATGGCTGATTATTCAGTTTTCCAAGTTGAAATCTCTAAGGGGTATGATACTACTGAATGGCATGAAGATTTAAAAG
TGATCTTAAGGAAATGTGCGGAAGGTGAGATGCAGGGTGTCTTCCTGTTTACAGATACTCAAATTAAAGAAGAGTCTTTTCTGGAAGATGTCAG
TAATCTGCTAAATGCTGGGGAGATTCCAAATCTCTTTGCATTAGATGAGAAGCAAGAGATATGTGATAAGATGCGTCAGTTAGATCGCCAGCGG
GATAAAACCAAGCAAACAGATGGCAGCCCCATAGCCCTTTTCAACATGTTTATTGATCATTGCCGCAGCCAACTGCATGTGGTCCTTGCCATGA
GTCCCATTGGAGATGCATTTCGGAATCGTCTTAGAAAGTTCCCTGCTCTTGTTAACTGCTGTACCATTGACTGGTTTCAGTCATGGCCTGAAGA
TGCACTCCAGGCAGTTGCCTCACGATTCTTGGAAGAAATTGAAATGTCAGAGGAAATACGAGATGGCTGTATCGACATGTGTAAAAGCTTCCAC
ACTTCTACTATAGATTTATCCAAATCTTTCTTTGTTGAACTTCAAAGATACAATTATGTGACTCCTACCTCTTACCTCGAATTAATCTCCACCT
TCAAACTGTTGTTAGAAAAGAAAAGAAGTGAAGTAATGAAAATGAAAAAGAGATATGAAGTGGGTTTGGAGAAACTGGATTCTGCTTCATCTCA
AGTAGCCACAATGCAGATGGAGTTGGAGGCACTACATCCTCAATTAAAAGTTGCTAGCAAAGAGGTTGATGAAATGATGATAATGATTGAGAAA
GAGTCTGTAGAAGTTGCCAAAACTGAAAAAATAGTGAAAGCTGATGAAACAATAGCGAATGAACAAGCTATGGCTTCCAAAGCCATCAAAGATG
AGTGCGATGCTGACCTGGCAGGTGCCTTGCCAATATTAGAGTCAGCACTGGCCGCCCTTGATACTCTTACTGCACAGGATATTACAGTGGTAAA
ATCCATGAAGAGTCCTCCTGCTGGTGTCAAGCTTGTTATGGAAGCTATATGCATCTTGAAAGGAATCAAAGCTGACAAAATCCCTGACCCAACA
GGTTCAGGGAAAAAAATTGAGGATTTCTGGGGCCCAGCTAAGAGACTTCTTGGTGACATGAGGTTTCTGCAGTCACTTCATGAATATGACAAGG
ACAATATTCCTCCAGCTTATATGAATATCATAAGAAAAAATTATATTCCAAATCCAGATTTTGTACCAGAAAAAATCAGAAATGCTTCTACAGC
GGCCGAAGGTCTGTGCAAATGGGTCATAGCAATGGATTCATATGATAAAGTGGCAAAAATAGTAGCTCCCAAAAAGATAAAACTGGCTGCAGCT
GAAGGGGAGCTTAAAATTGCCATGGATGGTCTTAGAAAGAAGCAGGCAGCCCTTAAGGAAGTTCAGGACAAGCTGGCCAGGCTTCAAGACACAC
TTGAATTAAATAAACAAAAGAAGGCTGACCTGGAAAACCAGGTTGACCTTTGCAGCAAAAAACTAGAACGAGCTGAACAGTTGATTGGAGGCCT
TGGAGGTGAGAAAACTCGATGGAGCCACACAGCTCTGGAGCTAGGTCAGCTGTACATCAACTTGACTGGGGATATCCTCATTTCCTCGGAGTG
GTTGCTTACCTCGGAGCCTTCACATCCACCTATAGACAGAATCAAACTAAAGAGTGGACAACTTTGTGCAAAGGAAGAGATATCCCCTGCTCAG
ATGATTGCTCTCTTATGGGTACCCTGGGAGAAGCTGTGACAATTCGAACTTGGAATATTGCTGGATTACCTTCTGACTCATTTTCCATTGATAA
TGGGATAATCATAATGAATGCAAGAAGGTGGCCTCTGATGATAGATCCTCAAAGTCAGGCTAATAAATGGATCAAGAACATGGAAAAAGCCAAT
AGTCTTTATGTGATTAAACTTAGTGAACCTGACTATGTCAGGACTCTGGAAAATTGCATCCAGTTTGGTACTCCTGTGTTGCTAGAAAATGTTG
GCGAAGAACTAGATCCTATTTTGGAACCTCTTCTACTAAAACAAACCTTTAAGCAGGGTGGGAGTACATGTATCCGGCTTGGGGACTCCACAAT
TGAATATGCACCTGACTTCCGCTTCTATATTACTACCAAGTTAAGAAATCCTCATTATCTTCCTGAAACATCAGTAAAGGTAACATTATTAAAC
TTCATGATAACCCCTGAGGGAATGCAAGATCAGCTTCTGGGAATTGTGGTGGCACAAGAAAGGCCAGACCTTGAAGAAGAAAAGCAAGCCTTGA
TATTACAAGGAGCTGAAAATAAAAGGCAGTTAAAAGAAATAGAAGACAAGATTTTAGAAGTTCTTTCATCTTCGGAAGGCAATATATTAGAAGA
TGAAACTGCTATTAAGATATTATCTTCCTCCAAGGCCTTGGCTAATGACATTTCTCAGAAGCAGGTAGCCGAAGAGACAGAGAAAAAGATT
GACACCACCCGCATGGGCTATCGTCCTATTGCCATCCATTCTTCCATCCTATTTTTTTCTCTTGCTGATTTAGCCAACATTGAGCCCATGTACC
AGTATTCACTGACCTGGTTTATTAACCTTTTCATCCTGTCTATTGAAAATTCAGAGAAATCAGAAATTTTGGCAAAAAGGCTTCAGATTCTCAA
GGATCACTTTACTTATTCACTGTATGTTAATGTCTGCCGGTCACTCTTTGAAAAGGATAAGCTGCTCTTTTCCTTTTGTCTAACCATAAATCTA
CTGCTGCATGAGCGGGCGATTAATAAAGCTGAGTGGAGATTTCTGCTAACTGGTGGCATTGGACTGGATAATCCTTATGCCAACCTTTGTACAT
GGCTTCCTCAGAAATCCTGGGATGAAATATGTCGATTAGATGATTTGCCTGCCTTCAAAACCATTCGTAGAGAGTTTATGCGCTTAAAGGATGG
ATGGAAGAAAGTATATGATAGTTTGGAACCACACCATGAGGTTTTCCCTGAAGAATGGAAGATAAAGCAAATGAGTTTCAAAGGATGCTTATT
ATTCGTTGCTTGAGGCCAGACAAGGTTATTCCAATGTTGCAGGAATTTATAATCAACAGATTGGGACGTGCATTCATTGAACCACCCCCCTTTG
ATTTAGCCAAGGCATTTGGAGACAGTAACTGCTGTGCACCACTGATTTTCGTGCTCTCTCCTGGAGCAGATCCCATGGCTGCCCTTCTAAAATT
TGCTGATGACCAGGGATATGGGGGATCAAAACTTAGCTCTTTATCTCTTGGTCAAGGCCAAGGGCCCATTGCTATGAAGATGTTAGAAAAAGCT
GTCAAGGAAGGAACATGGGTTGTTCTTCAGAATTGTCACCTTGCCACCTCTTGGATGCCAACCCTTGAGAAAGTCTGTGAGGAGTTAAGCCCAG

Fig. 9 (Continued)

AGTCAACACATCCAGATTTCCGAATGTGGCTAACGAGTTACCCATCTCCAAATTTCCCTGTGTCAGTACTGCAGAATGGAGTGAAAATGACCAA
TGAAGCACCAAAAGGTTTACGGGCTAATATCATTCGATCATACCTCATGGACCCGATCTCTGATCCGGAGTTCTTTGGCAGCTGCAAAAAGCCT
GAGGAATTCAAGAAATTGCTTTATGGCCTGTGTTTCTTTCATGCTTTGGTACAAGAAAGACGGAAATTTGGACCCCTAGGGTGGAATATTCCTT
ATGAGTTCAATGAGACAGATCTGAGAATCAGCGTACAGCAGCTCCACATGTTCCTGAACCAGTATGAGGAACTGCCGTATGAGGCTCTGCGGTA
CATGACTGGCGAATGCAATTACGGAGGCAGAGTGACCGATGACTGGGACCGGCGCACGCTGCGCAGCATTCTAAACAAATTCTTCAATCCCGAA
TTAGTTGAAAATTCAGACTATAAGTTCGACTCAAGTGGCATCTATTTTGTTCCTCCTTCTGGTGATCACAAAAGCTACATCGAATACACAAAGA
CTCTGCCACTGACCCCAGCACCAGAAATCTTTGGGATGAATGCCAATGCAGATATCACTAAGGATCAGTCAGAAACTCAGCTGCTATTTGATAA
CATTCTTCTTACACAGTCTCGTTCAGCAGGTGCTGGTGCAAAATCATCAGATGAAGTAGTGAATGAGGTCGCTAGTGACATCTTGGGCAAACTT
CCAAACAACTTCGACATCGAGGCTGCCATGAGGAGGTACCCAACAACTTATACTCAGAGCATGAACACTGTACTTGTCCAAGAGATGGGACGGT
TCAATAAGTTACTGAAGACCATAAGAGATTCGTGCGTAAATATTCAAAAAGCAATCAAGGGGCTTGCAGTCATGTCTACAGATCTTGAAGAAGT
GGTTAGCAGCATTTTGAATGTCAAAATTCCAGAAATGTGGATGGGTAAATCCTACCCAAGCCTTAAACCACTTGGCAGCTATGTGAATGACTTC
CTTGCAAGACTAAAATTCTTGCAGCAATGGTATGAGGTTGGTCCTCCTCCAGTCTTCTGGCTTTCTGGCTTCTTCTTCACACAAGCCTTCCTGA
CCGGTGCCCAGCAGAACTACGCCAGGAAATACACAATTCCTATTGATCTTCTTGGGTTTGACTATGAAGTGATGGAAGACAAAGAATACAAGCA
TCCTCCTGAGGATGGTGTTTTCATTCACGGATTATTTCTGGATGGAGCTTCCTGGAATAGAAAGATCAAGAAACTTGCAGAATCGCATCCCAAA
ATTCTTTATGATACAGTGCCTGTGATGTGGCTAAAGCCCTGTAAGAGGGCAGATATACCAAAACGGCCAAGTTATGTTGCTCCATTGTATAAGA
CAAGTGAGCGGAGAGGAGTATTATCCACCACTGGCCATTCCACGAATTTTGTGATTGCCATGACTCTTCCCTCTGACCAACCCAAGGAACACTG
GATTGGACGAGGTGTAGCACTGTTATGTCAACTTAATTCATAA

ID 45: DNAH8, *Homo sapiens*
ATGATGAAATTGTATATAGACAATGC
AGCCCCGGATAAACTAAAAGGACTGTGCATATTTTTTGTTCGTTGCCGTAATGATGTTGCTATAAATGTT
AAAACTATTCAAGAGGAAGCGCTCTTTACTGTTCTGGATGCGTCGAAAGGACTCTTAAATGGAATTAGGG
ATATGTTGGCAAATATATTTCTACCAGCTGTTCTTGCAACAAACAACTGGGGTGCTTTAAACCAGTCCAA
GCAGGGAGAATCTGAAAAACATATTTTCACTGAAACCATCAACAGATATCTTTCATTTTTAGATGGTGCT
AGAATAAGTATTGAGGGAACAGTGAAGTTAAAGACAATAGACAATGTTAATTTTTCCAAACTGCACACCT
TTGAAGAAGTAACTGCTGCAGCCAGCAACTCAGAAACTGTTCATCAGCTGGAGGAAGTGCTGATGGTATG
GTACAAACAGATCGAACAGGTACTTATTGAGAGTGAGCAGATGAGAAAAGAAGCTGGTGATTCAGGTCCA
CTCACTGAATTGGAACACTGGAAACGCATGTCAGCCAAGTTCAACTATATCATTGAGCAGATTAAAGGGC
CAAGTTGTAAGGCTGTCATAAATGTGCTAAATGTTGCACACTCCAAACTGCTAAAGAATTGGCGTGATTT
GGATGCAAGAATCACTGATACAGCAAATGAATCCAAAGATAATGTCAGATATTTGTATACTTTGGAAAAA
GTGTGTCAACCTCTCTATAACCATGACCTAGTTTCCATGGCACATGGAATACAAAATTTGATTAATGCCA
TCAGAATGATTCACGGTGTGTCAAGGTATTATAATACCTCAGAGAGAATGACCTCATTGTTTATCAAGGT
AACAAATCAAATGGTAACAGCATGTAAAGCATATATTACTGATGGAGGATTAAACCATGTATGGGATCAG
GAAACGCCAGTTGTACTAAAGAAAATTCAGGACTGCATTTTTCTATTCAAGGAATATCAGGCATCTTTTC
ATAAAACAAGGAAACTGATTTCAGAATCCTCAGGGGAAAAATCTTTTGAGGTTTCAGAAATGTATATATT
TGGAAAATTTGAAGCTTTTTGCAAAAGACTGGAGAAGATTACAGAAATGATAACTGTTGTGCAAACATAT
TCAACCTTGAGTAATTCTACCATAGAAGGAATAGATATTATGGCAATAAAATTCAGAAATATATACCAAG
GGGTTAAGAAAAAGCAATATGACATTCTGGATCCAAGAAGGACAGAATTTGACACAGATTTCTTAGATTT
CATGACAAAAATCAATGGTTTAGAGGTACAAATACAGGCATTTATGAACAGTAGTTTTGGGAAAATCTTA
TCTTCTCAGCAGGCTCTTCAGCTACTTCAAAGGTTTCAGAAGCTGAACATTCCCTGTCTGGGATTAGAAA
TAAACCACACAATAGAGCGTATTCTTCAGTACTATGTGGCTGAACTTGATGCTACTAAGAAGCTTTATCA
TTCTCAGAAAGATGACCCCCCTCTTGCTCGCAACATGCCCCCTATAGCAGGAAAAATACTCTGGGTGAGG
CAGCTCTATCGCCGGATAAGTGAGCCCATCAATTATTTCTTTAAAAACTCAGACATTTTATCAAGTCCGG
ACGGTAAAGCTGTCATCCGTCAGTATAACAAGATCTCCTATGTGCTGGTGGAATTCGAGGTGGTCTATCA
CACAGCCTGGGTCAGAGAGATTTCACAGTTGCATTACGCTTTACAAGCCACGCTTTTTGTGCGACATCCA
GAAACAGGGAAGTTGCTGGTTAATTTCGATCCCAAAATTTTGGAAGTTGTTCGGGAAACTAAGTGTATGA
TAAAAATGAAGTTGGATGTACCAGAACAGGCAAAGAGATTGCTAAAATTGGAAAGTAAATTGAAAGCAGA
CAAACTGTATTTGCAGGGTCTTCTGCAATATTATGATGAGTTATGTCAGGAAGTGCCTTCTGTGTTTGTC
AATCTGATGACCCCAAAAATGAAAAAGGTGGAATCTGTGTTGAGGCAAGGACTCACAGTGTTAACATGGT
CGTCTTTAACACTGGAAAGCTTCTTTCAAGAAGTCGAATTAGTTTTGGATATGTTCAATCAACTTTTAAA
GAAGATCAGTGACTTGTGTGAAATGCATATTGATACAGTTCTGAAGGAGATAGCCAAAACTGTGTTGATT
TCTCTGCCTGAAAGTGGTGCTACCAAAGTAGAAGATATGTTGACCCTCAATGAGACATACACAAAAGAAT
GGGCTGACATTCTAAACCACAAAAGTAAGCATGTGGAAGAAGCTGTCAGAGAACTTATATCAATATTTGA
GCAGATTTATGAACTGAAATACACTGGGAAAGTAGGAAAACACTCAGAACAGCGGAAACACGTTGTTTTT
GGAAGTGAAACAGAAGAGGGTGAAAACAATGACTATGAAGCTAATATTGTGAATGAGTTTGATACTCATG
ATAAAGAAGATGAATTTAAAAAGGAGTGTAAAGAGGTCTTTGCTTTTTTCTCTCATCAATTACTAGACAG
TCTTCAAAAAGCTACACGGTTATCTCTGGACACAATGAAAAGAAGAATATTTGTTGCAAGCCTTTATGGG
CGAAAGCAGTCAGAAGATATTATTTCGTTTATAAAAAGTGAAGTACATCTTGCAATTCCTAATGTGGTGA
TGATTCCTAGTTTGGATGACATTCAACAAGCCATTAACCGTATGATCCAGTTAACCCTGGAGGTCAGCAG
AGGAGTGGCTCACTGGGGGCAACAGCAAATCCGTCCCATCAAGTCTGTCATTCCCAGCCCCACCACTACT
GACGTGACCCATCAAAACACAGGAAAACTGCTGAAGAAGGAAGAAAGATCTTTTGAAGAAGCTATTCCTG
CGAGGAAGCTGAAGAATTTTTACCCGGGGGTAGCGGAGCACAAGGATATTTCTAAGTTGGTCCTGCTCCT
TTCTTCCTCTGTAAATTCCCTAAGAAAGGCAGCTCATGAGGCCCTGCAGGACTTTCAGAAGTACAAGACT
CTCTGGACAGAGGACCGCGATGTGAAAGTGAAGGAATTTTTGGCTAACAACCCCTCTCTGACTGAAATCA
GATCAGAAATTCTACACTATGCTACTTTTGAACAGGAGATTGATGAGTTGAAGCCTATTATTGTTGTAGG
AGCACTTGAATTACATACAGAGCCGATGAAATTGGCCTTATCCATCGAGGCCAAGGCATGGAAGATGTTA
CTCTGTCGATATCTGAATGAAGAATACAAAAAGAAAATGTCATACATGATAGCATTTATTAATGAATACT
TGAAAAAGTTATCTAGACCTATTCGTGATTTAGATGATGTCAGATTTGCAATGGAAGCCTTGTCTTGCAT
ACGTGATAATGAAATTCAAATGGACATGACTTTGGGACCAATTGAAGAAGCCTATGCTATTTTAAACAGA
TTTGAAGTTGAAGTAACCAAAGAAGAATCAGAAGCAGTTGATACCTTAAGATATTCTTTCAACAAATTGC
AGAGCAAAGCTGTTTCAGTACAAGAGGACCTAGTTCAAGTGCAGCCAAAGTTTAAAAGCAATCTACTTGA
GTCTGTGAAAGTTTTTCGTGAGGACGTGATAAACTTTGCAGAAGCATATGAATTGGAAGGACCTATGGTT
CCAAATATACCACCCCAAGAAGCTAGCAACAGGCTACAGATATTTCAGGCCAGTTTCGATGATCTGTGGA
GGAAATTTGTTACGTATTCATCTGGTGAACAACTTTTTGGATTGCCTGTGACTGATTATGAGGTTTTACA
CAAAACCAGAAAAGAACTCAACTTGCTGCAGAAGCTGTATGGATTGTATGACACCGTAATGAGCAGTATT
AGTGGTTATTATGAAATACTTTGGGGAGATGTAGATATTGAAAAAATTAATGCAGAACTGCTGGAATTTC
AAAACAGATGTCGTAAACTTCCAAAAGGACTTAAAGATTGGCAAGCTTTTTTGGATCTCAAAAAGAGAAT
TGATGATTTCAGTGAGTCATGTCCTCTACTGGAAATGATGACCAATAAGGCCATGAAACAGAGACACTGG
GATAGAATCTCCGAGTTAACTGGAACCCCATTTGATGTGGAATCTGATTCTTTTTGCCTTAGAAATATCA
TGGAAGCACCACTCCTTAAACATAAGGATGATATTGAGGATATTTGCATATCTGCCATTAAGGAGAAGGA

Fig. 9 (Continued)

TATCGAAGCCAAGCTGACTCAGGTGATTGAGAATTGGACCAACCAAAATCTGAGTTTTGCAGCATTTAAG
GGAAAAGGAGAGCTCCTGCTCAAAGGAACCGAATCGGGAGAAATTATCACTTTGATGGAGGATAGTTTAA
TGGTCTTAGGGTCTTTACTCAGCAACAGATACAATGCTCCATTTAAAAAAATATCCAGAATTGGGTGTA
TAAATTGTCCACTTCCTCAGATATAATTGAAGAGTGGCTCGTAGTACAGAACCTTTGGGTTTATCTTGAA
GCCGTCTTTGTAGGTGGAGATATTGCCAAACAGCTGCCTCAGGAAGCAAAACGTTTTCAGAATATTGACA
AGTCTTGGATAAAAATAATGCAGCGAGCTCATGAGAATCCCAATGTGATTAATTGCTGTGTTGGAGATGA
AACCATGGGACAACTTTTACCTCATTTACATGAGCAGTTGGAAGTATGTCAGAAGTCACTCACAGGGTAT
TTGGAGAAGAAACGATTACTGTTTCCAAGATTCTTCTTTGTATCTGATCCAGTTCTCCTGGAAATTCTTG
GACAAGCCAGTGATTCCCACACCATACAGCCACATCTCCCTGCAGTATCTGACAACATCAATGAGGTGAC
ATTTCATACAAAAGACTATGATCGCATCATGGCCGTCATATCAAGAGAAGGAGAAAAAATTGTTTTGGAT
AATTCTGTTATGGCCAAAGGTCCTGTGGAGATTTGGCTACTGGATTTGTTAAAAATGCAGATGTCATCAT
TACATAATATAATTAGATCCGCTTTCTATCAAATCAGTGATTCAGGATTTCAACTCTTACCATTCCTCAG
CCACTTTCCAGCACAGGTTGGACTTCTGGGAATTCAGATGTTGTGGACACACGATTCAGAAGAGGCTTTA
CGTAATGCAAAAGATGACAGGAAAATCATGCAAGTGACCAATCAGAAATTTTTGGATATTCTAAATACTC
TCATTAGTCAGACAACACATGATCTAAGCAAGTTTGATAGAGTGAAGTTCGAGACTCTAATTACCATCCA
TGTGCATCAGAGAGATATTTTTGATGACTTGGTAAAAATGCATATCAAATCACCTACTGACTTTGAATGG
CTAAAACAGAGTAGATTTTATTTTAAGGAAGATTTGGATCAAACTGTGGTGTCTATTACAGATGTTGATT
TTATTTACCAAAATGAATTTCTGGGATGTACTGATCGTCTTGTTATCACTCCATTAACAGATAGATGCTA
TATCACGTTAGCTCAGGCCTTGGGCATGAACATGGGAGGTGCTCCCGCAGGACCTGCTGGCACTGGCAAA
ACAGAAACCACAAAAGACATGGGAAGGTGTTTGGGAAAATATGTGGTCGTGTTCAATTGCTCAGATCAAA
TGGATTTCAGAGGCCTAGGAAGGATTTTCAAAGGTCTTGCACAGTCGGGTTCCTGGGGCTGTTTTGATGA
GTTTAACAGAATTGAATTGCCTGTATTATCAGTGGCAGCACAACAAATTTATATTGTTTTGACAGCAAGA
AAAGAAAGAAAGAAACAGTTCATTTTTTCTGATGGTGATTGTGTTGATTTAAATCCAGAATTTGGAATCT
TCTTAACGATGAACCCTGGATATGCTGGGCGCCAGGAACTACCAGAAAACCTAAAAATCCAGTTTAGAAC
TGTTGCTATGATGGTTCCTGATAGACAGATCATTATGAGAGTTAAACTTGCAAGCTGTGGTTTTCTTGAA
AATGTTATCTTGGCTCAAAAATTTTACGTTCTTTACAAACTCTGTGAAGAGCAACTTACTAAACAGGTTC
ATTATGACTTTGGATTGAGAAATATTCTGTCTGTATTGAGGACTCTTGGATCTCAAAAAAGAGCCAGACC
AGAAGATAGTGAATTAAGCATTGTCATGAGAGGACTAAGAGATATGAACCTTTCCAAACTGGTTGATGAA
GATGAACCCCTGTTCCTCAGCTTAATCAATGACCTGTTCCCAGGACTGCAACTGGATAGTAATACTTATG
CAGAACTGCAAAACGCAGTAGCCCATCAGGTTCAGATAGAGGGTTTGATTAACCATCCACCCTGGAACCT
GAAACTCGTGCAGTTATATGAGACGTCTTTGGTACGGCATGGCTTGATGACTCTTGGGCCCAGTGGTTCT
GGAAAGACAACCGTTATCACGATTCTAATGAAGGCGCAAACAGAATGCGGAAGGCCTCATAGAGAAATGC
GAATGAATCCAAAAGCCATTACTGCACCTCAGATGTTTGGCAGACTGGACACTGCTACCAATGACTGGAC
AGATGGGATTTTTTCTACTCTGTGGAGAAAAACATTAAAAGCTAAAAAAGGTGAAAACATTTTCCTCATT
TTAGATGGTCCTGTGGATGCCATCTGGATTGAGAACTTAAATTCCGTTTTGGATGACAATAAAACTCTGA
CGTTAGCTAATGGAGATCGCATTCCCATGGCCCCTAGTTGTAAGCTTCTGTTTGAAGTCCACAATATCGA
GAACGCCTCTCCTGCCACGGTTTCTAGGATGGGCATGGTCTATATCAGCAGCTCTGCTCTCAGCTGGAGG
CCAATCTTACAGGCATGGTTGAAGAAACGCACTGCACAGGAAGCTGCTGTATTCCTGACACTGTATGAGA
AAGTCTTTGAAGATACATACACATATATGAAACTAAATCTCAATCCCAAAATGCAGCTCTTGGAGTGCAA
CTATATTGTGCAATCTCTCAATCTTCTGGAAGGGTTAATTCCCTCCAAAGAAGAAGGCGGTGTTTCCTGT
GTCGAACATCTTCATAAATTATTTGTGTTTGGCCTAATGTGGAGTTTAGGAGCCCTTCTGGAATTAGAAA
GCAGAGAAAAGCTTGAAGCCTTCTTACGGCAGCATGAAAGCAAGTTGGACTTACCAGAAATACCTAAAGG
CTCAAATCAAACCATGTATGAGTTTTATGTTACTGATTATGGTGATTGGGAGCACTGGAATAAGAAACTT
CAGCCTTATTATTATCCAACTGACAGTATTCCGGAATATTCATCAATTTTGGTTCCAAATGTTGACAATA
TTAGAACAAATTTTTTGATAGACACCATTGCAAAACAACATAAAGCTGTTTTGCTCACAGGAGAGCAGGG
AACTGCAAAAACTGTCATGGTTAAGGCCTATTTGAAAAAATATGATCCTGAAGTACAGCTATCCAAAAGT
CTAAACTTTTCATCTGCCACAGAACCAATGATGTTTCAGAGAACAATTGAAAGCTATGTGGATAAGCGAA
TTGGAAGCACATATGGGCCACCAGGAGGGAGAAAAATGACTGTATTTATTGATGATATTAATATGCCTGT
GATTAATGAGTGGGGAGATCAGATAACTAATGAGATTGTGCGACAGATGATGGAAATGGAAGGAATGTAC
AGCTTGGACAAGCCTGGAGACTTCACTACTATTGTTGATGTGCAGCTCATAGCAGCAATGATCCACCCTG
GAGGTGGTCGAAATGATATTCCACAACGTTTAAAAAGACAATTTACTGTGTTTAATTGTACATTGCCTTC
AAATGCTTCAATAGACAAAATTTTTGGAATTATTGGATGTGGATACTTTGATCCTTGTAGAAGTTTCAAG
CCTCAAATATGTGAGATGATTGTGAATTTAGTCTCAGTGGGTAGAGTGCTGTGGCAATGGACTAAGGTGA
AGATGCTGCCAACTCCTTCTAAATTTCATTACATCTTCAATCTTCGAGATCTTTCCAGAATTTGGCAAGG
AATGTTGACCATAAAAGCTGAGGAGTGCGCTTCAATCCCTACTCTCCTGTCCCTTTTCAAACACGAGTGC
AGCAGAGTAATTGCAGACAGATTTATAACTCCTGAAGATGAGCAGTGGTTTAATGCACATCTTACTCGTG
CAGTTGAAGAAAATATTGGCTCTGATGCAGCGTCGTGTATTCTTCCTGAACCATACTTTGTGGATTTTCT
TCGTGAGATGCCAGAACCAACTGGTGATGAACCTGAAGACTCTGTGTTTGAAGTACCCAAAATATATGAA
TTGATGCCATCCTTTGACTTTCTGGCTGAAAAACTCCAGTTTTACCAGAGACAGTTCAATGAAATCATTA
GAGGAACATCTCTTGATCTGGTGTTTTTTAAAGATGCAATGACTCATCTTATTAAGATTTCACGAATAAT
TCGAACGTCGTGTGGAAATGCATTGCTGGTGGGTGTTGGTGGTTCCGGAAAACAAAGTCTTTCAAGATTG
GCCTCTTTTATTGCTGGCTATCAAATATTCCAGATAACATTAACCAGGTCTTACAATGTGACTAATCTAA
CAGATGATTTAAAAGCTTTGTACAAAGTTGCTGGTGCTGATGGAAAAGGCATCACTTTCATCTTTACTGA
CAGTGAAATAAAAGATGAGGCATTTCTAGAATACCTTAACAACTTGCTATCTTCAGGGGAGATCTCCAAC
TTGTTTGCACGAGATGAGATGGATGAAATCACCCAAGGTCTGATTTCAGTGATGAAGAGGGAGCTACCTC
GCCATCCTCCTACCTTTGATAATTTGTATGAATACTTCATTTCAAGATCAAGGAAGAACTTACATGTTGT
TCTCTGCTTTTCTCCAGTTGGTGAGAAGTTCCGTGCCCGTTCTTTGAAATTTCCTGGCTTGATATCAGGT
TGCACTATGGACTGGTTCAGCCGCTGGCCAAGGGAGGCTCTGATTGCTGTGGCCTCCTACTTCCTTTCAG
ACTATAATATTGTCTGCTCTAGTGAAATTAAAAGACAAGTTGTAGAAACAATGGGCCTGTTTCATGACAT
GGTTTCAGAGAGCTGTGAAAGTTATTTCCAAAGATACCGCCGAAGAGCACATGTGACTCCCAAATCTTAC
CTCTCATTTATAAATGGTTATAAAAACATTTATGCTGAAAAGGTGAAGTTCATTAATGAACAGGCTGAAC
GTATGAATATTGGTCTTGATAAACTAATGGAGGCAAGTGAATCTGTTGCTAAACTCTCTCAGGATCTTGC
AGTCAAGGAGAAGGAGTTGGCAGTGGCTTCCATAAAAGCAGACGAAGTATTAGCAGAAGTCACAGTAAGC
GCTCAGGCTTCAGCCAAAATTAAAAATGAAGTACAGGAGGTAAAGGACAAAGCCCAAAAAATTGTGGATG
AAATTGATAGTGAAAAAGTGAAAGCTGAAAGCAAGCTTGAGGCAGCTAAACCTGCACTGGAAGAAGCAGA
AGCAGCCCTGAATACTATCAAGCCAAATGATATTGCCACAGTCAGGAAACTTGCAAAACCACCACATCTT
ATTATGAGAATCATGGACTGTGTTCTGTTACTATTTCAAAAGAAAATTGACCCTGTTACTATGGATCCAG
AAAAATCTTGCTGTAAGCCATCATGGGGAGAGTCATTAAAGTTGATGAGTGCAACAGGATTCCTGTGGAG
CCTTCAGCAGTTCCCTAAGGACACTATAAATGAAGAGACTGTTGAGTTACTACAGCCATATTTTAATATG
GATGATTATACTTTTGAAAGTGCCAAAAAAGTCTGTGGGAATGTGGCTGGTCTCCTGTCTTGGACACTTG

Fig. 9 (Continued)

CTATGGCAATATTTTATGGCATCAATAGAGAAGTGTTGCCTCTGAAGGCCAACCTGGCCAAGCAGGAAGG
CCGGTTAGCAGTTGCTAATGCTGAGTTAGGGAAGGCACAAGCCCTGCTGGATGAGAAGCAAGCTGAGCTG
GATAAAGTACAGGCAAAATTTGATGCAGCAATGAATGAGAAAATGGATTTGCTTAATGACGCTGATACGT
GCCGGAAAAAGATGCAGGCCGCCTCCACTCTCATCGATGGGCTGAGTGGAGAAAAAATCCGGTGGACCCA
GCAAAGTAAAGAATTCAAAGCTCAGATTAATAGACTTGTAGGTGATATTCTGCTGTGCACGGGATTCCTT
TCCTACCTTGGTCCTTTCAATCAGATATTTAGGAACTATTTGCTTAAAGATCAATGGGAAATGGAGTTGA
GAGCACGGAAAATTCCTTTCACAGAAAACCTGAATCTTATTTCAATGTTGGTGGATCCTCCAACTATTGG
TGAGTGGGGGCTACAGGGATTACCAGGAGATGATCTCTCAATTCAGAATGGCATTATTGTGACAAAGGCC
ACCAGATACCCACTCCTCATAGACCCACAAACTCAAGGCAAAACTTGGATTAAATCAAAGGAAAAAGAAA
ATGATTTACAGGTGACATCTCTGAACCGTAAATATTTTCGCACACACTTGGAGGACAGCCTTTCCTTGGG
CCGACCCCTTCTCATTGAGGACATTCATGAAGAGCTGGATCCAGCCTTGGATAATGTATTAGAAAAGAAT
TTTATTAAATCTGGCACCACTTTCAAGGTGAAAGTCGGTGATAAGGAATGTGATATCATGGATACATTTA
AACTTTACATTACTACGAAGTTACCAAATCCTGCCTTTACCCCAGAGATTAATGCTAAAACGTCAGTCAT
TGATTTCACTGTTACAATGAAAGGACTTGAGAATCAGTTACTAAGGAGAGTCATTCTAACAGAGAAACAG
GAGTTAGAGGCTGAGAGGGTTAAACTTTTGGAGGATGTTACTTTTAATAAGCGGAAGATGAAAGAACTTG
AAGATAACCTCCTCTATAAATTAAGTGCTACAAAAGGCTCATTGGTAGATGACGAATCTCTCATTGGTGT
ACTTCGAACTACCAAGCAGACAGCAGCTGAGGTAAGTGAAAAGTTGCATGTGGCTGCAGAAACTGAGATC
AAGATCAACGCGGCTCAGGAGGAGTTCCGGCCCGCAGCCACCCGCGGAAGCATCCTCTACTTCCTCATCA
CAGAGATGAGCATGGTCAACATCATGTATCAGACGTCATTGGCCCAGTTCTTGAAGTTATTTGACCAGTC
CATGGCCAGATCTGAAAAGTCACCACTACCTCAAAAGAGAATTACAAATATTATCGAGTACCTGACATAT
GAAGTTTTTACATACTCTGTCAGAGGCCTATACGAAAACCACAAATTCCTGTTTGTACTCCTCATGACCT
TAAAGATTGACCTTCAGAGAGGGACAGTTAAGCACAGAGAGTTTCAAGCTCTCATTAAAGGGGGAGCAGC
TCTGGACCTGAAAGCCTGTCCTCCCAAACCCTATCGCTGGATCCTTGACATGACTTGGCTGAATCTTGTG
GAGCTGAGTAAACTTCCACAATTTGCAGAAATTATGAACCAGATATCTCGTAATGAGAAGGGGTGGAAAA
GCTGGTTTGATAAAGATGCTCCAGAGGAGGAAATTATCCCTGATGGATATAATGATTCACTAGATACCTG
CCATAAACTTTTACTTATCAGGTCTTGGTGCCCAGACCGTACTGTTTTTCAAGCAAGAAAGTATATTGCA
GATTCTTTGGAGGAGAAGTACACAGAACCAGTTATCTTAAATCTGGAGAAAACTTGGGAAGAAAGTGATA
CCCGGACACCTCTGATATGCTTCCTGTCCATGGGATCTGACCCCACCAATCAAATTGATGCATTGGCCAA
GAAACTGAAACTGGAATGTAGAACTATCTCAATGGGGCAAGGACAAGAAGTACATGCTCGAAAGCTGATT
CAGATGTCAATGCAGCAGGGTGGTTGGGTATTACTACAAAATTGCCACCTTGGCCTGGAATTCATGGAAG
AATTACTAGAGACGCTAATTACCACTGAAGCCAGTGATGATTCTTTCCGAGTATGGATAACTACGGAGCC
CCATGATCGATTTCCAATTACATTGCTTCAGACCTCTCTCAAATTCACTAATGAGCCACCCCAAGGTGTA
CGCGCAGGTTTGAAAAGAACATTTGCTGGAATTAATCAAGACCTTCTGGACATCAGTAATTTACCCATGT
GGAAGCCGATGCTTTACACAGTAGCATTTTTACACTCCACTGTGCAGGAGCGACGAAAATTTGGCCCCTT
AGGATGGAATATTCCCTACGAATTCAATTCTGCTGACTTTTCAGCCAGTGTTCAGTTTATTCAGAATCAC
CTTGATGAATGCGATATTAAGAAAGGTGTATCATGGAATACGGTTCGGTACATGATCGGAGAAGTACAAT
ATGGAGACAGAGTGACAGATGACTTTGACAAACGTCTACTTAATTGCTTTGCCAGAGTCTGGTTCAGTGA
GAAGATGTTTGAACCGTCATTCTGCTTTTATACTGGATATAAAATCCCCTTATGCAAAACCTTAGACCAG
TATTTTGAATACATCCAGTCACTGCCATCCCTAGATAACCCTGAAGTCTTTGGGCTTCACCCTAATGCTG
ATATCACGTATCAGAGTAACACTGCTTCTGCTGTTCTTGAAACAATTACCAACATTCAACCCAAAGAGAG
TGGAGGTGGTGTGGGAGAGACCCGGGAGGCTATTGTTTATAGATTATCTGAAGATATGCTGAGTAAACTC
CCTCCTGATTACATTCCTCATGAGGTGAAATCTCGTTTGATAAAGATGGGCCATCTTAATTCAATGAACA
TATTTCTTAGACAAGAAATTGACAGAATGCAAAGAGTCATTTCAGTACTCCGCAGTAGCCTGAGTGATCT
AAAATTGGCCATTGAAGGAACAATCATTATGAGTGAGAATCTGAGAGATGCTCTGGACAACATGTATGAT
GCTCGTATACCTCAGCTCTGGAAAAGAGTGTCTTGGGATTCGTCCACACTGGGCTTCTGGTTCACTGAAC
TTTTGGAAAGAAATGCTCAGTTTTCTACGTGGATATTTGAAGGGAGGCCTAATGTGTTTTGGATGACTGG
TTTCTTTAATCCCCAAGGCTTCCTCACAGCAATGAGGCAAGAAGTGACCCGTGCCCACAAAGGCTGGGCA
CTGGACACTGTGACCATCCACAATGAAGTTCTGAGACAGACCAAGGAGGAGATCACGTCACCCCCTGGGG
AAGGTGTGTATATTTATGGGCTCTACATGGATGGAGCAGCCTGGGACAGACGGAATGGGAAGCTCATGGA
ATCCACCCCCAAGGTACTCTTCACGCAGTTACCCGTGCTCCACATCTTTGCCATTAACTCCACGGCACCC
AAGGACCCCAAGCTGTATGTGTGTCCTATTTACAAGAAACCCAGGCGAACTGATTTGACCTTCATCACTG
TGGTATATTTACGAACAGTGTTGTCCCCGGATCACTGGATCCTGAGAGGAGTGGCCCTTTTGTGTGACAT
CAAGTAA

ID 46: DNAH9, *Homo sapiens*

ATGCGGCTCGCGGAGGAGCGGGCCGCGCTCGCGGCGGAGAACGCGGATGGGGAACCCGGCGCCGACCGACGACTGCGACTCCTGGGGACCTACG
TGGCCATGAGCCTGCGGCCGGCTGCGGGCGCCTGGGAGCGTTGCGCGGGGAGTGCTGAGGCGGAGCAGCTGCTCCAGGCCTTCCTGGGCCGCGA
TGCTGCCGAGGGGCCGCGGCCGCTGCTGGTGGTGCGGCCCGGGCCCAGGGGCCTGGCAATACGCCCCGGGCTGGAGGTGGGACCTGAGTCGGGC
CTGGCTGGCGCTAAGGCGCTTTTTTTCCTTCGCACCGGGCCCGAGCCTCCAGGGCCCGACAGCTTCCGCGGCGCAGTGGTCTGCGGGGACCTGC
CCGCGGCACCTCTGGAGCACCTAGCCGCGCTGTTCTCGGAGGTTGTTCTACCCGTCCTGGCCAATGAGAAGAATCGCCTAAACTGGCCCCACAT
GATATGTGAGGATGTCAGGCGGCACGCCCACAGCCTCCAATGTGACCTCTCAGTTATACTTGAGCAAGTGAAGGAAAAACTTTGCTGCCTCTT
CCAGCAGGCTCAGAAAAAATGGAGTTTGCGGATTCCAAAAGTGAGACAGTCTTGGATTCTATAGATAAGTCAGTCATCTATGCCATTGAGTCTG
CAGTGATCAAATGGAGCTACCAAGTCCAGGTGGTACTCAAGAGAGAGTCTTCCCAGCCACTCTTACAAGGGGAGAATCCCACCCCTAAGGTGGA
GTTGGAGTTCTGGAAGAGCAGGTATGAAGATCTGAAATACATCTATAATCAACTGAGAACAATAACGGTGAGGGGCATGGCCAAGCTCCTGGAC
AAGCTTCAGAGTAGCTACTTTCCAGCTTTCAAAGCCATGTACAGAGATGTTGTTGCAGCTCTAGCAGAGGCACAGGACATCCATGTGCACCTGA
TACCGCTCCAGCGCCACCTGGAAGCTCTGGAGAATGCAGAATTTCCGGAGGTGAAGCCCCAGCTGCGGCCCCTGCTCCACGTGGTCTGTCTGAT
TTGGGCCACATGCAAGTCCTACCGCTCCCCGGGAAGGCTGACTGTGCTGCTCCAGGAGATTTGCAACCTTCTCATCCAGCAGGCCTCTAATTAT
CTCAGCCCAGAAGACCTGCTGAGAAGTGAGGTAGAAGAAAGTCAGAGAAAACTGCAAGTGGTCTCAGACACTTTGAGCTTCTTCAAGCAAGAGT
TTCAGGACAGAAGGGAGAATCTCCACACTTACTTCAAACAGAACCAGGAAGTCAAGGAATGGGATTTCCAGTCTTCTTTGGTCTTTGTGCGATT
GGATGGCTTCCTGGGACAACTGCACGTGGTGGAGGGTCTTCTGAAGACGGCCCTGGATTTCCACAAACTGGGAAAGGTGGAGTTCAGCGGCGTC
AGAGGGAATGCTCTGAGTCAGCAGGTCCAGCAAATGCATGAAGAATTTCAAGAGATGTACAGGCTTCTCTCAGGATCCTCCTCCGACTGCCTGT
ACCTCCAAAGCACGGACTTTGAAAATGACGTCTCTGAATTTAACCAGAAAGTAGAAGATCTTGACCGAAGATTGGGGACTATCTTTATTCAAGC
TTTTGATGATGCACCTGGCTTGGAGCATGCCTTTAAGCTGCTAGACATAGCAGGAAACCTCCTTGAAAGACCGCTGGTAGCGAGGGATACATCT
GATAAATACCTGGTCCTCATCCAAATGTTCAACAAAGATCTGGATGCAGTGAGGATGATCTACAGTCAGCACGTCCAGGAGGAAGCAGAACTTG
GGTTCTCCCCGGTGCACAAGAACATGCCCACCGTGGCTGGCGGCCTCCGCTGGGCACAGGAGCTGAGGCAGCGCATCCAGGGTCCTTTCAGCAA
CTTTGGACGCATCACACACCCTTGCATGGAATCTGCAGAAGGAAAGCGAATGCAACAAAAATATGAAGATATGCTGTCATTGCTAGAAAAGTAT
GAGACAAGACTTTATGAGGATTGGTGCCGGACAGTATCAGAGAAGTCACAGTACAATCTTTCCCAACCACTTCTAAAACGTGACCCAGAGACGA
AGGAGATCACTATCAACTTTAACCCACAGCTGATTTCAGTGCTGAAAGAAATGAGCTATCTTGAACCCAGAGAGATGAAACACATGCCTGAGAC
AGCAGCAGCCATGTTCTCCTCCAGGGATTTCTATCGGCAGCTTGTGGCTAATTTAGAGTTGATGGCAAATTGGTACAACAAGGTTATGAAAACT
CTGCTGGAGGTGGAATTTCCATTAGTGGAGGAAGAGCTGCAAAATATTGATCTCCGCCTCAGAGCAGCAGAGGAGACTTTGAACTGGAAAACAG

Fig. 9 (Continued)

AAGGCATTTGCGATTATGTCACTGAAATCACCAGTAGTATTCATGATCTTGAACAAAGAATTCAGAAAACTAAAGACAATGTGGAAGAGATCCA
AAACATCATGAAAACATGGGTGACTCCAATATTTAAGACAAAAGATGGAAAAAGGGAATCCCTTCTTTCTCTGGATGATCGGCATGATCGAATG
GAAAAATATTACAATCTCATCAAGGAATCTGGCCTTAAGATCCACGCCCTTGTTCAGGAAAACCTGGGTCTATTTTCAGCAGACCCAACCTCCA
ATATCTGGAAGACTTATGTTAACTCTATTGACAATTTGTTGCTGAATGGATTCTTTCTTGCCATTGAGTGCTCCCTCAAGTATCTTCTGGAAAA
TACTGAGTGTAAGGCAGGACTTACCCCAATATTTGAAGCACAACTGAGTCTAGCCATCCCAGAGCTAGTTTTCTATCCGTCTCTGGAGTCTGGA
GTGAAGGGGGGTTTCTGTGACATTGTTGAGGGTCTCATCACCAGCATTTTTAGGATACCATCTCTGGTGCCACGGCTTTCCCCACAAAATGGCT
CTCCTCACTATCAGGTCGACCTGGACGGTATACCAGATTTGGCAAACATGCGGCGCACACTCATGGAGAGAGTCCAGAGAATGATGGGCCTCTG
CTGTGGCTATCAGAGCACCTTCAGCCAGTATTCGTACCTCTATGTGGAGGACCGGAAGGAGGTTCTGGGTCAGTTTCTGCTGTACGGGCACATC
CTCACTCCGGAAGAAATTGAAGACCATGTGGAAGATGGCATCCCAGAGAACCCTCCCCTCCTTTCTCAGTTTAAAGTGCAAATCGACTCCTATG
AAACGCTCTATGAAGAGGTGTGCAGGCTGGAACCCATCAAGGTGTTTGACGGCTGGATGAAAATTGATATTCGACCCTTTAAGGCATCTCTGCT
GAATATTATTAAGAGGTGGAGCCTCCTGTTCAAACAGCATCTTGTGGACCACGTCACTCACAGCTTGGCCAACCTGGATGCGTTTATAAAGAAG
AGTGAGAGCGGCTTACTCAAGAAAGTTGAAAAAGGAGATTTCCAAGGCTTGGTTGAGATCATGGGACACCTTATGGCTGTTAAAGAACGGCAGA
GTAACACTGATGAGATGTTTGAGCCCTTAAAGCAGACTATTGAATTGCTGAAGACCTATGAACAAGAATTGCCAGAAACAGTGTTTAAGCAGCT
GGAGGAGCTGCCTGAGAAATGGAACAACATAAAAAAGGTGGCCATTACTGTGAAGCAGCAGGTGGCCCCACTGCAGGCAAATGAAGTGACACTC
CTCCGCCAGAGGTGCACAGCCTTCGATGCAGAACAGCAGCAATTCTGGGAGCAATTCCACAAAGAAGCCCCGTTCAGGTTTGATAGCATCCACC
CTCATCAAATGCTGGATGCCAGGCACATCGAGATCCAGCAGATGGAATCCACTATGGCCTCCATTTCTGAGTCTGCCAGCTTATTTGAAGTCAA
TGTCCCTGACTATAAGCAGCTGAGGCAGTGCAGGAAGGAGGTCTGCCAGCTGAAGGAGCTCTGGGACACCATTGGAATGGTGACCTCCAGCATC
CATGCCTGGGAGACCACACCCTGGAGGAATATCAACGTGGAAGCCATGGAGTTGGAGTGCAAACAGTTTGCCCGGCATATCCGAAACCTGGACA
AGGAGGTCAGGGCCTGGGATGCATTCACAGGCCTGGAAAGCACTGTGTGGAACACGCTGAGCTCCCTGAGGGCAGTAGCTGAGCTGCAGAATCC
AGCCATCCGGGAGCGGCACTGGAGGCAGCTGATGCAGGCCACCGGTGTGAGCTTCACTATGGACCAGGACACCACCCTAGCGCACCTGCTGCAG
CTCCAGCTGCACCACTATGAGGATGAGGTCCGGGGCATTGTGGACAAAGCTGCAAAAGAGATGGGTATGGAGAAAACCTTAAAGGAGCTGCAGA
CTACCTGGGCTGGCATGGAATTCCAGTATGAGCCCCACCCACGGACCAATGTCCCCCTCCTGTGCTCTGATGAGGACCTCATAGAGGTTCTGGA
GGATAATCAAGTTCAACTTCAGAACCTGGTGATGTCCAAGTATGTTGCTTTCTTCTTGGAGGAGGTGTCGGGCTGGCAGAAGAAGCTGTCCACA
GTGGACGCTGTCATCTCTATCTGGTTTGAAGTGCAGCGAACATGGACTCACCTGGAAAGCATATTCACTGGATCTGAAGATATTCGGGCACAGC
TACCCCAGGATTCTAAAAGGTTTGAAGGCATCGACATTGACTTTAAAGAGCTAGCTTATGATGCCCAGAAAATTCCAAATGTAGTGCAAACCAC
CAACAAGCCAGGCCTGTATGAAAAGCTGGAGGATATTCAGGGCAGATTGTGCCTGTGTGAGAAGGCCCTGGCAGAGTACCTCGACACCAAGAGG
CTTGCCTTCCCGCGGTTTTACTTTCTCTCCTCCTCCGATCTGTTAGACATCCTTTCCAACGGCACAGCTCCACAACAGGTTCAACGTCACCTTT
CCAAACTCTTTGACAACATGGCCAAGATGCGATTCCAGCTAGATGCCAGTGGGGAACCAACCAAGACAAGCCTCGGCATGTACAGCAAAGAAGA
GGAGTATGTGGCTTTCAGTGAGCCCTGTGACTGCAGCGGGCAGGTAGAAATATGGCTGAACCATGTCCTTGGTCACATGAAGGCCACTGTGAGG
CATGAGATGACAGAAGGTGTAACTGCCTATGAAGAAAAGCCGAGGGAGCAGTGGCTTTTTGACCACCCAGCTCAGGTGGCCCTGACCTGTACTC
AGATCTGGTGGACAACAGAAGTGGGCATGGCATTTGCCAGGCTGGAGGAAGGCTATGAGAGTGCCATGAAGGACTATTATAAGAAGCAAGTGGC
CCAGCTCAAAACCCTTATCACCATGCTGATTGGCCAGCTCTCCAAGGGAGACCGGCAGAAGATTATGACTATATGCACCATCGATGTGCATGCC
CGGGATGTGGTAGCCAAGATGATTGCTCAGAAGGTAGACAATGCCCAGGCTTTCCTCTGGCTGTCTCAGCTGCGCCATCGTTGGGATGACGAGG
TCAAACACTGCTTTGCCAACATCTGTGATGCCCAGTTTTTGTATTCCTATGAGTACCTGGGAAACACACCTCGCTTGGTGATCACACCTTTGAC
TGACAGGTGCTACATCACCCTCACCCAGTCCCTGCACCTGACCATGAGTGGGGCTCCCGCAGGACCTGCAGGCACAGGCAAGACCGAGACCACC
AAGGACCTGGGCCGCGCACTGGGCATCCTGGTCTATGTGTTCAACTGCTCGGAGCAGATGGATTACAAGTCTTGTGGCAACATCTACAAAGGCC
TTGCTCAGACTGGTGCCTGGGGCTGCTTTGATGAGTTTAATCGAATCTCCGTGGAGGTCTTGTCAGTGGTGGCAGTGCAGGTAAAAAGCATTCA
AGATGCGATTAGAGATAAGAAGCAGTGGTTCAGCTTCCTTGGGGAGGAGATCAGCCTGAATCCTTCTGTCGGTATCTTCATCACCATGAACCCA
GGCTATGCTGGCCGCACAGAGCTGCCAGAGAATCTCAAGTCTCTCTTCAGGCCTTGTGCAATGGTGGTTCCAGACTTTGAATTGATCTGTGAAA
TCATGCTGGTGGCAGAAGGATTCATTGAAGCCCAGTCATTAGCCAGAAAGTTCATCACTCTTTACCAGTTGTGCAAAGAGCTTCTCTCCAAACA
GGATCACTACGACTGGGGCCTACGGGCCATCAAGTCCGTGCTGGTGGTGGCAGGATCCCTGAAGAGAGGAGACCCTGACCGGCCTGAGGACCAG
GTCCTGATGCGCTCCTTGCGGGATTTCAACATCCCCAAGATTGTGACTGATGACATGCCCATCTTCATGGGCCTGATCGGGGACCTCTTTCCCG
CCCTGGATGTCCCCCGGAGGAGAGACCCCAACTTCGAAGCTTTGGTTAGGAAGGCGATAGTGGATCTGAAGCTCCAGGCTGAGGACAACTTTGT
GCTCAAGGTGGTCCAGCTGGAGGAGCTCCTGGCTGTGCGGCACTCTGTATTTGTGGTGGGTGGCGCTGGTACCGGCAAGTCACAGGTGCTGAGG
TCCTTGCACAAGACCTATCAGATCATGAAACGGCGCCCCGTCTGGACTGACCTCAATCCCAAAGCAGTCACAAATGATGAGCTCTTTGGCATCA
TCAATCCAGCCACAGGAGAATGGAAGGATGGATTGTTCTCTTCCATCATGCGGGAGCTTGCCAACATCACCCATGATGGGCCCAAGTGGATTTT
ACTGGATGGCGACATAGATCCAATGTGGATTGAATCCCTGAATACTGTCATGGATGATAACAAGGTGCTGACATTGGCCAGCAATGAGAGGATT
CCTCTGAACCCCACCATGAAGCTCCTCTTTGAGATCAGCCACCTGCGCACAGCCACTCCAGCAACTGTCTCTAGAGCAGGGATCTTGTACATCA
ACCCGGCAGACTTGGGATGGAACCCTCCAGTGAGCAGCTGGATTGAGAAGAGGGAAATCCAGACAGAGAGAGCCAACTTAACCATTTTGTTCGA
CAAGTATCTTCCAACCTGCCTAGACACACTCAGAACCAGGTTTAAGAAGATCATTCCCATCCCAGAGCAGAGCATGGTTCAGATGGTGTGTCAC
CTTCTGGAATGTCTCCTGACCACGGAGGACATCCCTGCAGACTGCCCTAAGGAAATTTATGAGCATTATTTTGTGTTTGCTGCCATCTGGGCTT
TCGGCGGAGCAATGGTCCAAGATCAGCTTGTGGACTACCGGGCAGAGTTCAGCAAATGGTGGCTGACTGAGTTCAAAACAGTCAAGTTTCCTTC
CCAAGGAACCATCTTTGACTATTACATCGACCCAGAGACCAAGAAATTCGAGCCTTGGTCCAAGCTCGTCCCCCAGTTCGAATTTGACCCCGAG
ATGCCCTTGCAGGCGTGTTTGGTGCACACGAGTGAGACCATCCGTGTGTGCTACTTCATGGAGCGGTTGATGGCGCGGCAGCGGCCTGTCATGC
TGGTGGGCACGGCTGGCACTGGCAAGTCGGTGCTGGTGGGAGCTAAGCTGGCCAGCCTTGACCCCGAGGCATACCTGGTGAAAAACGTGCCATT
CAACTACTACACCACGTCAGCAATGCTGCAGGCTGTCCTGGAGAAGCCTCTGGAAAAGAAGGCTGGCAGAAACTATGGCCCTCCAGGGAACAAG
AAACTCATCTATTTCATTGATGACATGAACATGCCTGAGGTGGATGCCTACGGGACGGTGCAGCCCCACACCATCATCCGGCAGCATCTGGACT
ATGGCCACTGGTATGATCGGAGCAAGCTGTCCCTAAAGGAGATCACAAATGTACAGTATGTTTCCTGTATGAACCCCACGGCAGGCAGCTTCAC
CATCAACCCCCGGCTTCAGCGTCACTTCAGCGTGTTTGTCCTCTCCTTCCCGGGGGCAGATGCCCTGTCCTCTATCTACAGCATCATCCTCACT
CAGCATCTGAAGCTCGGAAACTTCCCGGCGTCCCTGCAGAAATCCATCCCCCCACTGATCGATCTGGCCCTCGCCTTCCACCAGAAAATTGCTA
CCACCTTCCTACCCACAGGAATCAAATTCCACTACATCTTCAACCTCAGAGATTTTGCCAACATTTTCCAGGGCATTCTCTTCTCCTCAGTGGA
ATGTGTGAAATCCACATGGGATCTTATAAGGCTCTATCTGCATGAATCAAATCGAGTTTATCGGGATAAGATGGTAGAAGAAAAGGACTTTGAT
CTTTTTGATAAAATCCAGACAGAAGTGCTCAAGAAAACTTTTGATGATATTGAAGACCCTGTGGAGCAGACCCAAAGCCCGAACCTGTATTGTC
ACTTTGCAAATGGTATTGGGGAGCCCAAATACATGCCTGTACAGTCTTGGGAACTTTTGACCCAGACTCTGGTGGAGGCCTTGGAGAACCACAA
TGAAGTCAACACAGTGATGGACCTAGTTCTCTTTGAGGATGCCATGCGCCATGTCTGCCATATCAATCGCATCTTGGAGTCCCCGCGGGGAAAT
GCTCTGCTGGTTGGTGTAGGTGGGAGCGGCAAGCAGAGCCTGACAAGGCTGGCAGCTTTCATCAGCTCCATGGATGTCTTCCAGATCACACTGC
GCAAAGGCTACCAGATCCAGGACTTCAAGATGGACCTGGCCAGCCTGTGTCTGAAAGCTGGAGTGAAGAATCTCAACACAGTGTTTCTCATGAC
TGATGCCCAAGTGGCTGATGAGAGGTTCCTTGTGCTCATCAATGATCTTTTGGCATCTGGGGAGATCCCAGATCTCTACTCTGATGATGAAGTT
GAAAACATCATAAGCAATGTGAGGAATGAAGTCAAGAGCCAGGGTCTGGTTGACAACAGAGAGAACTGTTGGAAGTTCTTTATAGATCGGATCC
GGCGACAGCTGAAGGTGACTCTCTGTTTCTCCCCTGTGGGAAACAAGCTAAGAGTCCGCAGCAGGAAGTTCCCAGCCATTGTGAACTGCACAGC
CATCCACTGGTTCCACGAGTGGCCTCAGCAAGCATTGGAGTCTGTCAGCCTCCGCTTCTTGCAGAACACAGAGGGCATTGAGCCCACAGTAAAG
CAGTCGATTAGCAAATTCATGGCCTTTGTCCACACAAGTGTCAACCAAACATCCCAGTCTTATCTGAGCAATGAACAGCGCTACAACTATACAA
CTCCCAAGTCCTTTCTGGAGTTCATCAGACTCTACCAGAGCTTGTTGCACAGGCACAGAAAAGAGCTCAAGTGCAAGACAGAGCGGTTGGAGAA
CGGGCTGCTGAAGCTGCATAGCACCTCTGCCCAGGTGGATGATCTGAAAGCAAAGCTGGCTGCCCAGGAAGTAGAGCTGAAGCAGAAAAATGAA
GATGCAGACAAACTGATTCAGGTCGTGGGTGTGGAGACTGACAAAGTGAGCAGAGAGAAAGCCATGGCAGATGAAGAGGAGCAGAAGGTGGCCG
TCATCATGCTAGAGGTGAAACAGAAGCAGAAGGACTGTGAGGAGGACCTGGCAAAGGCTGAGCCAGCACTCACAGCAGCGCAGGCAGCTCTCAA
CACCCTGAACAAGACCAACCTGACAGAGCTGAAGTCATTTGGCTCTCCGCCTCTGGCCGTCAGCAATGTCAGCGCTGCGGTGATGGTACTGATG
GCTCCCAGGGGTAGGGTGCCCAAGGACCGGAGCTGGAAGGCTGCTAAGGTCACCATGGCCAAAGTGGATGGCTTCCTGGACTCGCTAATAAACT
TCAACAAAGAGAACATTCACGAGAACTGCCTCAAAGCCATCAGGCCGTATCTGCAAGACCCCGAGTTCAATCCTGAGTTTGTGGCCACCAAATC
CTATGCGGCTGCAGGCCTCTGCTCCTGGGTCATCAATATTGTGAGATTTTATGAGGTGTTCTGTGATGTGGAACCCAAGCGCCAGGCACTGAAC

Fig. 9 (Continued)

AAAGCCACCGCGGACCTCACAGCTGCCCAGGAGAAGCTGGCTGCCATCAAAGCCAAGATCGCTCACCTTAATGAAAACCTGGCAAAGCTCACAG
CCAGGTTTGAGAAAGCAACAGCAGACAAACTCAAATGTCAGCAAGAAGCCGAAGTGACCGCAGTCACCATCTCCCTTGCCAACCGCCTGGTTGG
AGGACTCGCTTCTGAAAACGTGAGGTGGGCAGATGCCGTGCAGAACTTCAAACAGCAGGAAAGGACGTTATGTGGAGACATTTTACTTATAACG
GCTTTCATTTCCTACCTTGGCTTCTTCACAAAGAAATACCGGCAGAGCCTCCTGGACAGAACTTGGAGGCCCTACCTGAGCCAGCTGAAAACTC
CCATTCCAGTCACCCCAGCCCTGGATCCCCTGAGGATGCTGATGGATGATGCTGACGTGGCTGCCTGGCAGAACGAGGGCCTCCCAGCCGACCG
CATGTCCGTGGAGAATGCCACCATTCTCATCAACTGTGAGCGCTGGCCACTCATGGTTGACCCTCAGCTACAAGGCATCAAATGGATCAAGAAT
AAATATGGTGAAGATCTCCGGGTCACGCAGATTGGTCAGAAAGGCTACCTTCAAATCATAGAGCAGGCCCTGGAAGCTGGAGCTGTGGTGCTGA
TTGAAAATCTAGAGGAGTCCATTGATCCTGTTCTGGGACCCCTGCTTGGGAGAGAAGTCATTAAAAAGGACGATTCATTAAAATTGGAGACAA
AGAATGTGAATACAATCCCAAGTTCCGGCTCATCCTCCACACCAAGCTGGCTAATCCTCACTACCAGCCTGAGCTGCAGGCTCAGGCCACCCTG
ATCAACTTCACCGTGACCAGGGATGGCCTGGAGGACCAGTTGCTGGCCGCTGTGGTCAGCATGGAGAGGCCAGACTTGGAGCAGCTGAAGTCCG
ATCTCACAAAGCAGCAGAATGGATTCAAAATTACCCTGAAAACGTTGGAAGACAGTCTTCTCTCTCGCCTCTCCTCCGCCTCTGGGAACTTCCT
GGGAGAAACAGTGCTGGTGGAAAACCTAGAGATCACCAAGCAGACTGCTGCCGAAGTTGAGAAAAAGGTCCAGGAGGCCAAGGTGACTGAAGTG
AAAATCAACGAGGCCCGAGAGCACTACCGGCCAGCAGCTGCCAGGGCCTCACTGCTCTACTTCATCATGAACGACCTCAGCAAGATCCATCCAA
TGTACCAGTTTTCTCTCAAGGCCTTCAGTATCGTCTTCCAGAAGGCTGTGGAGAGGGCTGCTCCTGACGAAAGCCTCAGGGAGCGGGTGGCCAA
CCTAATAGACAGCATAACCTTCTCTGTGTACCAGTACACCATCCGCGGGCTCTTTGAGTGTGATAAGCTGACCTACCTTGCCCAGCTCACCTTT
CAGATTCTCCTCATGAACCGAGAAGTCAATGCAGTGGAGTTGGATTTCCTGCTTCGATCTCCAGTGCAGACGGGCACCGCCAGCCCCGTGGAGT
TCCTCTCCCATCAGGCGTGGGGAGCTGTCAAGGTACTTTCATCAATGGAAGAATTCTCTAATCTGGATCGGGACATAGAGGGATCTGCTAAGAG
CTGGAAAAAGTTTGTGGAGTCCGAATGTCCTGAGAAAGAGAAGCTCCCACAGGAGTGGAAGAACAAGACAGCCCTGCAGCGCCTCTGCATGCTG
AGAGCCATGCGGCCCGACCGGATGACCTATGCTTTGCGAGATTTTGTTGAAGAGAAGTTAGGAAGCAAATACGTGGTGGGAAGAGCCCTAGATT
TTGCAACCTCATTTGAAGAATCGGGACCAGCCACTCCTATGTTTTTCATCCTGTCTCCAGGGGTGGACCCACTGAAGGATGTAGAAAGTCAAGG
AAGAAAACTTGGATACACCTTCAACAATCAGAACTTTCACAACGTGTCTTTGGGGCAAGGACAGGAAGTGGTGGCTGAGGCTGCGCTGGACCTC
GCTGCCAAGAAAGGTCACTGGGTTATTTTGCAGAACATTCACCTGGTGGCCAAGTGGCTCAGCACCCTGGAGAAGAAGCTGGAGGAGCACAGTG
AGAACAGCCACCCAGAGTTCAGGGTCTTCATGAGTGCAGAGCCAGCACCCTCCCCTGAGGGCCACATCATCCCCCAGGGCATCCTGGAGAACTC
CATTAAGATCACCAATGAGCCCCCCACGGGCATGCATGCCAACCTGCACAAGGCCCTGGACAACTTCACTCAGGACACTCTGGAGATGTGTTCT
CGGGAGACGGAGTTTAAGAGCATCCTCTTTGCTCTTTGTTACTTCCATGCGGTGGTGGCAGAAAGACGAAAATTTGGCCCCCAGGGATGGAATC
GCTCATACCCCTTTAACACTGGAGACCTCACTATCTCTGTGAATGTCCTCTACAACTTCCTGGAGGCCAACGCAAAGGTCCCCTATGATGATTT
GCGCTACCTGTTTGGAGAGATCATGTATGGAGGCCATATCACAGATGACTGGGACAGAAGACTCTGCAGAACCTACCTGGGGGAATTCATTCGA
CCAGAAATGTTAGAAGGAGAACTGTCTTTGGCCCCAGGGTTCCCACTCCCAGGCAACATGGACTACAATGGTTATCATCAGTACATCGATGCTG
AGCTGCCCCCAGAATCCCCCTACCTCTATGGCCTCCACCCGAACGCAGAGATTGGCTTCCTGACCCAAACCTCAGAAAAGCTCTTCCGCACTGT
GCTGGAGCTGCAGCCTCGGGACAGCCAGGCCAGAGACGGAGCGGGCGCCACAAGAGAAGAAAAGGTCAAGGCACTTCTGGAAGAAATATTGGAG
CGGGTGACAGACGAGTTTAACATCCCAGAACTGATGGCCAAAGTGGAGGAGCGCACCCCTTACATTGTAGTTGCCTTCCAGGAGTGTGGCCGGA
TGAATATCCTCACCAGAGAGATTCAGCGCTCACTGAGGGAGCTGGAGCTCGGCTTAAAGGGGGAGCTGACTATGACCAGCCACATGGAGAACTT
ACAGAATGCCCTGTACTTCGATATGGTGCCAGAGTCCTGGGCTAGACGAGCCTACCCTTCCACAGCAGGCCTGGCAGCCTGGTTTCCAGACCTC
CTCAACAGAATCAAGGAGCTAGAGGCTTGGACGGGTGACTTTACAATGCCCTCCACTGTGTGGCTGACAGGCTTCTTCAACCCCCAGTCGTTCC
TGACTGCCATCATGCAGTCCACGGCTCGCAAGAATGAGTGGCCACTGGACCAGATGGCCCTGCAATGTGACATGACGAAGAAGAACAGAGAAGA
GTTTAGGAGTCCTCCTCGGGAAGGGGCCTACATCCATGGCCTCTTCATGGAAGGTGCCTGCTGGGACACACAGGCTGGGATCATTACAGAGGCA
AAGCTGAAGGATCTGACACCCCCTATGCCTGTGATGTTCATCAAGGCCATTCCTGCAGATAAGCAGGACTGCCGCAGTGTCTATTCCTGTCCTG
TGTACAAGACTAGTCAGCGGGGACCCACCTACGTGTGGACTTTCAACCTGAAGACTAAGGAAAACCCATCCAAGTGGGTTCTGGCTGGAGTAGC
CTTGCTTCTCCAGATTTAG

ID 47: DNAH10, *Homo sapiens*

ATGGTGCCGGAGGAGGTGGAGGTGGAGATTGATGAGATACCTGTCCTGTCTGAAGAGGGAGAAGAGGAAGAAGAGACTTATTCTCAAAAAGTGG
AGTCCGTGGATAAAGTGCGAGCTAAGCGTGTGTCACTGAGAACCGAATCTCTAGGCCAACCTCTAAACAGAGAGGATGAAGAAATGGACAAAGA
GATTTCAGAAAAACTCCCTTCCAAAAGAACTGCGAAGCACATCATGGAAAAGATGCATCTCCACATGCTCTGTACCCCTCTTCCCGAGGAGTTC
CTGGACCAAAACGTGGTGTTTTTCCTCAGAAATACCAAAGAGGCAATCTCTGAAGCTACCGACATGAAGGAAGCTATGGAAATTATGCCAGAAA
CACTGGAGTATGGAATTATAAACGCTAATGTGCTCCATTTTCTGAAGAATATTATATGTCAGGTTTTTTTGCCAGCATTGTCCTTCAATCAGCA
CAGGACGAGTACAACCGTGGGAGTCACATCTGGAGAAGTCTCTAATTCCTCTGAGCATGAATCAGACCTGCCGCCCATGCCTGGGGAGGCAGTA
GAATATCACAGTATTCAATTAATACGGGATGAATTTTTAATGAACGTGCAGAAATTTGCAAGTAATATTCAAAGAACCATGCAGCAACTTGAAG
GTGAGATCAAGTTAGAAATGCCAATCATCAGTGTGGAGGGAGAGGTGTCTGACCTGGCAGCTGACCCGGAAACCGTTGACATCTTGGAGCAGTG
TGTGATAAACTGGCTGAATCAGATATCCACAGCGGTTGAGGCCCAACTGAAGAAGACACCTCAGGGTAAAGGCCCTCTGGCTGAAATTGAATTC
TGGAGGGAAAGAAATGCAACCTTAAGTGCGCTGCATGAACAAACAAAGCTTCCAATAGTCAGAAAAGTCTTGGATGTGATCAAGGAATCCGACT
CCATGCTTGTGGCTAATCTGCAGCCAGTGTTCACCGAGTTATTCAAGTTCCACACGGAGGCCTCAGACAATGTGCGCTTTCTCTCCACCGTGGA
GCGTTATTTCAAGAACATAACGCACGGGTCTGGCTTCCACGTGGTCCTGGACACCATCCCCGCCATGATGAGTGCCCTGCGGATGGTGTGGATC
ATCTCCCGACACTACAACAAAGACGAGAGGATGATTCCGCTCATGGAGCGCATCGCCTGGGAAATCGCTGAGAGAGTCTGCCGAGTGGTCAACC
TGCGGACTTTGTTCAAAGAAAATCGAGCGAGTGCCCAAAGCAAAACCTTGGAAGCCAGGAACACCCTCAGGCTGTGGAAAAAGGCCTATTTTGA
CACCCGGGCCAAGATAGAGGCTTCGGGGAGGGAAGATCGGTGGGAGTTTGACCGGAAGCGGCTGTTCGAGAGGACGGATTATATGGCCACCATC
TGCCAGGACCTCTCCGACGTTCTGCAGATTTTGGAGGAATTTTATAACATATTTGGTCCAGAACTAAAGGCAGTGACGGGGGACCCCAAGCGCA
TTGATGATGTCCTATGCAGAGTGGACGGCCTAGTCACCCCCATGGAAAACCTGACCTTTGACCCCTTCAGCATCAAGTCCTCCCAGTTCTGGAA
ATATGTGATGGATGAATTCAAGATTGAAGTTCTGATTGACATCATTAATAAAATCTTTGTCCAGAACCTTGAAAATCCACCACTGTATAAGAAT
CACCCTCCAGTAGCAGGTGCAATATACTGGGAACGATCTCTGTTCTTTCGGATTAAGCATACCATCCTCCGATTTCAAGAGGTACAAGAGATAC
TGGACAGTGATCGAGGACAGGAGGTCAAACAAAAATATTTGGAAGTAGGTAGGACAATGAAGGAGTATGAAGACAGAAAGTATGAGCAGTGGAT
GGAGGTGACGGAGCAGGTGCTGCCAGCTCTCATGAAGAAGAGCCTTTTGACCAAGTCTTCCATCGCCACAGAGGAGCCTTCGACTTTAGAAAGG
GGAGCTGTTTTTGCAATCAACTTTTCACCGGCTCTCAGAGAGATTATTAATGAAACAAAGTACTTAGAGCAGCTGGGGTTCACTGTCCCTGAAT
TAGCAAGAAATGTTGCTCTCCAGGAAGACAAATTCCTTAGGTACACAGCTGGGATACAGCGCATGTTGGATCATTATCACATGCTCATAGGAAC
GTTAAACGATGCGGAGTCTGTGCTTCTCAAAGATCATTCCCAGGAACTGCTCCGAGTGTTTAGGTCGGGATATAAGAGGTTGAACTGGAACTCA
CTAGGTATCGGTGACTATATAACTGGTTGCAAACAGGCCATTGGGAAATTTGAGTCTCTCGTCCACCAGATTCATAAGAATGCAGATGACATTT
CTTCCAGGCTGACATTAATAGAGGCCATAAATCTCTTTAAATATCCAGCCGCTAAAAGTGAGGAAGAACTCCCAGGCGTGAAGGAATTTTTTGA
ACACATTGAGCGAGAAAGGGCCAGCGACGTGGACCACATGGTCCGGTGGTATCTTGCCATTGGACCACTGCTGACCAAAGTTGAGGGCCTGGTC
GTCCACACCAACACAGGCAAGGCCCCCAAGCTGGCCTCCTACTACAAATACTGGGAAAAGAAAATTTATGAGGTCCTGACAAAGCTCATCCTGA
AGAACTTGCAGTCTTTTAATTCTTTGATCCTTGGAAATGTCCCTCTGTTCCACACTGAAACCATTCTGACGGCACCTGAGATCATCCTTCATCC
CAACACAAATGAGATCGACAAGATGTGCTTCCATTGTGTCCGGAATTGCGTGGAGATCACCAAGCATTTTGTTCGTTGGATGAATGGCAGCTGC
ATAGAATGCCCACCTCAGAAGGGGGAGGAAGAGGAAGTTGTTATAATAAACTTTTACAATGATATCTCTCTGAACCCTCAGATAATTGAACAAG
CTGTTATGATCCCCCAAAATGTCCACAGGATTCTGATCAATCTTATGAAGTATCTACAAAAATGGAAGCGGTATCGACCTCTCTGGAAATTGGA
CAAAGCTATTGTGATGGAGAAATTTGCTGCCAAGAAACCTCCTTGTGTAGCATATGATGAAAAGTTGCAGTTCTATTCCAAGATAGCTTATGAG
GTTATGCGCCACCCTCTAATTAAGGATGAGCATTGCATCAGACTTCAGCTCAGGCATCTGGCAAACACAGTGCAGGAAAATGCCAAGTCCTGGG
TGATTTCGCTTGGAAAACTTCTCAATGAGTCAGCAAAAGAGGAGCTCTATAATCTCCATGAAGAGATGGAGCACCTGGCCAAAAACCTTAGGAA
GATCCCCAATACCCTTGAAGATCTCAAGTTTGTCCTTGCAACAATTGCAGAAATTAGAAGTAAATCTCTAGTCATGGAACTCAGATATAGGGAC
GTCCAGGAGCGATACCGTACCATGGCAATGTATAACCTCTTTCCTCCTGATGCAGAGAAAGAACTGGTTGATAAGATTGAGAGCATATGGTCCA
ATCTGTTTAATGATTCAGTGAATGTGGAGCATGCTCTTGGGGACATAAAGAGAACTTTCACAGAGCTTACTCGAGGCGAAATAATGAACTACAG
AGTTCAGATAGAGGAGTTTGCAAAGCGTTTTTACAGTGAAGGCCCTGGTTCTGTTGGTGATGATCTTGATAAAGGAGTAGAGCTTTTAGGTGTT

Fig. 9 (Continued)

TATGAAAGAGAGCTGGCAAGACATGAAAAGAGCCGTCAGGAACTGGCTAACGCTGAGAAACTTTTCGATCTTCCTATTACAATGTACCCAGAGC
TGCTGAAAGTGCAGAAGGAAATGAGTGGGCTGAGGATGATTTACGAGCTCTATGAAGGACTAAAGGTTGCAAAAGAAGAATGGTCTCAGACCCT
TTGGATCAACCTGAATGTGCAGATTCTCCAGGAAGGAATTGAAGGTTTTCTCAGGGCTCTCAGAAAGCTACCTCGGCCAGTCCGTGGCTTATCA
GTGACCTACTACTTGGAAGCAAAAATGAAGGCATTCAAAGACTCGATTCCTTTACTTCTTGACTTGAAAAACGAGGCACTAAGAGACAGGCATT
GGAAAGAACTTATGGAAAAAACGTCTGTCTTTTTTGAAATGACCGAAACGTTCACCTTGGAAAATATGTTTGCTATGGAACTGCACAAACACAC
AGATGTTCTCAATGAGATTGTCACAGCAGCAATCAAGGAGGTTGCCATTGAGAAGGCTGTGAAGGAAATCCTAGACACGTGGGAAAATATGAAA
TTCACTGTAGTCAAGTATTGCAAAGGCACACAGGAGCGAGGCTACATCCTGGGTTCTGTTGACGAAATTATTCAGTCTCTTGATGACAACACTT
TCAACCTGCAGAGCATCTCAGGAAGCAGATTTGTGGGGCCTTTTCTGCAAACTGTTCACAAATGGGAAAAAACGCTTTCTCTAATAGGGGAAGT
CATTGAGATTTGGATGTTGGTTCAGAGAAAATGGATGTATCTTGAAAGTATTTTTATTGGTGGAGATATAAGATCACAACTTCCGGAAGAGGCA
AAAAAGTTTGACAACATCGATAAAGTATTTAAAAGGATCATGGGTGAGACCTTAAAAGACCCCGTGATCAAGAGGTGCTGTGAAGCCCCAAACC
GCCTCAGTGACCTACAGAACGTCAGCGAGGGCCTGGAGAAATGCCAGAAAAGCCTCAACGACTACTTAGATTCGAAGAGAAATGCTTTCCCAAG
GTTCTTCTTCATTTCTGACGATGAGTTGCTTAGCATTCTGGGGAGCAGCGACCCACTCTGCGTCCAGGAGCACATGATCAAGATGTACGACAAC
ATAGCATCACTGAGGTTTAATGACGGCGATAGTGGAGAAAAACTGGTGTCCGCGATGATTTCAGCAGAAGGAGAAGTCATGGAGTTTCGGAAGA
TCTTGCGGGCTGAAGGGCGCGTGGAGGACTGGATGACGGCAGTTTTGAATGAGATGAGAAGAACTAATAGACTAATTACCAAAGAGGCTATTTT
TAGATACTGTGAAGACAGAAGCAGAGTCGACTGGATGCTCCTGTACCAGGGCATGGTGGTGCTGGCCGCTAGCCAGGTGTGGTGGACCTGGCAG
GTGGAAGACGTCTTCCACAAAGCGCAAAAAGGGGAGAAGCAGGCCATGAAGAACTATGGCAGGAAAATGCACCGGCAGATCGATGAGTTGGTAA
CGCGCATCACCATGCCGCTAAGCAAAAACGACAGGAAAAAATACAACACTGTTCTCATCATTGATGTGCATGCCAGAGACATAGTTGATTCTTT
CATAAGAGGCAGTATCCTGGAGGCCCGAGAGTTTGACTGGGAAAGTCAGTTGCGGTTTTATTGGACCGGGAGCCGGATGAGCTGAACATCCGC
CAGTGCACGGGAACCTTTGGCTACGGCTACGAGTACATGGGCCTGAACGGCAGGCTGGTCATCACGCCCCTCACCGATCGGATTTACCTGACGC
TCACCCAGGCGCTGTCCATGTATCTAGGTGGGGCCCCCGCCGGCCCAGCAGGAACCGGCAAAACCGAGACCACCAAGGACCTGGCGAAAGCCTT
GGGCTTGCTCTGTGTTGTCACCAACTGTGGCGAAGGCATGGATTACAGGGCCGTGGGAAGATTTTCTCTGGCCTGGCACAGTGCGGGGCTTGG
GGCTGCTTTGATGAGTTTAATCGAATCGATGCTTCTGTGCTCTCCGTGATCTCCTCCCAGATCCAGACGATCCGAAATGCTCTGATCCATCAGT
TAACCACGTTCCAGTTTGAAGGGCAGGAGATTTCCCTGGACTCCCGCATGGGCATCTTCATCACCATGAACCCCGGCTACGCAGGCCGCACGGA
GCTGCCCGAGTCGGTGAAGGCGCTGTTCAGGCCTGTGGTCGTGATCGTGCCCGACCTGCAGCAGATCTGTGAGATCATGCTCTTCTCTGAGGGC
TTCCTGGAGGCCAAGACTCTGGCGAAAAAGATGACGGTTCTGTATAAGCTGGCCCGGGAGCAGCTGTCCAAGCAGTATCACTATGATTTTGGAC
TCAGAGCCCTGAAATCGGTGCTGGTCATGGCTGGTGAGCTGAAGAGAGGCTCCTCTGACCTTAGGGAGGACGTGGTGCTGATGAGGGCCTTGCG
AGACATGAACTTGCCCAAATTTGTGTTTGAAGATGTTCCTCTTTTCCTTGGTTTGATTTCGGATCTGTTTCCTGGGCTGGACTGCCCTCGCGTC
CGCTACCCTGACTTCAACGATGCGGTAGAGCAGGTCCTGGAGGAGAACGGCTACGCGGTCCTACCCATCCAGGTGGATAAAGTGGTTCAAATGT
TCGAGACCATGTTAACCCGCCACACGACGATGGTGGTGGGGCCCACCAGAGGGGGCAAGTCCGTCGTCATTAACACTCTGTGTCAGGCCCAGAC
CAAGCTTGGGCTGACGACAAAGTTGTACATCCTGAACCCCAAAGCCGTGAGTGTCATAGAACTCTACGGCATCCTGGACCCAACCACCCGAGAC
TGGACAGATGGGGTGTTGTCAAACATCTTCAGGGAAATCAACAAGCCAACAGACAAGAAGGAGCGAAAGTATATTTTATTTGATGGTGATGTGG
ATGCTCTATGGGTGGAAAACATGAATTCTGTGATGGATGACAACAGGTTGTTGACATTGGCCAACGGGGAACGCATCCGGCTCCAAGCACACTG
TGCCCTGCTCTTTGAGGTTGGAGATTTACAGTATGCCTCCCCTGCAACTGTCTCTCGATGTGGAATGGTTTATGTGGATCCTAAAAACTTGAAA
TATCGACCATACTGGAAAAAATGGGTTAATCAAATACCAAACAAGGTGGAGCAATACAATTTGAATAGTCTCTTTGAGAAGTATGTGCCCTATC
TCATGGATGTGATAGTGGAAGGAATTGTGGATGGAAGACAAGCAGAAAAGCTGAAGACAATAGTTCCTCAGACAGACCTCAATATGGTAACCCA
GTTAGCCAAGATGTTGGATGCGTTGCTAGAAGGAGAAATAGAAGACCTTGACCTGCTGGAGTGCTACTTCCTGGAGGCTTTGTACTGCTCTCTG
GGAGCCTCCCTGCTTGAGGATGGAAGGATGAAATTTGACGAATATATCAAACGCCTTGCTTCTTTGTCTACTGTTGACACAGAAGGAGTTTGGG
CCAACCCTGGGGAACTGCCAGGTCAACTTCCAACCTTGTATGACTTTCATTTTGATAACAAACGGAATCAATGGGTCCCATGGAGTAAATTAGT
TCCAGAGTATATTCATGCCCCCGAGAGGAAATTCATCAACATCCTGGTTCACACAGTGGATACCACTCGGACTACCTGGATATTGGAACAAATG
GTTAAAATTAAGCAACCTGTTATTTTTGTTGGTGAATCTGGCACTTCTAAGACAGCCACTACCCAGAATTTCCTCAAAAATCTGAGTGAAGAAA
CTAACATTGTGTTAATGGTCAACTTCTCCTCCCGCACCACGTCCATGGATATCCAAAGAAATTTAGAAGCAAATGTGGAAAAGCGAACCAAAGA
TACTTACGGCCCACCCATGGGAAAACGCCTGCTGGTGTTCATGGATGACATGAATATGCCAAGGGTGGATGAATATGGCACGCAGCAGCCCATT
GCCTTGCTGAAGCTGCTGTTGGAAAAAGGCTACTTATATGACCGTGGGAAGGAGCTGAACTGTAAAAGCATTCGAGACCTTGGCTTTATTGCTG
CAATGGGAAAGGCTGGAGGAGGCCGCAATGAAGTTGACCCAAGATTTATTTCGCTATTCAGTGTCTTCAATGTGCCATTTCCTTCAGAGGAGTC
TCTGCATTTAATTTATTCCTCCATCCTGAAAGGCCACACCTCGACGTTTCATGAGAGCATTGTGGCTGTGAGTGGCAAGCTGACATTCTGCACG
CTAGCACTTTACAAAAATATTGTGCAAGACCTACCTCCCACTCCGTCAAAGTTCCATTACATCTTCAACCTTCGAGATCTCTCACGGGTTTTTA
ATGGTCTTGTCCTCACTAACCCGGAGCGATTCCAGACGGTGGCCCAGATGGTGAGAGTCTGGAGGAATGAGTGTCTGAGAGTCTTCCACGACCG
GCTGATCAGTGAAACAGACAAGCAGCTGGTACAACAGCACATAGGCAGCTTGGTTGTGGAACATTTTAAAGATGACGTGGAGGTGGTGATGAGG
GATCCCATATTGTTTGGAGACTTCCAGATGGCTCTGCACGAAGGAGAACCACGCATTTATGAAGACATCCAGGACTACGAGGCGGCCAAGGCTC
TGTTCCAGGAAATTCTTGAAGAGTATAATGAAAGCAACACCAAAATGAACTTGGTTCTCTTCGACGATGCTCTGGAGCATTTAACCCGGGTGCA
CCGTATCATCCGCATGGACCGCGGCCACGCCCTGCTGGTCGGGGTAGGGGGCTCAGGGAAGCAGTCTCTTTCGAGGCTGGCTGCCTTCACAGCC
AGCTGTGAGGTGTTTGAGATCCTGCTGAGCCGAGGCTACTCGGAGAACAGTTTCCGGGAAGACCTGAAGAGCCTCTATTTGAAACTTGGGATTG
AGAACAAAGCGATGATCTTTCTGTTCACGGATGCCCATGTGGCTGAGGAGGGCTTCCTGGAGCTCATCAACAACATGCTGACCTCAGGAATTGT
ACCTGCGCTTTTTTCTGAAGAGGAGAAAGAGTCTATCCTGAGTCAGATTGGACAGGAAGCTCTGAAGCAAGGCATGGGGCCGGCCAAGGAGTCT
GTGTGGCAGTACTTCGTGAACAAAAGTGCAAATAACCTGCACATTGTCCTGGGCATGTCGCCAGTGGGGGACACCCTGAGGACCTGGTGCAGAA
ACTTCCCAGGTATGGTAAATAACACTGGTATTGACTGGTTCATGCCCTGGCCTCCCCAAGCCCTCCATGCGGTCGCAAAGTCCTTTCTAGGGTA
TAATCCAATGATCCCGGCAGAAAATATAGAAAATGTGGTGAAGCATGTTGTCTTGGTTCACCAATCCGTGGACCACTACAGCCAACAGTTTCTA
CAGAAATTGAGGCGCAGCAACTATGTCACTCCCAAGAACTACCTTGATTTTATTAACACCTATTCAAAATTGCTGGATGAGAAAACTCAGTGTA
ATATAGCTCAGTGCAAGCGTCTGGATGGGGGACTGGACAAGCTGAAGGAGGCCACCATCCAGCTGGACGAGCTGAACCAGAAGCTGGCCGAGCA
GAAGATCGTGCTGGCGGAGAAGTCCGCCGCCTGCGAGGCCTTGCTGGAGGAGATCGCCGTCAACACCGCTGTAGCCGAGGAGAAGAAGAAACTG
GCAGAGGAAAAGGCCATGGAGATAGAGGAGCAGAACAAAGTCATTGCCATGGAGAAGGCCGAGGCCGAGACGACCCTGGCAGAGGTCATGCCCA
TCCTGGAGGCCGCCAAGCTGGAACTGCAGAAGCTGGACAAGTCGGACGTGACTGAGATTAGGTCGTTTGCTAAGCCCCCGAAGCAGGTGCAGAC
GGTCTGCGAATGCATCCTCATCATGAAAGGGTACAAAGAGCTGAACTGGAAAACAGCCAAGGGCGTGATGTCCGACCCGAATTTCCTGCGGTCT
CTGATGGAGATTGATTTTGATTCGATTACCCAGAGCCAAGTGAAAAACATCAAAGGCCTCTTGAAGACTCTTAATACCACAACTGAAGAAATGG
AAGCTGTCAGCAAAGCCGGGCTGGGGATGCTGAAATTTGTTGAAGCTGTAATGGGCTACTGTGATGTTTTCAGAGAAATCAAGCCCAAAAGAGA
GAAGGTGGCCAGGCTGGAGCGGAATTTTTACCTCACTAAACGGGAACTGGAAAGGATCCAGAATGAGTTGGCAGCAATTCAGAAAGAGCTGGAA
ACATTGGGTGCCAAATATGAGGCCGCCATACTGGAAAAGCAGAAGCTGCAGGAAGAAGCCGAGATCATGGAGAGGCGGCTGATTGCCGCAGACA
AACTCATCTCGGGTCTGGGGTCAGAAAACATCAGGTGGCTGAACGACCTGGATGAGCTGATGCACCGGCGCGTGAAGCTGCTGGGGGACTGCCT
GCTCTGCGCGGCTTTCCTCAGCTACGAGGGAGCCTTCACCTGGGAGTTCCGTGACGAGATGGTCAATCGGATTTGGCAAAATGACATCCTGGAG
CGGGAGATCCCCCTGAGCCAGCCTTTCCGGCTGGAAAGCCTGCTCACGGATGATGTTGAGATCAGCAGATGGGGATCCCAGGGCCTTCCCCCCG
ATGAGCTCTCCGTTCAGAATGGCATCCTCACCACCCGGGCCAGCCGCTTCCCTCTGTGTATCGACCCCCAGCAGCAGGCCCTCAACTGGATCAA
GAGAAAAGAGGAGAAGAACAATCTGCGGGTCGCTTCCTTTAATGACCCTGACTTCCTCAAGCAGCTAGAGATGTCCATAAAGTACGGGACCCCT
TTCCTGTTCCGCGATGTTGATGAATACATCGATCCTGTGATTGACAACGTCTTAGAAAAAAATATAAAAGTCTCCCAAGGACGGCAGTTTATTA
TCCTGGGAGACAAGGAAGTGGACTATGATTCAAATTTCAGACTGTACCTGAACACCAAGCTGGCCAATCCCAGATATTCCCCATCCGTGTTTGG
GAAAGCTATGGTGATCAATTACACTGTCACGCTGAAGGGCCTGGAGGACCAGCTGCTGAGCGTGCTGGTGGCTTACGAGAGGCGGGAGCTGGAG
GAGCAGCGGGAGCACCTCATCCAGGAGACCAGCGAGAACAAGAACCTGCTCAAGGACCTGGAAGATTCCCTCCTTCGGGAGCTGGCCACGTCCA
CGGGGAACATGCTGGACAATGTGGACCTGGTGCACACCCTGGAGGAGACCAAATCCAAGGCAACAGAGGTCTCAGAGAAACTCAAGCTGGCGGA
GAAGACAGCCTTGGACATCGACAGGCTGCGGGATGGCTACCGGCCAGCAGCCAGGAGGGGGCCATCCTGTTCTTCGTCCTGTCTGAGATGGCC
CTGGTGAACTCCATGTACCAGTACTCCCTGATTGCCTTCTTAGAGGTCTTCAGGCTGTCACTGAAGAAGTCGCTGCCTGATTCCATCCTCATGA
AACGCCTGAGGAACATCATGGACACGCTGACCTTCAGCATCTATAACCACGGCTGCACAGGGCTGTTTGAGAGGCACAAGCTACTCTTTTCTTT

Fig. 9 (Continued)

TAATATGACCATCAAGATAGAACAAGCAGAAGGGAGAGTCCCTCAAGAAGAACTAGATTTCTTTTTAAAAGGAAACATTTCCCTGGAGAAAAGC
AAAAGAAAAAAGCCCTGCGCTTGGTTGTCTGACCAAGGATGGGAAGATATCATTCTTTTATCAGAAATGTTTTCAGACAACTTTGGGCAACTTC
CTGATGATGTTGAGAATAATCAGACTGTCTGGCAGGAGTGGTATGACCTGGATTCACTGGAGCAGTTTCCCGTCCCCTTGGGTTACGATAACAA
CATCACCCCTTTCCAGAAGTTGCTTATTTTGCGCTGTTTCCGTGTGGATCGGGTCTATCGGGCCGTGACTGACTATGTGACTGTAACAATGGGA
GAGAAGTATGTGCAGCCCCCAATGATCAGCTTTGAAGCTATTTTTGAGCAGAGCACTCCACATTCGCCCATTGTGTTTATCCTGAGTCCTGGCT
CCGACCCTGCCACTGATCTTATGAAATTAGCAGAGCGAAGTGGTTTTGGAGGAAATCGCCTCAAATTCCTTGCAATGGGTCAAGGTCAAGAAAA
GGTGGCCCTGCAGCTGCTGGAGACGGCGGTGGCTCGGGGGCAGTGGCTGATGCTGCAGAACTGCCACCTCCTGGTCAAGTGGCTGAAAGATCTG
GAGAAGTCCCTGGAGAGGATCACCAAGCCCCACCCAGACTTCCGCCTGTGGCTCACCACGGACCCCACCAAGGGCTTCCCCATTGGGATTCTGC
AGAAGTCCCTAAAGGTTGTCACCGAGCCACCCAATGGGCTGAAACTCAACATGAGGGCAACTTACTTCAAGATCTCTCACGAAATGCTGGACCA
GTGCCCGCACCCTGCCTTCAAGCCGCTGGTCTACGTGCTGGCGTTCTTTCATGCTGTGGTGCAGGAGAGAAGGAAGTTTGGGAAGATTGGCTGG
AACGTGTACTATGACTTCAATGAGTCTGACTTCCAGGTCTGCATGGAAATTCTGAACACGTACTTAACGAAAGCCTTCCAGCAACGGGACCCAA
GGATCCCGTGGGGCAGCCTCAAGTACCTAATTGGAGAGGTCATGTATGGAGGACGGGCCATCGACAGCTTTGATCGCCGCATCCTGACCATCTA
CATGGATGAGTACCTGGGGGACTTCATTTTTGATACTTTCCAGCCATTCCACTTCTTCCGGAACAAGGAAGTGGACTACAAAATCCCTGTTGGT
GATGAAAAGGAGAAATTTGTTGAAGCCATCGAGGCCCTCCCGCTTGCCAACACGCCAGAAGTGTTTGGTCTCCACCCCAACGCTGAGATTGGCT
ATTACACGCAGGCGGCTCGAGACATGTGGGCTCACCTGCTGGAGCTGCAGCCTCAGACAGGGGAATCCAGCAGTGGTATCAGCCGCGATGATTA
TATTGGCCAAGTGGCCAAAGAAATAGAAAACAAGATGCCCAAAGTCTTTGACTTGGACCAGGTGAGGAAGCGCCTCGGAACAGGACTCTCCCCC
ACTTCGGTGGTGCTCCTGCAGGAACTGGAACGCTTCAACAAGCTTGTGGTCCGGATGACGAAGTCTCTGGCTGAACTTCAAAGGGCCTTGGCTG
GAGAAGTTGGAATGAGCAATGAGTTAGATGATGTGGCCAGGTCTCTTTTTATCGGGCATATCCCTAATATCTGGAGAAGGCTTGCTCCTGACAC
CTTAAAGTCCCTTGGAAACTGGATGGTCTACTTCCTGCGGCGGTTCAGCCAGTACATGTTGTGGGTGACCGAGAGCGAGCCCAGCGTGATGTGG
CTCTCGGGGCTGCACATCCCTGAGTCCTACCTCACGGCGCTGGTGCAGGCCACCTGCCGGAAGAACGGCTGGCCACTGGACCGCTCCACCTTGT
TCACACAAGTGACCAAGTTCCAGGATGCAGATGAAGTGAATGAGCGGGCGGGACAAGGATGCTTTGTCTCAGGACTGTACCTGGAAGGTGCTGA
CTGGGATATAGAAAAAGGATGTCTTATCAAGAGCAAACCCAAGGTGCTGGTTGTGGACCTGCCGATCCTGAAGATCATCCCCATTGAAGCCCAT
CGCCTCAAGCTGCAGAATACTTTCCGGACCCCCGTCTACACCACCTCCATGAGAAGGAACGCCATGGGAGTCGGCTTGGTTTTTGAAGCTGATC
TCTTTACCACGAGGCACATTTCTCACTGGGTGCTGCAAGGAGTATGCCTCACCCTGAATTCTGATTAA

ID 48: DNAH11, *Homo sapiens*
ATGGCAGCCCAGGTGGCAGCCCGGGAGGCGCGAGACTTC
AGAGAAGCCCCGACCCTTCGCCTAACCTCGGGGGCCGGCCTGGAGGCAGTGGGCGCTGTGGAGCTCGAGG
AGGAGGAGGAGAACGAGGAGGAGGCGGCGGCCAGGAGAGCGCGGAGTTTCGCCCAAGACGCGCGGGTGCG
CTTCCTCGGCGGCCGCCTGGCGATGATGCTGGGGTTCACGGAGGAGAAATGGAGCCAGTATTTGGAAAGC
GAGGACAACCGGCAGGTTCTTGGGGAGTTTCTGGAAAGCACCAGCCCGGCTTGCCTTGTGTTTAGCTTCG
CCGCCTCGGGGCGCCTTGCGGCTTCCCAGGAGATTCCAAGAGATGCAAACCATAAACTTGTTTTTATTTC
CAAGAAGATTACTGAAAGCATTGGAGTAAATGACTTTTCTCAAGTGGTTTTATTTGGAGAGTTACCTGCG
TTGTCTCTTGGACATGTATCTGCTTTCCTTGATGAGATTTTAGTGCCAGTTCTTTCTAATAAGAACAACC
ATAAGTCCTGGTCCTGTTTTACTTCACAAGATATGGAATATCACATAGAAGTCATGAAAAAGAAGATGTA
TATTTTTAGGGGCAAAATGTCTAGAAGAACTCTTCTACCAATTCCCACTGTTGCAGGAAAGATGGATCTG
GATCAGAATTGTTCAGAGAACAAGCCACCGTCAAATGAAAGGATAATACTTCATGCAATTGAATCTGTGG
TTATTGAATGGTCACATCAAATCCAAGAAATTATAGAAAGAGATTCAGTGCAGCGTTTGTTGAATGGTCT
TCACTTGTCTCCTCAAGCAGAACTAGATTTCTGGATGATGAGGAGAGAAAATCTGTCATGCATTTATGAT
CAACTTCAGGCACCTGTTGTCCTCAAAATGGTTAAGATCCTGACAACTAAACAAAGCAGCTATTTTCCTA
CTCTGAAGGACATTTTTCTGGCTGTGGAAAATGCTCTTCTCGAAGCCCAAGATGTGGAACTTTACCTGAG
ACCTCTGAGGAGACACATCCAGTGTCTCCAGGAGACGGAATTCCCACAGACACGCATATTAATCGCTCCA
TTATTTCATACCATCTGTCTGATCTGGAGTCATTCCAAGTTTTATAACACCCCAGCTCGGGTTATAGTTT
TATTGCAAGAGTTTTGTAATCTCTTCATTAACCAGGCAACAGCTTACCTTTCACCTGAGGACCTTTTGAG
GGGAGAAATAGAAGAGTCACTGGAAAAGGTGCAGGTGGCTGTTAACATCTTAAAGACTTTCAAAAACTCC
TTTTTCAACTATAGAAAAAAATTGGCAAGCTACTTTATGGAAGAAAGCTGAGACCATGGGATTTCCAGT
CTCATCTGGTGTTTTGCAGATTTGACAAGTTTCTTGATCGTTTAATAAAAATAGAGGATATATTTGCCAC
CACTTTGGAATTTGAAAAGCTGGAAAGACTGGAATTTGGTGGTACCAAAGGAGCAATTTTAAATGGACAA
GTCCACGAGATGAGTGAAGAACTTATGGAACTCTGTAAACTTTTTAAACAGAGCACTTATGACCCATCTG
ATTGCACTAACATGGAGTTTGAAAGTGATTATGTGGCATTTAAGTCCAAAACTCTGGAATTTGACAGAAG
GCTTGGGACAATTATTTGTGAAGCTTTCTTTAACTGCAATGGCTTAGAAGCTGCATTTAAGCTTTTGACC
ATATTTGGAAATTTTCTAGAGAAGCCAGTTGTCATGGAAATTTTCAGCCTACATTACAGCACACTAGTGC
ATATGTTTAATACAGAGCTGGATGTGTGTAAGCAACTGTATAATGAACACATGAAACAGATTGAATGTGG
TCATGTAGTTCTTAACAAGAACATGCCATTTACCTCAGGAAATATGAAATGGCCCAGCAGGTTCTCCAA
CGACTTCAAATGTTTTGGTCAAACTTTGCATCTCTCCGTTATCTATTTTTGGGCAATCCTGATCACGCTT
TAGTTTATCAAAAGTATGTTGAAATGACCACTTTGCTTGATCAATTTGAAAGTCGTATCTATAATGAATG
GAAAAGTAATGTGGATGAAATCTGTGAATTCAATTTGAATCAACCCTTGGTTAAATTCAGTGCCATAAAT
GGTCTTCTCTGTGTCAATTTTGACCCAAAGCTAGTGGCTGTATTGAGAGAAGTGAAATATCTTTTGATGT
TGAAGAAACAAGACATACCAGATTCAGCTTTAGCCATCTTCAAGAAAAGGAACACTATTTTAAAGTACAT
TGGAAATCTTGACCTTCTTGTGCAAGGGTATAATAAACTCAAACAGACGCTCCTGGAAGTTGAATACCCT
CTGATTGAAGATGAGCTGAGGGCTATTGACGAGCAGCTGACAGCAGCCACAACGTGGCTGACATGGCAGG
ATGACTGCTGGGGCTACATCGAGAGGGTGAGGGCAGCCACGTCCGAGTTGGAGCACAGAGTTGAGCGCAC
ACAGAAAAACGTGAAGGTGATCCAGCAGACCATGAGGGGCTGGGCCAGGTGCGTGCTACCTCCCAGGAGA
GAGCACAGACGAGAGGCAGCCTTCACCTTGGAGGACAAGGGTGATTTGTTTACAAAAAATACAAGTTAA
TCCAAGGAGATGGCTGCAAGATCCACAACTTGGTCGAGGAAAATAGGAAGCTCTTCAAAGCCAATCCCTC
TCTGGATACCTGGAAAATTTATGTAGAATTCATTGACGACATTGTGGTGGAAGGCTTTTTTCAGGCTATA
ATGCACGACTTAGACTTCTTTCTGAAGAATACAGAGAAACAATTGAAACCGGCACCGTTTTTTCAAGCAC
AAATGATCTTGTTGCCTCCTGAGATTGTGTTTAAACCTTCCCTAGACAGAGAGGCTGGGGATGGCTTCTA
TGATCTTGTAGAAGAAATGTTATGCAATAGTTTTAGAATGTCTGCCCAGATGAACCGAATAGCAACACAC
CTGGAAATTAAAAATTATCAGAATGATATGGATAACATGTTAGGCCTGGCAGAGGTCAGGCAGGAGATCA
TGAACAGAGTGGTGAATGTCATCAACAAAGTCTTAGATTTCAGAAACACCCTGGAGACCCACGCTTACCT
CTGGGTGGATGATCGAGCTGAGTTTATGAAGCATTTTCTCTTGTATGGCCATGCTGTGTCTTCCGATGAA
ATGGATGCTCATGCAAATGAAGAAATTCCCGAACAACCACCAACTCTTGAGCAATTCAAAGAACAGATTG
ACATTTATGAAGCTTTGTATGTTCAAATGAGCAAATTTGAGGACTTTAGAGTGTTTGATAGTTGGTTCAA
GGTGGACATGAAGCCTTTCAAAGTGAGCTTGTTAACCATAATTAAGAAATGGAGCTGGATGTTTCAGGAG
CATCTTTTGAGATTTGTCATTGACAGTCTGAATGAGCTACAAGAATTTATAAAGGAGACAGATTCCGGAC
TTCAGAGAGAATTAAATGAAGGTGATCATGATGGTTTAGTTGACATCATGGTGCATCTTCTGGCTGTAAG
AAGCCGACAGAGAGCTACTGATGAACTCTTTGAACCTCTAAAAGAAACGATCACCCTCTTGGAAAGCTAT
GGCCAGAAGATGCCTGAGCAGGTCTATATTCAGCTAGAGGAATTACCTGAAAGATGGGAAACTACCAAAA
AGATCGCAGCAACTGTCAGACATGAAGTCTCACCTCTCCATAATGCGGAAGTCACTCTTATAAGGAAAAA

Fig. 9 (Continued)

ATGTATTTTGTTTGACGCAAAGCAGGCAGAGTTCAGAGAGAGATTCAGACACTATGCCCCTCTTGGATTT
AATGCAGAAAATCCATACACAGCGCTTGATAAGGCAAATGAAGAGCTTGAGGCCTTAGAAGAAGAAATGT
TGCAGATGCAAGAATCTACTCGTCTTTTTGAAGTGGCTCTTCCAGAGTACAAACAAATGAAACAGTGTCG
CAAAGAAATAAAATTGCTCAAGGGACTGTGGGATGTCATTATTTATGTTCGAAGAAGCATTGATAATTGG
ACTAAAACCCAGTGGAGACAGATTCATGTGGAACAGATGGATGTAGAACTCAGAAGGTTTGCCAAGGCGA
GTTCCATAACTGAAATTTGGTCACTCAACAAGGAAGTCCGCGTCTGGGATGCTTACACGGGCCTGGAAGG
CACAGTTAAGGACATGACAGCCTCCCTGAGGGCCATCACAGAGTTACAGAGCCCTGCCCTCAGGCACAGG
CATTGGCACCAGCTGATGAAAGCTATTGGGGTCAAGTTTTTAATAAATGAAGCCACAACTTTGGCAGATT
TGTTAGCACTGCGGTTACACAGAGTGGAAGATGATGTCCGAAGGATTGTGGACAAGGCGGTGAAAGAGCT
GGGGACTGAGAAGGTTATTACTGAAATCAGTCAGACCTGGGCAACCATGAAGTTTTCTTACGAAGTTCAC
TATCGAACAGGCATTCCATTACTAAAGTCTGATGAACAACTTTTTGAAACTCTAGAGCACAACCAAGTTC
AGTTGCAGACTCTTCTTCAAAGCAAGTATGTAGAATATTTCATTGAGCAAGTGTTAAGCTGGCAAAATAA
ATTAAACATAGCAGACTTGGTCATCTTCACTTGGATGGAAGTCCAGCGAACTTGGTCTCACCTGGAAAGC
ATTTTTGTCTGTTCAGAAGATATTCGAATCCAGCTTGTGAAAGATGCTAGAAGATTTGATGCGGTGGATG
CTGAATTTAAGGAGTTAATGTTCAAGACAGCCAAAGTAGAAAATGTGTTAGAAGCAACGTGCAGACCTAA
TCTCTATGAAAAACTTAAAGATTTACAGTCCAGGCTTTCTCTTTGTGAAAAAGCTCTCGCTGAATACCTG
GAAACCAAGCGCATAGCCTTTCCTCGCTTCTATTTCGTCTCTTCTGCTGATTTACTTGACATTCTCTCAA
AAGGAGCTCAGCCTAAACAGGTAACATGTCACCTTGCCAAACTTTTCGACAGCATTGCAGATCTGCAGTT
TGAAGACAATCAGGATGTTTCTGCACACAGGGCAGTTGGAATGTACAGCAAAGAAAAGGAGTATGTCCCA
TTCCAAGCCGAGTGTGAATGTGTGGGCCATGTGGAAACATGGCTTCTGCAACTTGAACAGACTATGCAAG
AAACGGTGCGTCATTCTATAACAGAAGCCATAGTGGCCTACGAGGAAAAACCTAGGGAACTGTGGATTTT
TGATTTCCCAGCTCAGGTTGCACTAACCAGCTCACAAATATGGTGGACCACAGATGTAGGAATAGCCTTC
AGTAGACTGGAAGAAGGCTACGAAACAGCCCTGAAGGATTTCCATAAAAAACAGATTTCTCAGCTGAATA
CACTGATTACACTTTTGCTGGGAGAACTTCCACCTGGAGACAGACAGAAGATCATGACAATTTGTACCAT
AGATGTCCATGCCAGAGACGTGGTGGCAAAACTTATTTCTCAGAAGCAAGTTGTTGTCAGTCCCCAAGCT
TTTACATGGCTGTCTCAACTTCGTCACCGATGGGAGGATACCCAGAAACACTGCTTTGTTAATATTTGTG
ATGCCCAGTTCCAGTACTTCTATGAATACTTAGGAAACAGCCCTCGACTAGTGATCACTCCTCTAACTGA
CAGGTGTTATATTACCTTAACTCAATCACTTCATCTAACCATGAGTGGGGCTCCTGCTGGCCCAGCTGGT
ACCGGGAAAACAGAGACCACCAAAGACCTAGGACGTGCCCTTGGCATGATGGTCTATGTATTCAACTGTT
CAGAGCAAATGGACTACAAATCCATAGGCAATATCTATAAGGGATTGGTGCAGACAGGAGCTTGGGGCTG
CTTTGATGAGTTCAACCGAATCTCTGTGGAAGTTCTGTCAGTGGTGGCAGTACAAGTGAAAATGATTCAT
GATGCCATCAGAAACAGGAAGAAGAGATTTGTATTTCTTGGGGAAGCTATCACACTGAAGCCATCAGTTG
GAATATTTATTACTATGAACCCGGGTTATGCTGGTCGAACCGAATTACCGGAAAATCTCAAAGCTCTTTT
CAGACCCTGTGCCATGGTGGCCCCTGACATTGAGCTAATCTGTGAAATCTTGTTAGTTGCTGAAGGTTTT
GTGGATGCGCGTGCATTAGCCCGAAAGTTCATTACGTTGTACACGCTTTGCAAGGAGCTTCTCTCCAAGC
AGGATCATTACGACTGGGGACTTCGTGCTATTAAGTCTGTCTTGGTTGTGGCTGGATCTCTGAAACGAGG
AGATAAAAATAGACCCGAAGATCAGGTACTCATGAGAGCATTAAGGGATTTCAATATGCCCAAAATAGTG
ACTGACGACATCCCAGTGTTTCTGGGCCTGGTCGGTGACCTGTTTCCAGCCCTGGATGTGCCCCGGAGGA
GGAAGCTGCACTTTGAACAGATGGTCAGGCAGTCTACCCTGGAGCTCCGCCTGCAGCCTGAAGAGAGCTT
CATCCTCAAAGTTGTCCAGCTTGAGGAACTGTTGGCTGTGCGGCACTCGGTCTTTGTAGTTGGAAATGCA
GGCACAGGAAAGAGTAAGATTTTGAGAACACTGAACCGAACATATGTTAACATGAAACAGAAGCCGGTTT
GGAATGACTTAAACCCTAAAGCTGTGACAACAGATGAACTCTTTGGTTTCATACATCATGCTACCCGAGA
ATGGAAAGATGGCAAGATTGTTTACTCTTATTTTATAGGTCTCTTCTCATCCATTCTACGAGAACAAGCA
AATCTTAAGCATGATGGACCAAAATGGATAGTCCTGGATGGCGATATTGACCCCATGTGGATTGAATCAC
TGAATACTGTAATGGATGATAACAAGGTGCTGACCCTCGCCAGCAATGAGCGCATTGCACTCACTCCCTT
CATGAGGCTTCTGTTTGAGATACATCACTTAAGGAGCGCAACCCCGGCCACTGTTTCCAGAGCTGGTATT
CTGTATGTGAACCCACAAGATCTGGGCTGGAATCCGTATGTGGCCAGTTGGATAGACAGAAGGCGGCATC
AATCAGAAAAGGCCAATTTGACTATTCTTTTTGATAAATATGTCCCTGCATGCTTGGATAAACTGAGAAC
AAGCTTTAAAACCATCACTTCAATTCCTGAGAGTAGCCTGGTGCAGACTCTATGTGTTCTTTTGGAGTGC
TTGCTGACTCCTGAAAATGTACCTTCTGACAGCCCAAAAGAAGTTTATGAAGTCTATTTTGTATTTGCTT
GTATCTGGGCTTTTGGAGGCACCCTGCTACAAGATCAGATTTCTGATTATCAAGCTGACTTCAGTCGGTG
GTGGCAGAAAGAGATGAAAGCAGTGAAATTTCCGTCGCAGGGAACAATCTTTGATTATTATGTGGACCAC
AAAACTAAGAAATTATTGCCCTGGGCTGACAAAATTGCCCAGTTTACTATGGATCCAGATGTGCCTCTGC
AGACAGTTCTCGTTCACACAACAGAGACAGCTCGTCTTAGATATTTCATGGAGTTGTTGCTTGAGAAAGG
AAAACCTCTAATGCTAGTAGGAAATGCAGGAGTGGGAAAAACAGTCTTTGTAGGTGACACATTGGCAAGT
CTCTCTGAGGATTACATAGTATCCCGTGTGCCTTTCAACTACTACACAACATCCACAGCTCTGCAAAAAA
TTCTTGAGAAACCCCTAGAGAAAAAAGCTGGTCATAACTATGGTCCTGGAGGAAATAAAAAATTGATTTA
TTTTATCGACGACATGAACATGCCTGAAGTGGACTTATATGGCACCGTTCAGCCTCATACCCTGATCCGG
CAGCATATTGATTATGGACATTGGTATGATAGACAGAAGGTGATGCTTAAAGAAATCCATAACTGCCAGT
ATGTCGCCTGCATGAATCCGATGGTGGGCAGCTTCACCATCAGTCCCAGGCTACAGAGACATTTCACAGT
GTTTGCATTCAATTTTCCATCTTTGGATGCACTAAACACCATCTATGGCCAAATCTTTAGCTTCCATTTC
CAACAGCAAGCATTTGCTCCATCAATTCTCAGGAGTGGCCCCACTTTGATCCAGGCAACAATAGCATTCC
ATCAGACAATGATGTGTAACTTTTTACCCACGGCTATTAAATTCCACTACATCTTTAATCTGAGAGATTT
ATCAAACGTCTTCCAGGGGATTTTATTTGCTTCTCCTGAGTGTTTAAAAGGTCCACTTGATTTAATACAT
CTGTGGCTTCATGAATCTGCCCGTGTTTATGGAGACAAACTGATAGACAAAAAAGATTGTGATTTGTTTC
AGAGAAGAATGCTGGAAACTGCTTATAAATATTTTGAAGGTATAGATAGTCACATGCTGCTTCAACAGCC
CCTCATTTATTGCCACTTTGCTGATAGAGGGAAGGACCCACATTACATGCCAGTGAAGGACTGGGAAGTG
CTGAAGACGATTCTTACAGAAACGTTAGACAACTACAATGAACTAAATGCTGCCATGCACCTAGTTTTGT
TTGAAGATGCCATGCAACATGTGTGTCGCATCAGCCGGATCTTACGAACCCCTCAGGGCTGTGCTCTCTT
GGTTGGAGTTGGGGGCAGTGGCAAGCAGAGCTTGTCCAGGCTGGCAGCTTACCTTCGTGGCCTTGAGGTC
TTTCAGATCACTCTGACCGAGGGCTATGGAATCCAGGAACTTCGGGTAGATCTTGCCAATTTGTACATCC
GAACTGGAGCCAAGAACATGCCCACTGTGTTCCTGCTGACAGATGCCCAGGTTCTAGATGAGAGCTTCCT
CGTGCTGATTAATGACTTGCTGGCATCAGGAGAAATCCCAGATCTGTTCAGCGATGAAGATGTGGACAAG
ATAATTTCTGGAATTCATAATGAAGTTCATGCTCTGGGCATGGTAGACTCCAGGGAAAACTGTTGGAAAT
TCTTTATGGCCAGGGTGCGACTACAGCTCAAAATCATTTTGTGTTTCTCTCCAGTTGGTCGCACGCTGAG
AGTTAGAGCTCGGAAGTTCCCAGCCATAGTTAACTGCACGGCTATTGACTGGTTTCATGCGTGGCCGCAG
GAGGCTCTGGTCTCCGTCAGCAGGAGGTTCATTGAGGAAACCAAGGGAATTGAGCCAGTGCACAAAGACT
CTATTAGCCTTTTCATGGCACATGTTCACACCACTGTAAATGAAATGAGTACCAGATATTACCAGAATGA
GAGAAGACACAACTATACCACCCCAAAGAGTTTTCTAGAACAAATATCACTGTTTAAGAACCTGTTGAAG
AAGAAGCAAAATGAGGTATCCGAGAAAAAAGAACGCCTGGTGAACGGCATCCAAAAGCTAAAAACCACAG

Fig. 9 (Continued)

CCTCTCAGGTGGGAGATCTAAAAGCCAGACTTGCCTCTCAAGAAGCCGAGCTGCAACTGAGAAATCATGA
TGCCGAAGCTCTGATCACAAAGATCGGCCTTCAGACGGAGAAAGTGAGCCGGGAAAAGACCATCGCTGAT
GCTGAGGAGCGAAAGGTGACAGCCATTCAGACTGAAGTGTTCCAGAAACAGAGAGAATGTGAAGCTGACT
TACTCAAGGCTGAGCCTGCACTGGTGGCTGCTACAGCTGCACTCAATACACTCAACAGGGTCAACCTCAG
TGAGCTGAAAGCCTTTCCCAACCCTCCCATCGCAGTTACCAATGTTACTGCAGCCGTGATGGTCCTTCTG
GCTCCTCGGGGAAGAGTGCCCAAAGACCGAAGTTGGAAAGCAGCTAAAGTCTTCATGGGAAAGGTTGATG
ATTTTTTGCAAGCATTAATTAACTATGACAAAGAGCACATTCCAGAGAACTGTCTAAAAGTGGTGAATGA
ACACTATTTGAAAGACCCAGAGTTTAATCCAAACCTGATTCGAACCAAATCTTTTGCAGCAGCTGGCCTG
TGTGCCTGGGTCATCAACATCATTAAATTCTATGAGGTCTACTGTGATGTGGAGCCAAAACGCCAAGCAT
TAGCCCAAGCAAACTTAGAACTGGCTGCAGCTACTGAAAAACTAGAGGCTATCAGGAAAAAGCTTGTGGA
TCTGGATCGAAATCTGAGCAGACTCACGGCTTCATTTGAAAAAGCAACAGCTGAGAAAGTCCGGTGTCAA
GAAGAGGTGAACCAAACCAACAAAACCATCAAATTAGCTAACAGACTTGTCAAGGAACTTGAGGCAAAGA
AGATTCGCTGGGGTCAATCCATTAAGTCCTTTGAAGCTCAAGAGAAGACACTCTGTGGAGATGTTCTTCT
CACGGCGGCATTTGTGTCTTACGTCGGACCCTTCACAAGGCAGTATCGCCAGGAGCTGGTGCACTGCAAG
TGGTTCCCTTTCTTCAACAGAAGGTTTCCATTCCACTAACCGAAGGCCTGGACTTGATATCCATGTTGA
CGGATGATGCTACAATTGCCGCCTGGAATAACGAAGGACTGCCCAGTGACAGAATGTCCACCGAAAATGC
CGCTATCCTAACACACTGTGAGCGCTGGCCTCTGGTGATAGATCCCCAGCAACAGGGAATTAAGTGGATC
AAGAATAAGTATGGAATGGACCTGAAAGTCACACATTTGGGCCAGAAAGGGTTTTTGAATGCCATTGAAA
CTGCTTTGGCCTTTGGTGATGTCATCTTAATTGAAAATCTCGAGGAAACGATAGATCCAGTCCTGGATCC
ACTACTTGGCAGGAACACAATTAAAAAAGGAAAGTATATCAGGATTGGAGATAAAGAATGTGAATTTAAC
AAGAACTTTCGCCTTATCCTTCACACAAAATTGGCAAATCCTCACTATAAGCCGGAATTACAAGCTCAGA
CAACTCTCCTCAATTTCACAGTCACAGAAGATGGTCTAGAAGCCCAGCTGCTGGCAGAGGTTGTCAGTAT
TGAAAGGCCAGATTTGGAGAAACTTAAGTTGGTATTGACAAAGCACCAAAATGATTTTAAAATTGAGCTC
AAGTATCTGGAAGACGATCTCCTTTTGCGCCTTTCTGCGGCAGAGGGAAGCTTTCTGGATGACACCAAAC
TGGTAGAGAGATTGGAGGCAACAAAGACCACCGTGGCAGAGATAGAGCACAAGGTGATTGAAGCCAAAGA
AAATGAAAGAAAAATCAACGAGGCCCGAGAATGTTACAGACCATTGGCAGCAAGAGCATCTCTTCTTTAT
TTTGTTATTAATGACCTCCAAAAAATCAACCCCCTCTACCAATTCTCTTTGAAGGCTTTTAACGTGCTGT
TCCACAGAGCGATCGAGCAGGCTGACAAGGTGGAAGACATGCAGGGACGCATCTCTATCCTGATGGAGAG
CATCACCCACGCTGTCTTCCTCTACACCAGCCAGGCGCTGTTTGAGAAGGACAAGCTCACCTTCCTGTCC
CAGATGGCTTTTCAGATTTTGTTGAGAAAGAAAGAGATAGACCCTCTTGAATTGGATTTCCTGCTTCGAT
TCACAGTTGAACACACTCATCTGAGTCCCGTTGACTTCCTAACTTCTCAGTCATGGAGTGCTATCAAGGC
AATTGCCGTCATGGAAGAATTTCGAGGCATAGACCGAGATGTGGAAGGATCTGCCAAGCAGTGGAGGAAG
TGGGTAGAATCCGAGTGTCCAGAAAAAGAAAAATTACCTCAAGAATGGAAGAAGAAAAGTTTAATACAGA
AGCTGATTCTTCTGAGAGCAATGCGCCCTGACAGAATGACGTATGCTCTCAGAAATTTTGTAGAGGAAAA
ACTGGGTGCGAAGTATGTGGAGAGGACCAGATTGGACTTAGTTAAAGCATTCGAAGAAAGCAGCCCAGCC
ACCCCCATATTCTTCATCCTGTCTCCGGGGGTAGATGCCCTTAAAGACCTGGAGATTCTTGGCAAAAGAC
TTGGCTTTACAATTGACTCTGGAAAATTCCACAATGTGTCTTTAGGACAAGGTCAGGAGACGGTGGCAGA
AGTGGCCCTGGAGAAAGCTTCCAAAGGAGGACACTGGGTCATCCTCCAAAATGTTCATTTGGTAGCCAAG
TGGCTAGGAACCTTGGAGAAGCTCCTTGAAAGATTCAGCCAAGGAAGCCACAGAGATTACAGGGTTTTCA
TGAGTGCTGAGTCTGCACCTACACCAGATGAGCATATCATCCCTCAAGGACTCCTGGAAAATTCCATTAA
GATCACTAATGAACCCCCAACAGGGATGCTGGCCAATTTGCATGCCGCCCTGTACAACTTTGATCAGGAT
ACACTTGAAATATGCTCCAAGGAGCAGGAGTTTAAAAGCATCCTTTTTTCTCTCTGCTACTTCCACGCCT
GTGTTGCTGGGAGACTGAGGTTTGGCCCCCAGGGCTGGAGCCGAAGCTATCCTTTTAATCCTGGAGACCT
CACCATTTGTGCCAGTGTCCTCTACAACTACTTAGAGGCAAACTCTAAAGTCCCATGGGAAGATCTCCGT
TATCTCTTTGGTGAGATCATGTATGGAGGCCACATCACAGATGACTGGGATCGCAAACTGTGTCGGGTGT
ATTTAGAAGAATTCGTGAATCCATCTCTGACTGAAGATGAACTGATGCTGGCACCAGGTTTTGCTGCCCC
ACCCTACCTAGATTATGCAGGCTACCACCAGTACATAGAGGAGATGCTTCCTCCAGAAAGCCCGGCACTG
TATGGCCTCCACCCAAATGCTGAAATAGAATTCCTGACAGTGACATCCAACACTCTCTTCAGAACTTTGC
TGGAGATGCAGCCCAGGAATGCACTCAGTGGTGATGAACTGGGGCAGTCTACAGAAGAAAAGGTTAAGAA
TGTCTTGGATGACATTTTGGAGAAACTTCCAGAAGAGTTCAACATGGCAGAGATAATGCAAAAAAATTCA
AATAGAAGCCCATATGTTCTTGTTTGCTTCCAAGAATGTGAGAGGATGAATATTCTCATTCGGGAAATAC
GTATATCACTTGAACAACTGGACCTTAGTTTGAAGGGGGAATTGGCATTATCTCCTGCTGTGGAAGCCCA
GCAGTTTGCATTGAGTTATGACACGGTACCAGACACTTGGAGCAAACTGGCTTATCCTTCTACTTATGGC
CTAGCCCAGTGGTTCAATGACCTCCTCCTGCGATGCCGAGAACTCGATACTTGGACACAAGACCTTACCC
TTCCGGCTGTCGTGTGGCTATCCGGCTTCTTCAACCCTCAGTCCTTCTTAACTGCAATCATGCAGACGAT
GGCTCGAAAAAATGAGTGGCCCCTGGATAAAACGCGCTTGACTGCTGATGTTACCAAAAAAACAAAGGAA
GATTATGGACACCCGCCAAGGGAAGGTGCATACCTCCACGGACTCTTCATGGAGGGCGCCCGCTGGGACA
CCCAAGCAGGAACCATTGTTGAAGCCCGTCTCAAGGAGCTGGCATGCCCTATGCCGGTCATCTTTGCAAA
AGCCACCCCCGTGGACAGACAAGAAACCAAACAGACCTACGAGTGCCCTGTGTATAGAACCAAACTGAGA
GGCCCCAGCTACATCTGGACCTTCAGGCTGAAGAGCGAAGAGAAGACTGCAAAATGGGTTCTGGCTGGAG
TGGCTCTGCTTCTAGAAGCCTAA

ID 49: DNAH12, *Homo sapiens*
ATGTCAGATGCAAACAAAGCTGCCATTGCAGCAGAAAAGGAAGCTCTGAACTTGAAGTTACCCCCCATTGTCCATCTCCCAGAAAACATAGGCG
TTGATACACCAACACAAAGTAAGCTGCTAAAATACAGAAGATCCAAGGAGCAGCAGCAGAAAATTAATCAGTTAGTAATTGATGGAGCCAAAAG
AAATTTAGACAGAACACTGGGTAAAAGAACACCTCTATTACCACCACCTGATTATCCTCAAACTATGACCAGTGAAATGAAAAAAAAAGGATTC
AACTATATTTATATGAAGCAATGTGTAGAAAGTAGTCCTTTAGTACCTATTCAGCAGGAATGGCTGGATCACATGTTAAGGCTGATACCTGAGT
CTTTAAAGGAAGGGAAAGAAAGAGAAGAACTTCTTGAAAGTCTCATAAATGAGGTGTCAAGTGACTTTGAAAACAGCATGAAGAGATATTTGGT
GCAGAGCGTTCTTGTGAAACCACCAGTTAAATCGCTTGAAGATGAAGGAGGTCCTTTACCTGAATCTCCTGTAGGCCTAGATTATTCTAATCCT
TGGCATTCTAGCTATGTGCAGGCAAGAAATCAAATATTCTCTAATTTGCACATTATTCATCCAACTATGAAAATGTTACTGGACCTTGGTTATA
CAACATTTGCTGATACAGTTTTGTTGGACTTCACAGGAATTAGAGCTAAAGGTCCAATTGACTGTGAATCACTGAAAACTGATCTATCAATACA
AACTAGAAACGCAGAAGAGAAGATAATGAATACATGGTATCCAAAGGTTATAAATCTCTTTACCAAGAAGGAGGCACTAGAAGGTGTTAAACCT
GAAAAATTGGATGCATTTTATAGCTGTGTTTCCACACTTATGTCAAATCAGCTAAAGGATCTATTAAGGAGAACTGTAGAAGGATTTGTAAAAC
TCTTTGACCCAAAAGATCAACAAAGGCTGCCAATATTTAAGATAGAATTGACATTTGATGACGACAAAATGGAATTTTATCCTACCTTTCAAGA
TTTGGAAGATAATGTCTTGAGTTTGGTGGAACGAATAGCCGAAGCTCTGCAGAATGTCCAAACAATCCCCTCTTGGCTATCAGGAACTTCAACA
CCAGTAAATCTTGACACAGAACTTCCTGAACACGTGTTACACTGGGCTGTTGATACACTGAAGGCAGCAGTACATCGGAACTTAGAAGGTGCAA
GAAAGCATTATGAGACATATGTTGAAAAATATAATTGGCTCCTTGATGGGACTGCAGTTGAGAATATAGAGACTTTTCAGACAGAAGATCATAC
TTTTGATGAATATACAGAGGAGCTGGATTGCTGGGTGGTATGGGAAGTGTATTTTTAA ID 50: DNAH14, *Homo sapiens*

Fig. 9 (Continued)

ATGGAGACGTTTATACCCATTGATTTGACAACTGAAAATCAAGAGATGGACAAGGAGGAAACCAAGACAAAACCAAGACTTTTAAGATATGAAG
AGAAAAAATATGAAGATGTGAAACCATTAGAGACTCAACCAGCTGAAATAGCAGAAAAGGAAACATTGGAATATAAAACAGTTAGAACATTCTC
TGAATCTTTGAAGTCAGAGAAAACAGAAGATTACCTTAGAGAAAGTATAATTCAACAACATATGGTTTCTCCAGAGCCAGCTTCCCTTAAGGAG
AAAGGGAAGTCAAGGAGAAAAAAGGATCAAACTCATGCTTGTCCAAATGTTAGGAAAGCCAGGCCTGTGTCCTATGATAGAACAGAACCAAAAG
ATGATGATGTGATAAGAAATATTATTAGGCTACGAGAAAAGCTTGGTTGGCAAACTATATTACCGCAGCACAGTTTGAAATACGGAAGCTCCAA
AATTGCAATTCAGAAGATTACTTTAAAGAAACCTTTGGAAGATGATGGAGAATTTGTTTATTGCCTTCCTCGGAAAAGTCCTAAATCCCTTTAC
AATCCATATGATCTTCAGGTAGTATCGGCTCATACTGCTAAACATTGCAAAGAATTTTGGGTTATTACTGCTTCATTTATCTCAAAGGTTATTA
ATATAGTTGGTAGTGTAAAGGAAGTAGAACTCATACCTACTTTGGAATGGCTATCAGAAAGAAGACATTACTATTTATTACGGCAATTCAAGAT
ATTTTCTGATTTCCGAATGAATAAAGCATTTGTTACCTGGAAATTGAATGTTAAAAGAATTAAGACAGAGAAGAGCAGGTCATTTTTGTACCAC
CATCTTTTTTTGGCTGATGACTTGTTTCAAACCTGTTTGGTTTATATAAGAGGACTTTGTGAAGATGCAATTAATCTCAAAAATTATAATGACC
ATGAAAATAATCTATCTGCCATATGCCTTGTAAAGCTGGATAGTTCTCGAACATATTCTCTAGATGAATTTTGTGAAGAGCAGTTACAGCAAGC
TACCCAGGCATTGAAACAACTTGAGGACATCAGGAATAAAGCAATTTCAGAGATGAAAAGTACTTTTCTAAAGGTTGCAGAAAAGAATGAAATC
AAAGAGTATTTTGAGTCAAAACTCTCTGAAGATGACACAACACATTTCAAGCTGCCTAAATATAGACGTTTATTAGAAACATTTTTCAAGTTTG
TAATGCTGGTTGACTACATATTTCAGGAACTCATTCGTCAACTTATGAACACTGCAGTCACACTACTTTTGGAATTATTTAATGGTTCTGCTGG
AATGCCATTTTCAGTGGAAAAAAAGAATGAAAATCTTATCAGGTAA

ID 51: DNAI1, *Homo sapiens*
ATGATTCCTGCTTCTGCGAAGGCTCCCCATAAACAGCCTCATAAGCAGAGCATCAGCATAGGCAGAGGAACCAGGAAGAGAGATGAAGATTCAG
GGACTGAAGTGGGAGAAGGCACAGATGAATGGGCCCAATCCAAAGCCACAGTTAGACCCCCTGACCAGCTGGAGTTGACCGATGCGGAGTTAAA
GGAGGAGTTCACTCGGATTTTGACAGCCAACAACCCACACGCACCCCAGAACATTGTCAGGTACAGCTTCAAAGAAGGCACATATAAGCCTATT
GGCTTTGTGAACCAACTGGCAGTTCACTACACCCAGGTTGGGAACCTGATCCCCAAAGACTCAGATGAAGGACGGCGGCAGCATTACCGCGATG
AATTAGTGGCAGGTTCTCAGGAGTCTGTCAAGGTGATTTCAGAAACAGGAAACCTCGAAGAAGACGAAGAGCCCAAGGAGTTAGAAACTGAGCC
TGGGAGTCAAACAGATGTGCCTGCAGCTGGGGCAGCTGAAAAAGTGACTGAAGAAGAATTGATGACTCCTAAGCAGCCCAAGGAGAGAAAGCTC
ACTAACCAGTTCAACTTCAGTGAGAGGGCCTCACAGACCTACAACAACCCTGTCCGGGATCGAGAATGCCAGACGGAGCCTCCTCCCAGGACAA
ACTTTTCAGCCACAGCCAATCAGTGGGAGATCTATGATGCCTATGTAGAGGAACTTGAGAAGCAGGAAAAGACCAAAGAGAAGGAGAAGGCAAA
GACCCCAGTGGCTAAAAAATCAGGGAAGATGGCCATGAGGAAGCTGACATCTATGGAGTCTCAGACTGATGATCTCATCAAATTGTCCCAAGCT
GCTAAGATCATGGAGCGGATGGTCAACCAGAATACATATGATGACATTGCTCAAGATTTTAAGTACTATGACGATGCTGCTGATGAATACCGGG
ACCAGGTGGGTACCCTGCTGCCGCTCTGGAAGTTCCAAAATGACAAAGCCAAGCGCCTGTCCGTCACTGCCCTCTGCTGGAATCCAAAGTACAG
GGATCTGTTTGCAGTGGGATATGGCTCTTATGACTTCATGAAGCAGAGCCGGGGCATGCTGCTGCTCTACAGCCTGAAGAACCCCAGCTTCCCT
GAGTACATGTTCAGCAGCAACAGCGGCGTCATGTGTCTCGACATCCACGTGGACCACCCCTACCTGGTGGCAGTAGGCCACTATGACGGCAACG
TGGCCATTTACAACCTCAAGAAGCCCCACTCCCAGCCCTCCTTCTGCAGCTCAGCCAAGTCTGGCAAGCACTCAGACCCTGTGTGGCAGGTCAA
GTGGCAGAAGGATGACATGGACCAAAACCTTAACTTCTTCTCTGTGTCATCTGACGGCAGGATTGTGTCTTGGACTCTCGTGAAGAGAAAGCTG
GTTCACATAGATGTCATCAAGCTGAAGGTGGAAGGCAGCACCACGGAAGTTCCTGAGGGGTTGCAGCTGCACCCAGTGGGTTGTGGCACTGCCT
TTGACTTCCACAAAGAGATTGACTACATGTTCCTAGTGGGCACAGAGGAGGGAAAAATCTACAAGTGCTCTAAATCCTACTCCAGCCAATTCCT
CGACACCTATGACGCCCACAACATGTCAGTGGACACTGTGTCCTGGAACCCATACCACACCAAGGTCTTCATGTCCTGCAGCTCCGACTGGACA
GTGAAGATCTGGGACCACACCATCAAGACCCCGATGTTCATCTATGACCTGAACTCAGCCGTGGGTGATGTGGCCTGGGCGCCATACTCTTCTA
CTGTGTTCGCAGCAGTCACCACAGATGGGAAGGCCCACATATTTGACTTAGCCATCAACAAGTATGAGGCCATCTGCAACCAGCCTGTGGCGGC
CAAAAAGAACAGGCTCACCCACGTGCAGTTCAATCTCATCCACCCCATCATCATTGTGGGCGATGACCGTGGGCACATCATCAGCCTCAAGCTC
TCACCCAATTTGCGCAAGATGCCAAAGGAAAAGAAGGGGCAGGAGGTGCAGAAGGGTCCAGCTGTGGAGATTGCGAAACTGGACAAACTGCTGA
ACCTGGTGAGGGAAGTGAAAATCAAGACCTGA ID 52: DNAI2, *Homo sapiens*
ATGGAGATTGTGTACGTGTACGTCAAGAAGCGCAGCGAGTTCGGGAAGCAGTGCAATTTCTCGGACCGCCAGGCCGAGCTGAACATCGACATCA
TGCCCAACCCTGAGCTGGCCGAGCAGTTCGTGGAGCGGAACCCAGTGGACACGGGCATCCAGTGCTCGATCAGCATGTCGGAACACGAGGCCAA
CTCAGAGCGGTTTGAGATGGAGACCCGGGGAGTTAACCATGTCGAGGGGGGCTGGCCCAAGGACGTGAACCCCCTGGAGCTGGAGCAGACCATC
CGTTTCCGGAAGAAAGTGGAGAAAGATGAGAACTACGTTAACGCCATCATGCAGCTCGGCTCTATCATGGAGCACTGCATCAAGCAGAACAATG
CCATTGACATCTATGAAGAGTATTTCAATGACGAGGAGGCCATGGAAGTGATGGAGGAGGACCCTTCAGCTAAAACCATCAATGTGTTCAGGGA
CCCCCAGGAAATCAAGAGGGCTGCCACACACCTCTCCTGGCACCCCGATGGCAACAGGAAGTTGGCAGTGGCATACTCCTGCTTGGATTTTCAG
CGGGCACCTGTGGGCATGAGCAGCGATTCATACATCTGGGACCTGGAAAACCCCAACAAGCCTGAACTTGCTCTGAAGCCATCGTCTCCACTCG
TGACGTTGGAGTTCAACCCCAAAGATTCCCACGTACTCCTGGGTGGCTGCTACAATGGACAGATAGCCTGCTGGGACACCCGAAAGGGCAGCCT
GGTGGCGGAGCTATCCACCATTGAGTCCAGCCACCGAGACCCTGTGTATGGCACCATCTGGCTGCAGTCGAAGACGGGCACCGAGTGCTTCTCA
GCTTCCACGGATGGGCAGGTCATGTGGTGGGACATCCGAAAGATGAGCGAGCCCACTGAAGTTGTGATCTTGGACATCACCAAGAAGGAACAGT
TGGAAAATGCCTTGGGGGCCATCTCCCTGGAGTTCGAATCTACTTTGCCCACCAAGTTCATGGTGGGGACCGAGCAGGGCATCGTCATCTCCTG
CAACCGCAAGGCCAAGACGTCAGCTGAAAAGATTGTGTGCACCTTCCCGGGCCATCATGGCCCCATCTACGCCCTCCAGAGAAACCCCTTCTAC
CCGAAGAACTTCCTGACGGTTGGCGACTGGACAGCCCGCATTTGGTCTGAAGACAGCCGGGAATCGTCCATCATGTGGACCAAGTACCACATGG
CTTACCTCACTGATGCTGCCTGGAGCCCCGTGAGGCCGACCGTTTTCTTTACCACCAGGATGGACGGAACCCTGGATATCTGGGACTTCATGTT
CGAGCAGTGCGATCCCACCCTCAGCTTGAAGGTGTGTGACGAGGCCCTCTTCTGCCTCCGGGTGCAGGACAATGGGTGTCTCATCGCCTGCGGC
TCCCAGCTGGGGACAACCACCCTGCTGGAGGTCTCGCCTGGGCTCTCTACCCTCCAGAGGAATGAGAAGAACGTAGCCTCTTCCATGTTTGAGC
GTGAGACCCGGCGAGAGAAGATCCTGGAGGCCAGGCACCGGGAGATGCGGCTGAAGGAGAAGGGTAAGGCGGAGGGCAGGGATGAGGAGCAGAC
CGATGAGGAGCTGGCCGTAGACCTGGAGGCGCTGGTCAGCAAGGCCGAGGAGGAGTTCTTCGACATCATCTTCGCAGAGCTGAAGAAGAAGGAG
GCAGACGCCATAAAGCTGACGCCAGTGCCTCAGCAACCAAGTCCAGAAGAAGACCAGGTGGTGGAGGAGGGAGAGGAAGCAGCGGGGAAGAAG
GGGATGAAGAAGTGGAAGAAGACTTAGCCTAG ID 53: DNAL1, *Homo sapiens*
ATGGCGAAAGCAACAACAATCAAAGAAGCCTTAGCGAGATGGGAAGAGAAAACTGGCCAGAGGCCATCTGAAGCCAAAGAGATAAAACTTTATG
CCCAGATTCCCCCTATAGAGAAGATGGATGCATCCTTGTCCATGCTTGCTAATTGCGAGAAGCTTTCACTGTCTACAAACTGCATTGAAAAAAT
TGCCAACCTGAATGGCTTAAAAAACTTGAGGATATTATCTTTAGGAAGAAACAACATAAAGAACTTAAATGGACTGGAGGCAGTAGGGGACACA
TTAGAAGAACTGTGGATCTCCTACAATTTTATTGAGAAGTTGAAAGGGATCCACATAATGAAGAAATTGAAGATTCTCTACATGTCTAATAACC
TGGTAAAAGACTGGGCTGAGTTTGTGAAGCTGGCAGAACTGCCATGCCTCGAAGACCTGGTGTTTGTAGGCAATCCCTTGGAAGAGAAACATTC
TGCTGAGAATAACTGGATTGAAGAAGCAACCAAGAGAGTGCCCAAACTGAAAAAGCTGGATGGTACTCCAGTAATTAAAGGGGATGAGGAAGAA
GACAACTAA ID 54: DNAL4, *Homo sapiens*
ATGGGAGAAACAGAAGGGAAGAAAGATGAGGCTGATTATAAGCGACTGCAGACCTTCCCTCTGGTCAGGCACTCGGACATGCCAGAGGAGATGC
GCGTGGAGACCATGGAGCTATGTGTCACAGCCTGTGAGAAATTCTCCAACAACAACGAGAGCGCCGCCAAGATGATCAAAGAGACAATGGACAA
GAAGTTCGGCTCCTCCTGGCACGTGGTGATCGGCGAGGGCTTTGGGTTTGAGATCACCCACGAGGTGAAGAACCTCCTCTACCTGTACTTCGGG
GGCACCCTGGCTGTGTGCGTCTGGAAGTGCTCCTGA

**ID 55: Stathmin, *Homo sapiens***

Fig. 9 (Continued)

ATGGCTTCTTCTGATATCCAGGTGAAAGAACTGGAGAAGCGTGCCTCAGGCCAGGCTTTTGAGCTGATTCTCAGCCCTCGGTCAAAAGAATCTG
TTCCAGAATTCCCCCTTTCCCCTCCAAAGAAGAAGGATCTTTCCCTGGAGGAAATTCAGAAGAAATTAGAAGCTGCAGAAGAAAGACGCAAGTC
CCATGAAGCTGAGGTCTTGAAGCAGCTGGCTGAGAAACGAGAGCACGAGAAAGAAGTGCTTCAGAAGGCAATAGAAGAGAACAACAACTTCAGT
AAAATGGCAGAAGAGAAACTGACCCACAAAATGGAAGCTAATAAAGAGAACCGAGAGGCACAAATGGCTGCCAAACTGGAACGTTTGCGAGAGA
AGATGTACTTCTGGACTCACGGGCCTGGGGCCCACCCAGCACAGATCTCTGCTGAGCAATCTTGTCTCCACTCTGTTCCTGCCCTTTGCCCAGC
CCTGGGCCTCCAATCTGCATTGATTACCTGGTCTGATCTCTCTCACCATCACTAG

**ID 56: Gephyrin, *Homo sapiens***

ATGGCGACCGAGGGAATGATCCTTACTAACCACGACCATCAAATCCGTGTCGGAGTCCTTACAGTGAGTGATAGTTGCTTCAGGAATCTTGCAG
AAGACCGCAGTGGGATAAATCTCAAAGATCTCGTACAAGATCCTTCTTTGTTGGGTGGACTATATCAGCATACAAGATAGTACCAGATGAAAT
AGAAGAAATCAAGGAAACCCTGATAGATTGGTGTGATGAAAAGGAACTTAATTTGATATTAACAACTGGAGGAACAGGATTTGCACCACGAGAT
GTCACTCCAGAGGCCACAAAAGAAGTAATAGAACGGGAAGCACCAGGGATGGCCCTGGCAATGCTGATGGGATCACTTAATGTTACACCTCTGG
GCATGCTCTCTAGGCCTGTATGTGGAATCAGAGGGAAAACGCTCATAATTAACCTGCCAGGTAGCAAGAAAGGATCTCAGGAATGCTTTCAATT
CATACTGCCAGCTCTACCTCATGCCATTGACCTTTTACGTGATGCCATTGTAAAAGTAAAGGAGGTGCATGATGAACTTGAAGATTTGCCTTCC
CCACCTCCCCCTCTTTCCCCTCCTCCTACTACCAGCCCCCATAAACAGACAGAAGACAAAGGAGTTCAATGTGAGGAAGAGGAAGAAGAGAAGA
AAGACAGTGGTGTTGCTTCAACAGAAGATAGTTCCTCATCACATATAACTGCAGCAGCCATTGCTGCCAAGAAGCATCCATTCTACACCAGTCC
TGCTGTTGTCATGGCACACGGTGAACAGCCCATCCCTGGTCTCATCAATTATTCCCATCATTCAACAGATGAACGGATTCCAGACTCCATCATT
TCTCGTGGTGTTCAGGTGCTCCCACGAGACACAGCCTCCCTCAGCACTACTCCTTCAGAATCGCCTCGTGCTCAGGCTACATCTCGCCTCTCTA
CAGCTTCCTGCCCAACACCAAAAGTCCAGTCCAGGTGCAGCAGCAAGGAGAACATTCTCAGAGCCAGTCACAGTGCTGTCGATATCACCAAGGT
GGCTAGAAGACATCGCATGTCTCCTTTTCCTCTGACATCTATGGACAAAGCCTTTATCACAGTCCTGGAGATGACTCCGGTGCTTGGGACAGAA
ATCATCAATTACCGAGATGGAATGGGGCGAGTCCTTGCTCAAGATGTATATGCAAAAGACAATTTACCCCCCTTCCCAGCATCAGTAAAAGATG
GCTATGCTGTCCGAGCTGCTGATGGCCCAGGAGATCGTTTCATCATTGGGGAATCCCAAGCTGGTGAACAGCCAACTCAGACAGTAATGCCAGG
ACAAGTCATGCGGGTTACAACAGGTGCTCCAATACCCTGCGGTGCTGATGCAGTAGTACAAGTGGAAGATACCGAACTTATCAGGGAATCAGAT
GATGGCACTGAAGAACTTGAAGTGCGAATTCTGGTGCAAGCTCGGCCAGGCCAAGATATCAGACCCATCGGCCATGACATTAAAAGAGGGGAAT
GTGTTTTGGCCAAAGGAACCCACATGGGCCCCTCAGAGATTGGTCTTCTGGCAACTGTAGGTGTCACAGAGGTTGAAGTTAATAAGTTTCCAGT
GGTTGCAGTCATGTCAACAGGGAATGAGCTGCTAAATCCTGAAGATGACCTCTTACCAGGGAAGATTCGAGACAGCAATCGTTCAACTCTTCTA
GCAACAATTCAGGAACATGGTTACCCCACGATCAACTTGGGTATTGTAGGAGACAACCCAGATGACTTACTCAATGCCTTGAATGAGGGTATCA
GTCGTGCTGATGTCATCATCACATCAGGGGGTGTATCCATGGGGGAAAAGGACTATCTCAAGCAGGTGCTGGACATTGATCTTCATGCTCAGAT
CCATTTTGGCAGGGTTTTTATGAAACCAGGCTTGCCAACAACATTTGCAACTTTGGATATTGATGGTGTAAGAAAAATAATCTTTGCACTACCT
GGGAATCCTGTATCGGCTGTGGTCACCTGCAATCTCTTTGTTGTGCCTGCACTGAGGAAAATGCAGGGCATCTTGGATCCTCGGCCAACCATCA
TCAAAGCAAGGTTATCATGTGATGTAAAACTTGATCCTCGTCCAGAATACCATCGGTGTATACTAACTTGGCATCACCAAGAACCACTACCTTG
GGCACAGAGTACAGGTAATCAAATGAGCAGCCGTCTGATGAGCATGCGCAGTGCCAATGGATTGTTGATGCTACCTCCAAAGACAGAACAGTAC
GTGGAGCTCCACAAAGGCGAGGTGGTGGATGTCATGGTCATTGGACGGCTATGA

**ID 57: MAP1a, *Homo sapiens***

ATGGACGGCGTGGCTGAGTTCTCCGAGTATGTCTCTGAGACTGTGGACGTGCCATCCCCATTTGACCTACTAGAGCCCCCCACCTCAGGGGGCT
TCCTCAAGCTCTCCAAGCCTTGTTGCTACATCTTCCCAGGTGGTCGTGGGGACTCTGCCCTCTTTGCTGTCAATGGTTTCAACATCCTGGTGGA
TGGTGGCTCTGATCGCAAGTCCTGTTTTTGGAAGCTGGTACGGCACTTGGACCGCATTGACTCGGTGCTACTCACACACATTGGGCAGACAAC
CTGCCAGGCATCAATGGACTACTGCAGCGCAAAGTGGCAGAGCTAGAGGAGGAGCAGTCCCAGGGCTCTAGCAGTTACAGCGACTGGGTGAAGA
ACCTTATCTCTCCTGAGCTTGGAGTTGTCTTTTTCAACGTGCCTGAGAAGCTGCGGCTTCCTGATGCCTCCCGGAAAGCCAAGCGTAGCATTGA
GGAGGCCTGCCTCACTCTGCAGCACTTAAACCGCCTGGGCATCCAGGCTGAGCCTCTATATCGTGTGGTCAGCAATACCATTGAGCCACTGACC
CTCTTCCACAAAATGGGTGTGGGCCGGCTGGACATGTATGTCCTCAACCCTGTCAAGGACAGCAAGGAGATGCAGTTCCTCATGCAAAAGTGGG
CAGGCAATAGTAAAGCCAAGACAGGCATCGTGCTGCCCAATGGAAGGAGGCTGAGATCTCCGTGCCCTACCTTACCTCTATCACTGCTCTGGT
GGTCTGGCTACCAGCCAATCCCACTGAGAAGATTGTGCGTGTGCTTTTTCCAGGAAATGCTCCCCAAAACAAGATCTTGGAGGGCCTAGAAAAG
CTTCGGCATCTGGACTTCCTGCGTTACCCTGTGGCCACGCAGAAGGACCTGGCTTCTGGGGCTGTGCCTACCAACCTCAAGCCCAGCAAAATCA
AACAGCGGGCTGATAGCAAGGAGAGCCTCAAAGCCACTACCAAGACGGCCGTGAGCAAGTTGGCCAAACGGAGGAGGTGGTAGAAGAGGGAGC
CAAGGAGGCACGTTCAGAGCTGGCCAAGGAGTTAGCCAAGACAGAGAAGAAGGCAAAAGAGTCATCTGAGAAGCCCCCAGAGAAGCCTGCCAAG
CCTGAGAGGGTGAAGACAGAGTCAAGTGAGGCACTGAAGGCAGAGAAGCGAAAGCTGATCAAAGACAAGGTAGGGAAAAAGCACCTTAAAGAAA
AGATATCAAAGCTGGAAGAAAAAAAGACAAGGAGAAAAAAGAGATCAAAAAGGAGAGGAAAGAGCTCAAGAAGGATGAAGGAAGGAAGGAGGA
GAAGAAGGATGCCAAGAAGGAGGAGAAGAGGAAAGATACCAAACCTGAGCTCAAGAAGATTTCCAAGCCAGACCTAAAGCCCTTTACTCCTGAG
GTACGTAAGACCCTCTATAAAGCCAAGGTCCCTGGAAGAGTCAAAATAGACAGGAGCCGTGCTATCCGTGGGGAGAAGGAGCTGTCTTCTGAGC
CCCAGACACCCCCAGCCCAGAAGGGAACTGTACCACTCCCAACCATCAGTGGGCACAGGGAGCTGGTCCTATCCTCACCAGAGGACCTCACACA
GGACTTTGAGGAGATGAAGCGTGAGGAGAGGGCTTTGCTGGCTGAACAAAGGGACACAGGACTAGGAGATAAGCCATTCCCTCTAGACACTGCA
GAGGAGGGACCCCCAAGTACAGCTATCCAGGGAACACCACCCTCTGTTCCAGGGCTGGGACAAGAAGAACATGTCATGAAGGAGAAAGAGCTTG
TCCCAGAGGTCCCTGAGGAACAAGGCAGCAAGGACAGAGGCCTAGACTCTGGGGCTGAAACAGAGGAAGAGAAAGATACCTGGGAGGAAAAGAA
GCAGAGGGAAGCAGAGAGGCTCCCAGACAGAACAGAAGCCAGAGAGGAAAGTGAACCTGAAGTAAAGGAGGATGTGATAGAAAAGGCTGAGTTA
GAAGAAATGGAGGAGGTACACCCTTCAGATGAGGAGGAAGAGGACGCGACAAAAGCTGAGGGTTTTTACCAAAAACATATGCAGGAACCCTTGA
AGGTAACTCCAAGGAGCCGGGAGGCTTTTGGGGGTCGGGAATTGGGACTCCAGGGCAAGGCCCCTGAGAAGGAGACCTCGTTATTCCTAAGCAG
CCTGACCACACCTGCAGGAGCCACTGAGCATGTCTCTTACATCCAGGATGAGACAATCCCTGGCTACTCAGAGACTGAGCAGACCATCTCAGAT
GAGGAGATCCATGATGAGCCGGAGGAGCGCCCAGCTCCACCCAGATTTCATACAAGTACATATGACCTGCCCGGGCCTGAAGGTGCTGGCCCAT
TCGAAGCCAGCCAACCTGCCGATAGTGCTGTTCCTGCTACCTCTGGCAAAGTCTATGGAACGCCAGAGACTGAACTCACCTACCCCACTAACAT
AGTGGCTGCCCCTTTGGCTGAAGAGGAACATGTGTCCTCGGCCACTTCAATCACTGAGTGTGACAAACTTTCTTCCTTTGCCACATCAGTGGCT
GAGGACCAATCTGTGGCCTCACTTACAGCTCCCCAGACAGAGGAGACAGGCAAGAGCTCCCTGCTGCTTGACACAGTCACAAGCATCCCTTCCT
CCCGTACTGAAGCTACGCAGGGCTTGGACTATGTGCCATCAGCTGGTACCATCTCACCCACCTCCTCACTGGAAGAAGACAAGGGCTTCAAATC
ACCACCCTGTGAGGACTTCTCTGTGACTGGGGAGTCAGAGAAGAGAGGAGAGATCATAGGGAAAGGCTTGTCTGGAGAGAGAGCTGTGGAAGAG
GAAGAGGAGGAGACAGCAAACGTAGAGATGTCTGAGAAACTTTGCAGTCAATATGGAACTCCAGTGTTTAGTGCCCCTGGGCATGCCCTACATC
CAGGAGAACCAGCCCTTGGAGAAGCAGAGGAGCGGTGCCTTAGCCCAGATGACAGCACAGTGAAGATGGCTTCTCCTCCACCATCTGGCCCACC
CAGTGCCACCCACACACCCTTTCATCAGTCCCCAGTGGAAGAAAAGTCTGAGCCCCAAGACTTTCAGGAGGCAGACTCCTGGGGAGACACTAAG
CGCACACCAGGTGTGGGCAAAGAAGATGCTGCAGAGGAGACAGTCAAGCCAGGGCCTGAAGAGGGCACACTAGAGAAGGAAGAGAAAGTTCCTC
CTCCCAGGAGCCCCCAGGCCCAGGAAGCACCTGTCAACATTGATGAGGGGCTTACAGGCTGTACCATTCAACTGTTGCCAGCACAGGATAAAGC
AATAGTCTTTGAGATTATGGAGGCAGGAGAGCCCACAGGCCCAATTCTGGGAGCAGAAGCCCTTCCCGGAGGTTTGAGGACTTTACCCCAAGAA
CCTGGCAAACCTCAGAAAGATGAGGTGCTCAGATATCCTGACCGAAGCCTCTCTCCTGAAGATGCAGAATCCCTCTCTGTCCTCAGCGTGCCCT
CCCCAGACACTGCCAACCAAGAGCCTACCCCCAAGTCTCCCTGTGGCCTGACAGAACAGTACCTACACAAAGACCGTTGGCCAGAGGTATCTCC
AGAAGACACCCAGTCACTTTCTCTGTCAGAAGAGAGTCCCAGCAAGGAGACCTCCCTGGATGTCTCTTCTAAGCAGCTCTCTCCAGAAAGCCTT
GGCACCCTCCAGTTTGGGGAACTAAACCTTGGGAAGGAAGAAATGGGGCATCTGATGCAGGCCGAGGATACCTCTCACCACACAGCTCCCATGT
CTGTTCCAGAGCCCCATGCAGCCACAGCGTCACCTCCCACAGATGGGACAACTCGATACTCTGCACAGACAGACATCACAGATGACAGCCTTGA
CAGGAAGTCACCTGCCAGCTCATTCTCTCACTCTACACCTTCAGGAAATGGGAAGTACTTACCTGGGGCGATCACAAGCCCTGATGAACACATT
CTGACACCTGATAGCTCCTTCTCCAAGAGTCCTGAGTCTTTGCCAGGCCCTGCCTTGGAGGACATTGCCATAAAGTGGGAAGATAAAGTTCCAG
GGTTGAAAGACAGAACCTCAGAACAGAAGAAGGAACCTGAGCCAAAGGATGAAGTTTTACAGCAGAAAGACAAAACTCTGGAGCACAAGGAGGT
GGTAGAGCCGAAGGATACAGCCATCTATCAGAAAGATGAGGCTCTGCATGTAAAGAATGAGGCTGTGAAACAGCAGGATAAGGCTTTAGAACAA

Fig. 9 (Continued)

AAGGGCAGAGACTTAGAGCAAAAAGACACAGCCCTAGAACAGAAGGACAAGGCCCTGGAACCAAAAGACAAAGACTTAGAAGAAAAAGACAAGG
CCCTGGAACAGAAGGATAAGATTCCAGAAGAGAAAGACAAAGCCTTAGAACAAAAGGATACAGCCCTGGAACAGAAGGACAAGGCCCTGGAACC
AAAAGATAAAGACTTGGAACAAAAGGACAGGGTCCTAGAACAGAAGGAGAAGATCCCAGAAGAGAAAGACAAAGCCTTAGATCAAAAAGTCAGA
AGTGTTGAACATAAGGCTCCGGAGGACACGGTCGCTGAAATGAAGGACAGAGACCTAGAACAGACAGACAAAGCCCCTGAACAGAAACACCAGG
CCCAGGAACAAAAGGATAAAGTCTCAGAAAAGAAGGATCAGGCCTTAGAACAAAAATACTGGGCTTTGGGACAGAAGGATGAAGCCCTGGAACA
AAACATTCAGGCTCTGGAAGAGAACCACCAAACTCAGGAGCAGGAGAGCCTAGTGCAGGAGGATAAAACCAGGAAACCAAAGATGCTAGAGGAA
AAATCCCCAGAAAAGGTCAAGGCCATGGAAGAGAAGTTAGAAGCTCTTCTGGAGAAGACCAAAGCTCTGGGCCTGGAAGAGAGCCTAGTGCAGG
AGGGCAGGGCCAGAGAGCAGGAAGAAAAGTACTGGAGGGGGCAGGATGTGGTCCAGGAGTGGCAAGAAACATCTCCTACCAGAGAGGAGCCGGC
TGGAGAACAGAAAGAGCTTGCCCCGGCATGGGAGGACACATCTCCTGAGCAGGACAATAGGTATTGGAGGGGCAGAGAGGATGTGGCCTTGGAA
CAGGACACATACTGGAGGGAGCTAAGCTGTGAGCGGAAGGTCTGGTTCCCTCACGAGCTGGATGGCCAGGGGGCCCGCCCACACTACACTGAGG
AACGGGAAAGCACTTTCCTAGATGAGGGCCCAGATGATGAGCAAGAAGTACCCCTGCGGGAACACGCAACCCGGAGCCCCTGGGCCTCAGACTT
CAAGGATTTCCAGGAATCCTCACCACAGAAGGGGCTAGAGGTGGAGCGCTGGCTTGCTGAATCACCAGTTGGGTTGCCACCAGAGGAAGAGGAC
AAACTGACCCGCTCTCCCTTTGAGATCATCTCCCCTCCAGCTTCCCCACCTGAGATGGTTGGACAAAGGGTTCCTTCAGCCCCAGGACAAGAGA
GTCCTATCCCAGACCCTAAGCTCATGCCACACATGAAGAATGAACCCACTACTCCCTCATGGCTGGCTGACATCCCACCCTGGGTGCCCAAGGA
CAGACCCCTCCCCCCTGCACCCCTCTCCCCAGCTCCTGGTCCCCCCACACCTGCCCCGGAATCCCATACTCCTGCACCCTTCTCTTGGGGCACA
GCCGAGTATGACAGTGTGGTGGCTGCAGTGCAGGAGGGGGCAGCTGAGTTGGAAGGTGGGCCATACTCCCCCCTGGGGAAGGACTACCGCAAGG
CTGAAGGGGAAAGGGAAGAAGAAGGTAGGGCTGAGGCTCCTGACAAAAGCTCACACAGCTCAAAGGTACCAGAGGCCAGCAAAAGCCATGCCAC
CACGGAGCCTGAGCAGACTGAGCCGGAGCAGAGAGAGCCCACACCCTATCCTGATGAGAGAAGCTTTCAGTATGCAGACATCTATGAGCAGATG
ATGCTTACTGGGCTTGGCCCTGCATGCCCCACTAGAGAGCCTCCACTTGGAGCAGCTGGGGATTGGCCCCCATGCCTCTCAACCAAGGAGGCAG
CTGCCGGCCGAAACACATCTGCAGAGAAGGAGCTTTCATCTCCTATCTCACCCAAGAGCCTCCAGTCTGACACTCCAACCTTCAGCTATGCAGC
CCTGGCAGGACCCACTGTACCCCCAAGGCCAGAGCCAGGGCCAAGTATGGAGCCCAGCCTCACCCCACCTGCAGTTCCCCCCCGTGCTCCTATC
CTGAGCAAAGGCCCAAGCCCCCCTCTTAATGGTAACATCCTGAGCTGCAGCCCAGATAGGAGGTCCCCATCCCCCAAGGAATCAGGCCGGAGTC
ACTGGGATGACAGCACTAGTGACTCAGAACTGGAGAAGGGGGCTCGGGAACAGCCAGAAAAAGAGGCCCAATCCCCAAGTCCTCCTCACCCCAT
TCCTATGGGGTCCCCCACATTATGGCCAGAAACTGAGGCACATGTTAGCCCTCCCTTGGACTCACACCTGGGGCCTGCCCGACCCAGTCTGGAC
TTCCCTGCTTCAGCCTTTGGCTTCTCCTCATTGCAGCCAGCTCCCCCACAGCTGCCCTCTCCAGCTGAACCCCGCTCGGCACCCTGTGGCTCCC
TTGCCTTCTCTGGGGATCGAGCTCTGGCTCTGGCTCCAGGACCCCCCACCAGAACCCGGCATGATGAATACCTGGAAGTGACCAAGGCCCCCAG
CCTGGATTCCTCACTGCCCCAGCTCCCATCACCCAGTTCTCCTGGGGCCCCTCTCCTCTCCAATCTGCCACGACCTGCCTCACCAGCCCTGTCT
GAGGGCTCCTCCTCTGAGGCTACCACGCCTGTGATTTCAAGTGTGGCGGAGCGCTTCTCTCCAAGCCTTGAGGCTGCAGAACAGGAGTCTGGAG
AGCTGGACCCAGGAATGGAACCAGCTGCCCACAGCCTCTGGGACCTCACTCCTCTGAGCCCAGCACCCCCAGCTTCACTGGACTTGGCCCTAGC
TCCAGCTCCAAGCCTGCCTGGAGACATGGGTGATGGCATCCTGCCGTGCCACCTGGAGTGCTCAGAGGCAGCCACGGAGAAGCCAAGCCCCTTC
CAGGTTCCCTCTGAGGATTGTGCAGCCAATGGCCCAACTGAAACCAGCCCTAACCCCCCAGGCCCTGCCCCAGCCAAGGCTGAAAATGAAGAGG
CTGCGGCTTGCCCTGCCTGGGAACGTGGGGCCTGGCCTGAAGGAGCTGAGAGGAGCTCCCGGCCTGACACATTGCTCTCCCCTGAGCAGCCAGT
GTGTCCTGCAGGGGGCTCCGGGGGCCCACCCAGCAGTGCCTCTCCTGAGGTCGAAGCTGGGCCCCAGGGATGTGCCACTGAGCCTCGGCCCCAT
CGTGGGGAGCTCTCCCCATCCTTCCTGAACCCACCTCTGCCCCCATCCATAGATGATAGGGACCTCTCAACTGAGGAAGTTCGGCTAGTAGGAA
GAGGGGGGCGGCGCCGGGTAGGGGGGCCAGGGACCACTGGGGGCCCATGCCCTGTGACTGATGAGACACCCCCTACATCAGCCAGTGACTCAGG
CTCCTCACAGTCAGATTCTGATGTCCCGCCAGAAACTGAGGAGTGTCCGTCCATCACAGCTGAGGCAGCCCTCGACTCAGATGAAGATGGAGAC
TTCCTACCTGTGGACAAAGCTGGGGGTGTCAGTGGTACTCACCACCCCAGGCCTGGCCATGACCCACCTCCTCTCCCACAGCCAGACCCCCGCC
CATCCCCTCCCCGCCCTGATGTGTGCATGGCTGACCCCGAGGGGCTCAGCTCAGAGTCTGGGAGAGTAGAGAGGCTACGGGAGAAGGAAAAGGT
TCAGGGGCGAGTAGGGCGCAGGGCCCCAGGCAAGGCCAAGCCAGCGTCCCCTGCACGGCGTCTGGATCTTCGGGGAAAACGCTCACCCACCCCT
GGTAAAGGGCCTGCAGATCGAGCATCCCGGGCCCCACCTCGACCACGCAGCACCACAAGCCAGGTCACCCCAGCAGAGGAAAAGGATGGACACA
GCCCCATGTCCAAAGGCCTAGTCAATGGACTCAAGGCAGGACCAATGGCCTTGAGTTCCAAGGGCAGCTCTGGTGCCCCTGTATATGTGGATCT
CGCCTACATCCCGAATCATTGCAGTGGCAAGACTGCTGACCTTGACTTCTTCCGTCGAGTGCGTGCATCCTACTATGTGGTCAGTGGGAATGAC
CCTGCCAATGGCGAGCCAAGCCGGGCTGTGCTGGATGCCCTGCTGGAGGGCAAGGCCCAGTGGGGGGAGAATCTTCAGGTGACTCTGATCCCTA
CTCATGACACGGAGGTGACTCGTGAGTGGTACCAACAAACTCATGAGCAGCAGCAACAACTGAATGTCCTGGTCCTGGCTAGCAGCAGCACCGT
GGTGATGCAGGATGAGTCCTTCCCTGCCTGCAAGATTGAGTTCTGA

ID 58: MAP1b, *Homo sapiens*

ATGGCGACCGTGGTGGTGGAAGCCACCGAGCCGGAGCCGTCCGGCAGCATCGCCAACCCGGCGGCGTCCACCTCGCCTAGCCTGTCGCACCGCT
TCCTTGACAGCAAGTTCTACTTGCTGGTGGTCGTCGGCGAGATCGTGACCGAGGAGCACCTGCGGCGTGCCATCGGCAACATCGAGCTCGGAAT
CCGATCATGGGACACAAACCTGATTGAATGCAACTTGGACCAAGAACTCAAACTTTTTGTATCTCGACACTCTGCAAGATTCTCTCCTGAAGTC
CCAGGACAAAAGATCCTTCATCACCGAAGTGACGTTTTAGAAACAGTGGTCCTGATCAACCCTTCTGATGAAGCAGTCAGCACCGAGGTGCGCT
TAATGATCACTGATGCTGCCCGACACAAGCTGCTCGTGCTGACCGGGCAGTGCTTTGAAAATACCGGAGAGCTCATTCTCCAGTCCGGCTCTTT
CTCCTTCCAGAACTTCATAGAGATTTTCACCGATCAAGAGATCGGGGAGTTACTAAGCACCACCCATCCTGCCAACAAAGCCAGCTTAACCCTG
TTCTGTCCTGAAGAAGGGGACTGGAAGAACTCCAATCTTGACAGACACAATCTCCAAGACTTCATCAATATTAAACTCAATTCAGCTTCTATCT
TGCCAGAAATGGAAGGACTTTCTGAGTTTACCGAGTATCTCTCAGAATCAGTGGAAGTCCCATCTCCCTTTGACATCTTGGAACCTCCCACATC
GGGTGGATTTCTGAAGCTCTCCAAGCCCTGCTGTTATATTTTTCCAGGAGGGAGGGGCGATTCTGCCTTGTTTGCAGTGAATGGTTTCAATATG
CTCATCAATGGCGGATCAGAGAGAAAATCCTGCTTCTGGAAGCTCATCCGACACTTAGACCGAGTGGACTCCATCCTGCTCACCCACATTGGGG
ATGACAATTTGCCTGGAATAAACAGCATGTTACAGCGGAAAATTGCAGAGCTCGAGGAAGAACAGTCCCAGGGCTCCACCACAAATAGTGACTG
GATGAAAAACCTCATCTCCCCTGACTTAGGAGTTGTATTTCTCAATGTACCTGAAAATCTCAAAAATCCAGAGCCAAACATCAAGATGAAGAGA
AGCATAGAAGAAGCCTGCTTCACTCTCCAGTACCTAAACAAATTGTCCATGAAACCAGAACCTCTGTTTAGAAGTGTAGGCAATACTATTGATC
CTGTCATTCTTTTCCAAAAAATGGGAGTAGGTAAACTTGAGATGTATGTGCTTAATCCAGTCAAGAGCAGCAAGGAAATGCAGTATTTTATGCA
GCAGTGGACTGGTACCAACAAAGACAAGGCTGAATTCATTCTGCCTAATGGTCAAGAAGTAGATCTCCCGATTTCCTACTTAACTTCAGTCTCA
TCTTTGATTGTGTGGCATCCAGCAAACCCTGCGGAGAAAATCATCCGAGTCCTGTTTCCTGGGAACAGCACCCAGTACAACATCCTGGAAGGGT
TGGAAAAGCTCAAACATCTAGACTTTCTGAAGCAGCCACTGGCCACCCAAAAGGATCTCACTGGCCAGGTGCCCACTCCTGTGGTGAAACAAAC
AAAACTGAAACAGAGGGCTGATAGCCGAGAAAGTCTGAAGCCAGCCGCAAAACCACTTCCTAGCAAATCCGTGCGCAAGGAGTCAAAAGAAGAA
ACCCCTGAGGTCACAAAAGTGAATCACGTGGAAAAGCCACCCAAAGTTGAAAGCAAAGAAAAGGTAATGGTGAAAAAAGACAAGCCAATAAAAA
CAGAGACCAAACCTTCAGTGACTGAAAAGGAGGTTCCCAGCAAAGAAGAGCCATCTCCAGTGAAAGCCGAGGTGGCTGAGAAGCAAGCCACAGA
TGTCAAACCCAAAGCTGCCAAGGAGAAGACGGTGAAAAAGGAAACCAAGGTAAAGCCTGAAGACAAGAAAGAGGAGAAAGAAAAGCCAAAGAAA
GAAGTGGCTAAAAAGGAGGACAAAACACCTATCAAGAAGGAGGAAAAACCAAAAAGGAAGAGGTGAAAAAAGAAGTCAAAAAAGAGATCAAGA
AAGAAGAGAAAAAAGAACCCAAGAAAGAGGTTAAGAAAGAAACACCGCCAAAGGAAGTTAAGAAGGAAGTGAAGAAGGAAGAGAAGAAGGAAGT
GAAAAAGGAAGAAAAGGAACCCAAAAAAGAAATTAAGAAGCTCCCTAAAGACGCAAAGAAATCATCTACTCCTCTGTCTGAAGCAAAAAAACCA
GCTGCTTTAAAACCAAAAGTACCCAAGAAGGAAGAGTCTGTCAAGAAAGATTCTGTTGCTGCCGGAAAGCCAAAGGAGAAAGGGGAAAATAAAG
TCATTAAGAAGGAAGGCAAGGCCGCAGAGGCTGTCGCTGCAGCTGTCGGCACTGGAGCCACCACAGCAGCTGTCATGGCGGCAGCTGGAATAGC
AGCCATTGGCCCTGCCAAAGAACTCGAAGCTGAGAGGTCCCTTATGTCATCTCCTGAGGATCTAACCAAGGACTTTGAAGAGTTAAAGGCTGAA
GAGGTCGATGTAACAAAGGACATCAAGCCTCAGCTGGAGCTAATCGAAGACGAAGAGAAACTGAAGGAAACTGAGCCAGTCGAAGCCTACGTCA
TCCAGAAGGAGAGAGAAGTCACCAAAGGTCCTGCCGAGTCCCCTGATGAGGGAATCACTACCACTGAAGGGGAGGGCGAATGTGAACAGACACC
TGAGGAGCTGGAGCCCGTCGAGAAGCAGCGAGTAGACGACATTGAAAAATTTGAAGATGAAGGAGCCGGTTTTGAAGAATCTTCAGAGACTGGA
GACTATGAAGAGAAGGCAGAAACTGAGGAGGCTGAGGAGCCAGAAGAGGATGGGGAGGAACACGTATGTGTGAGCGCCTCCAAGCACAGCCCCA
CTGAGGATGAGGAAAGTGCCAAGGCGGAGGCTGATGCATACATCAGGGAGAAGAGGGAGTCTGTGGCCAGTGGGGATGACCGAGCCGAAGAAGA
CATGGATGAGGCCATTGAGAAAGGAGAGGCTGAACAATCTGAAGAGGAGGCTGATGAGGAGGACAAAGCTGAAGATGCCAGAGAGGAGGAATAT

Fig. 9 (Continued)

GAGCCGGAAAAAATGGAAGCTGAAGACTATGTGATGGCTGTGGTCGACAAGGCTGCAGAGGCTGGTGGTGCCGAGGAGCAGTATGGATTCCTCA
CCACACCAACCAAGCAACTAGGAGCCCAGTCTCCTGGCCGAGAACCTGCATCTTCAATTCATGATGAGACTTTACCTGGAGGCTCAGAGAGCGA
GGCCACCGCTTCTGATGAGGAGAATCGAGAAGACCAGCCTGAGGAATTCACTGCCACCTCTGGCTACACTCAGTCTACTATTGAGATATCCAGT
GAGCCCACCCCCATGGATGAGATGTCTACCCCTCGAGACGTGATGAGTGATGAGACCAACAATGAAGAGACGGAGTCCCCTTCTCAGGAATTCG
TAAATATCACCAAATATGAATCTTCATTGTATTCTCAGGAATACTCTAAACCTGCTGATGTTACACCGCTCAACGGATTTTCTGAAGGATCAAA
AACAGATGCCACTGATGGCAAGGATTACAATGCTTCAGCCTCTACCATATCACCACCCTCTTCCATGGAGGAAGACAAATTCAGCAGATCTGCT
TTACGTGATGCTTACTGCTCTGAAGTGAAAGCCAGCACCACTTTGGACATCAAAGATAGCATCTCAGCTGTTTCAAGTGAAAAGGTCAGCCCAT
CGAAGAGCCCGTCCCTGAGTCCATCTCCACCATCACCCTTAGAAAAGACCCCCCTGGGTGAACGTAGTGTGAACTTCTCTCTGACGCCCAATGA
GATTAAAGTCTCTGCAGAGGCAGAAGTAGCCCCGGTGTCTCCTGAGGTGACCCAAGAAGTAGTTGAAGAACATTGTGCTAGTCCTGAGGACAAG
ACTCTGGAAGTGGTGTCACCATCTCAGTCCGTGACTGGCAGTGCTGGTCACACACCTTACTATCAATCTCCTACTGACGAGAAATCCAGTCATC
TCCCTACAGAAGTCATTGAAAAACCACCAGCAGTTCCAGTGAGTTTTGAATTCAGTGATGCCAAAGATGAGAATGAAAGGGCTTCAGTAAGCCC
CATGGATGAGCCCGTGCCTGACTCAGAGTCTCCTATTGAAAAAGTTTTGTCTCCTTTACGCAGCCCGCCCCTCATTGGATCCGAGTCTGCTTAT
GAAAGTTTTCTAAGTGCTGATGACAAGGCTTCTGGCAGAGGTGCCGAAAGTCCTTTTGAAGAAAAGAGTGGAAAACAAGGCTCTCCAGACCAAG
TAAGTCCAGTTTCTGAAATGACTTCTACTAGTCTTTACCAAGACAAACAGGAAGGGAAAAGCACAGACTTTGCACCAATAAAAGAAGACTTTGG
CCAAGAAAAGAAAACTGATGATGTTGAAGCCATGAGTTCTCAACCAGCACTGGCTCTGGATGAAAGGAAATTAGGAGATGTTTCTCCCACACAA
ATAGATGTCAGTCAGTTTGGATCTTTTAAAGAAGACACTAAGATGTCCATTTCTGAAGGTACTGTCTCAGACAAGTCAGCTACTCCTGTTGATG
AGGGCGTAGCAGAAGACACGTACTCTCATATGGAGGGTGTGGCCTCAGTGTCCACAGCCTCAGTGGCTACGAGCTCATTTCCAGAGCCAACAAC
AGATGATGTGTCTCCATCTCTGCATGCTGAGGTTGGCTCCCCACATTCCACAGAAGTAGATGACTCCCTTTCAGTGTCTGTTGTGCAAACACCT
ACCACATTCCAGGAAACAGAAATGTCTCCATCTAAAGAAGAATGCCCAAGACCGATGTCAATTTCTCCACCAGATTTCTCCCCTAAAACTGCAA
AGTCCAGGACACCCGTTCAAGATCACAGATCTGAACAGTCCTCAATGTCTATTGAATTTGGCCAAGAATCTCCTGAGCAATCCCTTGCTATGGA
CTTCAGTCGACAGTCTCCAGATCACCCTACAGTGGGTGCAGGCGTGCTTCACATCACTGAAAATGGGCCAACTGAAGTGGACTACAGTCCTTCT
GACATGCAGGACTCCAGTTTATCACATAAGATACCACCTATGGAGGAGCCGTCCTACACCCAAGATAATGATCTTTCTGAGCTCATCTCAGTAT
CTCAGGTAGAGGCCTCCCCGTCCACCTCTTCTGCTCATACCCCTTCTCAGATCGCTTCTCCTCTCCAAGAAGATACTCTATCCGATGTTGCTCC
TCCCAGAGATATGTCCTTATATGCCTCACTCACCTCTGAAAAAGTGCAAAGTCTGGAAGGAGAGAAGCTCTCTCCAAAATCTGATATCTCTCCA
CTCACCCCACGAGAGTCCTCTCCTTTATATTCACCTACTTTTTCAGATTCTACCTCTGCAGTCAAAGAGAAAACAGCAACTTGCCACAGTTCCT
CTTCTCCACCAATAGATGCAGCATCCGCAGAGCCCTATGGCTTCCGTGCCTCAGTGTTATTCGATACAATGCAACACCATCTAGCCTTGAATAG
AGATTTGTCCACACCTGGCCTGGAGAAGGACAGTGGAGGGAAGACACCTGGTGACTTTAGCTATGCCTATCAAAAGCCTGAGGAAACAACCAGG
TCCCCAGATGAAGAAGATTATGACTATGAGTCTTATGAGAAGACCACCCGGACCTCAGATGTGGGTGGCTATTACTATGAGAAGATAGAGAGAA
CCACAAAATCTCCAAGTGACAGTGGCTACTCCTATGAGACCATTGGAAAACTACCAAGACCCCTGAAGATGGTGACTATTCCTATGAAATTAT
TGAGAAGACCACACGGACCCCTGAAGAGGGTGGGTACTCATATGACATAAGTGAAAAGACCACCAGCCCCCCCGAAGTGAGTGGTTACAGCTAT
GAAAAGACTGAGAGGTCTAGAAGGCTTCTGGATGACATCAGCAATGGCTATGATGACTCTGAGGATGGTGGCCACACACTTGGGGACCCCAGCT
ACTCTTATGAAACCACTGAGAAAATTACCAGTTTCCCTGAGTCTGAAGGTTATTCCTATGAGACATCTACAAAGACAACACGAACCCCTGATAC
TTCCACATACTGTTACGAGACTGCAGAGAAAATCACTAGAACCCCTCAGGCATCCACATATTCCTACGAGACTTCAGACCTATGCTACACTGCA
GAAAAGAAGTCCCCCTCAGAAGCCCGTCAGGATGTCGATTTATGCCTCGTGTCCTCTTGTGAATACAAGCACCCCAAGACAGAGCTTTCACCCT
CTTTCATTAATCCCAATCCTCTTGAGTGGTTTGCCAGTGAAGAACCCACTGAAGAATCTGAAAAGCCCCTCACTCAATCAGGGGGAGCCCCACC
GCCTCCAGGAGGAAAGCAACAGGGCCGACAGTGTGATGAAACCCCTCCCACCTCAGTCAGCGAGTCAGCCCCATCCCAGACCGACTCTGATGTT
CCCCCGGAGACTGAAGAGTGCCCCTCCATCACGGCCGATGCCAATATCGACTCTGAAGACGAGTCGGAAACCATCCCCACAGACAAAACTGTCA
CGTACAAACACATGGACCCACCTCCAGCTCCCGTGCAAGACCGCAGCCCTTCGCCACGCCACCCTGATGTGTCCATGGTGGACCCAGAGGCCTT
GGCCATTGAGCAGAACCTGGGCAAAGCTCTAAAGAAAGATCTGAAAGAGAAGACCAAAACCAAAAAGCCAGGTACAAAGACCAAGTCATCTTCA
CCTGTCAAAAAGAGTGATGGGAAGTCTAAGCCCTTGGCAGCTTCACCAAAACCAGCGGGCTTGAAAGAATCCTCGGATAAAGTGTCCAGGGTGG
CTTCTCCTAAGAAGAAAGAATCTGTGGAAAAGGCAGCAAAACCCACCACCACTCCTGAGGTCAAAGCTGCACGTGGGGAAGAGAAAGACAAGGA
GACCAAGAATGCTGCCAATGCCTCTGCATCCAAGTCGGCCAAGACCGCCACTGCAGGACCAGGAACTACCAAGACGACCAAGTCATCTGCTGTG
CCCCCAGGCCTCCCTGTGTATTTGGACCTGTGCTACATTCCTAACCACAGCAATAGTAAGAATGTTGATGTGGAATTTTTCAAGAGAGTGCGGT
CTTCCTACTACGTGGTGAGTGGGAATGACCCTGCTGCTGAGGAGCCCAGCCGGGCTGTCCTGGACGCTTTGTTGGAAGGAAAGGCTCAGTGGGG
CAGCAACATGCAGGTGACACTGATCCCAACTCATGACTCAGAAGTGATGAGGGAATGGTACCAGGAGACCCATGAGAAACAGCAAGATCTCAAC
ATCATGGTTTTAGCAAGCAGCAGCACAGTGGTTATGCAAGATGAATCCTTCCCTGCATGCAAGATTGAACTGTAA

**ID 59: MAP2, *Homo sapiens***

ATGGCAGATGAACGGAAAGATGAAGCAAAGGCACCTCACTGGACCTCAGCACCGCTAACAGAGGCATCTGCACACTCACATCCACCTGAGATTA
AGGATCAAGGCGGAGCAGGGGAAGGACTTGTCCGAAGCGCCAATGGATTCCCATACAGGGAGGATGAAGAGGGTGCCTTTGGAGAGCATGGGTC
ACAGGGCACCTATTCAAATACCAAAGAGAATGGGATCAACGGAGAGCTGACCTCAGCTGACAGAGAAACAGCAGAGGAGGTGTCTGCAAGGATA
GTTCAAGTAGTCACTGCTGAGGCTGTAGCAGTCCTGAAAGGTGAACAAGAGAAAGAAGCTCAACATAAAGACCAGACTGCAGCTCTGCCTTTAG
CAGCTGAAGAAACAGCTAATCTGCCTCCTTCTCCACCCCCATCACCTGCCTCAGAACAGACTGTCACAGTGGAGGAAGATTTACTTACAGCCTC
GAAGATGGAGTTCCACGATCAACAGGAATTGACTCCCTCTACAGCTGAGCCTTCAGACCAGAAGGAAAAGGAGTCAGAGAAGCAAAGTAAGCCT
GGTGAAGACCTTAAACATGCTGCCTTAGTTTCTCAGCCAGAGACAACTAAAACTTACCCTGATAAAAAGGACATGCAAGGCACGGAAGAAGAAA
AAGCACCCCTAGCTTTGTTTGGCACACTCTTGTTGCCAGCCTGGAAGACATGAAACAGAAGACAGAACCAAGCCTTGTAGTACCTGGCATTGA
CCTCCCTAAAGAGCCTCCAACTCCAAAAGAACAAAGGACTGGTTCATCGAAATGCCAACGGAAGCAAAAAAGGATGAGTGGGGTTTAGTTGCC
CCCATATCTCCTGGCCCTCTGACTCCCATGAGGGAAAAAGATGTATTTGATGATATCCCAAAATGGGAAGGGAAACAGTTTGATTCTCCCATGC
CAAGTCCCTTTCAAGGGGGAAGCTTCACTCTTCCTTTAGATGTCATGAAGAATGAAATAGTTACAGAAACATCGCCCTTTGCCCCTGCCTTTTT
ACAGCCAGATGACAAAAAATCTCTGCAACAAACCAGTGGCCCAGCTACTGCCAAAGATAGTTTTAAAATTGAAGAGCCCCATGAGGCTAAACCT
GACAAAATGGCAGAAGCACCACCCTCAGAGGCAATGACCTTACCCAAAGATGCTCACATTCCAGTTGTAGAAGAACATGTTATGGGGAAAGTTT
TAGAGGAAGAAAAGGAGGCCATAAATCAAGAGACTGTGCAGCAAAGGGATACTTTCACCCCCAGTGGACAGGAACCTATACTTACTGAAAAGGA
AACTGAGCTGAAGCTTGAAGAAAAAACCACCATTTCTGACAAAGAAGCTGTGCCAAAAGAGAGTAAACCCCCAAAACCTGCAGATGAAGAAATA
GGCATAATTCAGACCTCCACAGAGCACACTTTCTCAGAACAGAAAGACCAAGAGCCTACCACAGATATGTTGAAACAGGACTCGTTCCCTGTAA
GTTTGGAGCAAGCAGTTACAGATTCAGCCATGACCTCTAAAACACTGGAGAAAGCCATGACCGAACCATCTGCATTAATTGAAAAGAGCTCAAT
TCAGGAACTTTTTGAAATGAGAGTTGATGACAAAGATAAGATTGAAGGAGTTGGAGCTGCAACATCAGCTGAGCTTGATATGCCATTTTATGAA
GATAAATCAGGAATGTCCAAGTACTTTGAAACATCTGCCTTGAAAGAAGAAGCAACAAAAAGCATTGAGCCAGGCAGTGATTACTATGAACTGA
GTGACACTAGAGAAAGTGTCCATGAGTCTATTGATACCATGTCTCCCATGCATAAAAATGGTGACAAGGAGTTTCAAACAGGAAAAGAATCCCA
GCCCAGTCCTCCAGCACAAGAAGCAGGGTACAGCACTCTCGCACAGAGTTATCCATCAGATTTACCTGAAGAACCCAGTTCTCCTCAAGAAAGA
ATGTTCACTATTGATCCAAAAGTGTATGGAGAGAAAAGGGACCTCCACAGTAAGAATAAGGATGATTTGACCCTTAGCAGGAGTTTAGGACTTG
GTGGTAGGTCTGCAATAGAACAAAGAAGCATGTCAATCAATTTGCCGATGTCTTGCCTAGATTCCATAGCCCTTGGATTTAACTTTGGTCGGGG
ACATGATCTTTCTCCTCTGGCTTCCGATATTCTAACCAACACTAGTGGAAGTATGGATGAAGGGGATGATTACCTTCCAGCCACCACACCTGCA
CTGGAGAAAGCCCCTTGCTTCCCTGTAGAAAGCAAAGAGGAAGAACAGATAGAGAAAGTAAAAGCTACTGGAGAAGAAAGTACTCAAGCGGAGA
TATCATGTGAGTCTCCTTTCCTAGCCAAAGATTTTTACAAAAATGGTACTGTCATGGCACCTGACCTTCCTGAAATGCTAGATCTGGCAGGCAC
AAGGTCAAGATTGGCTTCTGTGAGTGCAGATGCTGAGGTTGCCAGGAGGAAATCAGTCCCATCAGAGACTGTGGTTGAGGATAGTCGTACTGGC
TTGCCCCCGGTAACTGATGAAAACCATGTCATTGTAAAAACGGACAGTCAGCTCGAAGACCTGGGCTACTGTGTGTTCAATAAGTACACAGTCC
CATTGCCATCACCTGTTCAAGACAGTGAGAATTTATCAGGGGAGAGTGGTACCTTTTACGAAGGCACTGATGATAAAGTTCGAAGAGATTTGGC
CACAGACCTTTCACTGATTGAAGTGAAACTGGCAGCAGCCGGAAGAGTCAAAGATGAGTTCAGTGTTGACAAAGAAGCATCCGCGCATATCTCT
GGTGACAAATCAGGACTGAGTAAGGAGTTTGACCAAGAGAAGAAAGCTAATGATAGGTTGGATACTGTACTAGAAAAGAGTGAAGAACATGCTG
ATTCAAAAGAACATGCCAAGAAAACTGAAGAGGCTGGTGATGAAATAGAAACATTCGGATTAGGAGTAACCTATGAGCAAGCTTTGGCCAAAGA

Fig. 9 (Continued)

TTTGTCAATACCAACAGATGCATCCTCTGAGAAAGCAGAGAAGGGTCTTAGTTCAGTGCCAGAGATAGCTGAGGTAGAACCATCCAAAAAGGTG
GAACAAGGTCTGGATTTTGCTGTCCAGGGTCAACTAGATGTTAAAATTAGTGACTTTGGACAGATGGCTTCAGGGCTAAACATAGATGATAGAA
GGGCAACAGAGCTAAAACTTGAGGCTACACAGGACATGACCCCCTCATCCAAAGCACCGCAGGAGGCAGATGCATTTATGGGTGTTGAGTCTGG
CCACATGAAAGAAGGCACTAAAGTTAGTGAGACAGAAGTCAAAGAGAAGGTGGCCAAGCCTGACTTGGTGCACCAGGAGGCTGTAGACAAGGAG
GAGTCCTATGAATCTAGTGGTGAGCATGAAAGTCTCACCATGGAGTCCTTGAAAGCTGATGAGGGCAAGAAGGAAACATCTCCAGAATCATCTC
TAATTCAAGATGAGATTGCCGTCAAATTGTCAGTGGAAATACCTTGCCCACCTGCTGTTTCAGAGGCTGATTTAGCCACAGATGAGAGAGCTGA
TGTCCAGATGGAATTTATTCAGGGGCCAAAAGAAGAAAGCAAAGAGACCCCAGATATATCCATCACGCCTTCTGATGTTGCAGAGCCATTGCAT
GAAACGATCGTATCTGAACCAGCAGAGATTCAGAGTGAGGAAGAAGAGATAGAAGCCCAGGGAGAATATGATAAACTGCTCTTCCGCTCAGACA
CCCTTCAGATAACTGACCTGGGTGTCTCAGGTGCCAGGGAGGAATTTGTGGAGACCTGCCCAAGTGAACACAAAGGAGTGATTGAGTCTGTTGT
GACCATCGAGGATGATTTCATCACTGTAGTGCAAACCACAACTGATGAAGGGGAGTCAGGGTCCCACAGCGTGCGTTTTGCAGCCCTAGAGCAG
CCTGAGGTGGAAAGGAGACCATCTCCTCATGATGAAGAAGAGTTTGAAGTAGAAGAGGCAGCTGAAGCCCAGGCAGAACCCAAAGATGGTTCCC
CAGAGGCTCCAGCTTCCCCTGAGAGAGAAGAGGTTGCACTTTCTGAATATAAGACAGAAACCTATGACGATTACAAAGATGAGACCACCATTGA
CGACTCCATCATGGACGCTGACAGCCTCTGGGTGGACACTCAAGATGATGATAGGAGCATCATGACAGAACAGTTAGAAACTATTCCTAAAGAG
GAGAAAGCTGAAAAGGAAGCTCGGAGATCATCTCTTGAGAAACATAGAAAAGAAAAGCCTTTTAAAACCGGGAGAGGCAGAATTTCCACTCCTG
AAAGAAAAGTAGCTAAAAAGGAACCTAGCACAGTCTCCAGAGATGAAGTGAGAAGGAAAAAAGCAGTTTATAAGAAGGCTGAACTTGCTAAAAA
AACAGAAGTTCAGGCCCACTCTCCCTCCAGGAAATTCATTTTAAAACCTGCTATCAAATATACTAGACCAACTCATCTCTCCTGTGTTAAGCGG
AAAACCACAGCAGCAGGTGGGGAATCAGCTCTGGCTCCCAGTGTATTTAAACAGGCAAAGGACAAAGTCTCTGACGGAGTAACCAAGAGCCCAG
AAAAGCGCTCTTCTCTCCCAAGACCTTCCTCCATTCTCCCTCCTCGGCGAGGTGTGTCAGGAGACAGAGATGAGAATTCCTTCTCTCTCAACAG
TTCTATCTCTTCTTCAGCACGGCGGACCACCAGGTCAGAGCCAATTCGCAGAGCAGGGAAGAGTGGTACCTCAACACCCACTACCCCTGGGTCT
ACTGCCATCACTCCTGGCACCCCACCAAGTTATTCTTCACGCACACCAGGCACTCCTGGAACCCCTAGCTATCCCAGGACCCCTCACACACCAG
GAACCCCCAAGTCTGCCATCTTGGTGCCGAGTGAGAAGAAGGTCGCCATCATACGTACTCCTCCAAAATCTCCTGCGACTCCCAAGCAGCTTCG
GCTTATTAACCAACCACTGCCAGACCTGAAGAATGTCAAATCCAAAATCGGATCAACAGACAACATCAAATACCAGCCTAAAGGGGGGCAGGTA
CAAATTGTTACCAAGAAAATAGACCTAAGCCATGTGACATCCAAATGTGGCTCTCTGAAGAACATCCGCCACAGGCCAGGTGGCGGACGTGTGA
AAATTGAGAGTGTAAAACTAGATTTCAAAGAAAAGGCCCAAGCTAAAGTTGGTTCTCTTGATAATGCTCATCATGTACCTGGAGGTGGTAATGT
CAAGATTGACAGCCAAAAGTTGAACTTCAGAGAGCATGCTAAAGCCCGTGTGGACCATGGGGCTGAGATCATTACACAGTCCCCAGGCAGATCC
AGCGTGGCATCACCCCGACGACTCAGCAATGTCTCCTCGTCTGGAAGCATCAACCTGCTCGAATCTCCTCAGCTTGCCACTTTGGCTGAGGATG
TCACTGCTGCACTCGCTAAGCAGGGCTTGTGA

ID 60: MAP4, *Homo sapiens*
ATGGCTGACCTCAGTCTTGCAGATGCATTAACAGAACCATCTCCAGACATTGAGGCAGAGATAAAGCGGGACTTCATTGCCACACTAGAGGCAG
AGGCCTTTGATGATGTTGTGGGAGAAACTGTTGGAAAAACAGACTATATTCCTCTCCTGGATGTTGATGAGAAAACCGGGAACTCAGAGTCAAA
GAAGAAACCGTGCTCAGAAACTAGCCAGATTGAAGATACTCCATCTTCTAAACCAACACTCCTAGCCAATGGTGGTCATGGAGTAGAAGGGAGC
GATACTACAGGGTCTCCAACTGAATTCCTTGAAGAGAAAATGGCCTACCAGGAATACCCAAATAGCCAGAACTGGCCAGAAGATACCAACTTTT
GTTTCCAACCTGAGCAAGTGGTCGATCCTATCCAGACTGATCCCTTTAAGATGTACCATGATGATGACCTGGCAGATTTGGTCTTTCCCTCCAG
TGCGACAGCTGATACTTCAATATTTGCAGGACAAAATGATCCCTTGAAAGACAGTTACGGTATGTCTCCCTGCAACACAGCTGTTGTACCTCAG
GGGTGGTCTGTGGAAGCCTTAAACTCTCCACACTCAGAGTCCTTTGTTTCCCCAGAGGCTGTTGCAGAACCTCCTCAGCCAACGGCAGTTCCCT
TAGAGCTAGCCAAGGAGATAGAAATGGCATCAGAAGAGAGGCCACCAGCACAAGCATTGGAAATAATGATGGGACTGAAGACTACTGACATGGC
ACCATCTAAAGAAACAGAGATGGCCCTCGCCAAGGACATGGCACTAGCTACAAAAACCGAGGTGGCATTGGCTAAAGATATGGAATCACCCACC
AAATTAGATGTGACACTGGCCAAGGACATGCAGCCATCCATGGAATCAGATATGGCCCTAGTCAAGGACATGGAACTACCCACAGAAAAAGAAG
TGGCCCTGGTTAAGGATGTCAGATGGCCCACAGAAACAGATGTATCTTCAGCCAAGAATGTGGTACTGCCCACAGAAACAGAGGTAGCCCCAGC
CAAGGATGTGACACTGTTGAAAGAAACAGAGAGGGCATCTCCTATAAAAATGGACTTAGCCCCTTCCAAGGACATGGGACCACCCAAAGAAAAC
AAGAAAGAAACAGAGAGGGCATCTCCTATAAAAATGGACTTGGCTCCTTCCAAGGACATGGGACCACCCAAAGAAAACAAGATAGTCCCAGCCA
AGGATTTGGTATTACTCTCAGAAATAGAGGTGGCACAGGCTAATGACATTATATCATCCACAGAAATATCCTCTGCTGAGAAGGTGGCTTTGTC
CTCAGAAACAGAGGTAGCCCTGGCCAGGGACATGACACTGCCCCCGGAAACCAACGTGATCTTGACCAAGGATAAAGCACTACCTTTAGAAGCA
GAGGTGGCCCCAGTCAAGGACATGGCTCAACTCCCAGAAACAGAAATAGCCCCGGCCAAGGATGTGGCTCCGTCCACAGTAAAAGAAGTGGGCT
TGTTGAAGGACATGTCTCCACTATCAGAAACAGAAATGGCTCTGGGCAAGGATGTGACTCCACCTCCAGAAACAGAAGTAGTTCTCATCAAGAA
CGTATGTCTGCCTCCAGAAATGGAGGTGGCCCTGACTGAGGATCAGGTCCCAGCCCTCAAAACAGAAGCACCCCTGGCTAAGGATGGGGTTCTG
ACCCTGGCCAACAATGTGACTCCAGCCAAAGATGTTCCACCACTCTCAGAAACAGAGGCAACACCAGTTCCAATTAAAGACATGGAAATTGCAC
AAACACAAAAAGGAATAAGTGAGGATTCCCATTTAGAATCTCTGCAGGATGTGGGGCAGTCAGCTGCACCTACTTTCATGATTTCACCAGAAAC
CGTCACAGGAACGGGGAAAAAGTGCAGCTTGCCGGCCGAGGAGGATTCTGTGTTAGAAAAACTAGGGGAAAGGAAACCATGCAACAGTCAACCT
TCTGAGCTTTCTTCAGAGACCTCAGGAATAGCCAGGCCAGAAGAAGGAAGGCCTGTGGTGAGTGGGACAGGAAATGACATCACCACCCCACCGA
ACAAGGAGCTCCCACCAAGCCCAGAGAAGAAAACAAAGCCTTTGGCCACCACTCAACCTGCAAAGACTTCAACATCGAAAGCCAAAACACAGCC
CACTTCTCTCCCTAAGCAGCCAGCTCCCACCACCATTGGTGGGTTGAATAAAAAACCCATGAGCCTTGCTTCAGGCTTAGTGCCAGCTGCCCCA
CCCAAACGCCCTGCCGTCGCCTCTGCCAGGCCTTCCATCTTACCTTCAAAAGACGTGAAGCCAAAGCCCATTGCAGATGCAAAGGCTCCTGAGA
AGCGGGCCTCACCATCCAAGCCAGCTTCTGCCCCAGCCTCCAGATCTGGGTCCAAGAGCACTCAGACTGTTGCAAAAACCACAACAGCTGCTGC
TGTTGCCTCAACTGGCCCAAGCAGTAGGAGCCCCTCCACGCTCCTGCCCAAGAAGCCCACTGCCATTAAGACTGAGGGAAAACCTGCAGAAGTC
AAGAAGATGACTGCAAAGTCTGTACCAGCTGACTTGAGTCGCCCAAAGAGCACCTCCACCAGTTCCATGAAGAAAACCACCACTCTCAGTGGGA
CAGCCCCCGCTGCAGGGGTGGTTCCCAGCCGAGTCAAGGCCACACCCATGCCCTCCCGGCCCTCCACAACTCCTTTCATAGACAAGAAGCCCAC
CTCGGCCAAACCCAGCTCCACCACCCCCCGGCTCAGCCGCCTGGCCACCAATACTTCTGCTCCTGATCTGAAGAATGTCCGCTCCAAGGTTGGC
TCCACGGAAAACATCAAGCATCAGCCTGGAGGAGGCCGGGCCAAAGTAGAGAAAAAAACAGAGGCAGCTGCTACAACCCGAAAGCCTGAATCTA
ATGCAGTCACTAAAACAGCCGGCCCAATTGCAAGTGCACAGAAACAACCTGCGGGGAAAGTCCAGATAGTCTCCAAAAAAGTGAGCTACAGCCA
TATTCAGTCCAAGTGTGGTTCCAAGGACAATATTAAGCATGTCCCTGGAGGTGGTAATGTTCAGATTCAGAACAAGAAAGTGGACATCTCTAAG
GTCTCCTCCAAGTGTGGGTCTAAGGCTAACATCAAGCACAAGCCTGGTGGAGGAGATGTCAAGATTGAAAGTCAGAAGTTGAACTTCAAGGAGA
AGGCCCAGGCCAAGGTGGGATCCCTCGATAATGTGGGCCACCTACCTGCAGGAGGTGCTGTGAAGACTGAGGGCGGTGGCAGCGAGGCTCCTCT
GTGTCCGGGTCCCCCTGCTGGGGAGGAGCCGGCCATCTCTGAGGCAGCGCCTGAAGCTGGCGCCCCCACTTCAGCCAGTGGCCTCAATGGCCAC
CCCACCCTGTCAGGGGGTGGTGACCAAAGGGAGGCCCAGACCTTGGACAGCCAGATCCAGGAGACAAGCATCTAA ID 61: XMAP5, *Homo sapiens*
ATGGGAGATGACAGTGAGTGGTTGAAACTGCCAGTTGATCAGAAATGTGAACACAAGCTGTGGAAAGCAAGGTTAAGTGGGTATGAAGAGGCCC
TGAAGATCTTCCAGAAAATAAAGGATGAAAAGAGCCCAGAGTGGTCCAAATTTTTAGGATTGATCAAAAAATTTGTCACTGATTCCAATGCAGT
GGTTCAATTGAAAGGATTAGAAGCTGCACTTGTTTATGTTGAAAATGCCCATGTAGCAGGAAAAACCACAGGAGAAGTTGTGTCAGGTGTTGTA
AGTAAGGTGTTCAATCAACCTAAAGCTAAAGCCAAGGAGCTGGGCATAGAGATCTGTCTTATGTACATAGAGATTGAGAAAGGAGAGGCTGTTC
AAGAAGAGCTCCTGAAAGGCTTGGACAATAAGAATCCCAAGATCATAGTGGCCTGTATAGAGACACTGAGGAAAGCCTTAAGTGAATTTGGTTC
CAAAATCATCTTGCTTAAGCCAATTATCAAAGTGTTGCCAAAACTCTTTGAGTCTCGAGAGAAGGCTGTTCGAGATGAAGCCAAACTAATTGCT
GTGGAGATTTACAGATGGATTCGGGATGCTCTGAGACCCCCATTACAAAATATAAACTCTGTTCAGTTGAAAGAACTAGAAGAAGAATGGGTCA
AACTGCCAACAAGTGCTCCTAGACCTACTCGATTTCTTCGTTCCCAACAAGAACTAGAAGCTAAATTGGAACAACAACAGTCTGCTGGTGGAGA
TGCTGAAGGAGGTGGTGATGATGGTGATGAGGTGCCACAAATAGATGCTTATGAGCTTTTAGAAGCTGTAGAAATCCTTTCCAAACTTCCCAAA
GACTTTTATGACAAAATTGAGGCAAAAAAATGCAAGAGAGAAAAGAGGCCCTGGAGTCTGTAGAAGTACTAATAAAAAACCCCAAACTGGAAG
CTGGCGATTATGCAGATTTAGTAAAAGCATTAAAGAAGGTTGTTGGAAAGGACACCAATGTCATGTTGGTGGCTTTGGCAGCAAAATGTCTTAC
TGGCCTGGCTGTTGGGCTAAGGAAGAAATTTGGACAATATGCAGGACATGTTGTGCCAACCATCTTGGAGAAATTCAAAGAGAAGAAACCTCAA

Fig. 9 (Continued)

GTGGTACAAGCCCTGCAGGAGGCAATTGATGCAATCTTCCTTACTACCACACTACAGAACATCAGTGAGGATGTTTTAGCAGTAATGGATAATA
AAAATCCAACCATCAAGCAGCAGACATCTCTTTTTATTGCAAGAAGTTTCCGCCACTGCACTGCTTCTACCCTGCCAAAGAGCTTGCTAAAGCC
CTTTTGTGCTGCACTACTTAAGCACATCAATGATTCTGCTCCTGAAGTCAGAGATGCCGCATTTGAAGCATTGGGTACTGCTTTGAAGGTGGTT
GGCGAGAAAGCAGTAAACCCATTCCTAGCTGATGTGGACAAACTCAAGCTTGATAAGATCAAAGAATGTTCAGAAAAGGTAGAACTGATACATG
GTAAGAAAGCTGGACTAGCTGCTGATAAGAAGGAATTCAAACCTCTGCCTGGAAGGACTGCTGCTTCAGGGGCTGCAGGAGATAAGGACACAAA
GGACATTTCTGCACCCAAACCAGGACCTCTAAAAAAGGCACCTGCTGCTAAGGCTGGTGGGCCACCAAAAAAGGGGAAACCAGCTGCACCAGGA
GGCGCAGGGAATACTGGAACCAAGAACAAGAAAGGACTGGAGACTAAAGAAATAGTGGAGCCTGAGCTCTCGATAGAAGTATGTGAAGAAAAAG
CTTCAGCTGTTCTTCCCCCTACCTGTATACAGCTTCTTGACAGCAGTAACTGGAAAGAAAGGCTGGCTTGTATGGAAGAGTTCCAGAAGGCTGT
TGAGCTAATGGACCGAACTGAAATGCCATGCCAGGCATTAGTGAGGATGCTAGCCAAGAAACCTGGATGGAAAGAAACTAATTTTCAGGTGATG
CAAATGAAGCTTCATATAGTTGCTTTGATTGCCCAGAAGGGAAATTTTTCCAAAACGTCAGCTCAGGTTGTATTAGATGGCCTTGTGGACAAGA
TTGGAGATGTGAAATGTGGGAACAATGCAAAAGAAGCTATGACAGCAATAGCCGAAGCCTGTATGTTACCATGGACTGCTGAACAGGTTGTGTC
AATGGCTTTCTCACAAAAGAATCCCAAAAATCAGTCAGAAACTCTGAATTGGCTATCAAATGCCATAAAAGAATTTGGTTTTTCTGGGTTGAAT
GTCAAAGCTTTCATTAGCAATGTGAAGACAGCTCTTGCTGCAACAAACCCAGCTGTGAGGACTGCTGCCATAACCCTGCTTGGCGTGATGTATC
TGTATGTTGGTCCCTCTTTGCGAATGTTCTTTGAGGATGAGAAGCCTGCCCTCCTATCCCAGATAGATGCAGAATTTGAGAAGATGCAGGGACA
AAGTCCACCTGCTCCAACCAGAGGAATTTCCAAGCATAGCACAAGTGGTACAGATGAAGGAGAAGATGGAGATGAACCAGATGACGGGAGCAAT
GATGTCGTTGATCTTTTGCCGAGGACGGAGATCAGTGATAAAATCACTTCAGAGTTGGTATCTAAGATTGGTGATAAGAATTGGAAGATTAGGA
AAGAAGGCCTAGATGAAGTGGCAGGTATTATTAATGACGCAAAATTTATCCAACCGAATATAGGTGAACTTCCAACTGCCTTGAAGGGTCGACT
CAATGATTCAAATAAAATCTTGGTACAGCAAACGCTGAATATCCTGCAACAACTGGCAGTAGCCATGGGCCCAAATATTAAGCAACATGTAAAA
AATTTAGGCATCCCTATCATCACAGTCCTTGGAGACAGCAAGAACAATGTTCGAGCTGCTGCCCTAGCGACTGTGAATGCTTGGGCAGAACAGA
CTGGCATGAAGGAATGGCTGGAAGGAGAAGATCTTTCTGAAGAGCTCAAAAAGGAAAATCCTTTCTTGAGGCAAGAGCTTCTGGGCTGGCTGGC
TGAGAAACTACCTACTCTTCGTTCCACCCCTACAGACCTTATCCTTTGTGTTCCTCATCTCTACTCCTGCCTAGAAGATCGAAATGGAGATGTG
CGAAAGAAGGCCCAAGATGCCTTGCCATTCTTCATGATGCATTTAGGATATGAAAAAATGGCCAAGGCTACTGGAAACTAAAGCCAACTTCTA
AAGATCAGGTATTGGCCATGCTAGAGAAAGCCAAAGTTAACATGCCAGCCAAGCCTGCTCCACCCACTAAAGCAACTTCTAAACCAATGGGAGG
GTCCGCTCCAGCCAAATTCCAGCCTGCATCAGCACCTGCTGAAGATTGTATTTCCAGCAGTACAGAACCCAAACCTGATCCAAAAAAGGCCAAA
GCTCCAGGATTATCCTCTAAAGCAAAGAGTGCACAAGGGAAGAAGATGCCAAGCAAAACCAGCTTAAAGGAGGATGAAGACAAATCCGGGCCTA
TTTTTATTGTTGTTCCAAATGGAAAAGAGCAAAGGATGAAAGATGAAAAAGGATTGAAGGTGCTAAAGTGGAATTTTACTACCCCACGGGATGA
ATACATTGAGCAACTAAAGACTCAAATGTCTAGCTGTGTGGCTAAATGGTTACAAGATGAGATGTTTCACTCAGACTTTCAGCATCATAACAAA
GCCCTTGCTGTTATGGTTGATCACTTGGAGAGTGAAAAAGAAGGAGTTATTGGTTGCCTGGATCTTATCTTAAAGTGGCTTACCCTGAGGTTTT
TTGACACCAATACAAGCGTCCTGATGAAAGCACTAGAATATTTAAAATTGCTCTTCACCTTGCTAAGTGAAGAAGAATATCATCTTACTGAGAA
TGAAGCATCTTCCTTCATCCCCTATCTTGTCGTCAAGGTTGGAGAACCAAAGGATGTCATTCGTAAAGATGTTCGTGCCATCCTGAACCGGATG
TGCCTTGTCTACCCAGCTAGCAAGATGTTTCCCTTTATCATGGAAGGAACCAAATCCAAAAACTCTAAGCAGAGAGCAGAGTGCCTGGAAGAGC
TGGGATGTCTGGTTGAGTCCTATGGCATGAATGTTTGCCAACCAACCCCAGGAAAAGCCTTAAAGGAAATAGCTGTTCACATAGGAGACCGTGA
CAATGCTGTACGCAATGCTGCACTCAACACCATTGTAACGGTGTACAATGTACATGGGGATCAGGTGTTCAAACTGATTGGAAATCTTTCTGAA
AAGGATATGAGCATGCTCGAGGAGAGGATTAAGCGGTCAGCAAAGAGACCCTCTGCTGCACCAATAAAACAGGTGGAAGAGAAACCTCAGCGTG
CACAGAACATAAGCTCCAATGCCAACATGTTACGCAAGGGACCAGCTGAGGACATGTCTTCCAAACTCAACCAAGCCCGAAGCATGAGTGGGCA
TCCTGAGGCAGCCCAGATGGTCCGCCGAGAATTCCAGCTGGATCTAGATGAGATTGAGAATGACAATGGTACAGTCCGATGTGAAATGCCAGAA
CTTGTTCAGCACAAACTGGATGACATTTTTGAGCCAGTCCTTATTCCTGAACCCAAGATCCGGGCTGTTTCTCCACACTTCGATGACATGCACA
GTAATACAGCATCCACAATCAATTTCATTATCTCCCAAGTAGCCAGTGGTGACATCAACACAAGTATCCAAGCTCTGACACAGATCGATGAGGT
CCTGAGACAGGAAGACAAAGCTGAAGCCATGTCCGGCCATATTGATCAGTTTCTGATAGCCACTTTTATGCAGCTAAGACTCATCTACAACACA
CACATGGCAGATGAGAAATTGGAGAAGGACGAGATCATCAAGTTGTATAGCTGTATCATTGGCAACATGATTTCGCTGTTTCAGATAGAGAGCC
TTGCCCGGGAGGCCTCCACTGGAGTACTAAAAGACCTAATGCATGGCCTCATCACCTTAATGCTGGATTCTCGGATTGAAGATCTTGAGGAAGG
ACAACAGGTCATCCGCTCTGTGAACCTCTTGGTGGTGAAGGTTCTGGAGAAGTCAGACCAGACCAACATCCTGAGTGCCCTACTTGTTTTGCTC
CAAGACAGCCTGCTAGCAACAGCCAGTTCTCCCAAATTCTCAGAGCTTGTTATGAAGTGTCTCTGGAGAATGGTTCGACTGTTGCCTGATACCA
TCAATAGCATTAACCTAGACAGAATTCTTCTGGATATCCACATTTTCATGAAGGTCTTCCCCAAAGAGAAACTGAAGCAATGCAAAAGTGAATT
TCCCATAAGGACCCTAAAGACCCTGCTACACACCTTATGCAAATTAAAAGGGCCCAAGATCCTGGACCACCTAACGATGATCGACAACAAAAAC
GAGTCTGAGCTGGAGGCCCATCTCTGCCGGATGATGAAGCACAGTATGGACCAGACTGCGGAGCAAGTCTGATAAGGAAACAGAAAAGGGAGCAT
CTCGAATAGATGAAAAATCATCAAAGGCCAAAGTGAATGATTTCTTAGCTGAGATTTTTAAGAAGATTGGCTCTAAAGAAAACACTAAAGAGGG
ACTAGCAGAGTTATATGAATATAAGAAGAAATACTCAGATGCTGACATTGAACCATTTCTGAAAAATTCCTCACAGTTCTTCCAGAGCTATGTC
GAAAGAGGCCTTCGGGTGATTGAGATGGAGAGGGAGGGCAAAGGTCGTATTTCCACTTCAACAGGCATCTCCCCTCAGATGGAAGTCACATGTG
TGCCCACGCCCACAAGCACAGTGTCCTCCATAGGTAACACAAATGGGGAAGAAGTGGGGCCATCTGTCTACTTGGAAAGGCTAAAGATCCTCCG
ACAGCGATGTGGTCTGGACAACACAAAGCAAGATGACCGACCTCCTTTGACCTCTTTGCTCTCCAAACCAGCAGTTCCTACTGTCGCCTCTTCC
ACAGACATGCTCCACAGCAAACTCTCTCAGCTCCGGGAGTCACGGAGCAGCACCAGCATTCAGACCTGGATTCTAACCAGACTCACTCTTCAG
GAACTGTGACCTCCTCCTCCTCCACAGCTAACATAGACGACTTGAAAAAAAGACTGGAGAGAATAAAGAGCAGTCGCAAATGA

**ID 62: MAP6, *Homo sapiens***

ATGGCGTGGCCGTGCATCACGAGGGCCTGCTGCATCGCCCGCTTCTGGAACCAGTTGGACAAAGCGGACATCGCTGTGCCGCTGGTTTTCACCA
AGTACTCGGAGGCCACCGAGCACCCGGGCGCCCCGCCGCAGCCACCGCCGCCGCAGCAGCAGGCGCAGCCGGCGCTCGCGCCCCCCTCGGCGCG
CGCGGTTGCCATAGAGACGCAGCCAGCCCAGGGCGAGTTGGATGCAGTTGCCCGGGCAACGGGGCCAGCGCCTGGGCCTACCGGCGAGCGCGAG
CCGGCGGCGGCGCCCGGCGCGGAGCGGGCCCGGGCCTGGGCTCCGGCTCCACCTCCGGCCCCGCGGACTCGGTGATGCGGCAGGATTACC
GAGCCTGGAAGGTGCAGCGGCCCGAGCCCAGCTGCCGGCCGCGCAGCGAATACCAGCCCTCCGACGCTCCCTTCGAGCGCGAGACCCAGTACCA
GAAGGACTTCCGCGCCTGGCCGCTGCCGCGCCGCGGGGACCACCCGTGGATCCCCAAGCCCGTGCAGATCTCTGCGGCCTCCCAGGCGTCGGCG
CCCATTCTCGGGGCGCCCAAGCGCCGGCCGCAGAGCCAGGAGCGCTGGCCAGTGCAGGCCGCCGCTGAGGCCCGGGAGCAGGAGGCGGCCCCCG
GCGGAGCGGGTGGCCTGGCGGCCGGAAAGGCGTCCGGGGCGGACGAGCGCGACACGCGCAGGAAGGCCGGGCCTGCCTGGATTGTGCGCCGCGC
CGAGGGCCTGGGGCACGAGCAGACGCCGCTGCCCGCGGCCCAGGCCAGGTCCAGGCCACCGGCCCCGAGGCTGGCAGGGGGCGCGCCGCGGCG
GACGCCCTCAACCGGCAAATCCGCGAGGAGGTGGCGAGTGCAGTGAGCAGCTCCTACAGGAATGAATTCAGGGCATGGACGGACATCAAGCCTG
TGAAACCAATAAAGGCCAAGCCCCAGTACAAGCCCCCAGATGATAAGATGGTTCATGAGACCAGCTACAGTGCTCAGTTCAAAGGAGAGGCCAG
CAAGCCAACAACAGCTGACAATAAGGTCATTGATCGCAGAAGAATACGCAGCCTCTACAGCGAACCCTTCAAGGAACCCCCAAAGGTGGAAAAA
CCTAGTGTTCAGAGTTCCAAACCAAAAAAGACCTCAGCGAGCCATAAGCCCACGAGGAAGGCCAAAGACAAGCAGGCGGTGTCAGGCCAGGCTG
CCAAGAAAAAGAGCGCGGAGGGCCCGAGTACCACCAAGCCAGACGACAAGGAGCAAAGCAAAGAGATGAACAATAAACTGGCTGAGGCGAAAGA
GAGCCTGGCTCAACCCGTCAGTGATTCAAGTAAGACTCAAGGTCCTGTAGCCACAGAGCCAGACAAGGATCAAGGTTCTGTGGTCCCAGGCCTT
CTGAAAGGTCAAGGTCCTATGGTGCAAGAGCCTCTGAAGAAGCAAGGTTCTGTGGTCCCAGGGCCTCCAAAGGATCTAGGTCCCATGATCCCAT
TACCAGTCAAGGATCAAGATCACACGGTCCCTGAGCCTTTAAAGAATGAAAGCCCTGTTATCTCAGCACCAGTCAAGGACCAAGGTCCCTCGGT
CCCAGTTCCTCCAAAGAATCAAAGTCCTATGGTTCCAGCAAAAGTTAAGGATCAAGGCTCTGTGGTACCAGAGTCTCTAAAGGATCAAGGTCCT
AGGATTCCTGAGCCTGTGAAGAATCAAGCTCCTATGGTCCCAGCACCTGTCAAGGATGAAGGTCCCATGGTCTCAGCATCTGTCAAGGATCAAG
GTCCCATGGTCTCAGCACCTGTCAAGGATCAAGGTCCCATAGTCCCAGCACCTGTCAAGGGTGAAGGTCCCATAGTCCCAGCACCTGTCAAGGA
TGAAGGTCCCATGGTCTCAGCACCTATCAAGGATCAAGATCCCATGGTCCCAGAGCATCCGAAGGATGAAAGTGCCATGGCCACAGCACCCATA
AAGAATCAAGGTTCCATGGTCTCTGAGCCTGTAAAGAATCAAGGTTTAGTGGTCTCAGGGCCAGTCAAGGATCAAGATGTTGTAGTCCCAGAGC
ATGCAAAGGTTCACGATTCTGCAGTTGTGGCACCTGTAAAGAATCAAGGTCCTGTGGTCCCCGAGTCCGTGAAGAATCAAGACCCCATTCTCCC
AGTACTAGTTAAGGATCAAGGCCCCACAGTCCTACAGCCTCCAAAGAATCAAGGTCGTATAGTCCCTGAACCTCTGAAGAATCAAGTTCCTATA

Fig. 9 (Continued)

GTCCCAGTGCCTCTGAAGGATCAAGATCCTCTGGTGCCAGTACCAGCAAAGGACCAAGGTCCTGCAGTCCCTGAACCTCTGAAGACTCAAGGTC
CCAGGGACCCTCAGCTACCTACTGTCTCACCTCTACCCCGAGTCATGATCCCAACTGCCCCCCATACGGAATACATTGAGAGCTCCCCTTGA

ID 63: MAP7, *Homo sapiens*
ATGCCTGGATCAGCTACAGCTCTCCGACATGAGAGACTGAAGAAGACCAATGCAAGGCCAATTCCTCTTGGTTTATTCACCATTAATGAGGAAG
ACGAACAGCAAAAGAATGGAAATTCCAGAAGACCAAAAGCACCCGACAGCTACAAAGTGCAAGATAAGAAAAATGCCTCCAGCCGCCCTGCCTC
TGCAATTTCAGGACAAAATAACAACCACTCAGGAAATAAACCAGACCCTCCGCCTGTGTTACGTGTTGATGACCGGCAGCGGCTGGCCCGGGAG
CGACGTGAGGAACGGGAGAAACAGCTAGCTGCAAGAGAAATAGTGTGGTTAGAAAGAGAAGAGCGAGCCAGGCAGCACTACGAGAAGCACCTGG
AAGAGCGGAAGAAGAGGTTGGAGGAGCAGAGGCAGAAGGAGGAGCGGAGGAGGGCTGCTGTGGAGGAGAAGCGGAGGCAGAGACTTGAGGAGGA
CAAAGAACGCCACGAAGCTGTTGTACGGCGCACAATGGAAAGGAGCCAGAAGCCAAAACAGAAGCATAACCGTTGGTCGTGGGGAGGCTCTCTC
CATGGGAGCCCTAGCATCCACAGTGCAGATCCAGACAGGCGGTCAGTTTCCACCATGAATCTTTCGAAATATGTTGATCCCGTCATTAGCAAGC
GGCTCTCCTCTTCATCTGCAACTTTACTAAATTCTCCAGATAGAGCTCGCCGCCTGCAGCTCAGCCCATGGGAGAGCAGCGTTGTTAACAGACT
CCTGACGCCCACACATTCGTTCCTGGCCAGAAGTAAAAGCACAGCTGCCTTGTCTGGAGAAGCAGCATCTTGCAGCCCCATCATCATGCCCTAC
AAAGCTGCACACTCTAGAAATTCGATGGATCGACCAAAACTCTTTGTAACACCACCTGAGGGCTCTTCTCGCAGGAGGATCATTCATGGCACAG
CGAGCTATAAAAAAGAAAGAGAGAGAGAAAATGTACTCTTCCTCACATCTGGCACCCGAAGGGCTGTATCTCCATCTAATCCCAAAGCAAGACA
ACCAGCTCGCTCCCGACTTTGGCTTCCGTCCAAGTCTCTTCCTCATTTGCCTGGCACACCCAGACCGACATCCTCCTTGCCACCCGGCTCAGTC
AAAGCTGCTCCTGCTCAGGTCCGGCCCCCATCCCCCGGCAACATCCGCCCTGTCAAGAGGGAAGTCAAAGTGGAGCCTGAGAAGAAAGATCCTG
AGAAGGAACCTCAGAAAGTTGCCAATGAGCCCTCACTAAAGGGCAGAGCACCTTTAGTGAAGGTAGAAGAAGCCACAGTTGAAGAGCGGACACC
TGCTGAACCAGAAGTTGGCCCTGCTGCTCCAGCCATGGCCCCAGCTCCAGCCTCGGCCCCAGCTCCAGCCTCGGCCCCAGCTCCAGCCCCGGTC
CCCACCCCAGCCATGGTCTCAGCCCCGTCATCCACTGTGAATGCCAGTGCTTCTGTTAAGACTTCTGCAGGCACCACCGACCCAGAGGAGGCCA
CAAGGCTTCTAGCTGAGAAGAGGCGGCTGGCCCGAGAGCAGAGAGAAAAGGAAGAAAGGGAGAGGAGGGAGCAGGAAGAGCTTGAAAGACAAAA
GAGAGAGGAATTGGCTCAACGTGTGGCTGAAGAGAGGACGACTCGCCGTGAGGAGGAGTCGCGCAGGCTGGAAGCCGAGCAGGCCCGGGAGAAG
GAGGAGCAGCTGCAGCGGCAGGCGGAGGAGCGGGCGCTGCGCGAGCGGGAGGAGGCAGAGCGCGCCCAGAGGCAGAAAGAAGAAGAAGCTCGCG
TTCGTGAAGAAGCAGAGAGGGTCCGGCAGGAACGAGAGAAGCATTTCCAGAGAGAAGAGCAAGAGCGCCTGGAGAGAAAGAAGCGACTTGAGGA
GATTATGAAAAGAACCAGGAGAACAGAAGCTACAGATAAGAAAACCAGTGATCAGAGAAACGGTGATATAGCCAAGGGAGCTCTCACTGGAGGA
ACAGAGGTGTCTGCACTTCCATGTACAACAAACGCTCCGGGAAATGGAAAGCCAGTTGGCAGCCCACATGTGGTTACCTCACACCAGTCAAAAG
TGACAGTGGAGAGCACTCCCGATTTGGAAAAACAACCAAATGAAAATGGTGTATCTGTTCAGAATGAAAATTTTGAAGAAATTATAAACTTACC
CATTGGATCTAAACCATCCAGATTAGATGTCACCAACAGTGAGAGCCCAGAAATTCCTTTGAATCCAATTTTGGCCTTTGATGATGAAGGGACA
CTTGGGCCCCTGCCTCAGGTAGATGGTGTTCAGACACAGCAGACTGCAGAAGTTATATGA

ID 64: MAP8, *Homo sapiens*
ATGGCGGCGGTGGCTGGATCTGGGGCTGCCGCGGCTCCGAGCTCACTGCTCCTCGTGGTGGGCAGCGAGTTCGGGAGCCCGGGGCTCCTCACCT
ACGTCCTGGAGGAGCTCGAAAGAGGCATCCGGTCTTGGGATGTCGATCCTGGCGTCTGCAACCTTGATGAACAGCTCAAGGTCTTTGTGTCCCG
ACACTCTGCCACCTTCTCCAGCATTGTGAAAGGCCAGCGGAGCCTGCACCACCGTGGAGACAACCTGGAGACCCTGGTCCTCCTGAACCCATCA
GACAAGTCCCTGTATGATGAGCTCCGGAACCTTCTGTTGGACCCTGCCTCTCACAAGCTACTGGTGTTGGCTGGGCCCTGCCTGGAGGAGACGG
GGGAGCTGCTGCTACAGACAGGGGGCTTCTCGCCTCACCACTTCCTCCAGGTCCTGAAGGACAGAGAGATCCGGGACATCCTGGCCACCACGCC
CCCACCTGTGCAGCCGCCCATACTCACCATCACCTGCCCCACCTTCGGTGACTGGGCTCAGCTGGCACCCGCTGTGCCTGGCCTTCAGGGGGCG
CTCCGGCTCCAGCTGCGGCTGAACCCCCCGGCGCAGCTGCCCAACTCTGAGGGCCTGTGCGAATTCCTGGAGTACGTGGCTGAGTCTCTGGAGC
CACCGTCCCCCTTCGAGCTGCTGGAGCCCCCGACCTCCGGGGGCTTCCTCAGGCTGGGCCGGCCCTGCTGCTACATCTTCCCTGGAGGCCTCGG
GGATGCCGCCTTCTTCGCCGTCAATGGCTTCACTGTGCTGGTCAACGGTGGCTCAAACCCCAAGTCCAGTTTCTGGAAGCTGGTGCGGCACCTG
GACCGCGTGGATGCCGTGCTGGTGACCCACCCTGGCGCCGACAGCCTCCCCGGCCTCAACAGCCTGCTGCGGCGCAAACTGGCGGAGCGCTCCG
AGGTGGCTGCTGGTGGGGGCTCCTGGGACGACAGGCTGCGCAGGCTCATCTCCCCCAACCTGGGGGTCGTGTTCTTCAACGCCTGCGAGGCCGC
GTCGCGGCTGGCGCGCGGCGAGGATGAGGCGGAGCTGGCGCTGAGCCTCCTGGCGCAGCTGGGCATCACGCCTCTGCCACTCAGCCGCGGCCCC
GTGCCAGCCAAACCCACCGTGCTCTTCGAGAAGATGGGCGTGGGCCGGCTGGACATGTATGTGCTGCACCCGCCCTCCGCCGGCGCCGAGCGCA
CGCTGGCCTCTGTGTGCGCCCTGCTGGTGTGGCACCCCGCCGGCCCCGGCGAGAAGGTGGTGCGCGTGCTGTTCCCCGGTTGCACCCCGCCCGC
CTGCCTCCTGGACGGCCTGGTCCGCCTGCAGCACTTGAGGTTCCTGCGAGAGCCCGTGGTGACGCCCCAGGACCTGGAGGGGCCGGGGCGAGCC
GAGAGCAAAGAGAGCGTGGGCTCCCGGGACAGCTCGAAGAGAGAGGGCCTCCTGGCCACCCACCCTAGACCTGGCCAGGAGCGCCCTGGGGTGG
CCCGCAAGGAGCCAGCACGGGCTGAGGCCCCACGCAAGACTGAGAAAGAAGCCAAGACCCCCCGGGAGTTGAAGAAAGACCCCAAACCGAGTGT
CTCCCGGACCCAGCCGCGGGAGGTGCGCCGGGCAGCCTCTTCTGTGCCCAACCTCAAGAAGACGAATGCCCAGGCGGCACCCAAGCCCCGCAAA
GCGCCCAGCACGTCCCACTCTGGCTTCCCGCCGGTGGCAAATGGACCCCGCAGCCCGCCCAGCCTCCGATGTGGAGAAGCCAGCCCCCCCAGTG
CAGCCTGCGGCTCTCCGGCCTCCCAGCTGGTGGCCACGCCCAGCCTGGAGCTGGGGCCGATCCCAGCCGGGGAGGAGAAGGCACTGGAGCTGCC
TTTGGCCGCCAGCTCAATCCCAAGGCCACGCACACCCTCCCCTGAGTCCCACCGGAGCCCCGCAGAGGGCAGCGAGCGGCTGTCGCTGAGCCCA
CTGCGGGGCGGGGAGGCCGGGCCAGACGCCTCACCCACAGTGACCACACCCACGGTGACCACGCCCTCACTACCCGCAGAGGTGGGCTCCCCGC
ACTCGACCGAGGTGGACGAGTCCCTGTCGGTGTCCTTTGAGCAGGTGCTGCCGCCATCCGCCCCCACCAGTGAGGCTGGGCTGAGCCTCCCGCT
GCGTGGCCCCCGGGCGCGGCGCTCGGCTTCCCCACACGATGTGGACCTGTGCCTGGTGTCACCCTGTGAATTTGAGCATCGCAAGGCGGTGCCA
ATGGCACCGGCACCTGCGTCCCCCGGCAGCTCGAATGACAGCAGTGCCCGGTCACAGGAACGGGCAGGTGGGCTGGGGGCCGAGGAGACGCCAC
CCACATCGGTCAGCGAGTCCCTGCCCACCCTGTCTGACTCGGATCCCGTGCCCCTGGCCCCCGGTGCGGCAGACTCAGACGAAGACACAGAGGG
CTTTGGAGTCCCTCGCCACGACCCTTTGCCTGACCCCCTCAAGGTCCCCCCACCACTGCCTGACCCATCCAGCATCTGCATGGTGGACCCCGAG
ATGCTGCCCCCCAAGACAGCACGGCAAACGGAGAACGTCAGCCGCACCCGGAAGCCCCTGGCCCGCCCCAACTCACGCGCTGCCGCCCCCAAAG
CCACTCCAGTGGCTGCTGCCAAAACCAAGGGGCTTGCTGGTGGGGACCGTGCCAGCCGACCACTCAGTGCCCGGAGTGAGCCCAGTGAGAAGGG
AGGCCGGGCACCCCTGTCCAGAAAGTCCTCAACCCCCAAGACTGCCACTCGAGGCCCGTCGGGGTCAGCCAGCAGCCGGCCCGGGGTGTCAGCC
ACCCCACCCAAGTCCCCGGTCTACCTGGACCTGGCCTACCTGCCCAGCGGGAGCAGCGCCCACCTGGTGGATGAGGAGTTCTTCCAGCGCGTGC
GCGCGCTCTGCTACGTCATCAGTGGCCAGGACCAGCGCAAGGAGGAAGGCATGCGGGCCGTCCTGGACGCGCTACTGGCCAGCAAGCAGCATTG
GGACCGTGACCTGCAGGTGACCCTGATCCCCACTTTCGACTCGGTGGCCATGCATACGTGGTACGCAGAGACGCACGCCCGGCACCAGGCGCTG
GGCATCACGGTGTTGGGCAGCAACAGCATGGTGTCCATGCAGGATGACGCCTTCCCGGCCTGCAAGGTGGAGTTCTAG

ID 65: MAP9, *Homo sapiens*
ATGTCTGATGAAGTTTTTAGCACCACTTTGGCATATACAAAGAGTCCAAAAGTTACCAAAAGAACTACTTTCCAGGATGAGCTAATAAGAGCAA
TTACAGCTCGCTCAGCCAGACAAAGGAGTTCTGAATACTCAGATGACTTTGACAGTGATGAGATTGTTTCTTTAGGTGATTTTTCTGACACTTC
AGCAGATGAAAATTCAGTTAATAAAAAAATGAATGACTTTCATATATCAGATGATGAAGAAAAGAATCCTTCAAAACTATTGTTTTTGAAAACC
AATAAATCAAACGGTAACATAACCAAAGATGAGCCAGTGTGTGCCATCAAAAATGAAGAGGAAATGGCACCTGATGGGTGTGAAGACATTGTTG
TAAAATCTTTCTCTGAATCTCAAAATAAGGATGAGGAATTTGAAAAAGACAAAATAAAAATGAAACCTAAACCCAGAATTCTTTCAATTAAAAG
CACATCTTCAGCAGAAAACAACAGCCTTGACACAGATGATCACTTTAAACCATCACCTCGGCCAAGGAGTATGTTGAAAAAGAAAAGTCACATG
GAGGAGAAGGATGGACTAGAAGATAAAGAAACTGCCCTCAGTGAAGAATTGGAGTTACATTCTGCACCTTCTTCCCTTCCAACGCCGAATGGCA
TACAATTAGAAGCTGAGAAAAAGCATTCTCTGAAAACCTTGATCCTGAGGATTCATGCTTAACAAGTCTAGCATCATCATCACTTAAACAAAT
TCTTGGAGATTCTTTTTCACCAGGATCTGAGGGAAACGCATCTGGAAAAGATCCAAATGAAGAAATCACTGAAAACCATAATTCCTTGAAATCA
GATGAAAATAAAGAGAATTCATTTTCAGCAGACCATGTGACTACTGCAGTTGAGAAATCCAAGGAAAGTCAAGTGACTGCTGATGACCTTGAAG
AAGAAAAGGCAAAAGCGGAACTGATTATGGATGATGACAGAACAGTTGATCCACTACTATCTAAATCTCAGAGTATCTTAATATCTACCAGTGC
AACAGCATCTTCAAAGAAAACAATTGAAGATAGAAATATAAAGAATAAAAAGTCAACAAATAATAGAGCATCCAGTGCATCTGCCAGATTAATG
ACCTCTGAGTTTTTGAAGAAATCTAGTTCTAAAAGGAGAACTCCATCGACAACTACCTCTTCTCACTATTTAGGGACTTTAAAAGTCTTGGACC

Fig. 9 (Continued)

AAAAACCTTCACAGAAACAGAGCATAGAACCTGATAGAGCAGATAACATAAGGGCAGCTGTTTATCAGGAGTGGTTAGAAAAGAAAAATGTGTA
TTTACATGAAATGCACAGAATAAAAAGAATTGAAAGTGAAAACTTAAGGATCCAAAATGAACAGAAAAAAGCTGCTAAAAGAGAAGAAGCATTA
GCATCATTTGAGGCCTGGAAGGCTATGAAAGAAAAGGAAGCAAAGAAAATAGCTGCCAAAAAGAGGCTTGAAGAAAAAAACAAGAAGAAAACTG
AAGAAGAAAATGCTGCAAGAAAAGGAGAAGCACTACAAGCTTTTGAAAAATGGAAAGAGAAAAAGATGGAATATCTTAAAGAGAAAAATAGAAA
GGAGAGAGAATATGAAAGAGCAAAGAAACAGAAAGAGGAGGAAACTGTTGCCGAGAAAAAGAAAGATAATTTAACTGCTGTTGAGAAATGGAAT
GAAAAAAAGGAAGCTTTTTCAAGCAAAAGGAAAAAGAAAAAATAAATGAGAAAAGAAAGGAAGAACTGAAAAGAGCTGAGAAAAAAGATAAAG
ATAAACAAGCTATTAATGAATATGAAAAATGGCTGGAAAATAAGGAAAAACAAGAAAGAATTGAACGAAAACAGAAGAAACGTCATTCCTTTCT
TGAAAGTGAGGCACTTCCTCCGTGGAGCCCTCCAAGCAGAACTGTGTTCGCAAAAGTGTTTTGA

ID 66: DCTN1, *Homo sapiens*
ATGGCACAGAGCAAGAGGCACGTGTACAGCCGGACGCCCAGCGGCAGCAGGATGAGTGCGGAGGCAAGCGCCCGGCCTCTGCGGGTGGGCTCCC
GTGTAGAGGTGATTGGAAAAGGCCACCGAGGCACTGTGGCCTATGTTGGAGCCACACTGTTTGCCACTGGCAAATGGGTAGGCGTGATTCTGGA
TGAAGCAAAGGGCAAAAATGATGGAACTGTTCAAGGCAGGAAGTACTTCACTTGTGATGAAGGGCATGGCATCTTTGTGCGCCAGTCCCAGATC
CAGGTATTTGAAGATGGAGCAGATACTACTTCCCCAGAGACACCTGATTCTTCTGCTTCAAAAGTCCTCAAAAGAGAGGGAACTGATACAACTG
CAAAGACTAGCAAACTGCGGGGACTGAAGCCTAAGAAGGCACCGACAGCCCGAAAGACCACAACTCGGCGACCCAAGCCCACGCGCCCAGCCAG
TACTGGGGTGGCTGGGGCCAGTAGCTCCCTGGGCCCCTCTGGCTCAGCGTCAGCAGGTGAGCTGAGCAGCAGTGAGCCCAGCACCCCGGCTCAG
ACTCCGCTGGCAGCACCCATCATCCCCACGCCGGTCCTCACCTCTCCTGGAGCAGTCCCCCCGCTTCCTTCCCCATCCAAGGAGGAGGAGGGAC
TAAGGGCTCAGGTGCGGGACCTGGAGGAGAAACTAGAGACCCTGAGACTGAAACGGGCAGAAGACAAAGCAAAGCTAAAAGAGCTGGAGAAACA
CAAAATCCAGCTGGAGCAGGTGCAGGAATGGAAGAGCAAAATGCAGGAGCAGCAGGCCGACCTGCAGCGGCGCCTCAAGGAGGCGAGAAAGGAA
GCCAAGGAGGCGCTGGAGGCAAAGGAACGCTATATGGAGGAGATGGCTGATACTGCTGATGCCATTGAGATGGCCACTTTGGACAAGGAGATGG
CTGAAGAGCGGGCTGAGTCCCTGCAGCAGGAGGTGGAGGCACTGAAGGAGCGGGTGGACGAGCTCACTACTGACTTAGAGATCCTCAAGGCTGA
GATTGAAGAGAAGGGCTCAGATGGCGCTGCATCCAGTTATCAGCTCAAGCAGCTTGAGGAGCAGAATGCCCGCCTGAAGGATGCCCTGGTGAGG
ATGCGGGATCTTTCTTCCTCAGAGAAGCAGGAGCATGTGAAGCTCCAGAAGCTCATGGAAAAGAAGAACCAAGAGCTGGAAGTTGTGAGGCAAC
AGCGGGAGCGTCTGCAGGAGGAGCTAAGCCAGGCAGAGAGCACCATTGATGAGCTCAAGGAGCAGGTGGATGCTGCTCTGGGTGCTGAGGAGAT
GGTGGAGATGCTGACAGATCGGAACCTGAATCTGGAAGAGAAAGTGCGCGAGTTGAGGGAGACTGTGGGAGACTTGGAAGCGATGAATGAGATG
AACGATGAGCTGCAGGAGAATGCACGTGAGACAGAACTGGAGCTGCGGGAGCAGCTGGACATGGCAGGCGCGCGGGTTCGTGAGGCCCAGAAGC
GTGTGGAGGCAGCCCAGGAGACGGTTGCAGACTACCAGCAGACCATCAAGAAGTACCGCCAGCTGACCGCCCATCTACAGGATGTGAATCGGGA
ACTGACAAACCAGCAGGAAGCATCTGTGGAGAGGCAACAGCAGCCACCTCCAGAGACCTTTGACTTCAAAATCAAGTTTGCTGAGACTAAGGCC
CATGCCAAGGCAATTGAGATGGAATTGAGGCAGATGGAGGTGGCCCAGGCCAATCGACACATGTCCCTGCTGACAGCCTTCATGCCTGACAGCT
TCCTTCGGCCAGGTGGGGACCATGACTGCGTTCTGGTGCTGTTGCTCATGCCTCGTCTCATTTGCAAGGCAGAGCTGATCCGGAAGCAGGCCCA
GGAGAAGTTTGAACTAAGTGAGAACTGTTCAGAGCGGCCTGGGCTGCGAGGAGCTGCTGGGGAGCAACTCAGCTTTGCTGCTGGACTGGTGTAC
TCGCTGAGCCTGCTGCAGGCCACGCTACACCGCTATGAGCATGCCCTCTCTCAGTGCAGTGTGGATGTGTATAAGAAAGTGGGCAGCCTGTACC
CTGAGATGAGTGCCCATGAGCGCTCCTTGGATTTCCTCATTGAACTGCTGCACAAGGATCAGCTGGATGAGACTGTCAATGTGGAGCCTCTCAC
CAAGGCCATCAAGTACTATCAGCATCTGTACAGCATCCACCTTGCCGAACAGCCTGAGGACTGTACTATGCAGCTGGCTGACCACATTAAGTTC
ACGCAGAGTGCTCTGGACTGCATGAGTGTGGAGGTAGGACGGCTGCGTGCCTTCTTGCAGGGTGGGCAGGAGGCTACAGATATTGCCCTCCTGC
TCCGGGATCTGGAAACTTCATGCAGTGACATCCGCCAGTTCTGCAAGAAGATCCGAAGGCGAATGCCAGGGACAGATGCTCCTGGGATCCCAGC
TGCACTGGCCTTTGGACCACAGGTATCTGACACGCTCCTAGACTGCAGGAAACACTTGACGTGGGTCGTGGCTGTGCTGCAGGAGGTGGCAGCT
GCTGCTGCCCAGCTCATTGCCCCACTGGCAGAGAATGAGGGGCTACTTGTGGCTGCTCTGGAGGAACTGGCTTTCAAAGCAAGCGAGCAGATCT
ATGGGACCCCCTCCAGCAGCCCCTATGAGTGTCTGCGCCAGTCATGCAACATCCTCATCAGTACCATGAACAAGCTGGCCACAGCCATGCAGGA
GGGGGAGTATGATGCAGAGCGGCCCCCCAGCAAGCCTCCACCGGTTGAACTGCGGGCTGCTGCCCTTCGTGCAGAGATCACAGATGCTGAAGGC
CTGGGTTTGAAGCTCGAAGATCGAGAGACAGTTATTAAGGAGTTGAAGAAGTCACTCAAGATTAAGGGAGAGGAGCTAAGTGAGGCCAATGTGC
GGCTGAGCCTCCTGGAGAAGAAGTTGGACAGTGCTGCCAAGGATGCAGATGAGCGCATCGAGAAAGTCCAGACTCGGCTGGAGGAGACCCAGGC
ACTGCTGCGAAAGAAGGAGAAAGAGTTTGAGGAGACAATGGATGCACTCCAGGCTGACATCGACCAGCTGGAGGCAGAGAAGGCAGAACTAAAG
CAGCGTCTGAACAGCCAGTCCAAACGCACGATTGAGGGACTCCGGGGCCCTCCTCCTTCAGGCATTGCTACTCTGGTCTCTGGCATTGCTGGTG
AAGAACAGCAGCGAGGAGCCATCCCTGGGCAGGCTCCAGGGTCTGTGCCAGGCCCAGGGCTGGTGAAGGACTCACCACTGCTGCTTCAGCAGAT
CTCTGCCATGAGGCTGCACATCTCCCAGCTCCAGCATGAGAACAGCATCCTCAAGGGAGCCCAGATGAAGGCATCCTTGGCATCCCTGCCCCCT
CTGCATGTTGCAAAGCTATCCCATGAGGGCCCTGGCAGTGAGTTACCAGCTGGAGCGCTGTATCGTAAGACCAGCCAGCTGCTGGAGACATTGA
ATCAATTGAGCACACACACGCACGTAGTAGACATCACTCGCACCAGCCCTGCTGCCAAGAGCCCGTCGGCCCAACTTATGGAGCAAGTGGCTCA
GCTTAAGTCCCTGAGTGACACCGTCGAGAAGCTCAAGGATGAGGTCCTCAAGGAGACAGTATCTCAGCGCCCTGGAGCCACAGTACCCACTGAC
TTTGCCACCTTCCCTTCATCAGCCTTCCTCAGGGCCAAGGAGGAGCAGCAGGATGACACAGTCTACATGGGCAAAGTGACCTTCTCATGTGCGG
CTGGTTTTGGACAGCGACACCGGCTGGTGCTGACCCAGGAGCAGCTGCACCAGCTTCACAGTCGCCTCATCTCCTAA ID 67: TUBA1, *Homo sapiens*
ATGCGTGAATGCATCTCAGTCCACGTGGGGCAGGCAGGTGTCCAGATGGGCAATGCCTGCTGGGAGCTCTATTGCTTGGAACATGGGATTCAGC
CTGATGGGCAGATGCCCAGTGACAAGACCATTGGTGGAGGGGACGACTCCTTCACCACCTTCTTCTGTGAAACTGGTGCTGGAAAACACGTACC
CCGGGCAGTTTTTGTGGATCTGGAGCCTACGGTCATTGATGAGATCCGAAATGGCCCATACCGACAGCTCTTCCACCCAGAGCAGCTCATCACT
GGGAAAGAGGATGCTGCCAACAACTATGCCCGTGGTCACTATACCATTGGCAAGGAGATCATTGACCCAGTGCTGGATCGGATCCGCAAGCTGT
CTGACCAGTGCACAGGACTTCAGGGCTTCCTGGTGTTCCACAGCTTTGGTGGGGGCACTGGCTCTGGCTTCACCTCACTCCTGATGGAGCGGCT
CTCTGTTGACTATGGCAAGAAATCCAAGCTGGAATTCTCCATCTACCCAGCCCCCCAGGTGTCTACAGCCGTGGTCGAGCCCTACAACTCTATC
CTGACCACCCACACCACCCTGGAGCACTCAGACTGTGCCTTCATGGTGGACAACGAAGCAATCTATGACATCTGCCGCCGCAACCTAGACATCG
AGCGCCCAACCTACACCAACCTCAATCGCCTCATTAGCCAAATTGTCTCCTCCATCACAGCTTCTCTGCGCTTTGACGGGGCCCTCAATGTGGA
CCTGACAGAGTTCCAGACCAACCTGGTGCCCTACCCTCGCATCCACTTCCCCCTGGCCACCTATGCACCAGTCATCTCTGCAGAAAAGGCATAC
CACGAGCAGCTGTCGGTGGCAGAGATCACCAATGCCTGCTTTGAGCCTGCCAACCAGATGGTAAAGTGTGATCCCCGGCACGGCAAGTACATGG
CCTGCTGCCTGCTGTACCGTGGAGATGTGGTGCCCAAGGATGTCAACGCTGCCATTGCCGCCATCAAGACCAAGCGCAGCATTCAGTTTGTGGA
CTGGTGCCCCACAGGCTTCAAGGTTGGTATCAACTACCAGCCTCCCACTGTGGTGCCTGGGGGTGACCTGGCCAAGGTGCAGCGTGCCGTGTGC
ATGCTGAGCAACACGACCGCCATCGCCGAGGCCTGGGCCCGCCTGGACCACAAGTTCGACCTGATGTATGCCAAGAGGGCGTTTGTGCACTGGT
ATGTGGGTGAGGGCATGGAGGAGGGTGAGTTCTCCGAGGCCCGTGAGGATATGGCTGCCCTGGAGAAGGATTATGAGGAGGTGGGCATCGACTC
CTATGAGGACGAGGATGAGGGAGAAGAATAA ID 68: TUBA2, *Homo sapiens*
ATGCGTGAGTGTATCTCTATCCACGTGGGGCAGGCAGGAGTCCAGATCGGCAATGCCTGCTGGGAACTGTACTGCCTGGAACATGGAATTCAGC
CCGATGGTCAGATGCCAAGTGATAAAACCATTGGTGGTGGGGACGACTCCTTCAACACGTTCTTCAGTGAGACTGGAGCTGGCAAGCACGTGCC
CAGAGCAGTGTTTGTGGACCTGGAGCCCACTGTGGTCGATGAAGTGCGCACAGGAACCTATAGGCAGCTCTTCCACCCAGAGCAGCTGATCACC
GGGAAGGAAGATGCGGCCAATAATTACGCCAGAGGCCATTACACCATCGGCAAGGAGATCGTCGACCTGGTCCTGGACCGGATCCGCAAACTGG
CGGATCTGTGCACGGGACTGCAGGGCTTCCTCATCTTCCACAGTTTTGGGGGTGGCACTGGCTCTGGGTTCGCATCTCTGCTCATGGAGCGGCT
CTCAGTGGATTACGGCAAGAAGTCCAAGCTAGAATTTGCCATTTACCCAGCCCCCCAGGTCTCCACGGCCGTGGTGGAGCCCTACAACTCCATC
CTGACCACCCACACGACCCTGGAACATTCTGACTGTGCCTTCATGGTCGACAATGAAGCCATCTATGACATATGTCGGCGCAACCTGGACATCG
AGCGTCCCACGTACACCAACCTCAATCGCCTGATTGGCCAGATCGTGTCCTCCATCACGGCCTCCCTGCGATTTGACGGGGCCCTGAATGTGGA
CTTGACGGAATTCCAGACCAACCTAGTGCCGTACCCCCGCATCCACTTCCCCCTGGCCACCTACGCCCCGGTCATCTCAGCCGAGAAGGCCTAC
CACGAGCAGCTGTCCGTGGCTGAGATCACCAATGCCTGCTTCGAGCCAGCCAATCAGATGGTCAAGTGTGACCCTCGCCACGGCAAGTACATGG

Fig. 9 (Continued)

CCTGCTGCATGTTGTACAGGGGGGATGTGGTCCCGAAAGATGTCAACGCGGCCATCGCCACCATCAAGACCAAGCGCACCATCCAGTTTGTAGA
TTGGTGCCCAACTGGATTTAAGGTGGGCATTAACTACCAGCCCCCCACGGTGGTCCCTGGGGGAGACCTGGCCAAGGTGCAGCGGGCTGTGTGC
ATGCTGAGCAACACCACGGCCATCGCGGAGGCCTGGGCTCGCCTGGACCATAAGTTCGATCTCATGTATGCCAAGCGGGCCTTTGTGCACTGGT
ACGTGGGAGAAGGCATGGAGGAGGGGGAGTTCTCTGAGGCCCGCGAGGACCTGGCAGCTCTGGAGAAGGATTATGAAGAGGTGGGCGTGGATTC
CGTGGAAGCCGAGGCTGAAGAAGGTGAAGAATACTGA

ID 69: TUBA3, *Homo sapiens*
ATGCGTGAGTGCATCTCCATCCACGTTGGCCAGGCTGGTGTCCAGATTGGCAATGCCTGCTGGGAGCTCTACTGCCTGGAACACGGCATCCAGC
CCGATGGCCAGATGCCAAGTGACAAGACCATTGGGGGAGGAGATGATTCCTTCAACACCTTCTTCAGTGAGACGGGGGCTGGCAAGCATGTGCC
CCGGGCAGTGTTTGTAGACTTGGAACCCACAGTCATTGATGAAGTTCGCACTGGCACCTACCGCCAGCTCTTCCACCCTGAGCAACTTATCACA
GGCAAAGAAGATGCTGCCAATAACTATGCCCGAGGGCACTACACCATTGGCAAGGAGATCATTGACCTCGTGTTGGACCGAATTCGCAAGCTGG
CCGACCAGTGCACGGGTCTCCAGGGCTTCTTGGTTTTCCACAGCTTTGGTGGGGGAACTGGTTCTGGGTTCACCTCGCTGCTCATGGAACGTCT
CTCAGTTGATTATGGCAAGAAGTCCAAGCTGGAGTTCTCTATTTACCCGGCCCCCCAGGTTTCCACAGCTGTAGTTGAGCCCTACAACTCCATC
CTCACCACCCACACCACCCTGGAGCACTCTGATTGTGCCTTCATGGTAGACAATGAGGCCATCTATGACATCTGTCGTAGAAACCTCGATATTG
AGCGTCCAACCTATACTAACCTGAATAGGTTAATAGGTCAAATTGTGTCCTCCATCACTGCTTCCCTGAGATTTGATGGAGCCCTGAATGTTGA
CCTGACAGAATTCCAGACCAACCTGGTGCCCTATCCCCGCATCCACTTCCCTCTGGCCACATATGCCCCTGTCATCTCTGCTGAGAAAGCCTAC
CATGAACAGCTTTCTGTAGCAGAGATCACCAATGCTTGCTTTGAGCCAGCCAACCAGATGGTCAAATGTGACCCTCGCCATGGTAAATACATGG
CTTGCTGCCTGTTGTACCGTGGTGACGTGGTTCCCAAAGATGTCAATGCTGCCATTGCCACCATCAAGACCAAGCGTACCATCCAGTTTGTGGA
TTGGTGCCCCACTGGCTTCAAGGTTGGCATCAACTACCAGCCTCCCACTGTGGTGCCTGGTGGAGACCTGGCCAAGGTACAGAGAGCTGTGTGC
ATGCTGAGCAACACCACAGCCATTGCTGAGGCCTGGGCTCGCCTGGACCACAAGTTTGACCTGATGTATGCCAAACGTGCCTTTGTTCACTGGT
ACGTTGGGGAGGGGATGGAGGAAGGTGAGTTTTCAGAGGCCCGTGAGGACATGGCTGCCCTTGAGAAGGATTATGAGGAGGTTGGTGTGGATTC
TGTTGAAGGAGAGGGTGAGGAAGAAGGAGAGGAATACTAA ID 70: TUBA4, *Homo sapiens*
GTCTCTGCCCATCCGCGCACCCGGGCTTCGGCTGGAGAGGGCCAGCTCGCTTCAGGAGGCCGAACCCCGT
TCCCACCAACCCTCTCAGCTCAGACGCGGGGTGCTGAGTCACGGGGGGGGGGTGGTTCTGTGGATAGTTG
GAATGCATACACAGAGGAAAGGGGGATGCGGCACCAGCAGACAGAGAGACAAGACCCCAGCCAGCCCCTG
TCCAGGCAGCATGGCACATACCGCCAGATCTTCCATCCAGAGCAGCTCATCACAGGCAAGGAAGATGCTG
CCAATAACTATGCCTGGGGCCACTACACCATTGGGAAGGAGTTCATCGACCTGCTACTGGACCGGATTCG
GAAGCTGGCTGACCAGTGCACAGGACTTCAGGGCTTCCTGGTGTTCCACAGCCTTGGTCGGGGCACTGGC
TCTGACGTCACCTCATTCCTGATGGAGTGGCTTTCTGTTAACTATGGCAAGAAATCCAAGCTGGGATTCT
CCATCTACCCAGCCCCCCAGGTGTCTACAGCCATGGTCCAGCCCTACAACTCTATCCTGACCACCCACAC
CACCCTGGAGCACTCAGACTGTGCCTTCATGGTGGACAACAAAGCAATCTATGACATCTGCCACCGCAAC
CTAGACATTGAGCGCCCAACCTACACCAACCTCAATCGCCTCATTAGCCAAATTGTCTCCTCCATCACAG
CTTCTCTGCGCTTTGACGGGGCCCTCAATGTGGACCTGACAGAGTTCCAGACCAACCTGGTGTCCTACCT
CACATCCACTTCCCCCTGGCCACCTATGCACCAGTCATCTCTGCAGAAAAAGTATACCACGAGCAGCTGT
CGGTGGCAGAGATTACCAATGCCTGCTTTGAGCCTGCCAACCAGATGGTGAAGTGTGATCCCCGGCACGG
CAAGTACATGGCCTGCTGCCTGCTATACCATGGAGATGTGGTGCCCAAGGATGTCAACGCTGCCATTGCT
GCCATCAAGACCAAGTGCAGCATTCAGTTTGTGGACTGGTGCCCCACAGGCTTTAAGGTTGATATCAATC
ACCAGCCTCCCACTGTGGTGCCTGGGAGTGACCTGGTAAAGTGCAACGTGCCATGTGCATGCTGAGCAAC
ATGACAGCCATCACTATGGCCTGGGCCCGCCTGGACCACAAGTTTGACCTGATGTATGCCAAGAGGGCGT
TTGGGCACTGATATGTGGGTGAGGGCATGGAGGAGGGTGAGTTCTCCAAGGCCCATGAGGATATGACTGC
CCTGGAGAAGGATTACAAGGAGGTGGGCATGGATAGTGTGGAGTGTGGGGAAGAAAAGATAGGGGGGATG
AATACTAGGGGAATACTGTGTGTCTGTCCTACATAAAGTGCTGTGGCCTT ID 71: TUBA6
ATGCGTGAGTGCATCTCCATCCACGTTGGCCAGGCTGGTGTCCAGATTGGCAATGCCTGCTGGGAGCTCTACTGCCTGGAACACGGCATCCAGC
CCGATGGCCAGATGCCAAGTGACAAGACCATTGGGGGAGGAGATGATTCCTTCAACACCTTCTTCAGTGAAACGGGTGCTGGCAAGCATGTGCC
CCGGGCAGTGTTTGTAGACTTGGAACCCACAGTCATTGATGAAGTTCGCACTGGCACTTACCGCCAGCTCTTCCACCCTGAGCAACTCATCACA
GGCAAGGAAGATGCTGCCAATAACTATGCCCGAGGGCACTACACCATTGGCAAGGAGATCATTGACCTCGTGTTGGACCGAATTCGCAAGCTGG
CTGACCAGTGCACCGGTCTTCAGGGCTTCTTGGTTTTCCACAGCTTTGGTGGGGGAACTGGTTCTGGGTTCACCTCGCTGCTCATGGAACGTCT
CTCAGTTGATTATGGCAAGAAGTCCAAGCTGGAGTTCTCCATTTACCCGGCGCCCCAGGTTTCCACAGCTGTAGTTGAGCCCTACAACTCCATC
CTCACCACCCACACCACCCTGGAGCACTCTGATTGTGCCTTCATGGTAGACAATGAGGCCATCTATGACATCTGTCGTAGAAACCTCGATATCG
AGCGCCCAACCTACACTAACCTTAACCGCCTTATTAGCCAGATTGTGTCCTCCATCACTGCTTCCCTGAGATTTGATGGAGCCCTGAATGTTGA
CCTGACAGAATTCCAGACCAACCTGGTGCCCTACCCCCGCATCCACTTCCCTCTGGCCACATATGCCCCTGTCATCTCTGCTGAGAAAGCCTAC
CACGAACAGCTTACTGTAGCAGAGATCACCAATGCTTGCTTTGAGCCAGCCAACCAGATGGTCAAATGTGACCCTCGCCATGGTAAATACATGG
CTTGCTGCCTGTTATACCGTGGTGACGTGGTTCCCAAAGATGTCAATGCTGCCATTGCCACCATCAAAACCAAGCGTACCATCCAGTTTGTGGA
TTGGTGCCCCACTGGCTTCAAGGTTGGCATTAATTACCAGCCTCCCACTGTGGTGCCTGGCGGAGACCTGGCCAAGGTACAGAGAGCTGTGTGC
ATGCTGAGCAATACCACAGCTGTTGCCGAGGCCTGGGCTCGCCTGGACCACAAGTTTGACCTGATGTATGCCAAGCGTGCCTTTGTTCACTGGT
ACGTGGGTGAGGGGATGGAGGAAGGCGAGTTTTCAGAGGCCCGTGAGGACATGGCTGCCCTTGAGAAGGATTATGAGGAGGTTGGAGCAGATAG
TGCTGACGGAGAGGATGAGGGTGAAGAGTATTAA ID 72: TUBA8
ATGCGGGAATGCATATCAGTCCACGTGGGCCAAGCGGGAGTTCAGATTGGCAATGCCTGCTGGGAGCTCTTCTGCCTGGAACACGGCATCCAGG
CAGACGGCACTTTTGATGCTCAAGCTAGCAAGATCAACGATGATGACTCCTTCACCACCTTTTTCAGCGAGACTGGCAATGGCAAGCATGTGCC
CCGGGCCGTCATGATAGATCTGGAGCCTACTGTAGTGGATGAGGTTCGGGCAGGAACCTACCGCCAGCTCTTCCATCCAGAGCAGCTGATCACA
GGAAAGGAGGATGCAGCCAACAACTATGCCCGGGGCCACTACACGGTGGGCAAGGAGAGCATTGACCTGGTGCTGGACCGCATACGGAAGCTGA
CAGATGCTTGCTCTGGCCTGCAGGGCTTCCTGATTTTCCACAGTTTTGGTGGGGGCACTGGCTCCGGCTTCACTTCTCTGCTGATGGAACGCCT
CTCCCTGGATTATGGCAAGAAATCCAAGCTGGAGTTTGCCATCTACCCAGCCCCCCAGGTCTCTACTGCAGTGGTGGAGCCCTACAACTCCATC
CTGACCACCCACACCACACTGGAACATTCAGATTGTGCCTTCATGGTGGACAACGAAGCCATCTATGACATCTGCCGCAGGAACCTTGACATTG
AGCGCCCTACCTATACCAACCTCAACCGCCTCATCAGTCAGATTGTGTCCTCAATCACTGCTTCTCTCCGCTTTGACGGGGCCCTCAATGTGGA
CCTCACTGAGTTCCAGACCAACCTGGTGCCCTACCCCCGCATCCACTTCCCGCTGGTCACCTACGCGCCCATCATCTCTGCCGAGAAAGCCTAT
CACGAACAGCTCTCTGTGGCCGAGATAACCAGCTCCTGCTTTGAGCCCAACAGCCAGATGGTGAAGTGCGACCCGAGACATGGCAAGTACATGG
CCTGCTGCATGCTCTACCGGGGCGACGTGGTGCCCAAGGATGTGAATGTCGCTATTGCTGCCATCAAGACCAAGAGGACCATCCAGTTTGTAGA
CTGGTGTCCCACAGGCTTCAAGGTGGGCATCAACTACCAGCCCCCGACCGTGGTCCCCGGGGGAGACCTGGCCAAGGTGCAGCGGGCCGTCTGC
ATGCTCAGCAACACCACGGCCATTGCGGAGGCCTGGGCCCGCCTCGACCACAAGTTCGACCTCATGTACGCCAAGCGGGCCTTTGTGCATTGGT
ATGTGGGAGAGGGGATGGAAGAAGGAGAATTTTCTGAGGCCAGGGAAGACTTAGCTGCCCTGGAGAAGGATTATGAAGAAGTGGGGACTGATTC
GTTTGAAGAAGAAAATGAAGGGGAGGAATTTTAA ID 73: TEKT1, *Homo sapiens*

Fig. 9 (Continued)

ATGGCTAAACTATTACAACCTCCACCCAAGTTCCTGCCCTCAGAGTGGCACATTGCTAACAAGAACCAGTACCACAGAGCAGACGCTCAAAGGT
CCCGATCAGAACGCCTGGTCGCAGAAAGCCAGAGGCTTGTGGATGAAATTGAAAAGACCACAAGAAAATCTCAAAGCGATGTGAACAAGAAACT
AGAACAGAGACTCGAGGAAGTCCAGTTCTGGAAGAAGGAGTTAGATGACAAACTTGAGCAGCTTGTGAATGTAACTGATGATCTACTCATATAT
AAGATCAGATTGGAAAAAGCCCTGGAGACCTTGAAAGAGCCCTTGCACATCACTGAGACATGCCTGGCATACAGGGAGAAGCGCATTGGCATTG
ACCTGGTGCACGACACAGTGGAGCATGAGCTGATAAAGGAGGCTGAGATCATCCAGGGCATTATGGCTCTGCTGACCCGTACCTTGGAGGAGGC
TTCCGAGCAGATTCGGATGAACCGCTCTGCCAAGTACAATCTTGAGAAGGATTTGAAGGACAAGTTTGTGGCCCTGACCATAGATGATATCTGC
TTCTCGCTCAACAACAACTCACCAAACATCAGATATTCTGAGAACGCCGTGAGGATTGAGCCAAACTCCGTGAGTCTGGAAGACTGGTTGGACT
TCTCCAGCACCAATGTGGAGAAGGCTGACAAGCAGCGGAACAACTCCCTGATGCTGAAAGCCCTGGTGGATCGAATCCTGTCCCAGACAGCCAA
TGATCTGCGCAAGCAGTGTGATGTGGTGGACACGGCATTCAAGAATGGGCTGAAGGATACAAAGGATGCCAGGGACAAGCTGGCTGATCATCTG
GCCAAGGTCATGGAAGAGATTGCTTCCCAGGAGAAAAATATTACAGCTCTTGAAAAGGCCATCCTTGACCAAGAAGGGCCAGCCAAGGTGGCTC
ATACGCGCTTGGAGACCAGGACACACCGGCCGAACGTGGAGCTGTGTCGTGATGTCGCACAATATAGGCTAATGAAGGAGGTTCAAGAGATCAC
CCACAATGTCGCAAGATTGAAGGAAACTTTAGCCCAAGCTCAGGCAGAGCTGAAAGGGCTGCATCGCAGACAGCTTGCCCTGCAGGAGGAGATC
CAGGTCAAAGAGAACACCATTTATATCGACGAAGTGCTGTGTATGCAGATGAGGAAATCCATCCCACTTCGGGATGGGGAAGACCATGGGGTCT
GGGCTGGGGGCCTCCGCCCTGATGCTGTCTGCTAA

ID 74: TEKT2, *Homo sapiens*
ATGGCCACGCTGAGCGTCAAGCCAAGTCGGCGCTTCCAGCTGCCCGACTGGCACACTAACAGCTACCTGCTATCCACCAATGCCCAGCTGCAGC
GAGATGCTTCCCATCAGATCCGCCAGGAGGCCCGGGTGCTCCGCAACGAGACCAACAACCAGACCATTTGGGATGAACATGACAACAGGACTCG
ACTGGTGGAGAGGATTGATACTGTCAACCGGTGGAAGGAGATGCTGGACAAGTGTCTGACAGATTTAGATGCCGAGATCGATGCCCTGACACAG
ATGAAGGAGTCAGCAGAGCAAAACCTGCAGGCCAAGAACCTGCCTCTGGATGTGGCCATTGAGTGCCTGACCCTGCGGGAAAGCCGGCGAGACA
TTGATGTGGTGAAGGACCCTGTGGAGGATGAGCTGCATAAAGAGGTGGAGGTCATCGAGGCCACCAAGAAGGCCTTGCAACAGAAGGTCAGCCA
GGCCTTCGAGCAGCTCTGCCTCTTGCAGGAAGTCCAACAGCAGCTCAACTCCGACCATCGGGGCAAAATGGAGACACTAGAGATCGACAGAGGC
TGTCTCTCTCTCAACCTCAGATCCCCAAACATCTCGCTGAAGGTTGACCCCACACGTGTACCTGATGGCTCCACCACACTCCAGCAGTGGGATG
ACTTCAGTCGGTTCAACAAGGACCGAGCGGAGGCTGAGATGAAGGCAGCCACAGAGCTGAGGGAGGCCACTGCTCTAACTATTGCTGAGACCAA
CAACGAGCTTGAAGCCCAGAGAGTTGCAACGGAATTTGCCTTCAGGAAGCGGCTGCGGGAGATGGAGAAAGTGTACAGTGAGCTCAAGTGGCAA
GAGAAGAATACCTTGGAGGAGATCGCTGAGCTGCAGGAGGACATCCGGCACCTGGAGGAGGATCTGCGCACAAAGCTCCTGAGCCTGAAGCTGT
CCCATACCCGGCTAGAGGCCAGAACCTACCGGCCCAACGTGGAACTCTGCCGGGACCAGGCACAGTACGGCCTCACCGACGAGGTTCACCAGCT
AGAGGCAACCATCGCTGCCCTGAAGCAGAAGCTGGCGCAAGCACAGGACGCACTGGACGCCCTGTGCAAGCACCTGGCCCGGCTGCAGGCTGAC
ATTGCCTGCAAGGCCAACTCCATGCTGCTGGACACCAAGTGCATGGACACACGGCGCAAGCTGACCGTGCCTGCTGAGAGGTTCGTGCCTGAGG
TGGACACCTTCACACGTACCACAAATAGCACCCTGAGTCCACTCAAAAGCTGCCAGCTCGAGCTGGCCTAG ID 75: TEKT3, *Homo sapiens*
ATGGAACGTGTAGGTTGTACTTTAACGACAACTTACGCCCACCCTAGACCAACACCAACCAACTTTCTACCAGCCATCAGTACCATGGCCTCAA
GCTACAGGGACCGCTTTCCCCACTCCAATTTGACCCATAGCCTGAGCCTTCCTTGGAGACCCAGCACATACTACAAAGTCGCCTCCAATTCCCC
AAGCGTGGCCCCGTACTGCACCAGATCACAGAGGGTGTCCGAGAATACCATGCTTCCCTTTGTTTCCAACAGAACCACTTTCTTCACAAGATAC
ACACCGGATGACTGGTACAGGTCCAATTTAACCAACTATCAAGAGTCCAACACTTCCCGACATAATTCGGAGAAACTAAGAGTGGATACATCTC
GCCTGATTCAAGACAAATATCAACAAACAAGAAAAACTCAGGCAGACACAACCCAAAATCTGGGAGAACGTGTCAATGACATAGGGTTTTGGAA
ATCTGAAATCATTCATGAGTTGGATGAAATGATTGGAGAGACAAATGCACTTACTGATGTGAAGAAAAGACTGGAGCGGGCTTTGATGGAGACT
GAAGCCCCTCTTCAGGTAGCCCGAGAATGTCTATTTCATCGAGAAAAGAGAATGGGAATCGACCTAGTTCACGATGAAGTTGAAGCACAACTGC
TGACGGAAGTTGATACTATTCTGTGTTGTCAAGAAAAGAATGAAGCTACATTTGGATAAGGCTATTGCCCAACTTGCAGCCAACAGAGCGTCCCA
GCATGAGCTGGAAAAGGACCTGAGTGACAAACAGACGGCTTACCGGATCGACGACAAATGCCACCACCTGCGCAACACATCAGACGGTGTCGGC
TACTTCCGCGGAGTGGAGAGGGTCGATGCAACTGTCTCAGTGCCTGAGTCCTGGGCCAAATTTACAGATGACAATATTCTCCGCTCCCAGAGTG
AACGGGCAGCTTCCGCTAAGCTAAGAGACGACATTGAAAACCTCTTGGTTGTGACTGCCAATGAGATGTGGAATCAATTCAACAAAGTGAACTT
GTCTTTCACCAATCGCATTGCTGAGACTGCAGATGCTAAGAATAAGATTCAGACGCACTTAGCAAAGACCCTGCAGGAGATTTTCCAGACTGAA
ATGACCATAGAATCCATCAAGAAGGCCATCAAGGACAAGACTGCCTTCCTGAAGGTGGCTCAGACCAGACTGGATGAGCGCACAAGACGGCCGA
ACATTGAGTTGTGCCGAGACATGGCTCAGCTACGCCTTGTTAACGAGGTACACGAGGTTGACGACACCATCCAGACCCTGCAGCAGCGCCTGAG
GGATGCAGAGGACACCCTGCAGTCGCTGGTCCACATCAAAGCCACACTCGAGTATGACCTGGCTGTCAAAGCCAATTCCCTGTACATCGACCAG
GAAAAATGCATGAGCATGCGCAAGAGCTACCCCAACACCCTCCGGCTGGTCGGCTTCTGCTAG ID 76: TEKT4, *Homo sapiens*
ATGGCGCAGACAGTGCCGCCCTGCGAGCTGCCCTGCAAAGAGTACGACGTGGCCCGTAACACGGGCGCCTACACGTCCTCCGGCCTGGCCACCG
CCAGCTTCCGCACCTCCAAGTACCTGCTGGAGGAGTGGTTCCAGAACTGCTATGCTCGCTACCACCAGGCCTTCGCCGACCGCGACCAGTCGGA
GCGGCAGCGGCACGAGAGCCAGCAGCTGGCCACAGAGACCCAGGCGCTGGCGCAGCGCACGCAGCAAGACTCCACGCGCACAGTGGGCGAGCGA
CTGCAGGACACGCACAGCTGGAAGTCGGAGCTGCAGCGTGAGATGGAGGCGCTGGCTGCGGAGACCAACTTGCTCCTGGCCCAGAAGCAACGGC
TGGAGCGCGCCCTGGACGCCACAGAGGTGCCCTTCTCCATCACCACTGACAACCTGCAGTGCCGTGAGCGCCGCGAGCACCCCAACCTCGTGCG
CGACCATGTGGAAACGGAGCTGCTGAAGGAAGCCGAGCTCATCCGGAACATTCAGGAGCTGCTGAAGAGAACCATCATGCAAGCAGTGAGCCAG
ATCCGACTGAACCGGGAGCACAAGGAGACCTGCGAGATGGACTGGTCAGACAAGATGGAGGCCTACAACATCGACGAGACCTGCGGGCGCCACC
ACAGCCAGAGCACCGAGGTGCAGGCTCATCCGTACTCCACCACCTTCCAAGAGAGCGCCTCCACCCCGGAGACCCGGGCCAAGTTCACGCAGGA
CAATCTGTGCCGTGCCCAGCGCGAGCGCCTGGCCTCGGCCAACCTGCGGGTGCTGGTGGACTGCATCCTTCGCGACACCTCCGAGGACCTGCGG
CTCCAGTGCGACGCCGTGAACCTGGCCTTCGGGCGCCGCTGTGAGGAGCTGGAGGACGCGCGGTACAAGCTGCATCACCACCTGCACAAGACAC
TGCGGGAAATCACAGATCAGGAACACAACGTGGCGGCACTGAAGCAGGCCATCAAGGACAAAGAGGCACCTCTGCACGTAGCCCAGACCCGGCT
GTACCTGCGCTCGCACCGGCCCAACATGGAGCTGTGCCGTGACGCAGCCCAGTTCAGGCTGTTGAGTGAGGTGGAGGAGCTGAACATGTCCCTC
ACAGCACTGCGAGAGAAGCTTCTAGAAGCGGAGCAGTCCCTGCGCAACCTCGAGGACATCCACATGAGCCTGGAGAAGGACATTGCCGCCATGA
CCAACAGTCTCTTCATCGACCGCCAGAAGTGCATGGCCCATCGTACTCGCTACCCCACCATCCTGCAGCTGGCTGGCTACCAGTGA ID 77: TEKT5, *Homo sapiens*
ATGGAGTTTCTTGGGACTACTCAGACCGCCAGTTACTGTGGTCCCAAGAAATGCTGTGGCTTGACCTCACTGCCAGCTGTACAGGCGCCAGTGA
TCCAGGAATGCTATCAGCCCTACTACCTGCCCGGGTACCGCTACCTCAATTCATGGAGGCCTAGCCTCTTCTACAAGATAGCCAACGTCCAGAC
CTGCCCGGACGAGAGCACCAGTACCCTGCGGCCGCCCACCATCCTGCCCACACTGCGCTCCGCACTCTTCTCTCGCTATAGCCCCCACGACTGG
GACCAGTCCAACCAGCTGCAGGTGCGTGGGCCGAGGCCTCCCGGCTGTGGCCAGCCGGCTGACGGATGACTCCATGAGGCTCTTGCAGGACA
AGGACCAGCTGACGCACCAGATGCAGGAGGGCACCTGCCGGAACCTGGGCCAGAGGCTGTCGGACATTGGCTTCTGGAAGTCAGAGCTGAGCTA
TGAGCTGGACAGGCTTCTGACTGAGAACCAGAACTTGGAGACGGTCAAGAGGCGGCTGGAGTGCGCGGCCAATGAGGTGAACTGCCCATTGCAG
GTGGCCTTGGAGTGTCTGTACCATCGAGAGAAGAGGATTGGGATTGATTTGGTCCATGACAACGTGGAGAAAAACCTTATCCGGGAAGTGGATT
TGCTAAAATGTTGCCAAGAACAGATGAGAAAATTAGCTCAAAGAATTGATATCCAGATGCGGGATAACCGGGATGCTCAGCACGTGCTGGAGAG
GGACCTCGAAGACAAAAGCTCGGCCCAGTGTATCGATGAGAAGTGCTTTAACCTGAGAAATACGTCAGACTGCATCAGCTTCTTCCACGGCATG
GAGAAAATTGACGGCACGATCTCCGTACCTGAGACCTGGGCCAAGTTCAGTAACGACAACATCAAACACTCTCAGAACATGCGGGCCAACTCCA
TCCAGCTGCGGGAGGAGGCGGAGCACCTCTTTGAGACCTTGTCGGATCAGATGTGGAGGCAGTTCACAGACACCAACCTGGCCTTCAACGCCCG
CATCTCTGAGGTGACGGATGTGAAGAATAAGCTGCAGACGCAGCTGGCGAAGACGCTGCAGGAGATCTTCCAGGCCGAGAACACCATCATGCTG
CTGGAAAGGTCCATCATGGCCAAGGAGGGCCCGCTGAAGGTGGCCCAGACAAGGCTGGAGTGCCGGACCCGGCGCCCCAACATGGAGCTGTGCA
GGGACATCCCGCAGTTGAAGCTGGTGAACGAGGTGTTCACCATCGACGACACCCTGCAGACCCTCAAGCTGCGGCTGCGGGAGACACAGGACAC

Fig. 9 (Continued)

GCTGCAGCTGCTGGTCATGACCAAGTGCCGGCTGGAGCACGAGCTCGCCATCAAGGCCAACACCCTCTGCATCGACAAGGAGAAGTGCATGGGC
ATGCGTAAGACCTTCCCCTGCACCCCGCGCCTGGTGGGCCACACCTGA

ID 78: DNM1, *Homo sapiens*
ATGGGCAACCGCGGCATGGAAGATCTCATCCCGCTGGTCAACCGGCTGCAAGACGCCTTCTCTGCCATCGGCCAGAACGCGGACCTCGACCTGC
CGCAGATCGCTGTGGTGGGCGGCCAGAGCGCCGGCAAGAGCTCGGTGCTCGAGAATTTCGTAGGCAGGGACTTCTTGCCTCGAGGATCTGGCAT
TGTCACCCGACGTCCCCTGGTCTTGCAGCTGGTCAATGCAACCACAGAATATGCCGAGTTCCTGCACTGCAAGGGAAAGAAATTCACCGACTTC
GAGGAGGTGCGCCTTGAGATCGAGGCCGAGACCGACAGGGTCACCGGCACCAACAAGGGCATCTCGCCGGTGCCTATCAACCTCCGCGTCTACT
CGCCGCACGTGCTGAACCTGACCCTGGTGGACCTGCCCGGAATGACCAAGGTCCCGGTGGGGGACCAACCTCCCGACATCGAGTTCCAGATCCG
AGACATGCTTATGCAGTTTGTCACCAAGGAGAACTGCCTCATCCTGGCCGTGTCCCCCGCCAACTCTGACCTGGCCAATTCTGACGCCCTCAAG
GTCGCCAAGGAGGTGGACCCCCAGGGCCAGCGCACCATCGGGGTCATCACCAAGCTGGACCTGATGGACGAGGGCACAGATGCCCGTGATGTGC
TGGAGAACAAGCTGCTCCCCCTGCGCAGAGGCTACATTGGAGTGGTGAACCGGAGCCAGAAGGACATTGATGGCAAGAAGGACATTACCGCCGC
CTTGGCTGCTGAACGAAAGTTCTTCCTCTCCCATCCATCTTATCGCCACTTGGCTGACCGTATGGGCACGCCCTACCTGCAGAAGGTCCTCAAT
CAGCAACTGACGAACCACATCCGGGACACACTGCCGGGGCTGCGGAACAAGCTGCAGAGCCAGCTACTGTCCATTGAGAAGGAGGTGGAGGAAT
ACAAGAACTTCCGCCCTGATGACCCAGCTCGCAAGACCAAGGCCCTGCTGCAGATGGTCCAGCAGTTCGCCGTAGACTTTGAGAAGCGCATTGA
GGGCTCAGGAGATCAGATCGACACCTACGAACTGTCAGGGGGAGCCCGCATTAACCGAATCTTCCACGAGCGCTTCCCTTTCGAGCTGGTCAAG
ATGGAGTTTGATGAGAAGGAACTCCGAAGGGAGATCAGCTATGCTATCAAGAATATCCATGGCATTAGAACGGGGCTGTTTACCCCAGACATGG
CCTTTGAGACCATTGTGAAAAAGCAGGTGAAGAAGATCCGAGAACCGTGTCTCAAGTGTGTGGACATGGTTATCTCGGAGCTAATCAGCACCGT
TAGACAGTGCACCAAGAAGCTCCAGCAGTACCCGCGGCTACGGGAGGAGATGGAGCGCATCGTGACCACCCACATCCGGGAGCGCGAGGGCCGC
ACTAAGGAGCAGGTCATGCTTCTCATCGATATCGAGCTGGCTTACATGAACACCAACCATGAGGACTTCATAGGCTTTGCCAATGCTCAGCAGA
GGAGCAACCAGATGAACAAGAAGAAGACTTCAGGGAACCAGGATGAGATTCTGGTCATCCGCAAGGGCTGGCTGACTATCAATAATATTGGCAT
CATGAAAGGGGGCTCCAAGGAGTACTGGTTTGTGCTGACTGCTGAGAATCTGTCCTGGTACAAGGATGATGAGGAGAAAGAGAAGAAATACATG
CTGTCTGTGGACAACCTCAAGCTGCGGGACGTGGAGAAGGGCTTTATGTCGAGCAAGCATATCTTTGCCCTCTTTAACACGGAGCAGAGGAATG
TCTACAAGGATTATCGGCAGCTGGAGCTAGCCTGTGAGACACAGGAGGAGGTGGACAGCTGGAAGGCCTCCTTCCTGAGGGCTGGCGTGTACCC
TGAGCGTGTTGGGGACAAAGAGAAAGCCAGCGAGACCGAGGAGAATGGCTCCGACAGCTTCATGCATTCCATGGACCCACAGCTGGAACGGCAA
GTGGAGACCATCCGGAATCTTGTGGACTCATACATGGCCATTGTCAACAAGACCGTGAGGGACCTCATGCCCAAGACCATCATGCACCTCATGA
TTAACAATACCAAGGAGTTCATCTTCTCGGAGCTGCTGGCCAACCTGTACTCGTGTGGGGACCAGAACACGCTGATGGAGGAGTCGGCGGAGCA
GGCACAGCGGCGCGACGAGATGCTGCGCATGTACCACGCACTGAAGGAGGCGCTCAGCATCATCGGCGACATCAACACGACCACCGTCAGCACG
CCCATGCCCCCGCCCGTGGACGACTCCTGGCTGCAGGTGCAGAGCGTACCGGCCGGACGCAGGTCGCCCACGTCCAGCCCCACGCCGCAGCGCC
GAGCCCCGCCGTGCCCCCAGCCCGGCCCGGGTCGCGGGCCCTGCTCCTGGGCCTCCGCCTGCTGGGTCCGCCCTGGGGGGGCGCCCCCGT
GCCCTCCAGGCCGGGGGCTTCCCCTGACCCTTTCGGCCCTCCCCCTCAGGTGCCCTCGCGCCCCAACCGCGCCCCGCCCGGGGTCCCCAGCCGA
TCGGGTCAGGCAAGTCCATCCCGTCCTGAGAGCCCCAGGCCCCCCTTCGACCTCTAA ID 79: DNM2, *Homo sapiens*
ATGGGCAACCGCGGGATGGAAGAGCTGATCCCGCTGGTCAACAAACTGCAGGACGCCTTCAGCTCCATCGGCCAGAGCTGCCACCTGGACCTGC
CGCAGATCGCTGTAGTGGGCGGCCAGAGCGCCGGCAAGAGCTCGGTGCTGGAGAACTTCGTGGGCCGGGACTTCCTTCCCCGCGGTTCAGGAAT
CGTCACCCGGCGGCCTCTCATTCTGCAGCTCATCTTCTCAAAAACAGAACATGCCGAGTTTTTGCACTGCAAGTCCAAAAAGTTTACAGACTTT
GATGAAGTCCGGCAGGAGATTGAAGCAGAGACCGACAGGGTCACGGGGACCAACAAAGGCATCTCCCCAGTGCCCATCAACCTTCGAGTCTACT
CGCCACACGTGTTGAACTTGACCCTCATCGACCTCCCGGGTATCACCAAGGTGCCTGTGGGCGACCAGCCTCCAGACATCGAGTACCAGATCAA
GGACATGATCCTGCAGTTCATCAGCCGGGAGAGCAGCCTCATTCTGGCTGTCACGCCCGCCAACATGGACCTGGCCAACTCCGACGCCCTCAAG
CTGGCCAAGGAAGTCGATCCCCAAGGCCTACGGACCATCGGTGTCATCACCAAGCTTGACCTGATGGACGAGGGCACCGACGCCAGGGACGTCT
TGGAGAACAAGTTGCTCCCGTTGAGAAGAGGCTACATTGGCGTGGTGAACCGCAGCCAGAAGGATATTGAGGGCAAGAAGGACATCCGTGCAGC
ACTGGCAGCTGAGAGGAAGTTCTTCCTCTCCCACCCGGCCTACCGGCACATGGCCGACCGCATGGGCACGCCACATCTGCAGAAGACGCTGAAT
CAGCAACTGACCAACCACATCCGGGAGTCGCTGCCGGCCCTACGTAGCAAACTACAGAGCCAGCTGCTGTCCCTGGAGAAGGAGGTGGAGGAGT
ACAAGAACTTTCGGCCCGACGACCCCACCCGCAAAACCAAAGCCCTGCTGCAGATGGTCCAGCAGTTTGGGGTGGATTTTGAGAAGAGGATCGA
GGGCTCAGGAGATCAGGTGGACACTCTGGAGCTCTCCGGGGGCGCCCGAATCAATCGCATCTTCCACGAGCGGTTCCCATTTGAGCTGGTGAAG
ATGGAGTTTGACGAGAAGGACTTACGACGGGAGATCAGCTATGCCATTAAGAACATCCATGGAGTCAGGACCGGGCTTTTCACCCCGGACTTGG
CATTCGAGGCCATTGTGAAAAAGCAGGTCGTCAAGCTGAAAGAGCCCTGTCTGAAATGTGTCGACCTGGTTATCCAGGAGCTAATCAATACAGT
TAGGCAGTGTACCAGTAAGCTCAGTTCCTACCCCCGGTTGCGAGAGGAGACAGAGCGAATCGTCACCACTTACATCCGGGAACGGGAGGGGAGA
ACGAAGGACCAGATTCTTCTGCTGATCGACATTGAGCAGTCCTACATCAACACGAACCATGAGGACTTCATCGGGTTTGCCAATGCCCAGCAGA
GGAGCACGCAGCTGAACAAGAAGAGAGCCATCCCCAATCAGGGGGAGATCCTGGTGATCCGCAGGGGCTGGCTGACCATCAACAACATCAGCCT
GATGAAAGGCGGCTCCAAGGAGTACTGGTTTGTGCTGACTGCCGAGTCACTGTCCTGGTACAAGGATGAGGAGGAGAAAGAGAAGAAGTACATG
CTGCCTCTGGACAACCTCAAGATCCGTGATGTGGAGAAGGGCTTCATGTCCAACAAGCACGTCTTCGCCATCTTCAACACGGAGCAGAGAAACG
TCTACAAGGACCTGCGGCAGATCGAGCTGGCCTGTGACTCCCAGGAAGACGTGGACAGCTGGAAGGCCTCGTTCCTCCGAGCTGGCGTCTACCC
CGAGAAGGACCAGGCAGAAAACGAGGATGGGGCCCAGGAGAACACCTTCTCCATGGACCCCCAACTGGAGCGGCAGGTGGAGACCATTCGCAAC
CTGGTGGACTCATACGTGGCCATCATCAACAAGTCCATCCGCGACCTCATGCCAAAGACCATCATGCACCTCATGATCAACAATACGAAGGCCT
TCATCCACCACGAGCTGCTGGCCTACCTATACTCCTCGGCAGACCAGAGCAGCCTCATGGAGGAGTCGGCTGACCAGGCACAGCGGCGGGACGA
CATGCTGCGCATGTACCATGCCCTCAAGGAGGCGCTCAACATCATCGGTGACATCAGCACCAGCACTGTGTCCACGCCTGTACCCCCGCCTGTC
GATGACACCTGGCTCCAGAGCGCCAGCAGCCACAGCCCCACTCCACAGCGCCGACCGGTGTCCAGCATACACCCCCCTGGCCGGCCCCCAGCAG
TGAGGGGCCCCACTCCAGGGCCCCCCTGATTCCTGTTCCCGTGGGGGCAGCAGCCTCCTTCTCGGCGCCCCCAATCCCATCCCGGCCTGGACC
CCAGAGCGTGTTTGCCAACAGTGACCTCTTCCCAGCCCCGCCTCAGATCCCATCTCGGCCAGTTCGGATCCCCCCAGGGATTCCCCCAGGAGTG
CCCAGCAGAAGACCCCCTGCTGCGCCCAGCCGGCCCACCATTATCCGCCCAGCCGAGCCATCCCTGCTCGACTAG ID 80: DNM3, *Homo sapiens*
ATGGGGAACCGGGAGATGGAGGAGCTGATCCCGCTGGTGAACCGTCTGCAGGACGCGTTTTCGGCGCTGGGACAGAGCTGCCTGCTGGAGCTGC
CGCAGATCGCCGTGGTGGGCGGCCAGAGCGCCGGCAAGAGCTCGGTGCTCGAGAACTTCGTGGGCAGGGACTTTCTCCCTCGAGGGTCGGGCAT
TGTAACAAGACGACCTCTTGTGCTGCAGCTTGTTACTTCTAAAGCAGAATATGCCGAGTTTCTACATTGCAAAGGAAAGAAATTTACAGATTTT
GATGAAGTTCGCCTTGAGATTGAAGCAGAAACAGATCGCGTGACTGGAATGAATAAAGGCATTTCCTCCATACCCATTAATTTACGAGTCTATT
CCCCACACGTGTTAAATCTAACCCTTATTGATCTACCTGGAATAACTAAAGTGCCTGTGGGAGATCAGCCACCAGATATCGAGTATCAGATCAG
AGAAATGATTATGCAGTTCATCACGAGGGAGAACTGTCTGATTTTAGCTGTTACTCCAGCCAACACTGATCTTGCAAACTCAGATGCGCTGAAG
CTAGCTAAAGAAGTTGATCCTCAAGGTCTGAGAACCATTGGAGTTATCACCAAACTGGACCTTATGGATGAAGGAACGGATGCCAGGGATGTTC
TAGAGAACAAACTGTTGCCTCTTCGCAGGGGTTACGTGGGGGTGGTAAACAGAAGCCAGAAGGACATAGATGGGAAGAAGGACATAAAGGCAGC
CATGCTGGCAGAGAGGAAGTTTTTCCTTTCCCACCCGGCTTACAGACATATCGCTGACCGAATGGGAACCCCACACCTGCAGAAGGTCCTTAAT
CAGCAACTTACCAACCACATTCGGGATACCCTACCAAACTTCAGGAACAAACTACAGGGACAGTTGCTCTCCATAGAACATGAAGTAGAAGCCT
ACAAAAATTTCAAACCAGAAGACCCAACAAGGAAGACCAAAGCATTGCTGCAGATGGTTCAGCAATTTGCTGTGGACTTTGAGAAGAGAATTGA
AGGGTCAGGGGATCAAGTAGATACCCTGGAACTCTCAGGTGGTGCTAAAATCAATCGTATTTTTCATGAACGCTTTCCTTTTGAGATAGTAAAG
ATGGAGTTCAATGAGAAAGAATTGCGAAGAGAAATAAGCTATGCAATCAAAAACATACATGGTATCAGGACAGGGTTGTTTACTCCAGACATGG
CATTTGAAGCGATAGTCAAGAAACAGATTGTAAAGTTGAAAGGGCCTTCCTTGAAGAGTGTGGATCTGGTAATACAAGAATTAATCAACACTGT
GAAGAAGTGTACCAAAAAACTGGCAAACTTCCCCAGACTCTGCGAGGAAACGGAAAGGATTGTTGCTAACCACATTCGTGAGCGAGAAGGGAAG
ACAAAGGACCAGGTATTGCTATTGATTGACATTCAAGTCTCTTACATCAACACCAACCATGAAGACTTCATTGGCTTCGCAAATGCTCAGCAGA GGAGCAGTCAGGTTCACAAGAAAACCACAGTTGGAAATCAGGTGATTCGCAAGGGGTGGCTCACCATCAGCAACATTGGCATCATGAAAGGCGG
CTCGAAGGGATACTGGTTCGTCCTTACTGCGGAAAGCTTGTCCTGGTATAAAGATGATGAGGAAAAAGAAAAGAAGTACATGCTTCCCTTGGAC
AACCTGAAAGTTCGGGATGTGGAAAAGAGCTTTATGTCTAGCAAGCACATCTTTGCACTCTTTAATACAGAGCAAAGGAATGTATACAAAGACT
ATCGCTTCCTTGAGCTGGCATGTGATTCCCAGGAGGATGTCGACAGCTGGAAGGCATCTCTACTAAGAGCTGGGGTCTATCCTGACAAATCTGT
AGGGAACAACAAAGCTGAAAATGATGAGAATGGACAAGCAGAAAACTTTTCCATGGACCCACAATTGGAGAGGCAAGTGGAGACCATTCGCAAC
CTCGTAGACTCCTACATGTCCATTATCAACAAATGTATCCGAGATCTAATTCCAAAAACAATAATGCACCTTATGATCAATAACGTTAAAGATT
TCATAAATTCCGAGCTCCTAGCACAGTTGTATTCTTCAGAGGACCAAAATACCCTGATGGAGGAATCTGCTGAGCAGGCTCAGCGCCGGGATGA
GATGCTTCGAATGTATCAAGCACTGAAAGAAGCCCTTGGGATAATTGGGGACATCAGCACAGCCACCGTGTCCACTCCGGCACCCCCTCCAGTG
GATGACTCCTGGATACAGCACTCTCGCAGGTCACCTCCTCCAAGCCCCACAACCCAAAGGAGGCCAACACTAAGTGCTCCCCTCGCAAGGCCCA
CATCCGGCCGAGGACCAGCTCCTGCCATTCCCTCTCCTGGCCCCCACTCTGGGGCTCCTCCAGTCCCATTCCGTCCAGGCCCATTACCTCCTTT
CCCCAGCAGCAGTGACTCCTTCGGAGCCCCTCCACAAGTTCCATCTAGGCCTACGAGGGCCCCGCCCAGTGTCCCAAGCCGGAGACCACCCCCA
TCACCAACTCGTCCCACTATAATCCGCCCACTAGAATCCTCCCTGTTAGACTAA

Fig. 9 (Continued)

SEQUENCE LISTING

<160> NUMBER OF SEQ ID NOS: 80

<210> SEQ ID NO 1
<211> LENGTH: 1173
<212> TYPE: DNA
<213> ORGANISM: Homo sapiens

<400> SEQUENCE: 1
atggctgaac cccgccagga gttcgaagtg atggaagatc acgctgggac gtacgggttg 60
ggggacagga aagatcaggg ggctacacc atgcaccaag accaagaggg tgacacggac 120
gctggcctga aagctgaaga agcaggcatt ggagacaccc ccagcctgga agacgaagct 180
gctggtcacg tgacccaagc tcgcatggtc agtaaaagca aagacgggac tggaagcgat 240
gacaaaaaag ccaagggggc tgatggtaaa acgaagatcg ccacaccgcg gggagcagcc 300
cctccaggcc agaagggcca ggccaacgcc accaggattc cagcaaaaac cccgcccgct 360
ccaaagacac cacccagctc tggtgaacct ccaaaatcag gggatcgcag cggctacagc 420
agccccggct ccccaggcac tcccggcagc cgctcccgca ccccggccct tccaacccca 480
cccacccggg agcccaagaa ggtggcagtg gtccgtactc cacccaagtc gccgtcttcc 540
gccaagagcc gcctgcagac agcccccgtg cccatgccag acctgaagaa tgtcaagtcc 600
aagatcggcg ccactgagaa cctgaagcac cagccgggag gcgggaaggt gcagataatt 660
aataagaagc tggatcttag caacgtccag tccaagtgtg gctcaaagga taatatcaaa 720
cacgtcccgg gaggcggcag tgtgcaaata gtctacaaac cagttgacct gagcaaggtg 780
acctccaagt gtggctcatt aggcaacatc catcataaac caggaggtgg ccaggtggaa 840
gtaaaatctg agaagcttga cttcaaggac agagtccagt cgaagattgg gtccctggac 900
aatatcaccc acgtccctgg cggaggaaat aaaaagattg aaacccacaa gctgaccttc 960
cgcgagaacg ccaaagccaa gacagaccac ggggcggaga tcgtgtacaa gtcgccagtg 1020
gtgtctgggg acacgtctcc acggcatctc agcaatgtct cctccaccgg cagcatcgac 1080
atggtagact cgccccagct cgccacgcta gctgacgagg tgtctgcctc cctggccaag 1140
cagggtttgc ccaaaaaaaa aaggaaagtg tga 1173

<210> SEQ ID NO 2
<211> LENGTH: 747
<212> TYPE: DNA
<213> ORGANISM: Homo sapiens

<400> SEQUENCE: 2
atggcccagg tgcagctggt ggagagcggt ggaggtgttg tgcaacctgg ccggtccctg 60
cgcctgtcct gctcctcgtc tggcttcatt ttcagtgaca attacatgta ttgggtgaga 120

-continued

```
caggcacctg gaaaaggtct tgagtgggtt gcaaccatta gtgatggtgg tagttacacc    180

tactatccag acagtgtgaa gggaagattt acaatatcga gagacaacag caagaacaca    240

ttgttcctgc aaatggacag cctgagaccc gaagacaccg ggtctatttt ttgtgcaaga    300

ggctactata ggtacgaggg ggctatggac tactggggcc aagggacccc ggtcaccgtg    360

agctcaggag gtggcggctc cggaggtgga ggcagcggag ggggcggatc cgacatccag    420

ctgacccaga gcccaagcag cctgagcgcc agcgtgggtg acagagtgac catcacctgt    480

aagtccagtc aaagtgtttt atacagttca aatcagaaga actacttggc ctggtaccag    540

cagaagccag gtaaggctcc aaagctgctg atctactggg catccactag ggaatctggt    600

gtgccaagca gattcagcgg tagcggtagc ggtaccgact tcaccttcac catcagcagc    660

ctccagccag aggacatcgc cacctactac tgccatcaat acctctcctc gtggacgttc    720

ggccaaggga ccaagctgga gatcaaa                                        747
```

```
<210> SEQ ID NO 3
<211> LENGTH: 1929
<212> TYPE: DNA
<213> ORGANISM: Homo sapiens

<400> SEQUENCE: 3
```

```
atggcccagg tgcagctggt ggagagcggt ggaggtgttg tgcaacctgg ccggtccctg     60

cgcctgtcct gctcctcgtc tggcttcatt ttcagtgaca attacatgta ttgggtgaga    120

caggcacctg gaaaaggtct tgagtgggtt gcaaccatta gtgatggtgg tagttacacc    180

tactatccag acagtgtgaa gggaagattt acaatatcga gagacaacag caagaacaca    240

ttgttcctgc aaatggacag cctgagaccc gaagacaccg ggtctatttt ttgtgcaaga    300

ggctactata ggtacgaggg ggctatggac tactggggcc aagggacccc ggtcaccgtg    360

agctcaggag gtggcggctc cggaggtgga ggcagcggag ggggcggatc cgacatccag    420

ctgacccaga gcccaagcag cctgagcgcc agcgtgggtg acagagtgac catcacctgt    480

aagtccagtc aaagtgtttt atacagttca aatcagaaga actacttggc ctggtaccag    540

cagaagccag gtaaggctcc aaagctgctg atctactggg catccactag ggaatctggt    600

gtgccaagca gattcagcgg tagcggtagc ggtaccgact tcaccttcac catcagcagc    660

ctccagccag aggacatcgc cacctactac tgccatcaat acctctcctc gtggacgttc    720

ggccaaggga ccaagctgga gatcaaagcg gccgcaatgg ctgaaccccg ccaggagttc    780

gaagtgatgg aagatcacgc tgggacgtac gggttggggg acaggaaaga tcaggggggc    840

tacaccatgc accaagacca agagggtgac acggacgctg gcctgaaagc tgaagaagca    900

ggcattggag acacccccag cctggaagac gaagctgctg gtcacgtgac ccaagctcgc    960

atggtcagta aaagcaaaga cgggactgga agcgatgaca aaaaagccaa gggggctgat   1020

ggtaaaacga agatcgccac accgcgggga gcagcccctc caggccagaa gggccaggcc   1080

aacgccacca ggattccagc aaaaaccccg cccgctccaa agacaccacc cagctctggt   1140

gaacctccaa aatcagggga tcgcagcggc tacagcagcc ccggctcccc aggcactccc   1200

ggcagccgct cccgcacccc ggcccttcca accccaccca cccgggagcc caagaaggtg   1260

gcagtggtcc gtactccacc caagtcgccg tcttccgcca agagccgcct gcagacagcc   1320

cccgtgccca tgccagacct gaagaatgtc aagtccaaga tcggcgccac tgagaacctg   1380

aagcaccagc cgggaggcgg gaaggtgcag ataattaata agaagctgga tcttagcaac   1440

gtccagtcca agtgtggctc aaaggataat atcaaacacg tcccgggagg cggcagtgtg   1500
```

caaatagtct acaaaccagt tgacctgagc aaggtgacct ccaagtgtgg ctcattaggc 1560
aacatccatc ataaaccagg aggtggccag gtggaagtaa aatctgagaa gcttgacttc 1620
aaggacagag tccagtcgaa gattgggtcc ctggacaata tcacccacgt ccctggcgga 1680
ggaaataaaa agattgaaac ccacaagctg accttccgcg agaacgccaa agccaagaca 1740
gaccacgggg cggagatcgt gtacaagtcg ccagtggtgt ctggggacac gtctccacgg 1800
catctcagca atgtctcctc caccggcagc atcgacatgg tagactcgcc ccagctcgcc 1860
acgctagctg acgaggtgtc tgcctccctg gccaagcagg gtttgcccaa aaaaaaaagg 1920
aaagtgtga 1929

<210> SEQ ID NO 4
<211> LENGTH: 732
<212> TYPE: DNA
<213> ORGANISM: Mus sp.

<400> SEQUENCE: 4
atggccgagg tgcaactgca gcagtctggg gctgaactgg tgaagcctgg ggcttcagtg 60
aagttgtcct gcaaggcttc cggctacacc ttcaccagcc actggatgca ctgggtgaag 120
cagagggctg gacaaggcct tgagtggatc ggagagttta atcccagcaa cggccgtact 180
aactacaatg agaaattcaa gagcaaggcc acactgactg tagacaaatc ctccagcaca 240
gcctacatgc aactcagcag cctgacatct gaggactctg cggtctatta ctgtgccagt 300
cgggactatg attacgacgg acggtacttt gactactggg gccaagggac cacggtcacc 360
gtctcctcag gtggcggtgg ctcgggcggt ggtgggtcgg gtggtggcgg atctgacatc 420
gagctcaccc agtctccagc aatcatgtct gcatctccag gggagaaggt cactatgacc 480
tgcagtgcca gctcaagtgt aacttacatg tattggtacc agcagaagcc aggatcctcc 540
cccagactcc tgatttatga cacatccaac ctggcttctg gagtccctgt tcgtttcagt 600
ggcagtgggt ctgggacctc ttactctctc acaatcagcc gaatggaggc tgaagatgct 660
gccacttatt actgccagca gtggagtagt cacatattca cgttcggctc ggggacagaa 720
ctcgagatca aa 732

<210> SEQ ID NO 5
<211> LENGTH: 1914
<212> TYPE: DNA
<213> ORGANISM: artificial sequence
<220> FEATURE:
<223> OTHER INFORMATION: Mus sp. and Homo sapiens

<400> SEQUENCE: 5
atggccgagg tgcaactgca gcagtctggg gctgaactgg tgaagcctgg ggcttcagtg 60
aagttgtcct gcaaggcttc cggctacacc ttcaccagcc actggatgca ctgggtgaag 120
cagagggctg gacaaggcct tgagtggatc ggagagttta atcccagcaa cggccgtact 180
aactacaatg agaaattcaa gagcaaggcc acactgactg tagacaaatc ctccagcaca 240
gcctacatgc aactcagcag cctgacatct gaggactctg cggtctatta ctgtgccagt 300
cgggactatg attacgacgg acggtacttt gactactggg gccaagggac cacggtcacc 360
gtctcctcag gtggcggtgg ctcgggcggt ggtgggtcgg gtggtggcgg atctgacatc 420
gagctcaccc agtctccagc aatcatgtct gcatctccag gggagaaggt cactatgacc 480
tgcagtgcca gctcaagtgt aacttacatg tattggtacc agcagaagcc aggatcctcc 540

-continued

```
cccagactcc tgatttatga cacatccaac ctggcttctg gagtccctgt tcgtttcagt    600

ggcagtgggt ctgggacctc ttactctctc acaatcagcc gaatggaggc tgaagatgct    660

gccacttatt actgccagca gtggagtagt cacatattca cgttcggctc ggggacagaa    720

ctcgagatca aagcggccgc aatggctgaa ccccgccagg agttcgaagt gatggaagat    780

cacgctggga cgtacgggtt gggggacagg aaagatcagg ggggctacac catgcaccaa    840

gaccaagagg gtgacacgga cgctggcctg aaagctgaag aagcaggcat tggagacacc    900

cccagcctgg aagacgaagc tgctggtcac gtgacccaag ctcgcatggt cagtaaaagc    960

aaagacggga ctggaagcga tgacaaaaaa gccaaggggg ctgatggtaa aacgaagatc   1020

gccacaccgc ggggagcagc ccctccaggc cagaagggcc aggccaacgc caccaggatt   1080

ccagcaaaaa ccccgcccgc tccaaagaca ccacccagct ctggtgaacc tccaaaatca   1140

ggggatcgca gcggctacag cagccccggc tccccaggca ctcccggcag ccgctcccgc   1200

accccggccc ttccaacccc acccacccgg gagcccaaga aggtggcagt ggtccgtact   1260

ccacccaagt cgccgtcttc cgccaagagc cgcctgcaga cagcccccgt gcccatgcca   1320

gacctgaaga atgtcaagtc caagatcggc gccactgaga acctgaagca ccagccggga   1380

ggcgggaagg tgcagataat taataagaag ctggatctta gcaacgtcca gtccaagtgt   1440

ggctcaaagg ataatatcaa acacgtcccg ggaggcggca gtgtgcaaat agtctacaaa   1500

ccagttgacc tgagcaaggt gacctccaag tgtggctcat taggcaacat ccatcataaa   1560

ccaggaggtg gccaggtgga agtaaaatct gagaagcttg acttcaagga cagagtccag   1620

tcgaagattg ggtccctgga caatatcacc cacgtccctg gcggaggaaa taaaaagatt   1680

gaaacccaca agctgacctt ccgcgagaac gccaaagcca agacagacca cggggcggag   1740

atcgtgtaca agtcgccagt ggtgtctggg gacacgtctc cacggcatct cagcaatgtc   1800

tcctccaccg gcagcatcga catggtagac tcgccccagc tcgccacgct agctgacgag   1860

gtgtctgcct ccctggccaa gcagggtttg cccaaaaaaa aaaggaaagt gtga         1914


<210> SEQ ID NO 6
<211> LENGTH: 735
<212> TYPE: DNA
<213> ORGANISM: Mus sp.

<400> SEQUENCE: 6

atggcccagg tcaagctgca ggagtcaggg actgaactgg caaagcctgg ggccgcagtg     60

aagatgtcct gcaaggcttc tggctacacc tttactgact actggatgca ctgggttaaa    120

cagaggcctg gacagggtct ggaatggatt ggatacatta atcctaacac tgcttatact    180

gactacaatc agaaattcaa ggacaaggcc acattgactg cagacaaatc ctccagcaca    240

gcctacatgc aactgcgcag cctgacctct gaggattctg cagtctatta ctgtgcaaaa    300

aagacaactc agactacgtg gggtttcct ttttggggcc aagggaccac ggtcaccgtc    360

tcctcaggtg gaggcggttc aggcggaggt ggctctggcg gtggcggatc ggacattgtg    420

ctgacccagt ctccaaaatc catggccatg tcagtcggag agagggtcac cttgagctgc    480

aaggccagtg agaatgtgga ttcttttgtt tcctggtatc aacagaaacc aggccagtct    540

cctaaactgc tgatatacgg ggcctccaac cggtacactg ggtccccga tcgcttcgca    600

ggcagtggat ctggaagaga tttcactctg accatcagca gtgtgcaggc tgaagacctt    660

gcagattatc actgtggaca gaattacagg tatccgctca cgttcggtgc tggcaccaag    720

ctggaaatca aacgg                                                     735
```

<210> SEQ ID NO 7
<211> LENGTH: 735
<212> TYPE: DNA
<213> ORGANISM: Artificial Sequence
<220> FEATURE:
<223> OTHER INFORMATION: Mus sp. and Homo sapiens

<400> SEQUENCE: 7
atggcccagg tcaagctgca ggagtcaggg actgaactgg caaagcctgg ggccgcagtg 60
aagatgtcct gcaaggcttc tggctacacc tttactgact actggatgca ctgggttaaa 120
cagaggcctg gacagggtct ggaatggatt ggatacatta atcctaacac tgcttatact 180
gactacaatc agaaattcaa ggacaaggcc acattgactg cagacaaatc ctccagcaca 240
gcctacatgc aactgcgcag cctgacctct gaggattctg cagtctatta ctgtgcaaaa 300
aagacaactc agactacgtg gggtttcct ttttggggcc aagggaccac ggtcaccgtc 360
tcctcaggtg gaggcggttc aggcggaggt ggctctggcg gtggcggatc ggacattgtg 420
ctgacccagt ctccaaaatc catggccatg tcagtcggag agagggtcac cttgagctgc 480
aaggccagtg agaatgtgga ttcttttgtt tcctggtatc aacagaaacc aggccagtct 540
cctaaactgc tgatatacgg ggcctccaac cggtacactg ggtccccga tcgcttcgca 600 ggcagtggat ctggaagaga tttcactctg accatcagca gtgtgcaggc tgaagacctt 660
gcagattatc actgtggaca gaattacagg tatccgctca cgttcggtgc tggcaccaag 720
ctggaaatca aacgg 735

<210> SEQ ID NO 8
<211> LENGTH: 741
<212> TYPE: DNA
<213> ORGANISM: Homo sapiens

<400> SEQUENCE: 8
atgacccagt ctccatcctc cctgtctgca tctgtaggag acagagtcac catcgcttgc 60
cgggcaagtc agaccattag caactattta aattggtatc agcagaaacc agggaaagcc 120
cctaagctcc tgatctatgg tgcatccagt ttgcaaagtg gggtcccatc aaggttcagt 180
ggcagtggat ctgggacaga tttcactctc accatcagca gtctgcaacc tgaagatttt 240
gcaacttact actgtcaaca gagttacagt accctccga cgtacacttt tggccagggg 300
accaagctgg agatcaaagg tggcggtggc tcgggcggtg gtgggtcggg tggcagcgga 360
tcatcggggg gcgacttggt ccagccgggg gggtccctga gagtctcctg tgtagcctct 420
ggatttacat ttaggaccta tgtgatgaac tgggtccgcc aggctccagg aaaggggctg 480
gagtgggtgg cccacataag tccagaggga actgaagaat actatgcgga ccctgtgaag 540
ggccgattta ccgtctccag agacaacgcg aagaattcag tatttctgca aatgaatagt 600
ctgagaggcg aggacacggc tgtgtattat tgcgcgagag tccgacgcta tggtccctct 660
acgctcagtc cgttcacctg gaaggacaat cactacgcca tggacgtctg gggccaaggg 720
acaacggtca ccgtctctcc a 741

<210> SEQ ID NO 9
<211> LENGTH: 1923
<212> TYPE: DNA
<213> ORGANISM: Homo sapiens

<400> SEQUENCE: 9

-continued

```
atgacccagt ctccatcctc cctgtctgca tctgtaggag acagagtcac catcgcttgc     60

cgggcaagtc agaccattag caactattta aattggtatc agcagaaacc agggaaagcc    120

cctaagctcc tgatctatgg tgcatccagt ttgcaaagtg gggtcccatc aaggttcagt    180

ggcagtggat ctgggacaga tttcactctc accatcagca gtctgcaacc tgaagatttt    240

gcaacttact actgtcaaca gagttacagt acccctccga cgtacacttt tggccagggg    300

accaagctgg agatcaaagg tggcggtggc tcgggcggtg gtgggtcggg tggcagcgga    360

tcatcggggg gcgacttggt ccagccgggg gggtccctga gagtctcctg tgtagcctct    420

ggatttacat ttaggaccta tgtgatgaac tgggtccgcc aggctccagg aaaggggctg    480

gagtgggtgg cccacataag tccagaggga actgaagaat actatgcgga ccctgtgaag    540

ggccgattta ccgtctccag agacaacgcg aagaattcag tatttctgca aatgaatagt    600

ctgagaggcg aggacacggc tgtgtattat tgcgcgagag tccgacgcta tggtccctct    660

acgctcagtc cgttcacctg gaaggacaat cactacgcca tggacgtctg gggccaaggg    720

acaacggtca ccgtctctcc agcggccgca atggctgaac ccgccagga gttcgaagtg    780

atggaagatc acgctgggac gtacgggttg ggggacagga aagatcaggg gggctacacc    840

atgcaccaag accaagaggg tgacacggac gctggcctga aagctgaaga agcaggcatt    900

ggagacaccc ccagcctgga agacgaagct gctggtcacg tgacccaagc tcgcatggtc    960

agtaaaagca aagacgggac tggaagcgat gacaaaaaag ccaagggggc tgatggtaaa   1020

acgaagatcg ccacaccgcg gggagcagcc cctccaggcc agaagggcca ggccaacgcc   1080

accaggattc cagcaaaaac cccgcccgct ccaaagacac cacccagctc tggtgaacct   1140

ccaaaatcag gggatcgcag cggctacagc agccccggct ccccaggcac tcccggcagc   1200

cgctcccgca ccccggccct tccaacccca cccacccggg agcccaagaa ggtggcagtg   1260

gtccgtactc cacccaagtc gccgtcttcc gccaagagcc gcctgcagac agcccccgtg   1320

cccatgccag acctgaagaa tgtcaagtcc aagatcggcg ccactgagaa cctgaagcac   1380

cagccgggag gcgggaaggt gcagataatt aataagaagc tggatcttag caacgtccag   1440

tccaagtgtg gctcaaagga taatatcaaa cacgtcccgg gaggcggcag tgtgcaaata   1500

gtctacaaac cagttgacct gagcaaggtg acctccaagt gtggctcatt aggcaacatc   1560

catcataaac caggaggtgg ccaggtggaa gtaaaatctg agaagcttga cttcaaggac   1620

agagtccagt cgaagattgg gtccctggac aatatcaccc acgtccctgg cggaggaaat   1680

aaaaagattg aaacccacaa gctgaccttc cgcgagaacg ccaaagccaa gacagaccac   1740

ggggcggaga tcgtgtacaa gtcgccagtg gtgtctgggg acacgtctcc acggcatctc   1800

agcaatgtct cctccaccgg cagcatcgac atggtagact cgccccagct cgccacgcta   1860

gctgacgagg tgtctgcctc cctggccaag cagggtttgc ccaaaaaaaa aaggaaagtg   1920

tga                                                                 1923
```

<210> SEQ ID NO 10
<211> LENGTH: 732
<212> TYPE: DNA
<213> ORGANISM: Homo sapiens

<400> SEQUENCE: 10

```
atggcccagg tgcagctggt gcagtctggg gctgaggtga agaagcctgg gtcctcggtg     60

agggtctcct gcaaggcttc tggaggcacc ttcagcagct atgctatcag ctgggtgcga    120

caggcccctg gacaagggct tgagtggatg ggagggatca tccctatctt tggtacagca    180
```

```
aactacgcac agaagttcca gggcagagtc acgattaccg cggacgaatc cacgagcaca    240

gcctacatgg agctgagcag cctgagatct gaggacacgg ctgtgtatta ctgtgcaaga    300

gacccgtttc ttcactattg gggccaaggt accctggtca ccgtctcgag tggtggaggc    360

ggttcaggcg gaggtggctc tggcggtggc ggatcggaaa ttgagctcac tcagtctcca    420

ctctccctgc ccgtcacccc tggagagccg gcctccatct cctgcaggtc tagtcagagc    480

ctcctgcata gtaatggata caactatttg gattggtacc tgcagaagcc agggcagtct    540

ccacagctcc tgatctattt gggttctaat cgggcctccg ggtccctga caggttcagt    600

ggcagtggat caggcacaga ttttacactg aaaatcagca gagtggaggc tgaggatgtt    660

ggggtttatt actgcatgca agctctacaa actttcactt tcggccctgg gaccaaggtg    720

gagatcaaac gt                                                        732
```

<210> SEQ ID NO 11
<211> LENGTH: 1914
<212> TYPE: DNA
<213> ORGANISM: Homo sapiens

<400> SEQUENCE: 11

```
atggcccagg tgcagctggt gcagtctggg gctgaggtga agaagcctgg gtcctcggtg     60

agggtctcct gcaaggcttc tggaggcacc ttcagcagct atgctatcag ctgggtgcga    120

caggcccctg gacaagggct tgagtggatg ggagggatca tccctatctt tggtacagca    180

aactacgcac agaagttcca gggcagagtc acgattaccg cggacgaatc cacgagcaca    240

gcctacatgg agctgagcag cctgagatct gaggacacgg ctgtgtatta ctgtgcaaga    300

gacccgtttc ttcactattg gggccaaggt accctggtca ccgtctcgag tggtggaggc    360

ggttcaggcg gaggtggctc tggcggtggc ggatcggaaa ttgagctcac tcagtctcca    420

ctctccctgc ccgtcacccc tggagagccg gcctccatct cctgcaggtc tagtcagagc    480

ctcctgcata gtaatggata caactatttg gattggtacc tgcagaagcc agggcagtct    540

ccacagctcc tgatctattt gggttctaat cgggcctccg ggtccctga caggttcagt    600

ggcagtggat caggcacaga ttttacactg aaaatcagca gagtggaggc tgaggatgtt    660

ggggtttatt actgcatgca agctctacaa actttcactt tcggccctgg gaccaaggtg    720

gagatcaaac gtgcggccgc aatggctgaa ccccgccagg agttcgaagt gatggaagat    780

cacgctggga cgtacgggtt gggggacagg aaagatcagg ggggctacac catgcaccaa    840

gaccaagagg gtgacacgga cgctggcctg aaagctgaag aagcaggcat tggagacacc    900

cccagcctgg aagacgaagc tgctggtcac gtgacccaag ctcgcatggt cagtaaaagc    960

aaagacggga ctggaagcga tgacaaaaaa gccaaggggg ctgatggtaa aacgaagatc   1020

gccacaccgc ggggagcagc ccctccaggc cagaagggcc aggccaacgc caccaggatt   1080

ccagcaaaaa ccccgcccgc tccaaagaca ccacccagct ctggtgaacc tccaaaatca   1140

ggggatcgca gcggctacag cagccccggc tccccaggca ctcccggcag ccgctcccgc   1200

accccggccc ttccaacccc acccacccgg gagcccaaga aggtggcagt ggtccgtact   1260

ccacccaagt cgccgtcttc cgccaagagc cgcctgcaga cagcccccgt gcccatgcca   1320

gacctgaaga atgtcaagtc caagatcggc gccactgaga acctgaagca ccagccggga   1380

ggcgggaagg tgcagataat taataagaag ctggatctta gcaacgtcca gtccaagtgt   1440

ggctcaaagg ataatatcaa acacgtcccg ggaggcggca gtgtgcaaat agtctacaaa   1500
```

```
ccagttgacc tgagcaaggt gacctccaag tgtggctcat taggcaacat ccatcataaa   1560

ccaggaggtg gccaggtgga agtaaaatct gagaagcttg acttcaagga cagagtccag   1620

tcgaagattg ggtccctgga caatatcacc cacgtccctg gcggaggaaa taaaaagatt   1680

gaaacccaca agctgacctt ccgcgagaac gccaaagcca agacagacca cggggcggag   1740

atcgtgtaca agtcgccagt ggtgtctggg gacacgtctc cacggcatct cagcaatgtc   1800

tcctccaccg gcagcatcga catggtagac tcgccccagc tcgccacgct agctgacgag   1860

gtgtctgcct ccctggccaa gcagggtttg cccaaaaaaa aaaggaaagt gtga         1914
```

```
<210> SEQ ID NO 12
<211> LENGTH: 174
<212> TYPE: DNA
<213> ORGANISM: Homo sapiens

<400> SEQUENCE: 12

atggcccagc cggccaatag tgactctgaa tgtcccctgt cccacgatgg gtactgcctc     60

catgatggtg tgtgcatgta tattgaagca ttggacaagt atgcatgcaa ctgtgttgtt    120

ggctacatcg gggagcgatg tcagtaccga gacctgaagt ggtgggaact gcgc          174
```

```
<210> SEQ ID NO 13
<211> LENGTH: 1356
<212> TYPE: DNA
<213> ORGANISM: Homo sapiens

<400> SEQUENCE: 13

atggcccagc cggccaatag tgactctgaa tgtcccctgt cccacgatgg gtactgcctc     60

catgatggtg tgtgcatgta tattgaagca ttggacaagt atgcatgcaa ctgtgttgtt    120

ggctacatcg gggagcgatg tcagtaccga gacctgaagt ggtgggaact gcgcgcggcc    180

gcaatggctg aaccccgcca ggagttcgaa gtgatggaag atcacgctgg gacgtacggg    240

ttgggggaca ggaaagatca gggggggctac accatgcacc aagaccaaga gggtgacacg   300

gacgctggcc tgaaagctga agaagcaggc attggagaca cccccagcct ggaagacgaa    360

gctgctggtc acgtgaccca agctcgcatg gtcagtaaaa gcaaagacgg gactggaagc    420

gatgacaaaa aagccaaggg ggctgatggt aaaacgaaga tcgccacacc gcggggagca    480

gcccctccag gccagaaggg ccaggccaac gccaccagga ttccagcaaa aaccccgccc    540

gctccaaaga caccacccag ctctggtgaa cctccaaaat caggggatcg cagcggctac    600

agcagccccg gctccccagg cactcccggc agccgctccc gcaccccggc ccttccaacc    660

ccacccaccc gggagcccaa gaaggtggca gtggtccgta ctccacccaa gtcgccgtct    720

tccgccaaga gccgcctgca gacagccccc gtgcccatgc cagacctgaa gaatgtcaag    780

tccaagatcg gcgccactga gaacctgaag caccagccgg gaggcgggaa ggtgcagata    840

attaataaga agctggatct tagcaacgtc cagtccaagt gtggctcaaa ggataatatc    900

aaacacgtcc cgggaggcgg cagtgtgcaa atagtctaca aaccagttga cctgagcaag    960

gtgacctcca agtgtggctc attaggcaac atccatcata aaccaggagg tggccaggtg   1020

gaagtaaaat ctgagaagct tgacttcaag gacagagtcc agtcgaagat tgggtccctg   1080

gacaatatca cccacgtccc tggcggagga aataaaaaga ttgaaaccca caagctgacc   1140

ttccgcgaga acgccaaagc caagacagac cacggggcgg agatcgtgta caagtcgcca   1200

gtggtgtctg gggacacgtc tccacggcat ctcagcaatg tctcctccac cggcagcatc   1260

gacatggtag actcgcccca gctcgccacg ctagctgacg aggtgtctgc ctccctggcc   1320
```

aagcagggtt tgcccaaaaa aaaaaggaaa gtgtga 1356

<210> SEQ ID NO 14
<211> LENGTH: 1866
<212> TYPE: DNA
<213> ORGANISM: Homo sapiens

<400> SEQUENCE: 14
atggcgaacg ttccgtgggc agaggtctgc gagaaattcc aggcggcgct cgctctgtcg 60
cgggtggaac tgcataaaaa tccggagaag gaaccataca agtccaaata cagcgcccgg 120
gcgctactgg aagaggtcaa ggcgctgctc ggccctgcgc ctgaggacga ggatgagcgg 180
cctgaggccg aggacggccc gggtgccggt gaccacgccc tggggctgcc ggctgaggtg 240
gtggagcccg aggggcccgt cgcccagcga gcggtgaggc tggcagtcat cgagttccac 300
ctcggggtga accacatcga cacggaggag ctgtcggcgg gggaggagca cctggtgaaa 360
tgcctgcggc tgctgcgcag gtaccggctc tcgcacgact gcatctctct ctgcatccag 420
gcgcagaata acctgggtat cttgtggtct gaaagagaag aaattgaaac tgcacaggct 480
tacctagagt catcagaagc actatataat cagtatatga aagaggttgg gagtcctcct 540
cttgatccta ctgagcgttt tcttcctgaa gaagagaaac ttactgaaca agagagatca 600
aaaagatttg aaaaggttta tactcataac ctatattacc tagctcaagt ctaccagcat 660
ctggaaatgt ttgagaaggc tgctcactat tgccatagta cactaaaacg ccagcttgag 720
cacaatgcct accatcctat agagtgggct atcaatgctg ctaccttgtc acagttttac 780
atcaataagc tatgctttat ggaggccagg cactgtttat cagctgctaa tgtcattttt 840
ggtcaaactg gaaagatctc agccacagaa gacactcctg aagctgaagg agaagtgcca 900
gagctttatc atcaaagaaa gggggaaata gcaaggtgct ggatcaaata ctgtttgact 960
ctcatgcaga atgcccaact ctccatgcag gacaacatag gagagcttga tcttgataaa 1020
cagtctgaac ttagagcttt aaggaaaaaa gaactagatg aggaggaaag cattcggaaa 1080
aaagctgtgc agtttggaac cggtgaactg tgtgatgcca tctctgcagt agaagagaaa 1140
gtgagctact tgagaccttt agattttgaa gaagccagag aacttttctt attgggtcag 1200
cactatgtct ttgaggcaaa agagttcttt cagattgatg gttatgtcac tgaccatatt 1260
gaagttgtcc aagaccacag tgctctgttt aaggtgcttg cattctttga aactgacatg 1320
gagagacggt gcaagatgca taaacgcaga atagccatgc tagagcccct aactgtagac 1380
ctgaatccac agtattatct gttggtcaac agacagatcc agtttgaaat tgcacatgct 1440
tactatgata tgatggattt gaaggttgcc attgctgaca ggctaaggga tcctgattca 1500
cacattgtaa aaaaaataaa taatcttaat aagtcagcac tgaagtacta ccagctcttc 1560
ttagactccc tgagagaccc aaataaagta ttccctgagc atatagggga agatgttctt 1620
cgccctgcca tgttagctaa gtttcgagtt gcccgtctct atggcaaaat cattactgca 1680
gatcccaaga aagagctgga aaatttggca acatcattgg aacattacaa atttattgtt 1740
gattactgtg aaaagcatcc tgaggccgcc caggaaatag aagttgagct agaacttagt 1800
aaagagatgg ttagtcttct cccaacaaaa atggagagat tcagaaccaa gatggccctg 1860
acttaa 1866

<210> SEQ ID NO 15
<211> LENGTH: 2235
<212> TYPE: DNA

<213> ORGANISM: Homo sapiens

<400> SEQUENCE: 15

```
atggcaacgg ccaacttcgg caagatccag atcgggattt acgtggagat caagcgcagc     60
gatggccgaa tacatcaagc aatggtaaca tctttaaatg aagataatga aagtgtaact    120
gttgaatgga tagaaaatgg agatacaaaa ggcaaagaga ttgacctgga gagcatcttt    180
tcacttaacc ctgaccttgt tcctgatgaa gaaattgaac ccagtccaga aacacctcca    240
cctccagcat cctcagccaa agtaaacaaa attgtaaaga atcgacggac tgtagcttct    300
attaagaatg accctccttc aagagataat agagtggttg gttcagcacg tgcacggccc    360
agtcaatttc ctgaacagtc ttcctctgca caacagaatg gtagtgtttc agatatatct    420
ccagttcaag ctgcaaaaaa ggaatttgga ccccccttcac gtagaaaatc taattgtgtg    480
aaagaagtag aaaaactgca agaaaaacga gagaaaagga gattgcaaca gcaagaactt    540
agagaaaaaa gagcccagga cgttgatgct acaaacccaa attatgaaat tatgtgtatg    600
atcagagact ttagaggaag tttggattat agaccattaa caacagcaga tcctattgat    660
gaacatagga tatgtgtgtg tgtaagaaaa cgaccactca ataaaaaaga aactcaaatg    720
aaagatcttg atgtaatcac aattcctagt aaagatgttg tgatggtaca tgaaccaaaa    780
caaaaagtag atttaacaag gtacctagaa aaccaaacat ttcgttttga ttatgccttt    840
gatgactcag ctcctaatga aatggtttac aggtttactg ctagaccact agtggaaact    900
atatttgaaa ggggaatggc tacatgcttt gcttatgggc agactggaag tggaaaaact    960
catactatgg gtggtgactt ttcaggaaag aaccaagatt gttctaaagg aatttatgca   1020
ttagcagctc gagatgtctt tttaatgcta aagaagccaa actataagaa gctagaactt   1080
caagtatatg caaccttctt tgaaatttat agtggaaagg tgtttgactt gctaaacagg   1140
aaaacaaaat taagagttct agaagatgga aaacagcagg ttcaagtggt gggattacag   1200
gaacgggagg tcaaatgtgt tgaagatgta ctgaaactca ttgacatagg caacagttgc   1260
agaacatccg gtcaaacatc tgcaaatgca cattcatctc ggagccatgc agtgtttcag   1320
attattctta gaaggaaagg aaaactacat ggcaaatttt ctctcattga tttggctgga   1380
aatgaaagag gagctgatac ttccagtgcg gacaggcaaa ctaggcttga aggtgctgaa   1440
attaataaaa gccttttagc actcaaggag tgcatcagag ccttaggtag aaataaacct   1500
catactcctt tccgtgcaag taaactcact caggtgttaa gagattcttt cataggtgaa   1560
aactctcgta cctgcatgat tgccacaatc tctccaggaa tggcatcctg tgaaaatact   1620
cttaatacat taagatatgc aaatagagta aaggagtttg gaattagtcc atcagacatt   1680
cccttctcac agggtagtgg cagtcgccct gatctctctc cttcttatga atatgacgac   1740
ttttctcctt cagttaccag ggtcaaagaa ttgactgtag atccaactgc tgctggtgat   1800
gttcgtccaa taatgcacca tccaccaaac cagattgatg acttagagac acagtggggt   1860
gtggggagtt cccctcagag agatgatcta aaacttcttt gtgaacaaaa tgaagaagaa   1920
gtctctccac agttgtttac tttccacgaa gctgtttcac aaatggtaga aatggaagaa   1980
caagttgtag aagatcacag ggcagtgttc caggaatcta ttcggtggtt agaagatgaa   2040
aaggccctct tagagatgac tgaagaagta gattatgatg tcgattcata tgctacacaa   2100
cttgaagcta ttcttgagca aaaaatagac attttaactg aactgcggga taaagtgaaa   2160
tctttccgtg cagctctaca agaggaggaa caagccagca agcaaatcaa cccgaagaga   2220
ccccgtgccc tttaa                                                    2235
```

<210> SEQ ID NO 16
<211> LENGTH: 3699
<212> TYPE: DNA
<213> ORGANISM: Homo sapiens

<400> SEQUENCE: 16
atgaaggaag aggtgaaggg aattcccgta agagtggcgc tgcgttgtcg ccctctggtc 60
cccaaagaga ttagcgaggg ctgccagatg tgcctttcct tcgtgcccgg agagcctcag 120
gtggtggttg gtacagataa atccttcacc tacgattttg tatttgatcc ctctactgaa 180
caggaagaag tcttcaatac agcagtagcg ccactcataa aaggtgtatt taaaggatat 240
aatgcaacgg tcctggccta tgggcagact ggctctggaa aaacctattc aatgggaggt 300
gcatatactg cagagcaaga gaatgaacca acagttgggg ttattcctag ggtaatacaa 360
ctgctcttca aagaaattga taaaaagagt gactttgaat ttactctgaa agtgtcttac 420
ttagagattt acaatgaaga aattttggat cttctatgcc catctcgtga gaaagctcaa 480
ataaatatac gagaggatcc taaggaaggc ataaagattg tgggactcac tgagaagact 540
gttttggttg ccttggatac tgtttcctgt ttggaacagg gcaacaactc taggactgtg 600
gcctccacgg ctatgaactc ccagtcgtcc cgatctcatg ccatctttac aatctcctta 660
gagcaaagaa agaaaagtga caagaatagc agctttcgct ccaagctgca tcttgtagac 720
ctcgctggat cagaaagaca gaagaaaacc aaggctgaag gggatcgtct aaaagagggt 780
attaatatta accgaggcct cctatgcttg ggaaatgtaa tcagtgctct tggagatgac 840
aaaaagggtg gctttgtgcc ctacagagat tccaagttga ctcgactgct tcaagattct 900
ctaggaggta atagccatac tcttatgata gcctgtgtga gtcctgctga ctccaatcta 960
gaggaaacat taaataccct tcgctatgct gacagagcaa gaaaaatcaa gaacaaacct 1020
attgttaata ttgatcccca gacagctgaa cttaatcatc taaagcaaca ggtacaacag 1080
ctacaagtct tgttgctaca ggcccatgga ggtaccctgc ctggatctat aactgtggaa 1140
ccatcagaga atctacaatc cctgatggag aagaatcagt ccctggtaga ggagaatgaa 1200
aaattaagtc gtggtctgag cgaggcagct ggtcagacag cccagatgtt ggagaggatc 1260
attttgacag agcaagcgaa tgaaaaaatg aacgccaagc tagaagagct caggcagcat 1320
gcggcctgca aactggatct tcaaaagcta gtggagactt tggaagacca ggaattgaaa 1380
gaaaatgtag agataatttg taacctgcag caattgatta cccagttatc ggatgaaact 1440
gttgcttgca tggctgcagc cattgatact gcggtggagc aagaagccca agtagaaacc 1500
agtccagaga cgagcaggtc ttctgacgct tttaccactc agcatgctct ccgtcaagcg 1560
cagatgtcta aggagctggt tgagttgaat aaagcgcttg cactgaaaga ggccctggct 1620
aggaagatga ctcagaatga cagccaactg cagcccattc agtaccaata ccaggataac 1680
ataaaagagc tagaattaga agtcatcaat ctgcaaaagg aaaaggaaga attggttctt 1740
gaacttcaga cagcaaagaa ggatgccaac caagccaagt tgagtgagcg ccgccgcaaa 1800
cgtctccagg agctggaggg tcaaattgct gatctgaaga agaaactgaa tgagcagtcc 1860
aaacttctga aactaaagga atccacagag cgtactgtct ccaaactgaa ccaggagata 1920
cggatgatga aaaaccagcg ggtacagtta atgcgtcaaa tgaaagaaga tgctgagaag 1980
tttagacagt ggaagcagaa aaaagacaaa gaagtaatac agttaaaaga acgagaccgt 2040
aagaggcaat atgagctgct gaaacttgaa agaaacttcc agaaacaatc caatgtgctc 2100

```
agacgtaaaa cggaggaggc agcagctgcc aacaagcgtc tcaaggatgc tctccagaaa   2160

caacgggagg ttgcagataa gcggaaagag actcagagcc gtggaatgga aggcactgca   2220

gctcgagtga agaattggct tggaaacgaa attgaggtta tggtcagtac tgaggaagcc   2280

aaacgccatc tgaatgacct ccttgaagat agaaagatcc tggctcaaga tgtggctcaa   2340

ctcaaagaaa aaaaggaatc tggggagaat ccacctccta aactccggag gcgtacattc   2400

tcccttactg aagtgcgtgg tcaagtttcg gagtcagaag attctattac aaagcagatt   2460

gaaagcctag agactgaaat ggaattcagg agtgctcaga ttgctgacct acagcagaag   2520

ctgctggatg cagaaagtga agacagacca aaacaacgct gggagaatat tgccaccatt   2580

ctggaagcca agtgtgccct gaaatatttg attggagagc tggtctcctc caaaatacag   2640

gtcagcaaac ttgaaagcag cctgaaacag agcaagacca gctgtgctga catgcagaag   2700

atgctgtttg aggaacgaaa tcattttgcc gagatagaga cagagttaca agctgagctg   2760

gtcagaatgg agcaacagca ccaagagaag gtgctgtacc ttctcagcca gctgcagcaa   2820

agccaaatgg cagagaagca gttagaggaa tcagtcagtg aaaaggaaca gcagctgctg   2880

agcacactga agtgtcagga tgaagaactt gagaaaatgc gagaagtgtg tgagcaaaat   2940

cagcagcttc tccgagagaa tgaaatcatc aagcagaaac tgaccctcct ccaggtagcc   3000

agcagacaga aacatcttcc taaggatacc cttctatctc cagactcttc ttttgaatat   3060

gtcccaccta agccaaaacc ttctcgtgtt aaagaaaagt tcctggagca aagcatggac   3120

atcgaggatc taaaatattg ttcagagcat tctgtgaatg agcatgagga tggtgatggt   3180

gatgatgatg agggggatga cgaggaatgg aagccaacaa aattagttaa ggtgtccagg   3240

aagaacatcc aagggtgttc ctgcaagggc tggtgtggaa acaagcagtg tgggtgcagg   3300

aagcaaaagt cagactgtgg tgtggactgt tgctgtgacc ccacaaagtg tcggaaccgc   3360

cagcaaggca aggatagctt gggcactgtt gaacggaccc aggattccga aggctccttc   3420

aaactggagg atcctaccga ggtgacccca ggattgagct tctttaatcc cgtctgtgcc   3480

acccccaata gcaagatcct gaaagagatg tgcgatgtgg agcaggtgct gtcaaagaag   3540

actcccccag ctccctcccc ttttgacctc ccagagttga aacatgtagc aacagaatac   3600

caagaaaaca aggctccagg gaagaaaaag aaacgggctc tggccagcaa caccagcttc   3660

ttctctggct gctcccctat cgaagaagag gcccactga                          3699


<210> SEQ ID NO 17
<211> LENGTH: 3099
<212> TYPE: DNA
<213> ORGANISM: Homo sapiens

<400> SEQUENCE: 17

atggcggaga ccaacaacga atgtagcatc aaggtgctct gccgattccg gcccctgaac     60

caggctgaga ttctgcgggg agacaagttc atccccattt tccaagggga cgacagcgtc    120

gttattgggg ggaagccata tgtttttgac cgtgtattcc ccccaaacac gactcaagag    180

caagtttatc atgcatgtgc catgcagatt gtcaaagatg tccttgctgg ctacaatggc    240

accattttg cttatggaca gacatcctca gggaaaacac ataccatgga gggaaagctg     300

cacgaccctc agctgatggg aatcattcct cgaattgccc gagacatctt caaccacatc    360

tactccatgg atgagaacct tgagttccac atcaaggttt cttactttga aatttacctg    420

gacaaaattc gtgaccttct ggatgtgacc aagacaaatc tgtccgtgca cgaggacaag    480

aaccgggtgc catttgtcaa gggttgtact gaacgctttg tgtccagccc ggaggagatt    540
```

-continued

```
ctggatgtga ttgatgaagg gaaatcaaat cgtcatgtgg ctgtcaccaa catgaatgaa    600
cacagctctc ggagccacag catcttcctc atcaacatca agcaggagaa catggaaacg    660
gagcagaagc tcagtgggaa gctgtatctg gtggacctgg cagggagtga gaaggtcagc    720
aagactggag cagagggagc cgtgctggac gaggcaaaga atatcaacaa gtcactgtca    780
gctctgggca atgtgatctc cgcactggct gagggcacta aaagctatgt tccatatcgt    840
gacagcaaaa tgacaaggat tctccaggac tctctcgggg gaaactgccg gacgactatg    900
ttcatctgtt gctcaccatc cagttataat gatgcagaga ccaagtccac cctgatgttt    960
gggcagcggg caaagaccat taagaacact gcctcagtaa atttggagtt gactgctgag   1020
cagtggaaga agaaatatga gaaggagaag gagaagacaa aggcccagaa ggagacgatt   1080
gcgaagctgg aggctgagct gagccggtgg cgcaatggag agaatgtgcc tgagacagag   1140
cgcctggctg gggaggaggc agccctggga gccgagctct gtgaggagac ccctgtgaat   1200
gacaactcat ccatcgtggt gcgcatcgcg cccgaggagc ggcagaaata cgaggaggag   1260
atccgccgtc tctataagca gcttgacgac aaggatgatg aaatcaacca acaaagccaa   1320
ctcatagaga agctcaagca gcaaatgctg gaccaggaag agctgctggt gtccacccga   1380
ggagacaacg agaaggtcca gcgggagctg agccacctgc aatcagagaa cgatgccgct   1440
aaggatgagg tgaaggaagt gctgcaggcc ctggaggagc tggctgtgaa ctatgaccag   1500
aagtcccagg aggtggagga gaagagccag cagaaccagc ttctggtgga tgagctgtct   1560
cagaaggtgg ccaccatgct gtccctggag tctgagttgc agcggctaca ggaggtcagt   1620
ggacaccagc gaaaacgaat tgctgaggtg ctgaacgggc tgatgaagga tctgagcgag   1680
ttcagtgtca ttgtgggcaa cggggagatt aagctgccag tggagatcag tggggccatc   1740
gaggaggagt tcactgtggc ccgactctac atcagcaaaa tcaaatcaga agtcaagtct   1800
gtggtcaagc ggtgccggca gctggagaac ctccaggtgg agtgtcaccg caagatggaa   1860
gtgaccgggc gggagctctc atcctgccag ctcctcatct ctcagcatga ggccaagatc   1920
cgctcgctta cggaatacat gcagagcgtg gagctaaaga agcggcacct ggaagagtcc   1980
tatgactcct tgagcgatga gctggccaag ctccaggccc aggaaactgt gcatgaagtg   2040
gccctgaagg acaaggagcc tgacactcag gatgcagatg aagtgaagaa ggctctggag   2100
ctgcagatgg agagtcaccg ggaggcccat caccggcagc tggcccggct ccgggacgag   2160
atcaacgaga agcagaagac cattgatgag ctcaaagacc taaatcagaa gctccagtta   2220
gagctagaga agcttcaggc tgactacgag aagctgaaga gcgaagaaca cgagaagagc   2280
accaagctgc aggagctgac atttctgtac gagcgacatg agcagtccaa gcaggacctc   2340
aagggtctgg aggagacagt tgcccgggaa ctccagaccc tccacaacct tcgcaagctg   2400
ttcgttcaag acgtcacgac tcgagtcaag aaaagtgcag aaatggagcc cgaagacagt   2460
ggggggattc actcccaaaa gcagaagatt tcctttcttg agaacaacct ggaacagctt   2520
acaaaggttc acaaacagct ggtacgtgac aatgcagatc tgcgttgtga gcttcctaaa   2580
ttggaaaaac gacttagggc tacggctgag agagttaagg ccctggaggg tgcactgaag   2640
gaggccaagg agggcgccat gaaggacaag cgccggtacc agcaggaggt ggaccgcatc   2700
aaggaggccg ttcgctacaa gagctcgggc aaacggggcc attctgccca gattgccaaa   2760
cccgtccggc ctggccacta cccagcatcc tcacccacca accccctatgg cacccggagc   2820
cctgagtgca tcagttacac caacagcctc ttccagaact accagaatct ctacctgcag   2880
```

-continued

```
gccacaccca gctccacctc agatatgtac tttgcaaact cctgtaccag cagtggagcc   2940

acatcttctg gcggcccctt ggcttcctac cagaaggcca acatggacaa tggaaatgcc   3000

acagatatca atgacaatag gagtgacctg ccgtgtggct atgaggctga ggaccaggcc   3060

aagcttttcc ctctccacca agagacagca gccagctaa                          3099
```

<210> SEQ ID NO 18
<211> LENGTH: 2892
<212> TYPE: DNA
<213> ORGANISM: Homo sapiens

<400> SEQUENCE: 18

```
atggcggacc tggccgagtg caacatcaaa gtgatgtgtc gcttcagacc tctcaacgag     60

tctgaagtga accgcggcga caagtacatc gccaagtttc agggagaaga cacggtcgtg    120

atcgcgtcca agccttatgc atttgatcgg gtgttccagt caagcacatc tcaagagcaa    180

gtgtataatg actgtgcaaa gaagattgtt aaagatgtac ttgaaggata taatggaaca    240

atatttgcat atggacaaac atcctctggg aagacacaca caatggaggg taaacttcat    300

gatccagaag gcatgggaat tattccaaga atagtgcaag atatttttaa ttatatttac    360

tccatggatg aaaatttgga atttcatatt aaggtttcat attttgaaat atatttggat    420

aagataaggg acctgttaga tgtttcaaag accaaccttt cagttcatga agacaaaaac    480

cgagttccct atgtaaaggg gtgcacagag cgttttgtat gtagtccaga tgaagttatg    540

gataccatag atgaaggaaa atccaacaga catgtagcag ttacaaatat gaatgaacat    600

agctctagga gtcacagtat atttcttatt aatgtcaaac aagagaacac acaaacggaa    660

caaaagctga gtggaaaact ttatctggtt gatttagctg gtagtgaaaa ggttagtaaa    720

actggagctg aaggtgctgt gctggatgaa gctaaaaaca tcaacaagtc actttctgct    780

cttggaaatg ttatttctgc tttggctgag ggtagtacat atgttccata tcgagatagt    840

aaaatgacaa gaatccttca agattcatta ggtggcaact gtagaaccac tattgtaatt    900

tgctgctctc catcatcata caatgagtct gaaacaaaat ctacactctt atttggccaa    960

agggccaaaa caattaagaa cacagtttgt gtcaatgtgg agttaactgc agaacagtgg   1020

aaaaagaagt atgaaaaaga aaaagaaaaa aataagatcc tgcggaacac tattcagtgg   1080

cttgaaaatg agctcaacag atggcgtaat ggggagacgg tgcctattga tgaacagttt   1140

gacaaagaga aagccaactt ggaagctttc acagtggata aagatattac tcttaccaat   1200

gataaaccag caaccgcaat tggagttata ggaaatttta ctgatgctga aagaagaaag   1260

tgtgaagaag aaattgctaa attatacaaa cagcttgatg acaaggatga agaaattaac   1320

cagcaaagtc aactggtaga gaaactgaag acgcaaatgt tggatcagga ggagcttttg   1380

gcatctacca gaagggatca agacaatatg caagctgagc tgaatcgcct tcaagcagaa   1440

aatgatgcct ctaaagaaga agtgaaagaa gttttacagg ccctagaaga acttgctgtc   1500

aattatgatc agaagtctca ggaagttgaa gacaaaacta aggaatatga attgcttagt   1560

gatgaattga atcagaaatc ggcaacttta gcgagtatag atgctgagct tcagaaactt   1620

aaggaaatga ccaaccacca gaaaaaacga gcagctgaga tgatggcatc tttactaaaa   1680

gaccttgcag aaataggaat tgctgtggga aataatgatg taaagcagcc tgagggaact   1740

ggcatgatag atgaagagtt cactgttgca agactctaca ttagcaaaat gaagtcagaa   1800

gtaaaaacca tggtgaaacg ttgcaagcag ttagaaagca cacaaactga gagcaacaaa   1860

aaaatggaag aaaatgaaaa ggagttagca gcatgtcagc ttcgtatctc tcaacatgaa   1920
```

gccaaaatca agtcattgac tgaatacctt caaaatgtgg aacaaaagaa aagacagttg 1980
gaggaatctg tcgatgccct cagtgaagaa ctagtccagc ttcgagcaca agagaaagtc 2040
catgaaatgg aaaaggagca cttaaataag gttcagactg caaatgaagt taagcaagct 2100
gttgaacagc agatccagag ccatagagaa actcatcaaa aacagatcag tagtttgaga 2160
gatgaagtag aagcaaaagc aaaacttatt actgatcttc aagaccaaaa ccagaaaatg 2220
atgttagagc aggaacgtct aagagtagaa catgagaagt tgaaagccac agatcaggaa 2280
aagagcagaa aactacatga acttacggtt atgcaagata gacgagaaca agcaagacaa 2340
gacttgaagg gtttggaaga gacagtggca aaagaacttc agactttaca caacctgcgc 2400
aaactctttg ttcaggacct ggctacaaga gttaaaaaga gtgctgagat tgattctgat 2460
gacaccggag gcagcgctgc tcagaagcaa aaaatctcct ttcttgaaaa taatcttgaa 2520
cagctcacta aagtgcacaa acagttggta cgtgataatg cagatctccg ctgtgaactt 2580
cctaagttgg aaaagcgact tcgagctaca gctgagagag tgaaagcttt ggaatcagca 2640
ctgaaagaag ctaaagaaaa tgcatctcgt gatcgcaaac gctatcagca agaagtagat 2700
cgcataaagg aagcagtcag gtcaaagaat atggccagaa gagggcattc tgcacagatt 2760
gctaaaccta ttcgtcccgg gcaacatcca gcagcttctc caactcaccc aagtgcaatt 2820
cgtggaggag gtgcatttgt tcagaacagc cagccagtgg cagtgcgagg tggaggaggc 2880
aaacaagtgt aa 2892

<210> SEQ ID NO 19
<211> LENGTH: 2445
<212> TYPE: DNA
<213> ORGANISM: Homo sapiens

<400> SEQUENCE: 19
atggtgaagc agactatcca gatattcgcg agggtgaagc cccctgtccg gaagcaccaa 60
caagggattt attccataga tgaagatgaa aaattaatac ctagcttgga aatcatctta 120
ccacgtgatt tggcagatgg gtttgtgaat aataagcgag aaagctacaa atttaaattt 180
caaagaattt ttgatcagga tgcaaaccaa gagaccgttt ttgaaaacat tgccaaacca 240
gttgctggga gtgtcctggc aggttacaat ggtaccatct ttgcatatgg gcaaacaggc 300
agcgggaaga cattcactat cacagggggt gcagagcgtt acagtgacag aggcattatc 360
ccaaggacac tgtcatacat ttttgaacag ttacaaaagg acagcagcaa aatatataca 420
acacacattt cctatttgga aatctacaat gaatgtggtt atgatctttt ggatccaaga 480
catgaagcct ccagtttgga agatttgccg aaagtgacaa tactggagga tcctgatcag 540
aacattcacc tgaaaaactt gactctccat caggcaacca cagaggaaga agctctgaat 600
ttgctttttt taggagacac caaccgaatg attgcagaga ctcctatgaa ccaagcttca 660
acccgttccc actgcatttt caccattcat ttgtcaagca aggaaccagg atctgcaact 720
gtacgacatg ccaaactcca tctggttgac ctggctggtt cagagcgagt tgcaaagact 780
ggagtagggg gccatcttct aacagaggcc aagtatatca acttgtcact acattactta 840
gaacaggtta tcattgccct ttcagaaaag caccgttcgc acattcctta tagaaactcc 900
atgatgacca gtgtcctaag agacagtttg ggagggaact gcatgacaac tatgattgca 960
acactctcct tggagaaaag gaatcttgat gagtctatat caacctgcag atttgcacag 1020
cgagtggcac tcataaagaa tgaagctgtt cttaatgaag aaattaaccc cagattagtg 1080
attaaacgcc tacaaaagga aatccaggaa ctgaaggatg aactggccat ggtcactggg 1140
gagcagagga cagaggcact cacagaagca gagctccttc agctggaaaa actaataaca 1200
tcctttttgg aagaccagga ttcagacagt agattagagg ttggcgcgga tatgcgtaaa 1260
gttcatcact gttttcatca tttaaagaaa ctattgaatg acaagaagat ccttgaaaac 1320
aatacagtct cctctgaaag caaagaccaa gattgtcaag aaccattaaa agaagaagaa 1380
tatagaaagc tacgagatat tctgaaacag agagataacg aaatcaatat cctggtcaac 1440
atgttaaaaa aagaaaagaa gaaagctcag gaggctctcc acttggctgg catggataga 1500
cgtgaattca gacagtccca gagcccaccc ttccgcctag gaaacccaga agaaggtcaa 1560
agaatgcgac tatcctcagc tccctcacag gcccaggact tcagcatttt ggggaaaaga 1620
tccagtttgc tccacaagaa aataggaatg agagaggaaa tgtcattagg atgccaggag 1680
gcttttgaaa tcttcaagag ggaccacgct gacagcgtta ccatcgatga caacaaacag 1740
attctgaaac agagattttc tgaagccaag gccctgggag aaagtataaa tgaagcaaga 1800
agtaaaattg gtcacctgaa ggaagaaatc acccagcggc atatacagca agtagcccta 1860
ggaatctcgg aaaacatggc cgtgcctctg atgccagacc agcaggagga gaagctgcga 1920
tcacaactgg aggaagaaaa gagaaggtat aaaacaatgt tcactcgcct gaaagccctg 1980
aaggtggaga tcgagcactt gcagctgctc atggacaaag ccaaggtgaa gctacagaaa 2040
gagtttgaag tctggtgggc agaggaggcc accaacctgc aggtaaattc tccagcagtg 2100
aattcactcg atcacacgaa gccatttctc cagacatctg actcccagca tgaatggtcc 2160
caactcctct ctaacaaaag ttctggaggc tgggaagtcc aagatcaagg cactggcaga 2220
ttcgatgtct gtgatgtgaa tgccaggaaa atcctgccct cgccttgccc cagtccacac 2280
agccagaaac agagcagcac cagcacccca ctggaagaca gcatccccaa gaggccagtg 2340
tcgtccatcc ctctcaccgg agacagccag acggactcgg acatcatcgc cttcatcaag 2400
gccagacaga gcattctgca gaagcaatgt ttgggaagca attga 2445

<210> SEQ ID NO 20
<211> LENGTH: 4032
<212> TYPE: DNA
<213> ORGANISM: Homo sapiens

<400> SEQUENCE: 20
atggggctgg aggctcagag gctgccaggg gctgaggagg ccccagtgcg ggttgccctg 60
cgagttcgac cactgctgcc caaggagctg ctgcacgggc atcagagctg cctgcaggtg 120
gagccagggc ttggccgcgt cactctgggc cgtgaccgac actttggctt ccacgtggtg 180
ctggccgagg atgcggggca ggaggccgtg taccaggcct gcgttcagcc cctccttgag 240
gccttcttcg agggcttcaa tgccactgtc tttgcctatg gtcagacggg ctcagggaag 300
acatacacca tgggggaggc cagtgtggcc tccctccttg aggatgagca gggcattgtc 360
ccgagggcca tggccgaggc cttcaagctc atcgatgaga acgacctgct tgactgtctg 420
gtacatgtgt cctacctgga agtgtacaag gaggagttcc gagacctgct cgaggtgggc 480
actgccagcc gtgacatcca gctccgggaa gatgagcgcg ggaatgttgt gctgtgcggg 540
gtgaaggagg tcgacgtgga gggcctggat gaggtgctga gcctcctgga gatgggcaac 600
gcggcgcggc acacgggagc cacgcacctc aaccacctgt ctagccgctc acacacggtc 660
ttcaccgtga ccctggagca gcgggggcgc gcccccagcc gcctaccccg ccccgccccg 720
ggccagctgc tcgtctccaa gttccacttc gtggacctgg cgggctcaga gagggtgctc 780

-continued

```
aagacgggca gcaccggcga gcggctcaag gagagcatcc agatcaacag cagcctcctg    840
gcgctgggca acgtcatcag cgccctgggg gaccctcagc gccggggcag ccacataccc    900
taccgcgact ccaagatcac ccggatcctc aaagactcgc tgggcgggaa cgccaagacg    960
gtgatgatcg cctgcgtcag cccttcctcc tccgacttcg acgagaccct caacaccctc   1020
aactacgcca gccgcgccca gaacatccgc aaccgcgcca cggtcaactg gcggcccgag   1080
gccgagcggc cacccgaaga gacggcgagc ggcgcgcggg gtccgccacg gcaccgctcc   1140
gagacccgca tcatccaccg cggccggcgc gccccaggcc cagccaccgc ctccgcggcg   1200
gccgccatgc gcctgggcgc cgagtgcgcg cgctaccggg cctgcaccga cgccgcctac   1260
agcctcttgc gcgagctgca ggccgagccc gggctgcccg gcgccgccgc ccgcaaggtg   1320
cgcgactggc tgtgcgccgt cgagggcgag cgcagcgccc tgagctccgc ctccgggccc   1380
gatagcggca tcgagagcgc ctccgtcgag gaccaggcgg cgcagggggc cggcgggcga   1440
aaggaggatg agggggcgca gcagctgctg accctgcaga accaggtggc gcggctggag   1500
gaggagaacc gagactttct ggctgcgctg gaggacgcca tggagcagta caaactgcag   1560
agcgaccggc tgcgtgagca gcaggaggag atggtggaac tgcggctgcg gttagagctg   1620
gtgcggccag gctggggggg cccgcggctc ctgaatggcc tgcctcccgg gtcctttgtg   1680
cctcgacctc atacagcccc cctggggggt gcccacgccc atgtgctggg catggtgccg   1740
cctgcctgcc tccctggaga tgaagttggc tctgagcaga ggggagagca ggtgacaaat   1800
ggcagggagg ctggagctga gttgctgact gaggtgaaca ggctgggaag tggctcttca   1860
gctgcttcag aggaggaaga ggaggaggag gagccgccca ggcggacctt acacctgcgc   1920
agaaatagga tcagcaactg cagtcagagg gcgggggcac gcccagggag tctgccagag   1980
aggaagggcc cagagctttg ccttgaggag ttggatgcag ccattccagg gtccagagca   2040
gttggtggga gcaaggcccg agttcaggcc cgccaggtcc cccctgccac agcctcagag   2100
tggcggctgg cccaggccca gcagaagatc cgggagctgg ctatcaacat ccgcatgaag   2160
gaggagctta ttggcgagct ggtccgcaca ggaaaggcag ctcaggccct gaaccgccag   2220
cacagccagc gtatccggga gctggagcag gaggcagagc aggtgcgggc cgagctgagt   2280
gaaggccaga ggcagctgcg ggagctcgag ggcaaggagc tccaggatgc tggcgagcgg   2340
tctcggctcc aggagttccg caggagggtc gctgcggccc agagccaggt gcaggtgctg   2400
aaggagaaga agcaggctac ggagcggctg gtgtcactgt cggcccagag tgagaagcga   2460
ctgcaggagc tcgagcggaa cgtgcagctc atgcggcagc agcagggaca gctgcagagg   2520
cggcttcgcg aggagacgga gcagaagcgg cgcctggagg cagaaatgag caagcggcag   2580
caccgcgtca aggagctgga gctgaagcat gagcaacagc agaagatcct gaagattaag   2640
acggaagaga tcgcggcatt ccagaggaag aggcgcagtg gcagcaacgg ctctgtggtc   2700
agcctggaac agcagcagaa gattgaggag cagaagaagt ggctggacca ggagatggag   2760
aaggtgctac agcagcggcg ggcgctggag gagctggggg aggagctcca caagcgggag   2820
gccatcctgg ccaagaagga ggccctgatg caggagaaga cggggctgga gagcaagcgc   2880
ctgagatcca gccaggccct caacgaggac atcgtgcgag tgtccagccg gctggagcac   2940
ctggagaagg agctgtccga gaagagcggg cagctgcggc agggcagcgc ccagagccag   3000
cagcagatcc gcggggagat cgacagcctg cgccaggaga aggactcgct gctcaagcag   3060
cgcctggaga tcgacggcaa gctgaggcag gggagtctgc tgtcccccga ggaggagcgg   3120
```

-continued

```
acgctgttcc agttggatga ggccatcgag gccctggatg ctgccattga gtataagaat   3180
gaggccatca catgccgcca gcgggtgctt cgggcctcag cctcgttgct gtcccagtgc   3240
gagatgaacc tcatggccaa gctcagctac ctctcatcct cagagaccag agccctcctc   3300
tgcaagtatt ttgacaaggt ggtgacgctc cgagaggagc agcaccagca gcagattgcc   3360
ttctcggaac tggagatgca gctggaggag cagcagaggc tggtgtactg gctggaggtg   3420
gccctggagc ggcagcgcct ggagatggac cgccagctga ccctgcagca gaaggagcac   3480
gagcagaaca tgcagctgct cctgcagcag agtcgagacc acctcggtga agggttagca   3540
gacagcagga ggcagtatga ggcccggatt caagctctgg agaaggaact gggccgttac   3600
atgtggataa accaggaact gaaacagaag ctcggcggtg tgaacgctgt aggccacagc   3660
aggggtgggg agaagaggag cctgtgctcg gagggcagac aggctcctgg aaatgaagat   3720
gagctccacc tggcacccga gcttctctgg ctgtccccc tcactgaggg ggccccccgc    3780
acccgggagg agacgcggga cttggtccac gctccgttac ccttgacctg gaaacgctcg   3840
agcctgtgtg gtgaggagca ggggtccccc gaggaactga ggcagcggga ggcggctgag   3900
cccctggtgg ggcgggtgct tcctgtgggt gaggcaggcc tgccctggaa ctttgggcct   3960
ttgtccaagc cccggcggga actgcgacga gccagcccgg ggatgattga tgtccggaaa   4020
aaccccctgt aa                                                       4032
```

<210> SEQ ID NO 21
<211> LENGTH: 2373
<212> TYPE: DNA
<213> ORGANISM: Homo sapiens

<400> SEQUENCE: 21

```
atgggtacta ggaaaaaagt tcatgcattt gtccgtgtca aacccaccga tgactttgct     60
catgaaatga tcagatacgg agatgacaaa agaagcattg atattcactt aaaaaaagac    120
attcggagag gagttgtcaa taaccaacag acagactggt cgtttaagtt ggatggagtt    180
cttcacgatg cctcccagga cttggtttat gagacagttg caaaggatgt ggtttctcag    240
gccctcgatg gctataatgg caccatcatg tgttatgggc agacgggagc tggcaagaca    300
tacaccatga tgggggcaac tgagaattac aagcaccggg ggatcctccc tcgtgccctg    360
cagcaggttt ttaggatgat cgaagaacgc cccacacatg ccatcactgt gcgtgtttcc    420
tacttggaaa tctataatga gagcctgttt gatctcctgt ccactctgcc ctatgttgga    480
ccctcagtca caccaatgac catcgtggaa aaccctcaag gagtcttcat taagggcttg    540
tcagttcacc tcacaagtca ggaggaggat gcattcagcc tcctttttga gggtgagacc    600
aacaggatta tagcctccca cactatgaac aaaaactctt ccagatcaca ctgcattttc    660
accatctact tagaggccca ttcccggacc ttatcagagg aaaagtacat cacttccaaa    720
attaacttgg tggatctggc aggctcagag aggctgggga agtctgggtc tgagggccaa    780
gtcctgaagg aagccaccta catcaacaaa tcgctctcat tcctggagca ggccatcatt    840
gcccttgggg accagaagcg ggaccacatc ccctttcggc agtgcaagct cacccacgct    900
ctgaaggact cgttaggggg aaactgcaat atggtcctcg tgacaaacat ctatggagaa    960
gctgcccagt tagaagaaac gctatcttca ctgagatttg ccagcaggat gaagctagtc   1020
accactgagc ctgccatcaa tgaaaagtat gatgctgaga gaatggtcaa gaacctggag   1080
aaggaactag cactactcaa gcaggagctg gctatccatg acagcctgac caaccgcacc   1140
tttgtgacct atgaccccat ggatgaaatc cagattgctg agatcaactc ccaggtgcgg   1200
```

aggtacctgg aggggacact ggacgagatc gacataatca gccttagaca gatcaaggag 1260
gtgttcaacc agttccgggt ggttctgagc caacaggaac aggaagtgga gtccactttg 1320
cgcaggaagt acaccctcat tgacaggaat gactttgcag ccatttctgc tatccagaag 1380
gcggggcttg tggatgttga tggccaccta gtgggtgagc ctgaaggaca aaactttgga 1440
ctcggagtcg cccctttctc taccaaacct gggaagaaag ccaagtccaa gaagacattc 1500
aaagagccac tcagctcctt ggcaagaaag gaaggtgcca gcagccctgt gaatgggaag 1560
gacttggatt acgtttccac ctccaagacc cagctggtcc catcctccaa agatggggat 1620
gtcaaagaca tgctttcgcg ggaccgggaa acttccagca ttgagcccct tccctcagac 1680
tccccgaagg aggaattacg cccaattagg cccgacaccc caccctccaa accagtggcc 1740
tttgaggagt ttaagaatga gcaaggtagt gagatcaacc gaattttcaa agaaaacaaa 1800
tccatcttga atgaacggag gaaaagggcc agcgagacca cacagcacat caatgccatc 1860
aagcgggaga ttgatgtgac caaggaggcc ctgaatttcc agaagtcact acgggagaag 1920
caaggcaagt acgaaaacaa ggggctgatg atcatcgatg aggaagaatt cctgctgatc 1980
ctcaagctca aagacctcaa gaagcagtac cgcagcgagt accaggacct gcgtgacctc 2040
agggctgaga tccagtattg ccagcaccta gtggatcagt gtcgccaccg cctgctcatg 2100
gaatttgaca tctggtacaa tgagtccttt gtcatccctg aggacatgca gatggcactg 2160
aagccaggcg gcagcatccg gccaggcatg gtccctgtga acaggattgt gtctctggga 2220
gaagatgacc aggacaaatt cagccagctg cagcagaggg tgcttcctga gggccctgat 2280
tccatctcct tctacaatgc caaagtcaag atagagcaga agcataatta cttgaaaacc 2340
atgatgggcc tccagcaggc acatagaaaa tag 2373

<210> SEQ ID NO 22
<211> LENGTH: 8106
<212> TYPE: DNA
<213> ORGANISM: Homo sapiens

<400> SEQUENCE: 22
atggcggagg aaggagccgt ggccgtctgc gtgcgagtgc ggccgctgaa cagcagagaa 60
gaatcacttg gagaaactgc ccaagtttac tggaaaactg acaataatgt catttatcaa 120
gttgatggaa gtaaatcctt caattttgat cgtgtctttc atggtaatga aactaccaaa 180
aatgtgtatg aagaaatagc agcaccaatc atcgattctg ccatacaagg ctacaatggt 240
actatatttg cctatggaca gactgcttca ggaaaaacat ataccatgat gggttcagaa 300
gatcatttgg gagttatacc cagggcaatt catgacattt tccaaaaaat taagaagttt 360
cctgataggg aatttctctt acgtgtatct tacatggaaa tatacaatga aaccattaca 420
gatttactct gtggcactca aaaaatgaaa cctttaatta ttcgagaaga tgtcaatagg 480
aatgtgtatg ttgctgatct cacagaagaa gttgtatata catcagaaat ggctttgaaa 540
tggattacaa agggagaaaa gagcaggcat tatggagaaa caaaaatgaa tcaaagaagc 600
agtcgttctc ataccatctt taggatgatt ttggaaagca gagagaaggg tgaaccttct 660
aattgtgaag gatctgttaa ggtatcccat ttgaatttgg ttgatcttgc aggcagtgaa 720
agagctgctc aaacaggcgc tgcaggtgtg cggctcaagg aaggctgtaa tataaatcga 780
agcttattta ttttgggaca agtgatcaag aaacttagtg atggacaagt tggtggtttc 840
ataaattatc gagatagcaa gttaacacga attctccaga attccttggg aggaaatgca 900

-continued

```
aagacacgta ttatctgcac aattactcca gtatcttttg atgaaacact tactgctctc    960
cagtttgcca gtactgctaa atatatgaag aatactcctt atgttaatga ggtatcaact   1020
gatgaagctc tcctgaaaag gtatagaaaa gaaataatgg atcttaaaaa acaattagag   1080
gaggtttctt tagagacgcg ggctcaggca atggaaaaag accaattggc ccaacttttg   1140
gaagaaaaag atttgcttca gaaagtacag aatgagaaaa ttgaaaactt aacacggatg   1200
ctggtgacct cttcttccct cacgttgcaa caggaattaa aggctaaaag aaaacgaaga   1260
gttacttggt gccttggcaa aattaacaaa atgaagaact caaactatgc agatcaattt   1320
aatataccaa caaatataac aacaaaaaca cataagcttt ctataaattt attacgagaa   1380
attgatgaat ctgtctgttc agagtctgat gttttcagta acactcttga tacattaagt   1440
gagatagaat ggaatccagc aacaaagcta ctaaatcagg agaatataga aagtgagttg   1500
aactcacttc gtgctgacta tgataatctg gtattagact atgaacaact acgaacagaa   1560
aaagaagaaa tggaattgaa attaaaagaa aagaatgatt tggatgaatt tgaggctcta   1620
gaaagaaaaa ctaaaaaaga tcaagagatg caactaattc atgaaatttc gaacttaaag   1680
aatttagtta agcatgcaga agtatataat caagatcttg agaatgaact cagttcaaaa   1740
gtagagctgc ttagagaaaa ggaagaccag attaagaagc tacaggaata catagactct   1800
caaaagctag aaaatataaa aatggacttg tcatactcat tggaaagcat tgaagaccca   1860
aaacaaatga agcagactct gtttgatgct gaaactgtag cccttgatgc caagagagaa   1920
tcagcctttc ttagaagtga aaatctggag ctgaaggaga aaatgaaaga acttgcaact   1980
acatacaagc aaatggaaaa tgatattcag ttatatcaaa gccagttgga ggcaaaaaag   2040
aaaatgcaag ttgatctgga gaaagaatta caatctgctt ttaatgagat aacaaaactc   2100
acctccctta tagatggcaa agttccaaaa gatttgctct gtaatttgga attggaagga   2160
aagattactg atcttcagaa agaactaaat aaagaagttg aagaaaatga agctttgcgg   2220
gaagaagtca ttttgctttc agaattgaaa tctttacctt ctgaagtaga aaggctgagg   2280
aaagagatac aagacaaatc tgaagagctc catataataa catcagaaaa agataaattg   2340
ttttctgaag tagttcataa ggagagtaga gttcaaggtt tacttgaaga aattgggaaa   2400
acaaaagatg acctagcaac tacacagtcg aattataaaa gcactgatca agaattccaa   2460
aatttcaaaa cccttcatat ggactttgag caaaagtata agatggtcct tgaggagaat   2520
gagagaatga atcaggaaat agttaatctc tctaaagaag cccaaaaatt tgattcgagt   2580
ttgggtgctt tgaagaccga gctttcttac aagacccaag aacttcagga gaaaacacgt   2640
gaggttcaag aaagactaaa tgagatggaa cagctgaagg aacaattaga aaatagagat   2700
tctacgctgc aaactgtaga aagggagaaa acactgatta ctgagaaact gcagcaaact   2760
ttagaagaag taaaaacttt aactcaagaa aaagatgatc taaaacaact ccaagaaagc   2820
ttgcaaattg agagggacca actcaaaagt gatattcacg atactgttaa catgaatata   2880
gatactcaag aacaattacg aaatgctctt gagtctctga aacaacatca agaaacaatt   2940
aatacactaa aatcgaaaat ttctgaggaa gtttccagga atttgcatat ggaggaaaat   3000
acaggagaaa ctaaagatga atttcagcaa aagatggttg gcatagataa aaaacaggat   3060
ttggaagcta aaaataccca aacactaact gcagatgtta aggataatga gataattgag   3120
caacaaagga agatattttc tttaatacag gagaaaaatg aactccaaca aatgttagag   3180
agtgttatag cagaaaagga acaattgaag actgacctaa aggaaaatat tgaaatgacc   3240
attgaaaacc aggaagaatt aagacttctt ggggatgaac ttaaaaagca acaagagata   3300
```

-continued

```
gttgcacaag aaaagaacca tgccataaag aaagaaggag agctttctag gacctgtgac   3360
agactggcag aagttgaaga aaaactaaag gaaaagagcc agcaactcca agaaaaacag   3420
caacaacttc ttaatgtaca agaagagatg agtgagatgc agaaaaagat taatgaaata   3480
gagaatttaa agaatgaatt aaagaacaaa gaattgacat tggaacatat ggaaacagag   3540
aggcttgagt tggctcagaa acttaatgaa aattatgagg aagtgaaatc tataaccaaa   3600
gaaagaaaag ttctaaagga attacagaag tcatttgaaa cagagagaga ccaccttaga   3660
ggatatataa gagaaattga agctacaggc ctacaaacca aagaagaact aaaaattgct   3720
catattcacc taaaagaaca ccaagaaact attgatgaac taagaagaag cgtatctgag   3780
aagacagctc aaataataaa tactcaggac ttagaaaaat cccataccaa attacaagaa   3840
gagatcccag tgcttcatga ggaacaagag ttactgccta atgtgaaaga agtcagtgag   3900
actcaggaaa caatgaatga actggagtta ttaacagaac agtccacaac caaggactca   3960
acaacactgg caagaataga aatggaaagg ctcaggttga atgaaaaatt tcaagaaagt   4020
caggaagaga taaaatctct aaccaaggaa agagacaacc ttaaaacgat aaaagaagcc   4080
cttgaagtta aacatgacca gctgaaagaa catattagag aaactttggc taaaatccag   4140
gagtctcaaa gcaaacaaga acagtcctta aatatgaaag aaaaagacaa tgaaactacc   4200
aaaatcgtga gtgagatgga gcaattcaaa cccaaagatt cagcactact aaggatagaa   4260
atagaaatgc tcggattgtc caaaagactt caagaaagtc atgatgaaat gaaatctgta   4320
gctaaggaga aagatgacct acagaggctg caagaagttc ttcaatctga aagtgaccag   4380
ctcaaagaaa acataaaaga aattgtagct aaacacctgg aaactgaaga ggaacttaaa   4440
gttgctcatt gttgcctgaa agaacaagag gaaactatta atgagttaag agtgaatctt   4500
tcagagaagg aaactgaaat atcaaccatt caaaagcagt tagaagcaat caatgataaa   4560
ttacagaaca agatccaaga gatttatgag aaagaggaac aatttaatat aaaacaaatt   4620
agtgaggttc aggaaaaagt gaatgaactg aaacaattca aggagcatcg caaagccaag   4680
gattcagcac tacaaagtat agaaagtaag atgctcgagt tgaccaacag acttcaagaa   4740
agtcaagaag aaatacaaat tatgattaag gaaaaagagg aaatgaaaag agtacaggag   4800
gcccttcaga tagagagaga ccaactgaaa gaaaacacta aagaaattgt agctaaaatg   4860
aaagaatctc aagaaaaaga atatcagttt cttaagatga cagctgtcaa tgagactcag   4920
gagaaaatgt gtgaaataga acacttgaag gagcaatttg agacccagaa gttaaacctg   4980
gaaaacatag aaacggagaa tataaggttg actcagatac tacatgaaaa ccttgaagaa   5040
atgagatctg taacaaaaga aagagatgac cttaggagtg tggaggagac tctcaaagta   5100
gagagagacc agctcaagga aaaccttaga gaaactataa ctagagacct agaaaaacaa   5160
gaggagctaa aaattgttca catgcatctg aaggagcacc aagaaactat tgataaacta   5220
agagggattg tttcagagaa aacaaatgaa atatcaaata tgcaaaagga cttagaacac   5280
tcaaatgatg ccttaaaagc acaggatctg aaaatacaag aggaactaag aattgctcac   5340
atgcatctga aagagcagca ggaaactatt gacaaactca gaggaattgt ttctgagaag   5400
acagataaac tatcaaatat gcaaaaagat ttagaaaatt caaatgctaa attacaagaa   5460
aagattcaag aacttaaggc aaatgaacat caacttatta cgttaaaaaa agatgtcaat   5520
gagacacaga aaaaagtgtc tgaaatggag caactaaaga aacaaataaa agaccaaagc   5580
ttaactctga gtaaattaga aatagagaat ttaaatttgg ctcagaaact tcatgaaaac   5640
```

-continued

```
cttgaagaaa tgaaatctgt aatgaaagaa agagataatc taagaagagt agaggagaca   5700
ctcaaactgg agagagacca actcaaggaa agcctgcaag aaaccaaagc tagagatctg   5760
gaaatacaac aggaactaaa aactgctcgt atgctatcaa aagaacacaa agaaactgtt   5820
gataaactta gagaaaaaat ttcagaaaag acaattcaaa tttcagacat tcaaaaggat   5880
ttagataaat caaaagatga attacagaaa aagatccaag aacttcagaa aaaagaactt   5940
caactgctta gagtgaaaga agatgtcaat atgagtcata aaaaaattaa tgaaatggaa   6000
cagttgaaga agcaatttga ggcccaaaac ttatctatgc aaagtgtgag aatggataac   6060
ttccagttga ctaagaaact tcatgaaagc cttgaagaaa taagaattgt agctaaagaa   6120
agagatgagc taaggaggat aaaagaatct ctcaaaatgg aaagggacca attcatagca   6180
accttaaggg aaatgatagc tagagaccga cagaaccacc aagtaaaacc tgaaaaaagg   6240
ttactaagtg atggacaaca gcaccttacg gaaagcctga gagaaaagtg ctctagaata   6300
aaagagcttt tgaagagata ctcagagatg gatgatcatt atgagtgctt gaatagattg   6360
tctcttgact tggagaagga aattgaattc caaaaagagc tttcaatgag agttaaagca   6420
aacctctcac ttccctattt acaaaccaaa cacattgaaa aactttttac tgcaaaccag   6480
agatgctcca tggaattcca cagaatcatg aagaaactga agtatgtgtt aagctatgtt   6540
acaaaaataa aagaagaaca acatgaatcc atcaataaat ttgaaatgga ttttattgat   6600
gaagtggaaa agcaaaagga attgctaatt aaaatacagc accttcaaca agattgtgat   6660
gtaccatcca gagaattaag ggatctcaaa ttgaaccaga atatggatct acatattgag   6720
gaaattctca aagatttctc agaaagtgag ttccctagca taaagactga atttcaacaa   6780
gtactaagta ataggaaaga aatgacacag tttttggaag agtggttaaa tactcgtttt   6840
gatatagaaa agcttaaaaa tggcatccag aaagaaaatg ataggatttg tcaagtgaat   6900
aacttcttta ataacagaat aattgccata atgaatgaat caacagagtt tgaggaaaga   6960
agtgctacca tatccaaaga gtgggaacag gacctgaaat cactgaaaga gaaaaatgaa   7020
aaactattta aaaactacca aacattgaag acttccttgg catctggtgc ccaggttaat   7080
cctaccacac aagacaataa gaatcctcat gttacatcaa gagctacaca gttaaccaca   7140
gagaaaattc gagagctgga aaattcactg catgaagcta aagaaagtgc tatgcataag   7200
gaaagcaaga ttataaagat gcagaaagaa cttgaggtga ctaatgacat aatagcaaaa   7260
cttcaagcca aagttcatga atcaaataaa tgccttgaaa aaacaaaaga gacaattcaa   7320
gtacttcagg acaaagttgc tttaggagct aagccatata aagaagaaat tgaagatctc   7380
aaaatgaagc ttgtgaaaat agacctagag aaaatgaaaa atgccaaaga atttgaaaag   7440
gaaatcagtg ctacaaaagc cactgtagaa tatcaaaagg aagttataag gctattgaga   7500
gaaaatctca gaagaagtca acaggcccaa gatacctcag tgatatcaga acatactgat   7560
cctcagcctt caaataaacc cttaacttgt ggaggtggca gcggcattgt acaaaacaca   7620
aaagctctta ttttgaaaag tgaacatata aggctagaaa aagaaatttc taagttaaag   7680
cagcaaaatg aacagctaat aaaacaaaag aatgaattgt taagcaataa tcagcatctt   7740
tccaatgagg tcaaaacttg gaaggaaaga acccttaaaa gagaggctca caaacaagta   7800
acttgtgaga attctccaaa gtctcctaaa gtgactggaa cagcttctaa aaagaaacaa   7860
attacaccct ctcaatgcaa ggaacggaat ttacaagatc ctgtgccaaa ggaatcacca   7920
aaatcttgtt tttttgatag ccgatcaaag tctttaccat cacctcatcc agttcgctat   7980
tttgataact caagtttagg cctttgtcca gaggtgcaaa atgcaggagc agagagtgtg   8040
```

gattctcagc caggtccttg gcacgcctcc tcaggcaagg atgtgcctga gtgcaaaact 8100
cagtag 8106

<210> SEQ ID NO 23
<211> LENGTH: 3171
<212> TYPE: DNA
<213> ORGANISM: Homo sapiens

<400> SEQUENCE: 23
atggcgtcgc agccaaattc gtctgcgaag aagaaagagg agaaggggaa gaacatccag 60
gtggtggtga gatgcagacc atttaatttg gcagagcgga aagctagcgc ccattcaata 120
gtagaatgtg atcctgtacg aaaagaagtt agtgtacgaa ctggaggatt ggctgacaag 180
agctcaagga aaacatacac ttttgatatg gtgtttggag catctactaa acagattgat 240
gtttaccgaa gtgttgtttg tccaattctg gatgaagtta ttatgggcta taattgcact 300
atctttgcgt atggccaaac tggcactgga aaaactttta caatggaagg tgaaaggtca 360
cctaatgaag agtatacctg ggaagaggat ccccttggctg gtataattcc acgtaccctt 420
catcaaattt ttgagaaact tactgataat ggtactgaat tttcagtcaa agtgtctctg 480
ttggagatct ataatgaaga gctttttgat cttcttaatc catcatctga tgtttctgag 540
agactacaga tgtttgatga tccccgtaac aagagaggag tgataattaa aggtttagaa 600
gaaattacag tacacaacaa ggatgaagtc tatcaaattt tagaaaaggg ggcagcaaaa 660
aggacaactg cagctactct gatgaatgca tactctagtc gttcccactc agttttctct 720
gttacaatac atatgaaaga aactacgatt gatggagaag agcttgttaa aatcggaaag 780
ttgaacttgg ttgatcttgc aggaagtgaa aacattggcc gttctggagc tgttgataag 840
agagctcggg aagctggaaa tataaatcaa tccctgttga ctttgggaag ggtcattact 900
gcccttgtag aaagaacacc tcatgttcct tatcgagaat ctaaactaac tagaatcctc 960
caggattctc ttggagggcg tacaagaaca tctataattg caacaatttc tcctgcatct 1020
ctcaatcttg aggaaactct gagtacattg gaatatgctc atagagcaaa gaacatattg 1080
aataagcctg aagtgaatca gaaactcacc aaaaaagctc ttattaagga gtatacggag 1140
gagatagaac gtttaaaacg agatcttgct gcagcccgtg agaaaaatgg agtgtatatt 1200
tctgaagaaa attttagagt catgagtgga aaattaactg ttcaagaaga gcagattgta 1260
gaattgattg aaaaaattgg tgctgttgag gaggagctga atagggttac agagttgttt 1320
atggataata aaaatgaact tgaccagtgt aaatctgacc tgcaaaataa aacacaagaa 1380
cttgaaacca ctcaaaaaca tttgcaagaa actaaattac aacttgttaa agaagaatat 1440
atcacatcag ctttggaaag tactgaggag aaacttcatg atgctgccag caagctgctt 1500
aacacagttg aagaaactac aaaagatgta tctggtctcc attccaaact ggatcgtaag 1560
aaggcagttg accaacacaa tgcagaagct caggatattt ttggcaaaaa cctgaatagt 1620
ctgtttaata atatggaaga attaattaag gatggcagct caaagcaaaa ggccatgcta 1680
gaagtacata agaccttatt tggtaatctg ctgtcttcca gtgtctctgc attagatacc 1740
attactacag tagcacttgg atctctcaca tctattccag aaaatgtgtc tactcatgtt 1800
tctcagattt ttaatatgat actaaaagaa caatcattag cagcagaaag taaaactgta 1860
ctacaggaat tgattaatgt actcaagact gatcttctaa gttcactgga aatgatttta 1920
tccccaactg tggtgtctat actgaaaatc aatagtcaac taaagcatat tttcaagact 1980

```
tcattgacag tggccgataa gatagaagat caaaaaaagg aactagatgg ctttctcagt   2040

atactgtgta acaatctaca tgaactacaa gaaaatacca tttgttcctt ggttgagtca   2100

caaaagcaat gtggaaacct aactgaagac ctgaagacaa taaagcagac ccattcccag   2160

gaactttgca agttaatgaa tctttggaca gagagattct gtgctttgga ggaaaagtgt   2220

gaaaatatac agaaaccact tagtagtgtc caggaaaata tacagcagaa atctaaggat   2280

atagtcaaca aaatgacttt tcacagtcaa aaattttgtg ctgattctga tggcttctca   2340

caggaactca gaaattttaa ccaagaaggt acaaaattgg ttgaagaatc tgtgaaacac   2400

tctgataaac tcaatggcaa cctggaaaaa atatctcaag agactgaaca gagatgtgaa   2460

tctctgaaca caagaacagt ttatttttct gaacagtggg tatcttcctt aaatgaaagg   2520

gaacaggaac ttcacaactt attggaggtt gtaagccaat gttgtgaggc ttcaagttca   2580

gacatcactg agaaatcaga tggacgtaag gcagctcatg agaaacagca taacattttt   2640

cttgatcaga tgactattga tgaagataaa ttgatagcac aaaatctaga acttaatgaa   2700

accataaaaa ttggtttgac taagcttaat tgctttctgg aacaggatct gaaactggat   2760

atcccaacag gtacgacacc acagaggaaa agttatttat acccatcaac actggtaaga   2820

actgaaccac gtgaacatct ccttgatcag ctgaaaagga aacagcctga gctgttaatg   2880

atgctaaact gttcagaaaa caacaaagaa gagacaattc cggatgtgga tgtagaagag   2940

gcagttctgg ggcagtatac tgaagaacct ctaagtcaag agccatctgt agatgctggt   3000

gtggattgtt catcaattgg cggggttcca tttttccagc ataaaaaatc acatggaaaa   3060

gacaaagaaa acagaggcat taacacactg gagaggtcta aagtggaaga aactacagag   3120

cacttggtta caaagagcag attacctctg cgagcccaga tcaaccttta a            3171
```

<210> SEQ ID NO 24
<211> LENGTH: 1542
<212> TYPE: DNA
<213> ORGANISM: Homo sapiens

<400> SEQUENCE: 24

```
atgcagagga ccttcgcctg gctgttggac cgcgtgcagc acctgggtgc ccctgtcacc     60

cttcgcgcct cttatctgga gatctacaat gagcaggttc gggacttgct gagcctgggg    120

tctccccggc ccctccctgt tcgctggaac aagactcggg gcttctatgt ggagcagctg    180

cgggtggtgg aatttgggag tctggaggcc ctgatggaac ttttgcaaac gggtctcagc    240

cgtcgaagga actcagccca caccctgaac caggcctcca gccgaagcca tgccctgctc    300

accctttaca tcagccgtca aactgcccag cagatgcctt ctgtggaccc tggggagccc    360

cctgttggtg ggaagctgtg ctttgtggac ctggcaggca gtgagaaggt agcagccacg    420

ggatcccgtg gggagctgat gcttgaggct aacagcatca accgaagcct gctggccctg    480

ggtcactgca tctccctgct gctggaccca cagcggaagc agagccacat cccctttccgg    540

gacagcaagc tcaccaagtt gctggcagac tcactgggag ggcgcggggt caccctcatg    600

gtggcctgcg tgtccccctc agcccagtgc cttcctgaga ctctcagcac cctgcgatat    660

gcaagccgag ctcagcgggt caccacccga ccacaggccc ccaagtctcc tgtggcaaag    720

cagccccagc gtttggagac agagatgctg cagctccagg aggagaaccg tcgcctgcag    780

ttccagctgg accaaatgga ctgcaaggcc tcagggctca gtggagcccg ggtggcctgg    840

gcccagcgga acctgtacgg gatgctacag gagttcatgc tagagaatga gaggctcagg    900

aaagaaaaga gccagctgca gaatagccga gacctggccc agaatgagca gcgcatcctg    960
```

gcccagcagg tccatgcact agagaggcgt ctcctctctg cctgctacca tcaccagcag 1020
ggtcctggcc tgaccccacc gtgtccctgc ttgatggccc cagctccccc ttgccatgca 1080
ctgccacccc tctactcctg cccctgctgc cacatctgcc cactgtgtcg agtgcccctg 1140
gcccactggg cctgcctgcc aggggagcac cacctgcccc aggtgttgga ccctgaggcc 1200
tcaggtggca ggcccccatc tgcccggccc ccaccctggg cacccccatg cagccctggc 1260
tctgccaagt gcccaagaga gaggagtcac agtgactgga ctcagacccg agtcctggca 1320
gagatgttga cggaggagga ggtggtacct tctgcacctc ccctgcctgt gaggcccccg 1380
aagacatcac cagggctcag aggtggggcc ggggttccaa acctggccca gagactggag 1440
gccctcagag accagattgg cagctccctg cgacgtggcc gcagccagcc accctgcagt 1500
gagggcgcac ggagcccagg ccaagtcctc cctccccatt ga 1542

<210> SEQ ID NO 25
<211> LENGTH: 5481
<212> TYPE: DNA
<213> ORGANISM: Homo sapiens

<400> SEQUENCE: 25
atgggggact ccaaagtgaa agtggcggtg cggatacgac ccatgaaccg gcgagagact 60
gacttgcata ccaaatgtgt ggtggatgtg gatgcaaaca aggttattct taatcctgta 120
aatacgaatc tttccaaagg agatgcccgg ggccagccga aggtgtttgc ttatgatcat 180
tgtttctggt ctatggatga atctgtcaaa gaaaagtatg caggtcaaga tattgttttc 240
aagtgccttg gagagaatat cctgcagaat gcttttgatg gctacaatgc atgtatcttt 300
gcctatggac agactggctc tggaaaatct tataccatga tgggcacagc tgaccaacct 360
ggattaatcc caagactttg cagtggactc tttgaacgaa ctcagaaaga ggaaaatgaa 420
gaacagagtt ttaaagtaga agtgtcctac atggaaattt ataatgaaaa agttcgagac 480
cttcttgatc ccaaaggaag ccgtcagacg ttgaaagtca gagagcatag tgtgttggga 540
ccttatgtcg acggactttc taaactggct gtcacaagct acaaggatat tgagtcgttg 600
atgtctgagg gtaacaaatc tcgcacagtt gctgcaacca acatgaacga ggagagtagc 660
cgatcccatg cagttttcaa aatcaccctc acacatactc tctacgatgt gaagtctggg 720
acatctggag agaaagtggg caaactcagc ctggtggatt tagctggcag tgaacgagca 780
acgaagacag gcgctgcagg ggacaggctg aaggaaggga gcaacattaa caagtccctc 840
acaaccctcg gtctggttat ctcagctctt gcagatcaga gtgctggcaa aaacaagaat 900
aaatttgttc catatcgtga ctcagttctc acttggctgc tcaaagacag cctcgggggt 960
aacagcaaga ccgccatggt ggctactgtg agtcctgcag ctgataacta tgatgaaacc 1020
ctctcaactc tgcggtatgc agatcgagcc aagcacattg taaaccacgc tgtggtgaat 1080
gaggacccta atgcccgaat tatccgggat ctccgggaag aagttgagaa actccgggag 1140
cagctgacca aagcagaggc aatgaaatct ccagagctaa aggaccggct ggaagaatct 1200
gagaagctaa tccaggaaat gactgtgacc tgggaggaga aattaaggaa aacggaggag 1260
attgcacagg aacgacagaa acagcttgag agtcttggaa tatctcttca gtcttcggga 1320
atcaaagttg gggatgataa atgcttcctt gtgaatctga atgctgaccc agctctgaat 1380
gagcttctgg tgtactattt aaaggaacat acattgatag ggtcagcaaa ttcccaagat 1440
atccaactgt gcggcatggg aattcttcct gaacactgta ttatagacat cacgtcagaa 1500

-continued

```
ggccaggtta tgctgactcc tcagaagaac accagaacat ttgtaaatgg gtcatctgtc   1560
tccagtccaa tacagctaca ccatggggac aggatattat ggggaaacaa tcatttcttc   1620
agactcaatt tgcctaaaaa gaaaaagaaa gcagaacgag aggatgagga ccaggatccc   1680
tccatgaaga acgagaatag ttctgagcag ctggatgtag acggagactc ctccagcgag   1740
gtgtccagtg aagttaactt taattacgaa tacgcacaga tggaggtcac catgaaggcc   1800
ctgggcagca atgatccgat gcagtccata ttaaacagct tagaacaaca gcatgaagaa   1860
gaaaaacgat ctgcactgga gcgccagagg cttatgtatg agcacgaatt ggagcagctc   1920
cggagaaggc tgtctcctga gaagcagaac tgccggagca tggacaggtt ttctttccac   1980
tcgcccagcg ctcagcaacg cttaagacag tgggctgagg agagagaagc aacgttgaat   2040
aacagcctga tgaggctgag ggaacaaatt gttaaggcca atctattggt gagagaagct   2100
aattacattg ctgaggagct ggataaaaga acagaataca aagttaccct acagattcca   2160
gcctccagcc tggatgccaa caggaagcga ggctctcttc ttagtgagcc tgcaatccag   2220
gtgagaagaa aaggaaaagg aaagcagatt tggtctttgg aaaaactgga caacaggctg   2280
ttggatatga gagaccttta tcaggagtgg aaagagtgtg aagaagataa cccagtaata   2340
cgatcatact tcaaacgtgc tgatccattc tatgatgagc aggaaaatca cagtctcatt   2400
ggggtggcca atgtcttcct cgagtcactt ttctatgatg tgaagttaca atacgctgtt   2460
cccatcatca accagaaagg agaggtggca ggtcggctgc acgtggaggt gatgcgactc   2520
agtggtgatg ttggggagag gatcgcagga ggcgatgagg tggcagaggt ctcctttgag   2580
aaggagaccc aggagaacaa actggtgtgc atggttaaaa tcctgcaagc tactgggttg   2640
ccacagcatc tgtcccactt tgtgttctgc aaatacagct tctgggatca acaggagccg   2700
gtgattgtcg ctcctgaagt ggacacctcc tcctcttccg tcagcaagga gccgcactgc   2760
atggttgtct ttgatcattg caatgagttt tctgttaaca tcaccgaaga ctttatcgag   2820
catctttccg aaggagcatt ggcaattgaa gtatatggac ataaaataaa cgatccccgg   2880
aaaaaccccg ccctgtggga tttgggaatc atccaagcaa agacacgtag tcttcgggac   2940
agatggagtg aagtgaccag gaaattggaa ttctgggttc aaatcttgga acagaatgag   3000
aatggtgaat actgccctgt agaagtgatt tctgcaaagg atgtcccaac aggaggaatc   3060
ttccagctcc ggcaggggca gtcccggaga gttcaagtcg aagtgaagtc agtgcaggaa   3120
tctgggactt taccactgat ggaagaatgt atactgtctg ttggcattgg atgtgtcaaa   3180
gttagaccgc tcagagcccc cagaacacat gagaccttcc atgaggaaga ggaagacatg   3240
gacagctacc aggatcgaga tttagagaga cttcgtagaa aatggctaaa tgcattaaca   3300
aaacgtcagg agtacttgga tcaacaattg caaaagcttg tcagtaaacg tgataaaaca   3360
gaggatgatg ctgaccgtga agcgcagctt ctggagatgc ggttgaccct aactgaggag   3420
aggaacgcgg tgatggtccc ctctgctggc agtggtattc caggggcccc agcagaatgg   3480
accccagtac ctgggatgga gacacacatt cctgttatat tcctggactt aaatgctgat   3540
gatttcagct ctcaggataa tcttgatgac ccagaagctg gtggatggga tgcgaccttg   3600
actggggaag aagaagagga gttctttgaa ttgcagattg tgaagcagca tgatggggag   3660
gtgaaagcag aagcctcctg ggactccgcg gtgcatggct gccctcagct cagcaggggc   3720
acgcccgtgg acgagcggtt gttcctgatc gtgcgcgtga cggtccagct cagccaccct   3780
gctgacatgc aactggtgtt acgcaagaga atctgtgtca atgttcacgg ccgccagggt   3840
tttgcacaga gtctcctaaa aaagatgtct catcgaagtt ctattcctgg ctgtggagtg   3900
```

```
acttttgaaa ttgtctccaa tattccagag gatgcccagg gagtggaaga acgggaagca   3960

ttagcaagaa tggcagccaa tgttgaaaac ccagcttctg ctgactcgga ggcttatatt   4020

gaaaagtacc tcaggagcgt gctggctgta gaaaacctcc tgactttaga tcgtctgcgc   4080

caggaagttg cagtgaagga acagttaaca ggaaaaggaa agttgagcag gaggagtatc   4140

agttctccaa atgtgaacag attgtctgga agccgacaag atctcattcc atcatacagt   4200

ctaggcagca acaagggccg gtgggaaagt cagcaggatg tatcccaaac cacagtttcc   4260

agaggaatag ctcctgcccc cgccctctct gtttctcccc aaaataacca ttctccagat   4320

ccaggactca gtaaccttgc agcatcctac ttgaatcctg tcaaatcctt cgtgccgcaa   4380

atgccaaagc tcctcaagtc tctctttccc gtccgcgatg agaagagggg caagcggccg   4440

tctcccctcg cacaccagcc cgtgccccgc atcatggtgc agtcagccag cccggacatc   4500

agggtgacca ggatggagga ggctcagccg gagatgggcc ctgacgtgct ggtgcagacg   4560

atgggggccc cggccttgaa gatctgcgac aaacctgcca aagtgccttc cccaccgcct   4620

gtcatagctg tcacagcggt caccccggct ccggaggcac aggacgggcc ccccagcccc   4680

ctgagtgaag cctctagcgg gtacttctcc cacagcgtct ccaccgcgac cctgtcggac   4740

gccctgggcc ccggcctgga cgctgcggcc ccgccggggt ccatgcccac cgcccctgag   4800

gccgagcccg aggcgcccat cagccacccc ccaccgccca cggccgtccc cgccgaggag   4860

ccccctggcc cccagcagct cgtgagcccc ggtcgggagc gccccgacct cgaggccccg   4920

gcgcccggct ccccgttccg cgtccggagg gtgcgggcct cggagttgcg ctccttctcg   4980

cgcatgctgg ctggggaccc cggctgctcc ccgggggccg aggggaatgc gccggccccg   5040

ggcgccgggg gacaggccct ggcctctgat tccgaggaag ctgacgaggt cccggagtgg   5100

ctccgagagg gcgagttcgt caccgtgggc gcccacaaaa cgggcgtggt gagatacgtg   5160

gggcctgccg acttccaaga gggcacgtgg gtcggcgtgg agctcgacct gccctcaggt   5220

aagaatgacg gttccatcgg cgggaagcag tacttcaggt gtaaccctgg ctacgggctg   5280

ctggtcaggc ccagccgggt ccgcagggcc acgggccctg tgcggcggcg cagcacagga   5340

ctccggctgg gtgcccccga ggcccgccgg agcgccaccc tctcgggctc cgccaccaac   5400

ctggcctcgc tgacagctgc cctggccaag gccgacagga gccacaagaa ccctgagaac   5460

cggaaatcct gggccagctg a                                              5481
```

<210> SEQ ID NO 26
<211> LENGTH: 4947
<212> TYPE: DNA
<213> ORGANISM: Homo sapiens

<400> SEQUENCE: 26

```
atgtcattac acagtactca taatagaaat aacagcggtg atattcttga tattccttct     60

tcccaaaata gttcatcact gaatgccctc acccacagta gccgacttaa gctgcatttg    120

aagtcggata tgtcagaatg tgaaaatgat gatccattat tgagatctgc aggtaaagtc    180

agagacataa atagaactta tgttatttct gccagtagaa aaacagcaga catgcccctt    240

acccctaatc ctgtaggtag attggcactt cagaggagaa ctacaaggaa caaagaatca    300

tctttgcttg ttagtgagtt ggaagacaca actgaaaaaa cagcagaaac acgtcttaca    360

ttacaacgtc gtgctaaaac agattctgca gaaaagtgga aaacagctga aatagattct    420

gtcaaaatga cactgaatgt gggaggtgaa acagaaaata atggtgtttc taaggaaagt    480
```

-continued

```
agaacaaatg taaggattgt aaataatgct aaaaactctt ttgttgcctc ttctgtacct    540
ttagatgaag atccacaggt cattgaaatg atggctgata agaaatacaa agaaacattt    600
tctgccccca gtagagcaaa tgaaaatgtt gcacttaagt actcaagtaa tagaccaccc    660
attgcttccc tgagtcagac tgaagttgtt agatcaggac acttgacaac gaaacctact    720
cagagcaagt tggatatcaa agtgttggga acaggaaact tgtatcatag aagtattggg    780
aaggaaattg caaaaacttc aaataaattt gggagcttag aaaaaagaac acctacaaaa    840
tgtacaacag aacacaaact gacaacaaag tgcagcctgc ctcagcttaa gagcccagct    900
ccatcaatac tgaagaatag aatgtctaac cttcaagtta aacaaagacc aaaaagttcc    960
tttcttgcaa ataaacagga aagatccgca gaaaatacaa ttcttcccga agaagaaact   1020
gtagttcaga acacctctgc aggaaaagac cccttaaaag tagagaatag tcaagtgaca   1080
gtggcagtac gcgtaagacc tttcaccaag agagagaaga ttgaaaaagc atcccaggta   1140
gtcttcatga gtgggaaaga aataactgtg gaacaccctg acacgaaaca agtttataat   1200
tttatttatg atgtttcatt ctggtctttt gatgaatgtc atcctcacta cgctagccag   1260
acaactgtct atgagaagct agcagcacca ctcctagaaa gagccttcga aggcttcaat   1320
acctgtcttt ttgcttatgg tcagactggc tctggaaaat catatacgat gatgggattt   1380
agtgaagaac caggaataat tccaagattt tgtgaagatc tttttctca agtagccaga   1440
aaacaaaccc aagaggtcag ctatcacatt gaaatgagct tctttgaagt atataatgaa   1500
aaaattcacg accttctggt ttgtaaagat gaaaatgggc agagaaagca accactgaga   1560
gtgagggaac atcctgttta tggaccatat gttgaagcac tgtcaatgaa cattgtcagt   1620
tcttacgctg atatccagag ttggctagaa ttgggaaata aacaaagagc tactgctgct   1680
actggtatga atgataaaag ttcccgatct cattcagttt tcaccctggt gatgacccag   1740
accaagacag aatttgtgga aggggaagaa cacgatcaca gaataacaag tcgaattaac   1800
ctaatagatc tggcaggcag tgagcgctgc tctacggctc acactaatgg agatcgacta   1860
aaggaaggtg tgagtattaa taagtccttg ctaactttgg gaaaagttat atctgcactt   1920
tcggaacaag caaaccaaag gagtgttttt attccttatc gtgaatctgt tcttacatgg   1980
ctgttaaaag aaagtctggg tggaaattca aaaactgcaa tgattgctac gattagtccc   2040
gctgccagca acatagaaga aacattaagc acacttagat atgctaacca agcccgttta   2100
atagtcaaca ttgctaaagt aaatgaagat atgaacgcta agttaattag agaattgaag   2160
gcagaaattg caaagctaaa agctgctcag agaaacagtc ggaatattga ccctgaacga   2220
tacaggctct gtcggcaaga aataacatcc ttaagaatga aactgcatca acaggagaga   2280
gacatggcag aaatgcaaag agtgtggaaa gaaaagtttg aacaagctga aaaaagaaaa   2340
cttcaagaaa caaaagagtt acagaaagca ggaattatgt ttcaaatgga caatcattta   2400
ccaaaccttg ttaatctgaa tgaagatcca caactatctg agatgctgct atatatgata   2460
aaagaaggaa caactacagt tggaaagtat aaaccaaact caagccatga tattcagtta   2520
tctggggtgc tgattgctga tgatcattgt actatcaaaa attttggtgg gacagtgagt   2580
attatcccag ttggggaagc aaagacatat gtaaatggaa aacatatttt ggaaatcaca   2640
gtattacgtc atggtgatcg agtgattctt ggtggagatc attattttag atttaatcat   2700
ccagtagaag tccagaaagg aaaaaggcca tctggaagag atactcctat aagtgagggt   2760
ccaaaagact ttgaatttgc aaaaaatgag ttgctcatgg cacagagatc acaacttgaa   2820
gcagaaataa aagaggctca gttgaaggca aaggaagaaa tgatgcaagg aatccagatt   2880
```

-continued

```
gcaaaagaaa tggctcagca agagctttct tctcaaaaag ctgcatatga aagcaaaata   2940
aaagcactgg aagcagaact gagagaagag tctcaaagga aaaaaatgca ggaaataaat   3000
aaccagaagg ctaatcacaa aattgaggaa ttagaaaagg caaagcagca tcttgaacag   3060
gaaatatatg tcaacaaaaa gcgattagaa atggaaacat tggctacaaa acaggcttta   3120
gaagaccata gcatccgcca tgcaagaatt ctggaagctt tagaaactga aaagcaaaaa   3180
attgctaaag aagtacaaat tctacagcag aatcggaata atagggataa aacttttaca   3240
gtgcagacaa cttggagctc tatgaaactc tcaatgatga ttcaggaagc caatgctatc   3300
agcagcaaat tgaaaacata ctatgttttt ggcagacatg atatatcaga taaaagtagt   3360
tctgacactt ctattcgggt tcgtaacctg aaactaggaa tctcaacatt ctggagtctg   3420
gaaaagtttg aatctaaact tgcagcaatg aaagaacttt atgagagtaa tggtagtaac   3480
aggggtgaag atgccttttg tgatcctgaa gatgaatggg aacccgacat tacagatgca   3540
ccagtttctt cactttctag aaggaggagt aggagtttga tgaagaacag aagaatttct   3600
ggttgtttac atgacataca agtccatcca attaagaatt tgcattcttc acattcatca   3660
ggtttaatgg acaaatcaag cactatttac tcaaattcag cagagtcctt tcttcctgga   3720
atttgcaaag aattgattgg ttcttcgtta gatttttttg gacagagtta tgatgaagaa   3780
agaactatag cagacagcct aattaatagt tttcttaaaa tttataatgg gctatttgcc   3840
atttccaagg ctcatgaaga acaagatgaa gaaagtcaag ataacttgtt ttcttctgat   3900
cgagcaatcc agtcacttac tattcagact gcatgtgctt ttgagcagct agtagtgcta   3960
atgaaacact ggctgagtga tttactgcct tgtaccaaca tagcaagact tgaggatgag   4020
ttgagacaag aagttaaaaa actgggaggc tacttacagt tatttttgca gggatgctgt   4080
ttggatattt catcaatgat aaaagaggct caaaagaatg caatccaaat tgtacaacaa   4140
gctgtaaagt atgtggggca gttagcagtt ctgaaaggga gcaagctaca ttttctagaa   4200
aacggtaaca ataaagctgc cagtgtccag gaggaattca tggatgctgt ttgtgatggt   4260
gtaggcttag gaatgaagat tttattagat tctggactgg aaaaagcaaa agaacttcag   4320
catgaactct ttaggcagtg tacaaaaaat gaggttacca aagaaatgaa aactaatgcc   4380
atgggattga ttagatctct tgaaaacatc tttgctgaat cgaaaattaa aagtttcaga   4440
aggcaagtac aagaagaaaa ctttgaatac caagatttca agaggatggt taatcgtgct   4500
ccagaattct taaagttaaa acattgctta gagaaagcta ttgaaattat tatttctgca   4560
ctgaaaggat gccatagtga tataaatctt ctccagactt gtgttgaaag tattcgcaac   4620
ttggccagtg atttttacag tgacttcagt gtgccttcta cttctgttgg cagctatgag   4680
agtagagtaa ctcacattgt ccaccaggaa ctagaatctc tagctaagtc tctcctcttt   4740
tgttttgaat ctgaagaaag ccctgatttg ttgaaaccct gggaaactta taatcaaaat   4800
accaaagaag aacaccaaca atctaaatca agcgggattg acggcagtaa gaataaaggt   4860
gtaccaaagc gtgtctatga gctccatggc tcatccccag cagtgagctc agaggaatgc   4920
acacccagta ggattcagtg ggtgtga                                       4947
```

<210> SEQ ID NO 27
<211> LENGTH: 4167
<212> TYPE: DNA
<213> ORGANISM: Homo sapiens

<400> SEQUENCE: 27

-continued

```
atggcacccg gctgcaaaac tgagttacgc agcgtgacaa atggtcagtc taaccaacca     60
agtaatgaag gtgatgccat caaagttttt gtgcgaattc gtcctcctgc agaaagatct    120
gggtcagctg atggagagca gaacttatgc ttatctgtgc tgtcctccac gagtctccgg    180
ctgcactcca accctgagcc caagaccttc acgtttgatc atgttgcaga tgtggatacc    240
actcaggaat ctgtattcgc aactgtggct aaaagcattg tggagtcttg catgagcggt    300
tataatggta ccatctttgc atatggacag actggctcag ggaagacatt tactatgatg    360
ggaccatctg aatctgataa tttttctcat aacctgagag gagtaatccc acgaagtttt    420
gaatatttgt tttccttaat tgatcgtgaa aaagaaaagg ctggagctgg aaagagtttc    480
ctttgtaagt gttcctttat tgaaatctac aacgagcaga tatatgatct actggactct    540
gcatcggctg gactgtactt aagggagcat atcaagaagg gagtctttgt tgttggtgcg    600
gtggagcagg tggtaacctc agctgctgaa gcctatcagg tgttgtctgg aggatggagg    660
aatagacgtg tggcatcaac atcaatgaac agagaatcgt ctaggtctca tgccgtcttt    720
acaattacaa tagagtcaat ggagaaaagt aatgagattg tgaatatacg gacctcccta    780
ctcaacctgg tggatttagc aggatctgaa aggcaaaaag atacccatgc agaagggatg    840
agattgaagg aagcaggtaa cataaatcga tcattgagct gcctgggcca agtgattaca    900
gcacttgtcg acgtgggtaa tggaaaacag agacatgttt gctacagaga ctccaaactt    960
accttcttac tacgggattc ccttggaggt aatgccaaaa cagccataat tgcaaatgtt   1020
catcctggat ccaggtgttt tggggaaacc ctatcaacac ttaactttgc tcaaagagcc   1080
aagctgatta aaaacaaggc agtagtaaat gaagacaccc aaggaaatgt gagccagctc   1140
caagctgaag tgaagaggct caaagaacaa ctggcggagc ttgcttcagg acagacacca   1200
ccagaaagct tcctgaccag agacaaaaag aagactaact atatggagta tttccaggaa   1260
gcaatgttat tctttaagaa atctgaacag gaaaagaagt ctctgataga aaaagttacc   1320
caattagaag acctcaccct caaaaaggaa aaatttattc aatctaataa aatgattgtg   1380
aaattccgag aggatcaaat aatacgcttg gaaaagctcc acaaggaatc ccggggaggt   1440
tttctgcctg aggagcagga tcgtttgctc tcagaattaa ggaatgagat tcaaactctg   1500
cgagaacaaa tagagcacca ccccagagtt gcaaagtatg ctatggaaaa tcattccctc   1560
agggaggaga atagaagact gagattatta gagcctgtga aaagagctca agaaatggat   1620
gcccagacca ttgcaaaact agaaaaagct ttctctgaaa taagtggcat ggagaaaagt   1680
gacaaaaatc agcaaggatt ttcacctaaa gctcagaaag agccatgttt gtttgcaaac   1740
actgagaagt taaaagcaca actcctgcaa attcagacag agctgaataa ttcaaagcaa   1800
gaatatgaag aattcaaaga acttactagg aaaaggcagc tagaattgga atcagagctt   1860
cagtctttgc aaaaagcgaa ccttaatctt gaaaaccttt tggaagcaac aaaagcctgc   1920
aagcggcaag aagtttctca gctgaataaa attcatgctg aaacacttaa gattataact   1980
acaccaacca aggcctacca acttcattcc cgaccagtac caaaattaag ccctgaaatg   2040
ggaagctttg gctctctata cactcagaat tctagcatat tagataatga tatattaaat   2100
gagccagttc ctcctgagat gaatgaacaa gcttttgagg ccatttctga agagcttaga   2160
acagtgcagg aacaaatgag tgctcttcaa gccaaactgg atgaagaaga gcataaaaac   2220
ctaaagcttc agcagcatgt tgacaaactg gaacatcatt ctacccaaat gcaggagctt   2280
ttctcatcag aaagaattga ttggaccaaa cagcaggaag agcttctctc acagttgaat   2340
gtccttgaaa agcagcttca agagactcaa actaaaaatg actttttgaa aagtgaggta   2400
```

```
catgacctgc gagtagtcct tcattctgct gacaaggagc tttcttcagt gaaattggaa   2460

tatagttcat tcaaaacgaa tcaggagaaa gaattcaaca aactttccga aagacacatg   2520

catgtacagc ttcaattaga taatctcagg ttagaaaacg aaaagctgct tgagagcaaa   2580

gcctgcctac aggattccta tgacaactta caagaaataa tgaaatttga gattgaccaa   2640

ctttcaagaa acctccaaaa cttcaaaaaa gaaaatgaaa ctctgaaatc tgatctgaat   2700

aatttgatgg agcttcttga ggcagaaaaa gaacgcaata acaaattatc attacagttt   2760

gaagaagata aagaaaacag ttctaaagaa atcttaaaag ttcttgaggc tgtacgtcag   2820

gagaaacaga aagagacggc caagtgtgag cagcagatgg caaaagtaca gaaactagaa   2880

gagagcttgc ttgctactga aaaagtgatc agttccctgg aaaagtctag agattctgat   2940

aagaaagttg tagctgacct catgaaccag atccaggagc taagaacatc ggtctgtgag   3000

aaaacagaaa ctatagacac cctgaaacaa gaactgaagg acataaattg caaatacaac   3060

tctgctttgg ttgacagaga agagagcaga gtgttgatca agaagcagga agtggatatt   3120

ctggatctga aagaaaccct taggctgaga atactttctg aggacataga gagggatatg   3180

ctctgtgagg acctggctca tgccactgag cagctgaaca tgctcacaga ggcctcaaaa   3240

aaacactcgg ggctgctgca gtctgcccag gaagaactga ccaagaagga agccctgatt   3300

caggaacttc agcacaagct aaaccaaaag aaagaggaag tagaacagaa gaagaatgaa   3360

tataacttca aaatgaggca actagaacat gtgatggatt ctgctgctga ggatccccag   3420

agtcctaaga caccacctca ctttcaaaca catttggcaa aactcctgga aacacaagaa   3480

caagagatag aagatggaag agcctctaag acttctttgg aacaccttgt aacaaagcta   3540

aatgaagaca gagaagtcaa aaatgctgaa atcctcagaa tgaaggagca gttgcgtgaa   3600

atggaaaacc tacgcctgga aagtcagcag ttaatagaga aaaactggct cctgcaaggt   3660

cagctggatg atattaaaag acaaaaggaa aacagtgatc agaatcatcc agataatcaa   3720

cagctgaaga atgaacaaga agaaagtatc aaagaaagac ttgcaaaaag taaaatagtt   3780

gaagaaatgc tgaaaatgaa agcagaccta gaagaagtcc aaagtgccct ttacaacaaa   3840

gagatggaat gccttagaat gactgatgaa gtcgaacgaa cccaaacttt ggagtctaaa   3900

gcattccagg aaaaagaaca actgagatca aagctggaag aaatgtatga agaaagagag   3960

agaacatccc aggagatgga aatgttaagg aagcaggtgg agtgtcttgc tgaggaaaat   4020

ggaaagttgg taggtcacca aaatttgcat cagaagattc agtacgtagt gcgactaaag   4080

aaggaaaatg tcaggcttgc tgaggagaca gaaaagttgc gtgccgaaaa tgtattttta   4140

aaagaaaaga aaagaagtga atcttga                                       4167
```

<210> SEQ ID NO 28
<211> LENGTH: 3090
<212> TYPE: DNA
<213> ORGANISM: Homo sapiens

<400> SEQUENCE: 28

```
atggcctccg aggcggtgaa ggttgtcgtg cgctgccgtc ccatgaacca gcgggagcga     60

gagctgcgct gccagcccgt ggtgactgtg gactgcgcgc gcgcccagtg ctgcatccag    120

aacccgggcg ccgccgacga gccgcccaag cagttcacct tcgacggcgc ctaccacgtg    180

gaccacgtca ccgagcagat ctacaacgag atcgcctatc cgctggtgga gggcgtcact    240

gagggctaca atggcaccat ctttgcctac ggccagacag gcagcgggaa gtccttcacc    300
```

-continued

```
atgcagggcc tgccggatcc gccctcccag agaggcatca tccccagggc cttcgagcac    360
gtgttcgaga gcgtccagtg tgcagagaac actaagttcc tggtccgggc ctcctacctg    420
gagatctaca atgaagatgt ccgggacctc cttggggctg acaccaagca gaagctggag    480
ctgaaggagc acccagagaa gggcgtgtac gtgaaggggc tgtccatgca cacggtgcac    540
agcgtggccc agtgtgagca catcatggag actggctgga agaaccgttc ggtcggctac    600
acgctgatga acaaggattc ctcacgctcg cactccatct tcaccatcag catcgagatg    660
tctgccgtgg atgagcgggg caaggaccac ctccgggcgg gcaagctgaa cctggtggac    720
ctggcgggca gcgagcggca gtccaagacc ggggccacgg gcgagcggct caaggaggcc    780
accaagatca acctgtcgct ctcggcactg ggcaatgtca tctcggcgct ggtggacggg    840
cgctgtaagc acgtccccta ccgtgactcg aagctgacgc ggctgctgca ggactcactg    900
ggcggcaaca ccaagacgct catggtggcc tgcctgtcgc ctgcggacaa caactacgat    960
gagacactca gcacgctgcg ctacgccaac cgggccaaga acatcaggaa caagccgcgc   1020
atcaatgagg accccaagga tgcgctgctt cgcgagtacc aggaggagat caagaagctc   1080
aaggccatcc tgacacagca gatgagcccc agcagcctgt cagccctgct gtccaggcag   1140
gtgcccccag accctgtgca ggtggaggag aagctgttgc cccaacctgt gatccagcat   1200
gacgtggagg ccgagaagca gctgatccgg gaggagtatg aagagcgcct ggcccggctg   1260
aaagccgact ataaggccga gcaggagtct cgggccaggc tggaggaaga catcactgcc   1320
atgcgcaact catatgacgt caggctgtcc acgctggagg agaacctgcg gaaggagaca   1380
gaggctgtcc tgcaggtggg agtcctctac aaggctgagg tcatgtccag ggctgagttt   1440
gccagcagcg ctgagtaccc gcctgctttt cagtatgaga cagtggtgaa acccaaggtc   1500
ttctccacga ctgacactct gcccagtgac gatgtctcca agactcaggt ttcctccagg   1560
tttgcggagc tgcccaaggt ggaaccctcc aaatctgaga tttctctggg ctccagtgag   1620
tcatcctcgc tcgaagaaac ctctgtgtcc gaggctttcc ctgggcctga ggagccctcc   1680
aacgtggagg tctccatgcc cactgaggag tccaggagca gatacttcct ggatgagtgc   1740
ctcgggcagg aggccgctgg gcacctgctg ggggaacaga actacctccc gcaagaggag   1800
ccgcaggagg tgcccctgca ggggttacta ggcctgcagg acccgtttgc cgaggtggaa   1860
gccaagctgg ccagactctc ctccaccgtg gccaggacag atgcacccca ggcagacgtc   1920
cccaaggtcc ctgtgcaggt ccctgcgccg acagacctgc tggagcccag tgatgccagg   1980
cccgaagccg aggcggctga tgacttcccg cccaggcctg aggtagatct ggcctcggaa   2040
gtggccttag aggtggtgcg gacagcagag cctggcgtgt ggttggaggc tcaggccccg   2100
gtggccctgg tggctcagcc tgagcccctg ccggccacag ctggtgtgaa gagggagagc   2160
gtgggcatgg aggtggcagt gctgactgat gacccgctgc ccgttgtgga ccagcagcag   2220
gtgctggccc gtctgcagct gttggagcag caggttgtgg gtggagagca ggccaagaac   2280
aaggacctga aggagaagca caagcggcgc aagcgctacg cagacgagcg caggaagcag   2340
ctggtggctg ccctgcagaa ctcggatgag gacagcgggg actgggtgct gcttaacgtc   2400
tacgactcca tccaggagga agtgcgggcc aagagcaagc tgctggagaa gatgcagagg   2460
aagcttcggg cagcagaggt ggagatcaaa gatctgcagt ccgagtttca gctggagaag   2520
atcgattact tggccaccat ccgccggcag gagcgtgact ccatgctctt gcagcagctc   2580
ctggagcagg tgcagcccct gattcgcagg gactgtaact acagcaacct ggagaagatt   2640
ctgcgtgagt cctgctggga cgaagataac ggcttctgga agatcccaca tcccgtcatc   2700
```

```
acaaaaacca gcctcccagt agcagtttca actgggccac agaacaaacc agcccgcaaa   2760
acctctgcag cagacaatgg cgagccgaac atggaggacg accgctacag gctcatgctc   2820
agtcggagca acagtgaaaa cattgccagc aactacttcc gatctaagcg ggccagccag   2880
atcctcagca cagacgccag gaagagcctc acacatcaca actcgccacc aggcctcagc   2940
tgcccactca gcaacaactc tgccatccca cccacccagg cccctgaaat gccccagccc   3000
cggcccttcc gcctcgagtc cctcgacatc cctttcacca aggccaagcg taagaaaagc   3060
aaaagcaact ttggcagtga gcctctgtga                                    3090
```

<210> SEQ ID NO 29
<211> LENGTH: 2997
<212> TYPE: DNA
<213> ORGANISM: Homo sapiens

<400> SEQUENCE: 29

```
atgaaggaca gcggggactc caaggaccag caactcatgg tggcgcttcg ggtccggccc     60
atcagcgtgg cagagctgga ggaaggagct accctcatcg cccataaagt ggatgagcag    120
atggtggttc tcatggaccc aatggaggat cccgacgaca tcctgcgggc gcatcgctcc    180
cgggagaagt cctacctgtt cgacgtggcc tttgacttca ccgccaccca ggagatggtg    240
tatcaggcca ccaccaagag cctcatcgag ggcgtcatct caggctacaa tgccactgtc    300
tttgcctatg gccccacagg ctgtgggaaa acctacacca tgctgggcac agaccaggag    360
cctggcatct atgttcagac cctcaacgac ctcttccgtg ccatcgagga gaccagcaat    420
gacatggagt atgaggtctc catgtcctac ctggagatct acaatgagat gatccgggac    480
ctgctgaacc cctccctggg ctacctggag ctgcgggagg actctaaggg ggtgatccag    540
gtggccggca tcaccgaagt ctccaccatc aatgccaagg agatcatgca gctgctgatg    600
aaggggaacc ggcagaggac ccaggagccc acggccgcca accagacgtc ctcccgctcc    660
cacgcggtac tgcaggtgac cgtgcgccag cgcagccggg tcaagaacat cttgcaggag    720
gtgcggcagg gccgcctgtt catgatcgac ctggctggct cagagcgcgc ctcgcagaca    780
cagaatcgtg ggcagcgtat gaaggagggg gcccacatca accgctcact gctggcactg    840
ggcaactgca tcaacgccct gagcgacaag ggtagcaaca agtacatcaa ctatcgcgac    900
agcaagctca cccggctcct gaaggactct ctgggaggaa acagccgcac agtgatgatc    960
gctcacatca gtcctgcgag cagtgccttc gaggagtccc ggaacaccct gacctacgcc   1020
ggccgggcca agaacattaa gactagggtg aagcagaacc tcctgaacgt ctcctaccac   1080
atcgcccagt acaccagcat catcgctgac ctgcggggcg agatccagcg actcaagcgc   1140
aagattgatg agcagactgg gcggggccag gcccggggcc ggcaggatcg gggtgacatc   1200
cgccacatcc aagctgaggt ccagctgcac agcgggcagg gtgagaaggc tggcatggga   1260
cagcttcggg agcagctcgc cagcgccttc caggagcaga tggatgtgcg gaggcgcctg   1320
ctggagctgg agaaccgcgc catggaggtc cagattgaca cctcccgaca cctgctcacc   1380
atcgccggct ggaagcatga gaagtcccgc cgggccctca aatggcggga ggagcagcga   1440
aaggagtgct acgctaagga cgacagcgag aaggactcag acacaggtga tgaccaacca   1500
gacatcctgg agccacccga ggtggccgca gcccgggaga gcattgcagc cctggtggac   1560
gagcagaagc aactgcgcaa gcagaagctg gcgctggagc agcgctgccg ggagctgcgc   1620
gcgcggggcc ggcgcctgga ggagacgctg ccgcggcgca tcggctccga ggagcagcgc   1680
```

```
gaggtgctca gcctgctgtg ccgcgtgcac gagctcgagg tggagaacac cgagatgcag   1740
tcgcacgcgc tgctccgcga cggtgcgctc cgccaccgcc acgaggccgt gcgccgcctg   1800
gagcagcacc gcagtctctg cgacgagatt atccagggcc agcggcagat catcgacgac   1860
tacaacctgg ccgtcccgca gcgcctggaa gagctctacg aagtgtacct gcgggagctg   1920
gaggagggca gcctggagca ggccaccatc atggaccaag tggcctccag ggccctgcag   1980
gacagctcct tgcccaaaat taccccagca ggaacctcac tgaccccaga ttctgacctg   2040
gagagtgtga agacattgag ctctgatgcc cagcacctgc agaacagcgc cctccctccc   2100
ctcagcacag agagtgaagg ccaccacgtg ttcaaggctg gtactggggc ctggcaggca   2160
aaaagctcct ctgtgcccac cccacctccc atccagctcg gcagcctggt gacgcaggag   2220
gccccggctc aggacagcct gggcagctgg atcaactctt cccctgacag cagtgagaac   2280
ctgtcggaga tccccttgtc ccacaaagag aggaaggaga tcctgactgg caccaagtgc   2340
atctgggtga aggccgcccg gcggcgctcg cgggccctgg gaaccgaggg gcgacacctg   2400
ctggcacccg cgacagagcg cagcagcctg tccctgcact cactgagcga gggcgacgat   2460
gcgcggccac caggcccact ggcctgcaag cggccgccca gccccacact acagcatgct   2520
gccagtgagg acaacctgtc cagcagcacg ggcgaggccc cgtcccgggc agtcggacat   2580
catggggacg gccccaggcc ctggctgcgt ggccagaaga aaagcctggg caagaaaagg   2640
gaggagtcgc tggaggcaaa gagaaggaag cggaggtccc gatccttcga ggtcaccggg   2700
caagggctct cccaccccaa gacacacctc ctggggcccc atcaggcgga gcgcatctcg   2760
gaccacagga tgccagtgtg caggcaccca gcccctggta tccggcatct gggaaaggtc   2820
acgctacctt tggccaaagt caaactccct ccaagccaga acacgggccc gggggactcc   2880
tcacccctgg ctgttccccc caacccaggt ggtggttctc gacgggctac ccgtgggccc   2940
cgcctgcccc acggcacaag cacccatggc aaagatggat gctcccggca taactga      2997
```

<210> SEQ ID NO 30
<211> LENGTH: 1998
<212> TYPE: DNA
<213> ORGANISM: Homo sapiens

<400> SEQUENCE: 30

```
atggccgcgg gcggctcgac gcagcagagg cgacgcgaga tggcggcagc ttcagcggcg     60
gcgatctcag gagctggtcg ctgtcggcta agcaagattg gagctactcg tcgtccacct    120
ccagctcgcg taagggtggc tgtgcgactg cggccatttg tggatggaac agcgggagca    180
agtgatcccc cctgtgtgcg gggcatggac agctgctctc tagagattgc taactggagg    240
aaccaccagg agactctcaa ataccagttt gatgccttct atggggagag gagtactcag    300
caggacatct atgcaggttc agtgcagccc atcctaaggc acttgctgga agggcagaat    360
gccagtgtgc ttgcctatgg acccacagga gctgggaaga cgcacacaat gctgggcagc    420
ccagagcaac ctggggtgat cccgcgggct ctcatggacc tcctgcagct cacaagggag    480
gagggtgccg agggccggcc atgggccctt tctgtcacca tgtcttacct agagatctac    540
caggagaagg tattagacct cctggaccct gcttcgggag acctggtaat ccgagaagac    600
tgccggggga atatcctgat tccgggtctc tcccagaagc ccatcagtag ctttgctgat    660
tttgagcggc acttcctgcc agccagtcga aatcggactg taggagccac ccggctcaac    720
cagcgctcct cccgcagtca tgctgtgctc ctggtcaagg tggaccagcg ggaacgtttg    780
gccccatttc gccagcgaga gggaaaactc tacctgattg acttggctgg gtcagaggac    840
```

aaccggcgca caggcaacaa gggccttcgg ctaaaagaga gtggagccat caacacctcc 900
ctgtttgtcc tgggcaaagt ggtagatgcg ctgaatcagg gcctccctcg tgtaccttat 960
cgggacagca agctcactcg cctattgcag gactctctgg gtggctcagc ccacagtatc 1020
cttattgcca acattgcccc tgagagacgc ttctacctag acacagtctc cgcactcaac 1080
tttgctgcca ggtccaagga ggtgatcaat cggcctttta ccaatgagag cctgcagcct 1140
catgccttgg gacctgttaa gctgtctcag aaagaattgc ttggtccacc agaggcaaag 1200
agagcccgag gccctgagga agaggagatc gggagccctg agcccatggc agctccagcc 1260
tctgcctccc agaaactcag ccccctacag aagctaagca gcatggaccc ggccatgctg 1320
gagcgcctcc tcagcttgga ccgtctgctt gcctcccagg ggagccaggg ggcccctctg 1380
ttgagtaccc caaagcgaga gcggatggtg ctaatgaaga cagtggaaga gaaggaccta 1440
gagattgaga ggcttaagac gaagcaaaaa gaactggagg ccaagatgtt ggcccagaag 1500
gctgaggaaa aggagaacca ttgtcccaca atgctccggc ccctttcaca tcgcacagtc 1560
acaggggcaa agcccctgaa aaaggctgtg gtgatgcccc tacagctaat tcaggagcag 1620
gcagcatccc caaatgccga gatccacatc ctgaagaata aaggccggaa gagaaagctg 1680
gagtccctgg atgccctaga gcctgaggag aaggctgagg actgctggga gctacagatc 1740
agcccggagc tactggctca tgggcgccaa aaaatactgg atctgctgaa cgaaggctca 1800
gcccgagatc tccgcagtct tcagcgcatt ggcccgaaga aggcccagct aatcgtgggc 1860
tggcgggagc tccacggccc cttcagccag gtggaggacc tggaacgcgt ggagggcata 1920
acggggaaac agatggagtc cttcctgaag gcaaacatcc tgggtctcgc cgccggccag 1980
cgctgtggcg cctcctga 1998

<210> SEQ ID NO 31
<211> LENGTH: 2883
<212> TYPE: DNA
<213> ORGANISM: Homo sapiens

<400> SEQUENCE: 31
atgaagtcag cgagagctaa gacaccccgg aaacctaccg tgaaaaaagg gtcccaaacg 60
aaccttaaag acccagttgg ggtatactgt agggtgcgcc cactgggctt tcctgatcaa 120
gagtgttgca tagaagtgat caataataca actgttcagc ttcatactcc tgagggctac 180
agactcaacc gaaatggaga ctataaggag actcagtatt catttaaaca agtatttggc 240
actcacacca cccagaagga actctttgat gttgtggcta atcccttggt caatgacctc 300
attcatggca aaaatggtct tctttttaca tatggtgtga cgggaagtgg aaaaaactcac 360 acaatgactg gttctccagg ggaaggaggg ctgcttcctc gttgtttgga catgatcttt 420
aacagtatag ggtcatttca agctaaacga tatgttttca aatctaatga taggaatagt 480
atggatatac agtgtgaggt tgatgcctta ttagaacgtc agaaaagaga agctatgccc 540
aatccaaaga cttcttctag caaacgacaa gtagatccag agtttgcaga tatgataact 600
gtacaagaat tctgcaaagc agaagaggtt gatgaagata gtgtctatgg tgtatttgtc 660
tcttatattg aaatatataa taattacata tatgatctat tggaagaggt gccgtttgat 720
cccataaaac ccaaacctcc acaatctaaa ttgcttcgtg aagataagaa ccataacatg 780
tatgttgcag gatgtacaga agttgaagtg aaatctactg aggaggcttt tgaagttttc 840
tggagaggcc agaaaaagag acgtattgct aatacccatt tgaatcgtga gtccagccgt 900

-continued

```
tcccatagcg tgttcaacat taaattagtt caggctccct tggatgcaga tggagacaat    960
gtcttacagg aaaaagaaca aatcactata agtcagttgt ccttggtaga tcttgctgga   1020
agtgaaagaa ctaaccggac cagagcagaa gggaacagat tacgtgaagc tggtaatatt   1080
aatcagtcac taatgacgct aagaacatgt atggatgtcc taagagagaa ccaaatgtat   1140
ggaactaaca agatggttcc atatcgagat tcaaagttaa cccatctgtt caagaactac   1200
tttgatgggg aaggaaaagt gcggatgatc gtgtgtgtga accccaaggc tgaagattat   1260
gaagaaaact tgcaagtcat gagatttgcg gaagtgactc aagaagttga agtagcaaga   1320
cctgtagaca aggcaatatg tggtttaacg cctgggagga gatacagaaa ccagcctcga   1380
ggtccagttg gaaatgaacc attggttact gacgtggttt tgcagagttt tccacctttg   1440
ccatcatgcg aaattttgga tatcaacgat gagcagacac ttccaaggct gattgaagcc   1500
ttagagaaac gacataactt acgacaaatg atgattgatg agtttaacaa acaatctaat   1560
gcttttaaag ctttgttaca agaatttgac aatgctgttt taagtaaaga aaaccacatg   1620
caagggaaac taaatgaaaa ggagaagatg atctcaggac agaaattgga aatagaacga   1680
ctggaaaaga aaaacaaaac tttagaatat aagattgaga ttttagagaa aacaactact   1740
atctatgagg aagataaacg caatttgcaa caggaacttg aaactcagaa ccagaaactt   1800
cagcgacagt tttctgacaa acgcagatta gaagccaggt tgcaaggcat ggtgacagaa   1860
acgacaatga agtgggagaa agaatgtgag cgtagagtgg cagccaaaca gctggagatg   1920
cagaataaac tctgggttaa agatgaaaag ctgaaacaac tgaaggctat tgttaccgaa   1980
cctaaaactg agaagccaga gagaccctct cgggagcgag atcgagaaaa agttactcaa   2040
agatctgttt ctccatcacc tgtgcctctt tctagtaact atattgctca gatttccaac   2100
ggccagcaac tcatgagcca gccacagcta cataggcgct ctaactcttg cagcagcatt   2160
tctgtagctt cctgtatttc ggaatgggag cagaaaattc ctacgtacaa cacacctctc   2220
aaagtcacat ctattgcaag gcgtaggcag caggagccag gacaaagcaa aacttgtatc   2280
gtgtcagaca gaaggcgagg gatgtactgg actgaaggca gggaggtggt tcctacattc   2340
agaaatgaga tagaaataga agaggatcat tgcggcaggt tactctttca acctgatcag   2400
aacgcaccac caattcgtct ccgacacaga cgatcacgct ctgcaggaga cagatgggta   2460
gatcataagc ccgcctctaa catgcaaact gaaacagtca tgcagccaca tgtccctcat   2520
gccatcacag tatctgttgc aaatgaaaag gcactagcta agtgtgagaa gtacatgctg   2580
acccaccagg aactagcctc cgatggggag attgaaacta aactaattaa gggtgatatt   2640
tataaaacaa ggggtggtgg acaatctgtt cagtttactg atattgagac tttaaagcaa   2700
gaatcaccaa atggtagtcg aaaacgaaga tcttccacag tagcacctgc ccaaccagat   2760
ggtgcagagt ctgaatggac cgatgtagaa acaaggtgtt ctgtggctgt ggagatgaga   2820
gcaggatccc agctgggacc tggatatcag catcacgcac aacccaagcg caaaaagcca   2880
tga                                                                 2883
```

<210> SEQ ID NO 32
<211> LENGTH: 4107
<212> TYPE: DNA
<213> ORGANISM: Homo sapiens

<400> SEQUENCE: 32

```
atggcatcct ggttatatga atgtctttgt gaagctgaac ttgcacagta ttattctcat     60
ttcactgccc ttggccttca gaaaatagat gaattagcca agattacaat gaaggactac    120
```

```
tccaaattag gagtccatga catgaacgac cgcaaacgtc tcttccaact tatcaaaatt    180
attaagatta tgcaagaaga agataaagca gtcagtatcc cagagcgtca tcttcagaca    240
agcagcctgc gcatcaaatc tcaggaatta agatctggcc ctcgcagaca gctgaatttt    300
gattctcctg ctgacaataa agacagaaat gccagcaatg atgggtttga aatgtgcagt    360
ttatcagatt tctctgcaaa tgaacagaag tccacttacc taaaagtgct agaacacatg    420
ctaccagatg attcccagta ccatacaaaa acaggaattc tgaatgccac agctggtgat    480
tcctatgtgc aaacagaaat cagcacttca ctcttttcac caaattacct ttctgcaata    540
ctgggggatt gtgatattcc cattattcaa agaatctctc atgtttcagg gtataactat    600
ggaatccctc attcttgtat cagacagaac acttcagaga aacagaatcc ttggactgag    660
atggagaaaa tcagagtttg tgttcgaaaa cgcccccctgg gcatgaggga ggtacgtcgt    720
ggagaaatta atattattac tgtagaagac aaagaaactc tacttgtgca tgagaagaaa    780
gaagcagttg acctcactca atatattctg cagcatgttt tttattttga tgaagtcttt    840
ggtgaggcgt gcaccaatca ggatgtatac atgaagacta ctcacccact tattcagcat    900
attttcaatg gaggcaatgc cacttgcttt gcttatggac agacaggtgc tggaaagacc    960
tacaccatga taggaactca tgagaaccca ggattgtatg ctctagctgc caaagatatc   1020
ttcaggcaac tagaagtgtc ccagccaaga aagcacctct ttgtgtggat cagcttctat   1080
gaaatttact gtggacagct ttatgacctc ctaaatagaa gaaaaaggct ctttgcaaga   1140
gaagatagca agcacatggt gcagatagtg ggactgcaag agcttcaggt ggacagtgtg   1200
gagctcctct tagaggtgat cttaaagggc agcaaggagc gcagcactgg ggccactgga   1260
gttaatgcag actcctcccg ctcccatgcc gtcatccaaa ttcagatcaa agattcagcc   1320
aagaggacat ttggcaggat ctcttttatt gacttggctg gcagtgaaag agcagcagat   1380
gcaagggact cagatagaca gacaaagatg gaaggtgcag aaataaatca gagtctactg   1440
gctctgaagg aatgtatccg agcactggat caggaacaca cccatactcc cttcaggcaa   1500
agcaaactaa ctcaggtcct gaaggactct ttcatcggca atgccaaaac ctgcatgatc   1560
gccaacatct caccaagcca cgtggccact gaacacactc tcaacacctt gcgctatgct   1620
gaccgggtca aagaactaaa gaaaggcatt aagtgttgca cttcagttac cagtcgaaat   1680
cggacatctg gaaactcctc tccaaaacga attcagagct cccctggggc tttgtcagag   1740
gacaaatgtt ctcccaaaaa agtcaagctg ggatttcagc agtcactcac agtggcagcc   1800
cctggttcca cgagagggaa ggtccatcct ctgaccagcc acccacccaa cattcctttt   1860
acttctgcac ctaaggtctc tggtaaaagg ggtggctcca gagggagtcc ttcacaagag   1920
tgggtcattc atgctagccc tgtgaaagga actgtgcgct ctggacatgt ggccaaaaaa   1980
aagccagaag agtcagcacc attgtgctct gagaaaaatc gaatgggcaa caaaactgtc   2040
cttgggtggg aaagcagggc ctcaggccca ggagaaggcc tagtgcgtgg taagctgtcc   2100
accaagtgca agaaagtgca gacagtgcag ccagtacaga agcagcttgt gtctcgagtt   2160
gagctctcct ttggcaacgc ccaccacagg gctgagtaca gtcaagacag ccagaggggc   2220
acgcctgcta ggcctgcctc tgaagcttgg acaaacatcc cgccacatca gaaggagagg   2280
gaggaacatc tgcgtttcta tcaccagcag ttccaacagc cacctctcct ccaacagaag   2340
ttaaaatacc aaccactgaa aaggtcttta cgccagtaca ggcccccaga gggtcagctc   2400
acgaatgaga ctccgcctct gttccactct tactctgaaa accatgatgg agcccaagta   2460
```

gaggaacttg atgacagtga tttcagtgaa gattcttttt cacacatctc tagtcagagg 2520
gccacaaagc aaaggaacac cctggagaat agcgaagact cattcttcct gcaccagacg 2580
tggggacagg gtcctgagaa gcaggtggca gaaagacagc agagtctgtt ttctagcccc 2640
aggacaggtg acaagaaaga tctaactaaa agctgggtgg actccaggga ccccataaac 2700
cacagaagag cagcactcga tcacagctgc agcccaagta aggggcccgt ggactggagc 2760
agagagaact ctacttcctc agggccttct cccagagaca gcctggcaga gaagccatac 2820
tgttcacagg tagatttcat atatagacag gaaagaggtg gaggctcttc ctttgatctc 2880
agaaaggatg cctcccaaag tgaggtttct ggggagaatg agggcaactt gccatcccca 2940
gaggaagatg gtttcactat ctcattgtcc cacgttgcag ttcctggatc cccagaccaa 3000
agagacacag tcaccacacc tctgagagaa gtcagtgcag acggcccaat ccaggtgacc 3060
agcactgtga aaaacggtca tgctgtccca ggagaggatc ctagggggca gttaggcacg 3120
catgctgaat atgcttctgg actcatgtct cccctcacca tgtccctcct ggagaaccca 3180
gacaacgaag ggtctcctcc ctcggagcag ctggtccagg atggggctac gcacagtcta 3240
gtggcagaga gcacaggggg cccagttgtg agccacacag tgccatctgg tgatcaagag 3300
gcagccttgc cagtgtcttc agcaactagg cacctgtggc tgtcctcatc tccccctgat 3360
aataagcctg gtggtgatct tccagctctg tccccatcac ccatccgtca gcacccagct 3420
gacaagctgc ccagcaggga ggcagaccta ggagaggcct gccagagcag agagactgta 3480
cttttctccc acgaacacat gggtagtgag cagtatgatg ctgatgcaga ggagacgggg 3540
ctggatggct cctggggttt cccaggaaag cccttcacca ccatacatat gggggtaccc 3600
cattctggac ctacactcac cccacgaaca ggaagtagtg atgtggctga ccagctctgg 3660
gcccaggaga gaaaacatcc tacaaggctt ggttggcagg agtttggttt gtccacagac 3720
cccatcaagt tgccctgcaa cagtgaaaat gtcacatggc tcaaacccag gccgatctca 3780
aggtgcttag caaggccaag ttctcccttg gttcccagct gctctcccaa gactgcaggg 3840
acactccgtc agcccaccct ggagcaagcg cagcaggtgg tcatccgagc acaccaggaa 3900
cagctggatg aaatggctga gctcggcttc aaggaggaga cgctgatgag ccagctggct 3960
tctaatgatt ttgaagattt tgtgacccag ctggatgaaa tcatggttct gaaatccaag 4020
tgtatccaga gtctgaggag ccagctgcag ctctatctca cctgccacgg gcccaccgca 4080
gcccctgagg gaacagtgcc gtcttag 4107

<210> SEQ ID NO 33
<211> LENGTH: 1155
<212> TYPE: DNA
<213> ORGANISM: Homo sapiens

<400> SEQUENCE: 33
atgacatgga cctcaggtca gcttcagcgt gagaagcagg ccaggcctgg gtctggagcc 60
gtcctggcct tcccagatga caaggacctc agggtttatg gtccagcaga gtctcagagc 120
gcggtctttg gagatgtgtg ccccctactc acttctctct tggatgggta caatgtttgt 180
gttatggcgt atggacagac gggcagcgga aagagctata ccatgctggg acgccattcg 240
gacgacggcc ctgttctgcc gcttgaccca cagagtgact taggaattat ccctagagtg 300
gctgaggagc tcttcaggct cattttggaa aatacctcaa gaagcccaaa ggttgaagtc 360
tccatagtgg aagtttacaa taatgacatt tttgaccttc tggccaaaga cagcattgca 420
gcagtgtcgg gggtcaagcg tgaggtggtg acagccaagg atggacggac agaggttgcg 480

-continued

```
ctgctggcct ctgaggctgt cggcagcgcc tcgaaactga tggagctcgt tcatggaggt    540

ctgcagctca gggcgaagca ccccaccctg gtgcacgcgg attcctccag gtctcacctg    600

ataattacgg tgactctaac cacagcctcc tgctctgaca gcactgcaga ccaagcctgc    660

agtgccaccc tccccaggga gcaaacagag gcaggaaggg caggaaggag ccgcagagct    720

tctcaagggg ccttggctcc acagctggtt cctgggaacc ccgcagggca tgcggagcag    780

gtgcaggctc gactacagct cgtggactcg gccggcagcg agtgcgttgg tgtgtctgga    840

gtgaccgggt tggccctgag ggagatggcg tgcatcagcc gcagccttgc ggccctggca    900

ggcgtcctgg gggctttgtt ggagcaccgt ggccatgccc cgtaccggaa cagcaggctc    960

acccacctcc ttcaggactg cctcggaggc gatgcgaagt tactggtgat tctctgcatt   1020

tctcccagcc agaggcacct ggcacagacg ttgcagggcc tgggtttcgg gatccgagct   1080

cggcaagtcc agcgaggccc tgcccgaaag aagccgccca gctcccaaac ggaggggaag   1140

aggaggccgg attga                                                    1155
```

```
<210> SEQ ID NO 34
<211> LENGTH: 4206
<212> TYPE: DNA
<213> ORGANISM: Homo sapiens

<400> SEQUENCE: 34

atggaagaaa taccagtaaa agttgctgta agaattagac ctctgctttg caaagaagct     60

cttcataatc atcaagtttg tgtgagagtt attccaaaca gccagcaagt tatcattggg    120

agagatagag tcttcacttt tgattttgtt tttggcaaaa attccactca agatgaagtt    180

tataacacat gtataaagcc cctagtgttg tcactcattg agggctataa tgcaactgtt    240

tttgcctatg gacaaactgg atctgggaag acatacacca ttggaggggg ccatattgct    300

tcagttgtgg agggccaaaa gggtatcatt cctcgagcta ttcaagaaat atttcaaagc    360

atctctgaac atcctagcat tgactttaat gtaaaagtat cttatataga agtgtacaag    420

gaagacctaa gagatcttct agaattggag acatccatga aggatcttca catccgagaa    480

gatgaaaaag gaaacacagt gattgttggg gccaaggaat gccatgtgga gagtgcaggt    540

gaagtgatga gtcttttgga gatggggaat gcagccagac atacaggtac cactcaaatg    600

aatgagcact ccagcagatc acatgcaatt tttacaatca gcatttgtca agttcataaa    660

aatatggagg cagctgaaga tggatcatgg tattcccctc ggcatattgt ctcaaagttc    720

cactttgtgg atttggcagg atcagaaaga gtaaccaaaa cggggaatac tggtgaacgg    780

ttcaaagaat ccattcaaat caatagtgga ttgctggctt taggaaatgt aataagcgct    840

cttggggacc cacgcaggaa gagttcacat attccatata gggatgctaa aattacccgg    900

cttctgaaag attctctggg aggcagtgct aagactgtca tgatcacatg tgtcagcccc    960

tcctcctcga attttgatga gtccttaaat tctctcaaat atgccaacag agcacggaac   1020

attagaaaca aacccactgt aaacttcagc cccgagtcag accgtataga tgaaatggaa   1080

tttgagatta aattgcttcg agaagctttg caaagccagc aggctggtgt cagccaaact   1140

acccagatca atcgagaagg gagtcctgat acaaatagga ttcattctct tgaggagcaa   1200

gtagctcagc ttcaaggaga atgtctgggt taccagtgtt gtgtagaaga agcctttacc   1260

ttcctggttg acctaaaaga tactgtcaga ctaaacgaaa agcagcaaca caaactgcag   1320

gagtggttta acatgatcca agaggtcagg aaggctgtcc tcacctcatt tcgaggaatc   1380
```

-continued

```
ggaggcactg caagtctgga agaaggacca cagcatgtta cagttctcca gctgaagaga   1440
gagcttaaga aatgccagtg tgtgcttgct gctgatgaag tagtatttaa tcagaaggaa   1500
ctggaggtga aggaactgaa gaatcaagtg cagatgatgg tacaggaaaa caaagggcat   1560
gctgtatctt tgaaagaagc gcaaaaagtg aatagactgc agaatgaaaa aataatagaa   1620
caacaacttc ttgtggatca actgagtgaa gaactaacaa aacttaacct gtcagtgact   1680
tcttcagcta aagaaaattg tggagatggg ccagatgcca ggatccctga aaggagacca   1740
tatactgtac catttgatac tcatttgggg cattatattt atatcccatc aagacaagat   1800
tccaggaagg tccacacaag tccgcctatg tactctctgg atcgaatatt tgctggattt   1860
cgaacacgaa gtcagatgct gttgggtcac atagaagaac aagataaggt cctccactgc   1920
caattttctg ataacagtga tgatgaagaa tcagaaggcc aagagaaatc tggaactaga   1980
tgtagaagtc gttcatggat tcagaagcca gactctgttt gttcccttgt tgaattgagt   2040
gatactcagg atgaaacaca aaagtcagat ttggagaatg aagatttaaa gattgattgt   2100
ctccaggaga gtcaagaatt gaatttgcaa aaattaaaga attcagaacg catacttact   2160
gaagctaaac aaaaaatgag agaacttaca attaacatca agatgaagga agatctgatt   2220
aaagaattaa taaaaacagg taatgatgcc aagtctgtaa gcaagcagta ttctttgaaa   2280
gtaacaaagc tagagcatga tgcagaacag gcaaaagtcg aactgattga aacacaaaag   2340
cagctacagg agctggaaaa caaagatctt tctgatgttg caatgaaggt aaaattacag   2400
aaagagtttc gtaaaaagat ggatgctgca aagctgagag ttcaggtctt gcagaagaag   2460
caacaagata gtaagaaact ggcatcactg tcaatccaaa atgagaaacg tgctaatgag   2520
ctagagcaga gtgtagatca catgaaatat caaaagatac agctacaaag aaaactacga   2580
gaagaaaatg aaaaaaggaa gcaactggat gcagtaatta agcgggacca gcaaaaaatc   2640
aaagaaatac aattaaaaac aggacaggaa gaaggtctaa aaccgaaagc tgaggacctt   2700
gatgcatgta acttgaaaag gagaaaaggt tcgtttggaa gtatagacca tctccagaaa   2760
ttggatgagc aaaagaaatg gttagatgaa gaagtagaga aagttctgaa ccaacgccaa   2820
gaattagagg agctggaagc agacttaaag aaacgggagg ccatagtttc taagaaggag   2880
gctctgttac aggagaagag tcacctggaa aataagaaat tgagatctag tcaggcctta   2940
aacacagata gtttgaaaat atcaactcgc ctgaacttac tggaacaaga gttgtctgaa   3000
aagaatgtgc agctccagac cagtacagct gaggagaaaa caaagatttc agaacaagtt   3060
gaagtcctcc agaaagaaaa ggatcagctc cagaaacgca gacacaatgt ggatgaaaaa   3120
cttaaaaatg gtagagtgtt atcacctgaa gaagaacatg ttcttttcca acttgaagaa   3180
gggattgaag ctttggaagc tgcaattgaa tacaggaatg aaagtatcca gaatcgccag   3240
aagtcactta gagcatcatt ccataacctc tctcgtggtg aagcaaatgt cttggaaaag   3300
ctagcttgcc tgagtcctgt tgagattaga actattcttt tcagatattt caataaggtg   3360
gtgaatttgc gagaagctga acggaaacaa cagttatata atgaagaaat gaaaatgaaa   3420
gttctggaac gggataatat ggttcgtgaa ttagaatctg cactggacca tctaaaattg   3480
cagtgtgacc ggagactgac cctccagcaa aaggaacacg aacaaaagat gcagttgcta   3540
ttacatcatt tcaaagaaca agatggagaa ggcattatgg aaactttcaa aacatatgaa   3600
gataaaatcc agcagttgga aaaagatctt tatttctata agaaaaccag ccgggatcat   3660
aagaagaaac ttaaggaact ggtaggggaa gcaattcggc ggcaactagc accatcagag   3720
tatcaagagg ctggagatgg agtcctgaag ccagaaggag gaggcatgct ttcagaagaa   3780
```

ttaaaatggg catccagacc tgaaagtatg aaattaagtg gaagagaaag agaaatggac 3840
agttcagcaa gcagcttaag aacacagcca aatcctcaaa agctctggga agatatccca 3900
gaattacctc caattcatag ttctttagca ccccccagtg ggcatatgtt aggtaatgag 3960
aataaaacag aaacagatga taatcagttt acaaaatctc acagtcgact gtcatcccaa 4020
attcaggttg tgggaaatgt gggacgactt catggtgtca cacctgtaaa actgtgtcga 4080
aaagaattac gtcaaatttc cgccttggaa ctatcattgc gacgttccag tcttggagtt 4140
ggcattggat caatggctgc tgattccatc gaagtatcta ggaaaccaag ggacttaaaa 4200
acttag 4206

<210> SEQ ID NO 35
<211> LENGTH: 4206
<212> TYPE: DNA
<213> ORGANISM: Homo sapiens

<400> SEQUENCE: 35
atggaagaaa taccagtaaa agttgctgta agaattagac ctctgctttg caaagaagct 60
cttcataatc atcaagtttg tgtgagagtt attccaaaca gccagcaagt tatcattggg 120
agagatagag tcttcacttt tgattttgtt tttggcaaaa attccactca agatgaagtt 180
tataacacat gtataaagcc cctagtgttg tcactcattg agggctataa tgcaactgtt 240
tttgcctatg gacaaactgg atctgggaag acatacacca ttggaggggg ccatattgct 300
tcagttgtgg agggccaaaa gggtatcatt cctcgagcta ttcaagaaat atttcaaagc 360
atctctgaac atcctagcat tgactttaat gtaaaagtat cttatataga agtgtacaag 420
gaagacctaa gagatcttct agaattggag acatccatga aggatcttca catccgagaa 480
gatgaaaaag gaaacacagt gattgttggg gccaaggaat gccatgtgga gagtgcaggt 540
gaagtgatga gtcttttgga gatggggaat gcagccagac atacaggtac cactcaaatg 600
aatgagcact ccagcagatc acatgcaatt tttacaatca gcatttgtca agttcataaa 660
aatatggagg cagctgaaga tggatcatgg tattcccctc ggcatattgt ctcaaagttc 720
cactttgtgg atttggcagg atcagaaaga gtaaccaaaa cggggaatac tggtgaacgg 780
ttcaaagaat ccattcaaat caatagtgga ttgctggctt taggaaatgt aataagcgct 840
cttggggacc cacgcaggaa gagttcacat attccatata gggatgctaa aattacccgg 900
cttctgaaag attctctggg aggcagtgct aagactgtca tgatcacatg tgtcagcccc 960
tcctcctcga attttgatga gtccttaaat tctctcaaat atgccaacag agcacggaac 1020
attagaaaca aacccactgt aaacttcagc cccgagtcag accgtataga tgaaatggaa 1080
tttgagatta aattgcttcg agaagctttg caaagccagc aggctggtgt cagccaaact 1140
acccagatca atcgagaagg gagtcctgat acaaatagga ttcattctct tgaggagcaa 1200
gtagctcagc ttcaaggaga atgtctgggt taccagtgtt gtgtagaaga agcctttacc 1260
ttcctggttg acctaaaaga tactgtcaga ctaaacgaaa agcagcaaca caaactgcag 1320
gagtggttta acatgatcca agaggtcagg aaggctgtcc tcacctcatt tcgaggaatc 1380
ggaggcactg caagtctgga agaaggacca cagcatgtta cagttctcca gctgaagaga 1440
gagcttaaga aatgccagtg tgtgcttgct gctgatgaag tagtatttaa tcagaaggaa 1500
ctggaggtga aggaactgaa gaatcaagtg cagatgatgg tacaggaaaa caaagggcat 1560
gctgtatctt tgaaagaagc gcaaaaagtg aatagactgc agaatgaaaa aataatagaa 1620

-continued

```
caacaacttc ttgtggatca actgagtgaa gaactaacaa aacttaacct gtcagtgact   1680
tcttcagcta aagaaaattg tggagatggg ccagatgcca ggatccctga aaggagacca   1740
tatactgtac catttgatac tcatttgggg cattatattt atatcccatc aagacaagat   1800
tccaggaagg tccacacaag tccgcctatg tactctctgg atcgaatatt tgctggattt   1860
cgaacacgaa gtcagatgct gttgggtcac atagaagaac aagataaggt cctccactgc   1920
caattttctg ataacagtga tgatgaagaa tcagaaggcc aagagaaatc tggaactaga   1980
tgtagaagtc gttcatggat tcagaagcca gactctgttt gttcccttgt tgaattgagt   2040
gatactcagg atgaaacaca aaagtcagat ttggagaatg aagatttaaa gattgattgt   2100
ctccaggaga gtcaagaatt gaatttgcaa aaattaaaga attcagaacg catacttact   2160
gaagctaaac aaaaaatgag agaacttaca attaacatca agatgaagga agatctgatt   2220
aaagaattaa taaaaacagg taatgatgcc aagtctgtaa gcaagcagta ttctttgaaa   2280
gtaacaaagc tagagcatga tgcagaacag gcaaaagtcg aactgattga aacacaaaag   2340
cagctacagg agctggaaaa caaagatctt tctgatgttg caatgaaggt aaaattacag   2400
aaagagtttc gtaaaaagat ggatgctgca aagctgagag ttcaggtctt gcagaagaag   2460
caacaagata gtaagaaact ggcatcactg tcaatccaaa atgagaaacg tgctaatgag   2520
ctagagcaga gtgtagatca catgaaatat caaaagatac agctacaaag aaaactacga   2580
gaagaaaatg aaaaaaggaa gcaactggat gcagtaatta agcgggacca gcaaaaaatc   2640
aaagaaatac aattaaaaac aggacaggaa gaaggtctaa aaccgaaagc tgaggacctt   2700
gatgcatgta acttgaaaag gagaaaaggt tcgtttggaa gtatagacca tctccagaaa   2760
ttggatgagc aaaagaaatg gttagatgaa gaagtagaga aagttctgaa ccaacgccaa   2820
gaattagagg agctggaagc agacttaaag aaacgggagg ccatagtttc taagaaggag   2880
gctctgttac aggagaagag tcacctggaa aataagaaat tgagatctag tcaggcctta   2940
aacacagata gtttgaaaat atcaactcgc ctgaacttac tggaacaaga gttgtctgaa   3000
aagaatgtgc agctccagac cagtacagct gaggagaaaa caaagatttc agaacaagtt   3060
gaagtcctcc agaaagaaaa ggatcagctc cagaaacgca gacacaatgt ggatgaaaaa   3120
cttaaaaatg gtagagtgtt atcacctgaa gaagaacatg ttcttttcca acttgaagaa   3180
gggattgaag ctttggaagc tgcaattgaa tacaggaatg aaagtatcca gaatcgccag   3240
aagtcactta gagcatcatt ccataacctc tctcgtggtg aagcaaatgt cttggaaaag   3300
ctagcttgcc tgagtcctgt tgagattaga actattcttt tcagatattt caataaggtg   3360
gtgaatttgc gagaagctga acggaaacaa cagttatata atgaagaaat gaaaatgaaa   3420
gttctggaac gggataatat ggttcgtgaa ttagaatctg cactggacca tctaaaattg   3480
cagtgtgacc ggagactgac cctccagcaa aaggaacacg aacaaaagat gcagttgcta   3540
ttacatcatt tcaaagaaca agatggagaa ggcattatgg aaactttcaa aacatatgaa   3600
gataaaatcc agcagttgga aaaagatctt tatttctata agaaaaccag ccgggatcat   3660
aagaagaaac ttaaggaact ggtaggggaa gcaattcggc ggcaactagc accatcagag   3720
tatcaagagg ctggagatgg agtcctgaag ccagaaggag gaggcatgct ttcagaagaa   3780
ttaaaatggg catccagacc tgaaagtatg aaattaagtg gaagagaaag agaaatggac   3840
agttcagcaa gcagcttaag aacacagcca aatcctcaaa agctctggga agatatccca   3900
gaattacctc caattcatag ttctttagca ccccccagtg ggcatatgtt aggtaatgag   3960
aataaaacag aaacagatga taatcagttt acaaaatctc acagtcgact gtcatcccaa   4020
```

-continued attcaggttg tgggaaatgt gggacgactt catggtgtca cacctgtaaa actgtgtcga 4080
aaagaattac gtcaaatttc cgccttggaa ctatcattgc gacgttccag tcttggagtt 4140
ggcattggat caatggctgc tgattccatc gaagtatcta ggaaaccaag ggacttaaaa 4200
acttag 4206

<210> SEQ ID NO 36
<211> LENGTH: 2022
<212> TYPE: DNA
<213> ORGANISM: Homo sapiens

<400> SEQUENCE: 36
atggatccgc agaggtcccc cctattggaa gtaaagggga acatagaact gaagagacct 60
ctgattaagg ccccttccca gctgcctctc tcaggaagca gactcaagag gaggcctgac 120
cagatggaag atggcctgga gcctgagaag aaacggacaa gaggcctggg tgcaacgacc 180
aaaattacca catcccaccc aagagttcca tccctcacta cagtgccaca gacacaaggc 240
cagaccacag ctcaaaaagt ttccaagaag acaggacccc ggtgttccac agctattgcc 300
acagggttga agaaccagaa gccagttcct gctgttcctg tccagaagtc tggcacatca 360
ggtgttcctc ccatggcagg agggaagaaa cccagcaaac gtccagcctg ggacttaaag 420
ggtcagttat gtgacctaaa tgcagaacta aaacggtgcc gtgagaggac tcaaacgttg 480
gaccaagaga accagcagct tcaggaccag ctcagagatg cccagcagca ggtcaaggcc 540
ctggggacag agcgcacaac actggagggg catttagcca aggtacaggc ccaggctgag 600
cagggccaac aggagctgaa gaacttgcgt gcttgtgtcc tggagctgga agagcggctg 660
agcacgcagg agggcttggt gcaagagctt cagaaaaaac aggtggaatt gcaggaagaa 720
cggaggggac tgatgtccca actagaggag aaggagagga ggctgcagac atcagaagca 780
gccctgtcaa gcagccaagc agaggtggca tctctgcggc aggagactgt ggcccaggca 840
gccttactga ctgagcggga agaacgtctt catgggctag aaatggagcg ccggcgactg 900
cacaaccagc tgcaggaact caagggcaac atccgtgtat tctgccgggt ccgccctgtc 960
ctgccggggg agcccactcc accccctggc ctcctcctgt ttccctctgg ccctggtggg 1020
ccctctgatc ctccaacccg ccttagcctc tcccggtctg acgagcggcg tgggaccctg 1080
agtggggcac cagctccccc aactcgccat gatttttcct ttgaccgggt attcccacca 1140
ggaagtggac aggatgaagt gtttgaagag attgccatgc ttgtccagtc agccctggat 1200
ggctatccag tatgcatctt tgcctatggc cagacaggca gtggcaagac cttcacaatg 1260
gagggtgggc ctgggggaga cccccagttg gaggggctga tccctcgggc cctgcggcac 1320
ctcttctctg tggctcagga gctgagtggt cagggctgga cctacagctt tgtagcaagc 1380
tacgtagaga tctacaatga gactgtccgg gacctgctgg ccactggaac ccggaagggt 1440
caagggggcg agtgtgagat tcgccgtgca gggccaggga gtgaggagct cactgtcacc 1500
aatgctcgat atgtccctgt ctcctgtgag aaagaagtgg acgccctgct tcatctggcc 1560
cgccagaatc gggctgtggc ccgcacagcc cagaatgaac ggtcatcacg cagccacagt 1620
gtattccagc tacagatttc tggggagcac tccagccgag gcctgcagtg tggggccccc 1680
ctcagtcttg tggacctggc cgggagtgag cgacttgacc ccggcttagc cctcggcccc 1740
ggggagcggg aacgccttcg ggaaacacag gccattaaca gcagcctgtc cacgctgggg 1800
ctggttatca tggccctgag caacaaggag tcccacgtgc cttaccggaa cagcaaactg 1860
acctacctgc tgcagaactc tctgggtggt agtgctaaga tgctcatgtt tgtgaacatt 1920
tctccactgg aagagaacgt ctccgagtcc ctcaactctc tacgctttgc ctccaaggtg 1980
aaccagtgtg ttattggtac tgctcaggcc aacaggaagt ga 2022

<210> SEQ ID NO 37
<211> LENGTH: 2517
<212> TYPE: DNA
<213> ORGANISM: Homo sapiens

<400> SEQUENCE: 37
atgtacgcct tttactcgtt gctcatctac atcttctaca gcctcttccg cagggatggt 60
ggcgccgcgg cggccgcgga gcccggggac cccgcccaga gagcccgcaa gccccggggt 120
cgccggcgcc cagacctgcc cgcgccagag ctgtggaccg agctgaccgg cctggccgcc 180
agctccgagc ctgaggatgg gtcggaaggc gcagccgagg gccgcgcggc cgcggtgtcc 240
ctggaagagg ccctactgcg cctcgccgag ttcctctccg tccagctggg ggcggaagag 300
agctgcgggg gcccggcgga cctgggccag tctggcgagg tcccctcact gttgacagtg 360
accagtcagc tcttggccct tctggcatgg cttcgaagcc ccaggggggag gcaggccctg 420 ctccagggga ctcagccagc ccctcgggtc cggcccccct ctccagatgg atccacatcc 480
caagaagaaa gcccttccca cttcaccgca gtcccaggcg agccactggg ggatgagacc 540
cagggacagc agcccctcca gttggaggag gatcagaggg cgtggcagcg gctggagcag 600
ctcatcctgg gacagctgga ggagctgaag cagcagctgg aacagcagga ggaggagttg 660
ggtcgactgc gcctgggcgt gggggcgacg gactcagaga aaagggttca gcatctgact 720
ctggagaacg aggccctgaa gcagagcctg agtctcatgc gggacctcct gctgcactgg 780
ggccccgggc cccccatcag ggctccgcag gaggaggcag aggcattgct agagctccag 840
ggccggcttc aggaggccca agacaccaca gaagccctcc gagcccagct gggggtgcag 900
gaggtgcagc tgcagggcct tcaaggggcc ctccagcagc tccagcagga gacggagcag 960
aactgcaggc gtgagctaca gcagatgcat gggcagctgg caggacttcg ggcacggatg 1020
gccagcctgc gtcagggctg cggggacctc cgaggtttgg tcagcacctt tacccagagc 1080
tgtcagggtt cgctgagtga ggcccggggc caggtgtcct gggccttggg ggcactgtca 1140
tctggagggc ctggcactca gctccctgag ggcagcaagg ggcccccagc cggatgccca 1200
gggcggctgc cagaactcaa gggaaatatc cgtgtgctgt gtcggctgag gccagggaca 1260
tcttctagcc ttgtgagtgt ggagcctggc ccagggggca ccgtcaccac ctgctaccgg 1320
gggcgccatc gtcgattccg cctagactgg gtcttccctc cagacgccag ccaggaggag 1380
gtcttcagag agctggaacc tgcggtgctg tcctgcctcc gaggctacag cgtctgcatc 1440
ttcacctatg gccagacagg caccgggaag acctacagca tggagggccc tcctgaggac 1500
cccggcatag ttcctagggc gctgcagtcg ctgttccggg agatgggggc cggccggcag 1560
caccgggtga cactcagcat ggtggagatc tacaatgagg ctgtcaggga cctccttgct 1620
ccagggcctc ccgagcgcct ggccgtgagg cagggcccag aaggccaggg cgggatccag 1680
gtggctggcc tcacccactg ggacgtgccc aacctggaga cattgcacca gatgctgaaa 1740
ctggggagga gcaaccgggc caccgccgcc accgccatga accagcgcag ctcccgctcg 1800
catgccctgg tcacgctgac gctgcgcgcg gcgtctccac cgcgcgctcc aggcaccgca 1860
ggcacgctgc acctggtgga cctggcggga tccgaacgcg cacggaaggc aggggcggcc 1920
ggcccgccgc ggggagaccc agacggcgcc cggcgcctgc gggaggccca gaccataaac 1980

```
cgctcgctgc tggcgctagg aggcgtgatg gccgcactgc gggcccaccg gccgcacgtg   2040
cccttccgcg actcgcagct cacgcgactg ctgcagccgg cgctgggccc aggcaccacc   2100
gcggtgctgc tgctgcaggt gggcgccggg gcggggcagg tgtgtgcgtg ccggtcgccg   2160
cccacccggg cccgcccacc cgcgcctctt gcccgcagat ctccacgcgg ccggaggatc   2220
tcggggagac agtctgctcc ctcaagttcg ccgaccgagt gggtcaagtg gagctggggc   2280
cagcccggcg ccgcagggtc ccgcgctcct ccgggacgcc ttcttccctc agcaccgaca   2340
ctccgctcac cgggaccccc tgcaccccta cgccgtcccc tggcagtcct ccatgcccca   2400
gtcccgacaa cggctcgggc tcggctctcg cgcccgcaga gggcctgccc ctctagtcct   2460
gggtcgcggc cctgcccatg gggtctcagg ccaggtctct gctggcagag gcggtag      2517
```

<210> SEQ ID NO 38
<211> LENGTH: 2502
<212> TYPE: DNA
<213> ORGANISM: Homo sapiens

<400> SEQUENCE: 38

```
atggtcccct ctcgcaggac gtggaacctg ggagccacgc cctcgctgcg gggcctgtgg     60
agagtgggcc gggccccgga gcccgagccg gggatggctc gccccgcccc agccccagcc    120
agcccggccg cccgcccttt cccacacacc ggcccgggga ggttgagaac tgggcgtgga    180
aaagataccc cagtctgcgg tgacgaggac tccagtgccc gaagtgcagc tcgcccagcc    240
ctagctcagt gccgagccct tagcgtggac tgggctggcc ccggaagccc ccacgggctc    300
tacctgaccc tgcaggtaga acacctgaag gagaagctca ttagccaggc ccaggaagtg    360
agccgactgc gatctgagct ggggggcacc gacttggaga agcaccggga cctgctgatg    420
gtggagaatg agcgactgag gcaggagatg cggcgctgtg aggccgagct gcaagagctg    480
cgcacaaagc cagcaggtcc ctgcccaggt tgtgagcaca gccaggagag cgcccagctc    540
cgtgacaagc tgtcccagct gcagctggag atggcggaaa gcaaaggcat gctgtcagag    600
ctgaacctag aggtgcagca gaagaccgac cggctggctg aggtggagct gcgactcaag    660
gactgcctgg ctgagaaggc acaggaggag gagcggctta gtcggcgcct gcgtgacagc    720
cacgagacca ttgccagcct gcgggcccag tccccacctg tcaagtatgt catcaagaca    780
gtggaggtgg agtcgtccaa gaccaagcag gccctcagcg agtcccaggc ccggaaccag    840
cacctgcagg agcaggtggc tatgcagagg caggtgctga aggagatgga acagcagctg    900
cagagctcac accagctgac cgcgcggctc cgggcgcaga ttgccatgta cgagtcagag    960
ctggagcggg cccatgggca gatgctggag gagatgcagt ccctggaaga ggacaagaac   1020
cgggccattg aggaggcctt tgccagagcc caggtggaga tgaaggctgt gcacgagaat   1080
ctagcaggcg tccggaccaa cttgctgacc ttgcagccgg cactgcggac cctcaccaac   1140
gactacaatg ggctcaagcg gcaggtgcgc ggcttcccac tgctgctgca ggaggccctc   1200
aggagtgtca aggccgagat aggccaggcc atcgaggagg tcaacagcaa caaccaggag   1260
ctgctgcgca agtaccgccg cgagctgcag ctgcgtaaga agtgccacaa tgagctcgtg   1320
cggctgaaag ggaacatccg agtgattgct cgtgtccggc cagtcaccaa agaggatggg   1380
gaaggacctg aggccaccaa tgctgtgact ttcgatgccg acgacgactc catcatccac   1440
ctgctgcaca agggcaagcc tgtgtccttc gagctggaca aggtcttctc cccacaggcc   1500
tcgcagcagg acgtgttcca ggaggtgcag gccctggtca cctcttgcat tgatggcttc   1560
```

aatgtctgca tctttgcgta cggccagacg ggcgccggca agacgtacac gatggagggg 1620
accgctgaga acccaggtat caaccagcgg gccctgcagc tgctcttctc cgaggtgcag 1680
gagaaggcgt ctgactggga gtacaccatc accgtcagcg ctgcggagat ctacaatgag 1740
gtcctcaggg acctgctagg gaaagagcct caggaaaaac tggagatccg gctgtgccca 1800
gacggcagtg ggcagctgta tgtaccaggg ctgactgagt tccaagtgca gagcgtggac 1860
gacatcaaca aggtgtttga gtttggccac actaatcgca cgaccgagtt caccaacctg 1920
aacgagcaca gctcccgctc gcacgcgctg ctcatcgtga cggtgcgagg cgtggactgc 1980
agcacaggcc tccgcaccac ggggaagctg aacctggtgg acttggctgg ctcggagcgc 2040
gtgggcaagt cgggggccga gggcagccgc ctgcgggagg cgcagcacat caacaagtcg 2100
ctgtcggctc tgggggacgt cattgctgcc ctgcgctccc gccagggcca cgtgcccttc 2160
cgcaactcca agctcaccta cctgctgcag gattcgctta gtggtgacag caagaccctc 2220
atggtggtac aggtgtcccc cgtggagaag aacactagcg agacgctcta ttccctcaag 2280
tttgctgaga gggtgcgctc tgtggagctg gggcctgggc tacgcagggc agagcttggg 2340
tcctggtcaa gccaggagca tctagagtgg gagccggctt gtcagacgcc acagccctcg 2400
gcacgggccc actcagcccc cagctctggg accagtagcc gccctggatc catccggagg 2460
aagctgcagc cctcggggaa gtcgcggcca ctgcctgtgt ga 2502

<210> SEQ ID NO 39
<211> LENGTH: 12798
<212> TYPE: DNA
<213> ORGANISM: Homo sapiens

<400> SEQUENCE: 39
atggagcagc ctaacagtaa aggctatagc ctgggaagga cccctcaggg cccagagtgc 60
agcagtgctc ctgcagtcca agtggggacc cacaggggcc tagagtataa cccggggaag 120
attcttccag gatcagacta tgggttggga aatcctccag cccttgaccc caagctccca 180
catttacccc tgcccccggc cccacccaca ctctcagact tggggcagcc acggaagtca 240
cccctgacag gcactgataa gaagtacccg ctgatgaagc agcgtgggtt ctactccgac 300
atcctcagcc ctggaacctt agatcaactt ggggaggtat gtcgtggccc ccgaatgagc 360
cagaacctcc tgcggcaggc tgaccttgac aagttcaccc caagagtcgg aagctttgag 420
gttcctgaag acttccagga gcgcatggag cagcagtgca tcgggtccac cacccggctg 480
ctcgcccaga ctgacttccc actgcaggcc tacgagccca agatgcaggt gcctttccag 540
gtgctgccag gccagcatcc tcgcaagatt gagatcgaga ggaggaaaca gcagtacctg 600
agcctggaca ttgagcagtt gctgttcagc cagggcatcg actccaacaa gctcatgccc 660
aggcacctgg accaccagca cccccaaacc atcgaacagg gccatgaccc aatcttcccc 720
atctacctcc cactgaaggt atttgacaat gaggactttg actgccggac tcccagagag 780
tggatcaaca tgggcttgga gccagggtct ctggacagga aacctgtccc gggaaaagcc 840
ctcttgccca ctgatgactt cctggggcat gaggacccca agagtcagaa gctgaagtac 900
aaatggtgcg aggtcggcgt cctggactac gacgaggaga agaagctata cctggtacac 960
aagacagacg agaaaggcct ggtgcgagat gagatgggga ggcccatcct gaatgcaggg 1020
gtcaccactg aaggaaggcc accccttcag gtctgtcagt actgggtgcc acggatccag 1080
cttctcttct gcgctgagga cccttgcatg ttcgcacaac gtgtggtcca ggccaacgcc 1140
ctgcgcaaga acacggaagc actgctgctc tacaacttgt atgtggactg catgccctct 1200

-continued

```
gacggccagc atgtcatcag tgaacagagc ctgagcaaga tcaagcagtg ggccctgagc   1260
acgcctcgga tgcgcaaagg cccctcggtt ctagagcacc tcagcagtct tgccagagaa   1320
gtgagcctgg actatgagcg cagcatgaac aagatcaact ttgaccacgt tgtctcttcc   1380
aagcccgaga ccttctccta cgtcaccctc cccaagaagg aggaggagca ggtgcctgag   1440
cgagggctgg tgagtgtccc caagtaccac ttctgggagc agaaggagga cttcactttc   1500
gtgtccctgc tcacacggcc agaggtcatc acggccctca gcaaggtgag ggccgagtgc   1560
aacaaggtga ccgccatgtc cctgttccac tcgagcctct ccaagtacag ccacctggag   1620
gaatttgagc agatccagtc acagaccttc tcccaggtgc agatgttcct caaggacagc   1680
tggatcagct cgctaaaggt ggccatgcgc agcagcctgc gcgacatgag caagggctgg   1740
tacaacctct acgagaccaa ctgggaggtg tacctcatgt ccaagctgcg caagctgatg   1800
gagctggtga agtacatgct gcaggacaca ctgcgcttcc tggtgcagga ctcacttgcc   1860
agcttctcac agttcatcag cgacacctgt tgcagcgtgc tcaactgcac cgatgacatg   1920
gtctggggtg acgacttaat taacagcccc tacaggcccc ggaagaatcc cctgttcatc   1980
atggacctgg tgctggacag ctctggggtg cactatagca ccccactgga gcagtttgag   2040
gcatctctgc tgaacctctt cgacaagggc atcctggcca cccatgccgt gccccagctg   2100
gagaagctgg tgatggagga catcttcatc agcggtgacc ccctgctgga gtccgtgggc   2160
cttcatgagc cactggtgga agagctacgg gccaccattg ccagtgccgt gtccaaggcc   2220
atgatcccac tgcaggccta cgccaaggag taccgaaagt acctggagct gaacaacaat   2280
gacattgcct cctttctcaa aacctaccag acgcagggcc tgttggccca ggaggtgcgg   2340
gaggtagtgc tcacccacct gcgggagaag gagatcctgg acagctcgct gcccagcagc   2400
atcatcattg ggcctttcta catcaacacc gacaatgtca agcagagcct gtccaagaaa   2460
cgcaaggccc tggccacttc cgtgctggac atccttgcca agaacctgca taaggaggtg   2520
gatagcatct gcgaggagtt ccgcagcatc agccgcaaga tctatgagaa gcccaacagc   2580
attgaggagc tggctgagct gcgagagtgg atgaagggca tcccggagag gctggtgggc   2640
ctggaggagc ggattgtgaa ggtcatggat gactaccagg tcatggatga attcctctac   2700
aacctcagct cagatgactt caatgacaaa tggattgcca gcaactggcc ttctaagatc   2760
cttgggcaga tagagctggt gcagcagcag catgtggagg atgaggagaa gttccgcaaa   2820
atccagatca tggatcagaa caacttccaa gagaagctgg aagggctgca gctggtagta   2880
gctggcttct ccatccatgt ggagatttca cgtgcacacg agatcgccaa cgaggtgcgg   2940
cgtgtcaaga agcagctgaa ggactgccag cagctggcca tgctctacaa caaccgcgag   3000
cgcatcttca gcttgcccat caccaattat gacaagctct ccaggatggt gaaggagttc   3060
caaccctacc tggacctttg gaccacagcg tctgactggc tgcgctggtc ggagagctgg   3120
atgaatgacc ccctctctgc catcgatgct gagcagctgg agaagaacgt ggttgaagcc   3180
ttcaagacca tgcacaagtg cgtgaagcag tttaaggaca tgccagcctg ccaggaagtg   3240
gccttggaca tccgggcccg catcgaggag ttcaaaccat acatcccact gatccagggg   3300
ctgcgcaacc ctggcatgcg gatccggcac tgggagacac tgtccaacca gatcaacatc   3360
aatgtcaggc ccaaggccaa cctgaccttt gctcgctgcc tggagatgaa cctgcaggac   3420
catatcgaga gcatcagcaa ggtggctgag gtggctggca aggagtacgc catcgagcag   3480
gcactggaca agatggagaa ggagtggtcg accatcctgt tcaatgtact gccctacaag   3540
```

-continued

```
gcgacagaca cctacatcct gaagagcccg gacgaggcct cacagctgct ggacgaccac   3600
atcgtcatga cccagaatat gtcattttca ccctacaaga agccctttga gcagcgcatc   3660
aactcctggg agaacaaact gaagctgacc caggaggttc tggaggagtg gctgaactgt   3720
cagcggtcct ggctctacct ggagcccatc tttagctctg aggacatcaa ccagcagctg   3780
cctgtggaga gcaagcgcta ccagaccatg gagcggatct ggaagaagat catgaagaat   3840
gcctacgaga accgggaggt gatcaatgtg tgttccgacc tgagaatgct ggacagcctg   3900
cgggactgca acaagattct ggacctggtg cagaagggcc tcagcgagta tctggagacc   3960
aagaggagcg ccttccccag attctacttc ctgtcagatg atgaactact agagatcttg   4020
tcgcagacaa aggaccccac ggccgtgcag ccacacctgc gcaagtgctt cgagaacatc   4080
gctcggctgc tattccagga ggacctggag atcacgcaca tgtactcagc cgagggggag   4140
gaggtacagt tgtgcttctc catctacccc tccagcaacg tggaggactg gctgcgggag   4200
gtggagcgca gcatgaaggc cagtgtgcac gacatcattg agaaggccat cagggcctac   4260
cccacgatgc ccaggaccca gtgggttctg aactggcctg gccaggtgac catcgctggg   4320
tgccagacct actggaccat ggaggtggca gaggctctgg aggccggcaa cctcagaagc   4380
caactgttcc cccagctctg ccagcagctc agtgatctgg tggcccttgt gcgggggaag   4440
ctgtcccgca tgcagcgggc agtgctgtca gcgctaatcg tcattgaggt ccatgccaag   4500
gacgtggtga gcaagctaat ccaggagaac gtggtcagcg tgaatgactt ccagtggatc   4560
tcacagctga ggtactactg gacaaataat gacctgtata tccgtgctgt gaatgctgag   4620
ttcatctatg gctatgagta cctgggcaac agtgggaggc tggtgatcac gcccctcacc   4680
gacaggtgct acctgacact gaccggagct ctgcacctca agtttggggg tgccccagct   4740
ggcccagctg gcacaggcaa aactgagacc accaaagacc tgggtaaggc cttggccata   4800
cagaccgttg tgttcaactg ctctgaccag ctcgacttca tggccatggg caagttcttc   4860
aagggcctgg ccagtgctgg ggcctgggcc tgcttcgacg agttcaatcg catcgacatc   4920
gaggtgctgt ctgtggtggc gcagcagatc accaccatcc agaaggcgca gcagcagcgg   4980
gtggaacgct tcatgtttga gggtgtggag atcccactgg tgccatcctg cgcagtgttt   5040
atcaccatga acccgggcta cgctggccgc acggagctgc ctgacaatct gaaggcgctc   5100
ttccgacccg tggccatgat ggttccagat tacgccatga tcactgagat ctccctctat   5160
tcctttggct ttaatgaggc cagtgtgctg gctaagaaga tcacaaccac cttcaagctg   5220
tcttctgagc agctcagctc ccaggatcac tatgacttcg ggatgagagc cgtgaaaact   5280
gtgatctcgg ctgctgggaa cctcaagcga gaaaacccca gcatgaatga ggagctgatc   5340
tgcctccggg ccatccgtga tgtgaacgtg cccaagttcc tgcaggagga cctcaagctc   5400
ttctctggca tcgtgtccga cctgtttccc accatcaagg aggaggacac ggactacggc   5460
atcctggatg aggccatccg cgaggcctgc aggaacagca acctcaagga tgtggagggc   5520
ttcctgacaa agtgcatcca gctctacgag accacggtgg tacgacacgg cctcatgctc   5580
gtcgggccca caggctccgg caagagtact tgttacagag tcctggcagc tgccatgacg   5640
tcactgaaag ggcagccatc catcagtggt ggcatgtacg aggctgtcaa ctactacgtg   5700
ctcaacccca agtccatcac gatgggccag ctgtacgggg agtttgacct cctcacccat   5760
gagtggacag acgggatatt ctcctcgttc atccgggcgg gggccatcac ctccgacacc   5820
aacaagaagt ggtacatgtt cgatgggccg gtggatgcca tctggattga gaacatgaac   5880
acggtgctgg atgacaacaa gaagctgtgc ctcagctctg ggagatcat caagctcaca    5940
```

```
gaggcaatga ccatgatgtt cgaggtgcaa gacctggcgg tggcttcacc agctacagtc   6000
tcccgctgtg gcatggtgta cctggagccc agcatcctgg ggctcatgcc cttcatcgag   6060
tgctggctga ggaagctgcc tcccttgctg aagccctatg aggagcattt caaggccctc   6120
tttgtcagct tcctggagga atccatctcc ttcgttcggt cctcagtgaa ggaggtgatc   6180
gcctcaacca actgcaacct gaccatgagc ctcctcaagc tgctggactg cttcttcaag   6240
ccctttctgc ctagagaggg cctcaagaaa ataccctctg aaaagctgag tcgcatcgta   6300
gagttgatcg agccctggtt catcttctcc ctgatctgga gcgtgggtgc cactggggac   6360
agcagtggcc gcaccagttt cagccactgg ctaaggctca agatggagaa cgaacagctg   6420
actctgcttt tcccagaaga ggggctggtg ttcgattaca ggctggagga cgcgggcatc   6480
agtggcacca acgacagtga ggatgaagag gaggaataca agcaggttgc ctgggtgaag   6540
tggatggact cctcagctcc attcaccatg gtaccagaca ccaactactg caacatcatt   6600
gtgcccacca tggacaccgt gcagatgtcc catttactgg acatgctgct caccaacaag   6660
aagcccgtgc tgtgcattgg gccaacaggc acggggaaga cgctcaccat ctctgacaag   6720
ctcctcaaga acctggcact ggattacatc agccacttcc tcaccttctc agcccgcact   6780
tcagccaacc agacccagga cttcattgac agcaagctgg acaagaggcg gaagggtgtg   6840
tttggaccac ctctggggcg caactttatc ttcttcatcg atgacctgaa catgccggcc   6900
ctggagacct acggtgcaca gccacccatc gagctgttgc gccagtggat ggaccacggc   6960
ggctggtacg accgcaagat cattggtgcc ttcaagaacc tagtggacat caactttgtc   7020
tgtgccatgg gcccccgggg tggaggcagg aacaccgtca ccccgcggct gatgcgtcac   7080
ttcaactacc tgtctttcgc tgagatggac gaggtcagca agaaacgcat cttctccacc   7140
atcctgggca actggttgga tggactcctt ggagaaaaaa gctaccggga gcgtgtgcct   7200
ggggcccccc acattgccca cttcacggag cccctgtgg aagccaccat catggtgtat    7260
gcaaccatca cctcccagct gctgcccact ccagccaagt cccactacac cttcaacctg   7320
agggacctct ccaaggtctt ccaaggcatg ctcatggctg acccggccaa ggtcgaggac   7380
caagtgcagc tgctgcgact gtggtatcac gagaactgcc gcgtgttccg ggaccgactg   7440
gtgaatgagg aggaccgcag ctggttcgac cagctcctca agcgctgcat ggagcagtgg   7500
gaggtgacct tcaacaaggt ctgccccttc cagcccattc tttacgggga cttcatgtca   7560
ccaggctccg atgtcaagtc ctacgagctc atcaccagtg agagtaagat gatgcaggtg   7620
atagaggagt acatagagga ctacaaccag atcaacacgg ccaagctgaa gctggtcctc   7680
ttcatggacg ccatgagcca catctgtcgc atcagccgca ccctacgcca ggcgctgggc   7740
aatgcactcc tgctgggcgt gggtggcagc ggccgcagct ccctcacaag gctcgcctcg   7800
cacatggccg agtacgagtg cttccagatt gaactatcca agaactacgg catgtccgag   7860
tggcgagatg atgtgaagaa ggtcctgctc aaggcgggcc tacagaacct acccatcacc   7920
ttcctcttct cagacaccca gatcaagaac gaatccttcc tggaagatat caacaacgtc   7980
ctaaactctg gtgacattcc caatctgtat actgcggacg agcaggacca gatcgtcagc   8040
accatgcggc cctatatcca ggagcagggc ctacagccca ccaaggccaa cctcatggct   8100
gcttacacag ggcgtgtgcg cagcaacatc cacatggtgc tgtgcatgag ccccatcgga   8160
gaggtcttcc gagctcgtct gaggcagttt ccctccctgg tcaactgctg taccatcgac   8220
tggtttaacg agtggccggc agaagccctg aagtctgtgg ccaccgtgtt cctcaatgag   8280
```

-continued

```
atcccagaac tggaatcctc ccaggaagaa atccaaggac tgatccaggt ctgtgtgtac   8340
atccaccagt cggtgtccaa gaagtgcatc gagtacctgg cagagctgac ccgccacaac   8400
tatgtgaccc ccaagagcta cttggagctg cttcatattt tctccatcct catcgggcag   8460
aagaaactgg agctgaaaac tgccaagaac cgcatgaaga gcggcctcga caagctgctg   8520
cgcacttctg aggatgtagc caagatgcag gaggacctgg agagtatgca ccccctgctg   8580
gaggaggctg ccaaggacac catgctcacc atggagcaga tcaaggtgga tacggccatc   8640
gccgaggaga cccggaattc agtgcagaca gaggagatca aagccaatga gaaggccaag   8700
aaggcacaag ctattgctga cgatgcccag aaggacctgg acgaggcgtt gccagccctg   8760
gatgcggctc tggccagcct gcgcaacctc aacaagaacg atgtgaccga ggtacgtgcc   8820
atgcagcggc cacccccggg tgtgaaactg gtcatagaag ctgtgtgcat tatgaaaggc   8880
atcaagccca agaaggtgcc tggagaaaag ccaggcacca aggtggatga ctactgggag   8940
cctggcaagg ggctgctgca ggacccgggc cacttccttg agagcctctt caagtttgac   9000
aaggacaaca ttggggatgt ggtgatcaaa gccatccagc cgtacatcga taatgaagag   9060
ttccagccag ccaccattgc caaggtgtcc aaggcttgca cctccatctg ccagtgggtg   9120
cgcgccatgc acaagtacca ctttgtggcc aaggccgtgg agcccaagcg gcaagccctg   9180
ctggaggccc aggatgacct gggggtgaca cagaggatcc tggatgaggc aaaacagcgc   9240
cttcgtgagg tggaggacgg catcgccaca atgcaggcta agtaccggga atgcattacc   9300
aagaaggagg agctggagct gaagtgtgag cagtgtgagc agcggctggg ccgagctggc   9360
aagctcatca acgggctgtc ggatgagaag gtgcgctggc aggagacggt ggagaacctg   9420
cagtacatgc tcaacaacat ctccggcgat gtcctggtgg ccgctggctt tgtggcctac   9480
ctgggcccct tcacgggcca gtaccgcacg gtgctctacg acagctgggt caagcagctc   9540
aggagccaca atgtcccaca cacctccgag cccacgctaa tcgggacgct ggggaaccct   9600
gtgaagatcc gatcgtggca gatcgctggc ctccccaacg acacactgtc agtggagaac   9660
ggggtcatca accagttttc ccagcgctgg acccacttca ttgaccctca gagccaggcc   9720
aacaaatgga tcaagaacat ggagaaggac aatgggctgg atgtgttcaa gttgagtgac   9780
cgcgacttcc tgcgcagcat ggagaacgcc atccgctttg gcaagccatg tctcctggag   9840
aacgtgggcg aggagctaga cccagccctg gagccagtgc tgctcaagca gacgtacaag   9900
cagcagggaa acacggtgct gaagctgggg gacacggtga tcccctacca tgaggacttc   9960
aggatgtaca tcaccaccaa gctgcccaac ccacactaca cgcccgagat ctccaccaaa  10020
ctcaccctca tcaacttcac cctgtcgccc agtggcctag aggaccagct actgggccag  10080
gtagtggcag aggagcgacc cgacctggag gaggccaaga accagctgat tatcagtaat  10140
gccaagatgc gccaggagct gaaggacatt gaggaccaga tcctgtaccg gctcagctcc  10200
tccgagggca accctgtaga tgacatggaa ctcatcaagg tgctggaagc ctccaagatg  10260
aaggctgctg agatccaggc caaagtcagg attgcagagc agacggagaa ggacatcgac  10320
ctgacgcgca tggagtacat acccgtggcc atccgcaccc agatcctctt cttctgtgtg  10380
tccgacctgg ccaacgtgga ccccatgtac cagtactccc ttgagtggtt tctcaacatc  10440
ttcctctcgg gcatcgccaa ctcagagaga gcagacaacc tgaagaagcg catctccaac  10500
atcaaccgct acctgaccta cagcctctac agcaacgtct gccgcagcct ctttgagaag  10560
cacaagctga tgtttgcctt cctgctgtgt gttcgcatca tgatgaacga gggcaaaatc  10620
aaccagagtg agtggcgata cctcctgtct gggggctcca tctcgatcat gactgagaat  10680
```

ccggcaccgg actggctgtc agaccgggct tggcgagaca tcctagcact ctcgaacctg 10740
ccaacctttt cctccttctc ttccgacttc gtgaagcacc tctcagaatt ccgggtcatc 10800
ttcgacagcc ttgagcccca ccgggagcct ttgcctggca tctgggacca gtacctagac 10860
cagttccaga agctgctagt cctccgctgc ctgcgtgggg acaaggttac caacgccatg 10920
caggactttg tggccaccaa cctggagcca cgcttcattg aaccccagac agccaatctg 10980
tcagtggtgt tcaaagactc caactccacc acacccctca tctttgtgct gtcacccggc 11040
acagaccctg ctgccgacct ctacaagttt gccgaagaaa tgaagttctc caaaaagctc 11100
tctgccatct ccctgggcca ggggcagggc cctcgggcag aagccatgat gcgcagctcc 11160
atagagaggg gcaaatgggt cttcttccag aactgccacc tggcaccaag ctggatgcca 11220
gccctagaac gcctcatcga gcacatcaac cccgacaagg tacacaggga cttccgcctc 11280
tggctcacca gcctgcccag caacaagttc ccagtgtcca tcctgcagaa cggctccaag 11340
atgaccattg agccgccacg cggtgtcagg gccaacctgc tgaagtccta tagtagcctt 11400
ggtgaagact tcctcaactc ctgccacaag gtgatggagt tcaagtctct gctgctgtct 11460
ctgtgcttgt tccatgggaa cgccctggag cgccataagt ttgggcccct gggcttcaac 11520
atcccctatg agttcacgga tggagatctg cgcatctgca tcagccagct caagatgttc 11580
ctggacgaat atgatgacat cccctacaag gtcctcaagt acacggcagg ggagatcaat 11640
tacgggggcc gtgtcactga tgactgggac cggcgctgca tcatgaacat cttggaggac 11700
ttctacaacc ctgacgtgct ctcccctgag cacagctaca gcgcctcggg catctaccac 11760
cagatcccgc ctacctacga cctccacggc tacctctcct acatcaagag cctcccactc 11820
aatgatatgc ctgagatctt tggcctgcat gacaatgcca acatcacctt tgcccagaac 11880
gagacgttcg ccctcctggg caccatcatc cagctgcaac ccaaatcatc ttctgcaggc 11940
agccagggcc gggaggagat agtggaggac gtcacccaaa acattctgct caaggtgcct 12000
gagcctatca acttgcaatg ggtgatggcc aagtacccag tgctgtatga ggaatcaatg 12060
aacacagtac tagtacaaga ggtcattagg tacaatcggc tgctgcaggt gatcacacag 12120
acactgcaag acctactcaa ggcactcaag gggctggtag tgatgtcctc tcagctggag 12180
ctgatggctg ccagcctgta caacaatact gtgcctgagc tctggagtgc caaggcctac 12240
ccatcgctca agcctctgtc atcatgggtc atggacctgc tgcaacgcct ggactttctg 12300
caggcctgga tccaagatgg catcccagct gtcttctgga tcagtggatt cttcttcccc 12360
caggctttct taacaggcac tctgcagaat tttgcccgca aatttgtcat ctccattgac 12420
accatctcct ttgatttcaa ggtgatgttt gaggcaccat cagagttaac acaaagaccc 12480
caagtagggt gctatatcca tggattattc ctggaaggtg cccgctggga tccagaggcc 12540
ttccagctgg ctgagtctca gcccaaggag ctgtacacag agatggccgt tatctggctc 12600
ttgccaacac ccaaccgcaa ggcccaggac caggactttt acctgtgccc catctacaag 12660
acactgactc gtgctggaac actatcaacc acaggacact ctaccaacta tgtcattgct 12720
gtggagatcc ccacccatca gccccagcga cactggataa agcgtggtgt ggccctcatc 12780
tgtgccctgg actactag 12798

<210> SEQ ID NO 40
<211> LENGTH: 13284
<212> TYPE: DNA
<213> ORGANISM: Homo sapiens -continued

<400> SEQUENCE: 40
atgtccagca aagctgagaa gaagcagcga ttgagtggcc gaggaagctc ccaggcaagc 60
tggtcagggc gggccactcg ggctgctgtg gccacacagg agcaggggaa tgccccggct 120
gtcagtgagc cagagctgca ggctgagctc cccaaggagg agcctgagcc acggttggag 180
ggacctcaag cacagagtga agaatcagtg gagcccgagg cagatgtgaa gcccctcttc 240
ctttcccgag ctgcgctgac aggactggcg gatgcagtgt ggacacagga gcatgatgcc 300
attctggaac actttgccca ggaccctaca gaatccatcc tcaccatctt cattgaccct 360
tgttttgggc tgaagctaga gctgggcatg cctgtacaga cccagaacca gcttgtctac 420
ttcattcgcc aagcaccagt tcccatcacc tgggagaact tcgaggcaac tgtgcagttt 480
gggacggtgc ggggccccta tatcccggcc ctgcttcggc tgctcggtgg agtctttgcc 540
cctcagatct ttgcaaacac aggctggcct gagagcatta gaaatcattt tgcttctcat 600
ctgcacaagt tcttggcctg cctgacagac actcggtaca aactggaggg gcacacggtc 660
ctctacatcc ctgcagaggc catgaacatg aagcctgaga tggtgataaa ggacaaagag 720
ctggtgcaac ggctagagac ctccatgatc cactggaccc ggcagataaa ggagatgctc 780
agtgcccagg agactgtgga gacaggagaa aatttaggtc ctctggagga gattgagttc 840
tggcgcaacc gatgcatgga cctgtctggc atcagtaagc agctggtgaa gaagggagtg 900
aagcacgttg aatccatcct gcaccttgcc aagtcgtcct acttggcgcc ctttatgaaa 960
ctggcacagc agatccagga tggctctcgt caagcacagt caaacctgac ctttttgtca 1020
atcctgaagg aaccttacca ggagttggct ttcatgaagc ccaaggacat ctctagcaag 1080
ctccctaagc tgatcagtct catccgcatc atctgggtca actctcccca ctacaacact 1140
cgggagagac tgacctcgct cttccgaaag gtatgtgact gtcagtatca cttcgcccgc 1200
tgggaagatg gcaagcaggg tccccttcct tgcttctttg gtgcccaggg gccacagata 1260
acacggaact tgctggagat tgaggacatc tttcataaaa atctgcacac gctgcgagcc 1320
gttcgcgggg gtatcctgga tgtcaagaac acctgttggc atgaagacta caataagttc 1380
cgtgccggaa tcaaggacct ggaggtgatg acccagaacc tgatcacctc agccttcgag 1440
ttggtgcggg acgtgccgca cggcgtgctt ctgctggaca ccttccacag gcttgcctcc 1500
cgcgaggcta tcaagcggac ttatgacaag aaggcggtgg atctctacat gctgttcaat 1560
agcgagctgg ccctggtgaa ccgtgaacgg aacaagaaat ggccagacct ggagccctac 1620
gtggcccagt attccggaaa ggcgcgctgg gtgcacatcc tccggcgtcg catcgacaga 1680
gtcatgacct gccttgctgg tgctcatttc ctgccccgta ttgggactgg aaaggagagt 1740
gtgcacacct atcagcagat ggtccaggcc attgatgagc tggttcgaaa aaccttccaa 1800
gagtggacat caagtctgga caaggattgc attcggcggt tggatacccc attgctgcga 1860
atcagccagg agaaggcggg catgctggat gtcaactttg acaagtccct tctgattctc 1920
tttgcggaaa ttgactactg ggagcggctg ctgtttgaga cgccccatta cgtggtgaac 1980
gtagctgagc gagccgagga cctgcgcatt ctgcgtgaaa atctgctact cgttgctaga 2040
gactacaata ggattattgc catgctgtcc ccagatgagc aggccctatt caaagagcgt 2100
attcggctcc tggataagaa gatccacccg ggactcaaga aactgcactg ggccttgaag 2160
ggggccagtg ccttcttcat cacggagtgc cgtatacatg ccagcaaggt gcagatgatt 2220
gtgaatgagt tcaaggcatc cactctgacc attggctggc gagcccaaga gatgtcagag 2280
aagctgctgg tacgcattag tggcaaacgg gtatacaggg acctggaatt tgaagaggac 2340

-continued

```
caaagagagc atcgggcagc tgtacagcag aaattgatga acctgcacca ggatgtggtg   2400
accatcatga ccaactccta tgaggtcttc aagaatgatg gtcctgagat tcagcagcag   2460
tggatgctgt acatgattcg gctggaccgc atgatggagg atgccctgcg cctgaatgtg   2520
aagtggtcac tgctagaact atccaaggct atcaacgggg atggaaagac cagcccaaac   2580
ccactcttcc aagtccttgt cattttgaag aatgatctgc aaggaagtgt ggcacaggtg   2640
gaattctcac ccactctgca gactttggca ggtgtggtca atgacattgg caaccacctc   2700
ttttccacca tctctgtctt ctgccacctc cctgacattc tcaccaagcg caagttacat   2760
cgtgaaccca tccaaacagt tgtggagcaa gatgaggaca tcaagaagat ccagacccaa   2820
atcagcagcg gcatgactaa caacgcaagc ctgctgcaga actacctcaa gacctgggac   2880
atgtaccggg agatctggga gatcaacaag gactccttca ttcatcgcta ccagcgcctc   2940
aaccctcctg tctcttcttt tgttgccgac attgcccgct acacggaagt tgctaataac   3000
gtgcagaagg aggagacagt caccaacatc cagtttgtgc tgctggactg ttcgcacctc   3060
aagttctccc tggtgcagca ctgcaatgaa tggcagaaca agttcgcgac tctgctcagg   3120
gagatggctg ctgggcgcct cctggagctg cacacctacc tgaaggagaa cgcagagaaa   3180
atcagccgcc ctccgcagac actggaggaa ctgggggtca gcttgcagct cgtggatgcc   3240
ctgaagcacg acttggccaa cgtggagact cagatccctc ccatacacga gcaatttgcc   3300
attcttgaaa agtacgaggt gccagtcgag gacagtgtcc tggagatgct ggacagtctc   3360
aacggggagt gggttgtctt ccaacaaact ctgctggaca gtaagcaaat gctgaagaaa   3420
cacaaggaga aattcaagac aggcctgatc cactcggcag atgacttcaa gaagaaagca   3480
catacacttc tggaagattt cgaattcaaa ggccatttca ccagcaacgt gggatacatg   3540
tctgccttag accagattac acaagtgcgg gccatgctga tggccatgcg ggaagaggaa   3600
aatagtctcc gagccaacct gggcatcttc aagatcgagc agccaccctc caaggacctt   3660
cagaacctgg agaaggagct cgatgccctc cagcaaatct gggagatcgc acgagactgg   3720
gaggagaact ggaatgagtg gaagactggc cggttcctga tcctgcagac ggaaaccatg   3780
gagaccacgg cccacgggct gtttcgtcgc ctcacaaaat tagccaaaga gtataaggac   3840
cgaaactggg aaattattga aaccactcgc tcaaaaatag agcagttcaa gaggaccatg   3900
cctctcatct cagacctgcg gaaccctgcc cttagagaga ggcactggga ccaggtccgg   3960
gatgagatcc agcgggagtt tgatcaggaa tctgaaagct tcaccttgga gcagattgtg   4020
gagcttggga tggatcagca tgtggagaaa attggggaga tctctgcttc agcaactaaa   4080
gagctggcta tagaagtggc tttacaaaac attgccaaga cctgggatgt gactcagctc   4140
gacatagtac cctacaagga taagggccat catcggctca gaggtacaga agaagtattc   4200
caggcactgg aagataacca ggtagctctg tctaccatga aggcatcacg ctttgtcaag   4260
gcctttgaga aggatgtgga ccactgggaa cgctgcctct ccctcatttt ggaggttatt   4320
gagatgattc tcacagtgca gcgtcagtgg atgtacttag agaatatctt cctaggagaa   4380
gacatccgca agcagctgcc caatgaatcg accttatttg accaggtcaa cagcaactgg   4440
aaagccatca tggacaggat gaacaaggac aacaatgctc tccggagcac ccatcaccca   4500
ggcctcctgg acacattgat agaaatgaat acaatcctgg aagatattca gaaatctctg   4560
gatatgtatt tagagaccaa gcgacatatt ttcccccgct tctacttctt gtccaatgat   4620
gacctgctgg agattctggg ccagtcccga aacccagagg ctgtgcagcc acacctcaaa   4680
```

-continued

```
aaatgctttg acaacatcaa gttgctgaga atccagaagg ttggagggcc cagcagcaaa   4740
tgggaagctg tggggatgtt ctcgggcgac ggcgagtaca ttgacttcct ccactcagta   4800
tttttagaag gccctgtgga gtcctggctt ggcgatgtgg aacagaccat gagggtgacc   4860
ctgcgggacc ttctccggaa ctgccacctg gccctcagga agttcctcaa caagagggac   4920
aaatgggtga aggagtgggc tggccaggtg gtgatcactg ccagtcagat ccagtggacg   4980
gctgatgtca ccaagtgcct gctgacagcg aaggagcggg cagacaagaa aatcctcaag   5040
gtcatgaaga agaaccaggt gtcaatcctg aataagtatt cagaagccat caggggggaac   5100
ttgaccaaga tcatgcggct taaaattgtg gctctggtga cgatagaaat tcatgcccgg   5160
gatgtgttgg agaagcttta caagagtggc ctcatggatg tcaattcctt tgactggctc   5220
agccaacttc ggttctactg ggagaaggat cttgatgact gtgtcatccg ccagaccaac   5280
acgcaatttc agtataatta tgagtacttg ggtaactcgg gccggctcgt catcaccccc   5340
ctgacggaca ggtgttacat gacactgacc acggcattgc acctgcaccg agggggctcc   5400
cccaaaggcc ctgcaggcac aggcaagacc gagaccgtca aggacctggg caaggccctg   5460
ggcatatatg tcattgtggt caactgctct gagggcctgg actacaagtc catgggccga   5520
atgtactcag gtctggccca gactggagct tggggctgct ttgatgagtt taaccgcatc   5580
aacatcgagg tgctgtcagt ggtggcccac cagatcctgt gcatcctgtc tgccctggct   5640
gccggcctca cccatttcca ttttgatggc tttgaaataa atctggtgtg gtcctgtggg   5700
atcttcatta ccatgaatcc tggctatgct ggccgcacag agcttcccga aaatcttaaa   5760
tccatgttcc gcccaattgc catggtggtg cctgactcca ccctcattgc agaaatcatt   5820
ctctttggag agggctttgg caactgcaag attctggcca agaaggtgta cacactctac   5880
tcactggctg tgcagcagct gtccagacag gaccactatg actttggcct gcgtgccctc   5940
acctcccttc tgcgctatgc tggcaagaag cgccgcctac agccggatct gactgatgaa   6000
gaggttctgc tgctctcaat gagagatatg aacatcgcca agctcacttc agttgatgca   6060
cccctgttca atgccatcgt gcaagatctg tttcccaaca ttgagctgcc tgtcattgac   6120
tatggcaagc tgcgggagac cgttgagcag gagattcgag acatgggcct gcaaagcacg   6180
ccgttcaccc tcaccaaggt tttccagttg tatgaaacca agaactcccg ccactccacc   6240
atgatcgtgg gctgcacggg cagcggcaag actgcctcat ggcgcattct acaggcctcc   6300
ctgtcctctc tgtgccgcgc cggagaccct aacttcaaca ttgttagaga gttccctttg   6360
aaccccaagg cattgtccct aggggaactg tatggggaat atgacctcag caccaatgaa   6420
tggacagatg gcatcttgtc cagtgtcatg cggacggcat gtgcagatga gaaacccgac   6480
gagaagtgga tcctgttcga tggccccgtg gacacactgt ggatcgagaa catgaactcc   6540
gtcatggacg ataacaaggt gttgaccctc atcaacggcg agcgcatcgc gatgcccgag   6600
caggtgtctc tcctgtttga agtggaggac ctggcaatgg cctctccggc cactgtatcc   6660
cgctgcggga tggtctacac tgactacgct gacctgggct ggaagcccta tgttcagtca   6720
tggctggaga agaggccaaa ggctgaggtg gagccccttc aacgcatgtt cgaaaagctc   6780
atcaacaaga tgctggcctt taagaaggac aactgcaagg agctggtgcc cctgcccgag   6840
tacagcggta tcacctccct ctgcaagctg tactctgccc tggccacgcc agagaatggg   6900
gtgaacccag ctgacggcga gaactatgtc accatggtag agatgacatt tgtgttcagc   6960
atgatctggt ctgtgtgtgc ctctgtggat gaggagggcc ggaagaggat cgacagctac   7020
ctccgagaga tcgagggctc ctttcccaat aaggacacgg tatatgagta ttttgtggac   7080
```

-continued

```
cccaaaatac ggagttggac atcatttgag gacaagctcc ctaagagttg gcgctaccct   7140
ccaaacgccc ccttctataa gatcatggtg cccaccgtcg acactgttcg ctacaactac   7200
ctggtgagca gcttggtggc caaccagaat cccattctgc tggtgggtcc cgtggggact   7260
gggaagacct ccatcgccca gagcgttctg cagtccctgc cctccagcca gtggtcggtg   7320
ctcgttgtca acatgtccgc acagaccaca tccaataacg tgcagagcat cattgagagc   7380
agggttgaga agcgaaccaa gggtgtctac gtgccattcg gggcaaaag catgatcacc    7440
tttatggatg acctaaatat gcccgctaag gacatgtttg ggtcccagcc acccctggag   7500
ctgatccgcc tctggattga ctatggcttc tggtatgacc gtacgaagca gaccatcaag   7560
tacattcgag aaatgttcct gatggctgcc atgggccccc ctgggggtgg acggactgtc   7620
atctccccaa ggctacggag tcgcttcaac attatcaaca tgaccttccc cacaaagtcc   7680
cagatcatcc gcatattcgg caccatgatc aatcagaagc ttcaggactt tgaggaagag   7740
gtgaagccca ttgggaacgt ggtgacagag gccaccctgg acatgtacaa caccgtggta   7800
cagcgcttcc tgcccacgcc caccaagatg cattacctct tcaaccttcg agacatctcc   7860
aaggtgttcc agggcatgct tagagccaac aaggacttcc atgataccaa gtccagcatc   7920
acacggctct ggatccatga atgtttcaga gtcttctctg accggctggt tgatgcggca   7980
gacacagaag ccttcatggg catcataagc gacaagctcg gctccttctt tgacctcaca   8040
tttcatcatc tctgtcccag caagcgtcct cctatctttg ggatttcct gaaggagccc    8100
aaggtgtatg aagacctcac ggatctgaca gtgctgaaga cagtcatgga gacagctcta   8160
aatgagtata acctgtcacc ctctgtcgtg cccatgcagc tagtgctctt ccgagaggct   8220
attgaacaca tcacacggat cgtgcgggtc attggacagc ctcggggcaa catgctcctg   8280
gtgggtatcg gggcagcgg acgccagagt ctggcccgcc tggcttcatc catctgcgac    8340
tacaccacct tccagatcga ggtcaccaaa cattatcgga agcaggagtt ccgagatgat   8400
atcaagcgtc tgtatcgcca ggctggggtg gagctcaaga ccacgtcctt catttttgtg   8460
gacacccaaa tagctgatga gtccttccta gaggacatca acaacatcct cagctcaggc   8520
gaggtgccca atctctacaa gcctgatgaa tttgaagaga tccagtcgca tatcatagac   8580
caggcccggg tggagcaggt gcctgagtca tcggacagcc tcttcgccta cctcattgaa   8640
cgcgtgcaga acaacctgca catcgtgctc tgcctcagcc ccatgggga tcccttcagg    8700
aactggatcc gccagtaccc agccttggtg aactgcacaa ccatcaactg gttctcagag   8760
tggccccaag aggccctgct cgaggtggct gagaagtgcc tcataggagt agacctggga   8820
actcaggaga atatccacag gaaggtggcc cagatctttg tcactatgca ctggtcagta   8880
gctcagtatt cccagaagat gctgttggaa ctgcggagac acaactatgt cacacccacc   8940
aaatacctgg aactcctgtc tggatataag aagttgctgg gagaaaaacg gcaggagctg   9000
ctggcccaag ccaataaact gcggacaggc ttgttcaaga tcgacgaaac tagggaaaag   9060
gtgcaagtga tgtcgttgga gctggaggat gccaagaaga aggtggctga gttccagaag   9120
cagtgtgagg agtacctggt catcattgtg cagcagaagc gggaggcaga tgagcagcag   9180
aaggccgtaa cagccaacag tgaaaagatt gcagttgagg aaatcaagtg tcaggcactg   9240
gctgacaatg cccagaaaga tctagaagag gcactgcccg ccctggaaga ggccatgcgg   9300
gccctggagt ctctgaacaa gaaggatata ggagagatca agtcttatgg acggccccca   9360
gcccaagtgg agatagtgat gcaggcagtt atgattcttc gaggcaacga gcccacatgg   9420
```

gcagaggcca agaggcagct aggggaacag aacttcatca agtcactgat caactttgat 9480
aaagacaata tctcagataa ggttctgaag aagattgggg cctactgcgc ccagcctgac 9540
ttccagcctg atatcatcgg ccgcgtctcc ctggctgcca agtccctctg catgtgggtg 9600
cgggccatgg agctgtatgg gcggctatat cgggtggtgg agcccaagcg aatccgaatg 9660
aacgctgcct tggctcagct tcgggagaag caagccgcgc tcgctgaggc ccaggagaag 9720
ctgcgggagg tagctgagaa actggagatg ctaaagaaac agtatgatga gaagctggca 9780
cagaaggagg agcttcgcaa gaagtctgaa gagatggagc tgaagctgga gcgagctggg 9840
atgctcgtgt cggggttggc tggcgagaag gccagatggg aggagacagt ccagggcctg 9900
gaggaggacc tgggctacct ggtgggggac tgtctcctgg cagctgcctt cctgtcctac 9960
atgggaccct tcctgaccaa ctaccgggat gagattgtca accaaatctg gatcgggaag 10020
atctgggagc ttcaggttcc ttgctcccct tctttcgcca tcgataactt cctgtgcaat 10080
cctaccaaag tccgggactg gaacatccaa gggttgccct cagacgcctt ctccactgag 10140
aatggcatca tcgtcacccg aggcaacagg tgggcactga tgatcgaccc tcaggcccag 10200
gccctgaaat ggattaagaa catggaagga ggccagggcc tgaagatcat cgacctgcag 10260
atgagcgatt acctgcgaat cctagaacac gccattcact ttggataccc ggtgctactt 10320
cagaacgtgc aggaatatct ggaccccaca ctgaacccca tgctcaacaa atctgtagcc 10380
cgaatcggtg gtcggctgtt gatgcgcatt ggcgataagg aggtggaata taataccaat 10440
ttccgtttct acatcaccac caagctctcc aacccccact acagcccaga gacctcagcc 10500
aagaccacca tcgtcaactt tgctgttaaa gaacagggcc tggaggccca gctgctgggc 10560
attgtggtgc ggaaggagcg gcctgagctg gaggagcaga aggactcact ggtcatcaac 10620
atcgcggctg gtaaaaggaa gctcaaggag ctggaggatg agatcctgcg gctgctgaat 10680
gaggccaccg gctccctgct ggatgatgtg cagctggtga acacgctgca tacctccaag 10740
atcacagcca cagaggtgac tgagcagctg gagaccagtg agaccacaga gatcaacact 10800
gacttggcgc gggaggctta ccgcccatgc gcccagcggg catcaatcct gttcttcgtg 10860
ctcaatgata tgggctgcat cgaccccatg taccagttct cactggatgc ctacatcagc 10920
ctctttattc tcagcattga caaaagccac cgcagcaata agctggagga ccgcattgac 10980
tacctgaatg actaccacac ctacgctgtc tacaggtaca cctgccgtac cctttcgaa 11040
cgccacaaac tactattcag ttttcatatg tgtgccaaaa tcttggagac ttctggcaag 11100
ctcaacatgg atgaatacaa cttctttcta cgtgggggtg tggtcttgga tcgggagggc 11160
caaatggaca atccatgtag tagctggctt gcagatgcct actgggataa catcacagag 11220
ctagacaaac tgaccaactt ccacggactc atgaactcct ttgagcagta ccctcgtgac 11280
tggcacctgt ggtataccaa tgctgccccg gagaaggcga tgctgccagg tgagtgggaa 11340
aatgcctgca atgaaatgca acggatgctg atcgttcgct ccctgcgcca ggaccgcgtg 11400
gccttctgcg tgacctcctt catcatcacc aaccttggct cccgcttcat cgagccgcct 11460
gtgctgaata tgaagtcggt gctggaggat tcaaccccac gatccccact cgtgttcatc 11520
ctgtcccctg gtgtggaccc caccagtgcc ctgctgcagc tggcagagca catgggcatg 11580
gcccagcgct tccacgccct gtccctgggc cagggccagg cccccatcgc tgctcggctc 11640
ctccgagagg gtgtgactca gggacactgg gtgttcctgg caaactgcca cctgtcactg 11700
tcttggatgc ctaatctgga caagctggtg gagcagctgc aggtggagga tcctcatcca 11760
tccttccgcc tctggctcag ctccatcccc cacccagact tccctatctc aatcttgcag 11820

-continued

```
gtcagcatca agatgaccac agagccacca aagggcctaa aggccaacat gacacgtctt  11880

taccaactga tgtcagaacc acagttttcc cgctgctcca aacctgccaa atataagaag  11940

ctgctgtttt cactctgttt cttccactct gtgttacttg aacgcaaaaa gttcctgcag  12000

cttggctgga acatcatcta tggcttcaat gactccgact ttgaggtgtc agaaaacttg  12060

ctgagcctct atctcgatga gtacgaggag acaccttggg acgcacttaa gtacctcatt  12120

gccggcatca actatggtgg acatgtcaca gatgactggg accggcgcct gctgaccacc  12180

tacatcaatg attatttctg tgaccagtct ctatcaactc ccttccaccg gttgtcagca  12240

ctggagactt atttcatccc caaggatggc agcctcgctt cttacaagga atacatcagc  12300

ttattgcctg gcatggaccc ccctgaggcc tttggccagc accccaatgc tgatgtggcc  12360

tctcagatca ctgaggcaca aaccctcttt gatactttgc tttccttgca acctcagatt  12420

acacccacca gggctggagg ccagacccgg gaagagaagg tccttgagtt ggccgctgat  12480

gtgaagcaga agatccctga aatgatcgac tatgagggga ctcaaaaact gctagctctc  12540

gacccctccc ccctcaatgt ggtccttctg caggagatcc agagatacaa cacactgatg  12600

cagaccatcc tgttctcact gacagaccta gagaaaggca tccagggtct catcgtcatg  12660

tctacaagcc tggaagagat tttcaattgc atctttgatg cccatgttcc tccgctctgg  12720

ggaaaggcat acccctcaca aaagccattg gctgcctgga cccgggactt ggccatgcgt  12780

gtggagcagt ttgagctgtg ggccagccgg gcccggcctc ctgtgatctt ctggttgtct  12840

ggtttcacct ttcccactgg cttcctcact gctgtgctgc agtcttcagc tcgccaaaac  12900

aacgtttcag tggacagcct ctcctgggag tttatcgttt ccactgtgga tgacagcaac  12960

ctagtgtatc cccccaagga tggtgtctgg gtccggggcc tgtacctgga aggtgctggc  13020

tgggaccgga agaactcctg cttggtggag gcagagccca tgcagcttgt ctgcctcatg  13080

cccacgatcc acttccggcc tgcagagagc cgcaagaaga gcgccaaggg catgtactcc  13140

tgcccctgct attactatcc caaccgggca ggcagctcag accgagcctc ctttgtcatc  13200

ggcattgacc tgcggtctgg ggccatgaca cctgatcatt ggatcaagag gggcactgct  13260

ctactcatga gcctggacag ctga                                         13284
```

<210> SEQ ID NO 41
<211> LENGTH: 12351
<212> TYPE: DNA
<213> ORGANISM: Homo sapiens

<400> SEQUENCE: 41

```
atgggagcta cagggcgcct cgagctcaca ctggccgccc ctccccatcc gggcccagcc     60

tttcagcgtt caaaagccag ggagacccaa ggagaggagg aagggagtga aatgcagatc    120

gccaaaagtg actccataca tcacatgagc cactcccagg ggcagccaga gctgcctcct    180

ctgcctgctt ctgctaatga ggaaccgtct ggactctatc agactgtcat gtcacacagc    240

ttttacccgc ccttgatgca acgcacgtca tggaccttgg ctgcaccctt caaagaacag    300

catcaccacc gtggacccag tgattccatc gccaacaact actccttgat ggcccaggac    360

ctgaagctga aagatctgct gaaggtctac caaccggcca ccatcagtgt ccctagggac    420

aggaccggtc aggggctgcc atcatcagga aatagaagct catcagagcc catgaggaaa    480

aaaacgaagt tttcctccag aaacaaagag gattccacta ggatcaagtt ggccttcaag    540

acgtcaatct tctcacccat gaagaaggag gtaaagacat ctttgacgtt cccaggaagc    600
```

-continued

```
agaccaatga gtccagaaca gcagctcgat gtcatgttac agcaggagat ggaaatggaa    660
agtaaagaaa agaagccatc tgaatcggac ctggagagat actattacta tctgaccaat    720
ggaattcgca aagacatgat tgcccctgag gagggtgaag tgatggttcg gatttcaaag    780
ctgatttcta acacgctgct gacgagtccc ttcctggagc ccctgatggt ggtcctcgtg    840
caggagaagg agaatgacta ttactgtagc ctcatgaaaa gcatcgttga ttacatcctc    900
atggacccaa tggagagaaa acggctcttt attgagagca tcccccgctt gtttcctcaa    960
agagtgatcc gggcccctgt gccctggcac agtgtctaca ggagcgccaa gaagtggaac   1020
gaggagcatc tgcacacggt gaaccccatg atgctcaggc tgaaagaact gtggtttgca   1080
gaattcagag acctcaggtt tgttcgaaca gcagaaatac tagcgggaaa attgcctctg   1140
cagcctcagg aattttggga tgtgatccag aaacactgcc tggaggcaca ccagactctt   1200
ctcaacaagt ggatccccac ctgcgcccag ctttttacct cacggaagga gcactggatt   1260
cattttgctc ccaagagcaa ctatgactca agtcgaaaca ttgaggaata ttttgcttct   1320
gtggcatcat tcatgtcgct gcagcttagg gagctggtca ttaagtcact tgaggacctc   1380
gtttcccttt tcatgataca caaagatggg aatgatttta aggagcccta ccaagagatg   1440
aagtttttca tacctcagct aatcatgatc aaacttgaag tcagtgaacc cattattgtc   1500
ttcaatccat cttttgatgg ctgctgggaa ttaatacgtg actctttcct ggaaattatt   1560
aagaactcta atgggatccc caagctgaaa tacataccac ttaagttctc cttcactgct   1620
gctgctgctg atcggcaatg tgtgaaagca gctgagccag gagagcccag catgcacgcg   1680
gctgccactg caatggcaga gctgaaagga tataatctgc tccttggaac tgttaacgca   1740
gaagaaaaac ttgtttctga tttttgatt caaactttca aggtatttca gaaaaatcaa    1800
gttggcccct gcaaatattt aaatgtctac aaaaagtatg ttgacttatt ggataacacg   1860
gcagagcaaa acatcgctgc gttcctgaaa gaaaatcatg acattgatga ttttgtgacg   1920
aagatcaatg ccataaagaa acggagaaat gaaattgcat ccatgaacat caccgtgcct   1980
ttagccatgt tctgccttga tgctacggcc ctaaatcatg atctctgtga gcgagctcaa   2040
aatcttaaag accatctgat tcaattccaa gtggatgtaa accgagacac caataccagc   2100
atttgtaatc agtacagcca catcgcagac aaagtcagtg aggttcctgc caacactaag   2160
gagctggtat ccctcattga attcctaaag aaatccagtg ctgtcactgt gttcaaactc   2220
aggaggcaac ttagagatgc aagtgaacgg ctggagttcc tgatggacta tgcagacttg   2280
ccgtaccaga ttgaagatat ctttgacaac agccggaact tgctccttca caagagggat   2340
caggcagaaa tggatctgat taaaagatgc tcagaatttg agttgagact tgagggctac   2400
cacagagaac tggaaagttt taggaagcgc gaagtgatga ctacagaaga aatgaagcac   2460
aatgttgaaa agcttaatga gctttcaaag aacctaaatc gggcgtttgc agagtttgag   2520
ttgatcaata aggaggaaga gctattggaa aaggagaaga gtacttaccc tcttctgcag   2580
gccatgctga agaacaaagt accttatgag cagctgtggt cgacagccta tgagttcagc   2640
atcaagtcag aggaatggat gaatggaccc ctcttcttac tgaatgctga gcaaattgcg   2700
gaggagatag ggaatatgtg gaggacaacg tataaactga tcaagacctt gtctgatgtg   2760
cctgcaccca ggcgcttagc agagaatgtg aagatcaaga tcgataagtt caagcagtac   2820
attcccatcc tcagtatttc ctgcaaccca ggaatgaaag accgacactg gcagcagatc   2880
agtgagattg ttggctatga gataaagccc accgaaacga cctgcctctc aaatatgctc   2940
gaatttggat tcggcaaatt cgttgaaaaa ttggagccca ttggtgcagc tgccagcaag   3000
```

-continued

```
gaatactctc tggagaaaaa cttggataga atgaagttgg attgggttaa cgtgacgttc   3060
agcttcgtga aatacaggga cactgataca aacatcttgt gtgcaattga tgacattcaa   3120
atgctacttg atgatcacgt gataaagacc cagaccatgt gtggctcccc attcatcaaa   3180
ccaatagaag cagaatgccg gaaatgggaa gaaaagctaa ttcgcataca agacaatttg   3240
gatgcctggt tgaaatgcca agccacctgg ctgtacctgg aaccaatctt cagttcagag   3300
gacatcatag cccagatgcc agaagagggg aggaaatttg gcattgttga tagttactgg   3360
aaatcactta tgtcccaagc ggtgaaagat aacaggattc tggtggcagc cgaccagcca   3420
cggatggcag agaagcttca agaagccaac tttctcttgg aggacatcca gaaagggctg   3480
aatgattact tggagaagaa gagactattc ttccccagat tcttcttcct atcaaacgat   3540
gagctgctgg aaatcttgtc cgagacaaag gaccctctcc gagtgcagcc gcacttgaag   3600
aagtgctttg aaggaattgc caagcttgag tttacagaca atctggaaat tgtgggcatg   3660
atcagctcgg aaaaagaaac tgttccattc atacagaaaa tctacccagc taatgccaag   3720
ggcatggtgg aaaagtggct ccagcaggtg gagcagatga tgctggccag tatgcgagaa   3780
gtcattggac ttgggattga agcatatgtc aaggtccctc gaaatcactg ggtcttacag   3840
tggcctggac aggtggttat ctgtgtctcc tccatctttt ggacccagga ggtgtcccaa   3900
gccctggcgg aaaatacctt actggatttt ctgaaaaaga gcaatgatca gattgcgcag   3960
attgtccagc tggtgcgagg gaagctgagc agtggagctc gactcactct cggggccctc   4020
acggtcatcg atgtccacgc ccgcgacgtg gtggccaagt tatctgagga cagggtctcc   4080
gatctgaatg atttccaatg gatctcacag ctgcgctact actgggtggc caaggatgtg   4140
caggtgcaga ttatcaccac agaagccttg tatggctatg agtacctggg aaactccccc   4200
cggctggtga tcacacccct caccgaccgc tgctacagga cactgatggg agctttgaag   4260
ctgaaccttg ggggtgctcc agagggtcca gctgggactg gcaagacaga aaccaccaaa   4320
gatttggcca aagccttggc taagcagtgt gtggtcttca actgctccga tggtttggat   4380
tacaaagcta tggggaagtt cttcaagggg ctggcacagg ctggagcatg ggcgtgcttt   4440
gatgagttca acaggatcga ggtagaagtg ctgtctgtgg tcgctcagca gatcctcagc   4500
atccaacaag ccatcattcg gaagctaaag acattcatct ttgaagggac tgagctctct   4560
ctgaacccaa cctgcgctgt gttcatcacc atgaaccccg ggtatgctgg cagggctgaa   4620
ctgcccgaca atctcaaggc cttgttccgg acagtggcca tgatggtccc agattacgcc   4680
ctcattggag aaatctccct ctactccatg gggtttctgg actccagaag tctcgcccag   4740
aagatcgttg cgacctaccg cctgtgctcg gaacaactgt cctctcagca tcactatgac   4800
tacggtatgc gcgctgtcaa gtctgtgctt actgccgcag gaaacctgaa gctcaagtat   4860
ccagaggaga atgaaagtgt cctgctgctc cgggcattgc ttgatgtcaa tctggccaag   4920
ttcttagcgc aagatgtccc tctgtttcag ggaattatat ctgatttatt tcctggagtt   4980
gttcttccaa agccagacta tgaagttttt ctgaaagtgc tgaatgataa catcaaaaag   5040
atgaaactcc agccagtacc ttggtttata gggaaaatta tccagatcta cgaaatgatg   5100
ctggtgagac atggctatat gattgtagga gaccccatgg gcggcaagac ctctgcttat   5160
aaagtgttgg ctgcagctct cggcgattta cacgcagcca atcagatgga ggagtttgct   5220
gtggagtaca agatcatcaa ccccaaggct atcacgatgg ggcagctgta tgggtgcttt   5280
gaccaagtga gccacgagtg gatggatggt gtccttgcca atgctttccg ggagcaagcg   5340
```

-continued

```
tcttcactct ctgatgatcg caagtggatt atatttgatg ggccagtgga tgctatttgg   5400
attgaaaata tgaacactgt tctggatgac aataaaaagc tgtgtctcat gagtggggaa   5460
attatccaga tgaactccaa gatgagcctg atcttcgagc ccgccgacct cgagcaagcc   5520
tctccagcca ctgtgagcag gtgtgggatg atctacatgg agccccatca actaggctgg   5580
aagcccctga aggattccta catggacacc ctgccctcca gtctcaccaa ggagcacaaa   5640
gaattggtca atgacatgtt catgtggctt gtccagccct gcctggaatt tggtcgcctt   5700
cattgtaaat ttgttgtcca gacatctccc atccaccttg ccttctcaat gatgagactg   5760
tactcttctc tgcttgatga aatcagggca gtagaagagg aggaaatgga attaggtgaa   5820
ggcctgtcaa gtcaacagat ctttctctgg ctccaaggac tgtttctctt ttccttggtg   5880
tggaccgtgg ctggcaccat caacgcagac agcagaaaga aatttgatgt gtttttccgc   5940
aacctgatca tgggcatgga tgataaccac ccaaggccca aaagcgtcaa actcaccaaa   6000
aacaacatct ttccagaaag aggaagcatc tatgattttt attttatcaa acaagctagt   6060
ggacattggg aaacgtggac acagtatatc accaaagagg aggaaaaagt tccagctggt   6120
gcaaaggtct cagaactcat catccccaca atggagacag cccggcagtc cttcttcttg   6180
aaaacctact tagaccatga gattccaatg ctgttcgtgg gtcccacagg cactggcaaa   6240
tcagccatca ccaacaactt ccttctccac cttcccaaaa atacgtacct acccaactgc   6300
atcaatttct ctgccagaac ctcagccaat cagacccagg atatcatcat gtccaagctg   6360
gatcgacgac ggaagggcct tttcgggcct cccataggga agaaagcagt ggtgtttgtg   6420
gatgacctca acatgccagc caaagaggtg tatggggccc agccacccat cgagctcctg   6480
aggcagtgga ttgaccatgg ttactggttt gacaaaaaag acacaaccag gctggacatc   6540
gtggacatgc tgctcgtgac agccatgggg ccccccgggg gaggaaggaa tgacattact   6600
ggacgattca ctcgccatct gaatatcatt tccatcaatg cctttgagga tgacatttta   6660
accaagattt tcagttcgat tgttgactgg cacttcggga aagggtttga tgtgatgttt   6720
ttaaggtacg gaaagatgct ggtccaagct actaagacaa tttatagaga tgcagtggag   6780
aacttcttgc caactccctc gaagtcacat tacgtcttta acctgcggga cttctcacga   6840
gtgattcaag ggtcctgct gtgccctcac acacacctgc aggatgtaga aaaatgtatc   6900
cggctttgga tccatgaggt ttatcgggtc ttctatgatc gtctgattga caaggaggac   6960
agacaggtct ttttcaacat ggtgaaggaa accacctcca attgcttcaa gcagaccata   7020
gagaaggtgc ttatccactt gtcacccact ggaaagatag tcgatgataa cattcgaagc   7080
ctcttctttg gagattattt caagccagaa agtgaccaaa aaatctacga tgagatcact   7140
gacctgaaac agctgactgt ggtcatggag cactatctgg aagaattcaa caacatcagc   7200
aaggccccca tgtccctggt catgttcagg tttgccattg agcacatctc taggatctgc   7260
cgtgtcctga agcaggacaa aggccacctg ctcctggtgg gcataggggg cagcgggcgg   7320
caaagtgccg ccaaactgtc cacattcatg aacgcatacg agctatacca gattgagatc   7380
accaagaact acgcaggcaa tgactggcga gaagatctta agaagatcat actgcaggtc   7440
ggtgtggcca ccaagagcac cgtgttcctc ttcgccgaca accagatcaa ggatgaatca   7500
ttcgtggagg acatcaacat gcttctgaac acaggtgacg tgcctaacat cttccctgct   7560
gacgagaagg ctgacatcgt ggagaagatg cagactgcag ccaggaccca aggagagaag   7620
gttgaagtca ctcctctttc tatgtataac ttctttattg agagggtaat taacaaaatc   7680
tcctttcat tagccatgag tccaataggg gatgccttca ggaaccgcct gcggatgttc   7740
```

-continued

```
ccttcgctga tcaattgctg tacgattgat tggttccagt cctggcccac agatgcccta   7800
gagttggtgg ctaacaaatt tctagaggat gtggagcttg atgacaacat tcgggtagag   7860
gtcgtgtcca tgtgcaaata tttccaagag agcgtcaaga agctgtcact cgattattac   7920
aacaaacttc gaagacacaa ctatgttacc cccacctcct accttgaatt gattctaacc   7980
ttcaagacgc tcctgaatag caagaggcaa gaggtggcta tgatgaggaa ccgctacctg   8040
acaggcttgc agaaactcga ctttgcagct tctcaggtag cggttatgca aagagaactg   8100
acagctcttc aacctcaact catcctcacc tccgaggaaa ctgccaagat gatggtgaaa   8160
attgaagcgg agacgagaga agctgatgga aagaaacttc tggtgcaggc agatgaaaaa   8220
gaagccaatg ttgctgctgc cattgcccaa ggaatcaaga acgaatgtga gggggaccta   8280
gctgaggcaa tgcctgcact cgaggctgca ctagctgctc tggacaccct gaacccggcc   8340
gacatctcgc tggtgaagtc gatgcagaac ccaccaggcc ctgtcaaact ggtcatggag   8400
agcatctgca tcatgaaagg gatgaagcca gagaggaagc cagaccccag tggctccggt   8460
aagatgatag aagattactg gggggtatcc aaaaagattc ttggggatct gaaattcttg   8520
gagagtctta agacatatga caaagacaac atccccccac tgaccatgaa gcggatccgg   8580
gaaaggttta tcaatcaccc ggaattccag ccagctgtca ttaaaaatgt atcgtcggcc   8640
tgcgagggtc tgtgcaagtg ggtgagggcc atggaggtgt acgatcgcgt ggccaaggtg   8700
gtggctccca aacgggagcg actgagggag gcagagggga agctggctgc acagatgcag   8760
aagctgaacc agaaaagagc agagctgaag ctggtggtag atcggctcca ggccctgaat   8820
gacgactttg aagagatgaa caccaagaaa aaggacttgg aggaaaacat tgaaatctgc   8880
tcccaaaagc tggtcagggc agagaaactg atcagtggtc ttgggggaga gaaggacaga   8940
tggaccgaag ctgcccgaca gctggggatc cgctatacta atctgactgg tgacgtgttg   9000
ctgtcctcag gaactgtggc ttacctgggc gcttttacag tggattatcg ggtccagtgc   9060
caaaatcagt ggttggctga atgtaaggac aaggtcatcc ctggcttcag tgacttcagt   9120
ctcagccaca cgttagggga tcccataaaa atccgtgcct ggcagattgc tgggcttccc   9180
gttgactcct tctccatcga caatggcatc attgtatcca attccagacg ctgggcctta   9240
atgattgacc ctcacgggca ggccaataaa tggattaaga acatggagaa ggcgaataaa   9300
ctggctgtca tcaagttctc tgatagcaac tacatgagga tgctggaaaa cgcgctgcag   9360
ttaggcaccc ctgtcttgat tgaaaacatt ggagaagagc tggatgcttc tatcgaacct   9420
atcttgctca aggcaacatt caaacagcaa ggagttgagt acatgaggct gggtgaaaac   9480
atcattgaat attccaggga ttttaagtta tacatcacaa cccgtttgag gaatccacat   9540
tacctcccag aagttgccgt gaaggtctgt ctcctcaact tcatgatcac cccccttgggt   9600
ctccaagatc aactccttgg catcgtggct gcgaaggaga agccagagct ggaagagaaa   9660
aagaaccagt tgattgtgga aagtgccaag aacaagaagc atctcaagga aattgaagat   9720
aagatcttgg aggttctctc catgtccaag ggtaacatcc tggaggatga aaccgccatc   9780
aaagttctgt cctcctccaa agtgctatct gaagagatct cagagaaaca gaaagttgct   9840
tccatgacag aaacgcagat tgacgagact cggatgggct acaagccagt ggctgtgcat   9900
tctgccacca tcttcttttg tatctcggac ctggccaaca tcgagccgat gtaccagtac   9960
tccctgactt ggttcataaa tctctacatg cattccttga cccacagcac gaagagcgag  10020
gaactgaatc tgcgcatcaa gtacatcatt gaccatttca ccctgagcat ctacaacaac  10080
```

```
gtgtgccgtt ctctgtttga gaaggacaag ctactcttct ctctcctcct gaccatcggc  10140
atcatgaaac agaagaagga aattacggag gaggtgtggt acttccttct cactggaggc  10200
atcgcactgg ataaccccta ccccaatcca gctccccaat ggctgtctga gaaggcatgg  10260
gcagagattg tccgtgcatc tgccttaccc aaactgcatg gcctgatgga gcatttggaa  10320
cagaacctgg gtgaatggaa gctgatctat gactcggcct ggccccatga ggagcaactc  10380
cctgggtctt ggaagttctc tcaaggattg gagaagatgg tgatccttcg atgtttgcgg  10440
cctgacaaaa tggtgccagc ggtccgggag ttcattgctg aacatatggg aaagctgtat  10500
atcgaagccc ctacgttcga tctccaggga tcctacaatg attccagctg ctgtgcgcct  10560
ttgatttttg tgttgtctcc aagtgcagac ccaatggcag gcctgctgaa gtttgctgat  10620
gatcttggta tgggaggtac cagaacacag accatctccc ttggccaagg ccaaggccct  10680
attgctgcca aaatgatcaa caatgccatc aaagacggga cctgggtggt cttacagaac  10740
tgccacctgg ccgcaagctg gatgcctacc ctggagaaga tttgtgagga ggtgattgtt  10800
cctgagagca ccaatgccag attcagactc tggctaacca gctatccatc agagaagttt  10860
ccagtcagca ttctccagaa tggaatcaaa atgaccaatg agcccccaa agggctccgg  10920
gccaacctgt tgcgctccta cctcaatgac cccatctcag atcctgtgtt cttccaaagc  10980
tgtgcaaagg cggtgatgtg gcaaaagatg ttatttggcc tttgtttctt ccacgccgtt  11040
gttcaagaga gaagaaactt cggcccccta gggtggaata ttccctatga attcaacgaa  11100
tctgacctga ggattagtat gtggcagatc cagatgtttc tcaatgacta caaggaggtg  11160
ccctttgatg ctctgaccta cctgacaggg gaatgtaatt acggaggcag agtgactgat  11220
gacaaagacc ggcgtctcct gctgtcactt ctgtccatgt tctactgtaa ggaaattgag  11280
gaggactatt actccctcgc tcctggagac acttactaca tccctcctca tggctcctac  11340
cagtcctata tcgactatct caggaatctc cccatcacag cccacccaga agtgttcggc  11400
ctccatgaga acgcagacat caccaaagac aaccaggaaa ccaaccagct gtttgagggg  11460
gtcctgctga ccctccctag acagtcagga ggaagtggca agtcccctca ggaagtggtt  11520
gaggagttgg cacaagacat tctctccaag cttcccagag actttgacct ggaagaggtc  11580
atgaagttgt accccgtggt ctatgaagaa tccatgaata ccgtcctaag gcaggagctc  11640
atcagattca acaggctgac caaagtggtt cggaggagcc tcatcaatct tggccgagcc  11700
atcaaaggac aggtcctgat gtcctcggag ctagaggaag tctttaacag catgcttgtg  11760
ggtaaagtgc cagccatgtg ggcagccaag tcttacccat cactgaagcc tctgggggc  11820
tacgtggctg acctgctggc ccgcctgacc ttcttccagg aatggattga caaggggccc  11880
cctgtggtat tttggatctc tggattctac ttcacacagt cttttttgac tggcgtctct  11940
caaaattatg cccggaaata taccatcccc attgaccaca ttggatttga gtttgaggta  12000
accccacaag aaacagtgat ggagaataac cccgaagatg gggcctacat caaagggctc  12060
ttcttagaag gtgcccgttg ggacaggaaa acgatgcaga ttggggaatc tctccccaaa  12120
atcctctatg acccactgcc catcatttgg ctgaaacctg ggagagagcgc aatgtttctg  12180
catcaggaca tctatgtgtg tccagtctac aaaacaagtg cccgcagagg aaccctctcc  12240
accacaggcc actctaccaa ctatgtcctc tccattgagc ttccaacaga catgccccag  12300
aagcactgga taaaccgagg ggtggcctca ctgtgccagc tggataactg a           12351
```

<210> SEQ ID NO 42
<211> LENGTH: 13875

<212> TYPE: DNA
<213> ORGANISM: Homo sapiens

<400> SEQUENCE: 42
atgtttagga ttgggaggag acagctctgg aagcatagcg tcactcgagt tttaacgcaa 60
agactgaagg gagagaagga agccaagcgg gctcttttgg atgcgaggca taactactta 120
tttgcaattg tggcttcctg tttggacctg aacaaaaccg aagtggagga tgccattctt 180
gaagggaatc agattgaaag aattgatcaa ctttttgctg ttggaggtct ccgacacctc 240
atgttttact atcaagatgt ggaggaagca gaaacaggac aacttggctc tctaggaggg 300
gtaaatcttg tttctggaaa gattaaaaaa cctaaggtgt tcgtgaccga gggaaacgat 360
gtggctctta ctggggtatg tgtgttcttc atcaggactg acccttccaa agccatcacc 420
cctgacaaca tccaccagga ggtgagtttt aacatgttag atgcggcaga tggaggcctg 480
ctcaacagtg tgagacgttt gctgtcggac atcttcattc ctgctctcag agccacgagc 540
catggctggg gcgagctcga gggccttcag gacgcagcta acattcgcca ggagttcttg 600
agctccctgg aaggctttgt gaacgtcctg tcgggtgcac aggagagtct gaaggagaag 660
gtgaaccttc gaaagtgtga catacttgaa ctgaaaaccc taaaggaacc tacggactac 720
ttgactctag caaataaccc tgagactttg ggaaaaatag aggattgcat gaaagtatgg 780
atcaaacaga cagaacaggt tcttgctgaa aacaatcagc tgctgaagga agcggatgac 840
gttgggccac gagcggagct ggagcactgg aaaaaaagac tctccaagtt taactacctt 900
ttggaacaat tgaaaagccc ggatgtgaag gctgtgctgg cagtgcttgc ggcggccaag 960
tcgaaactgc tgaagacttg gcgggagatg gatattcgaa tcactgatgc aactaatgaa 1020
gcaaaggaca atgtgaaata cttgtataca cttgaaaaat gttgtgaccc tttgtacagc 1080
agtgatcccc tatccatgat ggatgctatt cctacactta taaatgcaat taaaatgatc 1140
tatagtatct ctcattacta taatacctct gagaagatca catctctgtt tgtaaaggtg 1200
acaaatcaga ttatatctgc atgtaaagcc tatattacca ataatggaac cgcttccatc 1260
tggaaccagc cacaggatgt tgttgaagaa aaaatactat ctgcgattaa actgaaacag 1320
gaataccagc tctgctttca caagacaaaa caaaagctta aacaaaatcc aaatgcaaaa 1380
caatttgatt ttagcgagat gtatattttt ggaaaattcg aaacttttca ccgacgcctt 1440
gccaagataa tagacatctt tacaaccctc aagacgtatt cagtcctgca agattccaca 1500
attgaagggc tggaagacat ggccactaaa taccagggca ttgtggcaac cataaagaaa 1560
aaggaataca atttcctaga ccagcggaaa atggattttg accaagatta cgaagagttt 1620
tgcaagcaga ctaatgacct tcataacgag ttgcggaagt tcatggatgt tacatttgca 1680
aagattcaaa acacaaatca agctctaaga atgttgaaga aatttgaaag attgaatata 1740
cctaatcttg gtattgatga caaatatcaa cttatccttg agaactatgg ggctgacatt 1800
gatatgattt caaagctgta tacaaagcag aaatacgatc ctcctctggc tcgaaaccag 1860
cctcccatcg ctggaaagat tttgtgggcc cgccagctct tccataggat tcagcagccc 1920
atgcagcttt tccagcagca cccagctgtg ctaagcacgg cagaagccaa acctataatt 1980
cgcagttaca acaggatggc caaggtcctc ctggagtttg aggtcctctt ccacagggcg 2040
tggcttcggc aaattgaaga aattcatgta ggtcttgagg cttcattatt ggtgaaggct 2100
ccaggcacag gggaattgtt tgtaaacttt gaccctcaga tattaatctt atttagagaa 2160
acagagtgca tggcccagat gggtctggaa gtctctccac tggcaacttc cctcttccag 2220

```
aaacgagata gatacaaaag gaacttcagt aacatgaaga tgatgctagc tgaatatcag   2280
agagtgaagt caaaaatacc tgctgccatt gagcaattga ttgtccctca cttggccaaa   2340
gtggatgaag ctctccaacc tggcttggct gcactgacct ggacatcact gaatattgag   2400
gcttatttag aaaacacttt tgcaaagatc aaggacctgg agttgctgct tgacagggtc   2460
aatgatttga ttgagttccg cattgatgcc attctagaag aaatgagcag cacgcctctt   2520
tgtcagcttc cccaggagga gccactaacc tgtgaagagt ttctccaaat gacaaaggat   2580
ctttgtgtaa atggtgcaca aatactacat tttaaaagct cattagtgga ggaggcagtc   2640
aatgagcttg taaatatgtt gctggatgtg gaagttttat ctgaagaaga aagtgaaaaa   2700
atatccaatg agaatagtgt taattacaaa aatgaaagtt cagcaaaaag agaagaagga   2760
aattttgaca ccttgacatc atctattaat gccagggcca atgccctgct tttgacgaca   2820
gtcacgagga aaaagaaaga aactgagatg ttaggggaag aagcccgcga gttactctct   2880
catttcaacc atcagaacat ggatgctctt ctgaaagtta caaggaatac actagaggcc   2940
attcgcaaac gtattcattc ctctcacaca attaacttcc gggacagtaa cagtgcctct   3000
aacatgaagc agaacagttt gcccattttc cgggcaagcg tcactctggc cattcccaac   3060
atcgtcatgg cccctgccct ggaagatgta cagcagaccc tgaacaaagc cgtggagtgc   3120
atcatcagtg tccctaaggg ggtcagacag tggagcagtg aactgttgtc caagaaaaag   3180
atacaagaaa gaaaaatggc tgctttgcag agtaatgaag acagtgattc tgatgttgaa   3240
atgggagaaa atgaacttca agataccttg gagatagcat ctgtaaattt acccattccc   3300
gtgcaaacca agaactatta taagaatgtt tctgaaaaca aagagattgt aaaattagtt   3360
tctgtgctta gcacaattat caactccacc aaaaaggaag ttattacatc catggattgc   3420
ttcaaacgct acaatcacat ttggcaaaag ggaaaagaag aagccattaa gacatttatt   3480
acacagagcc ccttgctttc tgaatttgag tcccagattc tctatttcca aaacctagag   3540
caggaaatta atgctgagcc tgaatatgtc tgtgtgggtt ccattgctct gtacacagct   3600
gacttgaagt tcgccctgac tgctgagaca aaggcctgga tggttgtcat tggacgccac   3660
tgtaacaaaa aataccggag tgagatggaa aacattttta tgcttattga agaattcaat   3720
aagaaactaa atcgtccaat taaggaccta gatgatattc ggattgcaat ggcagcgctg   3780
aaagaaataa gggaggagca aatctccatt gactttcaag taggacctat tgaggaatct   3840
tatgccctgc ttaacagata tggacttctg atagcaaggg aagagataga caaagttgat   3900
acactgcact atgcttggga gaagctgctg gcacgtgctg gcgaagtcca gaataaatta   3960
gtctcactgc agcccagttt caagaaagag cttattagtg ctgtggaggt attcctccaa   4020
gattgtcacc agttttatct ggactatgat ttgaatggtc caatggctag cggcttgaag   4080
ccccaggaag ccagtgacag gcttatcatg tttcagaatc aatttgataa tatctatcgg   4140
aaatacatca catatactgg aggagaggag ctttttggcc tgccagctac acagtatcct   4200
cagcttcttg aaataaagaa gcaactaaat cttctacaga aaatatatac tctgtacaac   4260
agtgtcatag aaactgtaaa tagctattat gatattcttt ggtcagaggt gaatattgaa   4320
aaaattaaca atgaactctt agaattccag aacagatgtc gaaagcttcc ccgggccttg   4380
aaggactggc aggctttttt ggacctgaag aagatcattg atgatttcag cgagtgttgc   4440
ccgctgctgg aatacatggc cagtaaagcc atgatggagc ggcactggga aaggataacc   4500
accctcaccg ggcacagtct ggatgtgggg aatgaaagct ttaagttaag aaatatcatg   4560
gaggcacctc ttctgaaata taaagaggaa atagaggaca tctgtatcag tgcggtgaaa   4620
```

-continued

```
gagagagaca ttgagcaaaa gctgaagcaa gtgattaatg aatgggacaa taaaacattc   4680
accttcggca gctttaaaac ccgtggagag ctcctcttga gaggagacag tacctcggaa   4740
atcatcgcca acatggagga cagcttgatg ttgctgggat ccctactgag caacaggtac   4800
aatatgccat tcaaagccca gattcaaaaa tgggtgcagt acctttccaa ctcaacagac   4860
atcatcgaga gctggatgac ggtgcaaaac ctgtggattt atttagaagc tgtctttgtg   4920
ggaggagaca ttgccaagca gctgcccaag gaagccaagc ggttttctaa catagataaa   4980
tcttgggtga agatcatgac tcgggcacat gaagtgccca gtgtagtcca gtgctgtgtt   5040
ggagatgaga ccctggggca gctgttacca cacttgctgg accagttgga aatatgccag   5100
aaatccctta ctgggtactt ggagaaaaaa cgactgtgct ttcctcggtt tttcttcgtc   5160
tcagatcctg cccttctaga gattctgggg caggcgtcgg actcccacac tatacaggcc   5220
catttgctga atgtgtttga caacattaaa tctgtcaagt tccacgaaaa gatctatgat   5280
cgaattctgt caatttcctc tcaagagggt gagacgattg aattggataa acctgtcatg   5340
gcagagggca atgtggaagt ttggcttaat tctcttttgg aagaatctca gtcctcattg   5400
catcttgtga ttcgccaggc agccgcaaat attcaagaaa caggtttcca actaactgaa   5460
tttctttcat ccttccctgc tcaggttgga ttattaggaa ttcagatgat atggacacgg   5520
gattcagaag aagcccttag aaatgccaag tttgataaaa aaatcatgca gaaaactaat   5580
caggctttcc tggagctact caatacattg atagacgtca ccacgaggga tctgagttcc   5640
acggaacgag tgaaatacga gactctgatt actattcatg tgcaccaaag ggatatcttt   5700
gatgacctgt gtcatatgca tatcaagagt cccatggact ttgagtggct gaaacagtgc   5760
agattttact ttaacgaaga ttctgacaag atgatgattc acatcacaga tgtggcgttc   5820
atataccaga atgaattttt aggctgcact gacaggcttg taataactcc acttacagac   5880
agatgttaca tcacgctggc tcaagctctg ggaatgagca tgggggggagc ccctgctgga   5940
cctgcaggca caggcaaaac agaaaccact aaagacatgg gacgatgcct cgggaaatac   6000
gtcgtggttt tcaattgttc agaccagatg gatttccgag gacttggacg gatttttaag   6060
ggactggcac agtctggatc ctggggttgt tttgatgaat ttaaccgtat tgatctacca   6120
gttctctcgg ttgcagccca gcaaatttcc attattctga catgtaaaaa ggagcacaaa   6180
aagtctttta tctttactga tggagataat gtgactatga accctgaatt tgggcttttc   6240
ttaaccatga atcctggcta tgccggacgg caggaactcc ctgaaaactt gaagattaat   6300
ttccgctcag tggccatgat ggtgcctgac cgtcagatta tcataagggt gaagttggct   6360
agttgtggct tcattgacaa cgttgttttg gccaggaagt tttcacgct ctacaaactg   6420
tgtgaggagc agctttctaa gcaggttcat tatgactttg gcctgcgtaa cattctgtca   6480
gttcttcgga ccttgggagc agcaaaaaga gccaatccaa tggatacgga gtccacgatt   6540
gtcatgcgtg tactacggga catgaatctt tctaaactga ttgatgagga tgaacccttg   6600
tttttgagtt tgattgaaga tctctttcca aatattcttc tggacaaggc aggttaccct   6660
gaactggaag cagcaattag tagacaggtt gaagaagctg gtttaatcaa ccatcctcct   6720
tggaaactga aggtcatcca gctattcgaa acgcagagag tgcgacatgg gatgatgact   6780
ctggggccca gtggggctgg gaagaccacc tgcatccaca ccttgatgag agccatgaca   6840
gattgtggaa aaccacatcg ggaaatgagg atgaatccca aagcgattac tgccccacag   6900
atgtttggtc ggctggacgt tgccacaaat gactggactg atgggatatt ttctacgctt   6960
```

-continued

```
tggaggaaaa cattaagagc aaagaaaggg gaacatatct ggataattct tgatggtcca   7020
gtagatgcca tctggattga aaatctgaat tctgttttgg atgataacaa aactctaacc   7080
cttgccaatg gtgatcggat tcccatggct ccaaactgca agatcatttt cgagcctcat   7140
aacattgaca atgcttctcc tgccaccgtc tcaagaaatg gaatggtttt catgagctct   7200
tctatccttg attggagtcc tattcttgag ggttttctta agaaacgctc acctcaagaa   7260
gcagaaattc ttcgtcagct gtacaccgag tctttcccag acttgtatcg cttctgtatc   7320
cagaacttag aatacaagat ggaggtgctg gaggcctttg tcatcacaca gagcattaac   7380
atgcttcaag gcctgattcc tctgaaggag caaggcgggg aggtgagcca ggctcacctg   7440
gggcggctgt tcgtgttcgc gctgctgtgg agcgcggggg cggcgctgga gctggacgga   7500
cggcgccgcc tggagctctg gctgcgctct cggcccacag ggacgctgga gctgccgccg   7560
ccagcggggc ccggggacac cgccttcgac tactatgtgg cgcccgatgg tacatggacg   7620
cactggaaca cgcgtaccca ggaatacctg tatccgtctg ataccacccc agagtatggt   7680
tctattctgg tgccaaatgt tgacaatgtg aggactgact ttctaattca aaccattgct   7740
aaacagggca aggctgtgct attaattggt gaacaaggaa cagccaaaac agtaataatt   7800
aaaggattta tgtcaaaata tgatcctgaa tgtcacatga tcaagagtct gaatttttct   7860
tctgcaacca ccccactgat gttccagagg acgatagaga gctatgtgga taaacgaatg   7920
ggtacaacat atggccctcc tgcgggaaag aagatgactg tttttattga tgatgtgaat   7980
atgccaataa tcaatgagtg gggagatcag gttacgaatg agatagtgcg acagctgatg   8040
gaacaaaatg gattctataa tctagagaag cctggggagt tcaccagcat cgtggacatc   8100
cagtttttgg cagccatgat ccatcctggt ggtggacgca atgacatacc ccaaagactc   8160
aagaggcagt tctctatatt taattgcacg ttgccctctg aagcttctgt ggacaagatc   8220
tttggtgtga ttggggtagg ccactactgt actcagaggg gtttctcaga agaagtgaga   8280
gattctgtga caaaattggt gcctctgaca cgccgactat ggcagatgac caagattaaa   8340
atgcttccta cccctgcaaa attccattat gtgtttaacc tacgagatct ttctcgggtc   8400
tggcagggaa tgctgaacac tacttcagag gtcatcaagg aaccaaatga tctgttaaag   8460
ctgtggaagc atgagtgtaa acgtgttata gctgaccgtt tcacagtgtc cagtgatgtg   8520
acctggtttg ataaggcttt agtaagtttg gtagaggagg agtttggtga agagaaaaaa   8580
ctcttggtgg attgtggaat tgacacatat tttgtggatt tcttgagaga tgcacctgaa   8640
gctgcaggtg aaacatctga agaggctgat gctgaaacac ctaaaattta tgagccaatt   8700
gaatctttta gtcacctaaa agagcgtctg aatatgttcc tgcagctcta taatgagagc   8760
atccgtggcg ccggcatgga catggtgttc tttgcagatg ccatggttca cttagtcaag   8820
atctctcgtg tcattcgtac tcctcaggga aatgccctcc tggtcggggt gggcggatca   8880
ggaaagcaga gcctgacgag gttggcttca ttcattgctg gctacgtttc cttccagatc   8940
actctgacga gatcctacaa cacatcaaat ctgatggaag atctgaaggt tttgtatcga   9000
acagctggtc agcaaggcaa aggaatcact tttatttca cagacaatga gattaaagat   9060
gagtcatttt tggaatatat gaacaatgtt ttatcatcag gtgaggtctc taacctattt   9120
gctcgagatg aaattgatga aattaatagc gacctggcat cagtcatgaa aaaagaattc   9180
cccaggtgcc ttcctaccaa tgagaacctg cacgactact tcatgagtcg ggtccgacag   9240
aaccttcata ttgtgctctg cttctcgcca gtgggggaga aatttcgaaa cagagctttg   9300
aagttccctg ccctaatttc aggatgcaca attgactggt tcagccgatg gcccaaagat   9360
```

```
gctttagttg ctgtgtctga acacttcctc acttcctatg atattgactg cagtttggaa   9420
atcaagaagg aggtggtcca atgcatgggc tccttccagg atggggtggc tgagaagtgt   9480
gttgattatt ttcagagatt ccgacgttct acccacgtga cgcccaaatc atacctctcc   9540
tttattcagg gctataagtt catatatgga gaaaagcatg tggaggtgcg gaccctggcc   9600
aacagaatga atactggatt ggaaaagctc aaagaagctt cagagtctgt tgcagccttg   9660
agtaaagaac tggaagcgaa agaaaaggag ctacaagtgg ccaacgataa agccgacatg   9720
gtcttaaaag aagtgacaat gaaagcacag gctgctgaaa aggtcaaggc tgaggtacag   9780
aaggtgaagg acagggccca ggccattgtg gacagcatct ctaaagacaa agccattgct   9840
gaagaaaaac tggaagcagc aaaaccagct ttagaagagg cagaagctgc attgcagacc   9900
atcaggcctt cggacatcgc cactgttcgc acgttgggcc gcccccctca cctcatcatg   9960
cggatcatgg attgcgtact gctgctgttt caaaggaaag tcagtgctgt gaaaattgac  10020
ctggaaaaaa gctgtaccat gccctcctgg caggaatcct taaaattgat gactgcaggg  10080
aactttttac agaacttaca gcaattccca aaagacacaa tcaatgaaga ggtgatagaa  10140
tttttgagtc cttactttga aatgcctgac tataacatcg aaactgctaa acgcgtatgt  10200
ggaaatgtag ctggtctttg ttcctggacg aaagctatgg cttccttctt ttctataaac  10260
aaagaagtac tgcctctgaa ggccaacttg gtggtgcaag agaatcgcca tctcctggcc  10320
atgcaggatc tgcagaaagc ccaggccgag ttggatgaca agcaggcgga acttgacgtg  10380
gtgcaggctg agtatgaaca ggccatgact gaaaagcaga ccttgcttga agatgcagag  10440
cgatgcagac acaagatgca gacagcttcc acgctcatca gtggcttggc aggtgaaaaa  10500
gaaagatgga cagagcaaag ccaagagttt gctgcacaaa ctaaaagact tgtaggggat  10560
gtactgttgg ctacagcttt tctatcttat tctggtccat ttaaccaaga gtttcgtgat  10620
cttctgttaa atgactggcg gaaggaaatg aaagcccgga aaattccatt tggaaagaac  10680
ctaaatctca gtgagatgtt gattgatgct cctactatta gtgaatggaa cctccaaggt  10740
ctgccaaatg atgacttgtc cattcaaaat ggaattattg tcacgaaggc atctcgttac  10800
cctttgttaa ttgatccaca gactcaaggc aagatctgga ttaaaaataa agaaagccga  10860
aatgaactcc agatcacgtc tttaaatcac aagtacttca gaaaccacct ggaagacagc  10920
ctttctcttg gaaggccttt gcttattgaa gatgttggag aggaactaga tccagcacta  10980
gataatgttt tggaaagaaa cttcattaaa actgggtcta cctttaaggt gaaagttggt  11040
gacaaggaag tagatgtgtt ggatggcttt agactctaca ttaccaccaa attgcctaac  11100
ccagcctaca cccctgagat aagtgcccgt acctccatca ttgacttcac tgtcaccatg  11160
aaaggtctag aagatcagtt actggggagg gtcattctca cagagaagca ggaattggag  11220
aaagaaagaa ctcatctgat ggaagatgta actgcaaaca aaagaaggat gaaggaacta  11280
gaagataact tgctttaccg cctgacaagt acccaggggt ccctggtaga agatgaaagt  11340
ctcattgtcg tgctgagtaa cacaaaaagg acagccgagg aggtgacaca gaagctagaa  11400
atttctgctg agacagaagt tcaaattaac tcagcccggg aggaatacag acctgtggct  11460
acgcggggca gcatcctcta cttcctcatt actgagatgc gcttggttaa tgagatgtat  11520
cagacttcgc ttcgccagtt tctgggctta tttgaccttt ccttagccag gtctgtcaag  11580
agcccgatta caagcaagag gattgctaat atcatcgagc acatgaccta cgaggtttat  11640
aagtatgctg cccgagggct gtacgaggag cacaaattcc tgttcacctt gttgcttacc  11700
```

-continued

```
ctaaagattg acatccagag gaaccgagtc aagcatgaag agtttctcac tcttattaaa  11760

ggaggtgcct cattagacct taaagcttgt cctccaaaac catcaaaatg gatcctggac  11820

ataacatggc tgaatttggt ggaacttagc aaactcagac agttttcaga tgtccttgac  11880

cagatatcga gaaatgagaa aatgtggaaa atttggtttg ataaggaaaa cccggaggag  11940

gaacctcttc caaatgccta tgataaatct cttgactgct tcagacgtct tctccttatt  12000

agatcctggt gtcctgacag aaccatcgcc caggcccgca agtacatcgt ggactccatg  12060

ggagaaaaat atgccgaagg tgttatttta gacttggaga agacgtggga ggaatctgat  12120

ccacggacgc cactcatctg tctcctgtct atgggctcag accccacaga ttccatcatt  12180

gccttgggga agagattaaa aatagaaacc cgttatgtgt ccatgggcca gggccaggaa  12240

gtccatgctc ggaagctctt gcagcagacc atggcgaacg gaggatgggc acttctgcag  12300

aactgccatc tgggacttga tttcatggat gagctgatgg acataatcat agaaactgag  12360

cttgtacatg atgcgttccg cctctggatg accaccgagg ctcataagca gtttcccatt  12420

acactccttc agatgtccat taaatttgcc aacgatcctc cacaaggact ccgggcagga  12480

ctgaaaagaa catatagtgg tgtcagccaa gacctgctgg acgtgagctc tgggtcccag  12540

tggaagccca tgctgtacgc agtggctttc ctgcactcca ctgtccagga gaggcgcaag  12600

ttcggtgccc tggggtggaa tatcccctac gaatttaacc aagcggactt taatgccact  12660

gtgcagttca tccaaaacca cttggatgac atggatgtca aaaagggtgt ctcctggacc  12720

accatccgct acatgatagg agagattcaa tatggaggca gagtcactga cgactatgat  12780

aagagattgt tgaacacatt tgctaaggtt tggttcagtg aaaatatgtt tggaccagat  12840

ttcagttttt accaaggata caatattcca aaatgcagca cagtggataa ctatcttcag  12900

tatatccaga gtttgcctgc ctatgacagc cctgaggtgt ttgggctgca ccccaatgct  12960

gacatcacct accagagcaa gctggccaag gacgtgctgg acaccatcct aggcatccaa  13020

cccaaggaca cctctggtgg aggggatgag acccgggagg cggtggtggc ccggctggct  13080

gatgatatgc tggagaagct gcccccagac tatgtcccct ttgaagtaaa agagaggctg  13140

cagaagatgg ggccattcca gcctatgaac attttcctca ggcaggaaat agacagaatg  13200

caaagggtac tcagccttgt ccgcagcacc ctcactgagc tgaaacttgc tattgatggc  13260

accatcatca tgagcgaaaa tctgcgagat gcattggatt gcatgtttga tgctagaatc  13320

cctgcttggt ggaaaaaagc ttcttggatt tctagtacac tgggtttctg gtttactgaa  13380

cttatagaaa gaaacagcca gtttacctcg tgggttttca atggccgacc tcactgcttt  13440

tggatgacgg gttttttaa cccccaggga tttttaactg caatgcgaca ggaaataact  13500

cgggccaaca aaggctgggc tctggacaat atggtgcttt gcaatgaagt caccaaatgg  13560

atgaaggacg acatttctgc ccctcccaca gagggtgtct atgtctatgg cttatatctt  13620

gaaggtgctg gctgggacaa gaggaacatg aaactcattg aatcaaagcc aaaagtgctc  13680

tttgagttga tgcctgtcat aaggatttat gcagaaaaca atactttacg agatcctcgg  13740

ttttactcct gtcccatcta taagaagcca gttcgaacgg acttgaacta cattgccgct  13800

gtggatctca ggacagccca gacccctgaa cactgggtgc tccgtggggt tgcccttctg  13860

tgtgatgtca agtaa                                                   13875
```

<210> SEQ ID NO 43
<211> LENGTH: 12477
<212> TYPE: DNA
<213> ORGANISM: Homo sapiens

<400> SEQUENCE: 43

```
atgacttttc gggccacaga tagtgaattt gacctgacaa atattgaaga gtatgccgaa     60
aattctgcac tttcaagact gaataatata aaagccaaac aaagagtgag ttatgtgaca    120
tccacagaaa atgaatctga tacacaaatc ctaacgttta ggcacattac aaaagctcag    180
gagaagacaa gaaaacgaca gcagcctata aaactagagc ctttgccagt gctaaaagtc    240
taccaagatc ataagcagcc agaatacata catgaacaga accgatttca gttaatgact    300
gcaggaatca ttaaacgtcc agtaagcata gcaaaaaaaa gttttgccac atcatctact    360
cagtttcttg agcatcaaga tgctgtgaaa aaaatgcaga ttcatcggcc ctatgttgag    420
gtgttctctc cctctcctcc taaactgcca catactggta ttggaaaaag aggtctcttt    480
gggactagat cttcagctta ccctaagtac acttttcacg accgagaaga agttgttaaa    540
gccaacattc gtgatccctt gcaaatcatt aaaataatac gtgaaaatga acatcttgga    600
tttctttata tgatccctgc agtgccaaga tcatccattg aatatgatac atataatcta    660
aaagttgtaa gttatgagaa catcaataaa aatgactact atactattag ccaaagggca    720
gtaacacaca tttataatga agacattgaa tttatcgaaa ttgatcgatg ggaacaggaa    780
tatctgtatc acagagaact cactaagatt cccatatttt cactgttccg gaaatggaag    840
gcttttagtg tatggaggaa gaatgtccgc tccaagaaaa tcactggatg tcaaaaatct    900
ctacaaaaaa atttgttcat tgttaatcct catttgcgac cagctcttct taaaataaat    960
gaattgtgtt atcatttgag ttttatggga ctttgttata ttgaaaagtg tcacacctac   1020
accctgcagg aatttaaggc cgcacaagtc atacggctag cagaggtgac agaacgccta   1080
ggagaatttc gaaatgaggc aaaatatgta gtcaggaggg cttgtcgatt tgctttgcgt   1140
gctgcaggat ttgttcctga tgactgtgca tttggacctt ttgaggatta tcataaagtg   1200
cagagcagtg gaagtttcat taatacacca catgagttgc ccacttatgg agactctgag   1260
aaaatgacat atacagaaca ggccagcaaa aggcattatt gcatgaggct gacgtgcttt   1320
attcgtctaa acgactatct aattgagaac acaatgcaca tcttaacggt aaatgctgtt   1380
aattcgcttt tgaaccatct cactgacaag ctaaaacgaa caccttcagc agatgtcatt   1440
cagaaatgga ttactgaaga gaagcctgaa gtccctgata aaaaggggac ccttatggtg   1500
gaaaagcaag aagaagatga atctctcatc cccatgtttc tcacagaact aatgttgaca   1560
gtccagtcac tgctctttga gccttctctg gaagactttc tggatggtat tttgggtgca   1620
gttaatcact gtcaaaacac tgtgttatca gttcctaatc tcgtgcctga ttcgtatttt   1680
gatgctttca ccagccctta tattaacaac aaacttgaag gaaaaacctg tggaactggg   1740
ccaagtttag cagcagtatt tgaggatgat aagaattttc acacaattat ttctcaaata   1800
aaggaaacca ttcaggccgc atttgaatca gcccgcatct atgcagctac ctttgaaaag   1860
ttccagatat tcttcaagga aaatgaaagt cttgatttac aagctcttaa acttcaggaa   1920
cctgatatta actttttttag tgaacaactg gaaaaatatc acaaacagca caaggacgca   1980
gtagcgctca gacccaccag aaatgtagga ttgctgctca ttgatactag gcttctaaga   2040
gaaaaattaa ttccatcacc tttgcgatgc ttagaggtgc taaattttat gcttcctcgt   2100
caaagcaaga aaaaagtgga tgccattatc tttgaggcac aagatgcaga gtataaactt   2160
gagtttgttc caactactac cacagaatat gttcatagct tattatttct tgatgaaatt   2220
caggaacgga ttgaaagcct tgaagatgag gggaatatag tgactcaaat gtacaagctt   2280
```

-continued

```
atggaacaat atcaggtgcc cacacctcct gaagactttg ctgtttttgc aactatgaag   2340
ccatccattg ttgctgttcg gaatgccatt gataaatcag tgggtgatag agaatcaagc   2400
attaagcaat tttgtgtgca tttgggtagt gatcttgaag aattaaacaa cgaagtgaat   2460
gaagtaaaac tgcaagcaca ggatccacag attttagata tctctgctga ccaagacaaa   2520
ataaggctca tattgaataa tctgcaatct gttctggctg atcttcagaa acgtgcattt   2580
cagtataagt cctatcagaa gaattttaag gtagaagtgt ccaagtttga agctttggaa   2640
gaagtcagtg ctgaactgaa gctcaaacaa ttgctctggg attctttctc tgaatgggat   2700
aaactccaac aagaatggtt aaagtccaaa tttgattgcc tggatccaga agtcctaaac   2760
ggtcaagttt ctaaatatgc taaatttgtg actcaactgg aaaaaggctt gccacccaac   2820
agtgtagtgc cccagctcaa atacaaggtg gaaaaaatga aagaaaagct tccagttatc   2880
attgacttga ggaacccgac tttgaaggca agacattggg cagctattga acaaacagtt   2940
gatgccactc tagtggatgc tgaaattcca ttaaccttgg agaggctctc ccagttgcat   3000
gtttttgact ttggtcaaga aatccaggac atatctggac aggcttctgg agaagctgcc   3060
ttagaagcaa ttcttaaaaa ggtggaggac tcttggaaaa caactgaatt tgtcattctg   3120
cctcaccgtg actccaaaga tgtgtttata ctgggcggca cagatgacat acaggtcctt   3180
cttgatgata gcaccatcaa tgttgcaact cttgcctcat cacgttacct tggtccactg   3240
aaaactcgag tggatgaatg gcaaaaacaa cttgctttat ttaatcaaac actggaagag   3300
tggctgacct gccagagaaa ctggctctac ctagaaagta ttttcaatgc tccagacatt   3360
cagaggcaat tgcctgcaga ggccaagatg ttccttcagg tggataagtc atggaaagaa   3420
atcatgagaa aggtgaatcg gctgcctaat gctcttcgag ccgctactca gccaggactt   3480
ctggaaactt ttcaaaacaa taatgcatta cttgaccaaa ttcagaagtg cctagaggca   3540
tacttagaat caaaaagagt tatctttcca aggttttact tcttgtcaaa tgatgaactt   3600
ctggagattt tggcccagac acgaaatcca caggccgtgc agccacactt aaggaaatgc   3660
ttcgactcca tttcaaagct cgaatttgct ctcatgcctc ctgccgaagg aaagattcct   3720
ggtattgatg gagaaccaga aaaggtttat actaatgata ttttagcaat gctgtcacca   3780
gagggagaaa gggttagctt ggggaaaggc ctcaaggccc gaggcaatgt agaggaatgg   3840
cttggtaaag tggaagaagc catgttcaca tctctgcgtc gcctgtgcaa agctgccatc   3900
gctgactatc aggggaaact gaggacagac tgggtggttg ctggccaccc ttctcaagtt   3960
atcctgactg tttctcaaat tatgtggtgc cgtgatttga ctgaatgtct ggaaacagaa   4020
cacagtaatc atatacaggc cctgaagaat tttgaaaaag taaattttga gagattaaat   4080
gccctagctg caatagttca aggcagtctt cctaaattac acagaaacat cctaactgca   4140
ttgattacta ttgatgtgca tgcaagagat atagtcactg aacttgttca atccaaggtg   4200
gagacagttg aatcttttga ctggcagaga caactgcgct attactggga tatagacctg   4260
gataattgtg tggctagaat ggcgctctct cagtacactt atggctatga atatttgggt   4320
gcatgcccaa gattggttat tactccactc acagatcgct gctatctttg cctcatggga   4380
gctttgcagc ttgaccttgg gggtgcacca gctggtcctg ctggcactgg gaaaacagag   4440
actaccaaag atctggcaaa agctcttgcc atccagtgtg tggtctttaa ctgttcagat   4500
ggtttggact acaagatgat ggggcgcttc ttcagtggct tggcacagtc aggggcctgg   4560
tgctgctttg atgaatttaa tcgaattgac atagaagttc tgtccgtcat cgcgcagcaa   4620
ctcattacca ttaggaacgc caaagcggca aagctctcta gattcatgtt tgaggggcgg   4680
```

gaaataaagt tggtgatgac ttgtgcagcc ttcatcacaa tgaatcctgg ctatgcaggg 4740
agaactgaat tgccagataa tttgaaagcc ctgtttagac catttgcgat gatggttcca 4800
aattatgcct tgattgcaga ggtaattcta tattctgaag gatttgaatc cagtaaaata 4860
ttagcaagaa aaatgactca gatgtataag ctttgcagtg agcagctgtc tcagcaggat 4920
cactacgact ttggcatgag agctgtgaag tctgtcctgg tcatggctgg atctttaaaa 4980
agagaaaacc cagacctaaa tgaagatgtg gtgttgataa gagctttaca agactccaat 5040
ttgccaaaat ttctaacaga tgatgctctt ctgttcagtg gaatcatatc tgaccttttt 5100
cctggagtcc aaattccaga acatgattat ggtattttac aatcaacaat tgtggatgtc 5160
atgaatagac aaaatcttca gcctgagatg tgtatggtta gaaaggtgat acagttttat 5220
gaaactatgc tagtaaggca tggtgttatg ttagtcgggc caacaggagg cggcaagacc 5280
acagtttacc gaatactagc agaaacttta gggaatttac aaaaacttgg gatagaaaat 5340
tccttttacc aagcagttaa aacatatgtt ctcaacccta aatcaattac catgggtgaa 5400
ttatatggag aggttaataa cttaaccttg gaatggaaag atggtttgat ggcactaagt 5460
gtccgagcag ctgtgaatga tacttcagaa gaccataaat ggatcatcag tgatgggcca 5520
gtagatgctc tttggattga aaacatgaat acagtgctgg atgataacaa gatgctttgc 5580
ctggctaaca gtgagaggat taaactcaca cctcaaattc acatgctttt tgaggtgcaa 5640
gatctgcggg ttgcctcccc tgcaacagtc agtcgatgtg gaatggtgtt tgtggatcct 5700
gaagaactga aatggatgcc ttatgttaaa acttggatga agggtatttc taaaaaactg 5760
actgaggaaa cccaagaata tatattgaat cttttccaac gttatgttga tgaaggttta 5820
cattttatca ataaaaagtg cagccaagca attccacaag tggacatcag caaagttact 5880
acactctgtt gcttattgga gtccttgata cttgggaaag atggagttaa cttggcaatg 5940
gaacaaacaa aattgaacac tatactatgt cagacttttg tattctgtta tttgtggtct 6000
ttgggtggaa acctaactga aaactactat gattcttttg atacatttat tagaacacaa 6060
tttgatgata atcctgatgc caggcttccc aattctggtg atctgtggag cattcatatg 6120
gactttgaca ccaaacggct ggatccctgg gaacgaatca tacctacttt caaatacaac 6180
cgagatgttc catttttttga aatgcttgtc cccacaactg acacagtgcg ctatgggtat 6240
ctaatggaaa aactactggc agtcaagcat tccgtgttgt ttactggaat aactggagtg 6300
ggcaagtctg tgattgcaaa aggattgcta aataaaattc aagaatcagc tggctatgtc 6360
cctgtttatc taaatttttc tgctcaaact tcatctgcaa ggacacaaga gatcattgag 6420
tcaaaactgg agagaaaaag aaaaaatatt ctaggagcac cgggaaacaa acgaattgtg 6480
atttttgttg atgatttaaa catgcccaga ctggatcgct atggctctca gcctccgatt 6540
gaattacttc ggcagtatca agattttggg ggattttatg acagaaacaa actgttttgg 6600
aaagaaatac aggatgtaac aatcatatcg gcatgtgcac ctccaggcgg tggccgcaac 6660
cctgtgactc cccgcttcat cagacacttc agcatgctgt gcctcccaat gccctcagag 6720
cacagtctga aacagatttt tcaggccatc ttaaatggtt tcctgagtga ctttccacca 6780
gctgtaaagc aaactgcatc aagcattgta gaagcctcag ttgagattta taacaaaatg 6840
agtgttgacc tcctgccaac acccgccaag tcccattatg tctttaactt gagggactta 6900
tccaaatgtg tgcaaggtat cctccaatgt gatccaggaa caataagaga agaaattcag 6960
atatttagac tcttttgcca tgagtgccaa agggtcttcc atgatcgctt gattaataat 7020

-continued

```
gaagataagc actatttcca tgttattctg acagaaatgg ccaacaaaca ttttggaatt   7080
gcaattgacc tggaatattt tttgaataag cccatcatat ttggagattt cattaagttt   7140
ggagcagata aagctgatcg gatttatgat gacatgcctg atatagagaa aactgcaaat   7200
gttctacagg actatcttga tgattataat ctcacaaatc ccaaagaagt aaagttggtg   7260
ttcttccagg atgctataga acatgtttca aggattgctc ggatgatacg tcaagaaaga   7320
ggcaatgccc tgcttgttgg agtaggaggc acaggaaagc agtcactcac gagacttgca   7380
gctcatatat gcggttacaa atgtttgcag attgaactca gccggggata taattatgat   7440
agttttcatg aagacctgag gaagttgtac aaaatggctg gtgtagaaga caagaatatg   7500
gttttccttt tcactgacac ccagattgta gtggaggagt tcctagaaga tataaataac   7560
atcctgaact caggtgaagt gcctaattta tttgaaaagg atgaactgga gcaggtttta   7620
gcggccacca gaccaagagc aaaagaagta ggaatttctg aggggaacag agacgaggtg   7680
tttcaatact ttatcagcaa agtgcgtcag aagctgcaca ttgttctctg catgagccca   7740
gttggggagg cctttcggtc ccgatgcagg atgtttccat cccttgtgaa ttgctgcacc   7800
attgactggt ttgtgcagtg gcccagagaa gcacttcttt ctgtgtcaaa gacatttttc   7860
tcacaagtcg atgctggaaa tgaagaactg aaagaaaagc ttcccttgat gtgcgtgaac   7920
gttcacttga gtgtctccag catggcagag cgctattaca atgagctgcg caggcggtac   7980
tacacgacac ccacctccta cctggagctt atcaatcttt acctgtctat gctgtctgaa   8040
aaaaggaagc agattatttc agcacgagat cgggtgaaga atggtctcac caagctacta   8100
gaaacaaaca tactagtaga taaaatgaaa ctagatcttt cagctttaga gcctgtactt   8160
ttagcaaaat cagaagatgt tgaagccctg atggaaaaat tggcagtgga tcaagaaagt   8220
gccgatcagg tccgtaacac tgtgcaggag gatgaagcaa cagcaaaagt caaagctgaa   8280
gaaacccaag caatagctga tgatgctcaa agagatcttg acgaggcact acctgcacta   8340
gatgctgcca ataaagcact ggattcctta gataaggcag atatatctga aatcagagtt   8400
tttacaaagc cccccagattt ggtcatgaca gtaatggaag caatctccat tcttttgaat   8460
gccaagcctg attggccatc agcaaagcaa cttcttggtg actctaactt tctaaaaagg   8520
cttttagaat atgataagga gaacataaag cctcagatat tggcaaagct tcaaaagtat   8580
attaataatc ctgattttgt gcctgaaaaa gtggagaaag tgtccaaagc atgtaaatct   8640
atgtgcatgt gggtaagagc tatggatttg tactctcgag tggtcaaggt cgtcgaacca   8700
aaaagacaaa agctccgcgc cgcacaggct gaacttgaca ttaccatggc taccctgaga   8760
gaaaagcaag cattactaag acaagtagaa gatcaaatac aggccttaca agatgaatat   8820
gacaaaggtg taaatgaaaa agaaagcctg gcaaagacca tggccctgac aaaagcacgt   8880
ctagtacgtg ctggaaagct gacagcagca ttagaagatg agcaggttcg atgggaagaa   8940
agcatacaga agtttgagga agaaatatca aatatcactg ggaacgtgtt catagcagca   9000
gcttgtgtgg cctactatgg ggctttcaca gcccagtaca ggcagtcact tatagagtgt   9060
tggatccagg actgtcagtc tctggagatc ccaatcgatc cttccttcag tctcattaac   9120
attcttggag atccctacga gatacggcag tggaacactg atgggctgcc ccgtgacttg   9180
atatcaacag aaaatggcat tttggttact caaggcagaa gatggccttt gatgattgat   9240
ccccaagatc aggcaaaccg ttggataagg aacaaggaaa gcaaaagtgg tttaaagatc   9300
attaagctta cagatagtaa tttcttacga atactcgaga attcaatccg acttggttta   9360
cctgtcttac tggaagagct taaggaaacc ttggatccag ctctagaacc cattcttttg   9420
```

-continued

```
aaacaaattt ttatcagtgg tggccgacta ctcatccgtc ttggagactc agacattgat   9480
tatgacaaaa actttaggtt ctatatgaca accaaaatgc caaatcccca ctatctgcct   9540
gaggtatgca ttaaagttac cattatcaat ttcactgtaa caaaatcagg cctggaggat   9600
cagttgttaa gtgatgtggt gcgacttgaa aaacccaggt tggaagaaca aagaattaag   9660
ctcatcgtga ggatcaacac tgataaaaac cagttgaaaa ctatcgaaga gaaaatcctg   9720
agaatgctct ttacctctga aggaaatatt ctggacaatg aagaacttat tgacacactc   9780
caggattcaa agatcacttc tggtgccatt aaaaccaggc tggaagaagc agagtccact   9840
gagcagatga tcaatgtggc tcgtgagaag tatcgtccag tggccactca aggctctgta   9900
atgtactttg tcattgcaag cctctcagaa atagatccta tgtaccagta ctcattaaaa   9960
tactttaaac agttgttcaa taccaccatt gaaacttctg taaagacaga aaatctacaa  10020
cagcgcctgg acgtactact agaacaaact ctcctaactg cttatgtcaa tgtttcaaga  10080
ggacttttg agcaacataa actcatctac agctttatgc tttgtgttga gatgatgcgt  10140
cagcaaggaa ccctatctga tgctgaatgg aatttctttc tccgaggttc tgcaggattg  10200
gaaaaggaac gcccacctaa gcctgaagct ccctggctac ctactgctac atggttcgca  10260
tgctgtgact tggaagaatc atttccagtt tttcacggac ttacccaaaa tatattgtca  10320
catcctattt ccatacgctt aggatctttt gagacttata ttaacccaca gaaatgggaa  10380
ggctattcta aaatgaaaca cgaagataaa cacatgagac aggaaaagga ggcagcacac  10440
caagatccat ggagtgcagg attgagttct ttccataagc taattcttat taaatgttgt  10500
aaagaagaaa aggtggtttt tgctcttaca gactttgtga tagaaaatct tggaaaacag  10560
tttatagaga caccacctgt ggacctgcct accctgtatc aagacatgtc atgcaacact  10620
cccctggtat tcatcctaag cacaggctca gatcccatgg gtgcatttca gaggtttgcc  10680
agggaaagtg gatattcaga acgggtgcag tcaatttcac tggggcaagg acaaggacct  10740
attgctgaaa aaatggtcaa ggatgcaatg aaatcaggaa actgggtatt tttgcaaaat  10800
tgccatcttg ctgtttcttg gatgttggca atggaagagc tcattaaaac cttcacagat  10860
ccagatagtg ctatcaagga cacttttcga cttttttaa gctccatgcc tagtaataca  10920
tttcctgtta cagttcttca aaattctgtc aaggtgacca atgagcctcc aaaaggctta  10980
cgtgcaaata tcagacgagc atttactgaa atgacacctt cgtttttga agaaaatata  11040
cttggaaaaa aatggagaca aataatattt ggcatttgtt tcttccatgc aattattcag  11100
gagagaaaga agtttggccc ccttggttgg aatatctgct atgaatttaa tgacagtgac  11160
agggaatgtg ctttactgaa tctcaaactc tattgtaaag aaggaaagat tccctgggat  11220
gcactaattt acattactgg tgaaattact tatggtggta gagtcacaga cagctgggac  11280
caaagatgcc ttcgtactat cttgaaaaga tttttttctc ctgaaacatt agaagaagat  11340
tataaatact ctgaatcagg catctatttt gcacccatgg ctgacagcct acaagagttt  11400
aaggactaca ttgaaaatct gcctttgatc gatgacccag aaatttttgg aatgcatgaa  11460
aatgctaatc tagtcttcca gtacaaagag accagcactt taatcaacac catacttgag  11520
gttcagccaa ggtcatctac tggtggagag ggaaaaagca atgacgaaat tgttcaagaa  11580
cttgttgctt ctgtccagac cagagttcca gaaaaactgg aaatggaggg tgcttctgag  11640
agccttttg tcaaggatct tcaaggacgt ctgaactcct tgaccaccgt tcttggacag  11700
gaagtggacc ggtttaacaa cctgctgaag ttaattcata cttctctgga aacactcaac  11760
```

```
aaagccatcg ctggatttgt ggtgatgtct gaagaaatgg aaaaagtgta taacagtttc  11820
ctcaacaacc aggttcccgc tctgtggtcc aacacagcct acccatccct gaagccacta  11880
ggatcatggg tcaaagacct tatcctgagg acctcatttg tggatctgtg gctcaaaaga  11940
ggacagccta agtcctactg gatctctggt ttcttctttc ctcaaggatt tctaacagga  12000
actcttcaaa atcatgctcg aaaatacaat ttgcctatag atgagctgag tttcaaatac  12060
agcgtaattc ccacctatcg ggatcaagct gcagtgatag aagctgccaa gacagtgcaa  12120
tttggacaag aactgcccat ggacatggag ttgccctctc ctgaggatgg tgttcttgtt  12180
catgggatgt tcatggatgc ttctcgatgg gatgataagg agatggtgat agaagatgca  12240
ttgcccggac agatgaatcc agtgctgcct gtggtgcatt ttgaaccaca acaaaactat  12300
aagccaagcc caacacttta ccactgccca ctttataaaa caggagcccg ggcaggaaca  12360
ctctcaacca caggacattc aaccaatttt gtggtaaccg tcctgttacc ctccaagcgg  12420
tccaaagact actggattgc caagggatca gctttgctct gccagctgag cgaatga     12477
```

<210> SEQ ID NO 44
<211> LENGTH: 12075
<212> TYPE: DNA
<213> ORGANISM: Homo sapiens

<400> SEQUENCE: 44

```
atgagcagtg agcaggataa atcggccagc aaagaaaaat ccaagaaacc agtaagattt     60
ctaccacagc tgtctatgga gaaattagcc agcaaagaaa agttcaaggc accagcaaga    120
gctttaccac agctgtctat ggtgagtaca aagccccact ggcagcaggc agctccatca    180
ttccatttga gtgtaaagca ggatgatgag agtccagaac catttagtgt taaaaatgaa    240
cagtcccatg ctgaatacat ggaacgtttt ggaaaaaagg gcaaattacc ccaccaagtt    300
gatgatagtt atgttggacc atctacttcc aaatcaaagg gcaaatctcc acataaagaa    360
cgagaaaact ttagaagtac tcttgttaat gtcattatgc aacaagatgc tgacttagac    420
tcagctgtcc ctgatggaag cacaattcca aaaccgaccg cttctgctat agagaaagac    480
atcttgagat attactatta tattcaccat ggaattgata cagaccatgt agccccaatg    540
gaagattctt ggctagaaca cgtactggat ttagttccac aacatctgaa agtcttcact    600
gacagcatag ttacattatc tgatgaaatg agagaggatt atcttcttag tgtaaggaaa    660
tccatagttg attttgtttt aaaagatcct cgagagaaag gagatgataa gaagacagat    720
gaacttccag cccatcgtgc tgaaatggaa attctgccaa aaccttggag gaaatctttt    780
ttagctgcaa gcagttatat tagggatcac ttgaatgcaa tgaaccccac aatgctggct    840
gtactagatt tgtggcacac taattttaaa aaattacgtt tagttgatat caaagaattt    900
cataattgcc aggatgcatt agagctgtca agttttcaga acattatcat gagacacatg    960
gactctgcca aagagactct acttaaaatg tggtttccag aagtgcagaa tatttattac   1020
caaggtaata aaaaaaagca attgccaact ggtgacagca gtgccaaatt ggaatctttt   1080
ttcaactgtg ctgctgcact tatgacttta cagctgcagg acctcacttt agtctccatg   1140
caagatttca cggacttaat tgcacaaccc ccagattctg ttagagcttt tgaacatcca   1200
ggtttcatca tgaggctgat tcttgataat gacaccatta agtttgaacc tgagttgagt   1260
gactatatag atatctttct aaatgtttat gacgtcatga ttaaagctgt cagttttgtg   1320
ccaagagttg agacaaaatt gtattccaag tgggaaagta agtctaaacc aacaaccttg   1380
aagcccataa ttctgaatga aattgtagat gctcacaaag aaaagatcaa ggaagttatt   1440
```

```
atgaaagaga gtgtggcacc tactgagcac ctcagactct atgacaagta tgacttttta   1500
attaccagaa aagctgagcg agatgttgat aacttcctcg cagaaaatca tagttatgaa   1560
aaaataatag atgaaatttg caaataccag aaactaatag aggaaataca gtacacatcc   1620
ataaagacta ttcgtttagg aatgtttgaa atgcactgtg aggaattaat cagagctttg   1680
gtgaagcgag cagatattat ttgtgggaaa cttctagcta aaatgttcag agatcatcag   1740
gaagtaaata caagattatg cgatgaattt gagaggatag ctgaaaaagc tcttagcact   1800
cctccaaata cagcagaact aatggaaatg aaggcttaca ttcagaaagt ggaggtaact   1860
gatatgattg aactagaaca gagattagtg gattccaaaa actgcctcgc cttcctcatc   1920
gagtatgtca acttttctcc agcagacatg aggctaaata atagtgtttt ccagtggtat   1980
ggaaggatgg gagaaatttt tgaagaacac aggaaaatca ttaaagagaa aatagaacaa   2040
tatcaagaag gtctgaagtt acggtgtgaa cggtttgtgg aggaattgga gagttatgct   2100
aagcaatcag aagaatttta ttcatttgga gatcttcagg atgttcagcg gtacctaaaa   2160
aaggctcaaa tactgaatgg aaagttggat ttagctgcag ataagattga gcagtttaat   2220
gctgaagagg aagcatttgg ttggctacca tctgtatatc ctcaacgtaa aaaaatccaa   2280
gatggcttga acccttatct tcgtctttat gaaactgctg tcgaatttag cagcaactat   2340
agagcatgga cagaagggcc atatcataaa gtgaatccag accaagtaga agcagatatt   2400
ggaaattact ggagaggatt atataaactg gagaaaacct ttcatgattc tccatatgca   2460
ttggcaatga caaaaaaagt aagatcaaag gtggaagatt tcaagcagca cattcctctc   2520
attcaagtga tctgtaatcc tggtttgcgc cccaggcact gggaggccat gtctgccatt   2580
gttggttacc ctttgcagcc atcagatgac tccacagtct cctctttttt agacatgaat   2640
ctggaaccat atatagaccg atttgaaggt attagtgaag cagctagcaa agaatattct   2700
cttgaaaagg cgatggagaa gatgattact gagtgggatg cagtggaatt tgtcatccat   2760
tcttatagag aaactgggac atttattttg gcatcagttg atgaaattca gatgttgttg   2820
gatgaccata ttattaaaac acaaactatg cgaggatctc ctttcattaa gccttatgaa   2880
aaacaaatga gagaatggga gggcaagctc ctactgcttc aggagattct ggatgaatgg   2940
ctcaaagtcc aagccacgtg gctgtatctg gagcccattt tcagctctcc agacattatg   3000
tctcaaatgc ctgaggaagg cagacgattt acagctgtgg ataagacatg gagagatata   3060
atgagaagtg tcatgcagga taaacatgtt ctgacagttg taaccattga cagaatgctg   3120
gaaaggctga aaaaatctaa tgaacttttg gagctcattc ttaaaggact taatgaatat   3180
ttggaaaaga aacgcctctt tttccccaga ttcttttttt tgtccaatga tgaacttctt   3240
gagatactat ctgagactaa agatcccact agggtgcaac ctcacttgaa gaaatgtttt   3300
gaaggaatcg caaaggtaga atttacggaa actttagaca ttactcacat gaagagcagc   3360
gaaggagagg ttgtagaact catagagatt atttcaacag ccaaagccag aggtcaagtg   3420
gagaagtggt tggttgaatt agagagagtt atgattaact ccatccacaa ggtaactgga   3480
gatgcaactt ttgcctatac aaaatatgaa cgaattaact gggtaaggga ttggcctgga   3540
cagactgttc tctgtgtatc ccaaatcttt tggacaaaag aagtacaaac agctattcca   3600
atggggataa aggctcttga gcaatacttg aaaacatgta acagacaaat tgatgatatt   3660
gtcactttgg tgcgtggcaa attgtccatg cagaatcgcg taactctggg agcacttgtg   3720
gtactggatg tccatgctag agatgtcctc tcatcacttg taaaaaaaaa tattagcgat   3780
```

-continued

```
gactctgact ttgaatggtt aagtcagctt aggtactact ggcaagaaaa tcatttagaa   3840
acaaaaatga tcaatgctgg tttgcgatat ggatatgaat atctgggtaa ttcccctagg   3900
ctggttatta caccactcac ggatagatgt tacagaacct tatttggagc ccttcatttg   3960
caccttggag gagcacctga gggtccagct ggcactggga agactgaaac taccaaggat   4020
ttggcaaaag ctgtagccaa acaatgtgtt gttttcaact gctctgatgg gttggattat   4080
ttggctttgg gaaaattctt taagggactg ttatcttgtg gagcctgggc ttgctttgat   4140
gagtttaaca gaattgattt ggaagtactc tctgtggttg ctcaacaaat ccttactatc   4200
caaagaggta ttaatgcagg tgctgatata ctgatgtttg aaggaactga actaaaactt   4260
gaccccacat gtgctgtctt tataacaatg aaccctgggt atgctgggcg atcagaactg   4320
ccagataacc tgaaggctct ctttcggaca gtagcaatga tggtacctga ctatgccatg   4380
attgctgaaa tagtcctata ctcctgtggg tttgtcactg ctcgaccact gtctgtaaaa   4440
attgtggcta cgtatcgctt gtgttcagag cagctgtcat ctcaacatca ctacgactat   4500
ggaatgagag ccgtgaagtc agttcttact gctgctggga atctgaagct gaaatatcca   4560
aatgaaaatg aagaaatttt gctgcttaga tctatcattg atgtaaatct gccaaaattt   4620
ttatcccatg atttaccact ctttgaggga attacttcgg atttgtttcc tggggtaaaa   4680
ttaccaaaac cagattacaa tgatttgctg gcagctatca aagacaattg tgcctccatg   4740
aatttgcaaa tgactgcatt cttttccgag aagattcttc aagtatatga aatgatgatt   4800
gtgcgtcatg gttttatgat tgttggagaa ccatttggag gaaaaactag tgcatatcgt   4860
gtcttagctg gagcactaaa tgatatatgt gaaaaggggc taatggaaga aaacaaagtt   4920
caaataactg ttttaaatcc taagtctgtc accatgggcc aactgtacgg acagtttgat   4980
tcagtgtccc atgaatggtc tgatggggtc cttgctgtca gttttagagc atttgcctct   5040
tcagtgactc cagataggaa atggttaatt tttgatggcc cagtagatgc agtgtggatt   5100
gagaatatga acactgtgct ggatgacaac aagaagctat gtctgatgag tggggagatt   5160
attcagatgt caccacaaat gaatctaatt tttgagccaa tggatttaga agttgcttcc   5220
cctgccactg tttccagatg tggcatgatt tacatggagc ctcacatgtt aggctggaga   5280
ccactgatgt tgtcctgggt gaatctgtta cctgcgtcag tcagtgttat tcaaaaggaa   5340
ttcataatgg gcttatttga cagaatggtc cctgtttcgg ttgaatttat tagaaagcat   5400
acaaaggaat tatctcctac ttccgataca aacttggtcc ggtccttaat gaatctaata   5460
gactgtttta tggatgattt tgctgatgaa gtcaaactaa aggagagaaa tgatcgagaa   5520
acttactctt tgcttgaggg catttttctg ttttcattga tctggtccgt tggtgcttct   5580
tgtacagatg atgatcgatt gaaatttaat aagattcttc gagaactaat ggaaagtcca   5640
atttcagatc gaactcgaaa tacgtttaaa ttacagagtg gtactgagca aacatcctca   5700
aaggcactaa ctgtcccatt tcctgaaaaa ggaacaattt atgattatca atttgtcact   5760
gagggaatag gaaaatggga accatggata aagaaattga aagaagctcc tccaattcct   5820
aaagatgtaa tgtttaatga aatcattgtg ccaactctgg acacaattcg atactctgca   5880
ttaatggaat tgctgaccac ccatcaaaag ccttcaatat ttgtaggacc aacaggaact   5940
gggaaaagtg tttacattac gaattttctt ttaaatcaac taaataagga aatctacaaa   6000
cctctgctaa ttaacttctc agcacaaact acagcagctc aaactcagaa tattgtcatg   6060
tcaaaattgg acaagagaag aaagggagtt tttggtcctc ctttgggcaa gagaatggtt   6120
gtctttgtag atgatgtcaa tatgcctgct cgggaggtat atggggctca acctcccatt   6180
```

-continued

```
gagttactta gacagtggtt agaccactgg aactggtatg atctaaaaga ttgttccatg   6240
attaaactag tggacattca gatcatgtgt gctatgggac ctccaggtgg tggtcgaaat   6300
ccagtaactc ctcgatacat gcgacatttc aatattataa caatcaatga gtttagtgat   6360
aaatccatgt atacaatctt ctctagaatc ttaacttggc atttagaaat ctgttataaa   6420
tttccagatg aatttctaga tttgaccaca caaatcgtaa atggcacaat gactctgtat   6480
aaagaagcaa tgaagaatct cttgcctact ccagctaaat ctcactactt gttcaacctc   6540
cgtgatttct cccgtgtcat tcaaggtgtt tgtttgtcaa gaccagaaac aacagaaacc   6600
acagaagtga ttaaacgtct ttgggttcat gaggtccttc gagtgtatta tgaccgcctt   6660
ctggacaata cagacagaag ctggctcatc aactacattc aagaaatttt gagaaactac   6720
atgtatgaag attttcatga gctttttcag cgtttggatt ttgataatga tggcatggtg   6780
gaagcagatg acttacgcag cttaatgttt tgtgatttcc atgatcccaa gagggaggat   6840
accaactaca gagaaatcgc agatgtggat aatcttcgaa tgatagtaga aattcaccta   6900
gaagaataca acaatataag caaaaaaccc atgaaccttg tcttgtttcg atttgccata   6960
gagcacatca gcagaatttc caggatcctg aagcagcctc gcagccatgc tctcctagta   7020
ggggttggag ggagtggaag gcagtctgtc accagattag ctgcccacat ggctgattat   7080
tcagttttcc aagttgaaat ctctaagggg tatgatacta ctgaatggca tgaagattta   7140
aaagtgatct taaggaaatg tgcggaaggt gagatgcagg gtgtcttcct gtttacagat   7200
actcaaatta aagaagagtc ttttctggaa gatgtcagta atctgctaaa tgctggggag   7260
attccaaatc tctttgcatt agatgagaag caagagatat gtgataagat gcgtcagtta   7320
gatcgccagc gggataaaac caagcaaaca gatggcagcc ccatagccct tttcaacatg   7380
tttattgatc attgccgcag ccaactgcat gtggtccttg ccatgagtcc cattggagat   7440
gcatttcgga atcgtcttag aaagttccct gctcttgtta actgctgtac cattgactgg   7500
tttcagtcat ggcctgaaga tgcactccag gcagttgcct cacgattctt ggaagaaatt   7560
gaaatgtcag aggaaatacg agatggctgt atcgacatgt gtaaaagctt ccacacttct   7620
actatagatt tatccaaatc tttctttgtt gaacttcaaa gatacaatta tgtgactcct   7680
acctcttacc tcgaattaat ctccaccttc aaactgttgt tagaaaagaa aagaagtgaa   7740
gtaatgaaaa tgaaaaagag atatgaagtg ggtttggaga aactggattc tgcttcatct   7800
caagtagcca caatgcagat ggagttggag gcactacatc ctcaattaaa agttgctagc   7860
aaagaggttg atgaaatgat gataatgatt gagaaagagt ctgtagaagt tgccaaaact   7920
gaaaaaatag tgaaagctga tgaaacaata gcgaatgaac aagctatggc ttccaaagcc   7980
atcaaagatg agtgcgatgc tgacctggca ggtgccttgc caatattaga gtcagcactg   8040
gccgcccttg atactcttac tgcacaggat attacagtgg taaaatccat gaagagtcct   8100
cctgctggtg tcaagcttgt tatggaagct atatgcatct tgaaaggaat caaagctgac   8160
aaaatccctg acccaacagg ttcagggaaa aaaattgagg atttctgggg cccagctaag   8220
agacttcttg gtgacatgag gtttctgcag tcacttcatg aatatgacaa ggacaatatt   8280
cctccagctt atatgaatat cataagaaaa aattatattc caaatccaga ttttgtacca   8340
gaaaaaatca gaaatgcttc tacagcggcc gaaggtctgt gcaaatgggt catagcaatg   8400
gattcatatg ataaagtggc aaaaatagta gctcccaaaa agataaaact ggctgcagct   8460
gaaggggagc ttaaaattgc catggatggt cttagaaaga agcaggcagc ccttaaggaa   8520
```

-continued

```
gttcaggaca agctggccag gcttcaagac acacttgaat taaataaaca aaagaaggct   8580
gacctggaaa accaggttga cctttgcagc aaaaaactag aacgagctga acagttgatt   8640
ggaggccttg gaggtgagaa aactcgatgg agccacacag ctctggagct aggtcagctg   8700
tacatcaact tgactgggga tatcctcatt tcctccggag tggttgctta cctcggagcc   8760
ttcacatcca cctatagaca gaatcaaact aaagagtgga caactttgtg caaaggaaga   8820
gatatcccct gctcagatga ttgctctctt atgggtaccc tgggagaagc tgtgacaatt   8880
cgaacttgga atattgctgg attaccttct gactcatttt ccattgataa tgggataatc   8940
ataatgaatg caagaaggtg gcctctgatg atagatcctc aaagtcaggc taataaatgg   9000
atcaagaaca tggaaaaagc caatagtctt tatgtgatta aacttagtga acctgactat   9060
gtcaggactc tggaaaattg catccagttt ggtactcctg tgttgctaga aaatgttggc   9120
gaagaactag atcctatttt ggaacctctt ctactaaaac aaacctttaa gcagggtggg   9180
agtacatgta tccggcttgg ggactccaca attgaatatg cacctgactt ccgcttctat   9240
attactacca agttaagaaa tcctcattat cttcctgaaa catcagtaaa ggtaacatta   9300
ttaaacttca tgataacccc tgagggaatg caagatcagc ttctgggaat tgtggtggca   9360
caagaaaggc cagaccttga agaagaaaag caagccttga tattacaagg agctgaaaat   9420
aaaaggcagt taaaagaaat agaagacaag attttagaag ttctttcatc ttcggaaggc   9480
aatatattag aagatgaaac tgctattaag atattatctt cctccaaggc cttggctaat   9540
gagatttctc agaagcagga agtagccgaa gagacagaga aaaagattga caccacccgc   9600
atgggctatc gtcctattgc catccattct tccatcctat ttttttctct tgctgattta   9660
gccaacattg agcccatgta ccagtattca ctgacctggt ttattaacct tttcatcctg   9720
tctattgaaa attcagagaa atcagaaatt ttggcaaaaa ggcttcagat tctcaaggat   9780
cactttactt attcactgta tgttaatgtc tgccggtcac tctttgaaaa ggataagctg   9840
ctcttttcct tttgtctaac cataaatcta ctgctgcatg agcgggcgat taataaagct   9900
gagtggagat ttctgctaac tggtggcatt ggactggata atccttatgc caacctttgt   9960
acatggcttc ctcagaaatc ctgggatgaa atatgtcgat tagatgattt gcctgccttc  10020
aaaaccattc gtagagagtt tatgcgctta aaggatggat ggaagaaagt atatgatagt  10080
ttggaaccac accatgaggt ttccctgaa gaatgggaag ataaagcaaa tgagtttcaa  10140
aggatgctta ttattcgttg cttgaggcca gacaaggtta ttccaatgtt gcaggaattt  10200
ataatcaaca gattgggacg tgcattcatt gaaccacccc cctttgattt agccaaggca  10260
tttggagaca gtaactgctg tgcaccactg attttcgtgc tctctcctgg agcagatccc  10320
atggctgccc ttctaaaatt tgctgatgac cagggatatg gggatcaaa acttagctct   10380
ttatctcttg gtcaaggcca agggcccatt gctatgaaga tgttagaaaa agctgtcaag  10440
gaaggaacat gggttgttct tcagaattgt caccttgcca cctcttggat gccaaccctt  10500
gagaaagtct gtgaggagtt aagcccagag tcaacacatc cagatttccg aatgtggcta  10560
acgagttacc catctccaaa tttccctgtg tcagtactgc agaatggagt gaaaatgacc  10620
aatgaagcac caaaaggttt acgggctaat atcattcgat catacctcat ggacccgatc  10680
tctgatccgg agttctttgg cagctgcaaa aagcctgagg aattcaagaa attgctttat  10740
ggcctgtgtt tctttcatgc tttggtacaa gaaagacgga aatttggacc cctagggtgg  10800
aatattcctt atgagttcaa tgagacagat ctgagaatca gcgtacagca gctccacatg  10860
ttcctgaacc agtatgagga actgccgtat gaggctctgc ggtacatgac tggcgaatgc  10920
```

```
aattacggag gcagagtgac cgatgactgg gaccggcgca cgctgcgcag cattctaaac  10980

aaattcttca atcccgaatt agttgaaaat tcagactata agttcgactc aagtggcatc  11040

tattttgttc ctccttctgg tgatcacaaa agctacatcg aatacacaaa gactctgcca  11100

ctgaccccag caccagaaat ctttgggatg aatgccaatg cagatatcac taaggatcag  11160

tcagaaactc agctgctatt tgataacatt cttcttacac agtctcgttc agcaggtgct  11220

ggtgcaaaat catcagatga agtagtgaat gaggtcgcta gtgacatctt gggcaaactt  11280

ccaaacaact tcgacatcga ggctgccatg aggaggtacc caacaactta tactcagagc  11340

atgaacactg tacttgtcca agagatggga cggttcaata agttactgaa gaccataaga  11400

gattcgtgcg taaatattca aaaagcaatc aaggggcttg cagtcatgtc tacagatctt  11460

gaagaagtgg ttagcagcat tttgaatgtc aaaattccag aaatgtggat gggtaaatcc  11520

tacccaagcc ttaaaccact tggcagctat gtgaatgact tccttgcaag actaaaattc  11580

ttgcagcaat ggtatgaggt tggtcctcct ccagtcttct ggctttctgg cttcttcttc  11640

acacaagcct tcctgaccgg tgcccagcag aactacgcca ggaaatacac aattcctatt  11700

gatcttcttg ggtttgacta tgaagtgatg gaagacaaag aatacaagca tcctcctgag  11760

gatggtgttt tcattcacgg attatttctg gatggagctt cctggaatag aaagatcaag  11820

aaacttgcag aatcgcatcc caaaattctt tatgatacag tgcctgtgat gtggctaaag  11880

ccctgtaaga gggcagatat accaaaacgg ccaagttatg ttgctccatt gtataagaca  11940

agtgagcgga gaggagtatt atccaccact ggccattcca cgaattttgt gattgccatg  12000

actcttccct ctgaccaacc caaggaacac tggattggac gaggtgtagc actgttatgt  12060

caacttaatt cataa                                                   12075
```

```
<210> SEQ ID NO 45
<211> LENGTH: 13473
<212> TYPE: DNA
<213> ORGANISM: Homo sapiens

<400> SEQUENCE: 45
```

```
atgatgaaat tgtatataga caatgcagcc ccggataaac taaaaggact gtgcatattt     60

tttgttcgtt gccgtaatga tgttgctata aatgttaaaa ctattcaaga ggaagcgctc    120

tttactgttc tggatgcgtc gaaaggactc ttaaatggaa ttagggatat gttggcaaat    180

atatttctac cagctgttct tgcaacaaac aactggggtg ctttaaacca gtccaagcag    240

ggagaatctg aaaaacatat tttcactgaa accatcaaca gatatctttc atttttagat    300

ggtgctagaa taagtattga gggaacagtg aagttaaaga caatagacaa tgttaatttt    360

tccaaactgc acacctttga agaagtaact gctgcagcca gcaactcaga aactgttcat    420

cagctggagg aagtgctgat ggtatggtac aaacagatcg aacaggtact tattgagagt    480

gagcagatga gaaaagaagc tggtgattca ggtccactca ctgaattgga acactggaaa    540

cgcatgtcag ccaagttcaa ctatatcatt gagcagatta aagggccaag ttgtaaggct    600

gtcataaatg tgctaaatgt tgcacactcc aaactgctaa agaattggcg tgatttggat    660

gcaagaatca ctgatacagc aaatgaatcc aaagataatg tcagatattt gtatactttg    720

gaaaaagtgt gtcaacctct ctataaccat gacctagttt ccatggcaca tggaatacaa    780

aatttgatta atgccatcag aatgattcac ggtgtgtcaa ggtattataa tacctcagag    840

agaatgacct cattgtttat caaggtaaca aatcaaatgg taacagcatg taaagcatat    900
```

-continued

```
attactgatg gaggattaaa ccatgtatgg gatcaggaaa cgccagttgt actaaagaaa    960
attcaggact gcatttttct attcaaggaa tatcaggcat cttttcataa aacaaggaaa   1020
ctgatttcag aatcctcagg ggaaaaatct tttgaggttt cagaaatgta tatatttgga   1080
aaatttgaag ctttttgcaa aagactggag aagattacag aaatgataac tgttgtgcaa   1140
acatattcaa ccttgagtaa ttctaccata gaaggaatag atattatggc aataaaattc   1200
agaaatatat accaaggggt taagaaaaag caatatgaca ttctggatcc aagaaggaca   1260
gaatttgaca cagatttctt agatttcatg acaaaaatca atggtttaga ggtacaaata   1320
caggcattta tgaacagtag ttttgggaaa atcttatctt ctcagcaggc tcttcagcta   1380
cttcaaaggt ttcagaagct gaacattccc tgtctgggat tagaaataaa ccacacaata   1440
gagcgtattc ttcagtacta tgtggctgaa cttgatgcta ctaagaagct ttatcattct   1500
cagaaagatg accccctct tgctcgcaac atgcccccta tagcaggaaa aatactctgg   1560
gtgaggcagc tctatcgccg gataagtgag cccatcaatt atttctttaa aaactcagac   1620
attttatcaa gtccggacgg taaagctgtc atccgtcagt ataacaagat ctcctatgtg   1680
ctggtggaat tcgaggtggt ctatcacaca gcctgggtca gagagatttc acagttgcat   1740
tacgctttac aagccacgct ttttgtgcga catccagaaa cagggaagtt gctggttaat   1800
ttcgatccca aaattttgga agttgttcgg gaaactaagt gtatgataaa aatgaagttg   1860
gatgtaccag aacaggcaaa gagattgcta aaattggaaa gtaaattgaa agcagacaaa   1920
ctgtatttgc agggtcttct gcaatattat gatgagttat gtcaggaagt gccttctgtg   1980
tttgtcaatc tgatgacccc aaaaatgaaa aaggtggaat ctgtgttgag gcaaggactc   2040
acagtgttaa catggtcgtc tttaacactg gaaagcttct ttcaagaagt cgaattagtt   2100
ttggatatgt tcaatcaact tttaaagaag atcagtgact tgtgtgaaat gcatattgat   2160
acagttctga aggagatagc caaaactgtg ttgatttctc tgcctgaaag tggtgctacc   2220
aaagtagaag atatgttgac cctcaatgag acatacacaa aagaatgggc tgacattcta   2280
aaccacaaaa gtaagcatgt ggaagaagct gtcagagaac ttatatcaat atttgagcag   2340
atttatgaag tgaaatacac tgggaaagta ggaaaacagt cagaacagcg gaaacacgtt   2400
gtttttggaa gtgaaacaga agagggtgaa aacaatgact atgaagctaa tattgtgaat   2460
gagtttgata ctcatgataa agaagatgaa tttaaaaagg agtgtaaaga ggtctttgct   2520
tttttctctc atcaattact agacagtctt caaaaagcta cacggttatc tctggacaca   2580
atgaaaagaa gaatatttgt tgcaagcctt tatgggcgaa agcagtcaga agatattatt   2640
tcgtttataa aaagtgaagt acatcttgca attcctaatg tggtgatgat tcctagtttg   2700
gatgacattc aacaagccat taaccgtatg atccagttaa ccctggaggt cagcagagga   2760
gtggctcact gggggcaaca gcaaatccgt cccatcaagt ctgtcattcc cagcccccacc   2820
actactgacg tgacccatca aaacacagga aaactgctga agaaggaaga aagatctttt   2880
gaagaagcta ttcctgcgag gaagctgaag aatttttacc cgggggtagc ggagcacaag   2940
gatatttcta agttggtcct gctcctttct tcctctgtaa attccctaag aaaggcagct   3000
catgaggccc tgcaggactt tcagaagtac aagactctct ggacagagga ccgcgatgtg   3060
aaagtgaagg aatttttggc taacaacccc tctctgactg aaatcagatc agaaattcta   3120
cactatgcta cttttgaaca ggagattgat gagttgaagc ctattattgt tgtaggagca   3180
cttgaattac atacagagcc gatgaaattg gccttatcca tcgaggccaa ggcatggaag   3240
atgttactct gtcgatatct gaatgaagaa tacaaaaaga aaatgtcata catgatagca   3300
```

-continued

```
tttattaatg aatacttgaa aaagttatct agacctattc gtgatttaga tgatgtcaga   3360
tttgcaatgg aagccttgtc ttgcatacgt gataatgaaa ttcaaatgga catgactttg   3420
ggaccaattg aagaagccta tgctatttta aacagatttg aagttgaagt aaccaaagaa   3480
gaatcagaag cagttgatac cttaagatat tctttcaaca aattgcagag caaagctgtt   3540
tcagtacaag aggacctagt tcaagtgcag ccaaagttta aaagcaatct acttgagtct   3600
gtgaaagttt ttcgtgagga cgtgataaac tttgcagaag catatgaatt ggaaggacct   3660
atggttccaa atataccacc ccaagaagct agcaacaggc tacagatatt tcaggccagt   3720
ttcgatgatc tgtggaggaa atttgttacg tattcatctg gtgaacaact ttttggattg   3780
cctgtgactg attatgaggt tttacacaaa accagaaaag aactcaactt gctgcagaag   3840
ctgtatggat tgtatgacac cgtaatgagc agtattagtg gttattatga aatactttgg   3900
ggagatgtag atattgaaaa aattaatgca gaactgctgg aatttcaaaa cagatgtcgt   3960
aaacttccaa aaggacttaa agattggcaa gctttttttgg atctcaaaaa gagaattgat   4020
gatttcagtg agtcatgtcc tctactggaa atgatgacca ataaggccat gaaacagaga   4080
cactgggata gaatctccga gttaactgga accccatttg atgtggaatc tgattctttt   4140
tgccttagaa atatcatgga agcaccactc cttaaacata aggatgatat tgaggatatt   4200
tgcatatctg ccattaagga gaaggatatc gaagccaagc tgactcaggt gattgagaat   4260
tggaccaacc aaaatctgag ttttgcagca tttaagggaa aaggagagct cctgctcaaa   4320
ggaaccgaat cgggagaaat tatcactttg atggaggata gtttaatggt cttagggtct   4380
ttactcagca acagatacaa tgctccattt aaaaaaaata tccagaattg ggtgtataaa   4440
ttgtccactt cctcagatat aattgaagag tggctcgtag tacagaacct ttgggtttat   4500
cttgaagccg tctttgtagg tggagatatt gccaaacagc tgcctcagga agcaaaacgt   4560
tttcagaata ttgacaagtc ttggataaaa ataatgcagc gagctcatga gaatcccaat   4620
gtgattaatt gctgtgttgg agatgaaacc atgggacaac ttttacctca tttacatgag   4680
cagttggaag tatgtcagaa gtcactcaca gggtatttgg agaagaaacg attactgttt   4740
ccaagattct tctttgtatc tgatccagtt ctcctggaaa ttcttggaca agccagtgat   4800
tcccacacca tacagccaca tctccctgca gtatctgaca acatcaatga ggtgacattt   4860
catacaaaag actatgatcg catcatggcc gtcatatcaa gagaaggaga aaaaattgtt   4920
ttggataatt ctgttatggc caaaggtcct gtggagattt ggctactgga tttgttaaaa   4980
atgcagatgt catcattaca taatataatt agatccgctt tctatcaaat cagtgattca   5040
ggatttcaac tcttaccatt cctcagccac tttccagcac aggttggact tctgggaatt   5100
cagatgttgt ggacacacga ttcagaagag gctttacgta atgcaaaaga tgacaggaaa   5160
atcatgcaag tgaccaatca gaaatttttg gatattctaa atactctcat tagtcagaca   5220
acacatgatc taagcaagtt tgatagagtg aagttcgaga ctctaattac catccatgtg   5280
catcagagag atatttttga tgacttggta aaaatgcata tcaaatcacc tactgacttt   5340
gaatggctaa aacagagtag attttatttt aaggaagatt tggatcaaac tgtggtgtct   5400
attacagatg ttgattttat ttaccaaaat gaatttctgg gatgtactga tcgtcttgtt   5460
atcactccat taacagatag atgctatatc acgttagctc aggccttggg catgaacatg   5520
ggaggtgctc ccgcaggacc tgctggcact ggcaaaacag aaaccacaaa agacatggga   5580
aggtgtttgg gaaaatatgt ggtcgtgttc aattgctcag atcaaatgga tttcagaggc   5640
```

```
ctaggaagga ttttcaaagg tcttgcacag tcgggttcct ggggctgttt tgatgagttt   5700
aacagaattg aattgcctgt attatcagtg gcagcacaac aaatttatat tgttttgaca   5760
gcaagaaaag aaagaaagaa acagttcatt ttttctgatg gtgattgtgt tgatttaaat   5820
ccagaatttg gaatcttctt aacgatgaac cctggatatg ctgggcgcca ggaactacca   5880
gaaaacctaa aaatccagtt tagaactgtt gctatgatgg ttcctgatag acagatcatt   5940
atgagagtta aacttgcaag ctgtggtttt cttgaaaatg ttatcttggc tcaaaaattt   6000
tacgttcttt acaaactctg tgaagagcaa cttactaaac aggttcatta tgactttgga   6060
ttgagaaata ttctgtctgt attgaggact cttggatctc aaaaaagagc cagaccagaa   6120
gatagtgaat taagcattgt catgagagga ctaagagata tgaacctttc caaactggtt   6180
gatgaagatg aacccctgtt cctcagctta atcaatgacc tgttcccagg actgcaactg   6240
gatagtaata cttatgcaga actgcaaaac gcagtagccc atcaggttca gatagagggt   6300
ttgattaacc atccaccctg gaacctgaaa ctcgtgcagt tatatgagac gtctttggta   6360
cggcatggct tgatgactct tgggcccagt ggttctggaa agacaaccgt tatcacgatt   6420
ctaatgaagg cgcaaacaga atgcggaagg cctcatagag aaatgcgaat gaatccaaaa   6480
gccattactg cacctcagat gtttggcaga ctggacactg ctaccaatga ctggacagat   6540
gggatttttt ctactctgtg gagaaaaaca ttaaaagcta aaaaaggtga aaacattttc   6600
ctcattttag atggtcctgt ggatgccatc tggattgaga acttaaattc cgttttggat   6660
gacaataaaa ctctgacgtt agctaatgga gatcgcattc ccatggcccc tagttgtaag   6720
cttctgtttg aagtccacaa tatcgagaac gcctctcctg ccacggtttc taggatgggc   6780
atggtctata tcagcagctc tgctctcagc tggaggccaa tcttacaggc atggttgaag   6840
aaacgcactg cacaggaagc tgctgtattc ctgacactgt atgagaaagt ctttgaagat   6900
acatacacat atatgaaact aaatctcaat cccaaaatgc agctcttgga gtgcaactat   6960
attgtgcaat ctctcaatct tctggaaggg ttaattccct ccaaagaaga aggcggtgtt   7020
tcctgtgtcg aacatcttca taaattattt gtgtttggcc taatgtggag tttaggagcc   7080
cttctggaat tagaaagcag agaaaagctt gaagccttct tacggcagca tgaaagcaag   7140
ttggacttac cagaaatacc taaaggctca aatcaaacca tgtatgagtt ttatgttact   7200
gattatggtg attgggagca ctggaataag aaacttcagc cttattatta tccaactgac   7260
agtattccgg aatattcatc aattttggtt ccaaatgttg acaatattag aacaaatttt   7320
ttgatagaca ccattgcaaa acaacataaa gctgttttgc tcacaggaga gcagggaact   7380
gcaaaaactg tcatggttaa ggcctatttg aaaaaatatg atcctgaagt acagctatcc   7440
aaaagtctaa acttttcatc tgccacagaa ccaatgatgt ttcagagaac aattgaaagc   7500
tatgtggata agcgaattgg aagcacatat gggccaccag gagggagaaa aatgactgta   7560
tttattgatg atattaatat gcctgtgatt aatgagtggg gagatcagat aactaatgag   7620
attgtgcgac agatgatgga aatggaagga atgtacagct tggacaagcc tggagacttc   7680
actactattg ttgatgtgca gctcatagca gcaatgatcc accctggagg tggtcgaaat   7740
gatattccac aacgtttaaa aagacaattt actgtgttta attgtacatt gccttcaaat   7800
gcttcaatag acaaaatttt tggaattatt ggatgtggat actttgatcc ttgtagaagt   7860
ttcaagcctc aaatatgtga gatgattgtg aatttagtct cagtgggtag agtgctgtgg   7920
caatggacta aggtgaagat gctgccaact ccttctaaat ttcattacat cttcaatctt   7980
cgagatcttt ccagaatttg gcaaggaatg ttgaccataa aagctgagga gtgcgcttca   8040
```

atccctactc tcctgtccct tttcaaacac gagtgcagca gagtaattgc agacagattt 8100
ataactcctg aagatgagca gtggtttaat gcacatctta ctcgtgcagt tgaagaaaat 8160
attggctctg atgcagcgtc gtgtattctt cctgaaccat actttgtgga ttttcttcgt 8220
gagatgccag aaccaactgg tgatgaacct gaagactctg tgtttgaagt acccaaaata 8280
tatgaattga tgccatcctt tgactttctg gctgaaaaac tccagtttta ccagagacag 8340
ttcaatgaaa tcattagagg aacatctctt gatctggtgt tttttaaaga tgcaatgact 8400
catcttatta agatttcacg aataattcga acgtcgtgtg gaaatgcatt gctggtgggt 8460
gttggtggtt ccggaaaaca aagtctttca agattggcct cttttattgc tggctatcaa 8520
atattccaga taacattaac caggtcttac aatgtgacta atctaacaga tgatttaaaa 8580
gctttgtaca aagttgctgg tgctgatgga aaaggcatca ctttcatctt tactgacagt 8640
gaaataaaag atgaggcatt tctagaatac cttaacaact tgctatcttc aggggagatc 8700
tccaacttgt ttgcacgaga tgagatggat gaaatcaccc aaggtctgat ttcagtgatg 8760
aagagggagc tacctcgcca tcctcctacc tttgataatt tgtatgaata cttcatttca 8820
agatcaagga agaacttaca tgttgttctc tgcttttctc cagttggtga gaagttccgt 8880
gcccgttctt tgaaatttcc tggcttgata tcaggttgca ctatggactg gttcagccgc 8940
tggccaaggg aggctctgat tgctgtggcc tcctacttcc tttcagacta taatattgtc 9000
tgctctagtg aaattaaaag acaagttgta gaaacaatgg gcctgtttca tgacatggtt 9060
tcagagagct gtgaaagtta tttccaaaga taccgccgaa gagcacatgt gactcccaaa 9120
tcttacctct catttataaa tggttataaa aacatttatg ctgaaaaggt gaagttcatt 9180
aatgaacagg ctgaacgtat gaatattggt cttgataaac taatggaggc aagtgaatct 9240
gttgctaaac tctctcagga tcttgcagtc aaggagaagg agttggcagt ggcttccata 9300
aaagcagacg aagtattagc agaagtcaca gtaagcgctc aggcttcagc caaaattaaa 9360
aatgaagtac aggaggtaaa ggacaaagcc caaaaaattg tggatgaaat tgatagtgaa 9420
aaagtgaaag ctgaaagcaa gcttgaggca gctaaacctg cactggaaga agcagaagca 9480
gccctgaata ctatcaagcc aaatgatatt gccacagtca ggaaacttgc aaaaccacca 9540
catcttatta tgagaatcat ggactgtgtt ctgttactat ttcaaaagaa aattgaccct 9600
gttactatgg atccagaaaa atcttgctgt aagccatcat ggggagagtc attaaagttg 9660
atgagtgcaa caggattcct gtggagcctt cagcagttcc ctaaggacac tataaatgaa 9720
gagactgttg agttactaca gccatatttt aatatggatg attatacttt tgaaagtgcc 9780
aaaaaagtct gtgggaatgt ggctggtctc ctgtcttgga cacttgctat ggcaatattt 9840
tatggcatca atagagaagt gttgcctctg aaggccaacc tggccaagca ggaaggccgg 9900
ttagcagttg ctaatgctga gttagggaag gcacaagccc tgctggatga gaagcaagct 9960
gagctggata aagtacaggc aaaatttgat gcagcaatga atgagaaaat ggatttgctt 10020
aatgacgctg atacgtgccg gaaaaagatg caggccgcct ccactctcat cgatgggctg 10080
agtggagaaa aaatccggtg gacccagcaa agtaaagaat tcaaagctca gattaataga 10140
cttgtaggtg atattctgct gtgcacggga ttcctttcct accttggtcc tttcaatcag 10200
atatttagga actatttgct taaagatcaa tgggaaatgg agttgagagc acggaaaatt 10260
cctttcacag aaaacctgaa tcttatttca atgttggtgg atcctccaac tattggtgag 10320
tgggggctac agggattacc aggagatgat ctctcaattc agaatggcat tattgtgaca 10380
aaggccacca gatacccact cctcatagac ccacaaactc aaggcaaaac ttggattaaa 10440
tcaaaggaaa aagaaaatga tttacaggtg acatctctga accgtaaata ttttcgcaca 10500
cacttggagg acagcctttc cttgggccga ccccttctca ttgaggacat tcatgaagag 10560
ctggatccag ccttggataa tgtattagaa aagaatttta ttaaatctgg caccactttc 10620
aaggtgaaag tcggtgataa ggaatgtgat atcatggata catttaaact ttacattact 10680
acgaagttac caaatcctgc ctttacccca gagattaatg ctaaaacgtc agtcattgat 10740
ttcactgtta caatgaaagg acttgagaat cagttactaa ggagagtcat tctaacagag 10800
aaacaggagt tagaggctga gagggttaaa cttttggagg atgttacttt taataagcgg 10860
aagatgaaag aacttgaaga taacctcctc tataaattaa gtgctacaaa aggctcattg 10920
gtagatgacg aatctctcat tggtgtactt cgaactacca agcagacagc agctgaggta 10980
agtgaaaagt tgcatgtggc tgcagaaact gagatcaaga tcaacgcggc tcaggaggag 11040
ttccggcccg cagccacccg cggaagcatc ctctacttcc tcatcacaga gatgagcatg 11100
gtcaacatca tgtatcagac gtcattggcc cagttcttga agttatttga ccagtccatg 11160
gccagatctg aaaagtcacc actacctcaa aagagaatta caaatattat cgagtacctg 11220
acatatgaag tttttacata ctctgtcaga ggcctatacg aaaaccacaa attcctgttt 11280
gtactcctca tgaccttaaa gattgacctt cagagaggga cagttaagca cagagagttt 11340
caagctctca ttaaaggggg agcagctctg gacctgaaag cctgtcctcc caaaccctat 11400
cgctggatcc ttgacatgac ttggctgaat cttgtggagc tgagtaaact tccacaattt 11460
gcagaaatta tgaaccagat atctcgtaat gagaaggggt ggaaaagctg gtttgataaa 11520
gatgctccag aggaggaaat tatccctgat ggatataatg attcactaga tacctgccat 11580
aaacttttac ttatcaggtc ttggtgccca gaccgtactg tttttcaagc aagaaagtat 11640
attgcagatt ctttggagga gaagtacaca gaaccagtta tcttaaatct ggagaaaact 11700
tgggaagaaa gtgataccccg gacacctctg atatgcttcc tgtccatggg atctgacccc 11760
accaatcaaa ttgatgcatt ggccaagaaa ctgaaactgg aatgtagaac tatctcaatg 11820
gggcaaggac aagaagtaca tgctcgaaag ctgattcaga tgtcaatgca gcagggtggt 11880
tgggtattac tacaaaattg ccaccttggc ctggaattca tggaagaatt actagagacg 11940
ctaattacca ctgaagccag tgatgattct ttccgagtat ggataactac ggagccccat 12000
gatcgatttc caattacatt gcttcagacc tctctcaaat tcactaatga gccaccccaa 12060
ggtgtacgcg caggtttgaa aagaacattt gctggaatta atcaagacct tctggacatc 12120
agtaatttac ccatgtggaa gccgatgctt tacacagtag catttttaca ctccactgtg 12180
caggagcgac gaaaatttgg ccccttagga tggaatattc cctacgaatt caattctgct 12240
gacttttcag ccagtgttca gtttattcag aatcaccttg atgaatgcga tattaagaaa 12300
ggtgtatcat ggaatacggt tcggtacatg atcggagaag tacaatatgg agacagagtg 12360
acagatgact ttgacaaacg tctacttaat tgctttgcca gagtctggtt cagtgagaag 12420
atgtttgaac cgtcattctg cttttatact ggatataaaa tcccccttatg caaaacctta 12480
gaccagtatt ttgaatacat ccagtcactg ccatccctag ataaccctga agtctttggg 12540
cttcacccta atgctgatat cacgtatcag agtaacactg cttctgctgt tcttgaaaca 12600
attaccaaca ttcaacccaa agagagtgga ggtggtgtgg gagagacccg ggaggctatt 12660
gtttatagat tatctgaaga tatgctgagt aaactccctc ctgattacat tcctcatgag 12720
gtgaaatctc gtttgataaa gatgggccat cttaattcaa tgaacatatt tcttagacaa 12780
gaaattgaca gaatgcaaag agtcatttca gtactccgca gtagcctgag tgatctaaaa 12840
ttggccattg aaggaacaat cattatgagt gagaatctga gagatgctct ggacaacatg 12900
tatgatgctc gtatacctca gctctggaaa agagtgtctt gggattcgtc cacactgggc 12960
ttctggttca ctgaactttt ggaaagaaat gctcagtttt ctacgtggat atttgaaggg 13020
aggcctaatg tgttttggat gactggtttc tttaatcccc aaggcttcct cacagcaatg 13080
aggcaagaag tgacccgtgc ccacaaaggc tgggcactgg acactgtgac catccacaat 13140
gaagttctga gacagaccaa ggaggagatc acgtcacccc ctggggaagg tgtgtatatt 13200
tatgggctct acatggatgg agcagcctgg gacagacgga atgggaagct catggaatcc 13260
acccccaagg tactcttcac gcagttaccc gtgctccaca tctttgccat taactccacg 13320
gcacccaagg accccaagct gtatgtgtgt cctatttaca agaaacccag gcgaactgat 13380
ttgaccttca tcactgtggt atatttacga acagtgttgt ccccggatca ctggatcctg 13440
agaggagtgg ccctttttgtg tgacatcaag taa 13473

<210> SEQ ID NO 46
<211> LENGTH: 13461
<212> TYPE: DNA
<213> ORGANISM: Homo sapiens

<400> SEQUENCE: 46
atgcggctcg cggaggagcg ggccgcgctc gcggcggaga acgcggatgg ggaacccggc 60
gccgaccgac gactgcgact cctggggacc tacgtggcca tgagcctgcg gccggctgcg 120
ggcgcctggg agcgttgcgc ggggagtgct gaggcggagc agctgctcca ggccttcctg 180
ggccgcgatg ctgccgaggg gccgcggccg ctgctggtgg tgcggcccgg gcccaggggc 240
ctggcaatac gccccgggct ggaggtggga cctgagtcgg gcctggctgg cgctaaggcg 300 cttttttttcc ttcgcaccgg gcccgagcct ccagggcccg acagcttccg cggcgcagtg 360
gtctgcgggg acctgcccgc ggcacctctg gagcacctag ccgcgctgtt ctcggaggtt 420
gttctacccg tcctggccaa tgagaagaat cgcctaaact ggccccacat gatatgtgag 480
gatgtcaggc ggcacgccca cagcctccaa tgtgacctct cagttatact tgagcaagtg 540
aagggaaaaa ctttgctgcc tcttccagca ggctcagaaa aaatggagtt tgcggattcc 600
aaaagtgaga cagtcttgga ttctatagat aagtcagtca tctatgccat tgagtctgca 660
gtgatcaaat ggagctacca agtccaggtg gtactcaaga gagagtcttc ccagccactc 720
ttacaagggg agaatcccac ccctaaggtg gagttggagt tctggaagag caggtatgaa 780
gatctgaaat acatctataa tcaactgaga acaataacgg tgaggggcat ggccaagctc 840
ctggacaagc ttcagagtag ctactttcca gctttcaaag ccatgtacag agatgttgtt 900
gcagctctag cagaggcaca ggacatccat gtgcacctga taccgctcca gcgccacctg 960
gaagctctgg agaatgcaga atttccggag gtgaagcccc agctgcggcc cctgctccac 1020
gtggtctgtc tgatttgggc cacatgcaag tcctaccgct ccccgggaag gctgactgtg 1080
ctgctccagg agatttgcaa ccttctcatc cagcaggcct ctaattatct cagcccagaa 1140
gacctgctga gaagtgaggt agaagaaagt cagagaaaac tgcaagtggt ctcagacact 1200
ttgagcttct tcaagcaaga gtttcaggac agaagggaga atctccacac ttacttcaaa 1260
gagaaccagg aagtcaagga atgggatttc cagtcttctt tggtctttgt gcgattggat 1320
ggcttcctgg gacaactgca cgtggtggag ggtcttctga agacggccct ggatttccac 1380

-continued

```
aaactgggaa aggtggagtt cagcggcgtc agagggaatg ctctgagtca gcaggtccag   1440
caaatgcatg aagaatttca agagatgtac aggcttctct caggatcctc ctccgactgc   1500
ctgtacctcc aaagcacgga ctttgaaaat gacgtctctg aatttaacca gaaagtagaa   1560
gatcttgacc gaagattggg gactatcttt attcaagctt ttgatgatgc acctggcttg   1620
gagcatgcct ttaagctgct agacatagca ggaaacctcc ttgaaagacc gctggtagcg   1680
agggatacat ctgataaata cctggtcctc atccaaatgt tcaacaaaga tctggatgca   1740
gtgaggatga tctacagtca gcacgtccag gaggaagcag aacttgggtt ctccccggtg   1800
cacaagaaca tgcccaccgt ggctggcggc ctccgctggg cacaggagct gaggcagcgc   1860
atccagggtc ctttcagcaa ctttggacgc atcacacacc cttgcatgga atctgcagaa   1920
ggaaagcgaa tgcaacaaaa atatgaagat atgctgtcat tgctagaaaa gtatgagaca   1980
agactttatg aggattggtg ccggacagta tcagagaagt cacagtacaa tctttcccaa   2040
ccacttctaa aacgtgaccc agagacgaag gagatcacta tcaactttaa cccacagctg   2100
atttcagtgc tgaaagaaat gagctatctt gaacccagag agatgaaaca catgcctgag   2160
acagcagcag ccatgttctc ctccagggat ttctatcggc agcttgtggc taatttagag   2220
ttgatggcaa attggtacaa caaggttatg aaaactctgc tggaggtgga atttccatta   2280
gtggaggaag agctgcaaaa tattgatctc cgcctcagag cagcagagga gactttgaac   2340
tggaaaacag aaggcatttg cgattatgtc actgaaatca ccagtagtat tcatgatctt   2400
gaacaaagaa ttcagaaaac taaagacaat gtggaagaga tccaaaacat catgaaaaca   2460
tgggtgactc caatatttaa gacaaaagat ggaaaaaggg aatcccttct ttctctggat   2520
gatcggcatg atcgaatgga aaaatattac aatctcatca aggaatctgg ccttaagatc   2580
cacgcccttg ttcaggaaaa cctgggtcta ttttcagcag acccaacctc caatatctgg   2640
aagacttatg ttaactctat tgacaatttg ttgctgaatg gattctttct tgccattgag   2700
tgctccctca agtatcttct ggaaaatact gagtgtaagg caggacttac cccaatattt   2760
gaagcacaac tgagtctagc catcccagag ctagttttct atccgtctct ggagtctgga   2820
gtgaaggggg gtttctgtga cattgttgag ggtctcatca ccagcatttt taggatacca   2880
tctctggtgc cacggctttc cccacaaaat ggctctcctc actatcaggt cgacctggac   2940
ggtataccag atttggcaaa catgcggcgc acactcatgg agagagtcca gagaatgatg   3000
ggcctctgct gtggctatca gagcaccttc agccagtatt cgtacctcta tgtggaggac   3060
cggaaggagg ttctgggtca gtttctgctg tacgggcaca tcctcactcc ggaagaaatt   3120
gaagaccatg tggaagatgg catcccagag aaccctcccc tcctttctca gtttaaagtg   3180
caaatcgact cctatgaaac gctctatgaa gaggtgtgca ggctggaacc catcaaggtg   3240
tttgacggct ggatgaaaat tgatattcga ccctttaagg catctctgct gaatattatt   3300
aagaggtgga gcctcctgtt caaacagcat cttgtggacc acgtcactca cagcttggcc   3360
aacctggatg cgtttataaa gaagagtgag agcggcttac tcaagaaagt tgaaaaagga   3420
gatttccaag gcttggttga gatcatggga caccttatgg ctgttaaaga acggcagagt   3480
aacactgatg agatgtttga gcccttaaag cagactattg aattgctgaa gacctatgaa   3540
caagaattgc cagaaacagt gtttaagcag ctggaggagc tgcctgagaa atggaacaac   3600
ataaaaaagg tggccattac tgtgaagcag caggtggccc cactgcaggc aaatgaagtg   3660
acactcctcc gccagaggtg cacagccttc gatgcagaac agcagcaatt ctgggagcaa   3720
ttccacaaag aagccccgtt caggtttgat agcatccacc ctcatcaaat gctggatgcc   3780
```

-continued

```
aggcacatcg agatccagca gatggaatcc actatggcct ccatttctga gtctgccagc   3840
ttatttgaag tcaatgtccc tgactataag cagctgaggc agtgcaggaa ggaggtctgc   3900
cagctgaagg agctctggga caccattgga atggtgacct ccagcatcca tgcctgggag   3960
accacaccct ggaggaatat caacgtggaa gccatggagt tggagtgcaa acagtttgcc   4020
cggcatatcc gaaacctgga caaggaggtc agggcctggg atgcattcac aggcctggaa   4080
agcactgtgt ggaacacgct gagctccctg agggcagtag ctgagctgca gaatccagcc   4140
atccgggagc ggcactggag gcagctgatg caggccaccg gtgtgagctt cactatggac   4200
caggacacca ccctagcgca cctgctgcag ctccagctgc accactatga ggatgaggtc   4260
cggggcattg tggacaaagc tgcaaaagag atgggtatgg agaaaacctt aaaggagctg   4320
cagactacct gggctggcat ggaattccag tatgagcccc acccacggac caatgtcccc   4380
ctcctgtgct ctgatgagga cctcatagag gttctggagg ataatcaagt tcaacttcag   4440
aacctggtga tgtccaagta tgttgctttc ttcttggagg aggtgtcggg ctggcagaag   4500
aagctgtcca cagtggacgc tgtcatctct atctggtttg aagtgcagcg aacatggact   4560
cacctggaaa gcatattcac tggatctgaa gatattcggg cacagctacc ccaggattct   4620
aaaaggtttg aaggcatcga cattgacttt aaagagctag cttatgatgc ccagaaaatt   4680
ccaaatgtag tgcaaaccac caacaagcca ggcctgtatg aaaagctgga ggatattcag   4740
ggcagattgt gcctgtgtga gaaggccctg gcagagtacc tcgacaccaa gaggcttgcc   4800
ttcccgcggt tttactttct ctcctcctcc gatctgttag acatcctttc caacggcaca   4860
gctccacaac aggttcaacg tcacctttcc aaactctttg acaacatggc caagatgcga   4920
ttccagctag atgccagtgg ggaaccaacc aagacaagcc tcggcatgta cagcaaagaa   4980
gaggagtatg tggctttcag tgagccctgt gactgcagcg ggcaggtaga aatatggctg   5040
aaccatgtcc ttggtcacat gaaggccact gtgaggcatg agatgacaga aggtgtaact   5100
gcctatgaag aaaagccgag ggagcagtgg ctttttgacc acccagctca ggtggccctg   5160
acctgtactc agatctggtg gacaacagaa gtgggcatgg catttgccag gctggaggaa   5220
ggctatgaga gtgccatgaa ggactattat aagaagcaag tggcccagct caaaaccctt   5280
atcaccatgc tgattggcca gctctccaag ggagaccggc agaagattat gactatatgc   5340
accatcgatg tgcatgcccg ggatgtggta gccaagatga ttgctcagaa ggtagacaat   5400
gcccaggctt cctctggctt gtctcagctg cgccatcgtt gggatgacga ggtcaaacac   5460
tgctttgcca acatctgtga tgcccagttt ttgtattcct atgagtacct gggaaacaca   5520
cctcgcttgg tgatcacacc tttgactgac aggtgctaca tcaccctcac ccagtccctg   5580
cacctgacca tgagtggggc tcccgcagga cctgcaggca caggcaagac cgagaccacc   5640
aaggacctgg gccgcgcact gggcatcctg gtctatgtgt tcaactgctc ggagcagatg   5700
gattacaagt cttgtggcaa catctacaaa ggccttgctc agactggtgc ctggggctgc   5760
tttgatgagt ttaatcgaat ctccgtggag gtcttgtcag tggtggcagt gcaggtaaaa   5820
agcattcaag atgcgattag agataagaag cagtggttca gcttccttgg ggaggagatc   5880
agcctgaatc cttctgtcgg tatcttcatc accatgaacc caggctatgc tggccgcaca   5940
gagctgccag agaatctcaa gtctctcttc aggccttgtg caatggtggt tccagacttt   6000
gaattgatct gtgaaatcat gctggtggca gaaggattca ttgaagccca gtcattagcc   6060
agaaagttca tcactcttta ccagttgtgc aaagagcttc tctccaaaca ggatcactac   6120
```

-continued

```
gactggggcc tacgggccat caagtccgtg ctggtggtgg caggatccct gaagagagga   6180
gaccctgacc ggcctgagga ccaggtcctg atgcgctcct tgcgggattt caacatcccc   6240
aagattgtga ctgatgacat gcccatcttc atgggcctga tcggggacct ctttcccgcc   6300
ctggatgtcc cccggaggag agaccccaac ttcgaagctt tggttaggaa ggcgatagtg   6360
gatctgaagc tccaggctga ggacaacttt gtgctcaagg tggtccagct ggaggagctc   6420
ctggctgtgc ggcactctgt atttgtggtg ggtggcgctg gtaccggcaa gtcacaggtg   6480
ctgaggtcct tgcacaagac ctatcagatc atgaaacggc gccccgtctg gactgacctc   6540
aatcccaaag cagtcacaaa tgatgagctc tttggcatca tcaatccagc cacaggagaa   6600
tggaaggatg gattgttctc ttccatcatg cgggagcttg ccaacatcac ccatgatggg   6660
cccaagtgga ttttactgga tggcgacata gatccaatgt ggattgaatc cctgaatact   6720
gtcatggatg ataacaaggt gctgacattg gccagcaatg agaggattcc tctgaacccc   6780
accatgaagc tcctctttga gatcagccac ctgcgcacag ccactccagc aactgtctct   6840
agagcaggga tcttgtacat caacccggca gacttgggat ggaaccctcc agtgagcagc   6900
tggattgaga agagggaaat ccagacagag agagccaact taaccatttt gttcgacaag   6960
tatcttccaa cctgcctaga cacactcaga accaggttta agaagatcat tcccatccca   7020
gagcagagca tggttcagat ggtgtgtcac cttctggaat gtctcctgac cacggaggac   7080
atccctgcag actgccctaa ggaaatttat gagcattatt ttgtgtttgc tgccatctgg   7140
gctttcggcg gagcaatggt ccaagatcag cttgtggact accgggcaga gttcagcaaa   7200
tggtggctga ctgagttcaa aacagtcaag tttccttccc aaggaaccat ctttgactat   7260
tacatcgacc cagagaccaa gaaattcgag ccttggtcca agctcgtccc ccagttcgaa   7320
tttgaccccg agatgccctt gcaggcgtgt ttggtgcaca cgagtgagac catccgtgtg   7380
tgctacttca tggagcggtt gatggcgcgg cagcggcctg tcatgctggt gggcacggct   7440
ggcactggca agtcggtgct ggtgggagct aagctggcca gccttgaccc cgaggcatac   7500
ctggtgaaaa acgtgccatt caactactac accacgtcag caatgctgca ggctgtcctg   7560
gagaagcctc tggaaaagaa ggctggcaga aactatggcc ctccagggaa caagaaactc   7620
atctatttca ttgatgacat gaacatgcct gaggtggatg cctacgggac ggtgcagccc   7680
cacaccatca tccggcagca tctggactat ggccactggt atgatcggag caagctgtcc   7740
ctaaaggaga tcacaaatgt acagtatgtt tcctgtatga accccacggc aggcagcttc   7800
accatcaacc cccggcttca gcgtcacttc agcgtgtttg tcctctcctt cccgggggca   7860
gatgccctgt cctctatcta cagcatcatc ctcactcagc atctgaagct cggaaacttc   7920
ccggcgtccc tgcagaaatc catccccccca ctgatcgatc tggccctcgc cttccaccag   7980
aaaattgcta ccaccttcct acccacagga atcaaattcc actacatctt caacctcaga   8040
gattttgcca acattttcca gggcattctc ttctcctcag tggaatgtgt gaaatccaca   8100
tgggatctta taaggctcta tctgcatgaa tcaaatcgag tttatcggga taagatggta   8160
gaagaaaagg actttgatct tttgataaa atccagacag aagtgctcaa gaaaactttt   8220
gatgatattg aagaccctgt ggagcagacc caaagcccga acctgtattg tcactttgca   8280
aatggtattg gggagcccaa atacatgcct gtacagtctt gggaactttt gacccagact   8340
ctggtggagg ccttggagaa ccacaatgaa gtcaacacag tgatggacct agttctcttt   8400
gaggatgcca tgcgccatgt ctgccatatc aatcgcatct tggagtcccc gcggggaaat   8460
gctctgctgg ttggtgtagg tgggagcggc aagcagagcc tgacaaggct ggcagctttc   8520
```

atcagctcca tggatgtctt ccagatcaca ctgcgcaaag gctaccagat ccaggacttc 8580
aagatggacc tggccagcct gtgtctgaaa gctggagtga agaatctcaa cacagtgttt 8640
ctcatgactg atgcccaagt ggctgatgag aggttccttg tgctcatcaa tgatcttttg 8700
gcatctgggg agatcccaga tctctactct gatgatgaag ttgaaaacat cataagcaat 8760
gtgaggaatg aagtcaagag ccagggtctg gttgacaaca gagagaactg ttggaagttc 8820
tttatagatc ggatccggcg acagctgaag gtgactctct gtttctcccc tgtgggaaac 8880
aagctaagag tccgcagcag gaagttccca gccattgtga actgcacagc catccactgg 8940
ttccacgagt ggcctcagca agcattggag tctgtcagcc tccgcttctt gcagaacaca 9000
gagggcattg agcccacagt aaagcagtcg attagcaaat tcatggcctt tgtccacaca 9060
agtgtcaacc aaacatccca gtcttatctg agcaatgaac agcgctacaa ctatacaact 9120
cccaagtcct ttctggagtt catcagactc taccagagct tgttgcacag gcacagaaaa 9180
gagctcaagt gcaagacaga gcggttggag aacgggctgc tgaagctgca tagcacctct 9240
gcccaggtgg atgatctgaa agcaaagctg gctgcccagg aagtagagct gaagcagaaa 9300
aatgaagatg cagacaaact gattcaggtc gtgggtgtgg agactgacaa agtgagcaga 9360
gagaaagcca tggcagatga agaggagcag aaggtggccg tcatcatgct agaggtgaaa 9420
cagaagcaga aggactgtga ggaggacctg gcaaaggctg agccagcact cacagcagcg 9480
caggcagctc tcaacaccct gaacaagacc aacctgacag agctgaagtc atttggctct 9540
ccgcctctgg ccgtcagcaa tgtcagcgct gcggtgatgg tactgatggc tcccaggggt 9600
agggtgccca aggaccggag ctggaaggct gctaaggtca ccatggccaa agtggatggc 9660
ttcctggact cgctaataaa cttcaacaaa gagaacattc acgagaactg cctcaaagcc 9720
atcaggccgt atctgcaaga ccccgagttc aatcctgagt ttgtggccac caaatcctat 9780
gcggctgcag gcctctgctc ctgggtcatc aatattgtga gattttatga ggtgttctgt 9840
gatgtggaac ccaagcgcca ggcactgaac aaagccaccg cggacctcac agctgcccag 9900
gagaagctgg ctgccatcaa agccaagatc gctcacctta atgaaaacct ggcaaagctc 9960
acagccaggt ttgagaaagc aacagcagac aaactcaaat gtcagcaaga agccgaagtg 10020
accgcagtca ccatctccct tgccaaccgc ctggttggag gactcgcttc tgaaaacgtg 10080
aggtgggcag atgccgtgca gaacttcaaa cagcaggaaa ggacgttatg tggagacatt 10140
ttacttataa cggctttcat ttcctacctt ggcttcttca caaagaaata ccggcagagc 10200
ctcctggaca gaacttggag gccctacctg agccagctga aaactcccat tccagtcacc 10260
ccagccctgg atcccctgag gatgctgatg gatgatgctg acgtggctgc ctggcagaac 10320
gagggcctcc cagccgaccg catgtccgtg gagaatgcca ccattctcat caactgtgag 10380
cgctggccac tcatggttga ccctcagcta caaggcatca aatggatcaa gaataaatat 10440
ggtgaagatc tccgggtcac gcagattggt cagaaaggct accttcaaat catagagcag 10500
gccctggaag ctggagctgt ggtgctgatt gaaaatctag aggagtccat tgatcctgtt 10560
ctgggacccc tgcttgggag agaagtcatt aaaaaaggac gattcattaa aattggagac 10620
aaagaatgtg aatacaatcc caagttccgg ctcatcctcc acaccaagct ggctaatcct 10680
cactaccagc ctgagctgca ggctcaggcc accctgatca acttcaccgt gaccagggat 10740
ggcctggagg accagttgct ggccgctgtg gtcagcatgg agaggccaga cttggagcag 10800
ctgaagtccg atctcacaaa gcagcagaat ggattcaaaa ttaccctgaa aacgttggaa 10860
gacagtcttc tctctcgcct ctcctccgcc tctgggaact tcctgggaga aacagtgctg 10920
gtggaaaacc tagagatcac caagcagact gctgccgaag ttgagaaaaa ggtccaggag 10980
gccaaggtga ctgaagtgaa aatcaacgag gcccgagagc actaccggcc agcagctgcc 11040
agggcctcac tgctctactt catcatgaac gacctcagca agatccatcc aatgtaccag 11100
ttttctctca aggccttcag tatcgtcttc cagaaggctg tggagagggc tgctcctgac 11160
gaaagcctca gggagcgggt ggccaaccta atagacagca taaccttctc tgtgtaccag 11220
tacaccatcc gcgggctctt tgagtgtgat aagctgacct accttgccca gctcaccttt 11280
cagattctcc tcatgaaccg agaagtcaat gcagtggagt tggatttcct gcttcgatct 11340
ccagtgcaga cgggcaccgc cagccccgtg gagttcctct cccatcaggc gtggggagct 11400
gtcaaggtac tttcatcaat ggaagaattc tctaatctgg atcgggacat agagggatct 11460
gctaagagct ggaaaaagtt tgtggagtcc gaatgtcctg agaaagagaa gctcccacag 11520
gagtggaaga acaagacagc cctgcagcgc ctctgcatgc tgagagccat gcggcccgac 11580
cggatgacct atgctttgcg agattttgtt gaagagaagt taggaagcaa atacgtggtg 11640
ggaagagccc tagattttgc aacctcattt gaagaatcgg gaccagccac tcctatgttt 11700
ttcatcctgt ctccaggggt ggacccactg aaggatgtag aaagtcaagg aagaaaactt 11760
ggatacacct tcaacaatca gaactttcac aacgtgtctt tggggcaagg acaggaagtg 11820
gtggctgagg ctgcgctgga cctcgctgcc aagaaaggtc actgggttat tttgcagaac 11880
attcacctgg tggccaagtg gctcagcacc ctggagaaga agctggagga gcacagtgag 11940
aacagccacc cagagttcag ggtcttcatg agtgcagagc cagcaccctc ccctgagggc 12000
cacatcatcc cccagggcat cctggagaac tccattaaga tcaccaatga gccccccacg 12060
ggcatgcatg ccaacctgca caaggccctg gacaacttca ctcaggacac tctggagatg 12120
tgttctcggg agacggagtt taagagcatc ctctttgctc tttgttactt ccatgcggtg 12180
gtggcagaaa gacgaaaatt tgggccccag ggatggaatc gctcataccc ctttaacact 12240
ggagacctca ctatctctgt gaatgtcctc tacaacttcc tggaggccaa cgcaaaggtc 12300
ccctatgatg atttgcgcta cctgtttgga gagatcatgt atggaggcca tatcacagat 12360
gactgggaca gaagactctg cagaacctac ctgggggaat tcattcgacc agaaatgtta 12420
gaaggagaac tgtctttggc cccagggttc ccactcccag gcaacatgga ctacaatggt 12480
tatcatcagt acatcgatgc tgagctgccc ccagaatccc cctacctcta tggcctccac 12540
ccgaacgcag agattggctt cctgacccaa acctcagaaa agctcttccg cactgtgctg 12600
gagctgcagc ctcgggacag ccaggccaga gacggagcgg gcgccacaag agaagaaaag 12660
gtcaaggcac ttctggaaga aatattggag cgggtgacag acgagtttaa catcccagaa 12720
ctgatggcca aagtggagga gcgcacccct tacattgtag ttgccttcca ggagtgtggc 12780
cggatgaata tcctcaccag agagattcag cgctcactga gggagctgga gctcggctta 12840
aagggggagc tgactatgac cagccacatg gagaacttac agaatgccct gtacttcgat 12900
atggtgccag agtcctgggc tagacgagcc taccccttcca cagcaggcct ggcagcctgg 12960
tttccagacc tcctcaacag aatcaaggag ctagaggctt ggacgggtga ctttacaatg 13020
ccctccactg tgtggctgac aggcttcttc aacccccagt cgttcctgac tgccatcatg 13080
cagtccacgg ctcgcaagaa tgagtggcca ctggaccaga tggccctgca atgtgacatg 13140
acgaagaaga acagagaaga gtttaggagt cctcctcggg aaggggccta catccatggc 13200
ctcttcatgg aaggtgcctg ctgggacaca caggctggga tcattacaga ggcaaagctg 13260

-continued aaggatctga caccccctat gcctgtgatg ttcatcaagg ccattcctgc agataagcag 13320
gactgccgca gtgtctattc ctgtcctgtg tacaagacta gtcagcgggg acccacctac 13380
gtgtggactt tcaacctgaa gactaaggaa aacccatcca agtgggttct ggctggagta 13440
gccttgcttc tccagattta g 13461

<210> SEQ ID NO 47
<211> LENGTH: 13416
<212> TYPE: DNA
<213> ORGANISM: Homo sapiens

<400> SEQUENCE: 47
atggtgccgg aggaggtgga ggtggagatt gatgagatac ctgtcctgtc tgaagaggga 60
gaagaggaag aagagactta ttctcaaaaa gtggagtccg tggataaagt gcgagctaag 120
cgtgtgtcac tgagaaccga atctctaggc caacctctaa acagagagga tgaagaaatg 180
gacaaagaga tttcagaaaa actcccttcc aaaagaactg cgaagcacat catggaaaag 240
atgcatctcc acatgctctg taccccctctt cccgaggagt tcctggacca aaacgtggtg 300
tttttcctca gaaataccaa agaggcaatc tctgaagcta ccgacatgaa ggaagctatg 360
gaaattatgc cagaaacact ggagtatgga attataaacg ctaatgtgct ccatttctg 420 aagaatatta tatgtcaggt ttttttgcca gcattgtcct tcaatcagca caggacgagt 480
acaaccgtgg gagtcacatc tggagaagtc tctaattcct ctgagcatga atcagacctg 540
ccgcccatgc ctggggaggc agtagaatat cacagtattc aattaatacg ggatgaattt 600
ttaatgaacg tgcagaaatt tgcaagtaat attcaaagaa ccatgcagca acttgaaggt 660
gagatcaagt tagaaatgcc aatcatcagt gtggagggag aggtgtctga cctggcagct 720
gacccggaaa ccgttgacat cttggagcag tgtgtgataa actggctgaa tcagatatcc 780
acagcggttg aggcccaact gaagaagaca cctcagggta aaggccctct ggctgaaatt 840
gaattctgga gggaaagaaa tgcaacctta agtgcgctgc atgaacaaac aaagcttcca 900
atagtcagaa aagtcttgga tgtgatcaag gaatccgact ccatgcttgt ggctaatctg 960
cagccagtgt tcaccgagtt attcaagttc cacacggagg cctcagacaa tgtgcgcttt 1020
ctctccaccg tggagcgtta tttcaagaac ataacgcacg ggtctggctt ccacgtggtc 1080
ctggacacca tccccgccat gatgagtgcc ctgcggatgg tgtggatcat ctcccgacac 1140
tacaacaaag acgagaggat gattccgctc atggagcgca tcgcctggga aatcgctgag 1200
agagtctgcc gagtggtcaa cctgcggact ttgttcaaag aaaatcgagc gagtgcccaa 1260
agcaaaacct tggaagccag gaacaccctc aggctgtgga aaaaggccta ttttgacacc 1320
cgggccaaga tagaggcttc ggggagggaa gatcggtggg agtttgaccg gaagcggctg 1380
ttcgagagga cggattatat ggccaccatc tgccaggacc tctccgacgt tctgcagatt 1440
ttggaggaat tttataacat atttggtcca gaactaaagg cagtgacggg ggaccccaag 1500
cgcattgatg atgtcctatg cagagtggac ggcctagtca cccccatgga aaacctgacc 1560
tttgacccct tcagcatcaa gtcctcccag ttctggaaat atgtgatgga tgaattcaag 1620
attgaagttc tgattgacat cattaataaa atctttgtcc agaaccttga aaatccacca 1680
ctgtataaga atcaccctcc agtagcaggt gcaatatact gggaacgatc tctgttcttt 1740
cggattaagc ataccatcct ccgatttcaa gaggtacaag agatactgga cagtgatcga 1800
ggacaggagg tcaaacaaaa atatttggaa gtaggtagga caatgaagga gtatgaagac 1860

```
agaaagtatg agcagtggat ggaggtgacg gagcaggtgc tgccagctct catgaagaag   1920
agccttttga ccaagtcttc catcgccaca gaggagcctt cgactttaga aaggggagct   1980
gtttttgcaa tcaacttttc accggctctc agagagatta ttaatgaaac aaagtactta   2040
gagcagctgg ggttcactgt ccctgaatta gcaagaaatg ttgctctcca ggaagacaaa   2100
ttccttaggt acacagctgg gatacagcgc atgttggatc attatcacat gctcatagga   2160
acgttaaacg atgcggagtc tgtgcttctc aaagatcatt cccaggaact gctccgagtg   2220
tttaggtcgg gatataagag gttgaactgg aactcactag gtatcggtga ctatataact   2280
ggttgcaaac aggccattgg gaaatttgag tctctcgtcc accagattca taagaatgca   2340
gatgacattt cttccaggct gacattaata gaggccataa atctctttaa atatccagcc   2400
gctaaaagtg aggaagaact cccaggcgtg aaggaatttt ttgaacacat tgagcgagaa   2460
agggccagcg acgtggacca catggtccgg tggtatcttg ccattggacc actgctgacc   2520
aaagttgagg gcctggtcgt ccacaccaac acaggcaagg cccccaagct ggcctcctac   2580
tacaaatact gggaaaagaa aatttatgag gtcctgacaa agctcatcct gaagaacttg   2640
cagtctttta attctttgat ccttggaaat gtccctctgt tccacactga aaccattctg   2700
acggcacctg agatcatcct tcatcccaac acaaatgaga tcgacaagat gtgcttccat   2760
tgtgtccgga attgcgtgga gatcaccaag cattttgttc gttggatgaa tggcagctgc   2820
atagaatgcc cacctcagaa gggggaggaa gaggaagttg ttataataaa cttttacaat   2880
gatatctctc tgaaccctca gataattgaa caagctgtta tgatccccca aaatgtccac   2940
aggattctga tcaatcttat gaagtatcta caaaaatgga agcggtatcg acctctctgg   3000
aaattggaca aagctattgt gatggagaaa tttgctgcca agaaacctcc ttgtgtagca   3060
tatgatgaaa agttgcagtt ctattccaag atagcttatg aggttatgcg ccaccctcta   3120
attaaggatg agcattgcat cagacttcag ctcaggcatc tggcaaacac agtgcaggaa   3180
aatgccaagt cctgggtgat ttcgcttgga aaacttctca atgagtcagc aaaagaggag   3240
ctctataatc tccatgaaga gatggagcac ctggccaaaa accttaggaa gatccccaat   3300
acccttgaag atctcaagtt tgtccttgca acaattgcag aaattagaag taaatctcta   3360
gtcatggaac tcagatatag ggacgtccag gagcgatacc gtaccatggc aatgtataac   3420
ctctttcctc ctgatgcaga gaaagaactg gttgataaga ttgagagcat atggtccaat   3480
ctgtttaatg attcagtgaa tgtggagcat gctcttgggg acataaagag aactttcaca   3540
gagcttactc gaggcgaaat aatgaactac agagttcaga tagaggagtt tgcaaagcgt   3600
ttttacagtg aaggccctgg ttctgttggt gatgatcttg ataaaggagt agagctttta   3660
ggtgtttatg aaagagagct ggcaagacat gaaaagagcc gtcaggaact ggctaacgct   3720
gagaaacttt tcgatcttcc tattacaatg tacccagagc tgctgaaagt gcagaaggaa   3780
atgagtgggc tgaggatgat ttacgagctc tatgaaggac taaaggttgc aaaagaagaa   3840
tggtctcaga ccctttggat caacctgaat gtgcagattc tccaggaagg aattgaaggt   3900
tttctcaggg ctctcagaaa gctacctcgg ccagtccgtg gcttatcagt gacctactac   3960
ttggaagcaa aaatgaaggc attcaaagac tcgattcctt tacttcttga cttgaaaaac   4020
gaggcactaa gagacaggca ttggaaagaa cttatggaaa aaacgtctgt cttttttgaa   4080
atgaccgaaa cgttcacctt ggaaaatatg tttgctatgg aactgcacaa acacacagat   4140
gttctcaatg agattgtcac agcagcaatc aaggaggttg ccattgagaa ggctgtgaag   4200
gaaatcctag acacgtggga aaatatgaaa ttcactgtag tcaagtattg caaaggcaca   4260
```

caggagcgag gctacatcct gggttctgtt gacgaaatta ttcagtctct tgatgacaac 4320
actttcaacc tgcagagcat ctcaggaagc agatttgtgg ggccttttct gcaaactgtt 4380
cacaaatggg aaaaaacgct ttctctaata ggggaagtca ttgagatttg gatgttggtt 4440
cagagaaaat ggatgtatct tgaaagtatt tttattggtg gagatataag atcacaactt 4500
ccggaagagg caaaaaagtt tgacaacatc gataaagtat ttaaaaggat catgggtgag 4560
accttaaaag accccgtgat caagaggtgc tgtgaagccc caaaccgcct cagtgaccta 4620
cagaacgtca gcgagggcct ggagaaatgc cagaaaagcc tcaacgacta cttagattcg 4680
aagagaaatg ctttcccaag gttcttcttc atttctgacg atgagttgct tagcattctg 4740
gggagcagcg acccactctg cgtccaggag cacatgatca agatgtacga caacatagca 4800
tcactgaggt ttaatgacgg cgatagtgga gaaaaactgg tgtccgcgat gatttcagca 4860
gaaggagaag tcatggagtt tcggaagatc ttgcgggctg aagggcgcgt ggaggactgg 4920
atgacggcag ttttgaatga gatgagaaga actaatagac taattaccaa agaggctatt 4980
tttagatact gtgaagacag aagcagagtc gactggatgc tcctgtacca gggcatggtg 5040
gtgctggccg ctagccaggt gtggtggacc tgggaggtgg aagacgtctt ccacaaagcg 5100
caaaaagggg agaagcaggc catgaagaac tatggcagga aaatgcaccg gcagatcgat 5160
gagttggtaa cgcgcatcac catgccgcta agcaaaaacg acaggaaaaa atacaacact 5220
gttctcatca ttgatgtgca tgccagagac atagttgatt ctttcataag aggcagtatc 5280
ctggaggccc gagagtttga ctgggaaagt cagttgcggt tttattggga ccgggagccg 5340
gatgagctga acatccgcca gtgcacggga acctttggct acggctacga gtacatgggc 5400
ctgaacggca ggctggtcat cacgcccctc accgatcgga tttacctgac gctcacccag 5460
gcgctgtcca tgtatctagg tggggccccc gccggcccag caggaaccgg caaaaccgag 5520
accaccaagg acctggcgaa agccttgggc ttgctctgtg ttgtcaccaa ctgtggcgaa 5580
ggcatggatt acagggccgt ggggaagatt ttctctggcc tggcacagtg cggggcttgg 5640
ggctgctttg atgagtttaa tcgaatcgat gcttctgtgc tctccgtgat ctcctcccag 5700
atccagacga tccgaaatgc tctgatccat cagttaacca cgttccagtt tgaagggcag 5760
gagatttccc tggactcccg catgggcatc ttcatcacca tgaaccccgg ctacgcaggc 5820
cgcacggagc tgcccgagtc ggtgaaggcg ctgttcaggc ctgtggtcgt gatcgtgccc 5880
gacctgcagc agatctgtga gatcatgctc ttctctgagg gcttcctgga ggccaagact 5940
ctggcgaaaa agatgacggt tctgtataag ctggcccggg agcagctgtc caagcagtat 6000
cactatgatt ttggactcag agccctgaaa tcggtgctgg tcatggctgg tgagctgaag 6060
agaggctcct ctgaccttag ggaggacgtg gtgctgatga gggccttgcg agacatgaac 6120
ttgcccaaat ttgtgtttga agatgttcct cttttccttg gtttgatttc ggatctgttt 6180
cctgggctgg actgccctcg cgtccgctac cctgacttca acgatgcggt agagcaggtc 6240
ctggaggaga acggctacgc ggtcctaccc atccaggtgg ataaagtggt tcaaatgttc 6300
gagaccatgt taacccgcca cacgacgatg gtggtggggc ccaccagagg gggcaagtcc 6360
gtcgtcatta acactctgtg tcaggcccag accaagcttg ggctgacgac aaagttgtac 6420
atcctgaacc ccaaagccgt gagtgtcata gaactctacg gcatcctgga cccaaccacc 6480
cgagactgga cagatggggt gttgtcaaac atcttcaggg aaatcaacaa gccaacagac 6540
aagaaggagc gaaagtatat tttatttgat ggtgatgtgg atgctctatg ggtggaaaac 6600

```
atgaattctg tgatggatga caacaggttg ttgacattgg ccaacgggga acgcatccgg   6660
ctccaagcac actgtgccct gctctttgag gttggagatt tacagtatgc ctcccctgca   6720
actgtctctc gatgtggaat ggtttatgtg gatcctaaaa acttgaaata tcgaccatac   6780
tggaaaaaat gggttaatca aataccaaac aaggtggagc aatacaattt gaatagtctc   6840
tttgagaagt atgtgcccta tctcatggat gtgatagtgg aaggaattgt ggatggaaga   6900
caagcagaaa agctgaagac aatagttcct cagacagacc tcaatatggt aacccagtta   6960
gccaagatgt tggatgcgtt gctagaagga gaaatagaag accttgacct gctggagtgc   7020
tacttcctgg aggctttgta ctgctctctg ggagcctccc tgcttgagga tggaaggatg   7080
aaatttgacg aatatatcaa acgccttgct tctttgtcta ctgttgacac agaaggagtt   7140
tgggccaacc ctggggaact gccaggtcaa cttccaacct tgtatgactt tcattttgat   7200
aacaaacgga atcaatgggt cccatggagt aaattagttc cagagtatat tcatgccccc   7260
gagaggaaat tcatcaacat cctggttcac acagtggata ccactcggac tacctggata   7320
ttggaacaaa tggttaaaat taagcaacct gttatttttg ttggtgaatc tggcacttct   7380
aagacagcca ctacccagaa tttcctcaaa aatctgagtg aagaaactaa cattgtgtta   7440
atggtcaact tctcctcccg caccacgtcc atggatatcc aaagaaattt agaagcaaat   7500
gtggaaaagc gaaccaaaga tacttacggc ccacccatgg gaaaacgcct gctggtgttc   7560
atggatgaca tgaatatgcc aagggtggat gaatatggca cgcagcagcc cattgccttg   7620
ctgaagctgc tgttggaaaa aggctactta tatgaccgtg ggaaggagct gaactgtaaa   7680
agcattcgag accttggctt tattgctgca atgggaaagg ctggaggagg ccgcaatgaa   7740
gttgacccaa gatttatttc gctattcagt gtcttcaatg tgccatttcc ttcagaggag   7800
tctctgcatt taatttattc ctccatcctg aaaggccaca cctcgacgtt tcatgagagc   7860
attgtggctg tgagtggcaa gctgacattc tgcacgctag cactttacaa aaatattgtg   7920
caagacctac ctcccactcc gtcaaagttc cattacatct tcaaccttcg agatctctca   7980
cgggttttta atggtcttgt cctcactaac ccggagcgat tccagacggt ggcccagatg   8040
gtgagagtct ggaggaatga gtgtctgaga gtcttccacg accggctgat cagtgaaaca   8100
gacaagcagc tggtacaaca gcacataggc agcttggttg tggaacattt taaagatgac   8160
gtggaggtgg tgatgaggga tcccatattg tttggagact tccagatggc tctgcacgaa   8220
ggagaaccac gcatttatga agacatccag gactacgagg cggccaaggc tctgttccag   8280
gaaattcttg aagagtataa tgaaagcaac accaaaatga acttggttct cttcgacgat   8340
gctctggagc atttaacccg ggtgcaccgt atcatccgca tggaccgcgg ccacgccctg   8400
ctggtcgggg taggggctc agggaagcag tctctttcga ggctggctgc cttcacagcc    8460
agctgtgagg tgtttgagat cctgctgagc cgaggctact cggagaacag tttccgggaa   8520
gacctgaaga gcctctattt gaaacttggg attgagaaca aagcgatgat ctttctgttc   8580
acggatgccc atgtggctga ggagggcttc ctggagctca tcaacaacat gctgacctca   8640
ggaattgtac ctgcgctttt ttctgaagag gagaaagagt ctatcctgag tcagattgga   8700
caggaagctc tgaagcaagg catggggccg gccaaggagt ctgtgtggca gtacttcgtg   8760
aacaaaagtg caaataacct gcacattgtc ctgggcatgt cgccagtggg ggacaccctg   8820
aggacctggt gcagaaactt cccaggtatg gtaaataaca ctggtattga ctggttcatg   8880
ccctggcctc cccaagccct ccatgcggtc gcaaagtcct ttctagggta taatccaatg   8940
atcccggcag aaaatataga aaatgtggtg aagcatgttg tcttggttca ccaatccgtg   9000
```

-continued

```
gaccactaca gccaacagtt tctacagaaa ttgaggcgca gcaactatgt cactcccaag   9060
aactaccttg attttattaa cacctattca aaattgctgg atgagaaaac tcagtgtaat   9120
atagctcagt gcaagcgtct ggatgggga ctggacaagc tgaaggaggc caccatccag   9180
ctggacgagc tgaaccagaa gctggccgag cagaagatcg tgctggcgga gaagtccgcc   9240
gcctgcgagg ccttgctgga ggagatcgcc gtcaacaccg ctgtagccga ggagaagaag   9300
aaactggcag aggaaaaggc catggagata gaggagcaga acaaagtcat tgccatggag   9360
aaggccgagg ccgagacgac cctggcagag gtcatgccca tcctggaggc cgccaagctg   9420
gaactgcaga agctggacaa gtcggacgtg actgagatta ggtcgtttgc taagcccccg   9480
aagcaggtgc agacggtctg cgaatgcatc ctcatcatga aagggtacaa agagctgaac   9540
tggaaaacag ccaagggcgt gatgtccgac ccgaatttcc tgcggtctct gatggagatt   9600
gattttgatt cgattaccca gagccaagtg aaaaacatca aaggcctctt gaagactctt   9660
aataccacaa ctgaagaaat ggaagctgtc agcaaagccg ggctggggat gctgaaattt   9720
gttgaagctg taatgggcta ctgtgatgtt ttcagagaaa tcaagcccaa aagagagaag   9780
gtggccaggc tggagcggaa tttttacctc actaaacggg aactggaaag gatccagaat   9840
gagttggcag caattcagaa agagctggaa acattgggtg ccaaatatga ggccgccata   9900
ctggaaaagc agaagctgca ggaagaagcc gagatcatgg agaggcggct gattgccgca   9960
gacaaactca tctcgggtct ggggtcagaa aacatcaggt ggctgaacga cctggatgag  10020
ctgatgcacc ggcgcgtgaa gctgctgggg gactgcctgc tctgcgcggc tttcctcagc  10080
tacgagggag ccttcacctg ggagttccgt gacgagatgg tcaatcggat ttggcaaaat  10140
gacatcctgg agcgggagat ccccctgagc cagcctttcc ggctggaaag cctgctcacg  10200
gatgatgttg agatcagcag atggggatcc cagggccttc cccccgatga gctctccgtt  10260
cagaatggca tcctcaccac ccgggccagc cgcttccctc tgtgtatcga cccccagcag  10320
caggccctca actggatcaa gagaaaagag gagaagaaca atctgcgggt cgcttccttt  10380
aatgaccctg acttcctcaa gcagctagag atgtccataa agtacgggac ccctttcctg  10440
ttccgcgatg ttgatgaata catcgatcct gtgattgaca acgtcttaga aaaaaatata  10500
aaagtctccc aaggacggca gtttattatc ctgggagaca aggaagtgga ctatgattca  10560
aatttcagac tgtacctgaa caccaagctg gccaatccca gatattcccc atccgtgttt  10620
gggaaagcta tggtgatcaa ttacactgtc acgctgaagg gcctggagga ccagctgctg  10680
agcgtgctgg tggcttacga gaggcgggag ctggaggagc agcgggagca cctcatccag  10740
gagaccagcg agaacaagaa cctgctcaag gacctggaag attccctcct tcgggagctg  10800
gccacgtcca cggggaacat gctggacaat gtggacctgg tgcacaccct ggaggagacc  10860
aaatccaagg caacagaggt ctcagagaaa ctcaagctgg cggagaagac agccttggac  10920
atcgacaggc tgcgggatgg ctaccggcca gcagccagga gggggcccat cctgttcttc  10980
gtcctgtctg agatggccct ggtgaactcc atgtaccagt actccctgat tgccttctta  11040
gaggtcttca ggctgtcact gaagaagtcg ctgcctgatt ccatcctcat gaaacgcctg  11100
aggaacatca tggacacgct gaccttcagc atctataacc acggctgcac agggctgttt  11160
gagaggcaca agctactctt ttcttttaat atgaccatca agatagaaca agcagaaggg  11220
agagtccctc aagaagaact agatttcttt ttaaaaggaa acatttccct ggagaaaagc  11280
aaaagaaaaa agccctgcgc ttggttgtct gaccaaggat gggaagatat cattctttta  11340
```

tcagaaatgt tttcagacaa ctttgggcaa cttcctgatg atgttgagaa taatcagact 11400
gtctggcagg agtggtatga cctggattca ctggagcagt ttcccgtccc cttgggttac 11460
gataacaaca tcaccccttt ccagaagttg cttattttgc gctgtttccg tgtggatcgg 11520
gtctatcggg ccgtgactga ctatgtgact gtaacaatgg gagagaagta tgtgcagccc 11580
ccaatgatca gctttgaagc tatttttgag cagagcactc cacattcgcc cattgtgttt 11640
atcctgagtc ctggctccga ccctgccact gatcttatga aattagcaga gcgaagtggt 11700
tttggaggaa atcgcctcaa attccttgca atgggtcaag gtcaagaaaa ggtggccctg 11760
cagctgctgg agacggcggt ggctcggggg cagtggctga tgctgcagaa ctgccacctc 11820
ctggtcaagt ggctgaaaga tctggagaag tccctggaga ggatcaccaa gccccaccca 11880
gacttccgcc tgtggctcac cacggacccc accaagggct tccccattgg gattctgcag 11940
aagtccctaa aggttgtcac cgagccaccc aatgggctga aactcaacat gagggcaact 12000
tacttcaaga tctctcacga aatgctggac cagtgcccgc accctgcctt caagccgctg 12060
gtctacgtgc tggcgttctt tcatgctgtg gtgcaggaga gaaggaagtt tgggaagatt 12120
ggctggaacg tgtactatga cttcaatgag tctgacttcc aggtctgcat ggaaattctg 12180
aacacgtact taacgaaagc cttccagcaa cgggacccaa ggatcccgtg ggcagcctc 12240 aagtacctaa ttggagaggt catgtatgga ggacgggcca tcgacagctt tgatcgccgc 12300
atcctgacca tctacatgga tgagtacctg ggggacttca tttttgatac tttccagcca 12360
ttccacttct tccggaacaa ggaagtggac tacaaaatcc ctgttggtga tgaaaaggag 12420
aaatttgttg aagccatcga ggccctcccg cttgccaaca cgccagaagt gtttggtctc 12480
caccccaacg ctgagattgg ctattacacg caggcggctc gagacatgtg ggctcacctg 12540
ctggagctgc agcctcagac aggggaatcc agcagtggta tcagccgcga tgattatatt 12600
ggccaagtgg ccaaagaaat agaaaacaag atgcccaaag tctttgactt ggaccaggtg 12660
aggaagcgcc tcggaacagg actctccccc acttcggtgg tgctcctgca ggaactggaa 12720
cgcttcaaca agcttgtggt ccggatgacg aagtctctgg ctgaacttca aagggccttg 12780
gctggagaag ttggaatgag caatgagtta gatgatgtgg ccaggtctct ttttatcggg 12840
catatcccta atatctggag aaggcttgct cctgacacct taaagtccct tggaaactgg 12900
atggtctact tcctgcggcg gttcagccag tacatgttgt gggtgaccga gagcgagccc 12960
agcgtgatgt ggctctcggg gctgcacatc cctgagtcct acctcacggc gctggtgcag 13020
gccacctgcc ggaagaacgg ctggccactg gaccgctcca ccttgttcac acaagtgacc 13080
aagttccagg atgcagatga agtgaatgag cgggcgggac aaggatgctt tgtctcagga 13140
ctgtacctgg aaggtgctga ctgggatata gaaaaaggat gtcttatcaa gagcaaaccc 13200
aaggtgctgg ttgtggacct gccgatcctg aagatcatcc ccattgaagc ccatcgcctc 13260
aagctgcaga atactttccg gacccccgtc tacaccacct ccatgagaag gaacgccatg 13320
ggagtcggct tggtttttga agctgatctc tttaccacga ggcacatttc tcactgggtg 13380
ctgcaaggag tatgcctcac cctgaattct gattaa 13416

<210> SEQ ID NO 48
<211> LENGTH: 13572
<212> TYPE: DNA
<213> ORGANISM: Homo sapiens

<400> SEQUENCE: 48
atggcagccc aggtggcagc ccgggaggcg cgagacttca gagaagcccc gacccttcgc 60

-continued

```
ctaacctcgg gggccggcct ggaggcagtg ggcgctgtgg agctcgagga ggaggaggag    120
aacgaggagg aggcggcggc caggagagcg cggagtttcg cccaagacgc gcgggtgcgc    180
ttcctcggcg gccgcctggc gatgatgctg gggttcacgg aggagaaatg gagccagtat    240
ttggaaagcg aggacaaccg gcaggttctt ggggagtttc tggaaagcac cagcccggct    300
tgccttgtgt ttagcttcgc cgcctcgggg cgccttgcgg cttcccagga gattccaaga    360
gatgcaaacc ataaacttgt ttttatttcc aagaagatta ctgaaagcat tggagtaaat    420
gacttttctc aagtggtttt atttggagag ttacctgcgt tgtctcttgg acatgtatct    480
gctttccttg atgagatttt agtgccagtt ctttctaata agaacaacca taagtcctgg    540
tcctgtttta cttcacaaga tatggaatat cacatagaag tcatgaaaaa gaagatgtat    600
atttttaggg gcaaaatgtc tagaagaact cttctaccaa ttcccactgt tgcaggaaag    660
atggatctgg atcagaattg ttcagagaac aagccaccgt caaatgaaag gataatactt    720
catgcaattg aatctgtggt tattgaatgg tcacatcaaa tccaagaaat tatagaaaga    780
gattcagtgc agcgtttgtt gaatggtctt cacttgtctc ctcaagcaga actagatttc    840
tggatgatga ggagagaaaa tctgtcatgc atttatgatc aacttcaggc acctgttgtc    900
ctcaaaatgg ttaagatcct gacaactaaa caaagcagct attttcctac tctgaaggac    960
atttttctgg ctgtggaaaa tgctcttctc gaagcccaag atgtggaact ttacctgaga   1020
cctctgagga gacacatcca gtgtctccag gagacggaat tcccacagac acgcatatta   1080
atcgctccat tatttcatac catctgtctg atctggagtc attccaagtt ttataacacc   1140
ccagctcggg ttatagtttt attgcaagag ttttgtaatc tcttcattaa ccaggcaaca   1200
gcttaccttt cacctgagga ccttttgagg ggagaaatag aagagtcact ggaaaaggtg   1260
caggtggctg ttaacatctt aaagactttc aaaaactcct ttttcaacta tagaaaaaaa   1320
ttggcaagct actttatggg aagaaagctg agaccatggg atttccagtc tcatctggtg   1380
ttttgcagat ttgacaagtt tcttgatcgt ttaataaaaa tagaggatat atttgccacc   1440
actttggaat ttgaaaagct ggaaagactg gaatttggtg gtaccaaagg agcaatttta   1500
aatggacaag tccacgagat gagtgaagaa cttatggaac tctgtaaact ttttaaacag   1560
agcacttatg acccatctga ttgcactaac atggagtttg aaagtgatta tgtggcattt   1620
aagtccaaaa ctctggaatt tgacagaagg cttgggacaa ttatttgtga agctttcttt   1680
aactgcaatg gcttagaagc tgcatttaag cttttgacca tatttggaaa ttttctagag   1740
aagccagttg tcatggaaat tttcagccta cattacagca cactagtgca tatgtttaat   1800
acagagctgg atgtgtgtaa gcaactgtat aatgaacaca tgaaacagat tgaatgtggt   1860
catgtagttc ttaacaagaa catgccattt acctcaggaa atatgaaatg ggcccagcag   1920
gttctccaac gacttcaaat gttttggtca aactttgcat ctctccgtta tctatttttg   1980
ggcaatcctg atcacgcttt agtttatcaa aagtatgttg aaatgaccac tttgcttgat   2040
caatttgaaa gtcgtatcta taatgaatgg aaaagtaatg tggatgaaat ctgtgaattc   2100
aatttgaatc aacccttggt taaattcagt gccataaatg gtcttctctg tgtcaatttt   2160
gacccaaagc tagtggctgt attgagagaa gtgaaatatc ttttgatgtt gaagaaacaa   2220
gacataccag attcagcttt agccatcttc aagaaaagga acactatttt aaagtacatt   2280
ggaaatcttg accttcttgt gcaagggtat aataaactca aacagacgct cctggaagtt   2340
gaataccctc tgattgaaga tgagctgagg gctattgacg agcagctgac agcagccaca   2400
```

-continued

```
acgtggctga catggcagga tgactgctgg ggctacatcg agagggtgag ggcagccacg   2460
tccgagttgg agcacagagt tgagcgcaca cagaaaaacg tgaaggtgat ccagcagacc   2520
atgaggggct gggccaggtg cgtgctacct cccaggagag agcacagacg agaggcagcc   2580
ttcaccttgg aggacaaggg tgatttgttt acaaaaaaat acaagttaat ccaaggagat   2640
ggctgcaaga tccacaactt ggtcgaggaa aataggaagc tcttcaaagc caatccctct   2700
ctggatacct ggaaaattta tgtagaattc attgacgaca ttgtggtgga aggctttttt   2760
caggctataa tgcacgactt agacttcttt ctgaagaata cagagaaaca attgaaaccg   2820
gcaccgtttt ttcaagcaca aatgatcttg ttgcctcctg agattgtgtt taaaccttcc   2880
ctagacagag aggctgggga tggcttctat gatcttgtag aagaaatgtt atgcaatagt   2940
tttagaatgt ctgcccagat gaaccgaata gcaacacacc tggaaattaa aaattatcag   3000
aatgatatgg ataacatgtt aggcctggca gaggtcaggc aggagatcat gaacagagtg   3060
gtgaatgtca tcaacaaagt cttagatttc agaaacaccc tggagaccca cgcttacctc   3120
tgggtggatg atcgagctga gtttatgaag cattttctct tgtatggcca tgctgtgtct   3180
tccgatgaaa tggatgctca tgcaaatgaa gaaattcccg aacaaccacc aactcttgag   3240
caattcaaag aacagattga catttatgaa gctttgtatg ttcaaatgag caaatttgag   3300
gactttagag tgtttgatag ttggttcaag gtggacatga agcctttcaa agtgagcttg   3360
ttaaccataa ttaagaaatg gagctggatg tttcaggagc atcttttgag atttgtcatt   3420
gacagtctga atgagctaca agaatttata aaggagacag attccggact tcagagagaa   3480
ttaaatgaag gtgatcatga tggtttagtt gacatcatgg tgcatcttct ggctgtaaga   3540
agccgacaga gagctactga tgaactcttt gaacctctaa aagaaacgat caccctcttg   3600
gaaagctatg gccagaagat gcctgagcag gtctatattc agctagagga attacctgaa   3660
agatgggaaa ctaccaaaaa gatcgcagca actgtcagac atgaagtctc acctctccat   3720
aatgcggaag tcactcttat aaggaaaaaa tgtattttgt ttgacgcaaa gcaggcagag   3780
ttcagagaga gattcagaca ctatgcccct cttggattta atgcagaaaa tccatacaca   3840
gcgcttgata aggcaaatga agagcttgag gccttagaag aagaaatgtt gcagatgcaa   3900
gaatctactc gtctttttga agtggctctt ccagagtaca aacaaatgaa acagtgtcgc   3960
aaagaaataa aattgctcaa gggactgtgg gatgtcatta tttatgttcg aagaagcatt   4020
gataattgga ctaaaaccca gtggagacag attcatgtgg aacagatgga tgtagaactc   4080
agaaggtttg ccaaggcgag ttccataact gaaatttggt cactcaacaa ggaagtccgc   4140
gtctgggatg cttacacggg cctggaaggc acagttaagg acatgacagc ctccctgagg   4200
gccatcacag agttacagag ccctgccctc agggacaggc attggcacca gctgatgaaa   4260
gctattgggg tcaagttttt aataaatgaa gccacaactt tggcagattt gttagcactg   4320
cggttacaca gagtggaaga tgatgtccga aggattgtgg acaaggcggt gaaagagctg   4380
gggactgaga aggttattac tgaaatcagt cagacctggg caaccatgaa gttttcttac   4440
gaagttcact atcgaacagg cattccatta ctaaagtctg atgaacaact tttgaaact    4500
ctagagcaca accaagttca gttgcagact cttcttcaaa gcaagtatgt agaatatttc   4560
attgagcaag tgttaagctg gcaaaataaa ttaaacatag cagacttggt catcttcact   4620
tggatggaag tccagcgaac ttggtctcac ctggaaagca tttttgtctg ttcagaagat   4680
attcgaatcc agcttgtgaa agatgctaga agatttgatg gggtggatgc tgaatttaag   4740
gagttaatgt tcaagacagc caaagtagaa aatgtgttag aagcaacgtg cagacctaat   4800
```

-continued

```
ctctatgaaa aacttaaaga tttacagtcc aggctttctc tttgtgaaaa agctctcgct   4860
gaatacctgg aaaccaagcg catagccttt cctcgcttct atttcgtctc ttctgctgat   4920
ttacttgaca ttctctcaaa aggagctcag cctaaacagg taacatgtca ccttgccaaa   4980
cttttcgaca gcattgcaga tctgcagttt gaagacaatc aggatgtttc tgcacacagg   5040
gcagttggaa tgtacagcaa agaaaaggag tatgtcccat tccaagccga gtgtgaatgt   5100
gtgggccatg tggaaacatg gcttctgcaa cttgaacaga ctatgcaaga aacggtgcgt   5160
cattctataa cagaagccat agtggcctac gaggaaaaac ctagggaact gtggattttt   5220
gatttcccag ctcaggttgc actaaccagc tcacaaatat ggtggaccac agatgtagga   5280
atagccttca gtagactgga agaaggctac gaaacagccc tgaaggattt ccataaaaaa   5340
cagatttctc agctgaatac actgattaca cttttgctgg gagaacttcc acctggagac   5400
agacagaaga tcatgacaat ttgtaccata gatgtccatg ccagagacgt ggtggcaaaa   5460
cttatttctc agaagcaagt tgttgtcagt ccccaagctt ttacatggct gtctcaactt   5520
cgtcaccgat gggaggatac ccagaaacac tgctttgtta atatttgtga tgcccagttc   5580
cagtacttct atgaatactt aggaaacagc cctcgactag tgatcactcc tctaactgac   5640
aggtgttata ttaccttaac tcaatcactt catctaacca tgagtggggc tcctgctggc   5700
ccagctggta ccgggaaaac agagaccacc aaagacctag gacgtgccct tggcatgatg   5760
gtctatgtat tcaactgttc agagcaaatg gactacaaat ccataggcaa tatctataag   5820
ggattggtgc agacaggagc ttggggctgc tttgatgagt tcaaccgaat ctctgtggaa   5880
gttctgtcag tggtggcagt acaagtgaaa atgattcatg atgccatcag aaacaggaag   5940
aagagatttg tatttcttgg ggaagctatc acactgaagc catcagttgg aatatttatt   6000
actatgaacc cgggttatgc tggtcgaacc gaattaccgg aaaatctcaa agctcttttc   6060
agaccctgtg ccatggtggc ccctgacatt gagctaatct gtgaaatctt gttagttgct   6120
gaaggttttg tggatgcgcg tgcattagcc cgaaagttca ttacgttgta cacgctttgc   6180
aaggagcttc tctccaagca ggatcattac gactggggac ttcgtgctat taagtctgtc   6240
ttggttgtgg ctggatctct gaaacgagga gataaaaata gacccgaaga tcaggtactc   6300
atgagagcat taagggattt caatatgccc aaaatagtga ctgacgacat cccagtgttt   6360
ctgggcctgg tcggtgacct gtttccagcc ctggatgtgc cccggaggag gaagctgcac   6420
tttgaacaga tggtcaggca gtctaccctg gagctccgcc tgcagcctga agagagcttc   6480
atcctcaaag ttgtccagct tgaggaactg ttggctgtgc ggcactcggt ctttgtagtt   6540
ggaaatgcag gcacaggaaa gagtaagatt ttgagaacac tgaaccgaac atatgttaac   6600
atgaaacaga agccggtttg gaatgactta aaccctaaag ctgtgacaac agatgaactc   6660
tttggtttca tacatcatgc tacccgagaa tggaaagatg gcaagattgt ttactcttat   6720
tttataggtc tcttctcatc cattctacga gaacaagcaa atcttaagca tgatggacca   6780
aaatggatag tcctggatgg cgatattgac cccatgtgga ttgaatcact gaatactgta   6840
atggatgata acaaggtgct gaccctcgcc agcaatgagc gcattgcact cactcccttc   6900
atgaggcttc tgtttgagat acatcactta aggagcgcaa ccccggccac tgtttccaga   6960
gctggtattc tgtatgtgaa cccacaagat ctgggctgga atccgtatgt ggccagttgg   7020
atagacagaa ggcggcatca atcagaaaag gccaatttga ctattctttt tgataaatat   7080
gtccctgcat gcttggataa actgagaaca agctttaaaa ccatcacttc aattcctgag   7140
```

-continued

```
agtagcctgg tgcagactct atgtgttctt ttggagtgct tgctgactcc tgaaaatgta   7200
ccttctgaca gcccaaaaga agtttatgaa gtctattttg tatttgcttg tatctgggct   7260
tttggaggca ccctgctaca agatcagatt tctgattatc aagctgactt cagtcggtgg   7320
tggcagaaag agatgaaagc agtgaaattt ccgtcgcagg gaacaatctt tgattattat   7380
gtggaccaca aaactaagaa attattgccc tgggctgaca aaattgccca gtttactatg   7440
gatccagatg tgcctctgca gacagttctc gttcacacaa cagagacagc tcgtcttaga   7500
tatttcatgg agttgttgct tgagaaagga aaacctctaa tgctagtagg aaatgcagga   7560
gtgggaaaaa cagtctttgt aggtgacaca ttggcaagtc tctctgagga ttacatagta   7620
tcccgtgtgc ctttcaacta ctacacaaca tccacagctc tgcaaaaaat tcttgagaaa   7680
cccctagaga aaaaagctgg tcataactat ggtcctggag gaaataaaaa attgatttat   7740
tttatcgacg acatgaacat gcctgaagtg gacttatatg gcaccgttca gcctcatacc   7800
ctgatccggc agcatattga ttatggacat tggtatgata gacagaaggt gatgcttaaa   7860
gaaatccata actgccagta tgtcgcctgc atgaatccga tggtgggcag cttcaccatc   7920
agtcccaggc tacagagaca tttcacagtg tttgcattca attttccatc tttggatgca   7980
ctaaacacca tctatggcca aatctttagc ttccatttcc aacagcaagc atttgctcca   8040
tcaattctca ggagtggccc cactttgatc caggcaacaa tagcattcca tcagacaatg   8100
atgtgtaact tttacccac ggctattaaa ttccactaca tctttaatct gagagattta   8160
tcaaacgtct tccaggggat tttatttgct tctcctgagt gtttaaaagg tccacttgat   8220
ttaatacatc tgtggcttca tgaatctgcc cgtgtttatg gagacaaact gatagacaaa   8280
aaagattgtg atttgtttca gagaagaatg ctggaaactg cttataaata ttttgaaggt   8340
atagatagtc acatgctgct tcaacagccc ctcatttatt gccactttgc tgatagaggg   8400
aaggacccac attacatgcc agtgaaggac tgggaagtgc tgaagacgat tcttacagaa   8460
acgttagaca actacaatga actaaatgct gccatgcacc tagttttgtt tgaagatgcc   8520
atgcaacatg tgtgtcgcat cagccggatc ttacgaaccc ctcagggctg tgctctcttg   8580
gttggagttg gggcagtggg caagcagagc ttgtccaggc tggcagctta ccttcgtggc   8640
cttgaggtct ttcagatcac tctgaccgag ggctatggaa tccaggaact tcgggtagat   8700
cttgccaatt tgtacatccg aactggagcc aagaacatgc ccactgtgtt cctgctgaca   8760
gatgcccagg ttctagatga gagcttcctc gtgctgatta atgacttgct ggcatcagga   8820
gaaatcccag atctgttcag cgatgaagat gtggacaaga taatttctgg aattcataat   8880
gaagttcatg ctctgggcat ggtagactcc agggaaaact gttggaaatt ctttatggcc   8940
agggtgcgac tacagctcaa aatcattttg tgtttctctc cagttggtcg cacgctgaga   9000
gttagagctc ggaagttccc agccatagtt aactgcacgg ctattgactg gtttcatgcg   9060
tggccgcagg aggctctggt ctccgtcagc aggaggttca ttgaggaaac caagggaatt   9120
gagccagtgc acaaagactc tattagcctt ttcatggcac atgttcacac cactgtaaat   9180
gaaatgagta ccagatatta ccagaatgag agaagacaca actataccac cccaaagagt   9240
tttctagaac aaatatcact gtttaagaac ctgttgaaga agaagcaaaa tgaggtatcc   9300
gagaaaaaag aacgcctggt gaacggcatc caaaagctaa aaaccacagc ctctcaggtg   9360
ggagatctaa aagccagact tgcctctcaa gaagccgagc tgcaactgag aaatcatgat   9420
gccgaagctc tgatcacaaa gatcggcctt cagacggaga aagtgagccg ggaaaagacc   9480
atcgctgatg ctgaggagcg aaaggtgaca gccattcaga ctgaagtgtt ccagaaacag   9540
```

```
agagaatgtg aagctgactt actcaaggct gagcctgcac tggtggctgc tacagctgca   9600
ctcaatacac tcaacagggt caacctcagt gagctgaaag cctttcccaa ccctcccatc   9660
gcagttacca atgttactgc agccgtgatg gtccttctgg ctcctcgggg aagagtgccc   9720
aaagaccgaa gttggaaagc agctaaagtc ttcatgggaa aggttgatga tttttttgcaa   9780
gcattaatta actatgacaa agagcacatt ccagagaact gtctaaaagt ggtgaatgaa   9840
cactatttga aagacccaga gtttaatcca aacctgattc gaaccaaatc ttttgcagca   9900
gctggcctgt gtgcctgggt catcaacatc attaaattct atgaggtcta ctgtgatgtg   9960
gagccaaaac gccaagcatt agcccaagca aacttagaac tggctgcagc tactgaaaaa  10020
ctagaggcta tcaggaaaaa gcttgtggat ctggatcgaa atctgagcag actcacggct  10080
tcatttgaaa aagcaacagc tgagaaagtc cggtgtcaag aagaggtgaa ccaaaccaac  10140
aaaaccatca aattagctaa cagacttgtc aaggaacttg aggcaaagaa gattcgctgg  10200
ggtcaatcca ttaagtcctt tgaagctcaa gagaagacac tctgtggaga tgttcttctc  10260
acggcggcat ttgtgtctta cgtcggaccc ttcacaaggc agtatcgcca ggagctggtg  10320
cactgcaagt gggttccctt tcttcaacag aaggtttcca ttccactaac cgaaggcctg  10380
gacttgatat ccatgttgac ggatgatgct acaattgccg cctggaataa cgaaggactg  10440
cccagtgaca gaatgtccac cgaaaatgcc gctatcctaa cacactgtga gcgctggcct  10500
ctggtgatag atccccagca acagggaatt aagtggatca agaataagta tggaatggac  10560
ctgaaagtca cacatttggg ccagaaaggg tttttgaatg ccattgaaac tgctttggcc  10620
tttggtgatg tcatcttaat tgaaaatctc gaggaaacga tagatccagt cctggatcca  10680
ctacttggca ggaacacaat taaaaaagga aagtatatca ggattggaga taaagaatgt  10740
gaatttaaca agaactttcg ccttatcctt cacacaaaat tggcaaatcc tcactataag  10800
ccggaattac aagctcagac aactctcctc aatttcacag tcacagaaga tggtctagaa  10860
gcccagctgc tggcagaggt tgtcagtatt gaaaggccag atttggagaa acttaagttg  10920
gtattgacaa agcaccaaaa tgattttaaa attgagctca agtatctgga agacgatctc  10980
cttttgcgcc tttctgcggc agagggaagc tttctggatg acaccaaact ggtagagaga  11040
ttggaggcaa caaagaccac cgtggcagag atagagcaca aggtgattga agccaaagaa  11100
aatgaaagaa aaatcaacga ggcccgagaa tgttacagac cattggcagc aagagcatct  11160
cttctttatt ttgttattaa tgacctccaa aaaatcaacc ccctctacca attctctttg  11220
aaggctttta acgtgctgtt ccacagagcg atcgagcagg ctgacaaggt ggaagacatg  11280
cagggacgca tctctatcct gatggagagc atcacccacg ctgtcttcct ctacaccagc  11340
caggcgctgt ttgagaagga caagctcacc ttcctgtccc agatggcttt tcagattttg  11400
ttgagaaaga aagagataga ccctcttgaa ttggatttcc tgcttcgatt cacagttgaa  11460
cacactcatc tgagtcccgt tgacttccta acttctcagt catggagtgc tatcaaggca  11520
attgccgtca tggaagaatt tcgaggcata gaccgagatg tggaaggatc tgccaagcag  11580
tggaggaagt gggtagaatc cgagtgtcca gaaaaagaaa aattacctca agaatggaag  11640
aagaaaagtt taatacagaa gctgattctt ctgagagcaa tgcgccctga cagaatgacg  11700
tatgctctca gaaattttgt agaggaaaaa ctgggtgcga agtatgtgga gaggaccaga  11760
ttggacttag ttaaagcatt cgaagaaagc agcccagcca cccccatatt cttcatcctg  11820
tctccggggg tagatgccct taaagacctg gagattcttg gcaaaagact tggctttaca  11880
```

```
attgactctg gaaaattcca caatgtgtct ttaggacaag gtcaggagac ggtggcagaa  11940
gtggccctgg agaaagcttc caaaggagga cactgggtca tcctccaaaa tgttcatttg  12000
gtagccaagt ggctaggaac cttggagaag ctccttgaaa gattcagcca aggaagccac  12060
agagattaca gggttttcat gagtgctgag tctgcaccta caccagatga gcatatcatc  12120
cctcaaggac tcctggaaaa ttccattaag atcactaatg aaccccccaac agggatgctg  12180
gccaatttgc atgccgccct gtacaacttt gatcaggata cacttgaaat atgctccaag  12240
gagcaggagt ttaaaagcat ccttttttct ctctgctact tccacgcctg tgttgctggg  12300
agactgaggt ttggccccca gggctggagc cgaagctatc cttttaatcc tggagacctc  12360
accatttgtg ccagtgtcct ctacaactac ttagaggcaa actctaaagt cccatgggaa  12420
gatctccgtt atctctttgg tgagatcatg tatggaggcc acatcacaga tgactgggat  12480
cgcaaactgt gtcgggtgta tttagaagaa ttcgtgaatc catctctgac tgaagatgaa  12540
ctgatgctgg caccaggttt tgctgcccca ccctacctag attatgcagg ctaccaccag  12600
tacatagagg agatgcttcc tccagaaagc ccggcactgt atggcctcca cccaaatgct  12660
gaaatagaat tcctgacagt gacatccaac actctcttca gaactttgct ggagatgcag  12720
cccaggaatg cactcagtgg tgatgaactg gggcagtcta cagaagaaaa ggttaagaat  12780
gtcttggatg acattttgga gaaacttcca gaagagttca acatggcaga gataatgcaa  12840
aaaaattcaa atagaagccc atatgttctt gtttgcttcc aagaatgtga gaggatgaat  12900
attctcattc gggaaatacg tatatcactt gaacaactgg accttagttt gaagggggaa  12960
ttggcattat ctcctgctgt ggaagcccag cagtttgcat tgagttatga cacggtacca  13020
gacacttgga gcaaactggc ttatccttct acttatggcc tagcccagtg gttcaatgac  13080
ctcctcctgc gatgccgaga actcgatact tggacacaag accttaccct tccggctgtc  13140
gtgtggctat ccggcttctt caaccctcag tccttcttaa ctgcaatcat gcagacgatg  13200
gctcgaaaaa atgagtggcc cctggataaa acgcgcttga ctgctgatgt taccaaaaaa  13260
acaaaggaag attatggaca cccgccaagg gaaggtgcat acctccacgg actcttcatg  13320
gagggcgccc gctgggacac ccaagcagga accattgttg aagcccgtct caaggagctg  13380
gcatgcccta tgccggtcat ctttgcaaaa gccacccccg tggacagaca agaaaccaaa  13440
cagacctacg agtgccctgt gtatagaacc aaactgagag gccccagcta catctggacc  13500
ttcaggctga agagcgaaga gaagactgca aaatgggttc tggctggagt ggctctgctt  13560
ctagaagcgt aa                                                      13572
```

<210> SEQ ID NO 49
<211> LENGTH: 1374
<212> TYPE: DNA
<213> ORGANISM: Homo sapiens

<400> SEQUENCE: 49

```
atgtcagatg caaacaaagc tgccattgca gcagaaaagg aagctctgaa cttgaagtta     60
ccccccattg tccatctccc agaaaacata ggcgttgata caccaacaca aagtaagctg    120
ctaaaataca gaagatccaa ggagcagcag cagaaaatta atcagttagt aattgatgga    180
gccaaaagaa atttagacag aacactgggt aaaagaacac ctctattacc accacctgat    240
tatcctcaaa ctatgaccag tgaaatgaaa aaaaaaggat tcaactatat ttatatgaag    300
caatgtgtag aaagtagtcc tttagtacct attcagcagg aatggctgga tcacatgtta    360
aggctgatac ctgagtcttt aaaggaaggg aaagaaagag aagaacttct tgaaagtctc    420
```

ataaatgagg tgtcaagtga ctttgaaaac agcatgaaga gatatttggt gcagagcgtt 480
cttgtgaaac caccagttaa atcgcttgaa gatgaaggag gtcctttacc tgaatctcct 540
gtaggcctag attattctaa tccttggcat tctagctatg tgcaggcaag aaatcaaata 600
ttctctaatt tgcacattat tcatccaact atgaaaatgt tactggacct tggttataca 660
acatttgctg atacagtttt gttggacttc acaggaatta gagctaaagg tccaattgac 720
tgtgaatcac tgaaaactga tctatcaata caaactagaa acgcagaaga gaagataatg 780
aatacatggt atccaaaggt tataaatctc tttaccaaga aggaggcact agaaggtgtt 840
aaacctgaaa aattggatgc attttatagc tgtgtttcca cacttatgtc aaatcagcta 900
aaggatctat taaggagaac tgtagaagga tttgtaaaac tctttgaccc aaaagatcaa 960
caaaggctgc caatatttaa gatagaattg acatttgatg acgacaaaat ggaattttat 1020
cctacctttc aagatttgga agataatgtc ttgagtttgg tggaacgaat agccgaagct 1080
ctgcagaatg tccaaacaat cccctcttgg ctatcaggaa cttcaacacc agtaaatctt 1140
gacacagaac ttcctgaaca cgtgttacac tgggctgttg atacactgaa ggcagcagta 1200
catcggaact tagaaggtgc aagaaagcat tatgagacat atgttgaaaa atataattgg 1260
ctccttgatg ggactgcagt tgagaatata gagacttttc agacagaaga tcatactttt 1320
gatgaatata cagaggagct ggattgctgg gtggtatggg aagtgtattt ttaa 1374

<210> SEQ ID NO 50
<211> LENGTH: 1362
<212> TYPE: DNA
<213> ORGANISM: Homo sapiens

<400> SEQUENCE: 50
atggagacgt ttatacccat tgatttgaca actgaaaatc aagagatgga caaggaggaa 60
accaagacaa aaccaagact tttaagatat gaagagaaaa aatatgaaga tgtgaaacca 120
ttagagactc aaccagctga aatagcagaa aaggaaacat tggaatataa aacagttaga 180
acattctctg aatctttgaa gtcagagaaa acagaagatt accttagaga aagtataatt 240
caacaacata tggtttctcc agagccagct tcccttaagg agaaagggaa gtcaaggaga 300
aaaaaggatc aaactcatgc ttgtccaaat gttaggaaag ccaggcctgt gtcctatgat 360
agaacagaac caaaagatga tgatgtgata agaaatatta ttaggctacg agaaaagctt 420
ggttggcaaa ctatattacc gcagcacagt ttgaaatacg gaagctccaa aattgcaatt 480
cagaagatta ctttaaagaa acctttggaa gatgatggag aatttgttta ttgccttcct 540
cggaaaagtc ctaaatccct ttacaatcca tatgatcttc aggtagtatc ggctcatact 600
gctaaacatt gcaaagaatt ttgggttatt actgcttcat ttatctcaaa ggttattaat 660
atagttggta gtgtaaagga agtagaactc atacctactt tggaatggct atcagaaaga 720
agacattact atttattacg gcaattcaag atattttctg atttccgaat gaataaagca 780
tttgttacct ggaaattgaa tgttaaaaga attaagacag agaagagcag gtcatttttg 840
taccaccatc ttttttggc tgatgacttg tttcaaacct gtttggttta tataagagga 900
ctttgtgaag atgcaattaa tctcaaaaat tataatgacc atgaaaataa tctatctgcc 960
atatgccttg taaagctgga tagttctcga acatattctc tagatgaatt ttgtgaagag 1020
cagttacagc aagctaccca ggcattgaaa caacttgagg acatcaggaa taaagcaatt 1080
tcagagatga aaagtacttt tctaaaggtt gcagaaaaga atgaaatcaa agagtatttt 1140
gagtcaaaac tctctgaaga tgacacaaca catttcaagc tgcctaaata tagacgttta 1200
ttagaaacat ttttcaagtt tgtaatgctg gttgactaca tatttcagga actcattcgt 1260
caacttatga acactgcagt cacactactt ttggaattat ttaatggttc tgctggaatg 1320
ccattttcag tggaaaaaaa gaatgaaaat cttatcaggt aa 1362

<210> SEQ ID NO 51
<211> LENGTH: 2100
<212> TYPE: DNA
<213> ORGANISM: Homo sapiens

<400> SEQUENCE: 51
atgattcctg cttctgcgaa ggctccccat aaacagcctc ataagcagag catcagcata 60
ggcagaggaa ccaggaagag agatgaagat tcagggactg aagtgggaga aggcacagat 120
gaatgggccc aatccaaagc cacagttaga ccccctgacc agctggagtt gaccgatgcg 180
gagttaaagg aggagttcac tcggattttg acagccaaca acccacacgc accccagaac 240
attgtcaggt acagcttcaa agaaggcaca tataagccta ttggctttgt gaaccaactg 300
gcagttcact acacccaggt tgggaacctg atccccaaag actcagatga aggacggcgg 360
cagcattacc gcgatgaatt agtggcaggt tctcaggagt ctgtcaaggt gatttcagaa 420
acaggaaacc tcgaagaaga cgaagagccc aaggagttag aaactgagcc tgggagtcaa 480
acagatgtgc ctgcagctgg ggcagctgaa aaagtgactg aagaagaatt gatgactcct 540
aagcagccca aggagagaaa gctcactaac cagttcaact tcagtgagag ggcctcacag 600
acctacaaca accctgtccg ggatcgagaa tgccagacgg agcctcctcc caggacaaac 660
ttttcagcca cagccaatca gtgggagatc tatgatgcct atgtagagga acttgagaag 720
caggaaaaga ccaaagagaa ggagaaggca aagaccccag tggctaaaaa atcagggaag 780
atggccatga ggaagctgac atctatggag tctcagactg atgatctcat caaattgtcc 840
caagctgcta agatcatgga gcggatggtc aaccagaata catatgatga cattgctcaa 900
gattttaagt actatgacga tgctgctgat gaataccggg accaggtggg taccctgctg 960
ccgctctgga agttccaaaa tgacaaagcc aagcgcctgt ccgtcactgc cctctgctgg 1020
aatccaaagt acagggatct gtttgcagtg ggatatggct cttatgactt catgaagcag 1080
agccggggca tgctgctgct ctacagcctg aagaacccca gcttccctga gtacatgttc 1140
agcagcaaca gcggcgtcat gtgtctcgac atccacgtgg accaccccta cctggtggca 1200
gtaggccact atgacggcaa cgtggccatt tacaacctca agaagcccca ctcccagccc 1260
tccttctgca gctcagccaa gtctggcaag cactcagacc ctgtgtggca ggtcaagtgg 1320
cagaaggatg acatggacca aaaccttaac ttcttctctg tgtcatctga cggcaggatt 1380
gtgtcttgga ctctcgtgaa gagaaagctg gttcacatag atgtcatcaa gctgaaggtg 1440
gaaggcagca ccacggaagt tcctgagggg ttgcagctgc acccagtggg ttgtggcact 1500
gcctttgact tccacaaaga gattgactac atgttcctag tgggcacaga ggagggaaaa 1560
atctacaagt gctctaaatc ctactccagc caattcctcg acacctatga cgcccacaac 1620
atgtcagtgg acactgtgtc ctggaaccca taccacacca aggtcttcat gtcctgcagc 1680
tccgactgga cagtgaagat ctgggaccac accatcaaga ccccgatgtt catctatgac 1740
ctgaactcag ccgtgggtga tgtggcctgg gcgccatact cttctactgt gttcgcagca 1800
gtcaccacag atgggaaggc ccacatattt gacttagcca tcaacaagta tgaggccatc 1860
tgcaaccagc ctgtggcggc caaaaagaac aggctcaccc acgtgcagtt caatctcatc 1920

-continued caccccatca tcattgtggg cgatgaccgt gggcacatca tcagcctcaa gctctcaccc 1980
aatttgcgca agatgccaaa ggaaaagaag gggcaggagg tgcagaaggg tccagctgtg 2040
gagattgcga aactggacaa actgctgaac ctggtgaggg aagtgaaaat caagacctga 2100

<210> SEQ ID NO 52
<211> LENGTH: 1818
<212> TYPE: DNA
<213> ORGANISM: Homo sapiens

<400> SEQUENCE: 52
atggagattg tgtacgtgta cgtcaagaag cgcagcgagt tcgggaagca gtgcaatttc 60
tcggaccgcc aggccgagct gaacatcgac atcatgccca accctgagct ggccgagcag 120
ttcgtggagc ggaacccagt ggacacgggc atccagtgct cgatcagcat gtcggaacac 180
gaggccaact cagagcggtt tgagatggag acccggggag ttaaccatgt cgaggggggc 240
tggcccaagg acgtgaaccc cctggagctg gagcagacca tccgtttccg gaagaaagtg 300
gagaaagatg agaactacgt taacgccatc atgcagctcg gctctatcat ggagcactgc 360
atcaagcaga acaatgccat tgacatctat gaagagtatt tcaatgacga ggaggccatg 420
gaagtgatgg aggaggaccc ttcagctaaa accatcaatg tgttcaggga cccccaggaa 480
atcaagaggg ctgccacaca cctctcctgg caccccgatg gcaacaggaa gttggcagtg 540
gcatactcct gcttggattt tcagcgggca cctgtgggca tgagcagcga ttcatacatc 600
tgggacctgg aaaaccccaa caagcctgaa cttgctctga agccatcgtc tccactcgtg 660
acgttggagt tcaaccccaa agattcccac gtactcctgg gtggctgcta caatggacag 720
atagcctgct gggacacccg aaagggcagc ctggtggcgg agctatccac cattgagtcc 780
agccaccgag accctgtgta tggcaccatc tggctgcagt cgaagacggg caccgagtgc 840
ttctcagctt ccacggatgg gcaggtcatg tggtgggaca tccgaaagat gagcgagccc 900
actgaagttg tgatcttgga catcaccaag aaggaacagt tggaaaatgc cttgggggcc 960
atctccctgg agttcgaatc tactttgccc accaagttca tggtggggac cgagcagggc 1020
atcgtcatct cctgcaaccg caaggccaag acgtcagctg aaaagattgt gtgcaccttc 1080
ccgggccatc atggccccat ctacgccctc cagagaaacc ccttctaccc gaagaacttc 1140
ctgacggttg gcgactggac agcccgcatt tggtctgaag acagccggga atcgtccatc 1200
atgtggacca agtaccacat ggcttacctc actgatgctg cctggagccc cgtgaggccg 1260
accgttttct ttaccaccag gatggacgga accctggata tctgggactt catgttcgag 1320
cagtgcgatc ccaccctcag cttgaaggtg tgtgacgagg ccctcttctg cctccgggtg 1380
caggacaatg ggtgtctcat cgcctgcggc tcccagctgg ggacaaccac cctgctggag 1440
gtctcgcctg ggctctctac cctccagagg aatgagaaga acgtagcctc ttccatgttt 1500
gagcgtgaga cccggcgaga gaagatcctg gaggccaggc accgggagat gcggctgaag 1560
gagaagggta aggcggaggg cagggatgag gagcagaccg atgaggagct ggccgtagac 1620
ctggaggcgc tggtcagcaa ggccgaggag gagttcttcg acatcatctt cgcagagctg 1680
aagaagaagg aggcagacgc cataaagctg acgccagtgc ctcagcaacc aagtccagaa 1740
gaagaccagg tggtggagga gggagaggaa gcagcggggg aagaagggga tgaagaagtg 1800
gaagaagact tagcctag 1818

<210> SEQ ID NO 53

<211> LENGTH: 573
<212> TYPE: DNA
<213> ORGANISM: Homo sapiens

<400> SEQUENCE: 53
atggcgaaag caacaacaat caaagaagcc ttagcgagat gggaagagaa aactggccag 60
aggccatctg aagccaaaga gataaaactt tatgcccaga ttccccctat agagaagatg 120
gatgcatcct tgtccatgct tgctaattgc gagaagcttt cactgtctac aaactgcatt 180
gaaaaaattg ccaacctgaa tggcttaaaa aacttgagga tattatcttt aggaagaaac 240
aacataaaga acttaaatgg actggaggca gtaggggaca cattagaaga actgtggatc 300
tcctacaatt ttattgagaa gttgaaaggg atccacataa tgaagaaatt gaagattctc 360
tacatgtcta ataacctggt aaaagactgg gctgagtttg tgaagctggc agaactgcca 420
tgcctcgaag acctggtgtt tgtaggcaat cccttggaag agaaacattc tgctgagaat 480
aactggattg aagaagcaac caagagagtg cccaaactga aaaagctgga tggtactcca 540
gtaattaaag gggatgagga agaagacaac taa 573

<210> SEQ ID NO 54
<211> LENGTH: 318
<212> TYPE: DNA
<213> ORGANISM: Homo sapiens

<400> SEQUENCE: 54
atgggagaaa cagaagggaa gaaagatgag gctgattata agcgactgca gaccttccct 60
ctggtcaggc actcggacat gccagaggag atgcgcgtgg agaccatgga gctatgtgtc 120
acagcctgtg agaaattctc caacaacaac gagagcgccg ccaagatgat caaagagaca 180
atggacaaga agttcggctc ctcctggcac gtggtgatcg gcgagggctt tgggtttgag 240
atcacccacg aggtgaagaa cctcctctac ctgtacttcg gggcaccct ggctgtgtgc 300 gtctggaagt gctcctga 318

<210> SEQ ID NO 55
<211> LENGTH: 525
<212> TYPE: DNA
<213> ORGANISM: Homo sapiens

<400> SEQUENCE: 55
atggcttctt ctgatatcca ggtgaaagaa ctggagaagc gtgcctcagg ccaggctttt 60
gagctgattc tcagccctcg gtcaaaagaa tctgttccag aattccccct ttcccctcca 120
aagaagaagg atctttccct ggaggaaatt cagaagaaat tagaagctgc agaagaaaga 180
cgcaagtccc atgaagctga ggtcttgaag cagctggctg agaaacgaga gcacgagaaa 240
gaagtgcttc agaaggcaat agaagagaac aacaacttca gtaaaatggc agaagagaaa 300
ctgacccaca aaatggaagc taataaagag aaccgagagg cacaaatggc tgccaaactg 360
gaacgtttgc gagagaagat gtacttctgg actcacgggc ctggggccca cccagcacag 420
atctctgctg agcaatcttg tctccactct gttcctgccc tttgcccagc cctgggcctc 480
caatctgcat tgattacctg gtctgatctc tctcaccatc actag 525

<210> SEQ ID NO 56
<211> LENGTH: 2310
<212> TYPE: DNA
<213> ORGANISM: Homo sapiens

<400> SEQUENCE: 56

```
atggcgaccg agggaatgat ccttactaac cacgaccatc aaatccgtgt cggagtcctt     60
acagtgagtg atagttgctt caggaatctt gcagaagacc gcagtgggat aaatctcaaa    120
gatctcgtac aagatccttc tttgttgggt gggactatat cagcatacaa gatagtacca    180
gatgaaatag aagaaatcaa ggaaaccctg atagattggt gtgatgaaaa ggaacttaat    240
ttgatattaa caactggagg aacaggattt gcaccacgag atgtcactcc agaggccaca    300
aaagaagtaa tagaacggga agcaccaggg atggccctgg caatgctgat gggatcactt    360
aatgttacac ctctgggcat gctctctagg cctgtatgtg gaatcagagg gaaaacgctc    420
ataattaacc tgccaggtag caagaaagga tctcaggaat gctttcaatt catactgcca    480
gctctacctc atgccattga ccttttacgt gatgccattg taaaagtaaa ggaggtgcat    540
gatgaacttg aagatttgcc ttccccacct ccccctcttt cccctcctcc tactaccagc    600
ccccataaac agacagaaga caaaggagtt caatgtgagg aagaggaaga agagaagaaa    660
gacagtggtg ttgcttcaac agaagatagt tcctcatcac atataactgc agcagccatt    720
gctgccaaga agcatccatt ctacaccagt cctgctgttg tcatggcaca cggtgaacag    780
cccatccctg gtctcatcaa ttattcccat cattcaacag atgaacggat tccagactcc    840
atcatttctc gtggtgttca ggtgctccca cgagacacag cctccctcag cactactcct    900
tcagaatcgc ctcgtgctca ggctacatct cgcctctcta cagcttcctg cccaacacca    960
aaagtccagt ccaggtgcag cagcaaggag aacattctca gagccagtca cagtgctgtc   1020
gatatcacca aggtggctag aagacatcgc atgtctcctt ttcctctgac atctatggac   1080
aaagccttta tcacagtcct ggagatgact ccggtgcttg ggacagaaat catcaattac   1140
cgagatggaa tggggcgagt ccttgctcaa gatgtatatg caaaagacaa tttacccccc   1200
ttcccagcat cagtaaaaga tggctatgct gtccgagctg ctgatggccc aggagatcgt   1260
ttcatcattg gggaatccca agctggtgaa cagccaactc agacagtaat gccaggacaa   1320
gtcatgcggg ttacaacagg tgctccaata ccctgcggtg ctgatgcagt agtacaagtg   1380
gaagataccg aacttatcag ggaatcagat gatggcactg aagaacttga agtgcgaatt   1440
ctggtgcaag ctcggccagg ccaagatatc agacccatcg gccatgacat taaaagaggg   1500
gaatgtgttt tggccaaagg aacccacatg ggcccctcag agattggtct tctggcaact   1560
gtaggtgtca cagaggttga agttaataag tttccagtgg ttgcagtcat gtcaacaggg   1620
aatgagctgc taaatcctga agatgacctc ttaccaggga agattcgaga cagcaatcgt   1680
tcaactcttc tagcaacaat tcaggaacat ggttacccca cgatcaactt gggtattgta   1740
ggagacaacc cagatgactt actcaatgcc ttgaatgagg gtatcagtcg tgctgatgtc   1800
atcatcacat caggggggtgt atccatgggg gaaaaggact atctcaagca ggtgctggac   1860
attgatcttc atgctcagat ccattttggc agggttttta tgaaaccagg cttgccaaca   1920
acatttgcaa ctttggatat tgatggtgta agaaaaataa tctttgcact acctgggaat   1980
cctgtatcgg ctgtggtcac ctgcaatctc tttgttgtgc ctgcactgag gaaaatgcag   2040
ggcatcttgg atcctcggcc aaccatcatc aaagcaaggt tatcatgtga tgtaaaactt   2100
gatcctcgtc cagaatacca tcggtgtata ctaacttggc atcaccaaga accactacct   2160
tgggcacaga gtacaggtaa tcaaatgagc agccgtctga tgagcatgcg cagtgccaat   2220
ggattgttga tgctacctcc aaagacagaa cagtacgtgg agctccacaa aggcgaggtg   2280
gtggatgtca tggtcattgg acggctatga                                    2310
```

<210> SEQ ID NO 57
<211> LENGTH: 8412
<212> TYPE: DNA
<213> ORGANISM: Homo sapiens

<400> SEQUENCE: 57
atggacggcg tggctgagtt ctccgagtat gtctctgaga ctgtggacgt gccatcccca 60
tttgacctac tagagccccc cacctcaggg ggcttcctca agctctccaa gccttgttgc 120
tacatcttcc caggtggtcg tggggactct gccctctttg ctgtcaatgg tttcaacatc 180
ctggtggatg gtggctctga tcgcaagtcc tgtttttgga agctggtacg gcacttggac 240
cgcattgact cggtgctact cacacacatt ggggcagaca acctgccagg catcaatgga 300
ctactgcagc gcaaagtggc agagctagag gaggagcagt cccagggctc tagcagttac 360
agcgactggg tgaagaacct tatctctcct gagcttggag ttgtcttttt caacgtgcct 420
gagaagctgc ggcttcctga tgcctcccgg aaagccaagc gtagcattga ggaggcctgc 480
ctcactctgc agcacttaaa ccgcctgggc atccaggctg agcctctata tcgtgtggtc 540
agcaatacca ttgagccact gaccctcttc cacaaaatgg gtgtgggccg gctggacatg 600
tatgtcctca accctgtcaa ggacagcaag gagatgcagt tcctcatgca aaagtgggca 660
ggcaatagta aagccaagac aggcatcgtg ctgcccaatg ggaaggaggc tgagatctcc 720
gtgccctacc ttacctctat cactgctctg gtggtctggc taccagccaa tcccactgag 780
aagattgtgc gtgtgctttt tccaggaaat gctccccaaa acaagatctt ggagggccta 840
gaaaagcttc ggcatctgga cttcctgcgt taccctgtgg ccacgcagaa ggacctggct 900
tctggggctg tgcctaccaa cctcaagccc agcaaaatca aacagcgggc tgatagcaag 960
gagagcctca aagccactac caagacggcc gtgagcaagt tggccaaacg ggaggaggtg 1020
gtagaagagg gagccaagga ggcacgttca gagctggcca aggagttagc caagacagag 1080
aagaaggcaa aagagtcatc tgagaagccc ccagagaagc ctgccaagcc tgagagggtg 1140
aagacagagt caagtgaggc actgaaggca gagaagcgaa agctgatcaa agacaaggta 1200
gggaaaaagc accttaaaga aaagatatca aagctggaag aaaaaaaaga caaggagaaa 1260
aaagagatca aaaaggagag gaaagagctc aagaaggatg aaggaaggaa ggaggagaag 1320
aaggatgcca agaaggagga gaagaggaaa gataccaaac ctgagctcaa gaagatttcc 1380
aagccagacc taaagccctt tactcctgag gtacgtaaga ccctctataa agccaaggtc 1440
cctggaagag tcaaaataga caggagccgt gctatccgtg gggagaagga gctgtcttct 1500
gagccccaga caccccccagc ccagaaggga actgtaccac tcccaaccat cagtgggcac 1560
agggagctgg tcctatcctc accagaggac ctcacacagg actttgagga gatgaagcgt 1620
gaggagaggg ctttgctggc tgaacaaagg gacacaggac taggagataa gccattccct 1680
ctagacactg cagaggaggg acccccaagt acagctatcc agggaacacc accctctgtt 1740
ccagggctgg gacaagaaga acatgtgatg aaggagaaag agcttgtccc agaggtccct 1800
gaggaacaag gcagcaagga cagaggccta gactctgggg ctgaaacaga ggaagagaaa 1860
gatacctggg aggaaaagaa gcagagggaa gcagagaggc tcccagacag aacagaagcc 1920
agagaggaaa gtgaacctga agtaaaggag gatgtgatag aaaaggctga gttagaagaa 1980
atggaggagg tacacccttc agatgaggag gaagaggacg cgacaaaagc tgagggtttt 2040
taccaaaaac atatgcagga acccttgaag gtaactccaa ggagccggga ggcttttggg 2100
ggtcgggaat tgggactcca gggcaaggcc cctgagaagg agacctcgtt attcctaagc 2160

-continued agcctgacca cacctgcagg agccactgag catgtctctt acatccagga tgagacaatc 2220
cctggctact cagagactga gcagaccatc tcagatgagg agatccatga tgagccggag 2280
gagcgcccag ctccacccag atttcataca agtacatatg acctgcccgg gcctgaaggt 2340
gctggcccat tcgaagccag ccaacctgcc gatagtgctg ttcctgctac ctctggcaaa 2400
gtctatggaa cgccagagac tgaactcacc taccccacta acatagtggc tgcccctttg 2460
gctgaagagg aacatgtgtc ctcggccact tcaatcactg agtgtgacaa actttcttcc 2520
tttgccacat cagtggctga ggaccaatct gtggcctcac ttacagctcc ccagacagag 2580
gagacaggca agagctccct gctgcttgac acagtcacaa gcatcccttc ctcccgtact 2640
gaagctacgc agggcttgga ctatgtgcca tcagctggta ccatctcacc cacctcctca 2700
ctggaagaag acaagggctt caaatcacca ccctgtgagg acttctctgt gactggggag 2760
tcagagaaga gaggagagat catagggaaa ggcttgtctg gagagagagc tgtggaagag 2820
gaagaggagg agacagcaaa cgtagagatg tctgagaaac tttgcagtca atatggaact 2880
ccagtgttta gtgcccctgg gcatgcccta catccaggag aaccagccct tggagaagca 2940
gaggagcggt gccttagccc agatgacagc acagtgaaga tggcttctcc tccaccatct 3000
ggcccaccca gtgccaccca cacacccttt catcagtccc cagtggaaga aaagtctgag 3060
ccccaagact ttcaggaggc agactcctgg ggagacacta agcgcacacc aggtgtgggc 3120
aaagaagatg ctgctgagga gacagtcaag ccagggcctg aagagggcac actagagaag 3180
gaagagaaag ttcctcctcc caggagcccc caggcccagg aagcacctgt caacattgat 3240
gaggggctta caggctgtac cattcaactg ttgccagcac aggataaagc aatagtcttt 3300
gagattatgg aggcaggaga gcccacaggc ccaattctgg gagcagaagc ccttcccgga 3360
ggtttgagga ctttacccca agaacctggc aaacctcaga aagatgaggt gctcagatat 3420
cctgaccgaa gcctctctcc tgaagatgca gaatccctct ctgtcctcag cgtgccctcc 3480
ccagacactg ccaaccaaga gcctaccccc aagtctccct gtggcctgac agaacagtac 3540
ctacacaaag accgttggcc agaggtatct ccagaagaca cccagtcact ttctctgtca 3600
gaagagagtc ccagcaagga gacctccctg gatgtctctt ctaagcagct ctctccagaa 3660
agccttggca ccctccagtt tggggaacta aaccttggga aggaagaaat ggggcatctg 3720
atgcaggccg aggatacctc tcaccacaca gctcccatgt ctgttccaga gccccatgca 3780
gccacagcgt cacctcccac agatgggaca actcgatact ctgcacagac agacatcaca 3840
gatgacagcc ttgacaggaa gtcacctgcc agctcattct ctcactctac accttcagga 3900
aatgggaagt acttacctgg ggcgatcaca agccctgatg aacacattct gacacctgat 3960
agctccttct ccaagagtcc tgagtctttg ccaggccctg ccttggagga cattgccata 4020
aagtgggaag ataaagttcc agggttgaaa gacagaacct cagaacagaa gaaggaacct 4080
gagccaaagg atgaagtttt acagcagaaa gacaaaactc tggagcacaa ggaggtggta 4140
gagccgaagg atacagccat ctatcagaaa gatgaggctc tgcatgtaaa gaatgaggct 4200
gtgaaacagc aggataaggc tttagaacaa aagggcagag acttagagca aaaagacaca 4260
gccctagaac agaaggacaa ggccctggaa ccaaaagaca aagacttaga agaaaaagac 4320
aaggccctgg aacagaagga taagattcca gaagagaaag acaaagcctt agaacaaaag 4380
gatacagccc tggaacagaa ggacaaggcc ctggaaccaa aagataaaga cttggaacaa 4440
aaggacaggg tcctagaaca gaaggagaag atcccagaag agaaagacaa agccttagat 4500

-continued caaaaagtca gaagtgttga acataaggct ccggaggaca cggtcgctga aatgaaggac 4560
agagacctag aacagacaga caaagcccct gaacagaaac accaggccca ggaacaaaag 4620
gataaagtct cagaaaagaa ggatcaggcc ttagaacaaa aatactgggc tttgggacag 4680
aaggatgaag ccctggaaca aaacattcag gctctggaag agaaccacca aactcaggag 4740
caggagagcc tagtgcagga ggataaaacc aggaaaccaa agatgctaga ggaaaaatcc 4800
ccagaaaagg tcaaggccat ggaagagaag ttagaagctc ttctggagaa gaccaaagct 4860
ctgggcctgg aagagagcct agtgcaggag ggcagggcca gagagcagga agaaaagtac 4920
tggagggggc aggatgtggt ccaggagtgg caagaaacat ctcctaccag agaggagccg 4980
gctggagaac agaaagagct tgccccggca tgggaggaca catctcctga gcaggacaat 5040
aggtattgga ggggcagaga ggatgtggcc ttggaacagg acacatactg gagggagcta 5100
agctgtgagc ggaaggtctg gttccctcac gagctggatg gccagggggc ccgcccacac 5160
tacactgagg aacgggaaag cactttccta gatgagggcc cagatgatga gcaagaagta 5220
cccctgcggg aacacgcaac ccggagcccc tgggcctcag acttcaagga tttccaggaa 5280
tcctcaccac agaaggggct agaggtggag cgctggcttg ctgaatcacc agttgggttg 5340
ccaccagagg aagaggacaa actgacccgc tctccctttg agatcatctc ccctccagct 5400
tccccacctg agatggttgg acaaagggtt ccttcagccc caggacaaga gagtcctatc 5460
ccagacccta agctcatgcc acacatgaag aatgaaccca ctactccctc atggctggct 5520
gacatcccac cctgggtgcc caaggacaga cccctccccc ctgcacccct ctccccagct 5580
cctggtcccc ccacacctgc cccggaatcc catactcctg caccccttctc ttggggcaca 5640 gccgagtatg acagtgtggt ggctgcagtg caggaggggg cagctgagtt ggaaggtggg 5700
ccatactccc ccctggggaa ggactaccgc aaggctgaag gggaaaggga agaagaaggt 5760
agggctgagg ctcctgacaa aagctcacac agctcaaagg taccagaggc cagcaaaagc 5820
catgccacca cggagcctga gcagactgag ccggagcaga gagagcccac accctatcct 5880
gatgagagaa gctttcagta tgcagacatc tatgagcaga tgatgcttac tgggcttggc 5940
cctgcatgcc ccactagaga gcctccactt ggagcagctg gggattggcc cccatgcctc 6000
tcaaccaagg aggcagctgc cggccgaaac acatctgcag agaaggagct ttcatctcct 6060
atctcaccca agagcctcca gtctgacact ccaaccttca gctatgcagc cctggcagga 6120
cccactgtac ccccaaggcc agagccaggg ccaagtatgg agcccagcct caccccacct 6180
gcagttcccc cccgtgctcc tatcctgagc aaaggcccaa gcccccctct taatggtaac 6240
atcctgagct gcagcccaga taggaggtcc ccatccccca aggaatcagg ccggagtcac 6300
tgggatgaca gcactagtga ctcagaactg gagaaggggg ctcgggaaca gccagaaaaa 6360
gaggcccaat ccccaagtcc tcctcacccc attcctatgg ggtcccccac attatggcca 6420
gaaactgagg cacatgttag ccctcccttg gactcacacc tggggcctgc ccgacccagt 6480
ctggacttcc ctgcttcagc ctttggcttc tcctcattgc agccagctcc cccacagctg 6540
ccctctccag ctgaaccccg ctcggcaccc tgtggctccc ttgccttctc tggggatcga 6600
gctctggctc tggctccagg acccccccacc agaacccggc atgatgaata cctggaagtg 6660
accaaggccc ccagcctgga ttcctcactg ccccagctcc catcacccag ttctcctggg 6720
gcccctctcc tctccaatct gccacgacct gcctcaccag ccctgtctga gggctcctcc 6780
tctgaggcta ccacgcctgt gatttcaagt gtggcggagc gcttctctcc aagccttgag 6840
gctgcagaac aggagtctgg agagctggac ccaggaatgg aaccagctgc ccacagcctc 6900
tgggacctca ctcctctgag cccagcaccc ccagcttcac tggacttggc cctagctcca 6960
gctccaagcc tgcctggaga catgggtgat ggcatcctgc cgtgccacct ggagtgctca 7020
gaggcagcca cggagaagcc aagccccttc caggttccct ctgaggattg tgcagccaat 7080
ggcccaactg aaaccagccc taacccccca ggccctgccc cagccaaggc tgaaaatgaa 7140
gaggctgcgg cttgccctgc ctgggaacgt ggggcctggc ctgaaggagc tgagaggagc 7200
tcccggcctg acacattgct ctcccctgag cagccagtgt gtcctgcagg gggctccggg 7260
ggcccaccca gcagtgcctc tcctgaggtc gaagctgggc cccagggatg tgccactgag 7320
cctcggcccc atcgtgggga gctctcccca tccttcctga acccacctct gcccccatcc 7380
atagatgata gggacctctc aactgaggaa gttcggctag taggaagagg ggggcggcgc 7440
cgggtagggg ggccagggac cactgggggc ccatgccctg tgactgatga gacacccccct 7500 acatcagcca gtgactcagg ctcctcacag tcagattctg atgtcccgcc agaaactgag 7560
gagtgtccgt ccatcacagc tgaggcagcc ctcgactcag atgaagatgg agacttccta 7620
cctgtggaca aagctggggg tgtcagtggt actcaccacc ccaggcctgg ccatgaccca 7680
cctcctctcc cacagccaga cccccgccca tcccctcccc gccctgatgt gtgcatggct 7740
gaccccgagg ggctcagctc agagtctggg agagtagaga ggctacggga gaaggaaaag 7800
gttcaggggc gagtagggcg cagggcccca ggcaaggcca agccagcgtc ccctgcacgg 7860
cgtctggatc ttcggggaaa acgctcaccc accccctggta aagggcctgc agatcgagca 7920
tcccgggccc cacctcgacc acgcagcacc acaagccagg tcaccccagc agaggaaaag 7980
gatggacaca gccccatgtc caaaggccta gtcaatggac tcaaggcagg accaatggcc 8040
ttgagttcca agggcagctc tggtgcccct gtatatgtgg atctcgccta catcccgaat 8100
cattgcagtg gcaagactgc tgaccttgac ttcttccgtc gagtgcgtgc atcctactat 8160
gtggtcagtg ggaatgaccc tgccaatggc gagccaagcc gggctgtgct ggatgccctg 8220
ctggagggca aggcccagtg gggggagaat cttcaggtga ctctgatccc tactcatgac 8280
acggaggtga ctcgtgagtg gtaccaacaa actcatgagc agcagcaaca actgaatgtc 8340
ctggtcctgg ctagcagcag caccgtggtg atgcaggatg agtccttccc tgcctgcaag 8400
attgagttct ga 8412

<210> SEQ ID NO 58
<211> LENGTH: 7407
<212> TYPE: DNA
<213> ORGANISM: Homo sapiens

<400> SEQUENCE: 58
atggcgaccg tggtggtgga agccaccgag ccggagccgt ccggcagcat cgccaacccg 60
gcggcgtcca cctcgcctag cctgtcgcac cgcttccttg acagcaagtt ctacttgctg 120
gtggtcgtcg gcgagatcgt gaccgaggag cacctgcggc gtgccatcgg caacatcgag 180
ctcggaatcc gatcatggga cacaaacctg attgaatgca acttggacca agaactcaaa 240
ctttttgtat ctcgacactc tgcaagattc tctcctgaag tcccaggaca aaagatcctt 300
catcaccgaa gtgacgtttt agaaacagtg gtcctgatca acccttctga tgaagcagtc 360
agcaccgagg tgcgcttaat gatcactgat gctgcccgac acaagctgct cgtgctgacc 420
gggcagtgct ttgaaaatac cggagagctc attctccagt ccggctcttt ctccttccag 480
aacttcatag agattttcac cgatcaagag atcggggagt tactaagcac cacccatcct 540

-continued

```
gccaacaaag ccagcttaac cctgttctgt cctgaagaag gggactggaa gaactccaat    600
cttgacagac acaatctcca agacttcatc aatattaaac tcaattcagc ttctatcttg    660
ccagaaatgg aaggactttc tgagtttacc gagtatctct cagaatcagt ggaagtccca    720
tctccctttg acatcttgga acctcccaca tcgggtggat ttctgaagct ctccaagccc    780
tgctgttata tttttccagg agggaggggc gattctgcct tgtttgcagt gaatggtttc    840
aatatgctca tcaatggcgg atcagagaga aaatcctgct tctggaagct catccgacac    900
ttagaccgag tggactccat cctgctcacc cacattgggg atgacaattt gcctggaata    960
aacagcatgt tacagcggaa aattgcagag ctcgaggaag aacagtccca gggctccacc   1020
acaaatagtg actggatgaa aaacctcatc tcccctgact taggagttgt atttctcaat   1080
gtacctgaaa atctcaaaaa tccagagcca aacatcaaga tgaagagaag catagaagaa   1140
gcctgcttca ctctccagta cctaaacaaa ttgtccatga aaccagaacc tctgtttaga   1200
agtgtaggca atactattga tcctgtcatt cttttccaaa aaatgggagt aggtaaactt   1260
gagatgtatg tgcttaatcc agtcaagagc agcaaggaaa tgcagtattt tatgcagcag   1320
tggactggta ccaacaaaga caaggctgaa ttcattctgc ctaatggtca agaagtagat   1380
ctcccgattt cctacttaac ttcagtctca tctttgattg tgtggcatcc agcaaaccct   1440
gcggagaaaa tcatccgagt cctgtttcct gggaacagca cccagtacaa catcctggaa   1500
gggttggaaa agctcaaaca tctagacttt ctgaagcagc cactggccac ccaaaaggat   1560
ctcactggcc aggtgcccac tcctgtggtg aaacaaacaa aactgaaaca gagggctgat   1620
agccgagaaa gtctgaagcc agccgcaaaa ccacttccta gcaaatccgt gcgcaaggag   1680
tcaaaagaag aaacccctga ggtcacaaaa gtgaatcacg tggaaaagcc acccaaagtt   1740
gaaagcaaag aaaaggtaat ggtgaaaaaa gacaagccaa taaaaacaga gaccaaacct   1800
tcagtgactg aaaaggaggt tcccagcaaa gaagagccat ctccagtgaa agccgaggtg   1860
gctgagaagc aagccacaga tgtcaaaccc aaagctgcca aggagaagac ggtgaaaaag   1920
gaaacaaagg taaagcctga agacaagaaa gaggagaaag aaaagccaaa gaaagaagtg   1980
gctaaaaagg aggacaaaac acctatcaag aaggaggaaa aaccaaaaaa ggaagaggtg   2040
aaaaaagaag tcaaaaaaga gatcaagaaa gaagagaaaa aagaacccaa gaaagaggtt   2100
aagaaagaaa caccgccaaa ggaagtcaag aaggaagtta agaaggaaga gaagaaggaa   2160
gtgaaaaagg aagaaaagga acccaaaaaa gaaattaaga agctccctaa agacgcaaag   2220
aaatcatcta ctcctctgtc tgaagcaaaa aaaccagctg ctttaaaacc aaaagtaccc   2280
aagaaggaag agtctgtcaa gaaagattct gttgctgccg gaaagccaaa ggagaagggg   2340
aaaataaaag tcattaagaa ggaaggcaag gccgcagagg ctgtcgctgc agctgtcggc   2400
actggagcca ccacagcagc tgtcatggcg gcagctggaa tagcagccat tggccctgcc   2460
aaagaactcg aagctgagag gtcccttatg tcatctcctg aggatctaac caaggacttt   2520
gaagagttaa aggctgaaga ggtcgatgta acaaaggaca tcaagcctca gctggagcta   2580
atcgaagacg aagagaaact gaaggaaact gagccagtcg aagcctacgt catccagaag   2640
gagagagaag tcaccaaagg tcctgccgag tcccctgatg agggaatcac taccactgaa   2700
ggggagggcg aatgtgaaca gacacctgag gagctggagc ccgtcgagaa gcagggagta   2760
gacgacattg aaaaatttga agatgaagga gccggttttg aagaatcttc agagactgga   2820
gactatgaag agaaggcaga aactgaggag gctgaggagc cagaagagga tggggaggaa   2880
cacgtatgtg tgagcgcctc caagcacagc cccactgagg atgaggaaag tgccaaggcg   2940
```

-continued

```
gaggctgatg catacatcag ggagaagagg gagtctgtgg ccagtgggga tgaccgagcc   3000
gaagaagaca tggatgaggc cattgagaaa ggagaggctg aacaatctga agaggaggct   3060
gatgaggagg acaaagctga agatgccaga gaggaggaat atgagccgga aaaaatggaa   3120
gctgaagact atgtgatggc tgtggtcgac aaggctgcag aggctggtgg tgccgaggag   3180
cagtatggat tcctcaccac accaaccaag caactaggag cccagtctcc tggccgagaa   3240
cctgcatctt caattcatga tgagacttta cctggaggct cagagagcga ggccaccgct   3300
tctgatgagg agaatcgaga agaccagcct gaggaattca ctgccacctc tggctacact   3360
cagtctacta ttgagatatc cagtgagccc acccccatgg atgagatgtc taccccctcga   3420
gacgtgatga gtgatgagac caacaatgaa gagacggagt ccccttctca ggaattcgta   3480
aatatcacca aatatgaatc ttcattgtat tctcaggaat actctaaacc tgctgatgtt   3540
acaccgctca acggattttc tgaaggatca aaaacagatg ccactgatgg caaggattac   3600
aatgcttcag cctctaccat atcaccaccc tcttccatgg aggaagacaa attcagcaga   3660
tctgctttac gtgatgctta ctgctctgaa gtgaaagcca gcaccacttt ggacatcaaa   3720
gatagcatct cagctgtttc aagtgaaaag gtcagcccat cgaagagccc gtccctgagt   3780
ccatctccac catcaccctt agaaaagacc cccctgggtg aacgtagtgt gaacttctct   3840
ctgacgccca atgagattaa agtctctgca gaggcagaag tagccccggt gtctcctgag   3900
gtgacccaag aagtagttga agaacattgt gctagtcctg aggacaagac tctggaagtg   3960
gtgtcaccat ctcagtccgt gactggcagt gctggtcaca caccttacta tcaatctcct   4020
actgacgaga aatccagtca tctccctaca gaagtcattg aaaaaccacc agcagttcca   4080
gtgagttttg aattcagtga tgccaaagat gagaatgaaa gggcttcagt aagccccatg   4140
gatgagcccg tgcctgactc agagtctcct attgaaaaag ttttgtctcc tttacgcagc   4200
ccgcccctca ttggatccga gtctgcttat gaaagttttc taagtgctga tgacaaggct   4260
tctggcagag gtgccgaaag tccttttgaa gaaaagagtg gaaaacaagg ctctccagac   4320
caagtaagtc cagtttctga aatgacttct actagtcttt accaagacaa acaggaaggg   4380
aaaagcacag actttgcacc aataaaagaa gactttggcc aagaaaagaa aactgatgat   4440
gttgaagcca tgagttctca accagcactg gctctggatg aaaggaaatt aggagatgtt   4500
tctcccacac aaatagatgt cagtcagttt ggatctttta aagaagacac taagatgtcc   4560
atttctgaag gtactgtctc agacaagtca gctactcctg ttgatgaggg cgtagcagaa   4620
gacacgtact ctcatatgga gggtgtggcc tcagtgtcca cagcctcagt ggctacgagc   4680
tcatttccag agccaacaac agatgatgtg tctccatctc tgcatgctga ggttggctcc   4740
ccacattcca cagaagtaga tgactccctt tcagtgtctg ttgtgcaaac acctaccaca   4800
ttccaggaaa cagaaatgtc tccatctaaa gaagaatgcc caagaccgat gtcaatttct   4860
ccaccagatt tctcccctaa aactgcaaag tccaggacac ccgttcaaga tcacagatct   4920
gaacagtcct caatgtctat tgaatttggc caagaatctc ctgagcaatc ccttgctatg   4980
gacttcagtc gacagtctcc agatcaccct acagtgggtg caggcgtgct tcacatcact   5040
gaaaatgggc caactgaagt ggactacagt ccttctgaca tgcaggactc cagtttatca   5100
cataagatac cacctatgga ggagccgtcc tacacccaag ataatgatct ttctgagctc   5160
atctcagtat ctcaggtaga ggcctccccg tccacctctt ctgctcatac cccttctcag   5220
atcgcttctc ctctccaaga agatactcta tccgatgttg ctcctcccag agatatgtcc   5280
```

ttatatgcct cactcacctc tgaaaaagtg caaagtctgg aaggagagaa gctctctcca 5340
aaatctgata tctctccact caccccacga gagtcctctc ctttatattc acctactttt 5400
tcagattcta cctctgcagt caaagagaaa acagcaactt gccacagttc ctcttctcca 5460
ccaatagatg cagcatccgc agagccctat ggcttccgtg cctcagtgtt attcgataca 5520
atgcaacacc atctagcctt gaatagagat ttgtccacac ctggcctgga gaaggacagt 5580
ggagggaaga cacctggtga ctttagctat gcctatcaaa agcctgagga aacaaccagg 5640
tccccagatg aagaagatta tgactatgag tcttatgaga agaccacccg gacctcagat 5700
gtgggtggct attactatga gaagatagag agaaccacaa aatctccaag tgacagtggc 5760
tactcctatg agaccattgg gaaaactacc aagacccctg aagatggtga ctattcctat 5820
gaaattattg agaagaccac acggacccct gaagagggtg ggtactcata tgacataagt 5880
gaaaagacca ccagcccccc cgaagtgagt ggttacagct atgaaaagac tgagaggtct 5940
agaaggcttc tggatgacat cagcaatggc tatgatgact ctgaggatgg tggccacaca 6000
cttggggacc ccagctactc ttatgaaacc actgagaaaa ttaccagttt ccctgagtct 6060
gaaggttatt cctatgagac atctacaaag acaacacgaa cccctgatac ttccacatac 6120
tgttacgaga ctgcagagaa aatcactaga acccctcagg catccacata ttcctacgag 6180
acttcagacc tatgctacac tgcagaaaag aagtccccct cagaagcccg tcaggatgtc 6240
gatttatgcc tcgtgtcctc ttgtgaatac aagcacccca agacagagct ttcaccctct 6300
ttcattaatc ccaatcctct tgagtggttt gccagtgaag aacccactga agaatctgaa 6360
aagcccctca ctcaatcagg gggagcccca ccgcctccag gaggaaagca acagggccga 6420
cagtgtgatg aaacccctcc cacctcagtc agcgagtcag ccccatccca gaccgactct 6480
gatgttcccc cggagactga agagtgcccc tccatcacgg ccgatgccaa tatcgactct 6540
gaagacgagt cggaaaccat ccccacagac aaaactgtca cgtacaaaca catggaccca 6600
cctccagctc ccgtgcaaga ccgcagccct tcgccacgcc accctgatgt gtccatggtg 6660
gacccagagg ccttggccat tgagcagaac ctgggcaaag ctctaaagaa agatctgaaa 6720
gagaagacca aaaccaaaaa gccaggtaca aagaccaagt catcttcacc tgtcaaaaag 6780
agtgatggga agtctaagcc cttggcagct tcaccaaaac cagcgggctt gaaagaatcc 6840
tcggataaag tgtccagggt ggcttctcct aagaagaaag aatctgtgga aaaggcagca 6900
aaacccacca ccactcctga ggtcaaagct gcacgtgggg aagagaaaga caaggagacc 6960
aagaatgctg ccaatgcctc tgcatccaag tcggccaaga ccgccactgc aggaccagga 7020
actaccaaga cgaccaagtc atctgctgtg cccccaggcc tccctgtgta tttggacctg 7080
tgctacattc ctaaccacag caatagtaag aatgttgatg tggaattttt caagagagtg 7140
cggtcttcct actacgtggt gagtgggaat gaccctgctg ctgaggagcc cagccgggct 7200
gtcctggacg ctttgttgga aggaaaggct cagtggggca gcaacatgca ggtgacactg 7260
atcccaactc atgactcaga agtgatgagg gaatggtacc aggagaccca tgagaaacag 7320
caagatctca acatcatggt tttagcaagc agcagcacag tggttatgca agatgaatcc 7380
ttccctgcat gcaagattga actgtaa 7407

<210> SEQ ID NO 59
<211> LENGTH: 5484
<212> TYPE: DNA
<213> ORGANISM: Homo sapiens

<400> SEQUENCE: 59

-continued

```
atggcagatg aacggaaaga tgaagcaaag gcacctcact ggacctcagc accgctaaca     60
gaggcatctg cacactcaca tccacctgag attaaggatc aaggcggagc aggggaagga    120
cttgtccgaa gcgccaatgg attcccatac agggaggatg aagagggtgc ctttggagag    180
catgggtcac agggcaccta ttcaaatacc aaagagaatg ggatcaacgg agagctgacc    240
tcagctgaca gagaaacagc agaggaggtg tctgcaagga tagttcaagt agtcactgct    300
gaggctgtag cagtcctgaa aggtgaacaa gagaaagaag ctcaacataa agaccagact    360
gcagctctgc ctttagcagc tgaagaaaca gctaatctgc ctccttctcc acccccatca    420
cctgcctcag aacagactgt cacagtggag gaagatttac ttacagcctc gaagatggag    480
ttccacgatc aacaggaatt gactccctct acagctgagc cttcagacca gaaggaaaag    540
gagtcagaga agcaaagtaa gcctggtgaa gaccttaaac atgctgcctt agtttctcag    600
ccagagacaa ctaaaactta ccctgataaa aaggacatgc aaggcacgga agaagaaaaa    660
gcacccctag ctttgtttgg gcacactctt gttgccagcc tggaagacat gaaacagaag    720
acagaaccaa gccttgtagt acctggcatt gacctcccta aagagcctcc aactccaaaa    780
gaacaaaagg actggttcat cgaaatgcca acggaagcaa aaaaggatga gtggggttta    840
gttgcccccca tatctcctgg ccctctgact cccatgaggg aaaaagatgt atttgatgat    900
atcccaaaat gggaagggaa acagtttgat tctcccatgc caagtccctt tcaaggggga    960
agcttcactc ttcctttaga tgtcatgaag aatgaaatag ttacagaaac atcgcccttt   1020
gcccctgcct tttacagcc agatgacaaa aatctctgc aacaaaccag tggcccagct   1080
actgccaaag atagttttaa aattgaagag ccccatgagg ctaaacctga caaaatggca   1140
gaagcaccac cctcagaggc aatgacctta cccaaagatg ctcacattcc agttgtagaa   1200
gaacatgtta tggggaaagt tttagaggaa gaaaaggagg ccataaatca agagactgtg   1260
cagcaaaggg atactttcac ccccagtgga caggaaccta tacttactga aaaggaaact   1320
gagctgaagc ttgaagaaaa aaccaccatt tctgacaaag aagctgtgcc aaaagagagt   1380
aaacccccaa aacctgcaga tgaagaaata ggcataattc agacctccac agagcacact   1440
ttctcagaac agaaagacca agagcctacc acagatatgt tgaaacagga ctcgttccct   1500
gtaagtttgg agcaagcagt tacagattca gccatgacct ctaaaacact ggagaaagcc   1560
atgaccgaac catctgcatt aattgaaaag agctcaattc aggaactttt tgaaatgaga   1620
gttgatgaca aagataagat tgaaggagtt ggagctgcaa catcagctga gcttgatatg   1680
ccattttatg aagataaatc aggaatgtcc aagtactttg aaacatctgc cttgaaagaa   1740
gaagcaacaa aaagcattga gccaggcagt gattactatg aactgagtga cactagagaa   1800
agtgtccatg agtctattga taccatgtct cccatgcata aaaatggtga caaggagttt   1860
caaacaggaa aagaatccca gcccagtcct ccagcacaag aagcagggta cagcactctc   1920
gcacagagtt atccatcaga tttacctgaa gaacccagtt ctcctcaaga aagaatgttc   1980
actattgatc caaaagtgta tggagagaaa agggacctcc acagtaagaa taaggatgat   2040
ttgaccctta gcaggagttt aggacttggt ggtaggtctg caatagaaca aagaagcatg   2100
tcaatcaatt tgccgatgtc ttgcctagat tccatagccc ttggatttaa ctttggtcgg   2160
ggacatgatc tttctcctct ggcttccgat attctaacca acactagtgg aagtatggat   2220
gaaggggatg attaccttcc agccaccaca cctgcactgg agaaagcccc ttgcttccct   2280
gtagaaagca aagaggaaga acagatagag aaagtaaaag ctactggaga agaaagtact   2340
```

-continued

```
caagcggaga tatcatgtga gtctcctttc ctagccaaag atttttacaa aaatggtact   2400
gtcatggcac ctgaccttcc tgaaatgcta gatctggcag gcacaaggtc aagattggct   2460
tctgtgagtg cagatgctga ggttgccagg aggaaatcag tcccatcaga gactgtggtt   2520
gaggatagtc gtactggctt gcccccggta actgatgaaa accatgtcat tgtaaaaacg   2580
gacagtcagc tcgaagacct gggctactgt gtgttcaata agtacacagt cccattgcca   2640
tcacctgttc aagacagtga gaatttatca ggggagagtg gtacctttta cgaaggcact   2700
gatgataaag ttcgaagaga tttggccaca gacctttcac tgattgaagt gaaactggca   2760
gcagccggaa gagtcaaaga tgagttcagt gttgacaaag aagcatccgc gcatatctct   2820
ggtgacaaat caggactgag taaggagttt gaccaagaga agaaagctaa tgataggttg   2880
gatactgtac tagaaaagag tgaagaacat gctgattcaa aagaacatgc caagaaaact   2940
gaagaggctg gtgatgaaat agaaacattc ggattaggag taacctatga gcaagctttg   3000
gccaaagatt tgtcaatacc aacagatgca tcctctgaga aagcagagaa gggtcttagt   3060
tcagtgccag agatagctga ggtagaacca tccaaaaagg tggaacaagg tctggatttt   3120
gctgtccagg gtcaactaga tgttaaaatt agtgactttg gacagatggc ttcagggcta   3180
aacatagatg atagaagggc aacagagcta aaacttgagg ctacacagga catgaccccc   3240
tcatccaaag caccgcagga ggcagatgca tttatgggtg ttgagtctgg ccacatgaaa   3300
gaaggcacta aagttagtga gacagaagtc aaagagaagg tggccaagcc tgacttggtg   3360
caccaggagg ctgtagacaa ggaggagtcc tatgaatcta gtggtgagca tgaaagtctc   3420
accatggagt ccttgaaagc tgatgagggc aagaaggaaa catctccaga atcatctcta   3480
attcaagatg agattgccgt caaattgtca gtggaaatac cttgcccacc tgctgtttca   3540
gaggctgatt tagccacaga tgagagagct gatgtccaga tggaatttat tcaggggcca   3600
aaagaagaaa gcaaagagac cccagatata tccatcacgc cttctgatgt tgcagagcca   3660
ttgcatgaaa cgatcgtatc tgaaccagca gagattcaga gtgaggaaga agagatagaa   3720
gcccagggag aatatgataa actgctcttc cgctcagaca cccttcagat aactgacctg   3780
ggtgtctcag gtgccaggga ggaatttgtg gagacctgcc caagtgaaca caaaggagtg   3840
attgagtctg ttgtgaccat cgaggatgat ttcatcactg tagtgcaaac cacaactgat   3900
gaaggggagt cagggtccca cagcgtgcgt tttgcagccc tagagcagcc tgaggtggaa   3960
aggagaccat ctcctcatga tgaagaagag tttgaagtag aagaggcagc tgaagcccag   4020
gcagaaccca aagatggttc cccagaggct ccagcttccc ctgagagaga agaggttgca   4080
ctttctgaat ataagacaga aacctatgac gattacaaag atgagaccac cattgacgac   4140
tccatcatgg acgctgacag cctctgggtg gacactcaag atgatgatag gagcatcatg   4200
acagaacagt tagaaactat tcctaaagag gagaaagctg aaaaggaagc tcggagatca   4260
tctcttgaga aacatagaaa agaaaagcct tttaaaaccg ggagaggcag aatttccact   4320
cctgaaagaa aagtagctaa aaaggaacct agcacagtct ccagagatga agtgagaagg   4380
aaaaaagcag tttataagaa ggctgaactt gctaaaaaaa cagaagttca ggcccactct   4440
ccctccagga aattcatttt aaaacctgct atcaaatata ctagaccaac tcatctctcc   4500
tgtgttaagc ggaaaaccac agcagcaggt ggggaatcag ctctggctcc cagtgtattt   4560
aaacaggcaa aggacaaagt ctctgacgga gtaaccaaga gcccagaaaa gcgctcttct   4620
ctcccaagac cttcctccat tctccctcct cggcgaggtg tgtcaggaga cagagatgag   4680
aattccttct ctctcaacag ttctatctct tcttcagcac ggcggaccac caggtcagag   4740
```

ccaattcgca gagcagggaa gagtggtacc tcaacaccca ctacccctgg gtctactgcc 4800
atcactcctg gcaccccacc aagttattct tcacgcacac caggcactcc tggaacccct 4860
agctatccca ggacccctca cacaccagga acccccaagt ctgccatctt ggtgccgagt 4920
gagaagaagg tcgccatcat acgtactcct ccaaaatctc ctgcgactcc caagcagctt 4980
cggcttatta accaaccact gccagacctg aagaatgtca aatccaaaat cggatcaaca 5040
gacaacatca aataccagcc taaagggggg caggtacaaa ttgttaccaa gaaaatagac 5100
ctaagccatg tgacatccaa atgtggctct ctgaagaaca tccgccacag gccaggtggc 5160
ggacgtgtga aaattgagag tgtaaaacta gatttcaaag aaaaggccca agctaaagtt 5220
ggttctcttg ataatgctca tcatgtacct ggaggtggta atgtcaagat tgacagccaa 5280
aagttgaact tcagagagca tgctaaagcc cgtgtggacc atggggctga gatcattaca 5340
cagtccccag gcagatccag cgtggcatca ccccgacgac tcagcaatgt ctcctcgtct 5400
ggaagcatca acctgctcga atctcctcag cttgccactt tggctgagga tgtcactgct 5460
gcactcgcta agcagggctt gtga 5484

<210> SEQ ID NO 60
<211> LENGTH: 3459
<212> TYPE: DNA
<213> ORGANISM: Homo sapiens

<400> SEQUENCE: 60
atggctgacc tcagtcttgc agatgcatta acagaaccat ctccagacat tgagggagag 60
ataaagcggg acttcattgc cacactagag gcagaggcct ttgatgatgt tgtgggagaa 120
actgttggaa aaacagacta tattcctctc ctggatgttg atgagaaaac cgggaactca 180
gagtcaaaga agaaaccgtg ctcagaaact agccagattg aagatactcc atcttctaaa 240
ccaacactcc tagccaatgg tggtcatgga gtagaaggga gcgatactac agggtctcca 300
actgaattcc ttgaagagaa aatggcctac caggaatacc caaatagcca gaactggcca 360
gaagatacca acttttgttt ccaacctgag caagtggtcg atcctatcca gactgatccc 420
tttaagatgt accatgatga tgacctggca gatttggtct ttccctccag tgcgacagct 480
gatacttcaa tatttgcagg acaaaatgat cccttgaaag acagttacgg tatgtctccc 540
tgcaacacag ctgttgtacc tcaggggtgg tctgtggaag ccttaaactc tccacactca 600
gagtcctttg tttccccaga ggctgttgca gaacctcctc agccaacggc agttccctta 660
gagctagcca aggagataga aatggcatca gaagagaggc caccagcaca agcattggaa 720
ataatgatgg gactgaagac tactgacatg gcaccatcta aagaaacaga gatggccctc 780
gccaaggaca tggcactagc tacaaaaacc gaggtggcat tggctaaaga tatggaatca 840
cccaccaaat tagatgtgac actggccaag gacatgcagc catccatgga atcagatatg 900
gccctagtca aggacatgga actacccaca gaaaaagaag tggccctggt taaggatgtc 960
agatggccca cagaaacaga tgtatcttca gccaagaatg tggtactgcc cacagaaaca 1020
gaggtagccc cagccaagga tgtgacactg ttgaaagaaa cagagagggc atctcctata 1080
aaaatggact tagccccttc caaggacatg ggaccaccca aagaaaacaa gaaagaaaca 1140
gagagggcat ctcctataaa aatggacttg gctccttcca aggacatggg accacccaaa 1200
gaaaacaaga tagtcccagc caaggatttg gtattactct cagaaataga ggtggcacag 1260
gctaatgaca ttatatcatc cacagaaata tcctctgctg agaaggtggc tttgtcctca 1320
gaaacagagg tagccctggc cagggacatg acactgcccc cggaaaccaa cgtgatcttg 1380
accaaggata aagcactacc tttagaagca gaggtggccc cagtcaagga catggctcaa 1440
ctcccagaaa cagaaatagc cccggccaag gatgtggctc cgtccacagt aaaagaagtg 1500
ggcttgttga aggacatgtc tccactatca gaaacagaaa tggctctggg caaggatgtg 1560
actccacctc cagaaacaga agtagttctc atcaagaacg tatgtctgcc tccagaaatg 1620
gaggtggccc tgactgagga tcaggtccca gccctcaaaa cagaagcacc cctggctaag 1680
gatggggttc tgaccctggc caacaatgtg actccagcca aagatgttcc accactctca 1740
gaaacagagg caacaccagt tccaattaaa gacatggaaa ttgcacaaac acaaaaagga 1800
ataagtgagg attcccattt agaatctctg caggatgtgg ggcagtcagc tgcacctact 1860
ttcatgattt caccagaaac cgtcacagga acggggaaaa agtgcagctt gccggccgag 1920
gaggattctg tgttagaaaa actaggggaa aggaaaccat gcaacagtca accttctgag 1980
ctttcttcag agacctcagg aatagccagg ccagaagaag gaaggcctgt ggtgagtggg 2040
acaggaaatg acatcaccac cccaccgaac aaggagctcc caccaagccc agagaagaaa 2100
acaaagcctt tggccaccac tcaacctgca aagacttcaa catcgaaagc caaaacacag 2160
cccacttctc tccctaagca gccagctccc accaccattg gtgggttgaa taaaaaaccc 2220
atgagccttg cttcaggctt agtgccagct gccccaccca aacgccctgc cgtcgcctct 2280
gccaggcctt ccatcttacc ttcaaaagac gtgaagccaa agcccattgc agatgcaaag 2340
gctcctgaga agcgggcctc accatccaag ccagcttctg ccccagcctc cagatctggg 2400
tccaagagca ctcagactgt tgcaaaaacc acaacagctg ctgctgttgc ctcaactggc 2460
ccaagcagta ggagcccctc cacgctcctg cccaagaagc ccactgccat taagactgag 2520
ggaaaacctg cagaagtcaa gaagatgact gcaaagtctg taccagctga cttgagtcgc 2580
ccaaagagca cctccaccag ttccatgaag aaaaccacca ctctcagtgg gacagccccc 2640
gctgcagggg tggttcccag ccgagtcaag gccacaccca tgccctcccg gccctccaca 2700
actcctttca tagacaagaa gcccacctcg gccaaaccca gctccaccac cccccggctc 2760
agccgcctgg ccaccaatac ttctgctcct gatctgaaga atgtccgctc caaggttggc 2820
tccacggaaa acatcaagca tcagcctgga ggaggccggg ccaaagtaga gaaaaaaaca 2880
gaggcagctg ctacaacccg aaagcctgaa tctaatgcag tcactaaaac agccggccca 2940
attgcaagtg cacagaaaca acctgcgggg aaagtccaga tagtctccaa aaaagtgagc 3000
tacagccata ttcagtccaa gtgtggttcc aaggacaata ttaagcatgt ccctggaggt 3060
ggtaatgttc agattcagaa caagaaagtg gacatctcta aggtctcctc caagtgtggg 3120
tctaaggcta acatcaagca caagcctggt ggaggagatg tcaagattga aagtcagaag 3180
ttgaacttca aggagaaggc ccaggccaag gtgggatccc tcgataatgt gggccaccta 3240
cctgcaggag gtgctgtgaa gactgagggc ggtggcagcg aggctcctct gtgtccgggt 3300
ccccctgctg gggaggagcc ggccatctct gaggcagcgc ctgaagctgg cgccccccact 3360 tcagccagtg gcctcaatgg ccaccccacc ctgtcagggg gtggtgacca aagggaggcc 3420
cagaccttgg acagccagat ccaggagaca agcatctaa 3459

<210> SEQ ID NO 61
<211> LENGTH: 6099
<212> TYPE: DNA
<213> ORGANISM: Homo sapiens

<400> SEQUENCE: 61

-continued

```
atgggagatg acagtgagtg gttgaaactg ccagttgatc agaaatgtga acacaagctg     60
tggaaagcaa ggttaagtgg gtatgaagag gccctgaaga tcttccagaa aataaaggat    120
gaaaagagcc cagagtggtc caaattttta ggattgatca aaaaatttgt cactgattcc    180
aatgcagtgg ttcaattgaa aggattagaa gctgcacttg tttatgttga aaatgcccat    240
gtagcaggaa aaaccacagg agaagttgtg tcaggtgttg taagtaaggt gttcaatcaa    300
cctaaagcta aagccaagga gctgggcata gagatctgtc ttatgtacat agagattgag    360
aaaggagagg ctgttcaaga agagctcctg aaaggcttgg acaataagaa tcccaagatc    420
atagtggcct gtatagagac actgaggaaa gccttaagtg aatttggttc caaaatcatc    480
ttgcttaagc caattatcaa agtgttgcca aaactctttg agtctcgaga gaaggctgtt    540
cgagatgaag ccaaactaat tgctgtggag atttacagat ggattcggga tgctctgaga    600
cccccattac aaaatataaa ctctgttcag ttgaaagaac tagaagaaga atgggtcaaa    660
ctgccaacaa gtgctcctag acctactcga tttcttcgtt cccaacaaga actagaagct    720
aaattggaac aacaacagtc tgctggtgga gatgctgaag gaggtggtga tgatggtgat    780
gaggtgccac aaatagatgc ttatgagctt ttagaagctg tagaaatcct ttccaaactt    840
cccaaagact tttatgacaa aattgaggca aaaaaatggc aagagagaaa agaggccctg    900
gagtctgtag aagtactaat aaaaaacccc aaactggaag ctggcgatta tgcagattta    960
gtaaaagcat taaagaaggt tgttggaaag gacaccaatg tcatgttggt ggctttggca   1020
gcaaaatgtc ttactggcct ggctgttggg ctaaggaaga aatttggaca atatgcagga   1080
catgttgtgc caaccatctt ggagaaattc aaagagaaga aacctcaagt ggtacaagcc   1140
ctgcaggagg caattgatgc aatcttcctt actaccacac tacagaacat cagtgaggat   1200
gttttagcag taatggataa taaaaatcca accatcaagc agcagacatc tctttttatt   1260
gcaagaagtt tccgccactg cactgcttct accctgccaa agagcttgct aaagcccttt   1320
tgtgctgcac tacttaagca catcaatgat tctgctcctg aagtcagaga tgccgcattt   1380
gaagcattgg gtactgcttt gaaggtggtt ggcgagaaag cagtaaaccc attcctagct   1440
gatgtggaca aactcaagct tgataagatc aaagaatgtt cagaaaaggt agaactgata   1500
catggtaaga aagctggact agctgctgat aagaaggaat tcaaacctct gcctggaagg   1560
actgctgctt caggggctgc aggagataag gacacaaagg acatttctgc acccaaacca   1620
ggacctctaa aaaaggcacc tgctgctaag gctggtgggc caccaaaaaa ggggaaacca   1680
gctgcaccag gaggcgcagg gaatactgga accaagaaca agaaaggact ggagactaaa   1740
gaaatagtgg agcctgagct ctcgatagaa gtatgtgaag aaaaagcttc agctgttctt   1800
ccccctacct gtatacagct tcttgacagc agtaactgga aagaaaggct ggcttgtatg   1860
gaagagttcc agaaggctgt tgagctaatg gaccgaactg aaatgccatg ccaggcatta   1920
gtgaggatgc tagccaagaa acctggatgg aaagaaacta attttcaggt gatgcaaatg   1980
aagcttcata tagttgcttt gattgcccag aagggaaatt tttccaaaac gtcagctcag   2040
gttgtattag atggccttgt ggacaagatt ggagatgtga aatgtgggaa caatgcaaaa   2100
gaagctatga cagcaatagc cgaagcctgt atgttaccat ggactgctga acaggttgtg   2160
tcaatggctt tctcacaaaa gaatcccaaa aatcagtcag aaactctgaa ttggctatca   2220
aatgccataa aagaatttgg tttttctggg ttgaatgtca aagctttcat tagcaatgtg   2280
aagacagctc ttgctgcaac aaacccagct gtgaggactg ctgccataac cctgcttggc   2340
```

-continued

```
gtgatgtatc tgtatgttgg tccctctttg cgaatgttct ttgaggatga gaagcctgcc   2400
ctcctatccc agatagatgc agaatttgag aagatgcagg gacaaagtcc acctgctcca   2460
accagaggaa tttccaagca tagcacaagt ggtacagatg aaggagaaga tggagatgaa   2520
ccagatgacg ggagcaatga tgtcgttgat cttttgccga ggacggagat cagtgataaa   2580
atcacttcag agttggtatc taagattggt gataagaatt ggaagattag gaaagaaggc   2640
ctagatgaag tggcaggtat tattaatgac gcaaaattta tccaaccgaa tataggtgaa   2700
cttccaactg ccttgaaggg tcgactcaat gattcaaata aaatcttggt acagcaaacg   2760
ctgaatatcc tgcaacaact ggcagtagcc atgggcccaa atattaagca acatgtaaaa   2820
aatttaggca tccctatcat cacagtcctt ggagacagca agaacaatgt tcgagctgct   2880
gccctagcga ctgtgaatgc ttgggcagaa cagactggca tgaaggaatg gctggaagga   2940
gaagatcttt ctgaagagct caaaaaggaa aatcctttct tgaggcaaga gcttctgggc   3000
tggctggctg agaaactacc tactcttcgt tccaccccta cagaccttat cctttgtgtt   3060
cctcatctct actcctgcct agaagatcga aatggagatg tgcgaaagaa ggcccaagat   3120
gccttgccat tcttcatgat gcatttagga tatgaaaaaa tggccaaggc tactgggaaa   3180
ctaaagccaa cttctaaaga tcaggtattg gccatgctag agaaagccaa agttaacatg   3240
ccagccaagc ctgctccacc cactaaagca acttctaaac caatgggagg gtccgctcca   3300
gccaaattcc agcctgcatc agcacctgct gaagattgta tttccagcag tacagaaccc   3360
aaacctgatc caaaaaaggc caaagctcca ggattatcct ctaaagcaaa gagtgcacaa   3420
gggaagaaga tgccaagcaa aaccagctta aaggaggatg aagacaaatc cgggcctatt   3480
tttattgttg ttccaaatgg aaaagagcaa aggatgaaag atgaaaaagg attgaaggtg   3540
ctaaagtgga attttactac cccacgggat gaatacattg agcaactaaa gactcaaatg   3600
tctagctgtg tggctaaatg gttacaagat gagatgtttc actcagactt tcagcatcat   3660
aacaaagccc ttgctgttat ggttgatcac ttggagagtg aaaaagaagg agttattggt   3720
tgcctggatc ttatcttaaa gtggcttacc ctgaggtttt ttgacaccaa tacaagcgtc   3780
ctgatgaaag cactagaata tttaaaattg ctcttcacct tgctaagtga agaagaatat   3840
catcttactg agaatgaagc atcttccttc atcccctatc ttgtcgtcaa ggttggagaa   3900
ccaaaggatg tcattcgtaa agatgttcgt gccatcctga accggatgtg ccttgtctac   3960
ccagctagca agatgtttcc ctttatcatg gaaggaacca aatccaaaaa ctctaagcag   4020
agagcagagt gcctggaaga gctgggatgt ctggttgagt cctatggcat gaatgtttgc   4080
caaccaaccc caggaaaagc cttaaaggaa atagctgttc acataggaga ccgtgacaat   4140
gctgtacgca atgctgcact caacaccatt gtaacggtgt acaatgtaca tggggatcag   4200
gtgttcaaac tgattggaaa tctttctgaa aaggatatga gcatgctcga ggagaggatt   4260
aagcggtcag caaagagacc ctctgctgca ccaataaaac aggtggaaga gaaacctcag   4320
cgtgcacaga acataagctc caatgccaac atgttacgca agggaccagc tgaggacatg   4380
tcttccaaac tcaaccaagc ccgaagcatg agtgggcatc ctgaggcagc ccagatggtc   4440
cgccgagaat tccagctgga tctagatgag attgagaatg acaatggtac agtccgatgt   4500
gaaatgccag aacttgttca gcacaaactg gatgacattt ttgagccagt ccttattcct   4560
gaacccaaga tccgggctgt ttctccacac ttcgatgaca tgcacagtaa tacagcatcc   4620
acaatcaatt tcattatctc ccaagtagcc agtggtgaca tcaacacaag tatccaagct   4680
ctgacacaga tcgatgaggt cctgagacag gaagacaaag ctgaagccat gtccggccat   4740
```

attgatcagt ttctgatagc cacttttatg cagctaagac tcatctacaa cacacacatg 4800
gcagatgaga aattggagaa ggacgagatc atcaagttgt atagctgtat cattggcaac 4860
atgatttcgc tgtttcagat agagagcctt gcccgggagg cctccactgg agtactaaaa 4920
gacctaatgc atggcctcat caccttaatg ctggattctc ggattgaaga tcttgaggaa 4980
ggacaacagg tcatccgctc tgtgaacctc ttggtggtga aggttctgga gaagtcagac 5040
cagaccaaca tcctgagtgc cctacttgtt ttgctccaag acagcctgct agcaacagcc 5100
agttctccca aattctcaga gcttgttatg aagtgtctct ggagaatggt tcgactgttg 5160
cctgatacca tcaatagcat taacctagac agaattcttc tggatatcca cattttcatg 5220
aaggtcttcc ccaaagagaa actgaagcaa tgcaaaagtg aatttcccat aaggacccta 5280
aagaccctgc tacacacctt atgcaaatta aaagggccca agatcctgga ccacctaacg 5340
atgatcgaca acaaaaacga gtctgagctg gaggcccatc tctgccggat gatgaagcac 5400
agtatggacc agactgggag caagtctgat aaggaaacag aaaagggagc atctcgaata 5460
gatgaaaaat catcaaaggc caaagtgaat gatttcttag ctgagatttt taagaagatt 5520
ggctctaaag aaaacactaa agagggacta gcagagttat atgaatataa gaagaaatac 5580
tcagatgctg acattgaacc atttctgaaa aattcctcac agttcttcca gagctatgtc 5640
gaaagaggcc ttcgggtgat tgagatggag agggagggca aaggtcgtat ttccacttca 5700
acaggcatct cccctcagat ggaagtcaca tgtgtgccca cgcccacaag cacagtgtcc 5760
tccataggta acacaaatgg ggaagaagtg gggccatctg tctacttgga aaggctaaag 5820
atcctccgac agcgatgtgg tctggacaac acaaagcaag atgaccgacc tcctttgacc 5880
tctttgctct ccaaaccagc agttcctact gtcgcctctt ccacagacat gctccacagc 5940
aaactctctc agctccggga gtcacgggag cagcaccagc attcagacct ggattctaac 6000
cagactcact cttcaggaac tgtgacctcc tcctcctcca cagctaacat agacgacttg 6060
aaaaaaagac tggagagaat aaagagcagt cgcaaatga 6099

<210> SEQ ID NO 62
<211> LENGTH: 2442
<212> TYPE: DNA
<213> ORGANISM: Homo sapiens

<400> SEQUENCE: 62
atggcgtggc cgtgcatcac gagggcctgc tgcatcgccc gcttctggaa ccagttggac 60
aaagcggaca tcgctgtgcc gctggttttc accaagtact cggaggccac cgagcacccg 120
ggcgccccgc cgcagccacc gccgccgcag cagcaggcgc agccggcgct cgcgcccccc 180
tcggcgcgcg cggttgccat agagacgcag ccagcccagg gcgagttgga tgcagttgcc 240
cgggcaacgg ggccagcgcc tgggcctacc ggcgagcgcg agccggcggc gggccccggc 300
cggagcgggc cgggcccggg cctgggctcc ggctccacct ccggccccgc ggactcggtg 360
atgcggcagg attaccgagc ctggaaggtg cagcggcccg agcccagctg ccggccgcgc 420
agcgaatacc agccctccga cgctcccttc gagcgcgaga cccagtacca gaaggacttc 480
cgcgcctggc cgctgccgcg ccgcggggac cacccgtgga tccccaagcc cgtgcagatc 540
tctgcggcct cccaggcgtc ggcgcccatt ctcggggcgc ccaagcgccg gccgcagagc 600
caggagcgct ggccagtgca ggccgccgct gaggcccggg agcaggaggc ggcccccggc 660
ggagcgggtg gcctggcggc cggaaaggcg tccggggcgg acgagcgcga cacgcgcagg 720

```
aaggccgggc ctgcctggat tgtgcgccgc gccgagggcc tggggcacga gcagacgccg    780
ctgcccgcgg cccaggccca ggtccaggcc accggccccg aggctggcag ggggcgcgcc    840
gcggcggacg ccctcaaccg gcaaatccgc gaggaggtgg cgagtgcagt gagcagctcc    900
tacaggaatg aattcagggc atggacggac atcaagcctg tgaaaccaat aaaggccaag    960
ccccagtaca agcccccaga tgataagatg gttcatgaga ccagctacag tgctcagttc   1020
aaaggagagg ccagcaagcc aacaacagct gacaataagg tcattgatcg cagaagaata   1080
cgcagcctct acagcgaacc cttcaaggaa cccccaaagg tggaaaaacc tagtgttcag   1140
agttccaaac caaaaaagac ctcagcgagc cataagccca cgaggaaggc caaagacaag   1200
caggcggtgt caggccaggc tgccaagaaa aagagcgcgg agggcccgag taccaccaag   1260
ccagacgaca aggagcaaag caaagagatg aacaataaac tggctgaggc gaaagagagc   1320
ctggctcaac ccgtcagtga ttcaagtaag actcaaggtc ctgtagccac agagccagac   1380
aaggatcaag gttctgtggt cccaggcctt ctgaaaggtc aaggtcctat ggtgcaagag   1440
cctctgaaga agcaaggttc tgtggtccca gggcctccaa aggatctagg tcccatgatc   1500
ccattaccag tcaaggatca agatcacacg gtccctgagc ctttaaagaa tgaaagccct   1560
gttatctcag caccagtcaa ggaccaaggt ccctcggtcc cagttcctcc aaagaatcaa   1620
agtcctatgg ttccagcaaa agttaaggat caaggctctg tggtaccaga gtctctaaag   1680
gatcaaggtc ctaggattcc tgagcctgtg aagaatcaag ctcctatggt cccagcacct   1740
gtcaaggatg aaggtcccat ggtctcagca tctgtcaagg atcaaggtcc catggtctca   1800
gcacctgtca aggatcaagg tcccatagtc ccagcacctg tcaagggtga aggtcccata   1860
gtcccagcac ctgtcaagga tgaaggtccc atggtctcag cacctatcaa ggatcaagat   1920
cccatggtcc cagagcatcc gaaggatgaa agtgccatgg ccacagcacc cataaagaat   1980
caaggttcca tggtctctga gcctgtaaag aatcaaggtt tagtggtctc agggccagtc   2040
aaggatcaag atgttgtagt cccagagcat gcaaaggttc acgattctgc agttgtggca   2100
cctgtaaaga atcaaggtcc tgtggtcccc gagtccgtga agaatcaaga ccccattctc   2160
ccagtactag ttaaggatca aggccccaca gtcctacagc ctccaaagaa tcaaggtcgt   2220
atagtccctg aacctctgaa gaatcaagtt cctatagtcc cagtgcctct gaaggatcaa   2280
gatcctctgg tgccagtacc agcaaaggac caaggtcctg cagtccctga acctctgaag   2340
actcaaggtc ccagggaccc tcagctacct actgtctcac ctctaccccg agtcatgatc   2400
ccaactgccc cccatacgga atacattgag agctcccctt ga                       2442
```

<210> SEQ ID NO 63
<211> LENGTH: 2316
<212> TYPE: DNA
<213> ORGANISM: Homo sapiens

<400> SEQUENCE: 63

```
atgcctggat cagctacagc tctccgacat gagagactga agaagaccaa tgcaaggcca     60
attcctcttg gtttattcac cattaatgag gaagacgaac agcaaaagaa tggaaattcc    120
agaagaccaa aagcacccga cagctacaaa gtgcaagata agaaaaatgc ctccagccgc    180
cctgcctctg caatttcagg acaaaataac aaccactcag gaaataaacc agaccctccg    240
cctgtgttac gtgttgatga ccggcagcgg ctggcccggg agcgacgtga ggaacgggag    300
aaacagctag ctgcaagaga aatagtgtgg ttagaaagag aagagcgagc caggcagcac    360
tacgagaagc acctggaaga gcggaagaag aggttggagg agcagaggca gaaggaggag    420
```

```
cggaggaggg ctgctgtgga ggagaagcgg aggcagagac ttgaggagga caaagaacgc    480

cacgaagctg ttgtacggcg cacaatggaa aggagccaga agccaaaaca gaagcataac    540

cgttggtcgt ggggaggctc tctccatggg agccctagca tccacagtgc agatccagac    600

aggcggtcag tttccaccat gaatctttcg aaatatgttg atcccgtcat tagcaagcgg    660

ctctcctctt catctgcaac tttactaaat tctccagata gagctcgccg cctgcagctc    720

agcccatggg agagcagcgt tgttaacaga ctcctgacgc ccacacattc gttcctggcc    780

agaagtaaaa gcacagctgc cttgtctgga gaagcagcat cttgcagccc catcatcatg    840

ccctacaaag ctgcacactc tagaaattcg atggatcgac caaaactctt tgtaacacca    900

cctgagggct cttctcgcag gaggatcatt catggcacag cgagctataa aaaagaaaga    960

gagagagaaa atgtactctt cctcacatct ggcacccgaa gggctgtatc tccatctaat   1020

cccaaagcaa gacaaccagc tcgctcccga ctttggcttc cgtccaagtc tcttcctcat   1080

ttgcctggca cacccagacc gacatcctcc ttgccacccg gctcagtcaa agctgctcct   1140

gctcaggtcc ggcccccatc cccggcaac atccgccctg tcaagaggga agtcaaagtg   1200

gagcctgaga agaaagatcc tgagaaggaa cctcagaaag ttgccaatga gccctcacta   1260

aagggcagag cacctttagt gaaggtagaa gaagccacag ttgaagagcg gacacctgct   1320

gaaccagaag ttggccctgc tgctccagcc atggccccag ctccagcctc ggccccagct   1380

ccagcctcgg ccccagctcc agccccggtc cccaccccag ccatggtctc agccccgtca   1440

tccactgtga atgccagtgc ttctgttaag acttctgcag gcaccaccga cccagaggag   1500

gccacaaggc ttctagctga gaagaggcgg ctggcccgag agcagagaga aaaggaagaa   1560

agggagagga gggagcagga agagcttgaa agacaaaaga gagaggaatt ggctcaacgt   1620

gtggctgaag agaggacgac tcgccgtgag gaggagtcgc gcaggctgga agccgagcag   1680

gcccgggaga aggaggagca gctgcagcgg caggcggagg agcgggcgct gcgcgagcgg   1740

gaggaggcag agcgcgccca gaggcagaaa gaagaagaag ctcgcgttcg tgaagaagca   1800

gagagggtcc ggcaggaacg agagaagcat ttccagagag aagagcaaga gcgcctggag   1860

agaaagaagc gacttgagga gattatgaaa agaaccagga gaacagaagc tacagataag   1920

aaaaccagtg atcagagaaa cggtgatata gccaagggag ctctcactgg aggaacagag   1980

gtgtctgcac ttccatgtac aacaaacgct ccgggaaatg gaaagccagt tggcagccca   2040

catgtggtta cctcacacca gtcaaaagtg acagtggaga gcactcccga tttggaaaaa   2100

caaccaaatg aaaatggtgt atctgttcag aatgaaaatt ttgaagaaat tataaactta   2160

cccattggat ctaaaccatc cagattagat gtcaccaaca gtgagagccc agaaattcct   2220

ttgaatccaa ttttggcctt tgatgatgaa gggacacttg ggcccctgcc tcaggtagat   2280

ggtgttcaga cacagcagac tgcagaagtt atatga                             2316
```

<210> SEQ ID NO 64
<211> LENGTH: 3180
<212> TYPE: DNA
<213> ORGANISM: Homo sapiens

<400> SEQUENCE: 64

```
atggcggcgg tggctggatc tggggctgcc gcggctccga gctcactgct cctcgtggtg     60

ggcagcgagt tcgggagccc ggggctcctc acctacgtcc tggaggagct cgaaagaggc    120

atccggtctt gggatgtcga tcctggcgtc tgcaaccttg atgaacagct caaggtcttt    180
```

-continued

```
gtgtcccgac actctgccac cttctccagc attgtgaaag gccagcggag cctgcaccac    240
cgtggagaca acctggagac cctggtcctc ctgaacccat cagacaagtc cctgtatgat    300
gagctccgga accttctgtt ggaccctgcc tctcacaagc tactggtgtt ggctgggccc    360
tgcctggagg agacggggga gctgctgcta cagacagggg gcttctcgcc tcaccacttc    420
ctccaggtcc tgaaggacag agagatccgg gacatcctgg ccaccacgcc cccacctgtg    480
cagccgccca tactcaccat cacctgcccc accttcggtg actgggctca gctggcaccc    540
gctgtgcctg gccttcaggg ggcgctccgg ctccagctgc ggctgaaccc cccggcgcag    600
ctgcccaact ctgagggcct gtgcgaattc ctggagtacg tggctgagtc tctggagcca    660
ccgtcccccct tcgagctgct ggagcccccg acctccgggg gcttcctcag gctgggccgg    720
ccctgctgct acatcttccc tggaggcctc ggggatgccg ccttcttcgc cgtcaatggc    780
ttcactgtgc tggtcaacgg tggctcaaac cccaagtcca gtttctggaa gctggtgcgg    840
cacctggacc gcgtggatgc cgtgctggtg acccaccctg gcgccgacag cctccccggc    900
ctcaacagcc tgctgcggcg caaactggcg gagcgctccg aggtggctgc tggtgggggc    960
tcctgggacg acaggctgcg caggctcatc tcccccaacc tgggggtcgt gttcttcaac   1020
gcctgcgagg ccgcgtcgcg gctggcgcgc ggcgaggatg aggcggagct ggcgctgagc   1080
ctcctggcgc agctgggcat cacgcctctg ccactcagcc gcggccccgt gccagccaaa   1140
cccaccgtgc tcttcgagaa gatgggcgtg ggccggctgg acatgtatgt gctgcacccg   1200
ccctccgccg gcgccgagcg cacgctggcc tctgtgtgcg ccctgctggt gtggcacccc   1260
gccggccccg gcgagaaggt ggtgcgcgtg ctgttccccg gttgcacccc gcccgcctgc   1320
ctcctggacg gcctggtccg cctgcagcac ttgaggttcc tgcgagagcc cgtggtgacg   1380
ccccaggacc tggaggggcc ggggcgagcc gagagcaaag agagcgtggg ctcccgggac   1440
agctcgaaga gagagggcct cctggccacc caccctagac ctggccagga gcgccctggg   1500
gtggcccgca aggagccagc acgggctgag gccccacgca agactgagaa agaagccaag   1560
accccccggg agttgaagaa agaccccaaa ccgagtgtct cccggaccca gccgcgggag   1620
gtgcgccggg cagcctcttc tgtgcccaac ctcaagaaga cgaatgccca ggcggcaccc   1680
aagccccgca aagcgcccag cacgtcccac tctggcttcc cgccggtggc aaatggaccc   1740
cgcagcccgc ccagcctccg atgtggagaa gccagccccc ccagtgcagc ctgcggctct   1800
ccggcctccc agctggtggc cacgcccagc ctggagctgg ggccgatccc agccggggag   1860
gagaaggcac tggagctgcc tttggccgcc agctcaatcc caaggccacg cacaccctcc   1920
cctgagtccc accggagccc cgcagagggc agcgagcggc tgtcgctgag cccactgcgg   1980
ggcggggagg ccgggccaga cgcctcaccc acagtgacca cacccacggt gaccacgccc   2040
tcactacccg cagaggtggg ctccccgcac tcgaccgagg tggacgagtc cctgtcggtg   2100
tcctttgagc aggtgctgcc gccatccgcc cccaccagtg aggctgggct gagcctcccg   2160
ctgcgtggcc cccgggcgcg gcgctcggct tccccacacg atgtggacct gtgcctggtg   2220
tcaccctgtg aatttgagca tcgcaaggcg gtgccaatgg caccggcacc tgcgtccccc   2280
ggcagctcga atgacagcag tgcccggtca caggaacggg caggtgggct gggggccgag   2340
gagacgccac ccacatcggt cagcgagtcc ctgcccaccc tgtctgactc ggatcccgtg   2400
cccctggccc ccggtgcggc agactcagac gaagacacag agggctttgg agtccctcgc   2460
cacgaccctt tgcctgaccc cctcaaggtc cccccaccac tgcctgaccc atccagcatc   2520
tgcatggtgg accccgagat gctgcccccc aagacagcac ggcaaacgga gaacgtcagc   2580
```

cgcacccgga agcccctggc ccgccccaac tcacgcgctg ccgcccccaa agccactcca 2640
gtggctgctg ccaaaaccaa ggggcttgct ggtggggacc gtgccagccg accactcagt 2700
gcccggagtg agcccagtga gaagggaggc cgggcacccc tgtccagaaa gtcctcaacc 2760
cccaagactg ccactcgagg cccgtcgggg tcagccagca gccggcccgg ggtgtcagcc 2820
accccaccca agtccccggt ctacctggac ctggcctacc tgcccagcgg gagcagcgcc 2880
cacctggtgg atgaggagtt cttccagcgc gtgcgcgcgc tctgctacgt catcagtggc 2940
caggaccagc gcaaggagga aggcatgcgg gccgtcctgg acgcgctact ggccagcaag 3000
cagcattggg accgtgacct gcaggtgacc ctgatcccca ctttcgactc ggtggccatg 3060
catacgtggt acgcagagac gcacgcccgg caccaggcgc tgggcatcac ggtgttgggc 3120
agcaacagca tggtgtccat gcaggatgac gccttcccgg cctgcaaggt ggagttctag 3180

<210> SEQ ID NO 65
<211> LENGTH: 1944
<212> TYPE: DNA
<213> ORGANISM: Homo sapiens

<400> SEQUENCE: 65
atgtctgatg aagtttttag caccactttg gcatatacaa agagtccaaa agttaccaaa 60
agaactactt tccaggatga gctaataaga gcaattacag ctcgctcagc cagacaaagg 120
agttctgaat actcagatga ctttgacagt gatgagattg tttctttagg tgatttttct 180
gacacttcag cagatgaaaa ttcagttaat aaaaaaatga atgactttca tatatcagat 240
gatgaagaaa agaatccttc aaaactattg tttttgaaaa ccaataaatc aaacggtaac 300
ataaccaaag atgagccagt gtgtgccatc aaaaatgaag aggaaatggc acctgatggg 360
tgtgaagaca ttgttgtaaa atctttctct gaatctcaaa ataaggatga ggaatttgaa 420
aaagacaaaa taaaaatgaa acctaaaccc agaattcttt caattaaaag cacatcttca 480
gcagaaaaca acagccttga cacagatgat cactttaaac catcacctcg gccaaggagt 540
atgttgaaaa agaaaagtca catggaggag aaggatggac tagaagataa agaaactgcc 600
ctcagtgaag aattggagtt acattctgca ccttcttccc ttccaacgcc gaatggcata 660
caattagaag ctgagaaaaa agcattctct gaaaaccttg atcctgagga ttcatgctta 720
acaagtctag catcatcatc acttaaacaa attcttggag attctttttc accaggatct 780
gagggaaacg catctggaaa agatccaaat gaagaaatca ctgaaaacca taattccttg 840
aaatcagatg aaaataaaga gaattcattt tcagcagacc atgtgactac tgcagttgag 900
aaatccaagg aaagtcaagt gactgctgat gaccttgaag aagaaaaggc aaaagcggaa 960
ctgattatgg atgatgacag aacagttgat ccactactat ctaaatctca gagtatctta 1020
atatctacca gtgcaacagc atcttcaaag aaaacaattg aagatagaaa tataaagaat 1080
aaaaagtcaa caaataatag agcatccagt gcatctgcca gattaatgac ctctgagttt 1140
ttgaagaaat ctagttctaa aaggagaact ccatcgacaa ctacctcttc tcactattta 1200
gggactttaa aagtcttgga ccaaaaacct tcacagaaac agagcataga acctgataga 1260
gcagataaca taagggcagc tgtttatcag gagtggttag aaaagaaaaa tgtgtattta 1320
catgaaatgc acagaataaa aagaattgaa agtgaaaact taaggatcca aaatgaacag 1380
aaaaaagctg ctaaaagaga agaagcatta gcatcatttg aggcctggaa ggctatgaaa 1440
gaaaaggaag caaagaaaat agctgccaaa aagaggcttg aagaaaaaaa caagaagaaa 1500

```
actgaagaag aaaatgctgc aagaaaagga gaagcactac aagcttttga aaaatggaaa   1560
gagaaaaaga tggaatatct taaagagaaa aatagaaagg agagagaata tgaaagagca   1620
aagaaacaga aagaggagga aactgttgcc gagaaaaaga aagataattt aactgctgtt   1680
gagaaatgga atgaaaaaaa ggaagctttt ttcaagcaaa aggaaaaaga aaaaataaat   1740
gagaaaagaa aggaagaact gaaaagagct gagaaaaaag ataaagataa acaagctatt   1800
aatgaatatg aaaaatggct ggaaaataag gaaaaacaag aaagaattga acgaaaacag   1860
aagaaacgtc attcctttct tgaaagtgag gcacttcctc cgtggagccc tccaagcaga   1920
actgtgttcg caaaagtgtt ttga                                          1944
```

<210> SEQ ID NO 66
<211> LENGTH: 3837
<212> TYPE: DNA
<213> ORGANISM: Homo sapiens

<400> SEQUENCE: 66

```
atggcacaga gcaagaggca cgtgtacagc cggacgccca gcggcagcag gatgagtgcg     60
gaggcaagcg cccggcctct gcgggtgggc tcccgtgtag aggtgattgg aaaaggccac    120
cgaggcactg tggcctatgt tggagccaca ctgtttgcca ctggcaaatg ggtaggcgtg    180
attctggatg aagcaaaggg caaaaatgat ggaactgttc aaggcaggaa gtacttcact    240
tgtgatgaag ggcatggcat ctttgtgcgc cagtcccaga tccaggtatt tgaagatgga    300
gcagatacta cttccccaga gacacctgat tcttctgctt caaaagtcct caaaagagag    360
ggaactgata caactgcaaa gactagcaaa ctgcggggac tgaagcctaa gaaggcaccg    420
acagcccgaa agaccacaac tcggcgaccc aagcccacgc gcccagccag tactggggtg    480
gctggggcca gtagctccct gggcccctct ggctcagcgt cagcaggtga gctgagcagc    540
agtgagccca gcaccccggc tcagactccg ctggcagcac ccatcatccc cacgccggtc    600
ctcacctctc ctggagcagt ccccccgctt ccttccccat ccaaggagga ggagggacta    660
agggctcagg tgcgggacct ggaggagaaa ctagagaccc tgagactgaa acgggcagaa    720
gacaaagcaa agctaaaaga gctggagaaa cacaaaatcc agctggagca ggtgcaggaa    780
tggaagagca aaatgcagga gcagcaggcc gacctgcagc ggcgcctcaa ggaggcgaga    840
aaggaagcca aggaggcgct ggaggcaaag gaacgctata tggaggagat ggctgatact    900
gctgatgcca ttgagatggc cactttggac aaggagatgg ctgaagagcg ggctgagtcc    960
ctgcagcagg aggtggaggc actgaaggag cgggtggacg agctcactac tgacttagag   1020
atcctcaagg ctgagattga agagaagggc tcagatggcg ctgcatccag ttatcagctc   1080
aagcagcttg aggagcagaa tgcccgcctg aaggatgccc tggtgaggat gcgggatctt   1140
tcttcctcag agaagcagga gcatgtgaag ctccagaagc tcatggaaaa gaagaaccaa   1200
gagctggaag ttgtgaggca acagcgggag cgtctgcagg aggagctaag ccaggcagag   1260
agcaccattg atgagctcaa ggagcaggtg gatgctgctc tgggtgctga ggagatggtg   1320
gagatgctga cagatcggaa cctgaatctg gaagagaaag tgcgcgagtt gagggagact   1380
gtgggagact tggaagcgat gaatgagatg aacgatgagc tgcaggagaa tgcacgtgag   1440
acagaactgg agctgcggga gcagctggac atggcaggcg cgcgggttcg tgaggcccag   1500
aagcgtgtgg aggcagccca ggagacggtt gcagactacc agcagaccat caagaagtac   1560
cgccagctga ccgcccatct acaggatgtg aatcgggaac tgacaaacca gcaggaagca   1620
tctgtggaga ggcaacagca gccacctcca gagacctttg acttcaaaat caagtttgct   1680
```

-continued gagactaagg cccatgccaa ggcaattgag atggaattga ggcagatgga ggtggcccag 1740
gccaatcgac acatgtccct gctgacagcc ttcatgcctg acagcttcct tcggccaggt 1800
ggggaccatg actgcgttct ggtgctgttg ctcatgcctc gtctcatttg caaggcagag 1860
ctgatccgga agcaggccca ggagaagttt gaactaagtg agaactgttc agagcggcct 1920
gggctgcgag gagctgctgg ggagcaactc agctttgctg ctggactggt gtactcgctg 1980
agcctgctgc aggccacgct acaccgctat gagcatgccc tctctcagtg cagtgtggat 2040
gtgtataaga aagtgggcag cctgtaccct gagatgagtg cccatgagcg ctccttggat 2100
ttcctcattg aactgctgca caaggatcag ctggatgaga ctgtcaatgt ggagcctctc 2160
accaaggcca tcaagtacta tcagcatctg tacagcatcc accttgccga acagcctgag 2220
gactgtacta tgcagctggc tgaccacatt aagttcacgc agagtgctct ggactgcatg 2280
agtgtggagg taggacggct gcgtgccttc ttgcagggtg ggcaggaggc tacagatatt 2340
gccctcctgc tccgggatct ggaaacttca tgcagtgaca tccgccagtt ctgcaagaag 2400
atccgaaggc gaatgccagg gacagatgct cctgggatcc cagctgcact ggcctttgga 2460
ccacaggtat ctgacacgct cctagactgc aggaaacact tgacgtgggt cgtggctgtg 2520
ctgcaggagg tggcagctgc tgctgcccag ctcattgccc cactggcaga gaatgagggg 2580
ctacttgtgg ctgctctgga ggaactggct ttcaaagcaa gcgagcagat ctatgggacc 2640
ccctccagca gccccctatga gtgtctgcgc cagtcatgca acatcctcat cagtaccatg 2700
aacaagctgg ccacagccat gcaggagggg gagtatgatg cagagcggcc ccccagcaag 2760
cctccaccgg ttgaactgcg ggctgctgcc cttcgtgcag agatcacaga tgctgaaggc 2820
ctgggtttga agctcgaaga tcgagagaca gttattaagg agttgaagaa gtcactcaag 2880
attaagggag aggagctaag tgaggccaat gtgcggctga gcctcctgga gaagaagttg 2940
gacagtgctg ccaaggatgc agatgagcgc atcgagaaag tccagactcg gctggaggag 3000
acccaggcac tgctgcgaaa gaaggagaaa gagtttgagg agacaatgga tgcactccag 3060
gctgacatcg accagctgga ggcagagaag gcagaactaa agcagcgtct gaacagccag 3120
tccaaacgca cgattgaggg actccggggc cctcctcctt caggcattgc tactctggtc 3180
tctggcattg ctggtgaaga acagcagcga ggagccatcc ctgggcaggc tccagggtct 3240
gtgccaggcc cagggctggt gaaggactca ccactgctgc ttcagcagat ctctgccatg 3300
aggctgcaca tctcccagct ccagcatgag aacagcatcc tcaagggagc ccagatgaag 3360
gcatccttgg catccctgcc ccctctgcat gttgcaaagc tatcccatga gggccctggc 3420
agtgagttac cagctggagc gctgtatcgt aagaccagcc agctgctgga gacattgaat 3480
caattgagca cacacacgca cgtagtagac atcactcgca ccagccctgc tgccaagagc 3540
ccgtcggccc aacttatgga gcaagtggct cagcttaagt ccctgagtga caccgtcgag 3600
aagctcaagg atgaggtcct caaggagaca gtatctcagc gccctggagc cacagtaccc 3660
actgactttg ccaccttccc ttcatcagcc ttcctcaggg ccaaggagga gcagcaggat 3720
gacacagtct acatgggcaa agtgaccttc tcatgtgcgg ctggttttgg acagcgacac 3780
cggctggtgc tgacccagga gcagctgcac cagcttcaca gtcgcctcat ctcctaa 3837

<210> SEQ ID NO 67
<211> LENGTH: 1347
<212> TYPE: DNA
<213> ORGANISM: Homo sapiens

<400> SEQUENCE: 67

```
atgcgtgaat gcatctcagt ccacgtgggg caggcaggtg tccagatggg caatgcctgc     60
tgggagctct attgcttgga acatgggatt cagcctgatg ggcagatgcc cagtgacaag    120
accattggtg gaggggacga ctccttcacc accttcttct gtgaaactgg tgctggaaaa    180
cacgtacccc gggcagtttt tgtggatctg gagcctacgg tcattgatga gatccgaaat    240
ggcccatacc gacagctctt ccacccagag cagctcatca ctgggaaaga ggatgctgcc    300
aacaactatg cccgtggtca ctataccatt ggcaaggaga tcattgaccc agtgctggat    360
cggatccgca agctgtctga ccagtgcaca ggacttcagg gcttcctggt gttccacagc    420
tttggtgggg gcactggctc tggcttcacc tcactcctga tggagcggct ctctgttgac    480
tatggcaaga aatccaagct ggaattctcc atctacccag ccccccaggt gtctacagcc    540
gtggtcgagc cctacaactc tatcctgacc acccacacca ccctggagca ctcagactgt    600
gccttcatgg tggacaacga agcaatctat gacatctgcc gccgcaacct agacatcgag    660
cgcccaacct acaccaacct caatcgcctc attagccaaa ttgtctcctc catcacagct    720
tctctgcgct ttgacggggc cctcaatgtg gacctgacag agttccagac caacctggtg    780
ccctaccctc gcatccactt ccccctggcc acctatgcac cagtcatctc tgcagaaaag    840
gcataccacg agcagctgtc ggtggcagag atcaccaatg cctgctttga gcctgccaac    900
cagatggtaa agtgtgatcc ccggcacggc aagtacatgg cctgctgcct gctgtaccgt    960
ggagatgtgg tgcccaagga tgtcaacgct gccattgccg ccatcaagac caagcgcagc   1020
attcagtttg tggactggtg ccccacaggc ttcaaggttg gtatcaacta ccagcctccc   1080
actgtggtgc ctgggggtga cctggccaag gtgcagcgtg ccgtgtgcat gctgagcaac   1140
acgaccgcca tcgccgaggc ctgggcccgc ctggaccaca agttcgacct gatgtatgcc   1200
aagagggcgt ttgtgcactg gtatgtgggt gagggcatgg aggagggtga gttctccgag   1260
gcccgtgagg atatggctgc cctggagaag gattatgagg aggtgggcat cgactcctat   1320
gaggacgagg atgagggaga agaataa                                       1347
```

<210> SEQ ID NO 68
<211> LENGTH: 1353
<212> TYPE: DNA
<213> ORGANISM: Homo sapiens

<400> SEQUENCE: 68

```
atgcgtgagt gtatctctat ccacgtgggg caggcaggag tccagatcgg caatgcctgc     60
tgggaactgt actgcctgga acatggaatt cagcccgatg gtcagatgcc aagtgataaa    120
accattggtg gtggggacga ctccttcaac acgttcttca gtgagactgg agctggcaag    180
cacgtgccca gagcagtgtt tgtggacctg gagcccactg tggtcgatga agtgcgcaca    240
ggaacctata ggcagctctt ccacccagag cagctgatca ccgggaagga agatgcggcc    300
aataattacg ccagaggcca ttacaccatc ggcaaggaga tcgtcgacct ggtcctggac    360
cggatccgca aactggcgga tctgtgcacg ggactgcagg gcttcctcat cttccacagt    420
tttgggggtg gcactggctc tgggttcgca tctctgctca tggagcggct ctcagtggat    480
tacggcaaga agtccaagct agaatttgcc atttacccag ccccccaggt ctccacggcc    540
gtggtggagc cctacaactc catcctgacc acccacacga ccctggaaca ttctgactgt    600
gccttcatgg tcgacaatga agccatctat gacatatgtc ggcgcaacct ggacatcgag    660
cgtcccacgt acaccaacct caatcgcctg attgggcaga tcgtgtcctc catcacggcc    720
```

tccctgcgat ttgacggggc cctgaatgtg gacttgacgg aattccagac caacctagtg 780
ccgtaccccc gcatccactt cccccctggcc acctacgccc cggtcatctc agccgagaag 840
gcctaccacg agcagctgtc cgtggctgag atcaccaatg cctgcttcga gccagccaat 900
cagatggtca agtgtgaccc tcgccacggc aagtacatgg cctgctgcat gttgtacagg 960
ggggatgtgg tcccgaaaga tgtcaacgcg gccatcgcca ccatcaagac caagcgcacc 1020
atccagtttg tagattggtg cccaactgga tttaaggtgg gcattaacta ccagcccccc 1080
acggtggtcc ctgggggaga cctggccaag gtgcagcggg ctgtgtgcat gctgagcaac 1140
accacggcca tcgcggaggc ctgggctcgc ctggaccata agttcgatct catgtatgcc 1200
aagcgggcct ttgtgcactg gtacgtggga gaaggcatgg aggaggggga gttctctgag 1260
gcccgcgagg acctggcagc tctggagaag gattatgaag aggtgggcgt ggattccgtg 1320
gaagccgagg ctgaagaagg tgaagaatac tga 1353

<210> SEQ ID NO 69
<211> LENGTH: 1356
<212> TYPE: DNA
<213> ORGANISM: Homo sapiens

<400> SEQUENCE: 69
atgcgtgagt gcatctccat ccacgttggc caggctggtg tccagattgg caatgcctgc 60
tgggagctct actgcctgga acacggcatc cagcccgatg gccagatgcc aagtgacaag 120
accattgggg gaggagatga ttccttcaac accttcttca gtgagacggg ggctggcaag 180
catgtgcccc gggcagtgtt tgtagacttg gaacccacag tcattgatga agttcgcact 240
ggcacctacc gccagctctt ccaccctgag caacttatca caggcaaaga agatgctgcc 300
aataactatg cccgagggca ctacaccatt ggcaaggaga tcattgacct cgtgttggac 360
cgaattcgca agctggccga ccagtgcacg ggtctccagg gcttcttggt tttccacagc 420
tttggtgggg gaactggttc tgggttcacc tcgctgctca tggaacgtct ctcagttgat 480
tatggcaaga agtccaagct ggagttctct atttacccgg cgccccaggt ttccacagct 540
gtagttgagc cctacaactc catcctcacc acccacacca ccctggagca ctctgattgt 600
gccttcatgg tagacaatga ggccatctat gacatctgtc gtagaaacct cgatattgag 660
cgtccaacct atactaacct gaataggtta ataggtcaaa ttgtgtcctc catcactgct 720
tccctgagat ttgatggagc cctgaatgtt gacctgacag aattccagac caacctggtg 780
ccctatcccc gcatccactt ccctctggcc acatatgccc ctgtcatctc tgctgagaaa 840
gcctaccatg aacagctttc tgtagcagag atcaccaatg cttgctttga gccagccaac 900
cagatggtga aatgtgaccc tcgccatggt aaatacatgg cttgctgcct gttgtaccgt 960
ggtgacgtgg ttcccaaaga tgtcaatgct gccattgcca ccatcaagac caagcgtacc 1020
atccagtttg tggattggtg ccccactggc ttcaaggttg gcatcaacta ccagcctccc 1080
actgtggtgc ctggtggaga cctggccaag gtacagagag ctgtgtgcat gctgagcaac 1140
accacagcca ttgctgaggc ctgggctcgc ctggaccaca agtttgacct gatgtatgcc 1200
aaacgtgcct ttgttcactg gtacgttggg gaggggatgg aggaaggtga gttttcagag 1260
gcccgtgagg acatggctgc ccttgagaag gattatgagg aggttggtgt ggattctgtt 1320
gaaggagagg gtgaggaaga aggagaggaa tactaa 1356

<210> SEQ ID NO 70

<211> LENGTH: 1380
<212> TYPE: DNA
<213> ORGANISM: Homo sapiens

<400> SEQUENCE: 70

```
gtctctgccc atccgcgcac ccgggcttcg gctggagagg gccagctcgc ttcaggaggc     60
cgaaccccgt tcccaccaac cctctcagct cagacgcggg gtgctgagtc acgggggggg    120
ggtggttctg tggatagttg gaatgcatac acagaggaaa gggggatgcg gcaccagcag    180
acagagagac aagaccccag ccagcccctg tccaggcagc atggcacata ccgccagatc    240
ttccatccag agcagctcat cacaggcaag gaagatgctg ccaataacta tgcctggggc    300
cactacacca ttgggaagga gttcatcgac ctgctactgg accggattcg gaagctggct    360
gaccagtgca caggacttca gggcttcctg gtgttccaca gccttggtcg ggcactggc    420
tctgacgtca cctcattcct gatggagtgg ctttctgtta actatggcaa gaaatccaag    480
ctgggattct ccatctaccc agccccccag gtgtctacag ccatggtcca gccctacaac    540
tctatcctga ccacccacac caccctggag cactcagact gtgccttcat ggtggacaac    600
aaagcaatct atgacatctg ccaccgcaac ctagacattg agcgcccaac ctacaccaac    660
ctcaatcgcc tcattagcca aattgtctcc tccatcacag cttctctgcg ctttgacggg    720
gccctcaatg tggacctgac agagttccag accaacctgg tgtcctacct cacatccact    780
tccccctggc cacctatgca ccagtcatct ctgcagaaaa agtataccac gagcagctgt    840
cggtggcaga gattaccaat gcctgctttg agcctgccaa ccagatggtg aagtgtgatc    900
cccggcacgg caagtacatg gcctgctgcc tgctatacca tggagatgtg gtgcccaagg    960
atgtcaacgc tgccattgct gccatcaaga ccaagtgcag cattcagttt gtggactggt   1020
gccccacagg ctttaaggtt gatatcaatc accagcctcc cactgtggtg cctgggagtg   1080
acctggtaaa gtgcaacgtg ccatgtgcat gctgagcaac atgacagcca tcactatggc   1140
ctgggcccgc ctggaccaca agtttgacct gatgtatgcc aagagggcgt ttgggcactg   1200
atatgtgggt gagggcatgg aggagggtga gttctccaag gcccatgagg atatgactgc   1260
cctggagaag gattacaagg aggtgggcat ggatagtgtg gagtgtgggg aagaaaagat   1320
aggggggatg aatactaggg gaatactgtg tgtctgtcct acataaagtg ctgtggcctt   1380
```

<210> SEQ ID NO 71
<211> LENGTH: 1350
<212> TYPE: DNA
<213> ORGANISM: Homo sapiens

<400> SEQUENCE: 71

```
atgcgtgagt gcatctccat ccacgttggc caggctggtg tccagattgg caatgcctgc     60
tgggagctct actgcctgga acacggcatc cagcccgatg gccagatgcc aagtgacaag    120
accattgggg gaggagatga ttccttcaac accttcttca gtgaaacggg tgctggcaag    180
catgtgcccc gggcagtgtt tgtagacttg gaacccacag tcattgatga agttcgcact    240
ggcacttacc gccagctctt ccaccctgag caactcatca caggcaagga agatgctgcc    300
aataactatg cccgagggca ctacaccatt ggcaaggaga tcattgacct cgtgttggac    360
cgaattcgca agctggctga ccagtgcacc ggtcttcagg gcttcttggt tttccacagc    420
tttggtgggg gaactggttc tgggttcacc tcgctgctca tggaacgtct ctcagttgat    480
tatggcaaga agtccaagct ggagttctcc atttacccgg cgccccaggt ttccacagct    540
gtagttgagc cctacaactc catcctcacc acccacacca ccctggagca ctctgattgt    600
```

gccttcatgg tagacaatga ggccatctat gacatctgtc gtagaaacct cgatatcgag 660
cgcccaacct acactaacct taaccgcctt attagccaga ttgtgtcctc catcactgct 720
tccctgagat ttgatggagc cctgaatgtt gacctgacag aattccagac caacctggtg 780
ccctaccccc gcatccactt ccctctggcc acatatgccc ctgtcatctc tgctgagaaa 840
gcctaccacg aacagcttac tgtagcagag atcaccaatg cttgctttga gccagccaac 900
cagatggtga aatgtgaccc tcgccatggt aaatacatgg cttgctgcct gttataccgt 960
ggtgacgtgg ttcccaaaga tgtcaatgct gccattgcca ccatcaaaac caagcgtacc 1020
atccagtttg tggattggtg ccccactggc ttcaaggttg gcattaatta ccagcctccc 1080
actgtggtgc ctggcggaga cctggccaag gtacagagag ctgtgtgcat gctgagcaat 1140
accacagctg ttgccgaggc ctgggctcgc ctggaccaca agtttgacct gatgtatgcc 1200
aagcgtgcct ttgttcactg gtacgtgggt gaggggatgg aggaaggcga gttttcagag 1260
gcccgtgagg acatggctgc ccttgagaag gattatgagg aggttggagc agatagtgct 1320
gacggagagg atgagggtga agagtattaa 1350

<210> SEQ ID NO 72
<211> LENGTH: 1350
<212> TYPE: DNA
<213> ORGANISM: Homo sapiens

<400> SEQUENCE: 72
atgcgggaat gcatatcagt ccacgtgggc caagcgggag ttcagattgg caatgcctgc 60
tgggagctct tctgcctgga acacggcatc caggcagacg gcacttttga tgctcaagct 120
agcaagatca acgatgatga ctccttcacc acctttttca gcgagactgg caatgggaag 180
catgtgcccc gggccgtcat gatagatctg gagcctactg tagtggatga ggttcgggca 240
ggaacctacc gccagctctt ccatccagag cagctgatca caggaaagga ggatgcagcc 300
aacaactatg cccggggcca ctacacggtg ggcaaggaga gcattgacct ggtgctggac 360
cgcatacgga agctgacaga tgcttgctct ggcctgcagg gcttcctgat tttccacagt 420
tttggtgggg gcactggctc cggcttcact tctctgctga tggaacgcct ctccctggat 480
tatggcaaga aatccaagct ggagtttgcc atctacccag ccccccaggt ctctactgca 540
gtggtggagc cctacaactc catcctgacc acccacacca cactggaaca ttcagattgt 600
gctttcatgg tggacaacga agccatctat gacatctgcc gcaggaacct tgacattgag 660
cgccctacct ataccaacct caaccgcctc atcagtcaga ttgtgtcctc aatcactgct 720
tctctccgct ttgacggggc cctcaatgtg gacctcactg agttccagac caacctggtg 780
ccctaccccc gcatccactt cccgctggtc acctacgcgc ccatcatctc tgccgagaaa 840
gcctatcacg aacagctctc tgtggccgag ataaccagct cctgctttga gcccaacagc 900
cagatggtga agtgcgaccc gagacatggc aagtacatgg cctgctgcat gctctaccgg 960
ggcgacgtgg tgcccaagga tgtgaatgtc gctattgctg ccatcaagac caagaggacc 1020
atccagtttg tagactggtg tcccacaggc ttcaaggtgg gcatcaacta ccagcccccg 1080
accgtggtcc ccgggggaga cctggccaag gtgcagcggg ccgtctgcat gctcagcaac 1140
accacggcca ttgcggaggc ctgggcccgc ctcgaccaca agttcgacct catgtacgcc 1200
aagcgggcct ttgtgcattg gtatgtggga gaggggatgg aagaaggaga attttctgag 1260
gccagggaag acttagctgc cctggagaag gattatgaag aagtggggac tgattcgttt 1320
gaagaagaaa atgaagggga ggaattttaa 1350

<210> SEQ ID NO 73
<211> LENGTH: 1257
<212> TYPE: DNA
<213> ORGANISM: Homo sapiens

<400> SEQUENCE: 73
atggctaaac tattacaacc tccacccaag ttcctgccct cagagtggca cattgctaac 60
aagaaccagt accacagagc agacgctcaa aggtcccgat cagaacgcct ggtcgcagaa 120
agccagaggc ttgtggatga aattgaaaag accacaagaa aatctcaaag cgatgtgaac 180
aagaaactag aacagagact cgaggaagtc cagttctgga agaaggagtt agatgacaaa 240
cttgagcagc ttgtgaatgt aactgatgat ctactcatat ataagatcag attggaaaaa 300
gccctggaga ccttgaaaga gcccttgcac atcactgaga catgcctggc atacagggag 360
aagcgcattg gcattgacct ggtgcacgac acagtggagc atgagctgat aaaggaggct 420
gagatcatcc agggcattat ggctctgctg acccgtacct tggaggaggc ttccgagcag 480
attcggatga accgctctgc caagtacaat cttgagaagg atttgaagga caagtttgtg 540
gccctgacca tagatgatat ctgcttctcg ctcaacaaca actcaccaaa catcagatat 600
tctgagaacg ccgtgaggat tgagccaaac tccgtgagtc tggaagactg gttggacttc 660
tccagcacca atgtggagaa ggctgacaag cagcggaaca actccctgat gctgaaagcc 720
ctggtggatc gaatcctgtc ccagacagcc aatgatctgc gcaagcagtg tgatgtggtg 780
gacacggcat tcaagaatgg gctgaaggat acaaaggatg ccagggacaa gctggctgat 840
catctggcca aggtcatgga agagattgct tcccaggaga aaaatattac agctcttgaa 900
aaggccatcc ttgaccaaga agggccagcc aaggtggctc atacgcgctt ggagaccagg 960
acacaccggc cgaacgtgga gctgtgtcgt gatgtcgcac aatataggct aatgaaggag 1020
gttcaagaga tcacccacaa tgtcgcaaga ttgaaggaaa ctttagccca agctcaggca 1080
gagctgaaag ggctgcatcg cagacagctt gccctgcagg aggagatcca ggtcaaagag 1140
aacaccattt atatcgacga agtgctgtgt atgcagatga ggaaatccat cccacttcgg 1200
gatggggaag accatggggt ctgggctggg ggcctccgcc ctgatgctgt ctgctaa 1257

<210> SEQ ID NO 74
<211> LENGTH: 1293
<212> TYPE: DNA
<213> ORGANISM: Homo sapiens

<400> SEQUENCE: 74
atggccacgc tgagcgtcaa gccaagtcgg cgcttccagc tgcccgactg gcacactaac 60
agctacctgc tatccaccaa tgcccagctg cagcgagatg cttcccatca gatccgccag 120
gaggcccggg tgctccgcaa cgagaccaac aaccagacca tttgggatga acatgacaac 180
aggactcgac tggtggagag gattgatact gtcaaccggt ggaaggagat gctggacaag 240
tgtctgacag atttagatgc cgagatcgat gccctgacac agatgaagga gtcagcagag 300
caaaacctgc aggccaagaa cctgcctctg gatgtggcca ttgagtgcct gaccctgcgg 360
gaaagccggc gagacattga tgtggtgaag gaccctgtgg aggatgagct gcataaagag 420
gtggaggtca tcgaggccac caagaaggcc ttgcaacaga aggtcagcca ggccttcgag 480
cagctctgcc tcttgcagga agtccaacag cagctcaact ccgaccatcg gggcaaaatg 540
gagacactag agatcgacag aggctgtctc tctctcaacc tcagatcccc aaacatctcg 600

```
ctgaaggttg accccacacg tgtacctgat ggctccacca cactccagca gtgggatgac    660

ttcagtcggt tcaacaagga ccgagcggag gctgagatga aggcagccac agagctgagg    720

gaggccactg ctctaactat tgctgagacc aacaacgagc ttgaagccca gagagttgca    780

acggaatttg ccttcaggaa gcggctgcgg gagatggaga aagtgtacag tgagctcaag    840

tggcaagaga agaatacctt ggaggagatc gctgagctgc aggaggacat ccggcacctg    900

gaggaggatc tgcgcacaaa gctcctgagc ctgaagctgt cccatacccg gctagaggcc    960

agaacctacc ggcccaacgt ggaactctgc cgggaccagg cacagtacgg cctcaccgac   1020

gaggttcacc agctagaggc aaccatcgct gccctgaagc agaagctggc gcaagcacag   1080

gacgcactgg acgccctgtg caagcacctg gcccggctgc aggctgacat tgcctgcaag   1140

gccaactcca tgctgctgga caccaagtgc atggacacac ggcgcaagct gaccgtgcct   1200

gctgagaggt tcgtgcctga ggtggacacc ttcacacgta ccacaaatag caccctgagt   1260

ccactcaaaa gctgccagct ggagctggcc tag                                1293
```

```
<210> SEQ ID NO 75
<211> LENGTH: 1473
<212> TYPE: DNA
<213> ORGANISM: Homo sapiens

<400> SEQUENCE: 75

atggaacgtg taggttgtac tttaacgaca acttacgccc accctagacc aacaccaacc     60

aactttctac cagccatcag taccatggcc tcaagctaca gggaccgctt tccccactcc    120

aatttgaccc atagcctgag ccttccttgg agacccagca catactacaa agtcgcctcc    180

aattccccaa gcgtggcccc gtactgcacc agatcacaga gggtgtccga gaataccatg    240

cttccctttg tttccaacag aaccactttc ttcacaagat acacaccgga tgactggtac    300

aggtccaatt taaccaacta tcaagagtcc aacacttccc gacataattc ggagaaacta    360

agagtggata catctcgcct gattcaagac aaatatcaac aaacaagaaa aactcaggca    420

gacacaaccc aaaatctggg agaacgtgtc aatgacatag ggttttggaa atctgaaatc    480

attcatgagt tggatgaaat gattggagag acaaatgcac ttactgatgt gaagaaaaga    540

ctggagcggg ctttgatgga gactgaagcc cctcttcagg tagcccgaga atgtctattt    600

catcgagaaa agagaatggg aatcgaccta gttcacgatg aagttgaagc acaactgctg    660

acggaagttg atactattct gtgttgtcaa gaaagaatga agctacattt ggataaggct    720

attgcccaac ttgcagccaa cagagcgtcc cagcatgagc tggaaaagga cctgagtgac    780

aaacagacgg cttaccggat cgacgacaaa tgccaccacc tgcgcaacac atcagacggt    840

gtcggctact tccgcggagt ggagagggtc gatgcaactg tctcagtgcc tgagtcctgg    900

gccaaattta cagatgacaa tattctccgc tcccagagtg aacgggcagc ttccgctaag    960

ctaagagacg acattgaaaa cctcttggtt gtgactgcca atgagatgtg gaatcaattc   1020

aacaaagtga acttgtcttt caccaatcgc attgctgaga ctgcagatgc taagaataag   1080

attcagacgc acttagcaaa gaccctgcag gagattttcc agactgaaat gaccatagaa   1140

tccatcaaga aggccatcaa ggacaagact gccttcctga aggtggctca gaccagactg   1200

gatgagcgca caagacggcc gaacattgag ttgtgccgag acatggctca gctacgcctt   1260

gttaacgagg tacacgaggt tgacgacacc atccagaccc tgcagcagcg cctgagggat   1320

gcagaggaca ccctgcagtc gctggtccac atcaaagcca cactcgagta tgacctggct   1380
```

-continued gtcaaagcca attccctgta catcgaccag gaaaaatgca tgagcatgcg caagagctac 1440
cccaacaccc tccggctggt cggcttctgc tag 1473

<210> SEQ ID NO 76
<211> LENGTH: 1308
<212> TYPE: DNA
<213> ORGANISM: Homo sapiens

<400> SEQUENCE: 76
atggcgcaga cagtgccgcc ctgcgagctg ccctgcaaag agtacgacgt ggcccgtaac 60
acgggcgcct acacgtcctc cggcctggcc accgccagct tccgcacctc caagtacctg 120
ctggaggagt ggttccagaa ctgctatgct cgctaccacc aggccttcgc cgaccgcgac 180
cagtcggagc ggcagcggca cgagagccag cagctggcca cagagaccca ggcgctggcg 240
cagcgcacgc agcaagactc cacgcgcaca gtgggcgagc gactgcagga cacgcacagc 300
tggaagtcgg agctgcagcg tgagatggag gcgctggctg cggagaccaa cttgctcctg 360
gcccagaagc aacggctgga gcgcgccctg gacgccacag aggtgccctt ctccatcacc 420
actgacaacc tgcagtgccg tgagcgccgc gagcacccca acctcgtgcg cgaccatgtg 480
gaaacggagc tgctgaagga agccgagctc atccggaaca ttcaggagct gctgaagaga 540
accatcatgc aagcagtgag ccagatccga ctgaaccggg agcacaagga gacctgcgag 600
atggactggt cagacaagat ggaggcctac aacatcgacg agacctgcgg gcgccaccac 660
agccagagca ccgaggtgca ggctcatccg tactccacca ccttccaaga gagcgcctcc 720
accccggaga cccgggccaa gttcacgcag gacaatctgt gccgtgccca gcgcgagcgc 780
ctggcctcgg ccaacctgcg ggtgctggtg gactgcatcc ttcgcgacac ctccgaggac 840
ctgcggctcc agtgcgacgc cgtgaacctg gccttcgggc gccgctgtga ggagctggag 900
gacgcgcggt acaagctgca tcaccacctg cacaagacac tgcgggaaat cacagatcag 960
gaacacaacg tggcggcact gaagcaggcc atcaaggaca aagaggcacc tctgcacgta 1020
gcccagaccc ggctgtacct gcgctcgcac cggcccaaca tggagctgtg ccgtgacgca 1080
gcccagttca ggctgttgag tgaggtggag gagctgaaca tgtccctcac agcactgcga 1140
gagaagcttc tagaagcgga gcagtccctg cgcaacctcg aggacatcca catgagcctg 1200
gagaaggaca ttgccgccat gaccaacagt ctcttcatcg accgccagaa gtgcatggcc 1260
catcgtactc gctaccccac catcctgcag ctggctggct accagtga 1308

<210> SEQ ID NO 77
<211> LENGTH: 1458
<212> TYPE: DNA
<213> ORGANISM: Homo sapiens

<400> SEQUENCE: 77
atggagtttc ttgggactac tcagaccgcc agttactgtg gtcccaagaa atgctgtggc 60
ttgacctcac tgccagctgt acaggcgcca gtgatccagg aatgctatca gccctactac 120
ctgcccgggt accgctacct caattcatgg aggcctagcc tcttctacaa gatagccaac 180
gtccagacct gcccggacga gagcaccagt accctgcggc cgcccaccat cctgcccaca 240
ctgcgctccg cactcttctc tcgctatagc cccccacgact gggaccagtc caaccagctg 300
caggtgcgtg gggccgaggc ctcccggctg tgggccagcc ggctgacgga tgactccatg 360
aggctcttgc aggacaagga ccagctgacg caccagatgc aggagggcac ctgccggaac 420
ctgggccaga ggctgtcgga cattggcttc tggaagtcag agctgagcta tgagctggac 480
aggcttctga ctgagaacca gaacttggag acggtcaaga ggcggctgga gtgcgcggcc 540
aatgaggtga actgcccatt gcaggtggcc ttggagtgtc tgtaccatcg agagaagagg 600
attgggattg atttggtcca tgacaacgtg gagaaaaacc ttatccggga agtggatttg 660
ctaaaatgtt gccaagaaca gatgagaaaa ttagctcaaa gaattgatat ccagatgcgg 720
gataaccggg atgctcagca cgtgctggag agggacctcg aagacaaaag ctcggcccag 780
tgtatcgatg agaagtgctt taacctgaga aatacgtcag actgcatcag cttcttccac 840
ggcatggaga aaattgacgg cacgatctcc gtacctgaga cctgggccaa gttcagtaac 900
gacaacatca aacactctca gaacatgcgg gccaactcca tccagctgcg ggaggaggcg 960
gagcacctct ttgagacctt gtcggatcag atgtggaggc agttcacaga caccaacctg 1020
gccttcaacg cccgcatctc tgaggtgacg gatgtgaaga ataagctgca gacgcagctg 1080
gcgaagacgc tgcaggagat cttccaggcc gagaacacca tcatgctgct ggaaaggtcc 1140
atcatggcca aggagggccc gctgaaggtg gcccagacaa ggctggagtg ccggacccgg 1200
cgccccaaca tggagctgtg cagggacatc ccgcagttga agctggtgaa cgaggtgttc 1260
accatcgacg acaccctgca gaccctcaag ctgcggctgc gggagacaca ggacacgctg 1320
cagctgctgg tcatgaccaa gtgccggctg gagcacgagc tcgccatcaa ggccaacacc 1380
ctctgcatcg acaaggagaa gtgcatgggc atgcgtaaga ccttcccctg caccccgcgc 1440
ctggtgggcc acacctga 1458

<210> SEQ ID NO 78
<211> LENGTH: 2595
<212> TYPE: DNA
<213> ORGANISM: Homo sapiens

<400> SEQUENCE: 78
atgggcaacc gcggcatgga agatctcatc ccgctggtca accggctgca agacgccttc 60
tctgccatcg gccagaacgc ggacctcgac ctgccgcaga tcgctgtggt gggcggccag 120
agcgccggca agagctcggt gctcgagaat ttcgtaggca gggacttctt gcctcgagga 180
tctggcattg tcacccgacg tcccctggtc ttgcagctgg tcaatgcaac cacagaatat 240
gccgagttcc tgcactgcaa gggaaagaaa ttcaccgact tcgaggaggt gcgccttgag 300
atcgaggccg agaccgacag ggtcaccggc accaacaagg gcatctcgcc ggtgcctatc 360
aacctccgcg tctactcgcc gcacgtgctg aacctgaccc tggtggacct gcccggaatg 420
accaaggtcc cggtggggga ccaacctccc gacatcgagt tccagatccg agacatgctt 480
atgcagtttg tcaccaagga gaactgcctc atcctggccg tgtcccccgc caactctgac 540
ctggccaatt ctgacgccct caaggtcgcc aaggaggtgg acccccaggg ccagcgcacc 600
atcggggtca tcaccaagct ggacctgatg gacgagggca cagatgcccg tgatgtgctg 660
gagaacaagc tgctccccct gcgcagaggc tacattggag tggtgaaccg gagccagaag 720
gacattgatg gcaagaagga cattaccgcc gccttggctg ctgaacgaaa gttcttcctc 780
tcccatccat cttatcgcca cttggctgac cgtatgggca cgccctacct gcagaaggtc 840
ctcaatcagc aactgacgaa ccacatccgg gacacactgc cggggctgcg gaacaagctg 900
cagagccagc tactgtccat tgagaaggag gtggaggaat acaagaactt ccgccctgat 960
gacccagctc gcaagaccaa ggccctgctg cagatggtcc agcagttcgc cgtagacttt 1020
gagaagcgca ttgagggctc aggagatcag atcgacacct acgaactgtc agggggagcc 1080

-continued

```
cgcattaacc gaatcttcca cgagcgcttc cctttcgagc tggtcaagat ggagtttgat   1140

gagaaggaac tccgaaggga gatcagctat gctatcaaga atatccatgg cattagaacg   1200

gggctgttta ccccagacat ggcctttgag accattgtga aaaagcaggt gaagaagatc   1260

cgagaaccgt gtctcaagtg tgtggacatg gttatctcgg agctaatcag caccgttaga   1320

cagtgcacca agaagctcca gcagtacccg cggctacggg aggagatgga gcgcatcgtg   1380

accacccaca tccgggagcg cgagggccgc actaaggagc aggtcatgct tctcatcgat   1440

atcgagctgg cttacatgaa caccaaccat gaggacttca taggctttgc caatgctcag   1500

cagaggagca accagatgaa caagaagaag acttcaggga accaggatga gattctggtc   1560

atccgcaagg gctggctgac tatcaataat attggcatca tgaaaggggg ctccaaggag   1620

tactggtttg tgctgactgc tgagaatctg tcctggtaca aggatgatga ggagaaagag   1680

aagaaataca tgctgtctgt ggacaacctc aagctgcggg acgtggagaa gggctttatg   1740

tcgagcaagc atatctttgc cctctttaac acggagcaga ggaatgtcta caaggattat   1800

cggcagctgg agctagcctg tgagacacag gaggaggtgg acagctggaa ggcctccttc   1860

ctgagggctg gcgtgtaccc tgagcgtgtt ggggacaaag agaaagccag cgagaccgag   1920

gagaatggct ccgacagctt catgcattcc atggacccac agctggaacg gcaagtggag   1980

accatccgga atcttgtgga ctcatacatg gccattgtca acaagaccgt gagggacctc   2040

atgcccaaga ccatcatgca cctcatgatt aacaatacca aggagttcat cttctcggag   2100

ctgctggcca acctgtactc gtgtggggac cagaacacgc tgatggagga gtcggcggag   2160

caggcacagc ggcgcgacga gatgctgcgc atgtaccacg cactgaagga ggcgctcagc   2220

atcatcggcg acatcaacac gaccaccgtc agcacgccca tgcccccgcc cgtggacgac   2280

tcctggctgc aggtgcagag cgtaccggcc ggacgcaggt cgcccacgtc cagccccacg   2340

ccgcagcgcc gagcccccgc cgtgccccca gcccggcccg ggtcgcgggg ccctgctcct   2400

gggcctccgc ctgctgggtc cgccctgggg ggggcgcccc ccgtgccctc caggccgggg   2460

gcttcccctg accctttcgg ccctccccct caggtgccct cgcgccccaa ccgcgccccg   2520

cccggggtcc ccagccgatc gggtcaggca agtccatccc gtcctgagag ccccaggccc   2580

cccttcgacc tctaa                                                    2595
```

<210> SEQ ID NO 79
<211> LENGTH: 2613
<212> TYPE: DNA
<213> ORGANISM: Homo sapiens

<400> SEQUENCE: 79

```
atgggcaacc gcgggatgga agagctgatc ccgctggtca acaaactgca ggacgccttc     60

agctccatcg gccagagctg ccacctggac ctgccgcaga tcgctgtagt gggcggccag    120

agcgccggca agagctcggt gctggagaac ttcgtgggcc gggacttcct tccccgcggt    180

tcaggaatcg tcacccggcg gcctctcatt ctgcagctca tcttctcaaa aacagaacat    240

gccgagtttt tgcactgcaa gtccaaaaag tttacagact ttgatgaagt ccggcaggag    300

attgaagcag agaccgacag ggtcacgggg accaacaaag gcatctcccc agtgcccatc    360

aaccttcgag tctactcgcc acacgtgttg aacttgaccc tcatcgacct cccgggtatc    420

accaaggtgc ctgtgggcga ccagcctcca gacatcgagt accagatcaa ggacatgatc    480

ctgcagttca tcagccggga gagcagcctc attctggctg tcacgcccgc caacatggac    540

ctggccaact ccgacgccct caagctggcc aaggaagtcg atccccaagg cctacggacc    600
```

atcggtgtca tcaccaagct tgacctgatg gacgagggca ccgacgccag ggacgtcttg 660
gagaacaagt tgctcccgtt gagaagaggc tacattggcg tggtgaaccg cagccagaag 720
gatattgagg gcaagaagga catccgtgca gcactggcag ctgagaggaa gttcttcctc 780
tcccacccgg cctaccggca catggccgac cgcatgggca cgccacatct gcagaagacg 840
ctgaatcagc aactgaccaa ccacatccgg gagtcgctgc cggccctacg tagcaaacta 900
cagagccagc tgctgtccct ggagaaggag gtggaggagt acaagaactt tcggcccgac 960
gaccccaccc gcaaaaccaa agccctgctg cagatggtcc agcagtttgg ggtggatttt 1020
gagaagagga tcgagggctc aggagatcag gtggacactc tggagctctc cgggggcgcc 1080
cgaatcaatc gcatcttcca cgagcggttc ccatttgagc tggtgaagat ggagtttgac 1140
gagaaggact tacgacggga gatcagctat gccattaaga acatccatgg agtcaggacc 1200
gggcttttca ccccggactt ggcattcgag gccattgtga aaaagcaggt cgtcaagctg 1260
aaagagccct gtctgaaatg tgtcgacctg gttatccagg agctaatcaa tacagttagg 1320
cagtgtacca gtaagctcag ttcctacccc cggttgcgag aggagacaga gcgaatcgtc 1380
accacttaca tccgggaacg ggaggggaga acgaaggacc agattcttct gctgatcgac 1440
attgagcagt cctacatcaa cacgaaccat gaggacttca tcgggtttgc caatgcccag 1500
cagaggagca cgcagctgaa caagaagaga gccatcccca atcaggggga gatcctggtg 1560
atccgcaggg gctggctgac catcaacaac atcagcctga tgaaaggcgg ctccaaggag 1620
tactggtttg tgctgactgc cgagtcactg tcctggtaca aggatgagga ggagaaagag 1680
aagaagtaca tgctgcctct ggacaacctc aagatccgtg atgtggagaa gggcttcatg 1740
tccaacaagc acgtcttcgc catcttcaac acggagcaga gaaacgtcta caaggacctg 1800
cggcagatcg agctggcctg tgactcccag gaagacgtgg acagctggaa ggcctcgttc 1860
ctccgagctg gcgtctaccc cgagaaggac caggcagaaa acgaggatgg ggcccaggag 1920
aacaccttct ccatggaccc ccaactggag cggcaggtgg agaccattcg caacctggtg 1980
gactcatacg tggccatcat caacaagtcc atccgcgacc tcatgccaaa gaccatcatg 2040
cacctcatga tcaacaatac gaaggccttc atccaccacg agctgctggc ctacctatac 2100
tcctcggcag accagagcag cctcatggag gagtcggctg accaggcaca gcggcgggac 2160
gacatgctgc gcatgtacca tgccctcaag gaggcgctca acatcatcgg tgacatcagc 2220
accagcactg tgtccacgcc tgtacccccg cctgtcgatg acacctggct ccagagcgcc 2280
agcagccaca gccccactcc acagcgccga ccggtgtcca gcatacaccc ccctggccgg 2340
cccccagcag tgaggggccc cactccaggg cccccccctga ttcctgttcc cgtgggggca 2400
gcagcctcct tctcggcgcc cccaatccca tcccggcctg gaccccagag cgtgtttgcc 2460
aacagtgacc tcttcccagc cccgcctcag atcccatctc ggccagttcg gatcccccca 2520
gggattcccc caggagtgcc cagcagaaga ccccctgctg cgcccagccg gcccaccatt 2580
atccgcccag ccgagccatc cctgctcgac tag 2613

<210> SEQ ID NO 80
<211> LENGTH: 2592
<212> TYPE: DNA
<213> ORGANISM: Homo sapiens

<400> SEQUENCE: 80
atggggaacc gggagatgga ggagctgatc ccgctggtga accgtctgca ggacgcgttt 60

-continued

```
tcggcgctgg gacagagctg cctgctggag ctgccgcaga tcgccgtggt gggcggccag    120
agcgccggca agagctcggt gctcgagaac ttcgtgggca gggactttct ccctcgaggg    180
tcgggcattg taacaagacg acctcttgtg ctgcagcttg ttacttctaa agcagaatat    240
gccgagtttc tacattgcaa aggaaagaaa tttacagatt ttgatgaagt tcgccttgag    300
attgaagcag aaacagatcg cgtgactgga atgaataaag gcatttcctc catacccatt    360
aatttacgag tctattcccc acacgtgtta aatctaaccc ttattgatct acctggaata    420
actaaagtgc ctgtgggaga tcagccacca gatatcgagt atcagatcag agaaatgatt    480
atgcagttca tcacgaggga gaactgtctg attttagctg ttactccagc caacactgat    540
cttgcaaact cagatgcgct gaagctagct aaagaagttg atcctcaagg tctgagaacc    600
attggagtta tcaccaaact ggaccttatg gatgaaggaa cggatgccag ggatgttcta    660
gagaacaaac tgttgcctct tcgcaggggt tacgtggggg tggtaaacag aagccagaag    720
gacatagatg ggaagaagga cataaaggca gccatgctgg cagagaggaa gtttttcctt    780
tcccacccgg cttacagaca tatcgctgac cgaatgggaa ccccacacct gcagaaggtc    840
cttaatcagc aacttaccaa ccacattcgg gataccctac caaacttcag gaacaaacta    900
cagggacagt tgctctccat agaacatgaa gtagaagcct acaaaaattt caaaccagaa    960
gacccaacaa ggaagaccaa agcattgctg cagatggttc agcaatttgc tgtggacttt   1020
gagaagagaa ttgaagggtc aggggatcaa gtagataccc tggaactctc aggtggtgct   1080
aaaatcaatc gtatttttca tgaacgcttt ccttttgaga tagtaaagat ggagttcaat   1140
gagaaagaat tgcgaagaga aataagctat gcaatcaaaa acatacatgg tatcaggaca   1200
gggttgttta ctccagacat ggcatttgaa gcgatagtca agaaacagat tgtaaagttg   1260
aaagggcctt ccttgaagag tgtggatctg gtaatacaag aattaatcaa cactgtgaag   1320
aagtgtacca aaaaactggc aaacttcccc agactctgcg aggaaacgga aaggattgtt   1380
gctaaccaca ttcgtgagcg agaagggaag acaaaggacc aggtattgct attgattgac   1440
attcaagtct cttacatcaa caccaaccat gaagacttca ttggcttcgc aaatgctcag   1500
cagaggagca gtcaggttca caagaaaacc acagttggaa atcaggtgat tcgcaagggg   1560
tggctcacca tcagcaacat tggcatcatg aaaggcggct cgaagggata ctggttcgtc   1620
cttactgcgg aaagcttgtc ctggtataaa gatgatgagg aaaaagaaaa gaagtacatg   1680
cttcccttgg acaacctgaa agttcgggat gtggaaaaga gctttatgtc tagcaagcac   1740
atctttgcac tctttaatac agagcaaagg aatgtataca aagactatcg cttccttgag   1800
ctggcatgtg attcccagga ggatgtcgac agctggaagg catctctact aagagctggg   1860
gtctatcctg acaaatctgt agggaacaac aaagctgaaa atgatgagaa tggacaagca   1920
gaaaactttt ccatggaccc acaattggag aggcaagtgg agaccattcg caacctcgta   1980
gactcctaca tgtccattat caacaaatgt atccgagatc taattccaaa aacaataatg   2040
caccttatga tcaataacgt taaagatttc ataaattccg agctcctagc acagttgtat   2100
tcttcagagg accaaaatac cctgatggag gaatctgctg agcaggctca gcgccgggat   2160
gagatgcttc gaatgtatca agcactgaaa gaagcccttg ggataattgg ggacatcagc   2220
acagccaccg tgtccactcc ggcacccccct ccagtggatg actcctggat acagcactct   2280
cgcaggtcac ctcctccaag ccccacaacc caaaggaggc caacactaag tgctcccctc   2340
gcaaggccca catccggccg aggaccagct cctgccattc cctctcctgg cccccactct   2400
ggggctcctc cagtcccatt ccgtccaggc ccattacctc ctttccccag cagcagtgac   2460
```

-continued

```
tccttcggag cccctccaca agttccatct aggcctacga gggccccgcc cagtgtccca   2520

agccggagac cacccccatc accaactcgt cccactataa tccgcccact agaatcctcc   2580

ctgttagact aa                                                        2592
```

MICROTUBULE-MODIFYING COMPOUND

CROSS-REFERENCE TO RELATED APPLICATIONS

This application is a U.S. National Stage of Application No. PCT/EP2013/072257, filed Oct. 24, 2013, which claims priority to European Patent Application No. EP 12189804.3, dated 24 Oct. 2012, which is incorporated herein by reference in its entirety.

The present invention pertains to a compound, a polynucleotide encoding the compound of the invention, a process of manufacturing the compound of the invention, a vector comprising the polynucleotide of the invention, a cell comprising the vector of the invention, a medicament comprising the compound of the invention as well as the use of the compound in the treatment of proliferative diseases. Recombinant immunotoxins are chimeric proteins predominantly used to treat cancer. These proteins are composed of a binding domain, which is commonly an antibody or a fragment thereof, and a toxic domain, which is a protein usually derived from bacteria or plants. After binding of the antibody to a target cell antigen, the immunotoxin is internalized followed by endosomal processing and the final release of the toxin into the cytosol, where it exerts its toxic activity. In addition to antibodies as targeting units, several ligands including growth factors have been used [1-4].

In the beginning of immunotoxin development, antibodies were conjugated to the toxin via chemical coupling, which, however, bore many disadvantages, such as a required separate production and purification of targeting and toxic unit, low yields after conjugation, and an undirected coupling leading to a heterogeneous protein preparation [5].

To overcome these drawbacks and to allow the commercial development of immunotoxins, recombinant immunotoxins were generated by genetically fusing the ligand and the protein-based toxin resulting in a single chain DNA construct. To date, most immunotoxins can be easily expressed by fermentation of transformed *Escherichia coli* or by Mammalian or yeast cells and purified by standard chromatographic methods. The most prominent toxins which have been used so far are the plant-derived ricin, especially the A chain thereof, and the bacterial *Pseudomonas* Exotoxin A (ETA) and Diphtheria Toxin (DT) [6]. Both bacterial toxins are multidomain proteins comprising a cell binding and a toxic domain separated by a translocation domain.

For use in immunotoxins, truncated versions of ETA and DT were generated by deletion of the cell-binding domain. This has reduced the size of ETA and DT, respectively, making them even more suitable to be used as fusion proteins and it has increased their specificity preventing unwanted binding to healthy cells [7-11]. The most prominent shortened version of ETA is called PE38 (here referred to as ETA') [10]. Historically, due to their relatively strong side effects, immunotoxins have been implicated for use in life threatening disease only. Consequently, their clinical use has been restricted to indications such as cancer. Just recently, Madhumthi and Verma reviewed existing therapeutic targets for immunotherapy emphasizing that cancer, including solid tumors, lymphoma and leukemia, represents the dominating indication for classical immunotoxins [12].

Besides their toxic side effects, immunogenicity of chimeric immunotoxins composed of a murine or human antibody and a bacterial or plant toxin had to be considered as an obstacle to treatment [13]. Generation of neutralizing antibodies by the own immune system would lead to a less biologically active immunotoxin concomitant with the demand to administer higher doses. Different attempts have been done to reduce immunogenicity. For example, putative T- and B-cell epitopes on ETA have been identified and mutated expecting a more humanized version of the bacterial toxin [14, 15]. An alternative strategy was to modify the immunotoxin using polyethylene glycol, which has been proved to be efficient in preventing immunogenicity of interferon and L-asparaginase [16-18]. However, these strategies failed to significantly reduce immunogenicity.

Vascular leak syndrome triggered by binding of toxins to endothelial cells represents another disadvantage of chimeric immunotoxins. As counter-measures, receptor mutation, inhibitors preventing the binding to endothelial cells and administration of anti-inflammatory agents have been taken [19].

Another approach is the generation of fully human cytolytic fusion proteins. Fully human antibody fragments fused to human proteins, which are capable of directly or indirectly inducing apoptosis, are now gaining attention.

Human RNases like RNase 1, 2, 3 and 5 (angiogenin), which degrade RNA and induce apoptosis by inhibition of protein synthesis, have been used as enzymes [20]. Huhn et al. could show specific cytotoxicity of human angiogenin to CD30 overexpressing Hodgkin lymphoma-derived cell lines delivered by a CD30 ligand (CD30L) [21]. Tur et al. generated a fully human CD30L-based immunokinase and could show specific cytotoxicity of the human death associated protein kinase 2 towards several Hodgkin lymphoma cells in vitro and in vivo [22, 23].

Proapoptotic proteins such as Bik, Bak, Bax, DNA fragmentation factor 40, FAS-ligand, TNF-related apoptosis-inducing ligand proofed effective in melanoma, renal cancer, cutaneous T cell lymphoma, and AML [24]. A novel human cytolytic fusion protein composed of a single chain fragment (scFv) against CTLA4 and perforin was shown to kill CTLA-positive cell lines in vitro [25].

Potent classical anti-cancer agents are cytostatic molecules capable of intervening into the process of mitosis. Primarily, their cytotoxicity is conferred by stabilizing or destabilizing microtubules, which are known to be sensitive to changes in both mass and dynamics. Similar to bacteria- or plant-derived toxins, cytostatic small molecules are recognized as foreign leading to undesired side effects.

BRIEF DESCRIPTION OF THE INVENTION

One object of the invention is to provide an effective medicament for treating proliferative diseases.

Another object of the present invention is to provide a compound, which is able to treat proliferative diseases.

A further object of the present invention is to provide a medicament based on a compound having reduced side effects.

BRIEF DESCRIPTION OF THE FIGURES

FIG. 3: Shows sequences ID 1-13.

FIG. 8: Shows successful elimination hCD64-positive inflammatory macrophages for H22(scFv)-MAP.

FIG. 9: Shows ORFs of human MAPs corresponding to sequences ID 14-24.

Figure 1:
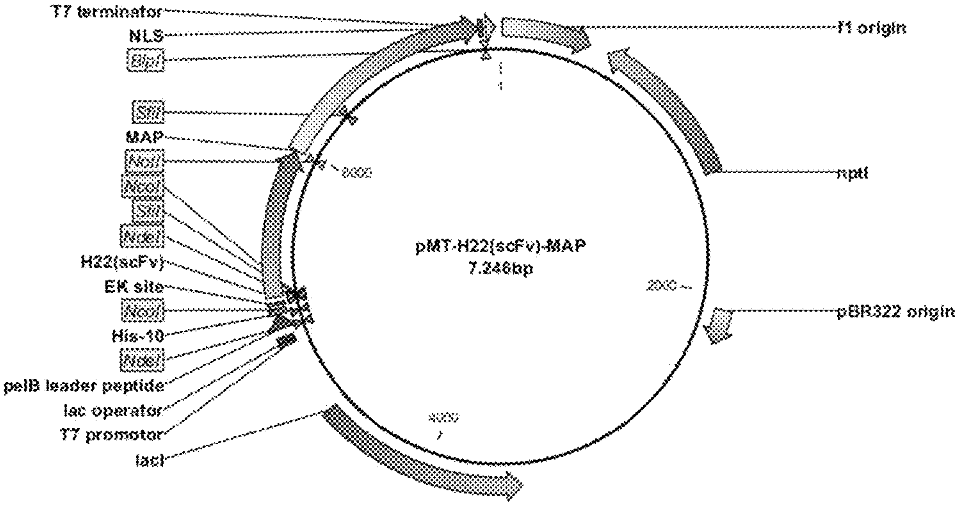
FIG. 1: Shows Construction of open reading frames for MAP-based human cytolytic fusion protein
Figure 2A:
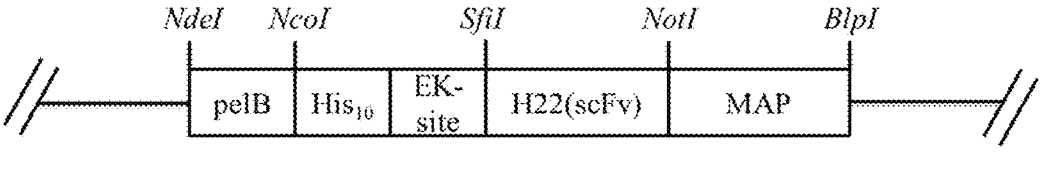
FIG. 2: Shows Complete expression cassettes for MAP-based human cytolytic fusion protein
Figure 2B:
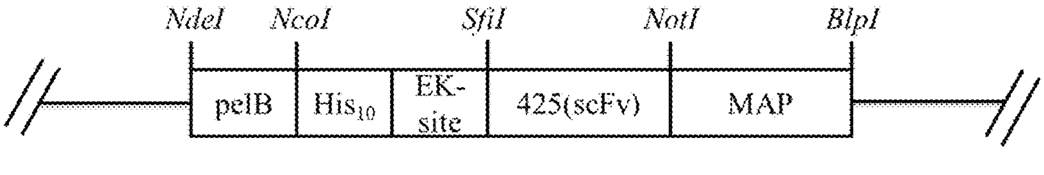
Figure 2C:
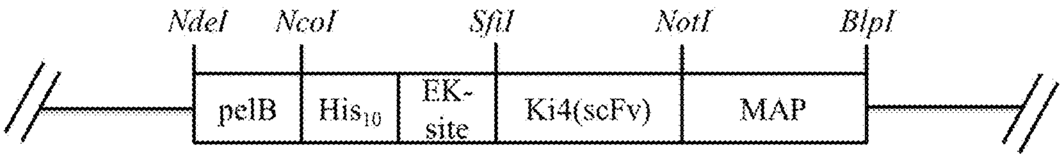
Figure 2D:
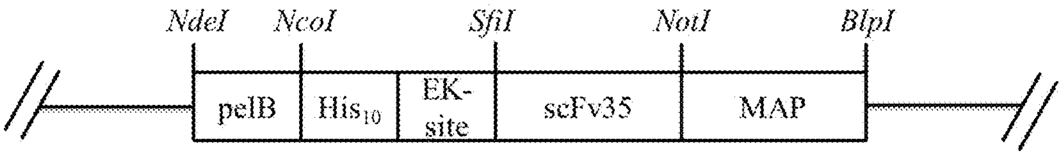
Figure 2E:
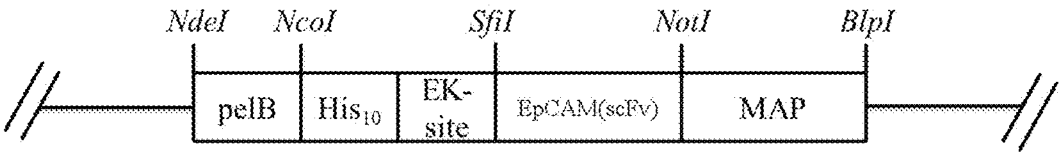
Figure 2F:
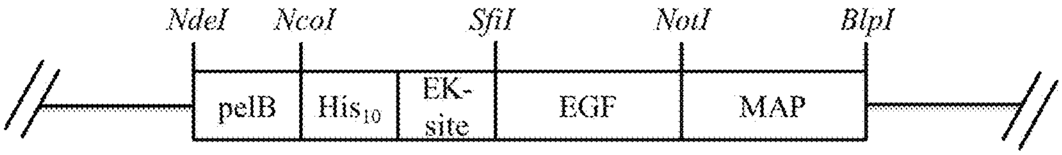

The present invention pertains to a compound formed from at least one component A comprising a binding domain for extra-cellular surface structures of a diseased cell that internalizes upon binding of component A of said compound, and at least one component B, characterized in that component B is a polypeptide which amino acid sequence comprises a microtubule-associated protein (MAP) or comprises at least a partial sequence of the MAP, the partial sequence having maintained the binding function of the MAP to a microtubule. In a specific embodiment the compound of the present invention is a human cytolytic fusion protein. The substances known to the skilled person as MAP are a specific class of compounds which show defined interaction with microtubules. The up-to-date skilled person's understanding of the term is e.g. summarized in Wikipedia (http://en.wikipedia.org/wiki/Microtubule-associated_protein).

It has to be noted, that in contrast to the classical approach to select for enzymes as toxic entity in an immunotoxin it has now surprisingly be found that proliferation of cells can be inhibited by coupling MAPs to a targeting protein which is an entity not exhibiting enzymatic activities.

The following references representing the prior art, however, are using the classical approach.

Bettina Stahnke, et al in Granzyme B-H22(scFv), a human immunotoxin targeting CD64 in acute myeloid leukemia of monocytic subtypes, Molecular Cancer Therapeutics, vol. 7, no. 9, pp. 2924-2932 present a novel fully human immunotoxin composed of an anti-CD64 antibody fragment [H22(scFv)] as binding ligand and the human serine protease granzyme B (Gb) as effector protein. After successful production in HEK293T cells and purification by affinity chromatography, the authors show that Gb-H22(scFv) has pro-apoptotic activity towards $CD64^+$ leukemia cells in vitro. In addition to cell lines, Gb-H22(scFv) also showed specific activity against primary $CD64^+$ acute myeloid leukemia cells. In contrast to the use of free cytosolic Gb, this article is the first report on a fully human Gb-based immunotoxin.

In Mrudula Mathew et al Humanized immunotoxins: A new generation of immunotoxins for targeted cancer therapy, Cancer Science vol. 100, no. 8, pp 1359-165 the authors review general aspects of chimeric immunotoxins, which classically comprise a cell-binding ligand and a chemically-linked or genetically fused toxin, usually derived from bacteria or plants. The authors point out that despite the success of these immunotoxins in pre-clinical studies, off-target effects and immunogenicity often are limiting their use in clinical applications. As countermeasure, a new generation of fusion proteins containing both human binding ligands and human pro-apoptotic effector proteins has emerged as a promising format. The authors present existing data on several human pro-apoptotic effector proteins, including members of the Bcl-2 family, DNA fragmentation factor-40, Fas ligand, TRAIL, granzyme B, and several RNAses.

In Dmitrij Hristodorov et al. Macrophage-Targeted Therapy: CD64-Based Immunotoxins for Treatment of Chronic Inflammatory Diseases, Toxins September 2012, vol. 4, no. 9, September 2012, pp 676-694, the authors describe the critical role of macrophages during chronic inflammation and how CD64-directed immunotoxins, such as H22(scFv)-ETA or H22-RicinA, can be used to target and eliminate activated macrophages in favor of resolution of chronic inflammation. In addition to the classical view on macrophages, which had been separated into a resting and an activated population in the past, the authors review recent findings on different subsets of polarized macrophages. Finally, the authors hypothesize that it will be possible to develop a subset-specific therapeutic approach using target-selective immunotoxins in near future.

In Keith R. Olson et al, Analysis of MAP4 function in living cells using green fluorescent protein (GFP) chimeras, JCB, The Rockefeller University Press, vol. 130, no. 3, 1995, pp. 639-650 the authors analyzed the function of the microtubule-associated protein 4 (MAP4) in living cells. Therefore, the sequences of MAP4 and the green fluorescent protein (GFP) were genetically fused and transfected into baby hamster kidney (BHK) or chinese hamster ovary (CHO) cells. Colocalization experiments revealed that GFP-MAP4 localized to and stabilized microtubules. To map the region of MAP4 that is responsible for binding to microtubules, the authors separated the known basic domain into a PGGG domain, which is shared between MAP4, MAP2, and the tau protein, and into a PSP domain, which is unique to MAP4. While the PSP domain maintained strong binding to microtubules, the PGGG domain showed only weak affinity, which brings the authors to the conclusion that this domain is dispensable for microtubule binding. Interestingly, this conclusion is in line with previously reported in vivo results for the PGGG domain of MAP2 and tau, however it is in contrast to numerous in vitro studies, which demonstrate pronounced affinity of this domain towards microtubules. In addition to the basic domain, this article shows that the acidic carboxy-terminus of MAP4 is critical for the binding affinity of the other domains to microtubules.

In Nikolai N. Sluchanko et al., Phosphorylation of more than one site is required for tight interaction of human tau protein with 14-3-3f, FEBS Letters, vol. 583, no. 17, (2009), pp. 2739-2742, the authors analyzed the role of phosphorylation of the human tau protein in regard to its interaction with the highly conserved regulatory protein 14-3-3. The authors generated several tau mutants, phosphorylated them in vitro and assessed their binding to 14-3-3 by native gel electrophoresis. The single mutant S156A, and the double mutants S156A/S267A and S156A/S235A showed reduced interaction with 14-3-3.

In one embodiment of the invention the component A of the compound of the invention is selected from the group of internalizing cell surface receptor binding structures consisting of antibodies or their derivatives or fragments thereof, synthetic peptides such as scFv, mimotopes, etc. or chemical molecules such as carbohydrates, lipids, nucleic acids, peptides, vitamins, etc., and/or small molecules with up to 100 atoms with receptor-binding activity like ligands, in particular single atoms, peptidic molecules, non-peptidic molecules, etc., and/or carbohydrate binding proteins and their ligands such as lectins, in particular calnexins, c-type lectins, I-type lectins, m-type lectins, p-type lectins, r-type lectins, galectins and their derivatives, and/or receptor binding molecules such as natural ligands to the cluster of differentiation (CD) antigens, like CD30, CD40, etc., cytokines such as chemokines, colony stimulating factors, type-1 cytokines, type-2 cytokines, interferons, interleukins, lymphokines, monokines, etc., and/or adhesion molecules including their derivatives and mutants, and/or derivatives or combinations of any of the above listed binding structures.

In particular component A is binding to a cell surface marker of a healthy or diseased cell belonging to the cluster of differentiation antigens (CD-antigens, Table 1).

In another embodiment of the invention, the component A is a chemokine or a specifically binding fragment thereof. According to the invention the chemokine is in particular selected from table 2. The chemokines introduced there are the CXC chemokine/receptor family such as CXCL1, CXCL2, CXCL3, CXCL4, CXCL5, CXCL6, CXCL7, CXCL8, CXCL9, CXCL10, CXCL11, CXCL12, CXCL13, CXCL14, KXCL15, CXCL16; or the C chemokine/receptor family, such as XCL1 and XCL2; or the $CX_3C$ chemokine/receptor family, such as CX3CL1, or the CC chemokine/receptor family, such as CCL1, CCL2, CCL3, CCL3L1, CCL4, CCL5, CCL6, CCL7, CCL8, CCL9/10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28.

In another embodiment of the invention, component A is an interleukin or a specifically binding fragment thereof like those provided in table 3 binding to its specific cellular receptor.

In a further embodiment of the invention the component B of the compound of the invention is selected from the group consisting of microtubule-associated proteins (MAPs [ID: 57-65]) including Kinesins (KIF1-27 [ID: 14-35], KIFC1-3 [ID: 36-38]), Dyneins (DNAH1−14 [ID: 39-50], DNAI1+2 [ID: 51-52], DNAL1+4 [ID: 53-54]), as well as Tau protein [ID: 1], Dynactin (DCTN1 [ID: 66]), Tubulins (TUBA1-8 [ID: 67-72]), Stathmin [ID: 55], Gephyrin [ID: 56], Tektins (TEKT1-5 [ID: 73-77]), Dynamins (DNM1-3 [ID: 78-80]).

In yet a further embodiment of the invention the components A, and/or B are chemically coupled in order to yield a conjugate or fused to each other by genetic engineering to obtain a fusion protein, such as exemplified by the proteins having one of the amino acid sequences encoded by the polynucleotide of one of the Seq ID Nos. 1-13.

Thus particular embodiments of the compound of the invention are formed by the following representatives: component A and KIF1, component A and KIF2A, component A and KIF4A, component A and KIF5A, component A and KIF5B, component A and KIF6, component A and KIF7, component A and KIF9, component A and KIF10, component A and KIF11, component A and KIF12, component A and KIF13B, component A and KIF14, component A and KIF15, component A and KIF17, component A and KIF19, component A and KIF22, component A and KIF23, component A and KIF24, component A and KIF25, component A and KIF26, component A and KIF27, component A and KIFC1, component A and KIFC2, component A and KIFC3, 5 component A and DNAH1, component A and DNAH2, component A and DNAH3, component A and DNAH5, component A and DNAH6, component A and DNAH7, component A and DNAH8, component A and DNAH9, component A and DNAH10, component A and DNAH11, component A and DNAH12, component A and DNAH14, component A and DNAI1, component A and DNAI2, component A and DNAL1, component A and DNAL4, component A and Tau, component A and Stathmin, component A and Gephyrin, component A and MAP1a, component A and MAP1b, component A and MAP2, component A and MAP4, component A and XMAP5, component A and MAP6, component A and MAP7, component A and MAP8, component A and MAP9, component A and DCTN1, component A and TUBA1, component A and TUBA2, component A and TUBA3, component A and TUBA4, component A and TUBA6, component A and TUBA8, component A and TEKT1, component A and TEKT2, component A and TEKT3, component A and TEKT4, component A and TEKT5, component A and DNM1, component A and DNM2, as well as component A and DNM3.

Still further particular embodiments of the compound of the invention are formed by the following representatives: a chemokine or a specifically binding fragment thereof and KIF1, a chemokine or a specifically binding fragment thereof and KIF2A, a chemokine or a specifically binding fragment thereof and KIF4A, a chemokine or a specifically binding fragment thereof and KIF5A, a chemokine or a specifically binding fragment thereof and KIF5B, a chemokine or a specifically binding fragment thereof and KIF6, a chemokine or a specifically binding fragment thereof and KIF7, a chemokine or a specifically binding fragment thereof and KIF9, a chemokine or a specifically binding fragment thereof and KIF10, a chemokine or a specifically binding fragment thereof and KIF11, a chemokine or a specifically binding fragment thereof and KIF12, a chemokine or a specifically binding fragment thereof and KIF13B, a chemokine or a specifically binding fragment thereof and KIF14, a chemokine or a specifically binding fragment thereof and KIF15, a chemokine or a specifically binding fragment thereof and KIF17, a chemokine or a specifically binding fragment thereof and KIF19, a chemokine or a specifically binding fragment thereof and KIF22, a chemokine or a specifically binding fragment thereof and KIF23, a chemokine or a specifically binding fragment thereof and KIF24, a chemokine or a specifically binding fragment thereof and KIF23, a chemokine or a specifically binding fragment thereof and KIF26, a chemokine or a specifically binding fragment thereof and KIF27, a chemokine or a specifically binding fragment thereof and KIFC1, a chemokine or a specifically binding fragment thereof and KIFC2, a chemokine or a specifically binding fragment thereof and KIFC3, a chemokine or a specifically binding fragment thereof and DNAH1, a chemokine or a specifically binding fragment thereof and DNAH2, a chemokine or a specifically binding fragment thereof and DNAH3, a chemokine or a specifically binding fragment thereof and DNAH5, a chemokine or a specifically binding fragment thereof and DNAH6, a chemokine or a specifically binding fragment thereof and DNAH7, a chemokine or a specifically binding fragment thereof and DNAH8, a chemokine or a specifically binding fragment thereof and DNAH9, a chemokine or a specifically binding fragment thereof and DNAH10, a chemokine or a specifically binding fragment thereof and DNAH11, a chemokine or a specifically binding fragment thereof and DNAH12, a chemokine or a specifically binding fragment thereof and DNAH14, a chemokine or a specifically binding fragment thereof and DNAI1, a chemokine or a specifically binding fragment thereof and DNAI2, a chemokine or a specifically binding fragment thereof and DNAL1, a chemokine or a specifically binding fragment thereof and DNAL4, a chemokine or a specifically binding fragment thereof and Tau, a chemokine or a specifically binding fragment thereof and Stathmin, a chemokine or a specifically binding fragment thereof and Gephyrin, a chemokine or a specifically binding fragment thereof and MAP1a, a chemokine or a specifically binding fragment thereof and MAP1b, a chemokine or a specifically binding fragment thereof and MAP2, a chemokine or a specifically binding fragment thereof and MAP4, a chemokine or a specifically binding fragment thereof and XMAP5, a chemokine or a specifically binding fragment thereof and MAP6, a chemokine or a specifically binding fragment thereof and MAP7, a chemokine or a specifically binding fragment thereof and MAP8, a chemokine or a specifically binding fragment thereof and MAP9, a chemokine or a specifically binding fragment thereof and DCTN1, a chemokine or a specifically binding fragment thereof and TUBA1, a chemokine or a specifically binding fragment thereof and TUBA2, a chemokine or a specifically binding fragment thereof and TUBA3, a chemokine or a specifically binding fragment thereof and TUBA4, a chemokine or a specifically binding fragment thereof and TUBA6, a chemokine or a specifically binding fragment thereof and TUBA8, a chemokine or a specifically binding fragment thereof and TEKT1, a chemokine or a specifically binding fragment thereof and TEKT2, a chemokine or a specifically binding fragment thereof and TEKT3, a chemokine or a specifically binding fragment thereof and TEKT4, a chemokine or a specifically binding fragment thereof and TEKT5, a chemokine or a specifically binding fragment thereof and DNM1, a chemokine or a specifically binding fragment thereof and DNM2, as well as a chemokine or a specifically binding fragment thereof and DNM3.

Further particular embodiments of the compound of the invention are formed by the following representatives: an interleukin or a specifically binding fragment thereof and KIF1, an interleukin or a specifically binding fragment thereof and KIF2A, an interleukin or a specifically binding fragment thereof and KIF4A, an interleukin or a specifically binding fragment thereof and KIF5A, an interleukin or a specifically binding fragment thereof and KIF5B, an interleukin or a specifically binding fragment thereof and KIF6, an interleukin or a specifically binding fragment thereof and KIF7, an interleukin or a specifically binding fragment thereof and KIF9, an interleukin or a specifically binding fragment thereof and KIF10, an interleukin or a specifically binding fragment thereof and KIF11, an interleukin or a specifically binding fragment thereof and KIF12, an interleukin or a specifically binding fragment thereof and KIF13B, an interleukin or a specifically binding fragment thereof and KIF14, an interleukin or a specifically binding fragment thereof and KIF15, an interleukin or a specifically binding fragment thereof and KIF17, an interleukin or a specifically binding fragment thereof and KIF19, an interleukin or a specifically binding fragment thereof and KIF22, an interleukin or a specifically binding fragment thereof and KIF23, an interleukin or a specifically binding fragment thereof and KIF24, an interleukin or a specifically binding fragment thereof and KIF25, an interleukin or a specifically binding fragment thereof and KIF26, an interleukin or a specifically binding fragment thereof and KIF27, an interleukin or a specifically binding fragment thereof and KIFC1, an interleukin or a specifically binding fragment thereof and KIFC2, an interleukin or a specifically binding fragment thereof and KIFC3, an interleukin or a specifically binding fragment thereof and DNAH1, an interleukin or a specifically binding fragment thereof and DNAH2, an interleukin or a specifically binding fragment thereof and DNAH3, an interleukin or a specifically binding fragment thereof and DNAH5, an interleukin or a specifically binding fragment thereof and DNAH6, an interleukin or a specifically binding fragment thereof and DNAH7, an interleukin or a specifically binding fragment thereof and DNAH8, an interleukin or a specifically binding fragment thereof and DNAH9, an interleukin or a specifically binding fragment thereof and DNAH10, an interleukin or a specifically binding fragment thereof and DNAH11, an interleukin or a specifically binding fragment thereof and DNAH12, an interleukin or a specifically binding fragment thereof and DNAH14, an interleukin or a specifically binding fragment thereof and DNAI1, an interleukin or a specifically binding fragment thereof and DNAI2, an interleukin or a specifically binding fragment thereof and DNAL1, an interleukin or a specifically binding fragment thereof and DNAL4, an interleukin or a specifically binding fragment thereof and Tau, an interleukin or a specifically binding fragment thereof and Stathmin, an interleukin or a specifically binding fragment thereof and Gephyrin, an interleukin or a specifically binding fragment thereof and MAP1a, an interleukin or a specifically binding fragment thereof and MAP1b, an interleukin or a specifically binding fragment thereof and MAP2, an interleukin or a specifically binding fragment thereof and MAP4, an interleukin or a specifically binding fragment thereof and XMAP5, an interleukin or a specifically binding fragment thereof and MAP6, an interleukin or a specifically binding fragment thereof and MAP7, an interleukin or a specifically binding fragment thereof and MAP8, an interleukin or a specifically binding fragment thereof and MAP9, an interleukin or a specifically binding fragment thereof and DCTN1, an interleukin or a specifically binding fragment thereof and TUBA1, an interleukin or a specifically binding fragment thereof and TUBA2, an interleukin or a specifically binding fragment thereof and TUBA3, an interleukin or a specifically binding fragment thereof and TUBA4, an interleukin or a specifically binding fragment thereof and TUBA6, an interleukin or a specifically binding fragment thereof and TUBA8, an interleukin or a specifically binding fragment thereof and TEKT1, an interleukin or a specifically binding fragment thereof and TEKT2, an interleukin or a specifically binding fragment thereof and TEKT3, an interleukin or a specifically binding fragment thereof and TEKT4, an interleukin or a specifically binding fragment thereof and TEKT5, an interleukin or a specifically binding fragment thereof and DNM1, an interleukin or a specifically binding fragment thereof and DNM2, as well as an interleukin or a specifically binding fragment thereof and DNM3.

Further particular embodiments of the compound of the invention are formed by the following representatives: a ligand binding to a cluster of differentiation antigens (CD-antigens, Table 1) and KIF1, a ligand binding to a cluster of differentiation antigens (CD-antigens, Table 1) and KIF2A, a ligand binding to a cluster of differentiation antigens (CD-antigens, Table 1) and KIF4A, a ligand binding to a cluster of differentiation antigens (CD-antigens, Table 1) and KIF5A, a ligand binding to a cluster of differentiation antigens (CD-antigens, Table 1) and KIF5B, a ligand binding to a cluster of differentiation antigens (CD-antigens, Table 1) and KIF6, a ligand binding to a cluster of differentiation antigens (CD-antigens, Table 1) and KIF7, a ligand binding to a cluster of differentiation antigens (CD-antigens, Table 1) and KIF9, a ligand binding to a cluster of differentiation antigens (CD-antigens, Table 1) and KIF10, a ligand binding to a cluster of differentiation antigens (CD-antigens, Table 1) and KIF11, a ligand binding to a cluster of differentiation antigens (CD-antigens, Table 1) and KIF12, a ligand binding to a cluster of differentiation antigens (CD-antigens, Table 1) and KIF13B, a ligand binding to a cluster of differentiation antigens (CD-antigens, Table 1) and KIF14, a ligand binding to a cluster of differentiation antigens (CD-antigens, Table 1) and KIF15, a ligand binding to a cluster of differentiation antigens (CD-antigens, Table 1) and KIF17, a ligand binding to a cluster of differentiation antigens (CD-antigens, Table 1) and KIF19, a ligand binding to a cluster of differentiation antigens (CD-antigens, Table 1) and KIF22, a ligand binding to a cluster of differentiation antigens (CD-antigens, Table 1) and KIF23, a ligand binding to a cluster of differentiation antigens (CD-antigens, Table 1) and KIF24, a ligand binding to a cluster of differentiation antigens (CD-antigens, Table 1) and KIF25, a ligand binding to a cluster of differentiation antigens (CD-antigens, Table 1) and KIF26, a ligand binding to a cluster of differentiation antigens (CD-antigens, Table 1) and KIF27, a ligand binding to a cluster of differentiation antigens (CD-antigens, Table 1) and KIFC1, a ligand binding to a cluster of differentiation antigens (CD-antigens, Table 1) and KIFC2, a ligand binding to a cluster of differentiation antigens (CD-antigens, Table 1) and KIFC3, a ligand binding to a cluster of differentiation antigens (CD-antigens, Table 1) and DNAH1, a ligand binding to a cluster of differentiation antigens (CD-antigens, Table 1) and DNAH2, a ligand binding to a cluster of differentiation antigens (CD-antigens, Table 1) and DNAH3, a ligand binding to a cluster of differentiation antigens (CD-antigens, Table 1) and DNAH5, a ligand binding to a cluster of differentiation antigens (CD-antigens, Table 1) and DNAH6, a ligand binding to a cluster of differentiation antigens (CD-antigens, Table 1) and DNAH7, a ligand binding to a cluster of differentiation antigens (CD-antigens, Table 1) and DNAH8, a ligand binding to a cluster of differentiation antigens (CD-antigens, Table 1) and DNAH9, a ligand binding to a cluster of differentiation antigens (CD-antigens, Table 1) and DNAH10, a ligand binding to a cluster of differentiation antigens (CD-antigens, Table 1) and DNAH11, a ligand binding to a cluster of differentiation antigens (CD-antigens, Table 1) and DNAH12, a ligand binding to a cluster of differentiation antigens (CD-antigens, Table 1) and DNAH14, a ligand binding to a cluster of differentiation antigens (CD-antigens, Table 1) and DNAI1, a ligand binding to a cluster of differentiation antigens (CD-antigens, Table 1) and DNAI2, a ligand binding to a cluster of differentiation antigens (CD-antigens, Table 1) and DNAL1, a ligand binding to a cluster of differentiation antigens (CD-antigens, Table 1) and DNAL4, a ligand binding to a cluster of differentiation antigens (CD-antigens, Table 1) and Tau, a ligand binding to a cluster of differentiation antigens (CD-antigens, Table 1) and Stathmin, a ligand binding to a cluster of differentiation antigens (CD-antigens, Table 1) and Gephyrin, a ligand binding to a cluster of differentiation antigens (CD-antigens, Table 1) and MAP1a, a ligand binding to a cluster of differentiation antigens (CD-antigens, Table 1) and MAP1b, a ligand binding to a cluster of differentiation antigens (CD-antigens, Table 1) and MAP2, a ligand binding to a cluster of differentiation antigens (CD-antigens, Table 1) and MAP4, a ligand binding to a cluster of differentiation antigens (CD-antigens, Table 1) and XMAP5, a ligand binding to a cluster of differentiation antigens (CD-antigens, Table 1) and MAP6, a ligand binding to a cluster of differentiation antigens (CD-antigens, Table 1) and MAP7, a ligand binding to a cluster of differentiation antigens (CD-antigens, Table 1) and MAP8, a ligand binding to a cluster of differentiation antigens (CD-antigens, Table 1) and MAP9, a ligand binding to a cluster of differentiation antigens (CD-antigens, Table 1) and DCTN1, a ligand binding to a cluster of differentiation antigens (CD-antigens, Table 1) and TUBA1, a ligand binding to a cluster of differentiation antigens (CD-antigens, Table 1) and TUBA2, a ligand binding to a cluster of differentiation antigens (CD-antigens, Table 1) and TUBA3, a ligand binding to a cluster of differentiation antigens (CD-antigens, Table 1) and TUBA4, a ligand binding to a cluster of differentiation antigens (CD-antigens, Table 1) and TUBA6, a ligand binding to a cluster of differentiation antigens (CD-antigens, Table 1) and TUBA8, a ligand binding to a cluster of differentiation antigens (CD-antigens, Table 1) and TEKT1, a ligand binding to a cluster of differentiation antigens (CD-antigens, Table 1) and TEKT2, a ligand binding to a cluster of differentiation antigens (CD-antigens, Table 1) and TEKT3, a ligand binding to a cluster of differentiation antigens (CD-antigens, Table 1) and TEKT4, a ligand binding to a cluster of differentiation antigens (CD-antigens, Table 1) and TEKT5, a ligand binding to a cluster of differentiation antigens (CD-antigens, Table 1) and DNM1, a ligand binding to a cluster of differentiation antigens (CD-antigens, Table 1) and DNM2, as well as a ligand binding to a cluster of differentiation antigens (CD-antigens, Table 1) and DNM3.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307;

CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF1. In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF2A.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF4A.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E;

CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF5A.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF5B.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164;

CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF6.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF7.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284;

CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF9.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; KIF10.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF11.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37;

CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF12.

In another embodiment the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and MAP11.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139;

CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF13B.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF14.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243;

CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF15

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF17.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF19.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10;

CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF22.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF23.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118;

CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF24.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF25.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222;

CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF26.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIF27.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIFC1.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIFC2.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and KIFC3.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85;

CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH1.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH2.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185;

CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH3.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH5.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318;

CD319; CD320; CD321; CD322; CD324; CDw325; CD326; CDw327; CDw328; CDw329; CD331; CD332; CD333; CD334; CD335; CD336; CD337; CDw338; CD339; and DNAH6.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH7.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH8.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E;

CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH9.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH10.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164;

CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH11.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH12.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284;

CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAH14.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAI1.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAI2.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37;

CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAL1.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNAL4.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139;

CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and Tau.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and Stathmin.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243;

CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and Gephyrin.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and MAP1a.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and MAP1b.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10;

CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and MAP2.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and MAP4.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118;

CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and XMAP5.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and MAP6.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222;

CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and MAP7.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and MAP8.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and MAP9.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DCTN1.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TUBA1.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85;

CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TUBA2.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TUBA3.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185;

CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TUBA4.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243;

CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TUBA4.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318;

CD319; CD320; CD321; CD322; CD324; CDw325; CD326; CDw327; CDw328; CDw329; CD331; CD332; CD333; CD334; CD335; CD336; CD337; CDw338; CD339; and TUBA6.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TUBA8.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TEKT1.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E;

CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TEKT2.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TEKT3.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164;

CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TEKT4.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and TEKT5.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284;

CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNM1.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNM2.

In a particular embodiment, the compound of the invention is formed by the combination of a ligand binding to the following clusters of differentiation: CD1a; CD1b; CD1c; CD1d; CD1e; CD2; CD3delta; CD3epsilon; CD3gamma; CD4; CD5; CD6; CD7; CD8alpha; CD8beta; CD9; CD10; CD11a; CD11b; CD11c; CDw12; CD13; CD14; CD15u; CD16a; CD16b; CDw17; CD18; CD19; CD20; CD21; CD22; CD23; CD24; CD25; CD26; CD27; CD28; CD29; CD30; CD31; CD32; CD33; CD34; CD35; CD36; CD37; CD38; CD39; CD40; CD41; CD42a; CD42b; CD42c; CD42d; CD43; CD44; CD44R; CD45; CD46; CD47R; CD48; CD49a; CD49b; CD49c; CD49d; CD49e; CD49f; CD50; CD51; CD52; CD53; CD54; CD55; CD56; CD57; CD58; CD59; CD60a; CD60b; CD60c; CD61; CD62E; CD62L; CD62P; CD63; CD64; CD65; CD65s; CD66a; CD66b; CD66c; CD66d; CD66e; CD66f; CD68; CD69; CD70; CD71; CD72; CD73; CD74; CD75; CD75s; CD77; CD79a; CD79b; CD80; CD81; CD82; CD83; CD84; CD85; CD86; CD87; CD88; CD89; CD90; CD91; CD92; CDw93; CD94; CD95; CD96; CD97; CD98; CD99; CD100; CD101; CD102; CD103; CD104; CD105; CD106; CD107a; CD107b; CD108; CD109; CD110; CD111; CD112; CDw113; CD114; CD115; CD116; CD117; CD118; CDw119; CD120a; CD120b; CD121a; CDw121b; CD122; CD123; CD124; CDw125; CD126; CD127; CDw128a; CDw128b; CD129; CD130; CD131; CD132; CD133; CD134; CD135; CDw136; CDw137; CD138; CD139; CD140a; CD140b; CD141; CD142; CD143; CD144; CDw145; CD146; CD147; CD148; CDw149; CD150; CD151; CD152; CD153; CD154; CD155; CD156a; CD156b; CDw156C; CD157; CD158; CD159a; CD159c; CD160; CD161; CD162; CD162R; CD163; CD164; CD165; CD166; CD167a; CD168; CD169; CD170; CD171; CD172a; CD172b; CD172g; CD173; CD174; CD175; CD175s; CD176; CD177; CD178; CD179a; CD179b; CD180; CD181; CD182; CD183; CD184; CD185; CDw186; CD191; CD192; CD193; CD195; CD196; CD197; CDw198; CDw199; CDw197; CD200; CD201; CD202b; CD203c; CD204; CD205; CD206; CD207; CD208; CD209; CDw210; CD212; CD213a1; CD213a2; CDw217; CDw218a; CDw218b; CD220; CD221; CD222; CD223; CD224; CD225; CD226; CD227; CD228; CD229; CD230; CD231; CD232; CD233; CD234; CD235a; CD235b; CD235ab; CD236; CD236R; CD238; CD239; CD240CE; CD240D; CD240DCE; CD241; CD242; CD243; CD244; CD245; CD246; CD247; CD248; CD249; CD252; CD253; CD254; CD256; CD257; CD258; CD261; CD262; CD263; CD264; CD265; CD266; CD267; CD268; CD269; CD271; CD272; CD273; CD274; CD275; CD276; CD277; CD278; CD279; CD280; CD281; CD282; CD283; CD284; CD289; CD292; CDw293; CD294; CD295; CD296; CD297; CD298; CD299; CD300a; CD300c; CD300e; CD301; CD302; CD303; CD304; CD305; CD306; CD307; CD309; CD312; CD314; CD315; CD316; CD317; CD318; CD319; CD320; CD321; CD322; CD324; CDw325; CD326; CDw327; CDw328; CDw329; CD331; CD332; CD333; CD334; CD335; CD336; CD337; CDw338; CD339; and DNM3.

In yet another embodiment the compound of the invention is formed by the combination of the following chemokines: Members of table 2; and KIF1.

In another embodiment the compound of the invention is formed by the combination of the following chemokines: Members of table 2; and KIF2A.

In another embodiment the compound of the invention is formed by the combination of the following chemokines: Members of table 2; and KIF4A.

In another embodiment the compound of the invention is formed by the combination of the following chemokines: Members of table 2; and KIF5A.

In another embodiment the compound of the invention is formed by the combination of the following chemokines: Members of table 2; and KIF5B.

In another embodiment the compound of the invention is formed by the combination of the following chemokines: Members of table 2; and KIF6.

In another embodiment the compound of the invention is formed by the combination of the following chemokines: Members of table 2; and KIF7.

In another embodiment the compound of the invention is formed by the combination of the following chemokines: Members of table 2; and KIF9.

In another embodiment the compound of the invention is formed by the combination of the following chemokines: Members of table 2; and KIF10.

In another embodiment the compound of the invention is formed by the combination of the following chemokines: Members of table 2; and KIF11.

In another embodiment the compound of the invention is formed by the combination of the following chemokines: Members of table 2; and KIF12.

In another embodiment the compound of the invention is formed by the combination of the following chemokines: Members of table 2; and KIF13B.

In yet another embodiment the compound of the invention is formed by the combination of the following chemokines: Members of table 2; and KIF14.

In yet another embodiment the compound of the invention is formed by the combination of the following chemokines: Members of table 2; and KIF15.

In yet another embodiment the compound of the invention is formed by the combination of the following chemokines: Members of table 2; and KIF17.

In yet another embodiment the compound of the invention is formed by the combination of the following chemokines: Members of table 2; and KIF19.

In yet another embodiment the compound of the invention is formed by the combination of the following chemokines: Members of table 2; and KIF22.

In yet another embodiment the compound of the invention is formed by the combination of the following chemokines: Members of table 2; and KIF23.

In yet another embodiment the compound of the invention is formed by the combination of the following chemokines: Members of table 2; and KIF24.

In yet another embodiment the compound of the invention is formed by the combination of the following chemokines: Members of table 2; and KIF25.

In yet another embodiment the compound of the invention is formed by the combination of the following chemokines: Members of table 2; and KIF26.

In yet another embodiment the compound of the invention is formed by the combination of the following chemokines: Members of table 2; and KIF27.

In yet another embodiment the compound of the invention is formed by the combination of the following chemokines: Members of table 2; and KIFC1.

In yet another embodiment the compound of the invention is formed by the combination of the following chemokines: Members of table 2; and KIFC2.

In yet another embodiment the compound of the invention is formed by the combination of the following chemokines: Members of table 2; and KIFC3.

In yet another embodiment the compound of the invention is formed by the combination of the following chemokines: Members of table 2; and DNAH1.

In yet another embodiment the compound of the invention is formed by the combination of the following chemokines: Members of table 2; and DNAH2.

In yet another embodiment the compound of the invention is formed by the combination of the following chemokines: Members of table 2; and DNAH3.

In yet another embodiment the compound of the invention is formed by the combination of the following chemokines: Members of table 2; and DNAH5.

In yet another embodiment the compound of the invention is formed by the combination of the following chemokines: Members of table 2; and DNAH6.

In yet another embodiment the compound of the invention is formed by the combination of the following chemokines: Members of table 2; and DNAH7.

In yet another embodiment the compound of the invention is formed by the combination of the following chemokines: Members of table 2; and DNAH8.

In yet another embodiment the compound of the invention is formed by the combination of the following chemokines: Members of table 2; and DNAH9.

In yet another embodiment the compound of the invention is formed by the combination of the following chemokines: Members of table 2; and DNAH10.

In yet another embodiment the compound of the invention is formed by the combination of the following chemokines: Members of table 2; and DNAH11.

In yet another embodiment the compound of the invention is formed by the combination of the following chemokines: Members of table 2; and DNAH12.

In yet another embodiment the compound of the invention is formed by the combination of the following chemokines: Members of table 2; and DNAH14.

In yet another embodiment the compound of the invention is formed by the combination of the following chemokines: Members of table 2; and DNAI1.

In yet another embodiment the compound of the invention is formed by the combination of the following chemokines: Members of table 2; and DNAI2.

In yet another embodiment the compound of the invention is formed by the combination of the following chemokines: Members of table 2; and DNAL1.

In yet another embodiment the compound of the invention is formed by the combination of the following chemokines: Members of table 2; and DNAL4.

In yet another embodiment the compound of the invention is formed by the combination of the following chemokines: Members of table 2; and Tau.

In yet another embodiment the compound of the invention is formed by the combination of the following chemokines: Members of table 2; and Stathmin.

In yet another embodiment the compound of the invention is formed by the combination of the following chemokines: Members of table 2; and Gephyrin.

In yet another embodiment the compound of the invention is formed by the combination of the following chemokines: Members of table 2; and MAP1a.

In yet another embodiment the compound of the invention is formed by the combination of the following chemokines: Members of table 2; and MAP1b.

In yet another embodiment the compound of the invention is formed by the combination of the following chemokines: Members of table 2; and MAP2.

In yet another embodiment the compound of the invention is formed by the combination of the following chemokines: Members of table 2; and MAP4.

In yet another embodiment the compound of the invention is formed by the combination of the following chemokines: Members of table 2; and XMAP5.

In yet another embodiment the compound of the invention is formed by the combination of the following chemokines: Members of table 2; and MAP6.

In yet another embodiment the compound of the invention is formed by the combination of the following chemokines: Members of table 2; and MAP7.

In yet another embodiment the compound of the invention is formed by the combination of the following chemokines: Members of table 2; and MAP8.

In yet another embodiment the compound of the invention is formed by the combination of the following chemokines: Members of table 2; and MAP9.

In yet another embodiment the compound of the invention is formed by the combination of the following chemokines: Members of table 2; and DCTN1.

In yet another embodiment the compound of the invention is formed by the combination of the following chemokines: Members of table 2; and TUBA1.

In yet another embodiment the compound of the invention is formed by the combination of the following chemokines: Members of table 2; and TUBA2.

In yet another embodiment the compound of the invention is formed by the combination of the following chemokines: Members of table 2; and TUBA3.

In yet another embodiment the compound of the invention is formed by the combination of the following chemokines: Members of table 2; and TUBA4.

In yet another embodiment the compound of the invention is formed by the combination of the following chemokines: Members of table 2; and TUBA6.

In yet another embodiment the compound of the invention is formed by the combination of the following chemokines: Members of table 2; and TUBA8.

In yet another embodiment the compound of the invention is formed by the combination of the following chemokines: Members of table 2; and TEKT1.

In yet another embodiment the compound of the invention is formed by the combination of the following chemokines: Members of table 2; and TEKT2.

In yet another embodiment the compound of the invention is formed by the combination of the following chemokines: Members of table 2; and TEKT3.

In yet another embodiment the compound of the invention is formed by the combination of the following chemokines: Members of table 2; and TEKT4.

In yet another embodiment the compound of the invention is formed by the combination of the following chemokines: Members of table 2; and TEKT5.

In yet another embodiment the compound of the invention is formed by the combination of the following chemokines: Members of table 2; and DNM1.

In yet another embodiment the compound of the invention is formed by the combination of the following chemokines: Members of table 2; and DNM2.

In yet another embodiment the compound of the invention is formed by the combination of the following chemokines: Members of table 2; and DNM3.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF1.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF2A.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF4A.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF5A.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF5B.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF6.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF7.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF9.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF10.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF11.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF12.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF13B.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF14.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF15.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF17.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF19.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF22.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF23.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF24.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF25.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF26.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIF27.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIFC1.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIFC2.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and KIFC3.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH1.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH2.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH3.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH5.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH6.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH7.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH8.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH9.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH10.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH11.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH12.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAH14.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAI1.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAI2.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAL1.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNAL4.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and Tau.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and Stathmin.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and Gephyrin.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and MAP1a.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and MAP1b.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and MAP2.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and MAP4.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and XMAP5.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and MAP6.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and MAP7.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and MAP8.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and MAP9.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DCTN1.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TUBA1.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TUBA2.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TUBA3.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TUBA4.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TUBA6.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TUBA8.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TEKT1.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TEKT2.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TEKT3.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TEKT4.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and TEKT5.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNM1.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNM2.

In another embodiment the compound of the invention is formed by the combination of the following interleukins: IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; and DNM3.

In another embodiment of the invention the compound of the invention is encoded by a polynucleotide having the nucleotide sequences of one of the Seq ID Nos. 3, 5, 7, 9, 11 and/or 13.

Subject matter of the invention is also a polynucleotide having the Seq ID Nos. 3, 5, 7, 9, 11 and/or 13. These polynucleotides can be used for manufacturing a genetically fused compound the invention. In addition the polynucleotides of Seq ID Nos. 2, 4, 6, 8, 10, and 12 coding for representatives of component A can be used in combination with polynucleotides coding for representatives of component B having the Seq ID Nos. 1, and 14 to 80.

Further, the polynucleotides of Seq. ID Nos. 1, and 14 to 80 encoding proteins of component B can also be used for obtaining the expressed proteins which proteins can then be linked to a representative of the component A to yield a conjugated protein of component A and B, in particular linked via a linker group. In particular, the proteins of component A encoded by polynucleotides having the sequence of one of the Seq ID Nos. 2, 4, 6, 8, 10, 12, and those represented in Tables 1-3 can be attached to proteins of component B encoded by the polynucleotides of Seq. ID Nos. 1, and 14 to 80.

Another subject matter of the invention is a process for manufacturing the compound of the invention by cloning a component B to yield a polynucleotide; and fuse said polynucleotide coding for component B with a polynucleotide coding for a protein of component A to yield a polynucleotide coding for the compound of the invention;

expressing said polynucleotide coding for the compound of the invention in suitable host, such as *E. coli;* isolation and purification of the compound of the invention.

Subject matter of the invention is further a vector comprising at least one polynucleotide of the invention and a cell having the vector of the invention.

Further a medicament comprising the compound of the invention is also subject matter of the invention as well as a composition of matter comprising the compound of the invention for use in the treatment of a cancer disease, in particular for use in the treatment of proliferating diseases.

The present invention uses human microtubule-associated proteins (MAPs). This approach combines two major advantages: (1) prevention of undesired side effects as described for chimeric immunotoxins; (2) increase of specificity of the human cytolytic fusion protein for proliferating cells including cancer.

DETAILED DESCRIPTION OF THE INVENTION

The compound according to the invention is a compound comprising at least two domains, i.e. one domain having a microtubule-associated protein (MAP) and at least one cell-specific binding domain. The compound according to the invention is usable for therapy of proliferating diseases.

As used herein, the term "immunotoxin" refers to chimeric molecules in which a cell-binding monoclonal antibody or fragments thereof are chemically coupled or genetically fused to a bacterial or plant protein-based toxin. Immunotoxins per se as well as their constructions are well known to the person skilled in the art.

As used herein, the term "human cytolytic fusion protein" refers to a completely human immunotoxins in which a cell-binding human ligand or fragments thereof are chemically coupled or genetically fused to a human enzyme especially a microtubule-associated protein (MAP) or at least a partial sequence of the MAP, the partial sequence having maintained the binding function to a microtubule.

As used herein, the term "component A" of the compound represents the proliferating cell-specific binding structure of the compound of present invention. The component A is selected from the group of internalizing cell surface receptor binding structures consisting of antibodies or their derivatives or fragments thereof, synthetic peptides such as scFv, mimotopes, etc. or chemical molecules such as carbohydrates, lipids, nucleic acids, peptides, vitamins, etc., and/or small molecules with up to 100 atoms with receptor-binding activity like ligands, in particular single atoms, peptidic molecules, non-peptidic molecules, etc., and/or carbohydrate binding proteins and their ligands such as lectins, in particular calnexins, c-type lectins, I-type lectins, m-type lectins, p-type lectins, r-type lectins, galectins and their derivatives, and/or receptor binding molecules such as natural ligands to the cluster of differentiation (CD) antigens, like CD30, CD40, etc., cytokines such as chemokines, colony stimulating factors, type-1 cytokines, type-2 cytokines, interferons, interleukins, lymphokines, monokines, etc., and/or adhesion molecules including their derivatives and mutants, and/or derivatives or combinations of any of the above listed binding structures.

In an additional object of the present invention, component A is binding to a cell surface marker of a healthy or diseased cell belonging to the cluster of differentiation antigens (CD-antigens, Table 1).

In another specific embodiment, the component A is a chemokine or a specifically binding fragment thereof like those provided in table 2 binding to its specific cellular receptors.

In another embodiment, component A is an interleukin or a specifically binding fragment thereof like those provided in table 3 binding to its specific cellular receptor.

As used herein, the term "antibody" refers to polyclonal antibodies, monoclonal antibodies, humanized antibodies, single-chain antibodies, and fragments thereof such as Fab, F(ab)2, Fv, and other fragments which retain the antigen binding function and specificity of the parent antibody.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab)2, Fv, and others which retain the antigen binding function and specificity of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "human antibodies" means that the framework regions of an immunoglobulin are derived from human immunoglobulin sequences.

As used herein, the term "single chain antibody fragments" (scFv) refers to antibodies prepared by determining the binding domains (both heavy and light chains) of a binding antibody, and supplying a linking moiety, which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

The "component B" of the present invention is a protein which interacts with microtubule by stabilizing the microtubule due to the interaction. The skilled person designates such protein as microtubules associated protein (MAP). These protein MAPs are binding to the tubulin subunits that make up microtubules to regulate their stability. Different MAPs have been identified in different cell types, and they have been found to carry out defined functions which include both stabilizing and destabilizing microtubules, guiding microtubules towards specific cellular locations, cross-linking microtubules and mediating the interactions of microtubules with other proteins in the cell.

It is characteristic, that within the cell, MAPs bind directly to the tubulin dimers of microtubules. This binding can occur with either polymerized or depolymerized tubulin, and in most cases leads to the stabilization of microtubule structure, further encouraging polymerization. Usually, it is the C-terminal domain of the MAP that interacts with tubulin, while the N-terminal domain can bind with cellular vesicles, intermediate filaments or other microtubules. MAP-microtubule binding is believed to be regulated through MAP phosphorylation. This is accomplished through the function of the microtubule-affinity-regulating-kinase (MARK) protein. Phosphorylation of the MAP by the MARK causes the MAP to detach from any bound microtubules. This detachment is usually associated with a destabilization of the microtubule causing it to fall apart. In this way the stabilization of microtubules by MAPs is regulated within the cell through phosphorylation.

The numerous identified MAPs have been largely divided into two categories: Type I including MAP1 proteins and type II including MAP2, MAP4 and tau proteins.

MAP1a and MAP1b which make up the MAP1 family, bind to microtubules differently than other MAPs, utilizing charged interactions. While the C-terminals of these MAPs bind the microtubules, the N-terminals bind other parts of the cytoskeleton or the plasma membrane to control spacing of the microtubule within the cell. Members of the MAP1 family are found in the axons and dendrites of nerve cells.

Also found exclusively in nerve cells are the most well studied MAPs, MAP2 and tau (MAPT) as representatives of type II, which participate in determining the structure of different parts of nerve cells—MAP2 being found mostly in dendrites and tau in the axon. These proteins have a conserved C-terminal microtubule-binding domain and variable N-terminal domains projecting outwards probably interacting with other proteins. MAP2 and tau stabilize microtubules, and thus shift the reaction kinetics in favor of addition of new subunits, accelerating microtubule growth. Both MAP2 and tau have been shown to stabilize microtubules by binding to the outer surface of the microtubule protofilaments. MAP2 binds in a cooperative manner with many MAP2 proteins binding a single microtubule to promote stabilization. Tau as well helps to stabilize microtubules, however it forms the additional, important function of facilitating bundling of microtubules within the nerve cell.

The function of tau has been linked to the neurological condition known as Alzheimer's Disease. In the nervous tissue of Alzheimer's patients tau forms abnormal aggregates. This aggregated tau is often severely modified, most commonly through hyperphosphorylation. Phosphorylation of MAPs causes them to detach from microtubules. Thus, the hyperphosphorylation of tau leads to massive detachment which in turn greatly reduces the stability of microtubules in nerve cells. This increase in microtubule instability may be one of the main causes of the symptoms of Alzheimer's Disease.

In contrast to the MAPs described above, MAP4 is not confined to just nerve cells, but rather can be found in nearly all types of cells. Like MAP2 and tau, MAP4 is responsible for stabilization of microtubules. MAP4 has also been linked to the process of cell division.

Besides the classic MAP groups, MAPs have been identified that bind the length of the microtubules. These include STOP (also known as MAP6), and enscosin (also known as MAP7).

In addition, plus end tracking proteins, which bind to the very tip of growing microtubules, have also been identified. These include EB1, EB2, EB3, p150Glued, Dynamitin, Lisl, CLIP170, CLIP115, CLASP1, and CLASP2.

Another MAP whose function has been investigated during cell division is known as XMAP215 (the "X" stands for *Xenopus*). XMAP215 has generally been linked to microtubule stabilization. During mitosis the dynamic instability of microtubules has been observed to rise approximately tenfold. This is partly due to phosphorylation of XMAP215, which makes catastrophes (rapid depolymerization of microtubules) more likely. In this way the phosphorylation of MAPs plays a role in mitosis.

There are many other proteins which affect microtubule behavior, such as catastrophin, which destabilizes microtubules, katanin, which severs them, and a number of motor proteins that transport vesicles along them. Certain motor proteins were originally designated as MAPs before it was found that they utilized ATP hydrolysis to transport cargo. In general, all these proteins are not considered "MAPs" because they do not bind directly to tubulin monomers, a defining characteristic of MAPs. MAPs bind directly to microtubules to stabilize or destabilize them and link them to various cellular components including other microtubules. That is why the skilled person regards MAPs by its clear function as a well defined molecular species rather than an arbitrary collection of proteins.

In particular the component B of the compound of the invention is selected from the group consisting of MAP ($\tau$-protein) represented by the protein having the amino acid sequence encoded by the polynucleotide of the Seq ID No. 1, KIF1, KIF2A, KIF4A, KIF5A, KIF5B, KIF6, KIF7, KIF9, KIF10, KIF11, KIF12, KIF13B, KIF14, KIF15, KIF17, KIF19, KIF22, KIF23, KIF24, KIF25, KIF26, KIF27, KIFC1, KIFC2, KIFC3, DNAH1, DNAH2, DNAH3, DNAH5, DNAH6, DNAH7, DNAH8, DNAH9, DNAH10, DNAH11, DNAH12, DNAH14, DNAI1, DNAI2, DNAL1, DNAL4, Tau, Stathmin, Gephyrin, MAP1a, MAP1b, MAP2, MAP4, XMAP5, MAP6, MAP7, MAP8, MAP9, DCTN1, TUBA1, TUBA2, TUBA3, TUBA4, TUBA6, TUBA8, TEKT1, TEKT2, TEKT3, TEKT4, TEKT5, DNM1, DNM2, and DNM3, such as represented by the proteins having one of the amino acid sequences encoded by the polynucleotide of one of the Seq ID Nos. 14-80. The term "target cell" refers to cells carrying an extracellular surface structure to which the component A of the compound actively or passively binds. Target cells are thus cells to which the component A of the compound can bind. The target cells are further characterized by their ability to internalize the compound according to the present invention upon binding of component A.

The term "soluble" refers to the ability of the compound to stay in solution when recombinantly expressed, in particular during protein purification, enabling high yields. The term "soluble" also refers to the state of the compound in fluidic systems inside an organism, until specifically attached to the target cell/tissue. The term also refers to the state of the compound inside a cell upon release from any kind of incorporation vesicles.

The term "endogenous" refers to the localization of the compound in the surrounding/environment of a given target cell.

The term "synthetic" refers to a man-made compound, not found in nature. The term also comprises the meaning of "recombinant".

The term "recombinant" refers to the preparation of molecules, in particular the covalent joining of molecules from different sources, by any one of the known methods of molecular biology. As used in the present invention, the term "recombinant" refers in particular to the fusion of the antibody part to the protein, which interacts with microtubule, by any one of the known methods of molecular biology, such as through production of single chain antibodies. The recombinant DNA molecule encoding the recombinant compound—in this case a fusion protein—comprising the antibody part and the protein, which interacts with microtubule, are recombinantly expressed. Recombinant human cytolytic fusion proteins produced in this way may be isolated by any technique known in the field of recombinant DNA expression technology suitable for this purpose.

The compound of the invention can be a soluble, endogenous, synthetic and/or recombinantly manufactured compound.

The term "derivative" refers to a mutated or modified protein, which has retained its characterizing activity, i.e. binding activity or microtubules stabilizing activity. Particular preferred are constitutively active derivatives. The term derivative comprises proteins, which carry at least one amino acid substitution, deletion, addition, a swapping of a single domain or at least one modification of at least one amino acid. Preferred are derivatives, which carry 20 such changes, more preferred are those with 10 such changes and most preferred are those with 1 to 5 such changes. Modifications, which can occur, are phosphorylation, acetylation, methylation, prenylation and sulfation.

As used herein, the term "vector" comprises DNA and RNA forms of a plasmid, a cosmid, a phage, phagemid, derivatives of them, or a virus. A vector comprises control sequences and coding sequences.

The term "expression of the recombinant genes encoding the recombinant compound", wherein the recombinant compound is a single chain antibody-toxin moiety fusion polypeptide, refers to the transformation and/or transfection of a host cell with a nucleic acid or vector encoding such a compound, and culturing said host cells selected from the group of bacteria, such as *E. coli*, and/or in yeast, such as in *S. cerevisiae*, and/or in established mammalian or insect cell lines, such as CHO, COS, BHK, 293T and MDCK cells, and/or in primary cells, such as human cells, non-human vertebrate cells, and/or in invertebrate cells such as insect cells, and the synthesis and translation of the corresponding mRNA, finally giving rise to the recombinant protein, the recombinant compound. In more detail, the term "expression of the recombinant genes encoding the recombinant compound", comprises the following steps:

Transformation of an appropriate cellular host with a recombinant vector, in which a nucleotide sequence coding for the fusion protein had been inserted under the control of the appropriate regulatory elements, particularly a promoter recognized by the polymerases of the cellular host. In the case of a prokaryotic host, an appropriate ribosome-binding site (RBS) also precedes the nucleotide sequence coding for the fusion protein, enabling the translation in said cellular host. In the case of an eukaryotic host any artificial signal sequence or pre/pro sequence may be provided, or the natural signal sequence may be employed. The transformed cellular host is cultured under conditions enabling the expression of said insert.

The compound of the invention, in particular soluble, endogenous compound can also be manufactured by chemically linking a representative of component A with one of component B. The skilled person has an arsenal of methods at his or her disposal to chemically combine two proteins. It is e.g. possible to directly couple component A and B, however, for reasons known to the skilled person when considering coupling reactions and proteins to be coupled, he or she provides for a "spacer" between the two components. The spacer between the two proteins is advantageous since the two proteins are kept apart to some extent e.g. reducing possible sterical interaction between the two components.

The term "supplementary component S", refers to an additional component of the compound comprising A and B. The supplementary component S contributes features and properties to the compound, which allow efficient preparation and/or modify the effectiveness of the compound:

- translocation of the apoptotic agents into the target cells (e.g., translocation domain, membrane transfer peptides, amphiphatic sequences);
- intracellular activation/separation of component B (intracellular proteases).

Thus the supplementary component S is selected from the group of translocation domain, membrane transfer peptides, amphiphatic sequences and consensus sequences for intracellular proteases.

The invention also relates to nucleic acid molecules, such as DNA and/or RNA, or vectors, which code for the compound of the present invention or for individual components for preparing the compound. The feasibility of the expression of the nucleic acids encoding a recombinant compound in eukaryotic cells of human origin is successfully documented here, as well as the feasibility to use the compound as a specific agent in eukaryotic cells of human origin for interaction to microtubules. This suggests the suitability of nucleic acids coding for a compound according to the invention also for non germ line gene-therapeutic approaches. A person skilled in the art is capable of recognizing the various aspects and possibilities of gene-therapeutic interventions in connection with the various diseases to be treated.

Also claimed are cells or in vitro translation systems, which synthesize complete compounds according to the invention or individual components thereof, after transformation and/or transfection with, or addition of the nucleic acid molecules or vectors according to the invention.

Cells or organisms according to the invention are either of prokaryotic origin, especially from *E. coli, B. subtilis, S. carnosus, S. coelicolor, Marinococcus* sp., or eukaryotic origin, especially from *Saccharomyces* sp., *Aspergillus* sp., *Spodoptera* sp., *P. pastoris*, primary or cultivated mammalian cells, eukaryotic cell lines (e.g., CHO, Cos or 293) or plants (e.g. *N. tabacum*).

The invention also relates to medicaments comprising the compound according to the present invention and/or the nucleic acid or vectors encoding the compound of present invention. Typically, the compounds according to the invention are administered in physiologically acceptable dosage forms. These include, for example, Tris, NaCl, phosphate buffers and all approved buffer systems, especially including buffer systems, which are characterized by the addition of approved protein stabilizers. The administration is effected, in particular, by parenteral, intravenous, subcutaneous, intramuscular, intratumoral, transnasal administrations, and by transmucosal application.

The dosage of the compounds according to the invention to be administered must be established for each application in each disease to be newly treated by clinical phase I studies (dose-escalation studies).

Nucleic acids or vectors, which code for a compound according to the invention, are advantageously administered in physiologically acceptable dosage forms. These include, for example, Tris, NaCl, phosphate buffers and all approved buffer systems, especially including buffer systems, which are characterized by the addition of approved stabilizers for the nucleic acids and/or vectors to be used. The administration is effected, in particular, by parenteral, intravenous, subcutaneous, intramuscular, intratumoral, transnasal administrations, and by transmucosal application.

The compound according to the invention, nucleic acid molecules coding therefore and/or cells or in vitro translation systems can be used for the preparation of a medicament for treating tumor diseases, in particular leukemia such as acute myeloid leukemia.

The invention is further described—by way of example—by the cloning of a selected MAP candidate as fusion to H22(scFv) specific for binding to CD64, which is upregulated on cells of AML and CML patients, and expressed this human cytolytic fusion protein in *E. coli*. After affinity purification, identity and purity of obtained proteins were confirmed by SDS-PAGE followed by Coomassie staining and Western Blotting. Specific binding was verified by flow cytometry. Proliferation-dependent anti-tumor cytotoxicity was finally demonstrated in viability assays in vitro. In vivo efficacy was confirmed in a cutaneous inflammation model in mice. The results demonstrate how fully human MAPs can be exploited as effective component of a compound of the invention, in particular the human cytolytic fusion protein in form of a fusion protein for therapy of proliferative diseases including cancer. In addition, the cytostatic nature of human MAPs renders anti-cancer human cytolytic fusion protein even more selective as non-proliferating cells also expressing the target molecule are not affected.

All references cited herein are incorporated by reference to the full extent to which the incorporation is not inconsistent with the express teachings herein.

The invention is further disclosed in greater detail in the following non-limiting examples. It has to be noted, that although using the wt-MAP tau works according to the invention it was decided to use—instead of the even more easily available wt-tau—a double mutation in order to quench two potential phosphorylation sites of the tau protein. As explained before highly phosphorylated tau-protein has been connected with the etiology of Alzheimer's disease.

EXAMPLES

Construction of Open Reading Frames for Human MAP-Based Cytolytic Fusion Proteins Different components A like antibody fragments and natural ligands for receptors including soluble ligands, receptors, chemokines, growth factors or interleukins or fragments thereof were cloned in an open reading frame (ORF) together with different MAPs (component B). The ORF of MAPs was modified with 5'-NotI and 3'-BlpI restriction sites by PCR followed by ligation into a NotI/BlpI-linearized pMT vector already containing the sequence for component A (e.g. H22(scFv)) thus replacing the OFR of ETA (FIG. 1). Furthermore, two point mutations resulting in the removal of two putative phosphorylation sites S156A and S204A and a 3' nuclear localization sequence (NLS) were introduced into the ORF of MAP by PCR. Complete expression cassettes for MAP-based cytolytic fusion proteins are exemplified in FIG. 2*a-f*. Successful cloning was confirmed by test digestion and sequencing. The exemplified ORFs are listed by their sequences. See list of sequences ID 1-13 in FIG. 3.

Expression and Purification of Recombinant Human MAP-Based Cytolytic Fusion Proteins MAP-based MAP-based cytolytic fusion proteins were expressed in *Escherichia coli* BL21 (DE3) (*E. coli*) using the protocol for periplasmic stress expression in the presence of compatible solutes as described previously [26]. Briefly, after transformation bacteria were grown to an OD of 1.6 followed by stress induction with 500 mM D-sorbitol, 10 mM betaine monohydrate and 4% (w/w) NaCl. After an incubation of 30 min at 26° C. with shaking (180 rpm), protein expression was induced by 2 mM IPTG. Bacteria were harvested 18 h after induction by centrifugation (4,000×g, 10 min, 4° C.) and frozen at −80° C. overnight. The frozen pellet was resuspended in preparation buffer (75 mM Tris-HCl, 300 mM NaCl, 5 mM DTT, 10 mM EDTA, 10% (v/w) glycerol, pH 8.0 containing a complete protease inhibitor cocktail (Roche, Germany)) at 4° C. and sonicated 5 times for 60 sec at 200 W. Cell debris were removed by centrifugation (24,000×g, 20 min, 4° C.) and for removal of EDTA protein preparation was dialyzed against PBS (pH 7.4) at 4° C. overnight. Human MAP-based cytolytic fusion proteins were purified by immobilized metal-ion affinity chromatography (IMAC) using Ni-NTA Sepharose (Qiagen, Germany) and size exclusion chromatography (SEC) against PBS (pH 7.4) with Bio-Prep SE-100/17 (Bio-Rad, Germany) columns according to the manufacturers' instructions.

SDS-PAGE and Western Blot Analysis

Figure 4:
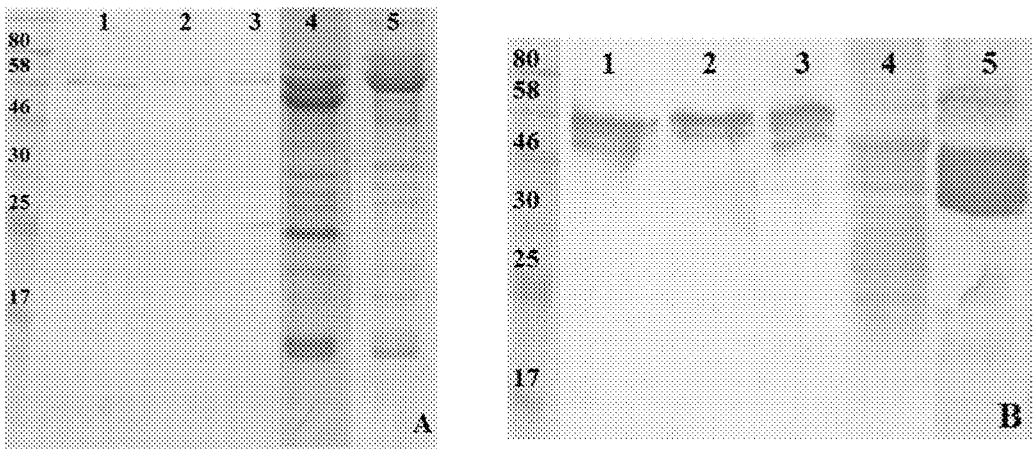
FIG. 4 Shows a 12% SDS-PAGE gel of different MAP-based human cytolytic fusion protein after purification via IMAC and SEC.

Purity and quantity were assessed by sodium dodecylsulfate polyacrylamide gel electrophoresis (SDS-PAGE) and Western blot as described previously [27]. Protein concentration were quantified by densitometry using AIDA software after Coomassie staining in comparison with bovine serum albumin standards and verified by Bradford assays (Bio-Rad, Germany). Detection of human MAP-based cytolytic fusion proteins on Western Blot was achieved using anti-human MAP (1:25,000; Thermo Scientific, Germany) or mouse-anti-Penta-His (1:5,000; Qiagen, Germany) in combination with an alkaline phosphatase-conjugated antimouse-IgG mAb (1:5,000; Sigma, Germany) followed by staining with Tris-HCl (pH 8.0) and 0.2 mg/ml naphtol-AS-Bi-phosphate (Sigma, Germany) supplemented with 1 mg/ml Fast-Red (Serva, Germany). FIG. 4 shows a 12% SDS-PAGE gel (A: Coomassie stained; B: Western Blot) of different human MAP-based cytolytic fusion proteins after purification via IMAC and SEC. The gel contains: 1, 425 (scFv)-MAP; 2, scFv35-MAP; 3, H22(scFv)-MAP; 4, EGF-MAP; 5, anti-EpCAM(scFv)-MAP. Protein size is shown in kDa.

Binding Analysis Via Flow Cytometry

Cell binding activity of purified human MAP-based cytolytic fusion proteins was assessed by flow cytometry.

Figure 5A:
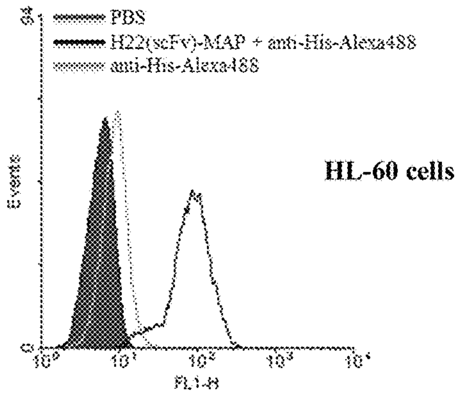
FIG. 5: shows cell binding activity of purified MAP-based human cytolytic fusion protein assessed by flow cytometry.
Figure 5B:
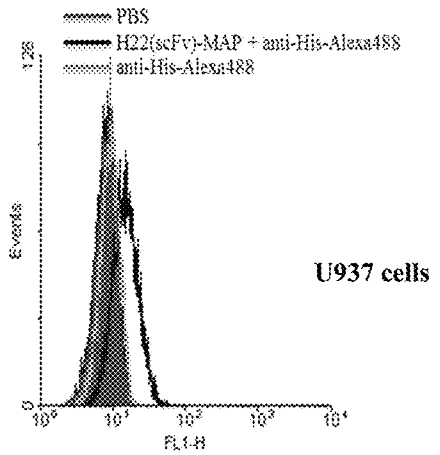
Figure 5C:
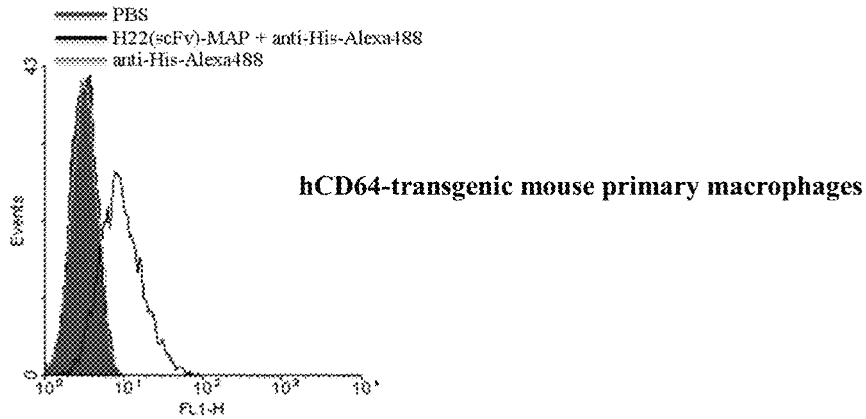
Figure 5D:
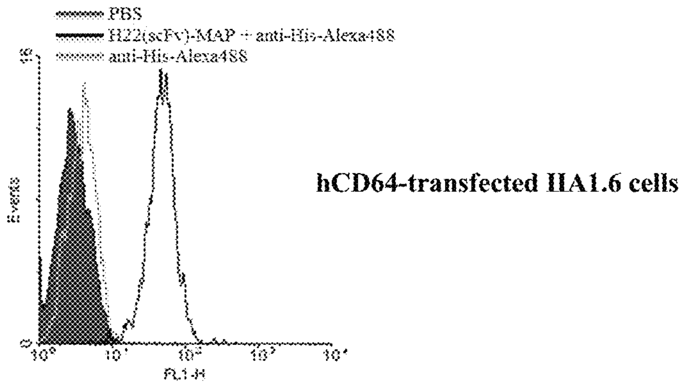
Figure 5E:
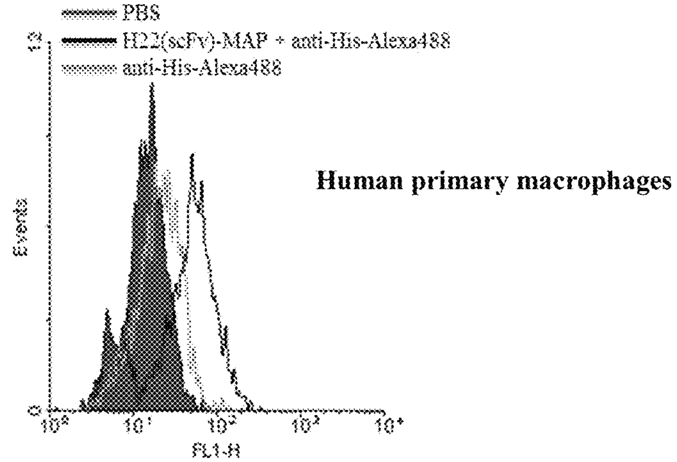

For H22(scFv)-MAP, binding was tested on human CD64 (hCD64)-positive leukemia cell lines HL-60 (FIG. 5*a*) and U937 (FIG. 5*b*), a mouse B-cell/macrophage cell line stably transfected with hCD64 IIA1.6 (FIG. 5*c*), murine peritoneal macrophages derived from hCD64-transgenic mice (FIG. 5*d*), or peripheral blood mononuclear cells derived (PBMC) human macrophages (FIG. 5*e*). All cells were stimulated with IFN-γ (50 U/ml for HL-60, U937 and IIA1.6; 100 U/ml for murine and human primary macrophages; Peprotech, Germany) 24 h prior to analysis.

Figure 5F:
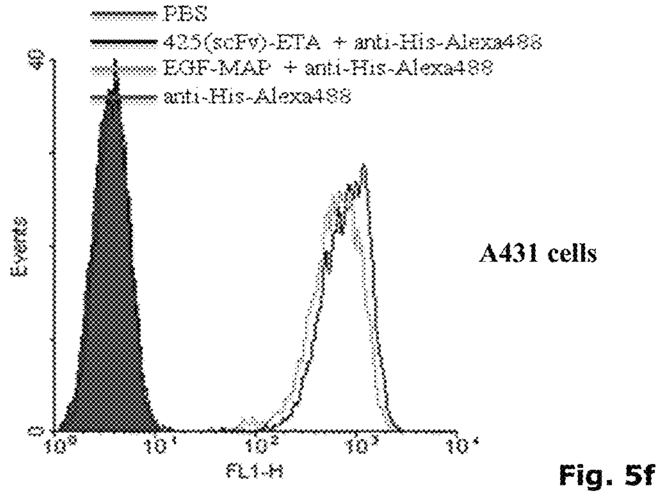
Figure 5G:
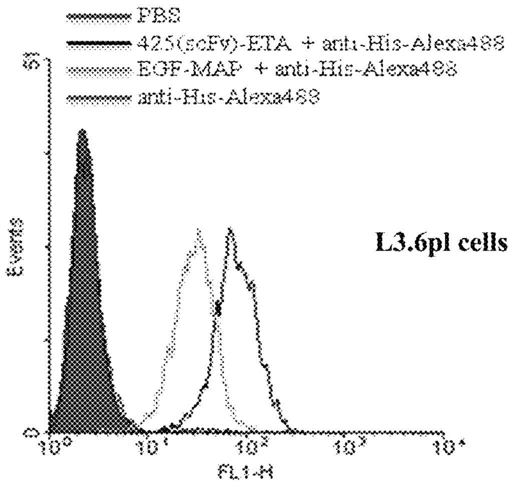
Figure 5H:
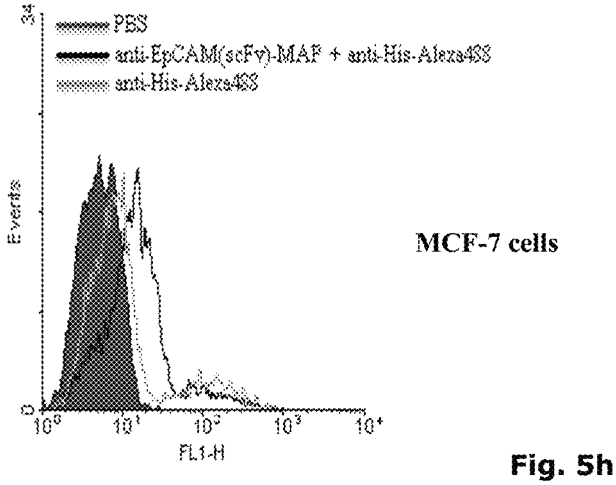
Figure 5I:
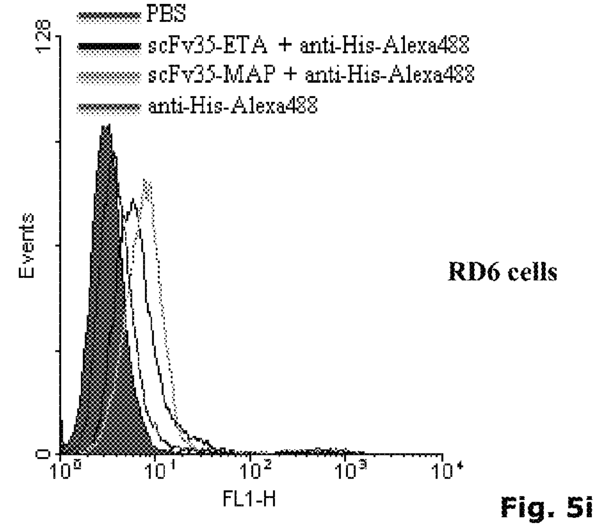
Figure 5J:
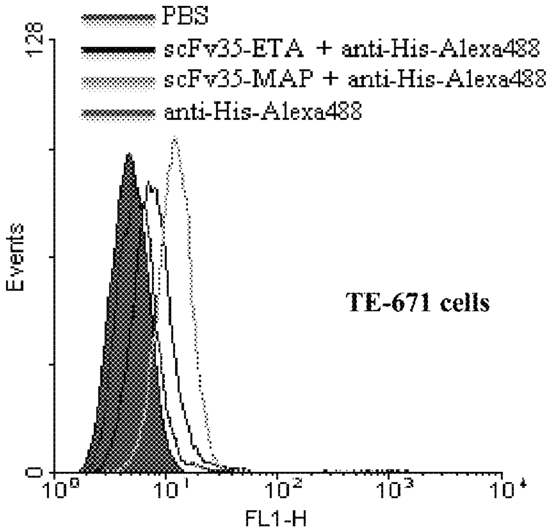
Figure 5K:
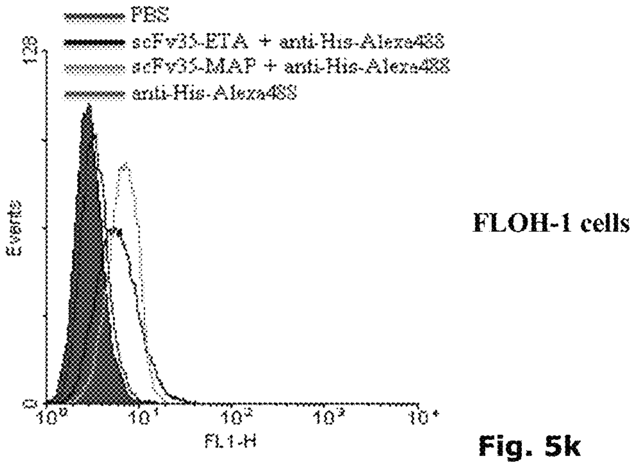
Figure 5L:
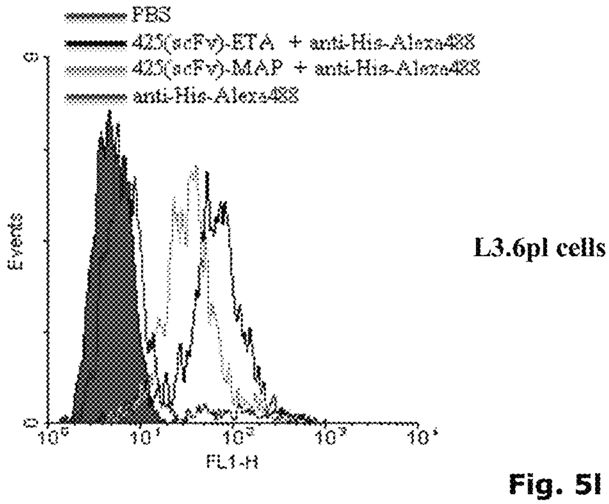
Figure 5M:
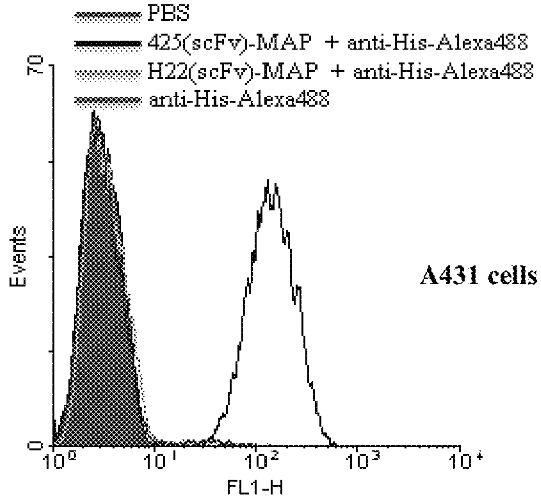
Figure 6A:
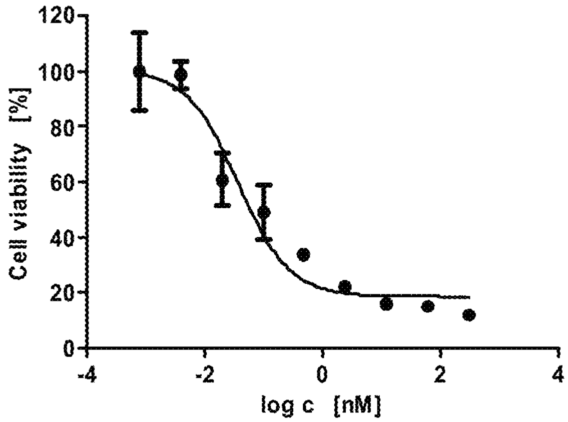
FIG. 6: Shows the results of cytotoxicity analysis.
Figure 6B:
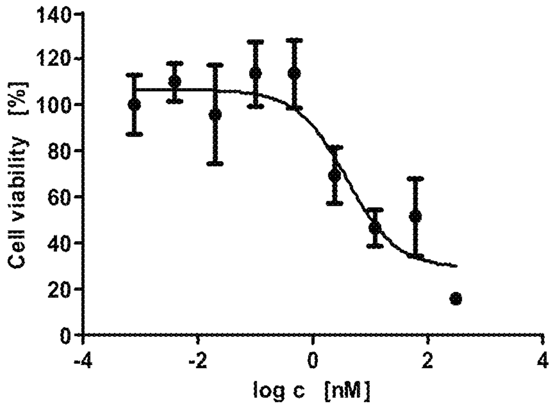
Figure 6C:
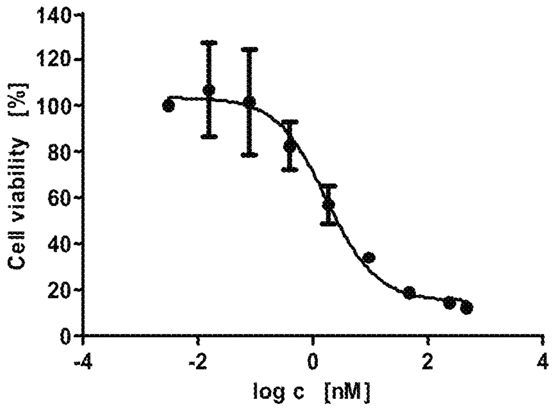
Figure 6D:
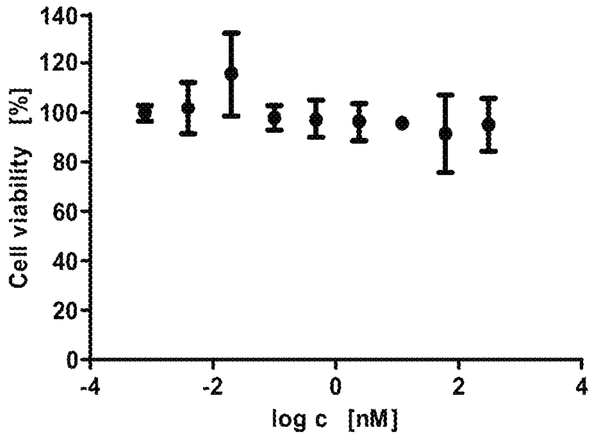
Figure 6E:
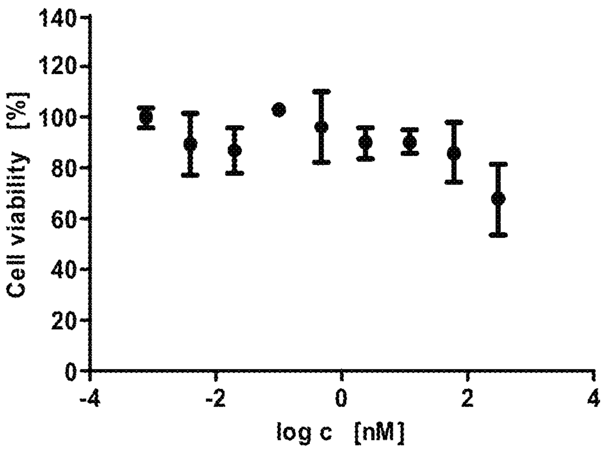
Figure 6F:
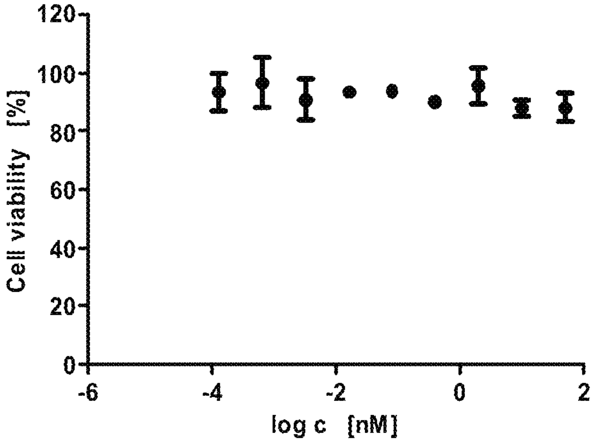
Figure 6G:
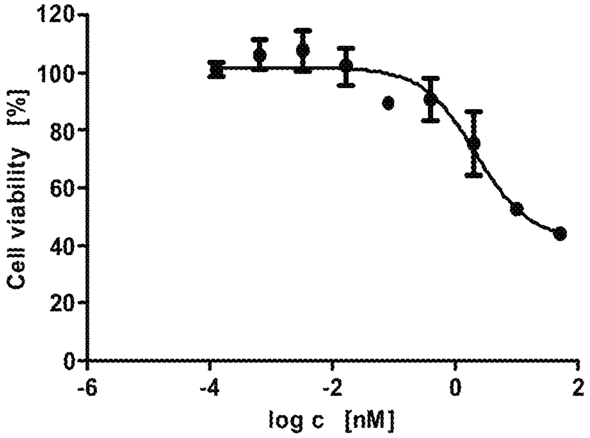
Figure 6H:
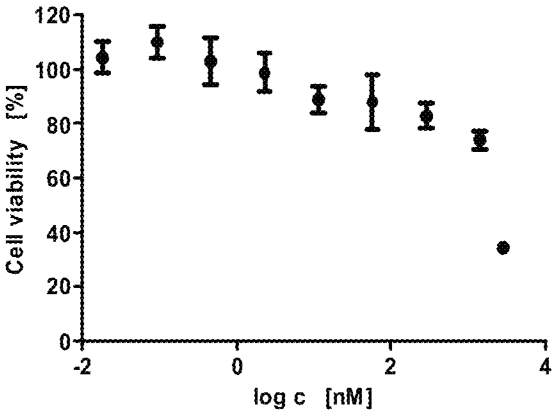
Figure 6I:
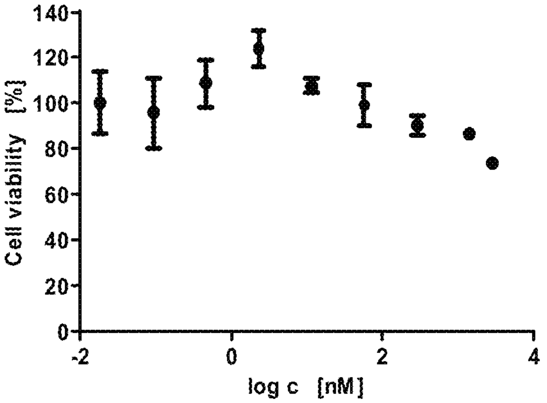
Figure 6J:
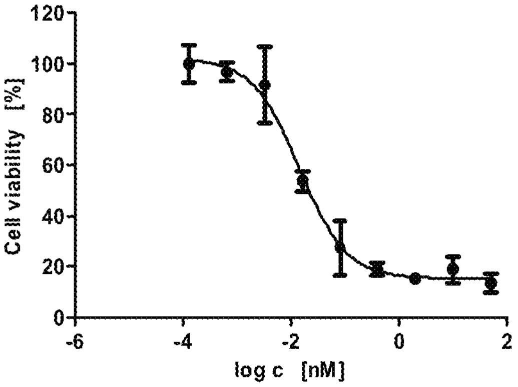
Figure 6K:
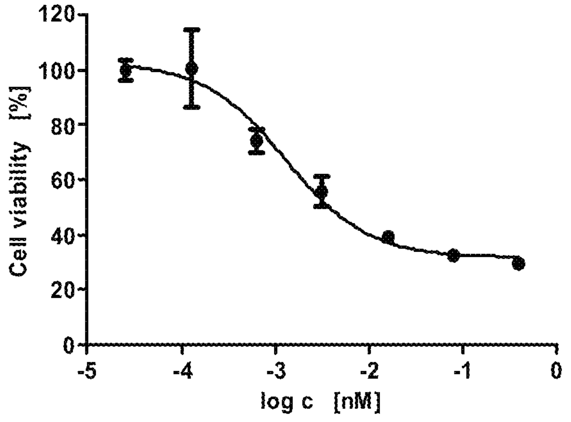
Figure 6L:
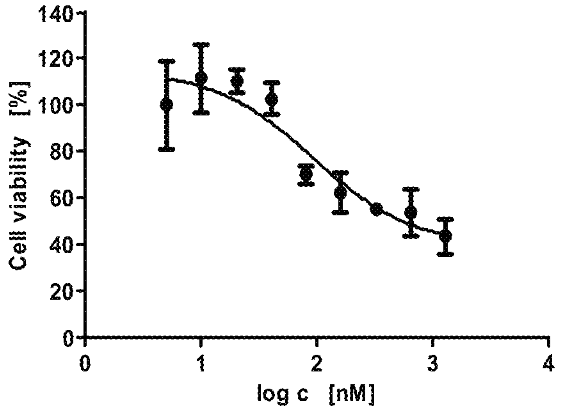
Figure 6M:
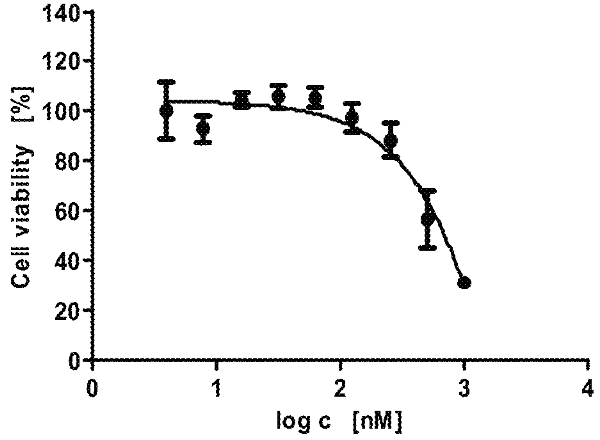
Figure 6O:
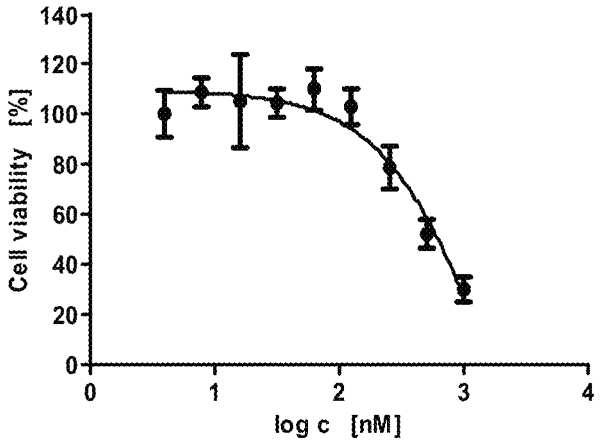
Figure 6N:
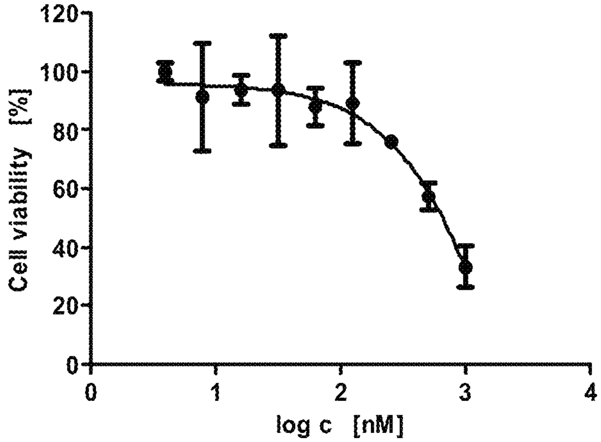

For 425(scFv)-MAP and EGF-MAP, the EGFR-positive cell lines A431 (FIG. 5*m* and FIG. 5*f*, respectively) and L3.6pl (FIG. 5*l* and FIG. 5*g*, respectively) were used.

For scFv35-MAP, the fAchR-positive cell lines FLOH-1 (FIG. 5*k*), RD6 (FIG. 5*i*) and TE-671 (FIG. 5*j*) were used.

For anti-EpCAM(scFv)-MAP, the EpCAM-positive cell line MCF-7 (FIG. 5*h*) was used.

For Ki4-MAP, the CD30-positive cell lines L540 and L428 were used (data not shown).

A total of $4\times10^5$ cells were incubated with 50-100 nM of the human MAP-based cytolytic fusion protein for 30 min on ice followed by washing with PBS containing 0.5% BSA and 2 mM EDTA. Finally, cells were incubated with Penta-His-Alexa Fluor 488 Conjugate (1:100; Qiagen, Germany) for 30 min on ice, washed twice as described above and analyzed by FACS Calibur (Becton Dickinson, Germany). FIG. 5*a-m* exemplifies the results of binding analysis.

In Vitro Cellular Cytotoxicity

Figure 7:
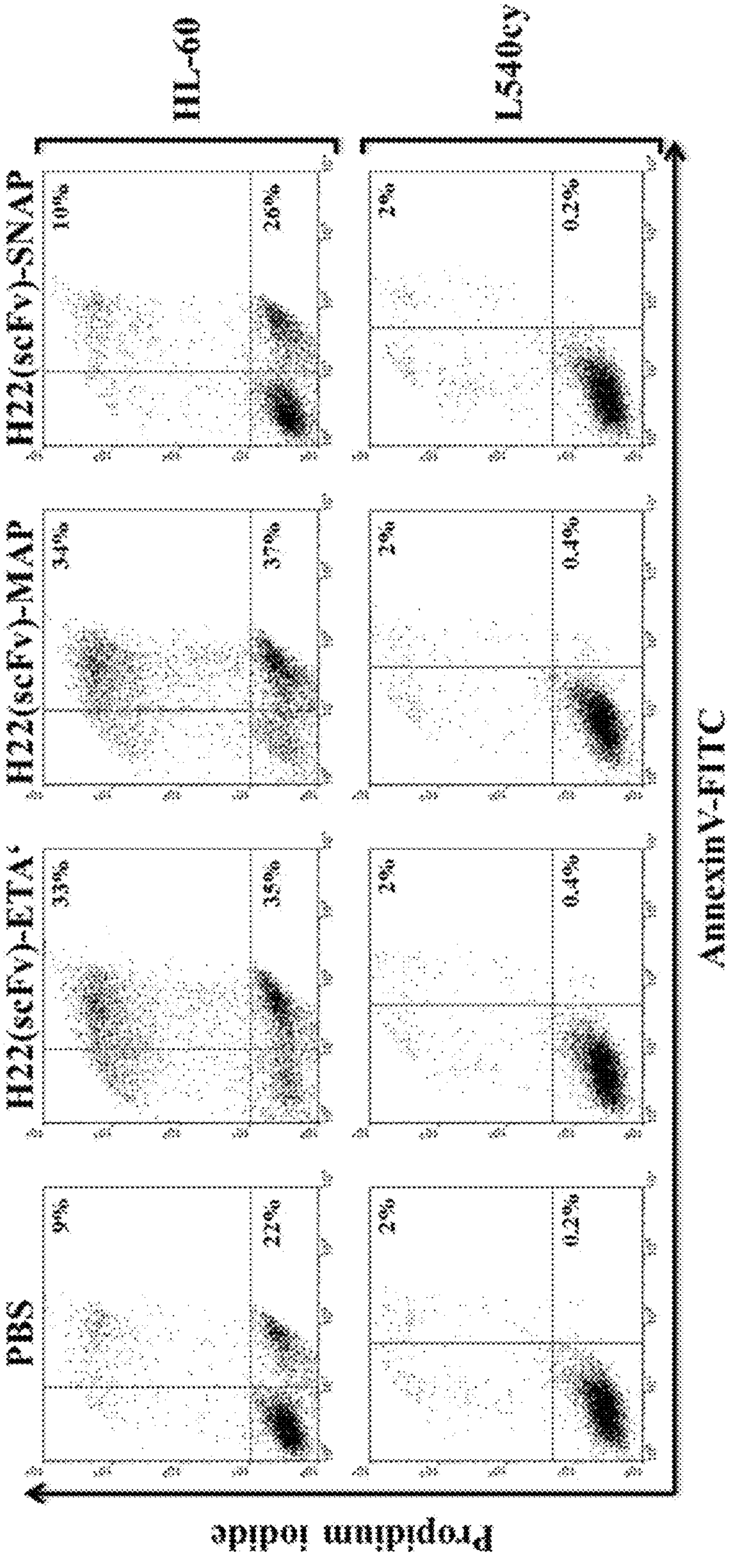
FIG. 7: Shows the results of an AnnexinV/PI assay.
Figure 7:
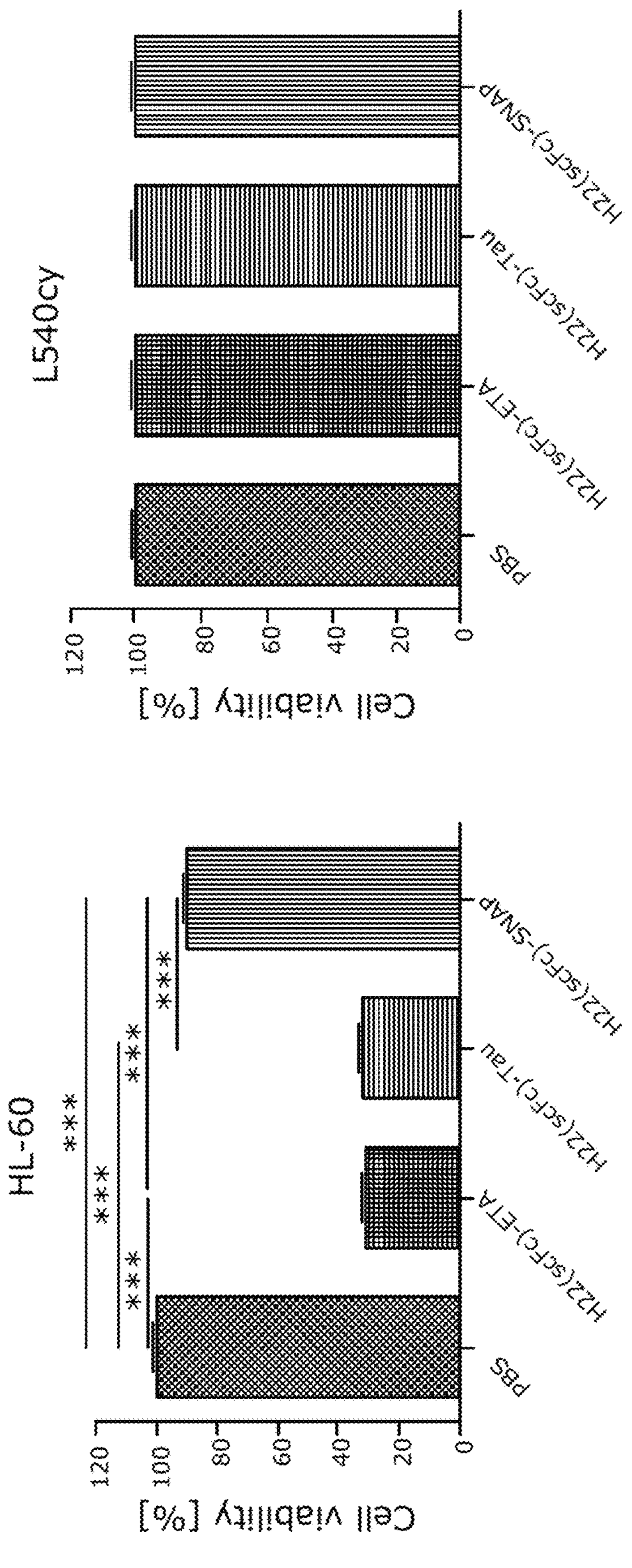

The cytotoxic effect of human MAP-based cytolytic fusion proteins towards target cells was assessed by measuring the conversion of XTT to a water soluble orange formazan dye. For H22(scFv)-MAP, $1\text{-}5\times10^5$ cells/well were seeded into a 96-well microtiter plate and stimulated with 50-100 U/ml IFN-γ or 20 ng/ml phorbol 12-myristate 13-acetate (PMA) for induction of proliferation arrest for 24 h at 37° C., 5% $CO_2$ and 100% humidity. After stimulation, various dilutions of the human MAP-based cytolytic fusion proteins were added to the wells and cells were incubated for further 72 h at conditions mentioned above. For all other MAP-based constructs, $1\text{-}5\times10^5$ cells/well were seeded into a 96-well microtiter plate and incubated with various dilutions of the human cytolytic fusion protein for 72 h at conditions mentioned above. For the read out, 50 μl of XTT/phenanzine methosulfate (100:1; Serva and Sigma-Aldrich, Germany) solution were added to each well followed by incubation for 3-4 h. Absorbances at 450 and 630 nm were measured using an Epoch Microplate Spectrophotometer (Biotek, Germany). The concentration required to achieve 50% reduction of protein synthesis ($IC_{50}$) relative to untreated control cells was calculated using GraphPad Prism (GraphPad Software, USA). All experiments were carried out in triplicates. FIG. 6 exemplifies the results of cytotoxicity analysis as follows:

a: IFN-γ stimulated (proliferating) HL-60 cells+H22(scFv)-MAP/$IC_{50}$: 36 pM b: IFN-γ stimulated (proliferating) U937 cells+H22(scFv)-MAP/$IC_{50}$: 3.8 nM c: IFN-γ stimulated (proliferating) hCD64_IIA1.6 cells+H22(scFv)-MAP/$IC_{50}$: 1.7 nM d: IFN-γ stimulated (non-proliferating) mouse primary macrophages+H22(scFv)-MAP e: IFN-γ stimulated (non-proliferating) human primary macrophages+H22(scFv)-MAP f: PMA stimulated (non-proliferating) HL-60 cells+H22 (scFv)-MAP g: PMA stimulated (non-proliferating) HL-60 cells+H22 (scFv)-ETA h: L3.6pl cells (non-proliferating; induced by binding of 425(scFv))+425(scFv)-MAP i: A431 cells (non-proliferating; induced by binding of 425(scFv))+425(scFv)-MAP j: A431 cells (non-proliferating; induced by binding of 425(scFv))+425(scFv)-ETA k: L3.6pl cells (non-proliferating; induced by binding of 425(scFv))+425(scFv)-ETA l: MCF-7 cells+anti-EpCAM(scFv)-MAP m: fAChR-positive FLOH-1 cells+scFv35-MAP n: fAChR-positive RD6 cells+scFv35-MAP o: fAChR-positive TE-671 cells+scFv35-MAP Apoptosis Assay To determine the mechanism of killing exhibited by human MAP-based cytolytic fusion proteins, an AnnexinV/PI assay was performed. For H22(scFv)-MAP, HL-60 cells were stimulated with 50 U/ml of IFN-γ (Peprotech, Germany) for 24 h followed by addition of 50 nM H22(scFv)-MAP. The same amount of H22(scFv)-ETA and H22(scFv)-SNAP were used as controls. The CD64-negative cell line L540cy was used as negative control (FIG. 7). After incubation for further 24 h with the human MAP-based cytolytic fusion protein, cells were washed twice with 1× AnnexinV binding buffer (10 mM Hepes/NaOH (pH 7.4), 140 mM NaCl, 2.5 mM $CaCl_2$) and stained with AnnexinV-FITC (eBioscience, Germany) for 30 min at RT. Finally, cells were washed again as described above, resuspended in 1× AnnexinV buffer containing 10 μg/ml propidium iodide and analyzed by flow cytometry using a FACS Calibur (Becton Dickinson, Germany).

In Vivo Efficacy

H22(scFv)-MAP

Nude transgenic male C57/Bl6/SKH1-E mice (>6 weeks) expressing hCD64 were used in all experiments. Non-transgenic male C57/Bl6/SKH1-E mice were used as controls. To induce chronic cutaneous inflammation, 5% (m/v) SDS in PBS was applied to a 1.5×1.5 cm skin surface area on both flanks of each mouse daily for 11 consecutive days. For administration of the human MAP-based cytolytic fusion protein, animals were anaesthetized with isofluran. Three intradermal injections of 20 μl of 1 μM human MAP-based cytolytic fusion protein, or PBS control, were administered contralaterally. The immunotoxin H22(scFv)-ETA' was used as a positive control. Finally, animals were sacrificed and skin biopsies were taken, snap frozen in liquid nitrogen, and stored at −80° C. prior to use.

Immunohistochemistry

Biopsies were cut into 8 μm sections on a freezing microtome and mounted on coated slides. After drying for 48-72 h, sections were fixed for 10 min with dry acetone and air-dried. Slides were incubated with FITC-conjugated primary antibody (1:40) in PBS 1% normal mouse serum for 45 min. Slides were washed three times for 5 min with PBS, 0.05% Tween, after which alkaline phosphatase (AP) conjugated sheep anti-FITC (Southern Biotech, Germany, 1:400) in PBS (1% sheep serum for 30 min) was added. After washing twice in PBS/Tween and once in Tris-HCl (0.1 M, pH 8.5), AP activity was demonstrated using naphthol AS-BI phosphate (sodium salt, 50 mg/100 ml; Sigma-Aldrich, Germany) as substrate and new fuchsin (10 mg/100 ml; Merck, USA) as chromogen dissolved in 0.1 M Tris-HCl, pH 8.5, resulting in pink/red staining. Endogenous AP activity was inhibited by addition of levamisole (35 mg/100 ml, Sigma-Aldrich, Germany) to the reaction mixture. Slides were lightly counterstained with hematoxylin. For H22 (scFv)-MAP, successful elimination hCD64-positive inflammatory macrophages is shown in FIG. 8. Further MAPs potentially suitable as cytostatic proteins The herein presented approach of generating fully human cytolytic fusion proteins by fusing a binding domain with a human MAP describes a general mechanism. Hence, the choice of the MAP is not limited to the sequence presented here but can be extended to other MAPs. Further exemplified ORFs of human MAPs are listed by their sequences. See list of sequences ID 14-80 in FIG. 9.

REFERENCES

1. Cawley, D. B., et al. (1980) Epidermal growth factor-toxin A chain conjugates: EGF-ricin A is a potent toxin while EGF-diphtheria fragment A is nontoxic. *Cell.* 22, 563-570.
2. Hu, C. C., et al. (2010) Investigation of a plasmid containing a novel immunotoxin VEGF165-PE38 gene for antiangiogenic therapy in a malignant glioma model. *Int J Cancer.* 127, 2222-2229.
3. Murphy, J. R., et al. (1986) Genetic construction, expression, and melanoma-selective cytotoxicity of a diphtheria toxin-related alpha-melanocyte-stimulating hormone fusion protein. *Proc Natl Acad Sci USA.* 83, 8258-8262.
4. Williams, D. P., et al. (1987) Diphtheria toxin receptor binding domain substitution with interleukin-2: genetic construction and properties of a diphtheria toxin-related interleukin-2 fusion protein. *Protein Eng.* 1, 493-498.
5. Kreitman, R. J. (2009) Recombinant immunotoxins for the treatment of chemoresistant hematologic malignancies. *Curr Pharm Des.* 15, 2652-2664.
6. Blythman, H. E., et al. (1981) Immunotoxins: hybrid molecules of monoclonal antibodies and a toxin subunit specifically kill tumour cells. *Nature.* 290, 145-146.
7. Chaudhary, V. K., D. J. FitzGerald, and I. Pastan (1991) A proper amino terminus of diphtheria toxin is important for cytotoxicity. *Biochem Biophys Res Commun.* 180, 545-551.
8. Kondo, T., et al. (1988) Activity of immunotoxins constructed with modified *Pseudomonas* exotoxin A lacking the cell recognition domain. *J Biol Chem.* 263, 9470-9475.
9. Kreitman, R. J., et al. (1993) Single-chain immunotoxin fusions between anti-Tac and *Pseudomonas* exotoxin: relative importance of the two toxin disulfide bonds. *Bioconjug Chem.* 4, 112-120.
10. Siegall, C. B., et al. (1989) Functional analysis of domains II, Ib, and III of *Pseudomonas* exotoxin. *J Biol Chem.* 264, 14256-14261.
11. Williams, D. P., et al. (1990) Structure/function analysis of interleukin-2-toxin (DAB486-IL-2). Fragment B sequences required for the delivery of fragment A to the cytosol of target cells. *J Biol Chem.* 265, 11885-11889.
12. Madhumathi, J. and R. S. Verma (2012) Therapeutic targets and recent advances in protein immunotoxins. *Curr Opin Microbiol.*
13. Kreitman, R. J. (2006) Immunotoxins for targeted cancer therapy. *AAPS J.* 8, E532-551.
14. Roscoe, D. M., et al. (1994) Primate antibody response to immunotoxin: serological and computer-aided analysis of epitopes on a truncated form of *Pseudomonas* exotoxin. *Infect Immun.* 62, 5055-5065.
15. Roscoe, D. M., L. H. Pai, and I. Pastan (1997) Identification of epitopes on a mutant form of *Pseudomonas* exotoxin using serum from humans treated with *Pseudomonas* exotoxin containing immunotoxins. *Eur J Immunol.* 27, 1459-1468.
16. Graham, M. L. (2003) Pegaspargase: a review of clinical studies. *Adv Drug Deliv Rev.* 55, 1293-1302.
17. Reddy, K. R. (2004) Development and pharmacokinetics and pharmacodynamics of pegylated interferon alfa-2a (40 kD). *Semin Liver Dis.* 24 Suppl 2, 33-38.
18. Tsutsumi, Y., et al. (2000) Site-specific chemical modification with polyethylene glycol of recombinant immunotoxin anti-Tac(Fv)-PE38 (LMB-2) improves antitumor activity and reduces animal toxicity and immunogenicity. *Proc Natl Acad Sci USA.* 97, 8548-8553.
19. Li, Z., et al. (2005) Immunotoxins and cancer therapy. *Cell Mol Immunol.* 2, 106-112.
20. Mathew, M. and R. S. Verma (2009) Humanized immunotoxins: a new generation of immunotoxins for targeted cancer therapy. *Cancer Sci.* 100, 1359-1365.
21. Huhn, M., et al. (2001) Human angiogenin fused to human CD30 ligand (Ang-CD30L) exhibits specific cytotoxicity against CD30-positive lymphoma. *Cancer Res.* 61, 8737-8742.
22. Tur, M. K., et al. (2009) Immunokinases, a novel class of immunotherapeutics for targeted cancer therapy. *Curr Pharm Des.* 15, 2693-2699.
23. Tur, M. K., et al. (2009) Targeted restoration of down-regulated DAPK2 tumor suppressor activity induces apoptosis in Hodgkin lymphoma cells. *J Immunother.* 32, 431-441.
24. ten Cate, B., et al. (2010) Targeted elimination of leukemia stem cells; a new therapeutic approach in hemato-oncology. *Curr Drug Targets.* 11, 95-110.
25. Wan, L., et al. (2006) Expression, purification, and refolding of a novel immunotoxin containing humanized single-chain fragment variable antibody against CTLA4 and the N-terminal fragment of human perforin. *Protein Expr Purif.* 48, 307-313.
26. Barth, S., et al. (2000) Compatible-solute-supported periplasmic expression of functional recombinant proteins under stress conditions. *Appl Environ Microbiol.* 66, 1572-1579.
27. Hetzel, C., et al. (2008) Small cleavable adapters enhance the specific cytotoxicity of a humanized immunotoxin directed against CD64-positive cells. *J Immunother.* 31, 370-376.

TABLE 1

| CD molecule | Alternate Names |
|---|---|
| CD1a | R4; HTA1 |
| CD1b | R1 |
| CD1c | M241; R7 |
| CD1d | R3 |
| CD1e | R2 |
| CD2 | CD2R; E-rosette receptor; T11; LFA-2 |
| CD3delta | CD3d |
| CD3epsilon | CD3e |
| CD3gamma | CD3g |
| CD4 | L3T4; W3/25 |
| CD5 | Leu-1; Ly-1; T1; Tp67 |
| CD6 | T12 |
| CD7 | gp40 |
| CD8alpha | Leu2; Lyt2; T cell co-receptor; T8 |
| CD8beta | Leu2; CD8; Lyt3 |
| CD9 | DRAP-27; MRP-1; p24 |
| CD10 | EC 3.4.24.11; neprilysin; CALLA; enkephalinase; gp100; NEP |
| CD11a | AlphaL integrin chain; LFA-1alpha |
| CD11b | AlphaM integrin chain; AlphaM-beta2; C3biR; CR3; Mac-1; Mol |
| CD11c | AlphaX integrin chain; Axb2; CR4; leukocyte surface antigen p150, 95 |

TABLE 1-continued

| CD molecule | Alternate Names |
|---|---|
| CDw12 | p90-120 |
| CD13 | APN; EC 3.4.11.2; gp150 |
| CD14 | LPS-R |
| CD15u | Sulphated CD15 |
| CD16a | FCRIIIA |
| CD16b | FCRIIIB |
| CDw17 | LacCer |
| CD18 | CD11a beta subunit; CD11b beta subunit; CD11c beta subunit; beta-2 integrin chain |
| CD19 | B4 |
| CD20 | B1; Bp35 |
| CD21 | C3d receptor; CR2; EBV-R |
| CD22 | BL-CAM; Lyb8 |
| CD23 | B6; BLAST-2; FceRII; Leu-20; Low affinity IgE receptor |
| CD24 | BA-1; HSA |
| CD25 | IL-2R alpha chain; IL-2R; Tac antigen |
| CD26 | EC 3.4.14.5; ADA-binding protein; DPP IV ectoenzyme |
| CD27 | S152; T14 |
| CD28 | T44; Tp44 |
| CD29 | Platelet GPIIa; VLA-beta chain; beta-1 integrin chain |
| CD30 | Ber-H2 antigen; Ki-1 antigen |
| CD31 | GPiia'; endocam; PECAM-1 |
| CD32 | FCR II; Fc gamma RII |
| CD33 | gp67; p67 |
| CD34 | gp105-120 |
| CD35 | C3bR; C4bR; CR1; Immune Adherence Receptor |
| CD36 | GPIIIb; GPIV; OKM5-antigen; PASIV |
| CD37 | gp52-40 |
| CD38 | T10; cyclic ADP-ribose hydrolase |
| CD39 | |
| CD40 | Bp50 |
| CD41 | GPIIb; alpha IIb integrin chain |
| CD42a | GPIX |
| CD42b | GPIbalpha; Glycocalicin |
| CD42c | GPIb-beta |
| CD42d | GPV |
| CD43 | gpL115; leukocyte sialoglycoprotein; leukosialin; sialophorin |
| CD44 | ECMR III; H-CAM; HUTCH-1; Hermes; Lu, In-related; Pgp-1; gp85 |
| CD44R | CD44v; CD44v9 |
| CD45 | B220; CD45R; CD45RA; CD45RB; CD45RC; CD45RO; EC 3.1.3.4; LCA; T200; Ly5 |
| CD46 | MCP |
| CD47R | Rh-associated protein; gp42; IAP; neurophilin; OA3; MEM-133; formerly CDw149 |
| CD48 | BCM1; Blast-1; Hu Lym3; OX-45 |
| CD49a | Alpha-1 integrin chain; VLA-1 alpha chain |
| CD49b | Alpha-2 integrin chain; GPIa; VLA-2 alpha chain |
| CD49c | Alpha-3 integrin chain; VLA-3 alpha chain |
| CD49d | Alpha-4 integrin chain; VLA-4 alpha chain |
| CD49e | Alpha-5 integrin chain; FNR alpha chain; VLA-5 alpha chain |
| CD49f | Alpha-6 integrin chain; Platelet gpI; VLA-6 alpha chain |
| CD50 | ICAM-3 |
| CD51 | VNR-alpha chain; alpha V integrin chain; vitronectin receptor |
| CD52 | |
| CD53 | |
| CD54 | ICAM-1 |
| CD55 | DAF |
| CD56 | Leu-19; NKH1; NCAM |
| CD57 | HNK1; Leu-7 |
| CD58 | LFA-3 |
| CD59 | 1F-5Ag; H19; HRF20; MACIF; MIRL; P-18; Protectin |
| CD60a | GD3 |
| CD60b | 9-O-acetyl-GD3 |
| CD60c | 7-O-acetyl-GD3 |
| CD61 | CD61A; GPIIb/IIIa; beta 3 integrin chain |
| CD62E | E-selectin; ELAM-1; LECAM-2 |
| CD62L | L-selectin; LAM-1; LECAM-1; Leu-8; MEL-14; TQ-1 |

TABLE 1-continued

| CD molecule | Alternate Names |
|---|---|
| CD62P | P-selectin; GMP-140; PADGEM |
| CD63 | LIMP; MLA1; PTLGP40; gp55; granulophysin; LAMP-3; ME491; NGA |
| CD64 | FC gammaRI; FCR I |
| CD65 | Ceramide-dodecasaccharide; VIM-2 |
| CD65s | Sialylated-CD65; VIM2 |
| CD66a | NCA-160; BGP |
| CD66b | CD67; CGM6; NCA-95 |
| CD66c | NCA; NCA-50/90 |
| CD66d | CGM1 |
| CD66e | CEA |
| CD66f | Pregnancy specific b1 glycoprotein; SP-1; PSG |
| CD68 | gp110; macrosialin |
| CD69 | AIM; EA 1; MLR3; gp34/28; VEA |
| CD70 | CD27-ligand; Ki-24 antigen |
| CD71 | T9; transferrin receptor |
| CD72 | Ly-19.2; Ly-32.2; Lyb-2 |
| CD73 | Ecto-5'-nucleotidase |
| CD74 | Class II-specific chaperone; Ii; Invariant chain |
| CD75 | Lactosamines |
| CD75s | Alpha-2,6-sialylated lactosamines (formerly CDw75 and CDw76) |
| CD77 | Pk blood group antigen; BLA; CTH; Gb3 |
| CD79a | Ig alpha; MB1 |
| CD79b | B29; Ig beta |
| CD80 | B7; BB1 |
| CD81 | TAPA-1 |
| CD82 | 4F9; C33; IA4; KAI1; R2 |
| CD83 | HB15 |
| CD84 | |
| CD85 | ILT/LIR family |
| CD86 | B7-2; B70 |
| CD87 | uPAR |
| CD88 | C5aR |
| CD89 | Fcalpha-R; IgA Fc receptor; IgA receptor |
| CD90 | Thy-1 |
| CD91 | ALPHA2M-R; LRP |
| CD92 | CTL1; formerly CDw92 |
| CDw93 | |
| CD94 | Kp43 |
| CD95 | APO-1; Fas; TNFRSF6; APT1 |
| CD96 | TACTILE |
| CD97 | |
| CD98 | 4F2; FRP-1; RL-388 |
| CD99 | CD99R; E2; MIC2 gene product |
| CD100 | SEMA4D |
| CD101 | IGSF2; P126; V7 |
| CD102 | ICAM-2 |
| CD103 | ITGAE; HML-1; integrin alphaE chain |
| CD104 | beta 4 integrin chain; TSP-1180; beta 4 |
| CD105 | endoglin |
| CD106 | INCAM-110; VCAM-1 |
| CD107a | LAMP-1 |
| CD107b | LAMP-2 |
| CD108 | SEMA7A; JMH human blood group antigen; formerly CDw108 |
| CD109 | 8A3; E123; 7D1 |
| CD110 | MPL; TPO-R; C-MPL |
| CD111 | PVRL1; PRR1; HevC; nectin-1; HIgR |
| CD112 | HVEB; PRR2; PVRL2; nectin 2 |
| CDw113 | PVRL3, Nectin3; poliovirus receptor-related 3; nectin-3 |
| CD114 | CSF3R; HG-CSFR; G-CSFR |
| CD115 | c-fms; CSF-1R; M-CSFR |
| CD116 | GM-CSF receptor alpha chain |
| CD117 | c-KIT; SCFR |
| CD118 | LIFR; leukemia inhibitory factor receptor |
| CDw119 | IFNgR; IFNgRa |
| CD120a | TNFRI; p55 |
| CD120b | TNFRII; p75; TNFR p80 |
| CD121a | IL-1R; type 1 IL-1R |
| CDw121b | IL-1R, type 2 |
| CD122 | IL-2Rbeta |
| CD123 | IL-3Ralpha |
| CD124 | IL-4R |
| CDw125 | IL-SRalpha |
| CD126 | IL-6R |
| CD127 | IL-7R; IL-7R alpha; p90 I17 R |

TABLE 1-continued

| CD molecule | Alternate Names |
|---|---|
| CDw128a | CXCR1; IL-8RA |
| CDw128b | CXCR2; IL-8R6 |
| CD129 | Reserved |
| CD130 | gp130 |
| CD131 | common beta subunit |
| CD132 | IL2RG; common cytokine receptor gamma chain; common gamma chain |
| CD133 | PROML1; AC133; hematopoietic stem cell antigen; prominin-like 1 |
| CD134 | OX40 |
| CD135 | fit3; Flk-2; STK-1 |
| CDw136 | msp receptor; ron; p158-ron |
| CDw137 | 4-1BB; ILA |
| CD138 | heparan sulfate proteoglycan; syndecan-1 |
| CD139 | |
| CD140a | PDGF-R; PDGFRa |
| CD140b | PDGFRb |
| CD141 | fetomodulin; TM |
| CD142 | F3; coagulation Factor III; thromboplastin; TF |
| CD143 | EC 3.4.15.1; ACE; kininase II; peptidyl dipeptidase A |
| CD144 | cadherin-5; VE-Cadherin |
| CDw145 | |
| CD146 | MCAM; A32; MUC18; Mel-CAM; S-endo |
| CD147 | 5A11; Basigin; CE9; HT7; M6; Neurothelin; OX-47; EMMPRIN; gp42 |
| CD148 | HPTP-eta; DEP-1; p260 |
| CDw149 | new designation is CD47R |
| CD150 | SLAM; IPO-3; fomerly CDw150 |
| CD151 | PETA-3; SFA-1 |
| CD152 | CTLA-4 |
| CD153 | CD30L |
| CD154 | CD40L; T-BAM; TRAP; gp39 |
| CD155 | PVR |
| CD156a | ADAMS; MS2 human; fomerly CD156 |
| CD156b | ADAM17; TACE; cSVP |
| CDw156C | ADAM10; a disintegrin and metalloproteinase domain 10 |
| CD157 | BP-3/IF-7; BST-1; Mo5 |
| CD158 | KIR family |
| CD159a | NKG2A |
| CD159c | NKG2C; killer cell lectin-like receptor subfamily C, member 2 |
| CD160 | BY55 antigen; NK1; NK28 |
| CD161 | KLRB1; NKR-P1A; killer cell lectin-like receptor subfamily B, member 1 |
| CD162 | PSGL-1, PSGL |
| CD162R | PEN5 (a post-translational modification of PSGL-1) |
| CD163 | GHI/61; M130; RM3/1 |
| CD164 | MUC-24; MGC-24v |
| CD165 | AD2; gp37 |
| CD166 | BEN; DM-GRASP; KG-CAM; Neurolin; SC-1; ALCAM |
| CD167a | trkE; trk6; cak; eddr1; DDR1; MCK10; RTK6; NTRK4 |
| CD168 | HMMR; IHABP; RHAMM |
| CD169 | sialoadhesin; siglec-1 |
| CD170 | Siglec-5 |
| CD171 | L1; L1CAM; N-CAM L1 |
| CD172a | SIRP alpha |
| CD172b | SIRPbeta; signal-regulatory protein beta 1 |
| CD172g | SIRPgamma; signal-regulatory protein beta 2 |
| CD173 | Blood group H type 2 |
| CD174 | Lewis y |
| CD175 | Tn |
| CD175s | Sialyl-Tn |
| CD176 | TF |
| CD177 | NB1 |
| CD178 | fas-L; TNFSF6; APT1LG1; CD95-L |
| CD179a | VpreB; VPREB1; IGVPB |
| CD179b | IGLL1; lambda5; immunoglobulin omega polypeptide; IGVPB; 14.1 chain |
| CD180 | LY64; RP105 |
| CD181 | CXCR1; (was CDw128A), IL8Ralpha |
| CD182 | CXCR2; (was CDw128B), IL8Rbeta |
| CD183 | CXCR3; GPR9; CKR-L2; IP10-R; Mig-R |
| CD184 | CXCR4; fusin; LESTR; NPY3R; HM89; FB22 |

TABLE 1-continued

| CD molecule | Alternate Names |
|---|---|
| CD185 | CXCR5; Chemokine (C-X-C motif) Receptor 5, Burkitt lymphoma receptor 1 |
| CDw186 | CXCR6; Chemokine (C-X-C motif) Receptor 6 |
| CD191 | CCR1; Chemokine (C-C motif) Receptor 1, RANTES Receptor |
| CD192 | CCR2; Chemokine (C-C motif) Receptor 2, MCP-1 receptor |
| CD193 | CCR3; Chemokine (C-C motif) Receptor 3, eosinophileotaxin receptor |
| CD195 | CCR5 |
| CD196 | CCR6; Chemokine (C-C motif) Receptor 6 |
| CD197 | CCR7; (was CDw197) Chemokine (C-C motif) Receptor 7 |
| CDw198 | CCR8; Chemokine (C-C motif) Receptor 8 |
| CDw199 | CCR9; Chemokine (C-C motif) Receptor 9 |
| CDw197 | CCR7 |
| CD200 | OX2 |
| CD201 | EPC R |
| CD202b | tie2; tek |
| CD203c | NPP3; PDNP3; PD-Ibeta; 610; gp13ORB13-6; ENPP3; bovine intestinal phosphodiesterase |
| CD204 | macrophage scavenger R |
| CD205 | DEC205 |
| CD206 | MRC1; MMR |
| CD207 | Langerin |
| CD208 | DC-LAMP |
| CD209 | DC-SIGN |
| CDw210 | IL-10 R |
| CD212 | IL-12 R |
| CD213a1 | IL-13 R alpha 1 |
| CD213a2 | IL-13 R alpha 2 |
| CDw217 | IL-17 R |
| CDw218a | IL18Ralpha; IL18Ralpha |
| CDw218b | IL18Rbeta; IL18Rbeta |
| CD220 | Insulin R |
| CD221 | IGF1 R |
| CD222 | Mannose-6-phosphate/IGF2 R |
| CD223 | LAG-3 |
| CD224 | GGT; EC2.3.2.2 |
| CD225 | Leu13 |
| CD226 | DNAM-1; PTA1; TLiSA1 |
| CD227 | MUC1; episialin; PUM; PEM; EMA; DF3 antigen; H23 antigen |
| CD228 | melanotransferrin |
| CD229 | Ly9 |
| CD230 | Prion protein |
| CD231 | TM4SF2; A15; TALLA-1; MXS1; CCG-B7; TALLA |
| CD232 | VESP R |
| CD233 | band 3; erythrocyte membrane protein band 3; AE1; SLC4A1; Diego blood group; EPB3 |
| CD234 | Fy-glycoprotein; Duffy antigen |
| CD235a | Glycophorin A |
| CD235b | Glycophorin B |
| CD235ab | Glycophorin A/B crossreactive mabs |
| CD236 | Glycophorin C/D |
| CD236R | Glycophorin C |
| CD238 | Kell |
| CD239 | B-CAM |
| CD240CE | Rh30CE |
| CD240D | Rh30D |
| CD240DCE | Rh30D/CE crossreactive mabs |
| CD241 | RhAg |
| CD242 | ICAM-4 |
| CD243 | MDR-1 |
| CD244 | 2B4; NAIL; p38 |
| CD245 | p220/240 |
| CD246 | Anaplastic lymphoma kinase |
| CD247 | Zeta chain |
| CD248 | TEM1, Endosialin; CD164 sialomucin-like 1, tumor endothelial marker 1 |
| CD249 | Aminopeptidase A; APA, gp160 |
| CD252 | OX40L; TNF (ligand) superfamily member 4, CD134 ligand |
| CD253 | TRAIL; TNF (ligand) superfamily member 10, APO2L |
| CD254 | TRANCE; TNF (ligand) superfamily member 11, RANKL |

TABLE 1-continued

| CD molecule | Alternate Names |
|---|---|
| CD256 | APRIL; TNF (ligand) superfamily member 13, TALL2 |
| CD257 | BLYS; TNF (ligand) superfamily, member 13b, TALL1, BAFF |
| CD258 | LIGHT; TNF (ligand) superfamily, member 14 |
| CD261 | TRAIL-R1; TNFR superfamily, member 10a, DR4, APO2 |
| CD262 | TRAIL-R2; TNFR superfamily, member 10b, DR5 |
| CD263 | TRAIL-R3; TNFR superfamily, member 10c, DCR1 |
| CD264 | TRAIL-R4; TNFR superfamily, member 10d, DCR2 |
| CD265 | TRANCE-R; TNFR superfamily, member 11a, RANK |
| CD266 | TWEAK-R; TNFR superfamily, member 12A, type I transmembrane protein Fn14 |
| CD267 | TACI; TNFR superfamily, member 13B, transmembrane activator and CAML interactor |
| CD268 | BAFFR; TNFR superfamily, member 13C, B cell-activating factor receptor |
| CD269 | BCMA; TNFR superfamily, member 17, B-cell maturation factor |
| CD271 | NGFR (p75); nerve growth factor receptor (TNFR superfamily, member 16) |
| CD272 | BTLA; B and T lymphocyte attenuator |
| CD273 | B7DC, PDL2; programmed cell death 1 ligand 2 |
| CD274 | B7H1, PDL1; programmed cell death 1 ligand 1 |
| CD275 | B7H2, ICOSL; inducible T-cell co-stimulator ligand (ICOSL) |
| CD276 | B7H3; B7 homolog 3 |
| CD277 | BT3.1; B7 family: butyrophilin, subfamily 3, member A1 |
| CD278 | ICOS; inducible T-cell co-stimulator |
| CD279 | PD1; programmed cell death 1 |
| CD280 | ENDO180; uPARAP, mannose receptor, C type 2, TEM22 |
| CD281 | TLR1; TOLL-like receptor 1 |
| CD282 | TLR2; TOLL-like receptor 2 |
| CD283 | TLR3; TOLL-like receptor 3 |
| CD284 | TLR4; TOLL-like receptor 4 |
| CD289 | TLR9; TOLL-like receptor 9 |
| CD292 | BMPR1A; Bone Morphogenetic Protein Receptor, type IA |
| CDw293 | BMPR1B; Bone Morphogenetic Protein Receptor, type IB |
| CD294 | CRTH2; PGRD2; G protein-coupled receptor 44, |
| CD295 | LEPR; Leptin Receptor |
| CD296 | ART1; ADP-ribosyltransferase 1 |
| CD297 | ART4; ADP-ribosyltransferase 4; Dombrock blood group glycoprotein |
| CD298 | ATP1B3; Na+/K+ -ATPase beta 3 subunit |
| CD299 | DCSIGN-related; CD209 antigen-like, DC-SIGN2, L-SIGN |

TABLE 1-continued

| CD molecule | Alternate Names |
|---|---|
| CD300a | CMRF35 FAMILY; CMRF-35H |
| CD300c | CMRF35 FAMILY; CMRF-35A |
| CD300e | CMRF35 FAMILY; CMRF-35L1 |
| CD301 | MGL; CLECSF14, macrophage galactose-type C-type lectin |
| CD302 | DCL1; Type I transmembrane C-type lectin receptor DCL-1 |
| CD303 | BDCA2; C-type lectin, superfamily member 11 |
| CD304 | BDCA4; Neuropilin 1 |
| CD305 | LAIR1; Leukocyte-Associated Ig-like Receptor 1 |
| CD306 | LAIR2; Leukocyte-Associated Ig-like Receptor 2 |
| CD307 | IRTA2; Immunoglobulin superfamily Receptor Translocation Associated 2 |
| CD309 | VEGFR2; KDR (a type III receptor tyrosine kinase) |
| CD312 | EMR2 ; EGF-like module containing, mucin-like, hormone receptor-like 2 |
| CD314 | NKG2D; Killer cell lectin-like receptor subfamily K, member 1 |
| CD315 | CD9P1; Prostaglandin F2 receptor negative regulator |
| CD316 | EWI2; Immunoglobulin superfamily, member 8 |
| CD317 | BST2; Bone Marrow Stromal cell antigen 2 |
| CD318 | CDCP1; CUB domain-containing protein 1 |
| CD319 | CRACC; SLAM family member 7 |
| CD320 | 8D6; 8D6 Antigen; FDC |
| CD321 | JAM1; F11 receptor |
| CD322 | JAM2; Junctional Adhesion Molecule 2 |
| CD324 | E-Cadherin; cadherin 1, type 1, E-cadherin (epithelial) |
| CDw325 | N-Cadherin; cadherin 2, type 1, N-cadherin (neuronal) |
| CD326 | Ep-CAM; tumor-associated calcium signal transducer 1 |
| CDw327 | siglec6; sialic acid binding Ig-like lectin 6 |
| CDw328 | siglec7; sialic acid binding Ig-like lectin 7 |
| CDw329 | siglec9; sialic acid binding Ig-like lectin 9 |
| CD331 | FGFR1; Fibroblast Growth Factor Receptor 1 |
| CD332 | FGFR2; Fibroblast Growth Factor Receptor 2 (keratinocyte growth factor receptor) |
| CD333 | FGFR3; Fibroblast Growth Factor Receptor 3 (achondroplasia, thanatophoric dwarfism) |
| CD334 | FGFR4; Fibroblast Growth Factor Receptor 4 |
| CD335 | NKp46; NCR1, (Ly94); natural cytotoxicity triggering receptor 1 |
| CD336 | NKp44; NCR2, (Ly95); natural cytotoxicity triggering receptor 2 |
| CD337 | NKp30; NCR3 |
| CDw338 | ABCG2; ATP-binding cassette, sub-family G (WHITE), member 2 |
| CD339 | Jagged-1; Jagged 1 (Alagille syndrome) |

TABLE 2

| Systematic name | Human chromosome | Human ligand | Mouse ligand | Chemokine receptor(s) |
|---|---|---|---|---|
| | | CXC chemokine/receptor family | | |
| CXCL1 | 4q21.1 | GROα/MGSA-α | GRO/MIP-2/KC? | CXCR2 > CXCR1 |
| CXCL2 | 4q21.1 | GROβ/MGSA-β | GRO/MIP-2/KC? | CXCR2 |
| CXCL3 | 4q21.1 | GROγ/MGSA-γ | GRO/MIP-2/KC? | CXCR2 |
| CXCL4 | 4q21.1 | PF4 | PF4 | Unknown |
| CXCL5 | 4q21.1 | ENA-78 | GCP-2/LIX? | CXCR2 |
| CXCL6 | 4q21.1 | GCP-2 | GCP-2/LIX? | CXCR1. CXCR2 |
| CXCL7 | 4q21.1 | NAP-2 | Unknown | CXCR2 |
| CXCL8 | 4q21.1 | IL-8 | Unknown | CXCR1. CXCR2 |
| CXCL9 | 4q21.1 | Mig | Mig | CXCR3[a] |
| CXCL10 | 4q21.1 | 1P-10 | 1P-10/CRG-2 | CXCR3[a] |
| CXCL11 | 4q21.1 | 1-TAC | 1-TAC | CXCR3[a] |
| CXCL12 | 10q11.21 | SDF-1 α/β | SDF-1/PBSF | CXCR4[b] |
| CXCL13 | 4q21.1 | BCA-1 | BLC | CXCR5 |
| CXCL14 | 5q31.1 | BRAK/bolekine | BRAK | Unknown |

TABLE 2-continued

| Systematic name | Human chromosome | Human ligand | Mouse ligand | Chemokine receptor(s) |
|---|---|---|---|---|
| (CXCL15) | | Unknown | Lungkine/WECHE | Unknown |
| CXCL16 | 17p13 | | | CXCR6 |
| | | C chemokine/receptor family | | |
| XCL1 | 1q24.2 | Lymphotactin/SCM-1α/ ATAC | Lymphotactin | XCR1 |
| XCL2 | 1q24.2 | SCM-1β | Unknown | XCR1 |
| | | $CX_3C$ chemokine/receptor family | | |
| CXC3L1 | 16q13 | Fractalkine | Neurotactin/ABCD-3 | CXC3R1 |
| | | CC chemokine/receptor family | | |
| CCL1 | 17q11.2 | 1-309 | TCA-3/P500 | CCR8 |
| CCL2 | 17q11.2 | MCP-1/MCA/TDCF | JE? | CCR2 |
| CCL3 | 17q12 | MIP-1α/LD78α | MIP-1α | CCR1, CCR5 |
| CCL3L1 | 17q12 | LD78β | Unknown | CCR1, CCR5 |
| CCL4 | 17q12 | MIP-1β | MIP-1β | CCR5[b] |
| CCL5 | 17q12 | RANTES | RANTES | CCR1, CCR3, CCR5[c] |
| (CCL6) | | Unknown | C10-MRP-1 | Unknown |
| CCL7 | 17q11.2 | MCP-3 | MARC? | CCR1, CCR3, CCR3 |
| CCL8 | 17q11.2 | MCP-2 | MCP-2? | CCR3, CCR5[c] |
| (CCL9/10) | | Unknown | MCP-2/CCF18/MIP-1γ | CCR1 |
| CCL11 | 17q11.2 | Eotaxin | Eotaxin | CCR3 |
| (CCL12) | | Unknown | MCP-5 | CCR2 |
| CCL13 | 17q11.2 | MCP-4 | Unknown | CCR2, CCR3 |
| CCL14 | 17q12 | HCC-1 | Unknown | CCR1, CCR5 |
| CCL15 | 17q12 | HCC-2/Lkn-1/MIP-1 | Unknown | CCR1, CCR3 |
| CCL16 | 17q12 | HCC-4/LEC/LCC-1 | Unknown | CCR1, CCR2 |
| CCL17 | 16q13 | TARC | TARC/ABCD-2 | CCR4 |
| CCL18 | 17q12 | DC-CK1/PARC/AMAC-1 | Unknown | Unknown |
| CCL19 | 9p13.3 | MIP-3β/ELC/exodus-3 | MIP-3β/ELC/exodus-3 | CCR7[d] |
| CCL20 | 2q36.3 | MIP-3α/LARC/exodus-1 | MIP-3α/LARC/exodus-1 | CCR6 |
| CCL21 | 9p13.3 | 6Ckine/SLC/exodus-2 | 6Ckine/SLC/exodus-2/ TCA-4 | CCR7[d] |
| CCL22 | 16q13 | MDC/STCP-1 | ABCD-1 | CCR4 |
| CCL23 | 17q12 | MPIF-1/CKβ8/CKβ8-1 | Unknown | CCR1 |
| CCL24 | 7q11.23 | Eotaxin-2/MPIF-2 | MPIF-2 | CCR3 |
| CCL25 | 19p13.3 | TECK | TECK | CCR9 |
| CCL26 | 7q11.23 | Eotaxin-3 | Unknown | CCR3 |
| CCL27 | 9p13.3 | CTACK/ILC | ALP/CTACK/ILC/ESkine | CCR10 |
| CCL28 | 5p12 | MEC | | CCR3/CCR10 |

[a]CD183.
[b]CD184
[c]CD195.
[d]$CD_x$ 197.
Extracted from R. Thorpe et al. , Cytokine 21 (2003) 48-49

TABLE 3

| Name | Source | Target receptors | Target cells | Function |
|---|---|---|---|---|
| IL-1 | macrophages, B cells, monocytes, dendritic cells | CD121a/ IL1R1, CD121b/ IL1R2 | T helper cells | co-stimulation |
| | | | B cells | Maturation & proliferation |
| | | | Nk cells | activation |
| | | | macrophages, endothelium, other | inflammation, small amounts induce acute phase reaction, large amounts induce fever |
| IL-2 | TH1-cells | CD25/ IL2RA, CD122/ IL2RB, CD132/ IL2RG | activated T cells and B cells, NK cells, macrophages, oligodendro-cytes | stimulates growth and differentiation of T cell response. Can be used in immunotherapy to treat cancer or suppressed for transplant patients. |

TABLE 3-continued

| Name | Source | Target receptors | Target cells | Function |
|---|---|---|---|---|
| IL-3 | activated T helper cells[3], mast cells, NK cells, endothelium, eosinophils | CD123/ IL3RA, CD131/ IL3RB | hematopoietic stem cells | growth and differentiation to e.g. erythrocytes, granulocytes |
| | | | mast cells | growth and histamine release |
| IL-4 | TH2-cells, just activated naive CD4+ cell, memory CD4+ cells, mast cells, macrophages | CD124/ IL4R, CD132/ IL2RG | activated B cells | proliferation and differentiation, IgG1 and IgE synthesis. Important role in allergic response (IgE) |
| | | | T cells | proliferation |
| IL-5 | TH2-cells, mast cells, eosinophils | CD125/ IL5RA, CD131/ IL3RB | eosinophils | production |
| | | | B cells | differentiation, IgA production |

TABLE 3-continued

| Name | Source | Target receptors | Target cells | Function |
|---|---|---|---|---|
| IL-6 | macrophages, TH2-cells, B cells, astrocytes, endothelium | CD126/ IL6RA, CD130/ IR6RB | activated B cells | differentiation into plasma cells |
| | | | plasma cells | antibody secretion |
| | | | hematopoietic stem cells | differentiation |
| | | | T cells, others | induces acute phase reaction, hematopoiesis, differentiation, inflammation |
| IL-7 | bone marrow stromal cells and thymus stromal cells | CD127/ IL7RA, CD132/ IL2RG | pre/pro-B cell, pre/pro-T cell, NK cells | involved in B, T, and NK cell survival, development, and homeostasis, ↑proinflammatory cytokines |
| IL-8 | macrophages, lymphocytes, epithelial cells, endothelial cells | CXCR1/ IL8RA, CXCR2/ IL8RB/ CD128 | neutrophils, basophils, lymphocytes | Neutrophil chemotaxis |
| IL-9 | Th2-cells, specifically by CD4+ helper cells | CD129/ IL9R | T cells, B cells | Potentiates IgM, IgG, IgE, stimulates mast cells |
| IL-10 | monocytes, TH2-cells, CD8+ T cells, mast cells, macrophages, B cell subset | CD210/ IL10RA, CDW210B/ IL10RB | macrophages | cytokine production |
| | | | B cells | activation |
| | | | Th1 cells | inhibits Th1 cytokine production (IFN-γ, TNF-β, IL-2) |
| | | | Th2 cells | Stimulation |
| IL-11 | bone marrow stroma | IL11RA | bone marrow stroma | acute phase protein production, osteoclast formation |
| IL-12 | dendritic cells, B cells, T cells, macrophages | CD212/ IL12RB1, IR12RB2 | activated [3] T cells, | differentiation into Cytotoxic T cells with IL-2[3], ↑ IFN-γ, TNF-α, ↓ IL-10 |
| | | | NK cells | ↑ IFN-γ, TNF-α |
| IL-13 | activated TH2-cells, mast cells, NK cells | IL13R | TH2-cells, B cells, macro-phages | Stimulates growth and differentiation of B-Cells (IgE), inhibits TH1-cells and the production of macrophage inflammatory cytokines (e.g. IL-1, IL-6), ↓ IL-8, IL-10, IL-12 |
| IL-14 | T cells and certain malignant B cells | | activated B cells | controls the growth and proliferation of B cells, inhibits Ig secretion |

TABLE 3-continued

| Name | Source | Target receptors | Target cells | Function |
|---|---|---|---|---|
| IL-15 | mononuclear phagocytes (and some other cells), especially macrophages following infection by virus(es) | IL15RA | T cells, activated B cells | Induces production of Natural Killer Cells |
| IL-16 | lymphocytes, epithelial cells, eosinophils, CD8+ T cells | CD4 | CD4+T cells | CD4+ chemoattractant |
| IL-17 | subsets of T cells | CDw217/ IL17RA, IL17RB | epithelium, endothelium, other | osteoclastogenesis, angiogenesis, ↑ inflammatory cytokines |
| IL-18 | macrophages | CDw218a/ IL18R1 | Th1 cells, NK cells | Induces production of IFNγ, ↑ NK cell activity |
| IL-19 | — | IL20R | | — |
| IL-20 | — | IL20R | | regulates proliferation and differentiation of keratinocytes |
| IL-21 | — | IL21R | | |
| IL-22 | — | IL22R | | Activates STAT1 and STAT3 and increases production of acute phase proteins such as serum amyloid A, Alpha 1-antichymotrypsin and haptoglobin in hepatoma cell lines |
| IL-23 | — | IL23R | | Increases angiogenesis but reduces CD8 T-cell infiltration |
| IL-24 | — | IL20R | | Plays important roles in tumor suppression, wound healing and psoriasis by influencing cell survival. |
| IL-25 | — | LY6E | | Induces the production IL-4, IL- 5 and IL-13, which stimulate eosinophil expansion |
| IL-26 | — | IL20R1 | | Enhances secretion of IL-10 and IL-8 and cell surface expression of CD54 on epithelial cells |
| IL-27 | — | IL27RA | | Regulates the activity of B lymphocyte and T lymphocytes |
| IL-28 | — | IL28R | | Plays a role in immune defense against viruses |
| IL-29 | — | | | Plays a role in host defenses against microbes |

TABLE 3-continued

| Name | Source | Target receptors | Target cells | Function |
| --- | --- | --- | --- | --- |
| IL-30 | — | | | Forms one chain of IL-27 |
| IL-31 | — | IL31RA | | May play a role in inflammation of the skin |
| IL-32 | — | | | Induces monocytes and macrophages to secrete TNF-α, IL-8 and CXCL2 |
| IL-33 | — | | | Induces helper T cells to produce type 2 cytokine |
| IL-35 | regulatory T cells | | | Suppression of T helper cell activation |

The invention claimed is:

1. A compound formed from at least one component A comprising a binding domain for extra-cellular surface structures of a diseased proliferating cell that is internalized upon binding of component A of said compound, wherein said extra-cellular surface structures are selected from the group consisting of CD64, EGFR, AchR, EpCAM, and CD30, and at least one component B, characterized in that component B is a polypeptide whose amino acid sequence comprises a microtubule-associated protein (MAP).

2. The compound according to claim 1, wherein component A is selected from the group of internalizing cell surface receptor binding structures consisting of antibodies or fragments thereof which retain antigen binding function and specificity of a parent antibody.

3. The compound according to claim 1, wherein component A has higher valency by comprising one or more binding structures selected from any one of those listed in claim 2.

4. The compound according to claim 1, wherein component B is selected from the group consisting of microtubule-associated proteins (MAPs), Kinesins, KIFC1-3, Dyneins, DNAI1 and 2, DNAL1 and 4, Tau protein, Dynactin DCTN1, Tubulins, Stathmin, Gephyrin, Tektins, and Dynamins.

5. The compound according to claim 1 formed by component A and KIF1, component A and KIF2A, component A and KIF4A, component A and KIF5A, component A and KIF5B, component A and KIF6, component A and KIF7, component A and KIF9, component A and KIF10, component A and KIF11, component A and KIF12, component A and KIF13B, component A and KIF14, component A and KIF15, component A and KIF17, component A and KIF19, component A and KIF22, component A and KIF23, component A and KIF24, component A and KIF25, component A and KIF26, component A and KIF27, component A and KIFC1, component A and KIFC2, component A and KIFC3, component A and DNAH1, component A and DNAH2, component A and DNAH3, component A and DNAH5, component A and DNAH6, component A and DNAH7, component A and DNAH8, component A and DNAH9, component A and DNAH10, component A and DNAH11, component A and DNAH12, component A and DNAH14, component A and DNAI1, component A and DNAI2, component A and DNAL1, component A and DNAL4, component A and Tau, component A and Stathmin, component A and Gephyrin, component A and MAP1a, component A and MAP1b, component A and MAP2, component A and MAP4, component A and XMAP5, component A and MAP6, component A and MAP7, component A and MAP5, component A and MAP5, component A and DCTN1, component A and TUBA1, component A and TUBA2, component A and TUBA3, component A and TUBA4, component A and TUBA6, component A and TUBA8, component A and TEKT1, component A and TEKT2, component A and TEKT3, component A and TEKT4, component A and TEKT5, component A and DNM1, component A and DNM2, or component A and DNM3.

6. The compound according to claim 1, wherein the components are chemically coupled or fused to each other by genetic engineering.

7. A compound formed from at least one component A comprising a binding domain for extra-cellular surface structures of a diseased proliferating cell that is internalized upon binding of component A of said compound, wherein said extra-cellular surface structures are selected from the group consisting of CD64, EGFR, AchR, EpCAM, and CD30, and at least one component B, characterized in that component B is a polypeptide whose amino acid sequence comprises a microtubule-associated protein (MAP) or comprises at least a partial sequence of the MAP, the partial sequence having maintained the binding function of the MAP to a microtubule;

wherein the compound is encoded by a polynucleotide having the nucleotide sequences of SEQ ID NO: 3, 11 and/or 13.

8. A polynucleotide encoding the compound of claim 1, having the SEQ ID NO: 3, 11 and/or 13.

9. A process for manufacturing the fused compound of claim 6 comprising cloning a component B to yield a polynucleotide;

fusing said polynucleotide coding for component B with a polynucleotide coding for a protein of component A to yield a polynucleotide coding for the compound of claim 1;

expressing said polynucleotide coding for the compound of claim 1 in suitable host; and isolating and purifying the compound of claim 1.

10. A vector comprising at least one polynucleotide of claim 8.

11. A cell comprising the vector of claim 10.

12. A medicament comprising a compound of claim 1.

13. A method for treating a cancer or a proliferating disease, wherein a cell of the cancer or the proliferating disease expresses a receptor selected from the group consisting of CD64, EGFR, AchR, EpCam and CD30, said method comprising administering to a subject having the cancer or proliferating disease an effective amount of a compound of claim 1.

14. The compound according to claim 2, wherein the antibody fragment is a scFv.

15. The compound according to claim 4, wherein a. the MAP has one of SEQ ID NOs: 57-65;

b. the kinesin is KIF1-27 having SEQ ID NO: 14 or SEQ ID NO: 35;

c. the KIFC1-3 has one of SEQ ID NOs: 36-38;

d. the dynein is DNAH1-14 having one of SEQ ID NOs: 39-50;

e. the DNAI1 and 2 have SEQ ID NOs: 51 or 52, respectively;

f. the DNAL1 and 4 have SEQ ID NOs: 53 or 54, respectively;

g. the Tau protein is a Tau protein having deleted phosphorylation sites, wherein said Tau protein is encoded by SEQ ID NO: 1;

h. the Dynactin is DCTN1 having SEQ ID NO: 66;

i. the Tubulin is TUBA1-8 having one of SEQ ID NOs: 67-72;

j. the Stathmin has SEQ ID NO: 55;

k. the Gephyrin has SEQ ID NO: 56;

l. the Tektin is TEKT1-5 having one of SEQ ID NOs: 73-77; and m. the Dynamin is DNM1-3 having one of SEQ ID NOs: 78-80.

16. The compound according to claim 1, wherein component A is an H22(scFv) encoded by a polynucleotide having the SEQ ID NO: 2.

* * * * *